(12) United States Patent
Dave et al.

(10) Patent No.: US 10,047,400 B2
(45) Date of Patent: Aug. 14, 2018

(54) MICRORNA AND USE THEREOF IN IDENTIFICATION OF B CELL MALIGNANCIES

(71) Applicant: Duke University, Durham, NC (US)

(72) Inventors: Sandeep Dave, Chapel Hill, NC (US); Cassandra Love, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/317,879

(22) Filed: Jun. 27, 2014

(65) Prior Publication Data
US 2015/0057165 A1 Feb. 26, 2015

Related U.S. Application Data

(62) Division of application No. 13/513,757, filed as application No. PCT/US2010/058952 on Dec. 3, 2010, now abandoned.

(60) Provisional application No. 61/266,733, filed on Dec. 4, 2009.

(51) Int. Cl.
C07H 21/02 (2006.01)
C07H 21/04 (2006.01)
C12Q 1/6886 (2018.01)

(52) U.S. Cl.
CPC ...... *C12Q 1/6886* (2013.01); *C12Q 2600/112* (2013.01); *C12Q 2600/158* (2013.01); *C12Q 2600/16* (2013.01); *C12Q 2600/178* (2013.01)

(58) Field of Classification Search
CPC .......................... C12N 2310/11; C12N 15/113
See application file for complete search history.

(56) References Cited

U.S. PATENT DOCUMENTS

| 8,362,230 B2 | 1/2013 | Plasterk et al. | |
|---|---|---|---|
| 2006/0199233 A1 | 9/2006 | Dahlberg et al. | |
| 2007/0072204 A1* | 3/2007 | Hannon et al. | C12N 15/113 |
| 2008/0200416 A1* | 8/2008 | Li et al. | C12N 2310/11 |
| 2009/0143326 A1 | 6/2009 | Obad et al. | |
| 2012/0302626 A1 | 11/2012 | Dave et al. | |

FOREIGN PATENT DOCUMENTS

| WO | WO 2007/112754 | 10/2007 | |
|---|---|---|---|
| WO | WO 2009/012263 A2 * | 1/2009 | ........... C12N 15/113 |
| WO | WO 2009/036236 A1 * | 3/2009 | ......... C12N 2310/11 |

OTHER PUBLICATIONS

Zhang et al. (Blood, May 2009, vol. 113, No. 19, 4586-4594).*
United States Patent Office Action for U.S. Appl. No. 13/513,757 dated Mar. 20, 2014 (8 pages).
Altschul et al., "Basic Local Alignment Search Tool," J. Mol. Biol. 215:403-410 [1990].
Ambros, V., et al., "A uniform system for microRNA annotation," RNA (2003);9(3):277-279.
Baek et al., "The impact of microRNAs on protein output," Nature. 2008; 455:64-71.
Baltimore et al., "MicroRNAs: new regulators of immune cell development and function," Nat Immunol. 2008;9:839-845.
Blast Help Manual, NCBI, 2008, online only, (http://www.ncbi.nlm.nih.gov/books/NBK1762/).
Calin et al., "A Micro RNA Signature Associated with Prognosis and Progression in Chronic Lymphocytic Leukemia," N Engl J Med. 2005;353: 1793-1801.
Carillo, H., and Lipman, D., "The Multiple Sequence Alignment Problem in Biology," Siam J. Applied Math., 48:1073 (1988).
Cattoretti et al., "Deregulated BCL6 expression recapitulates the pathogenesis of human diffuse large B cell lymphomas in mice," Cancer Cell. 2005;7:445-455.
Chang et al., "BCL-6, a POZ/zinc-finger protein, is a sequence-specific transcriptional repressor," Proc Natl Acad Sci USA. 1996;93:6947-6952.
Chen et al., "MicroRNAs Modulate Hematopoietic Lineage Differentiation," Science. 2004; 303 :83-86.
Chen, C., et al., "Real-time quantification of microRNAs by stem-loop RT-PCR," Nucleic Acids Res. (2005);33(20):e179.
Dave et al., "Molecular Diagnosis of Burkitt's Lymphoma," N Engl J Med. 2006; 354:2431-2442.
Dave et al., "Prediction of Survival in Follicular Lymphoma Based on Molecular Features of Tumor infiltrating Immune Cells," (2004) N. Engl. J. Med. 351: 2159-2169.
Devereux, et al., "A comprehensive set of sequence analysis programs for the VAX," Nucleic Acids Research 12:387-395 [1984].
Doleshal et al., "Evaluation and Validation of Total RNA Extraction Methods for MicroRNA Expression Analyses in Formalin-Fixed, Paraffin-Embedded Tissues," J Mol Diagn. 2008; 10:203-211.
Dorsett et al., "MicroRNA-155 Suppresses Activation-Induced Cytidine Deaminase-Mediated Myc-Igh Translocation," Immunity 2008; 28:630-638.
Gottwein et al., "A viral microRNA functions as an orthologue of cellular miR-155," Nature. 2007; 450:1096-1099.
Gribskov, et al., "Sequence Analysis Primer," M. Stockton Press, New York, 1991 (7 pages).
Hacein-Bey-Abina et al., "LM02-Associated Clonal T Cell Proliferation in Two Patients after Gene Therapy for SCID-X1," Science. 2003; 302:415-419.
Hans et al., "Confirmation of the molecular classification of diffuse large 13-celllymphoma by immunohistochemistry using a tissue microarray," (2004) Blood 103: 275-282.
He et al., "A microRNA component of the p53 tumour suppressor network," Nature. 2007; 447:1130-1134.

(Continued)

*Primary Examiner* — Amy H Bowman
(74) *Attorney, Agent, or Firm* — Michael Best & Friedrich LLP

(57) ABSTRACT

Disclosed are nucleic acid sequences, including microRNA sequences and cDNA sequences, as well as vectors, DNA libraries, microarrays, and recombinant cells comprising the nucleic acid sequences described herein. Methods of determining the B cell stage from which a B cell malignancy is derived. Methods of identifying B cell malignancies are also provided. Methods of diagnosing B cell malignancies are provided. Such methods comprise, in certain embodiments, detecting one or more microRNAs or cDNAs as disclosed herein.

7 Claims, 15 Drawing Sheets

(56) References Cited

OTHER PUBLICATIONS

Hummel et al., "A Biologic Definition of Burkitt's Lymphoma from Transcriptional and Genomic Profiling," N Engl J Med. 2006; 354:2419-2430.
Johnnidis et al., "Regulation of progenitor cell proliferation and granulocyte function by microRNA-223," Nature. 2008; 451:1125-1129.
Klein et al., "Gene Expression Profiling of B Cell Chronic Lymphocytic Leukemia Reveals a Homogeneous Phenotype Related to Memory B Cells," J Exp Med. 2001; 194:1625-1638.
Klein et al., "Transcriptional analysis of the B cell germinal center reaction," Proc Natl Acad Sci USA. 2003; 100:2639-2644.
Landgraf et al., "A Mammalian micro RNA Expression Atlas Based on Small RNA Library Sequencing," Cell. 2007; 129:1401-1414.
Larsson et al., "Considerations when using the significance analysis of microarrays (SAM) algorithm," BMC Bioinformatics. 2005; 6:129.
Li et al., "miR-181a Is an Intrinsic Modulator of T Cell Sensitivity and Selection," Cell. 2007;129:147-161.
Lim et al., "MicroaiTay analysis shows that some microRNAs downregulate large numbers of target mRNAs," Nature. 2005;433:769-773.
Lu et al., "MicroRNA expression profiles classify human cancers," Nature 2005; 435:834-838.
Martins et al., "Regulation and Functions of Blimp-1 in T and B Lymphocytes," Annu Rev Immunol. 2008; 26:133-169.
Needleman and Wunsch, "A General Method Applicable to the Search for Similarities in the Amino Acid Sequence of Two Proteins," J. Mol Biol. 48:443-453 (1970).
Nutt et al., "Commitment to the B-lymphoid lineage depends on the transcription factor Pax5," Nature. 1999;401 :556-562.
O'Donnell et al., "c-Myc-regulated microRNAs modulate E2F1 expression," Nature. 2005;435:839-843.
Rosenwald et al., "The Use of Molecular Profiling to Predict Survival After Chemotherapy for Diffuse Large-B-Cell Lymphoma," N Engl J Med. 2002; 346: 1937-1947.
Sanz et al., "Phenotypic and functional heterogeneity of human memory B cells," Semin Immunol. 2008; 20:67-82.
Schebesta et al., "Transcriptional control of B-cell development," Curr Opin Immunol. 2002;14:216-223.
Selbach et al., "Widespread changes in protein synthesis induced by microRNAs," Nature. 2008;455:58-63.
Shaffer et al., "Signatures of the Immune Response," Immunity 2001; 15: 375-385.
Shaffer et al., "XBP1, Downstream of Blimp-1, Expands the Secretory Apparatus and Other Organelles, and Increases Protein Synthesis in Plasma Cell Differentiation," Immunity 2004; 21 :81-93.
Turner et al., "Blimp-1, a Novel Zinc Finger-Containing Protein That Can Drive the Maturation of B Lymphocytes into Immunoglobulin-Secreting Cells," Cell. 1994;77:297-306.
Tusher et al., "Significance analysis of microarrays applied to the ionizing radiation response," Proc Natl Acad Sci USA. 2001;98:5116-5121.
Ventura et al., "Targeted Deletion Reveals Essential and Overlapping Functions of the miR-17~92 Family of miRNA Clusters," Cell. 2008; 132:875-886.
Volkheimer et al., "Progressive immunoglobulin gene mutations in chronic lymphocytic leukemia: evidence for antigen-driven intraclonal diversification," (2007) Blood 109: 1559-1567.
West et al., "Predicting the clinical status of human breast cancer by using gene expression profiles," Proc Natl Acad Sci USA. 2001; 98:11462-11467.
Xi et al., "Systematic analysis of microRNA expression of RNA extracted from fresh frozen and formalin-fixed paraffin-embedded samples," Rna. 2007;13:1668-1674.
Xiao et al., "Lymphoproliferative disease and autoimmunity in mice with increased miR-17-92 expression in lymphocytes," Nat Immunol 2008;9:405-414.
Zheng, Q., et al., "GOEAST: a web-based software toolkit for Gene Ontology enrichment analysis," Nucleic acids Res. 2008;36, Web Server issue:W358-363.
Invitation to Pay Additional Fees and Where Applicable, Protest Fee for Application No. PCT/US10/58952 dated Mar. 25, 2011 (2 pages).
International Search Report and Written Opinion for Application No. PCT/US2010/58952 dated Jun. 2, 2011 (11 pages).
International Preliminary Report for Patentability for Application No. PCT/US2010/58952 dated Jun. 5, 2012 (7 pages).
United States Patent Office Action for U.S. Appl. No. 13/513,757 dated Oct. 9, 2013 (10 pages).
Array Express Accession No. GSE22898, Aug. 25, 2010.
Gene Expression Omnibus database (GSE12366), Aug. 7, 2008.

* cited by examiner

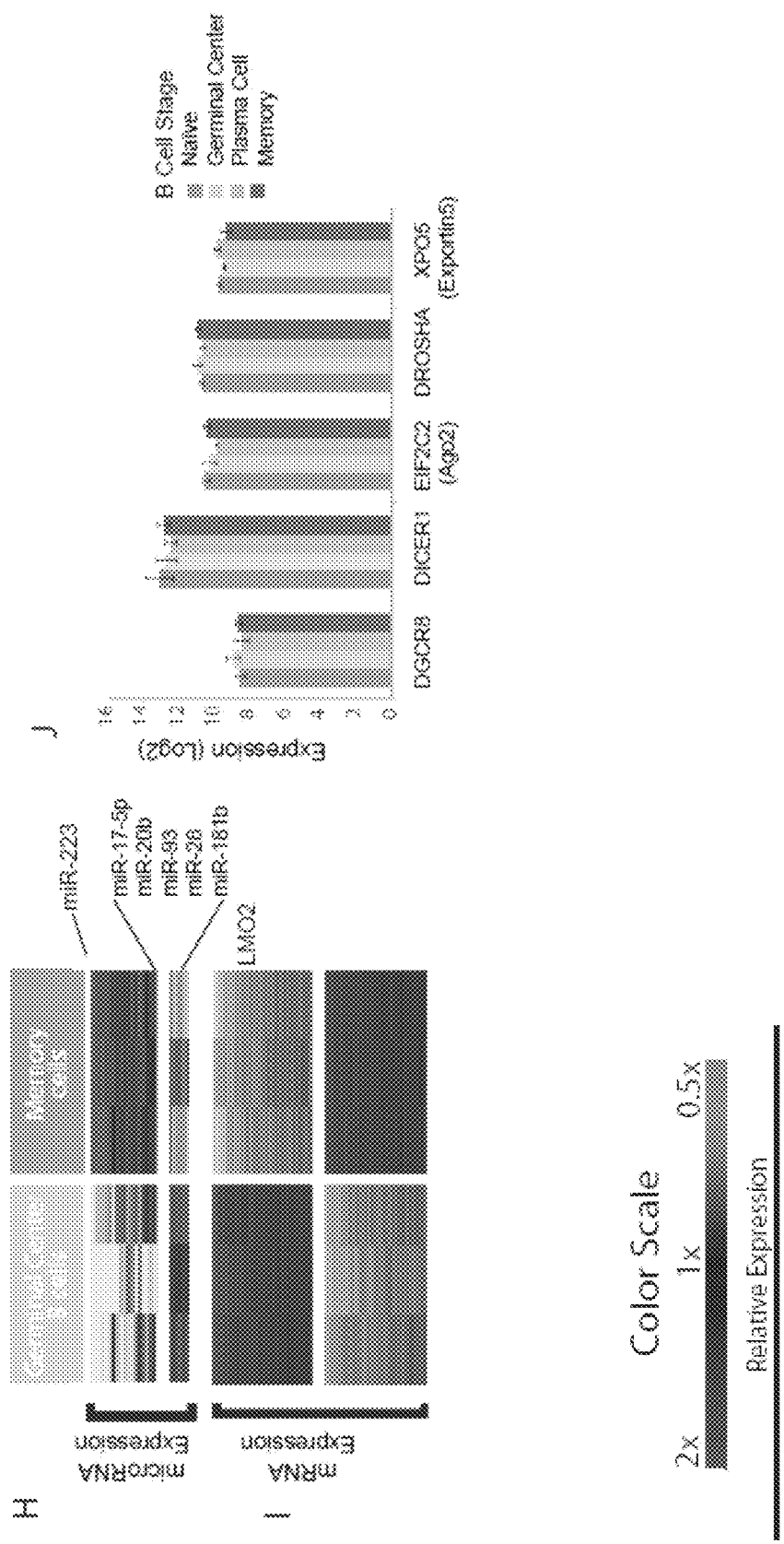
Figure 1 (con't)

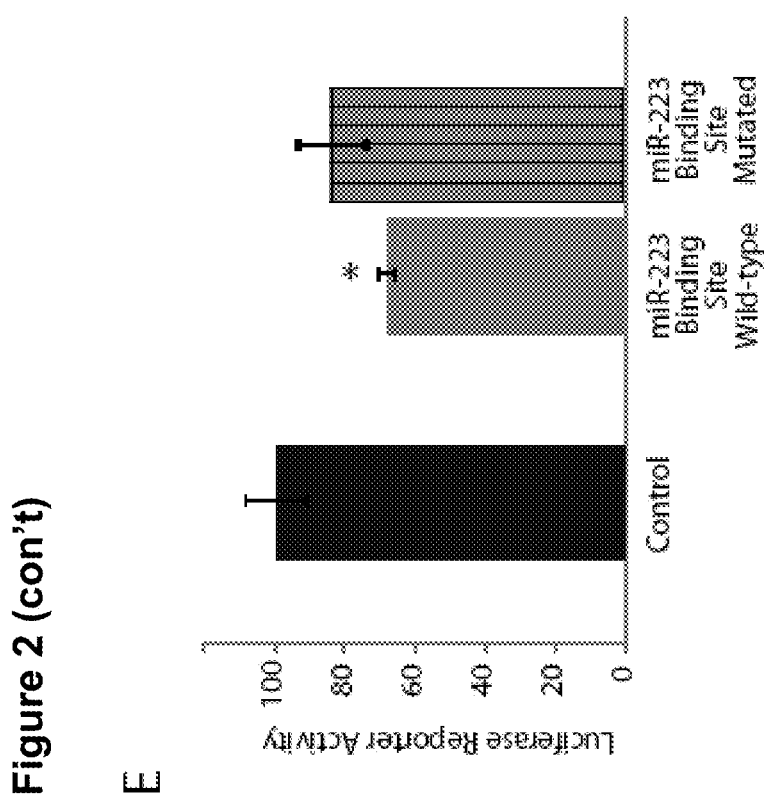
Figure 2 (con't)

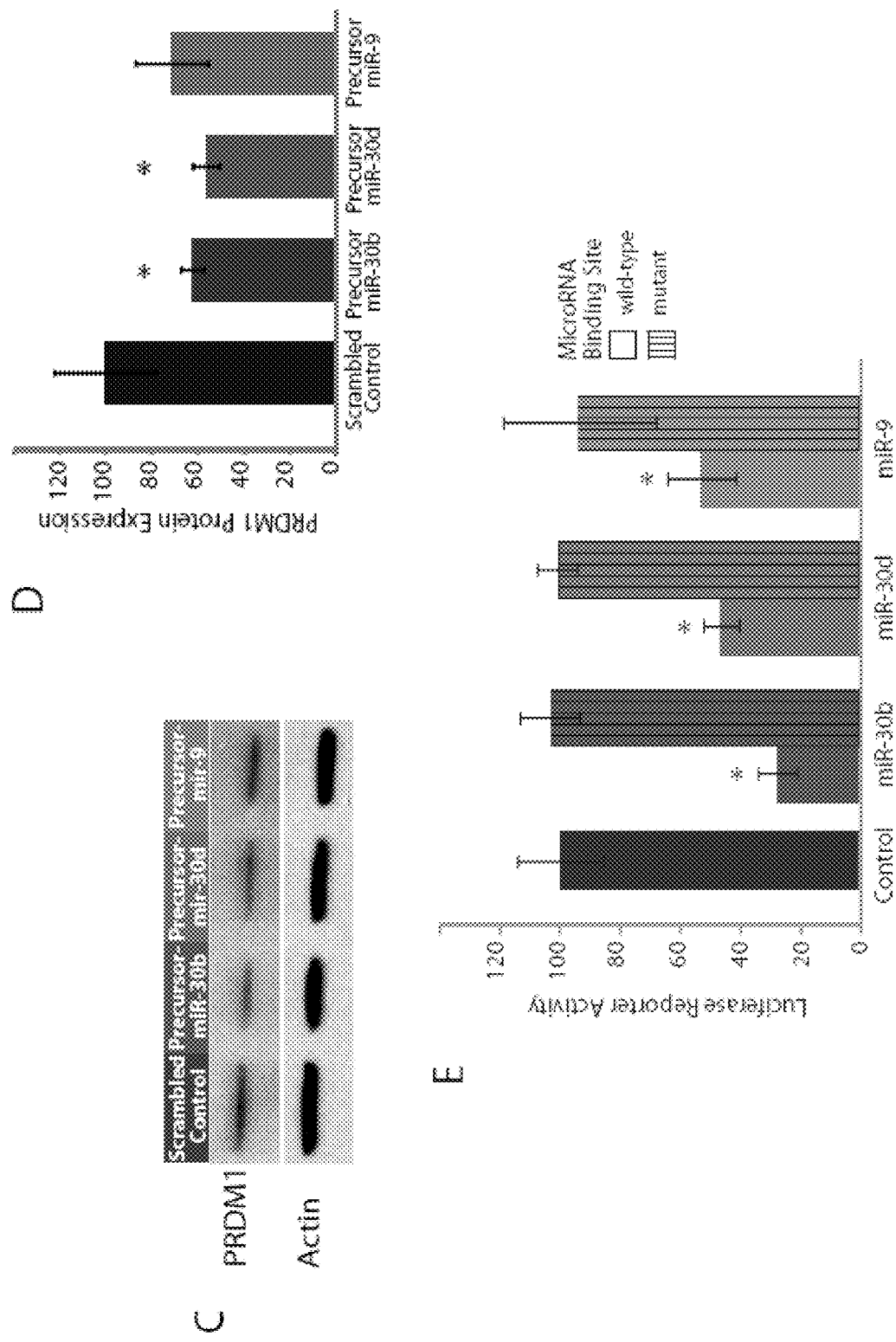
Figure 3 (con't)

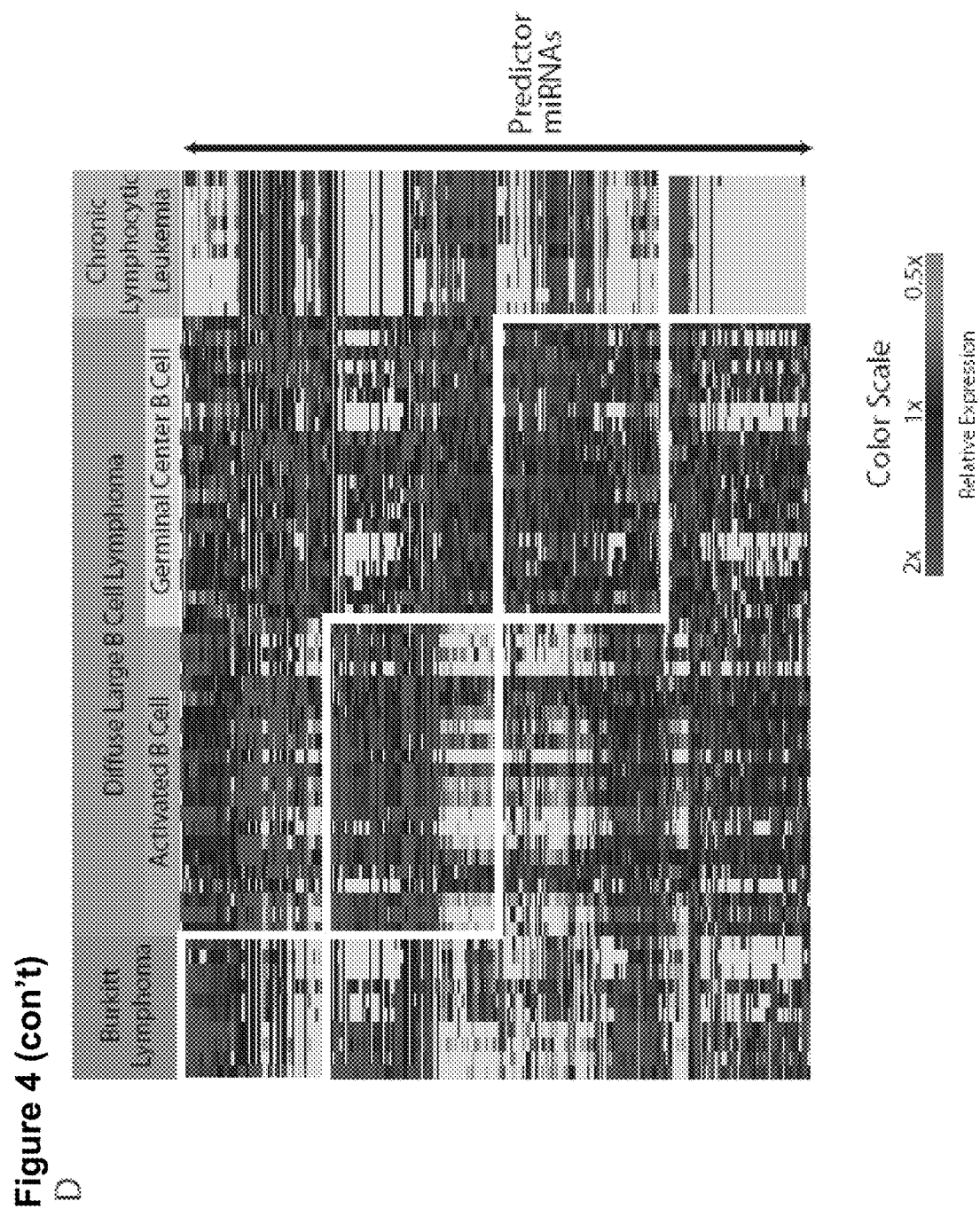
Figure 4 (con't)
D

SEQUENCE LISTING

<160> NUMBER OF SEQ ID NOS: 1565

<210> SEQ ID NO 1
<211> LENGTH: 22
<212> TYPE: RNA
<213> ORGANISM: homo sapiens

<400> SEQUENCE: 1
cugcgcaagc uacugccuug cu                                              22

<210> SEQ ID NO 2
<211> LENGTH: 22
<212> TYPE: RNA
<213> ORGANISM: homo sapiens

<400> SEQUENCE: 2
ccacggaugu uugagcaugu gc                                               22

<210> SEQ ID NO 3
<211> LENGTH: 22
<212> TYPE: RNA
<213> ORGANISM: homo sapiens

<400> SEQUENCE: 3
ccacggaugu uugagcaugu gc                                               22

<210> SEQ ID NO 4
<211> LENGTH: 22
<212> TYPE: RNA
<213> ORGANISM: homo sapiens

<400> SEQUENCE: 4
uacugcaaug uaagcacuuc uu                                               22

<210> SEQ ID NO 5
<211> LENGTH: 21
<212> TYPE: RNA
<213> ORGANISM: homo sapiens

<400> SEQUENCE: 5
cauuauuacu uuugguacgc g                                                21

<210> SEQ ID NO 6
<211> LENGTH: 22
<212> TYPE: RNA
<213> ORGANISM: homo sapiens

<400> SEQUENCE: 6
aagcccuuac cccaaaaagu au                                               22

<210> SEQ ID NO 7
<211> LENGTH: 22
<212> TYPE: RNA
<213> ORGANISM: homo sapiens

<400> SEQUENCE: 7
aagcccuuac cccaaaaagc au                                               22

<210> SEQ ID NO 8
<211> LENGTH: 22
<212> TYPE: RNA
<213> ORGANISM: homo sapiens

<400> SEQUENCE: 8
ucuacagugc acgucucc ag                                                 22

<210> SEQ ID NO 9
<211> LENGTH: 22
<212> TYPE: RNA
<213> ORGANISM: homo sapiens

<400> SEQUENCE: 9
cugguacagg ccuggggac ag                                                22

<210> SEQ ID NO 10
<211> LENGTH: 22
<212> TYPE: RNA
<213> ORGANISM: homo sapiens

<400> SEQUENCE: 10
acugcaguga aggcacuugu ag                                               22

<210> SEQ ID NO 11
<211> LENGTH: 21
<212> TYPE: RNA
<213> ORGANISM: homo sapiens

<400> SEQUENCE: 11
ugaauuaccg aagggccaua a                                                21

<210> SEQ ID NO 12
<211> LENGTH: 22
<212> TYPE: RNA
<213> ORGANISM: homo sapiens

<400> SEQUENCE: 12
aggggcuggc uuuccucugg uc                                               22

<210> SEQ ID NO 13
<211> LENGTH: 23
<212> TYPE: RNA
<213> ORGANISM: homo sapiens

<400> SEQUENCE: 13
acugcccuaa gugcuccuuc ugg                                              23

<210> SEQ ID NO 14
<211> LENGTH: 22
<212> TYPE: RNA
<213> ORGANISM: homo sapiens

<400> SEQUENCE: 14
aacuggccua caaaguccca gu                                               22

<210> SEQ ID NO 15
<211> LENGTH: 22
<212> TYPE: RNA
<213> ORGANISM: homo sapiens

<400> SEQUENCE: 15
cgggguuuug agggcgagau ga                                               22

<210> SEQ ID NO 16
<211> LENGTH: 23
<212> TYPE: RNA
<213> ORGANISM: homo sapiens

<400> SEQUENCE: 16
cccaguguuc agacuaccug uuc                                              23

<210> SEQ ID NO 17
<211> LENGTH: 22
<212> TYPE: RNA
<213> ORGANISM: homo sapiens

<400> SEQUENCE: 17
uaguuuugca uaguugcacu ac                                               22

<210> SEQ ID NO 18
<211> LENGTH: 23
<212> TYPE: RNA
<213> ORGANISM: homo sapiens

<400> SEQUENCE: 18
aguuuugcag guuugcaucc agc                                                23

<210> SEQ ID NO 19
<211> LENGTH: 22
<212> TYPE: RNA
<213> ORGANISM: homo sapiens

<400> SEQUENCE: 19
acuguaguau gggcacuucc ag                                                 22

<210> SEQ ID NO 20
<211> LENGTH: 22
<212> TYPE: RNA
<213> ORGANISM: homo sapiens

<400> SEQUENCE: 20
accuggcaua caauguagau uu                                                 22

<210> SEQ ID NO 21
<211> LENGTH: 21
<212> TYPE: RNA
<213> ORGANISM: homo sapiens

<400> SEQUENCE: 21
ggguuccugg caugcugauu u                                                  21

<210> SEQ ID NO 22
<211> LENGTH: 21
<212> TYPE: RNA
<213> ORGANISM: homo sapiens

<400> SEQUENCE: 22
aggcggagac uugggcaauu g                                                  21

<210> SEQ ID NO 23
<211> LENGTH: 22
<212> TYPE: RNA
<213> ORGANISM: homo sapiens

<400> SEQUENCE: 23
agagcuuagc ugauugguga ac                                                 22

<210> SEQ ID NO 24
<211> LENGTH: 22
<212> TYPE: RNA
<213> ORGANISM: homo sapiens

<400> SEQUENCE: 24
cugggaggug gauguuuacu uc                                                 22

<210> SEQ ID NO 25
<211> LENGTH: 22
<212> TYPE: RNA
<213> ORGANISM: homo sapiens

<400> SEQUENCE: 25
cugggagagg guuguuuacu cc                                                 22

<210> SEQ ID NO 26
<211> LENGTH: 22
<212> TYPE: RNA
<213> ORGANISM: homo sapiens

```
<400> SEQUENCE: 26
cugggagaag gcuguuuacu cu                                              22

<210> SEQ ID NO 27
<211> LENGTH: 22
<212> TYPE: RNA
<213> ORGANISM: homo sapiens

<400> SEQUENCE: 27
cuuucagucg gauguuuaca gc                                              22

<210> SEQ ID NO 28
<211> LENGTH: 23
<212> TYPE: RNA
<213> ORGANISM: homo sapiens

<400> SEQUENCE: 28
ucccuguccu ccaggagcuc acg                                             23

<210> SEQ ID NO 29
<211> LENGTH: 23
<212> TYPE: RNA
<213> ORGANISM: homo sapiens

<400> SEQUENCE: 29
ucucacacag aaaucgcacc cgu                                             23

<210> SEQ ID NO 30
<211> LENGTH: 22
<212> TYPE: RNA
<213> ORGANISM: homo sapiens

<400> SEQUENCE: 30
aaucagcaag uauacugccc ua                                              22

<210> SEQ ID NO 31
<211> LENGTH: 23
<212> TYPE: RNA
<213> ORGANISM: homo sapiens

<400> SEQUENCE: 31 uccccaggu gugauucuga uuu                                              23

<210> SEQ ID NO 32
<211> LENGTH: 24
<212> TYPE: RNA
<213> ORGANISM: homo sapiens

<400> SEQUENCE: 32
aauccuugga accuaggugu gagu                                            24

<210> SEQ ID NO 33
<211> LENGTH: 22
<212> TYPE: RNA
<213> ORGANISM: homo sapiens

<400> SEQUENCE: 33
agggacuuuc aggggcagcu gu                                              22

<210> SEQ ID NO 34
<211> LENGTH: 22
<212> TYPE: RNA
```

```
<213> ORGANISM: homo sapiens

<400> SEQUENCE: 34
cuuaucagau uguauuguaa uu                                          22

<210> SEQ ID NO 35
<211> LENGTH: 22
<212> TYPE: RNA
<213> ORGANISM: homo sapiens

<400> SEQUENCE: 35
cuuagcaggu uguauuauca uu                                          22

<210> SEQ ID NO 36
<211> LENGTH: 23
<212> TYPE: RNA
<213> ORGANISM: homo sapiens

<400> SEQUENCE: 36
agguuacccg agcaacuuug cau                                         23

<210> SEQ ID NO 37
<211> LENGTH: 21
<212> TYPE: RNA
<213> ORGANISM: homo sapiens

<400> SEQUENCE: 37
caaaacguga ggcgcugcua u                                           21

<210> SEQ ID NO 38
<211> LENGTH: 22
<212> TYPE: RNA
<213> ORGANISM: homo sapiens

<400> SEQUENCE: 38
uaugugccuu uggacuacau cg                                          22

<210> SEQ ID NO 39
<211> LENGTH: 22
<212> TYPE: RNA
<213> ORGANISM: homo sapiens

<400> SEQUENCE: 39
gucauacacg gcucuccucu cu                                          22

<210> SEQ ID NO 40
<211> LENGTH: 22
<212> TYPE: RNA
<213> ORGANISM: homo sapiens

<400> SEQUENCE: 40
ugucuuacuc ccucaggcac au                                          22

<210> SEQ ID NO 41
<211> LENGTH: 22
<212> TYPE: RNA
<213> ORGANISM: homo sapiens

<400> SEQUENCE: 41
ugucuuacuc ccucaggcac au                                          22

<210> SEQ ID NO 42
<211> LENGTH: 22
```

<212> TYPE: RNA
<213> ORGANISM: homo sapiens

<400> SEQUENCE: 42
gaaaucaagc gugggugaga cc                                            22

<210> SEQ ID NO 43
<211> LENGTH: 22
<212> TYPE: RNA
<213> ORGANISM: homo sapiens

<400> SEQUENCE: 43
auucuaauuu cuccacgucu uu                                            22

<210> SEQ ID NO 44
<211> LENGTH: 24
<212> TYPE: RNA
<213> ORGANISM: homo sapiens

<400> SEQUENCE: 44
ucagaacaaa ugccgguucc caga                                          24

<210> SEQ ID NO 45
<211> LENGTH: 22
<212> TYPE: RNA
<213> ORGANISM: homo sapiens

<400> SEQUENCE: 45
gagcuuauuc auaaaagugc ag                                            22

<210> SEQ ID NO 46
<211> LENGTH: 22
<212> TYPE: RNA
<213> ORGANISM: homo sapiens

<400> SEQUENCE: 46
gggggucccc ggugcucgga uc                                            22

<210> SEQ ID NO 47
<211> LENGTH: 22
<212> TYPE: RNA
<213> ORGANISM: homo sapiens

<400> SEQUENCE: 47
gacuauagaa cuuuccccu ca                                             22

<210> SEQ ID NO 48
<211> LENGTH: 22
<212> TYPE: RNA
<213> ORGANISM: homo sapiens

<400> SEQUENCE: 48
uggugggccg cagaacaugu gc                                            22

<210> SEQ ID NO 49
<211> LENGTH: 23
<212> TYPE: RNA
<213> ORGANISM: homo sapiens

<400> SEQUENCE: 49
aggaagcccu ggaggggcug gag                                           23

<210> SEQ ID NO 50

```
<211> LENGTH: 22
<212> TYPE: RNA
<213> ORGANISM: homo sapiens

<400> SEQUENCE: 50
aacuagacug ugagcuucua ga                                              22

<210> SEQ ID NO 51
<211> LENGTH: 22
<212> TYPE: RNA
<213> ORGANISM: homo sapiens

<400> SEQUENCE: 51
caacaaauca cagucugcca ua                                              22

<210> SEQ ID NO 52
<211> LENGTH: 22
<212> TYPE: RNA
<213> ORGANISM: homo sapiens

<400> SEQUENCE: 52
auaaagcuag auaaccgaaa gu                                              22

<210> SEQ ID NO 53
<211> LENGTH: 22
<212> TYPE: RNA
<213> ORGANISM: homo sapiens

<400> SEQUENCE: 53
auaaagcuag auaaccgaaa gu                                              22

<210> SEQ ID NO 54
<211> LENGTH: 22
<212> TYPE: RNA
<213> ORGANISM: homo sapiens

<400> SEQUENCE: 54
agggacggga cgcggugcag ug                                              22

<210> SEQ ID NO 55
<211> LENGTH: 22
<212> TYPE: RNA
<213> ORGANISM: homo sapiens

<400> SEQUENCE: 55
auaaagcuag auaaccgaaa gu                                              22

<210> SEQ ID NO 56
<211> LENGTH: 22
<212> TYPE: RNA
<213> ORGANISM: homo sapiens

<400> SEQUENCE: 56
ugagguagua gguuguauag uu                                              22

<210> SEQ ID NO 57
<211> LENGTH: 22
<212> TYPE: RNA
<213> ORGANISM: homo sapiens

<400> SEQUENCE: 57
ugagguagua gguuguauag uu                                              22
```

```
<210> SEQ ID NO 58
<211> LENGTH: 22
<212> TYPE: RNA
<213> ORGANISM: homo sapiens

<400> SEQUENCE: 58
ugagguagua gguuguaugg uu                                              22

<210> SEQ ID NO 59
<211> LENGTH: 22
<212> TYPE: RNA
<213> ORGANISM: homo sapiens

<400> SEQUENCE: 59
ugagguagga gguuguauag uu                                              22

<210> SEQ ID NO 60
<211> LENGTH: 22
<212> TYPE: RNA
<213> ORGANISM: homo sapiens

<400> SEQUENCE: 60
ugagguagua gauuguauag uu                                              22

<210> SEQ ID NO 61
<211> LENGTH: 22
<212> TYPE: RNA
<213> ORGANISM: homo sapiens

<400> SEQUENCE: 61
ugagguagua guuuguacag uu                                              22

<210> SEQ ID NO 62
<211> LENGTH: 22
<212> TYPE: RNA
<213> ORGANISM: homo sapiens

<400> SEQUENCE: 62
ugagguagua guuugugcug uu                                              22

<210> SEQ ID NO 63
<211> LENGTH: 22
<212> TYPE: RNA
<213> ORGANISM: homo sapiens

<400> SEQUENCE: 63
aacccguaga uccgaacuug ug                                              22

<210> SEQ ID NO 64
<211> LENGTH: 21
<212> TYPE: RNA
<213> ORGANISM: homo sapiens

<400> SEQUENCE: 64
uacaguacug ugauaacuga a                                               21

<210> SEQ ID NO 65
<211> LENGTH: 22
<212> TYPE: RNA
<213> ORGANISM: homo sapiens

<400> SEQUENCE: 65
guacaguacu gugauaacug aa                                              22
```

```
<210> SEQ ID NO 66
<211> LENGTH: 23
<212> TYPE: RNA
<213> ORGANISM: homo sapiens

<400> SEQUENCE: 66
agcagcauug uacagggcua uga                                              23

<210> SEQ ID NO 67
<211> LENGTH: 23
<212> TYPE: RNA
<213> ORGANISM: homo sapiens

<400> SEQUENCE: 67
agcagcauug uacagggcua uga                                              23

<210> SEQ ID NO 68
<211> LENGTH: 22
<212> TYPE: RNA
<213> ORGANISM: homo sapiens

<400> SEQUENCE: 68
aaaugcucag acuccugugg ug                                               22

<210> SEQ ID NO 69
<211> LENGTH: 22
<212> TYPE: RNA
<213> ORGANISM: homo sapiens

<400> SEQUENCE: 69
aaaugcucag acuccugugg ug                                               22

<210> SEQ ID NO 70
<211> LENGTH: 23
<212> TYPE: RNA
<213> ORGANISM: homo sapiens

<400> SEQUENCE: 70
aaaagugcuu acagugcagg uag                                              23

<210> SEQ ID NO 71
<211> LENGTH: 21
<212> TYPE: RNA
<213> ORGANISM: homo sapiens

<400> SEQUENCE: 71
uaaagugcug acagugcaga u                                                21

<210> SEQ ID NO 72
<211> LENGTH: 23
<212> TYPE: RNA
<213> ORGANISM: homo sapiens

<400> SEQUENCE: 72
agcagcauug uacagggcua uca                                              23

<210> SEQ ID NO 73
<211> LENGTH: 23
<212> TYPE: RNA
<213> ORGANISM: homo sapiens

<400> SEQUENCE: 73
uacccuguag auccgaauuu gug                                              23
```

<210> SEQ ID NO 74
<211> LENGTH: 23
<212> TYPE: RNA
<213> ORGANISM: homo sapiens

<400> SEQUENCE: 74
uacccuguag aaccgaauuu gug                                         23

<210> SEQ ID NO 75
<211> LENGTH: 22
<212> TYPE: RNA
<213> ORGANISM: homo sapiens

<400> SEQUENCE: 75
uggaauguaa agaaguaugu au                                          22

<210> SEQ ID NO 76
<211> LENGTH: 22
<212> TYPE: RNA
<213> ORGANISM: homo sapiens

<400> SEQUENCE: 76
uggaauguaa agaaguaugu au                                          22

<210> SEQ ID NO 77
<211> LENGTH: 22
<212> TYPE: RNA
<213> ORGANISM: homo sapiens

<400> SEQUENCE: 77
uggaguguga caauggucuu ug                                          22

<210> SEQ ID NO 78
<211> LENGTH: 20
<212> TYPE: RNA
<213> ORGANISM: homo sapiens

<400> SEQUENCE: 78
uaaggcacgc ggugaaugcc                                             20

<210> SEQ ID NO 79
<211> LENGTH: 20
<212> TYPE: RNA
<213> ORGANISM: homo sapiens

<400> SEQUENCE: 79
uaaggcacgc ggugaaugcc                                             20

<210> SEQ ID NO 80
<211> LENGTH: 20
<212> TYPE: RNA
<213> ORGANISM: homo sapiens

<400> SEQUENCE: 80
uaaggcacgc ggugaaugcc                                             20

<210> SEQ ID NO 81
<211> LENGTH: 22
<212> TYPE: RNA
<213> ORGANISM: homo sapiens

<400> SEQUENCE: 81

```
acccgucccg uucgucccg ga                                          22

<210> SEQ ID NO 82
<211> LENGTH: 21
<212> TYPE: RNA
<213> ORGANISM: homo sapiens

<400> SEQUENCE: 82
acggugcugg auguggccuu u                                          21

<210> SEQ ID NO 83
<211> LENGTH: 22
<212> TYPE: RNA
<213> ORGANISM: homo sapiens

<400> SEQUENCE: 83
agaaggaaau ugaauucauu ua                                         22

<210> SEQ ID NO 84
<211> LENGTH: 24
<212> TYPE: RNA
<213> ORGANISM: homo sapiens

<400> SEQUENCE: 84
agccuggaag cuggagccug cagu                                       24

<210> SEQ ID NO 85
<211> LENGTH: 23
<212> TYPE: RNA
<213> ORGANISM: homo sapiens

<400> SEQUENCE: 85
aggaugagca aagaaaguag auu                                        23

<210> SEQ ID NO 86
<211> LENGTH: 22
<212> TYPE: RNA
<213> ORGANISM: homo sapiens

<400> SEQUENCE: 86
aggcauugac uucucacuag cu                                         22

<210> SEQ ID NO 87
<211> LENGTH: 21
<212> TYPE: RNA
<213> ORGANISM: homo sapiens

<400> SEQUENCE: 87
cguaccguga guaauaaugc g                                          21

<210> SEQ ID NO 88
<211> LENGTH: 22
<212> TYPE: RNA
<213> ORGANISM: homo sapiens

<400> SEQUENCE: 88
augggugaau uuguagaagg au                                         22

<210> SEQ ID NO 89
<211> LENGTH: 22
<212> TYPE: RNA
<213> ORGANISM: homo sapiens

<400> SEQUENCE: 89
```

```
augguacccu ggcauacuga gu                                              22

<210> SEQ ID NO 90
<211> LENGTH: 22
<212> TYPE: RNA
<213> ORGANISM: homo sapiens

<400> SEQUENCE: 90
caggaugugg ucaaguguug uu                                              22

<210> SEQ ID NO 91
<211> LENGTH: 23
<212> TYPE: RNA
<213> ORGANISM: homo sapiens

<400> SEQUENCE: 91
ccucagggcu guagaacagg gcu                                             23

<210> SEQ ID NO 92
<211> LENGTH: 22
<212> TYPE: RNA
<213> ORGANISM: homo sapiens

<400> SEQUENCE: 92
cuggacugag ccgugcuacu gg                                              22

<210> SEQ ID NO 93
<211> LENGTH: 23
<212> TYPE: RNA
<213> ORGANISM: homo sapiens

<400> SEQUENCE: 93
cuggagauau ggaagagcug ugu                                             23

<210> SEQ ID NO 94
<211> LENGTH: 22
<212> TYPE: RNA
<213> ORGANISM: homo sapiens

<400> SEQUENCE: 94
cuuggcaccu agcaagcacu ca                                              22

<210> SEQ ID NO 95
<211> LENGTH: 22
<212> TYPE: RNA
<213> ORGANISM: homo sapiens

<400> SEQUENCE: 95
ucggauccgu cugagcuugg cu                                              22

<210> SEQ ID NO 96
<211> LENGTH: 22
<212> TYPE: RNA
<213> ORGANISM: homo sapiens

<400> SEQUENCE: 96
uacguagaua uauauguauu uu                                              22

<210> SEQ ID NO 97
<211> LENGTH: 22
<212> TYPE: RNA
<213> ORGANISM: homo sapiens
```

```
<400> SEQUENCE: 97
uaguacugug cauaucaucu au                                          22

<210> SEQ ID NO 98
<211> LENGTH: 21
<212> TYPE: RNA
<213> ORGANISM: homo sapiens

<400> SEQUENCE: 98
ucacagugaa ccggucucuu u                                           21

<210> SEQ ID NO 99
<211> LENGTH: 21
<212> TYPE: RNA
<213> ORGANISM: homo sapiens

<400> SEQUENCE: 99
ucacagugaa ccggucucuu u                                           21

<210> SEQ ID NO 100
<211> LENGTH: 21
<212> TYPE: RNA
<213> ORGANISM: homo sapiens

<400> SEQUENCE: 100
cuuuuugcgg ucugggcuug c                                           21

<210> SEQ ID NO 101
<211> LENGTH: 21
<212> TYPE: RNA
<213> ORGANISM: homo sapiens

<400> SEQUENCE: 101
cuuuuugcgg ucugggcuug c                                           21

<210> SEQ ID NO 102
<211> LENGTH: 22
<212> TYPE: RNA
<213> ORGANISM: homo sapiens

<400> SEQUENCE: 102
ugugagguug gcauuguugu cu                                          22

<210> SEQ ID NO 103
<211> LENGTH: 21
<212> TYPE: RNA
<213> ORGANISM: homo sapiens

<400> SEQUENCE: 103
uuaggccgca gaucugggug a                                           21

<210> SEQ ID NO 104
<211> LENGTH: 22
<212> TYPE: RNA
<213> ORGANISM: homo sapiens

<400> SEQUENCE: 104
uucauucggc uguccagaug ua                                          22

<210> SEQ ID NO 105
<211> LENGTH: 24
<212> TYPE: RNA
<213> ORGANISM: homo sapiens
```

```
<400> SEQUENCE: 105
uugcagcugc cugggaguga cuuc                                          24

<210> SEQ ID NO 106
<211> LENGTH: 22
<212> TYPE: RNA
<213> ORGANISM: homo sapiens

<400> SEQUENCE: 106
cgguuugagg cuacagugag au                                            22

<210> SEQ ID NO 107
<211> LENGTH: 18
<212> TYPE: RNA
<213> ORGANISM: homo sapiens

<400> SEQUENCE: 107
acguuggcuc uggugguG                                                 18

<210> SEQ ID NO 108
<211> LENGTH: 22
<212> TYPE: RNA
<213> ORGANISM: homo sapiens

<400> SEQUENCE: 108
acucggcgug gcgucggucg ug                                            22

<210> SEQ ID NO 109
<211> LENGTH: 22
<212> TYPE: RNA
<213> ORGANISM: homo sapiens

<400> SEQUENCE: 109
cagugcaaug uuaaaagggc au                                            22

<210> SEQ ID NO 110
<211> LENGTH: 22
<212> TYPE: RNA
<213> ORGANISM: homo sapiens

<400> SEQUENCE: 110
cagugcaaug augaaagggc au                                            22

<210> SEQ ID NO 111
<211> LENGTH: 22
<212> TYPE: RNA
<213> ORGANISM: homo sapiens

<400> SEQUENCE: 111
uaacagucua cagccauggu cg                                            22

<210> SEQ ID NO 112
<211> LENGTH: 22
<212> TYPE: RNA
<213> ORGANISM: homo sapiens

<400> SEQUENCE: 112
accguggcuu ucgauuguua cu                                            22

<210> SEQ ID NO 113
<211> LENGTH: 22
<212> TYPE: RNA
```

```
<213> ORGANISM: homo sapiens

<400> SEQUENCE: 113
ugugacuggu ugaccagagg gg                                            22

<210> SEQ ID NO 114
<211> LENGTH: 23
<212> TYPE: RNA
<213> ORGANISM: homo sapiens

<400> SEQUENCE: 114
uauggcuuuu cauuccuaug uga                                           23

<210> SEQ ID NO 115
<211> LENGTH: 23
<212> TYPE: RNA
<213> ORGANISM: homo sapiens

<400> SEQUENCE: 115
acuccauuug uuuugaugau gga                                           23

<210> SEQ ID NO 116
<211> LENGTH: 23
<212> TYPE: RNA
<213> ORGANISM: homo sapiens

<400> SEQUENCE: 116
agcugguguu gugaaucagg ccg                                           23

<210> SEQ ID NO 117
<211> LENGTH: 23
<212> TYPE: RNA
<213> ORGANISM: homo sapiens

<400> SEQUENCE: 117
agcugguguu gugaaucagg ccg                                           23

<210> SEQ ID NO 118
<211> LENGTH: 22
<212> TYPE: RNA
<213> ORGANISM: homo sapiens

<400> SEQUENCE: 118
uggagacgcg gcccuguugg ag                                            22

<210> SEQ ID NO 119
<211> LENGTH: 21
<212> TYPE: RNA
<213> ORGANISM: homo sapiens

<400> SEQUENCE: 119
uaccacaggg uagaaccacg g                                             21

<210> SEQ ID NO 120
<211> LENGTH: 22
<212> TYPE: RNA
<213> ORGANISM: homo sapiens

<400> SEQUENCE: 120
uaacacuguc ugguaaagau gg                                            22

<210> SEQ ID NO 121
<211> LENGTH: 20
```

```
<212> TYPE: RNA
<213> ORGANISM: homo sapiens

<400> SEQUENCE: 121
cccauaaagu agaaagcacu                                               20

<210> SEQ ID NO 122
<211> LENGTH: 21
<212> TYPE: RNA
<213> ORGANISM: homo sapiens

<400> SEQUENCE: 122
ugagaugaag cacuguagcu c                                             21

<210> SEQ ID NO 123
<211> LENGTH: 22
<212> TYPE: RNA
<213> ORGANISM: homo sapiens

<400> SEQUENCE: 123
ggauaucauc auauacugua ag                                            22

<210> SEQ ID NO 124
<211> LENGTH: 23
<212> TYPE: RNA
<213> ORGANISM: homo sapiens

<400> SEQUENCE: 124
guccaguuuu cccaggaauc ccu                                           23

<210> SEQ ID NO 125
<211> LENGTH: 22
<212> TYPE: RNA
<213> ORGANISM: homo sapiens

<400> SEQUENCE: 125
ugagaacuga auuccauggg uu                                            22

<210> SEQ ID NO 126
<211> LENGTH: 22
<212> TYPE: RNA
<213> ORGANISM: homo sapiens

<400> SEQUENCE: 126
ugagaacuga auuccauagg cu                                            22

<210> SEQ ID NO 127
<211> LENGTH: 22
<212> TYPE: RNA
<213> ORGANISM: homo sapiens

<400> SEQUENCE: 127
ucagugcacu acagaacuuu gu                                            22

<210> SEQ ID NO 128
<211> LENGTH: 22
<212> TYPE: RNA
<213> ORGANISM: homo sapiens

<400> SEQUENCE: 128
ucagugcauc acagaacuuu gu                                            22

<210> SEQ ID NO 129
```

```
<211> LENGTH: 22
<212> TYPE: RNA
<213> ORGANISM: homo sapiens

<400> SEQUENCE: 129
ucucccaacc cuuguaccag ug                                                 22

<210> SEQ ID NO 130
<211> LENGTH: 21
<212> TYPE: RNA
<213> ORGANISM: homo sapiens

<400> SEQUENCE: 130
cuagacugaa gcuccuugag g                                                  21

<210> SEQ ID NO 131
<211> LENGTH: 21
<212> TYPE: RNA
<213> ORGANISM: homo sapiens

<400> SEQUENCE: 131
ucagugcaug acagaacuug g                                                  21

<210> SEQ ID NO 132
<211> LENGTH: 23
<212> TYPE: RNA
<213> ORGANISM: homo sapiens

<400> SEQUENCE: 132
uuaaugcuaa ucgugauagg ggu                                                23

<210> SEQ ID NO 133
<211> LENGTH: 22
<212> TYPE: RNA
<213> ORGANISM: homo sapiens

<400> SEQUENCE: 133
uagcagcaca uaaugguuug ug                                                 22

<210> SEQ ID NO 134
<211> LENGTH: 22
<212> TYPE: RNA
<213> ORGANISM: homo sapiens

<400> SEQUENCE: 134
uagcagcaca ucaugguuua ca                                                 22

<210> SEQ ID NO 135
<211> LENGTH: 22
<212> TYPE: RNA
<213> ORGANISM: homo sapiens

<400> SEQUENCE: 135
uagcagcacg uaaauauugg cg                                                 22

<210> SEQ ID NO 136
<211> LENGTH: 22
<212> TYPE: RNA
<213> ORGANISM: homo sapiens

<400> SEQUENCE: 136
uagcagcacg uaaauauugg cg                                                 22
```

```
<210> SEQ ID NO 137
<211> LENGTH: 23
<212> TYPE: RNA
<213> ORGANISM: homo sapiens

<400> SEQUENCE: 137
caaagugcuu acagugcagg uag                                                23

<210> SEQ ID NO 138
<211> LENGTH: 23
<212> TYPE: RNA
<213> ORGANISM: homo sapiens

<400> SEQUENCE: 138
aacauucaac gcugucggug agu                                                23

<210> SEQ ID NO 139
<211> LENGTH: 23
<212> TYPE: RNA
<213> ORGANISM: homo sapiens

<400> SEQUENCE: 139
aacauucaac gcugucggug agu                                                23

<210> SEQ ID NO 140
<211> LENGTH: 23
<212> TYPE: RNA
<213> ORGANISM: homo sapiens

<400> SEQUENCE: 140
aacauucauu gcugucggug ggu                                                23

<210> SEQ ID NO 141
<211> LENGTH: 23
<212> TYPE: RNA
<213> ORGANISM: homo sapiens

<400> SEQUENCE: 141
aacauucauu gcugucggug ggu                                                23

<210> SEQ ID NO 142
<211> LENGTH: 22
<212> TYPE: RNA
<213> ORGANISM: homo sapiens

<400> SEQUENCE: 142
aacauucaac cugucgguga gu                                                 22

<210> SEQ ID NO 143
<211> LENGTH: 23
<212> TYPE: RNA
<213> ORGANISM: homo sapiens

<400> SEQUENCE: 143
aacauucauu guugucggug ggu                                                23

<210> SEQ ID NO 144
<211> LENGTH: 24
<212> TYPE: RNA
<213> ORGANISM: homo sapiens

<400> SEQUENCE: 144
uuuggcaaug guagaacuca cacu                                               24
```

```
<210> SEQ ID NO 145
<211> LENGTH: 22
<212> TYPE: RNA
<213> ORGANISM: homo sapiens

<400> SEQUENCE: 145
uauggcacug guagaauuca cu                                                22

<210> SEQ ID NO 146
<211> LENGTH: 22
<212> TYPE: RNA
<213> ORGANISM: homo sapiens

<400> SEQUENCE: 146
uggacggaga acugauaagg gu                                                22

<210> SEQ ID NO 147
<211> LENGTH: 22
<212> TYPE: RNA
<213> ORGANISM: homo sapiens

<400> SEQUENCE: 147
uggagagaaa ggcaguuccu ga                                                22

<210> SEQ ID NO 148
<211> LENGTH: 22
<212> TYPE: RNA
<213> ORGANISM: homo sapiens

<400> SEQUENCE: 148
caaagaauuc uccuuuuggg cu                                                22

<210> SEQ ID NO 149
<211> LENGTH: 21
<212> TYPE: RNA
<213> ORGANISM: homo sapiens

<400> SEQUENCE: 149
caucccuugc augguggagg g                                                 21

<210> SEQ ID NO 150
<211> LENGTH: 23
<212> TYPE: RNA
<213> ORGANISM: homo sapiens

<400> SEQUENCE: 150
uaaggugcau cuagugcaga uag                                               23

<210> SEQ ID NO 151
<211> LENGTH: 23
<212> TYPE: RNA
<213> ORGANISM: homo sapiens

<400> SEQUENCE: 151
caacggaauc ccaaaagcag cug                                               23

<210> SEQ ID NO 152
<211> LENGTH: 21
<212> TYPE: RNA
<213> ORGANISM: homo sapiens

<400> SEQUENCE: 152
cugaccuaug aauugacagc c                                                 21
```

```
<210> SEQ ID NO 153
<211> LENGTH: 22
<212> TYPE: RNA
<213> ORGANISM: homo sapiens

<400> SEQUENCE: 153
ugggucuuug cgggcgagau ga                                              22

<210> SEQ ID NO 154
<211> LENGTH: 22
<212> TYPE: RNA
<213> ORGANISM: homo sapiens

<400> SEQUENCE: 154
aacuggcccu caaagucccg cu                                              22

<210> SEQ ID NO 155
<211> LENGTH: 22
<212> TYPE: RNA
<213> ORGANISM: homo sapiens

<400> SEQUENCE: 155
uguaacagca acuccaugug ga                                              22

<210> SEQ ID NO 156
<211> LENGTH: 21
<212> TYPE: RNA
<213> ORGANISM: homo sapiens

<400> SEQUENCE: 156
uagcagcaca gaaauauugg c                                               21

<210> SEQ ID NO 157
<211> LENGTH: 22
<212> TYPE: RNA
<213> ORGANISM: homo sapiens

<400> SEQUENCE: 157
uagguaguuu cauguuguug gg                                              22

<210> SEQ ID NO 158
<211> LENGTH: 22
<212> TYPE: RNA
<213> ORGANISM: homo sapiens

<400> SEQUENCE: 158
uagguaguuu cauguuguug gg                                              22

<210> SEQ ID NO 159
<211> LENGTH: 22
<212> TYPE: RNA
<213> ORGANISM: homo sapiens

<400> SEQUENCE: 159
uagguaguuu ccuguuguug gg                                              22

<210> SEQ ID NO 160
<211> LENGTH: 22
<212> TYPE: RNA
<213> ORGANISM: homo sapiens

<400> SEQUENCE: 160
```
uucaccaccu ucuccaccca gc                                           22

<210> SEQ ID NO 161
<211> LENGTH: 22
<212> TYPE: RNA
<213> ORGANISM: homo sapiens

<400> SEQUENCE: 161
acaguagucu gcacauuggu ua                                           22

<210> SEQ ID NO 162
<211> LENGTH: 22
<212> TYPE: RNA
<213> ORGANISM: homo sapiens

<400> SEQUENCE: 162
acaguagucu gcacauuggu ua                                           22

<210> SEQ ID NO 163
<211> LENGTH: 22
<212> TYPE: RNA
<213> ORGANISM: homo sapiens

<400> SEQUENCE: 163
acaguagucu gcacauuggu ua                                           22

<210> SEQ ID NO 164
<211> LENGTH: 23
<212> TYPE: RNA
<213> ORGANISM: homo sapiens

<400> SEQUENCE: 164
ugugcaaauc uaugcaaaac uga                                          23

<210> SEQ ID NO 165
<211> LENGTH: 23
<212> TYPE: RNA
<213> ORGANISM: homo sapiens

<400> SEQUENCE: 165
ugugcaaauc caugcaaaac uga                                          23

<210> SEQ ID NO 166
<211> LENGTH: 23
<212> TYPE: RNA
<213> ORGANISM: homo sapiens

<400> SEQUENCE: 166
ugugcaaauc caugcaaaac uga                                          23

<210> SEQ ID NO 167
<211> LENGTH: 22
<212> TYPE: RNA
<213> ORGANISM: homo sapiens

<400> SEQUENCE: 167
uaacacuguc ugguaacgau gu                                           22

<210> SEQ ID NO 168
<211> LENGTH: 22
<212> TYPE: RNA
<213> ORGANISM: homo sapiens

<400> SEQUENCE: 168

```
uaauacugcc ugguaaugau ga                                              22

<210> SEQ ID NO 169
<211> LENGTH: 23
<212> TYPE: RNA
<213> ORGANISM: homo sapiens

<400> SEQUENCE: 169
uaauacugcc ggguaaugau gga                                             23

<210> SEQ ID NO 170
<211> LENGTH: 22
<212> TYPE: RNA
<213> ORGANISM: homo sapiens

<400> SEQUENCE: 170
uuccuaugca uauacuucuu ug                                              22

<210> SEQ ID NO 171
<211> LENGTH: 22
<212> TYPE: RNA
<213> ORGANISM: homo sapiens

<400> SEQUENCE: 171
gugaaauguu uaggaccacu ag                                              22

<210> SEQ ID NO 172
<211> LENGTH: 22
<212> TYPE: RNA
<213> ORGANISM: homo sapiens

<400> SEQUENCE: 172
uucccuuugu cauccuaugc cu                                              22

<210> SEQ ID NO 173
<211> LENGTH: 22
<212> TYPE: RNA
<213> ORGANISM: homo sapiens

<400> SEQUENCE: 173
uccuucauuc caccggaguc ug                                              22

<210> SEQ ID NO 174
<211> LENGTH: 22
<212> TYPE: RNA
<213> ORGANISM: homo sapiens

<400> SEQUENCE: 174
uggaauguaa ggaagugugu gg                                              22

<210> SEQ ID NO 175
<211> LENGTH: 23
<212> TYPE: RNA
<213> ORGANISM: homo sapiens

<400> SEQUENCE: 175
uaaagugcuu auagugcagg uag                                             23

<210> SEQ ID NO 176
<211> LENGTH: 23
<212> TYPE: RNA
<213> ORGANISM: homo sapiens
```

<400> SEQUENCE: 176
caaagugcuc auagugcagg uag                                               23

<210> SEQ ID NO 177
<211> LENGTH: 22
<212> TYPE: RNA
<213> ORGANISM: homo sapiens

<400> SEQUENCE: 177
uagcuuauca gacugauguu ga                                                22

<210> SEQ ID NO 178
<211> LENGTH: 22
<212> TYPE: RNA
<213> ORGANISM: homo sapiens

<400> SEQUENCE: 178
cugugcgugu gacagcggcu ga                                                22

<210> SEQ ID NO 179
<211> LENGTH: 21
<212> TYPE: RNA
<213> ORGANISM: homo sapiens

<400> SEQUENCE: 179
uaacagucuc cagucacggc c                                                 21

<210> SEQ ID NO 180
<211> LENGTH: 22
<212> TYPE: RNA
<213> ORGANISM: homo sapiens

<400> SEQUENCE: 180
acagcaggca cagacaggca gu                                                22

<210> SEQ ID NO 181
<211> LENGTH: 18
<212> TYPE: RNA
<213> ORGANISM: homo sapiens

<400> SEQUENCE: 181
ugaccuauga auugacag                                                     18

<210> SEQ ID NO 182
<211> LENGTH: 22
<212> TYPE: RNA
<213> ORGANISM: homo sapiens

<400> SEQUENCE: 182
aaaucucugc aggcaaaugu ga                                                22

<210> SEQ ID NO 183
<211> LENGTH: 22
<212> TYPE: RNA
<213> ORGANISM: homo sapiens

<400> SEQUENCE: 183
auacugcauc aggaacugau ug                                                22

<210> SEQ ID NO 184
<211> LENGTH: 22
<212> TYPE: RNA
<213> ORGANISM: homo sapiens -continued

```
<400> SEQUENCE: 184
agaguugagu cuggacgucc cg                                              22

<210> SEQ ID NO 185
<211> LENGTH: 22
<212> TYPE: RNA
<213> ORGANISM: homo sapiens

<400> SEQUENCE: 185
aagcugccag uugaagaacu gu                                              22

<210> SEQ ID NO 186
<211> LENGTH: 23
<212> TYPE: RNA
<213> ORGANISM: homo sapiens

<400> SEQUENCE: 186
agcuacauug ucugcugggu uuc                                             23

<210> SEQ ID NO 187
<211> LENGTH: 21
<212> TYPE: RNA
<213> ORGANISM: homo sapiens

<400> SEQUENCE: 187
agcuacaucu ggcuacuggg u                                               21

<210> SEQ ID NO 188
<211> LENGTH: 22
<212> TYPE: RNA
<213> ORGANISM: homo sapiens

<400> SEQUENCE: 188
cguguauuug acaagcugag uu                                              22

<210> SEQ ID NO 189
<211> LENGTH: 21
<212> TYPE: RNA
<213> ORGANISM: homo sapiens

<400> SEQUENCE: 189
caagucacua gugguuccgu u                                               21

<210> SEQ ID NO 190
<211> LENGTH: 21
<212> TYPE: RNA
<213> ORGANISM: homo sapiens

<400> SEQUENCE: 190
aucacauugc cagggauuuc c                                               21

<210> SEQ ID NO 191
<211> LENGTH: 21
<212> TYPE: RNA
<213> ORGANISM: homo sapiens

<400> SEQUENCE: 191
aucacauugc cagggauuac c                                               21

<210> SEQ ID NO 192
<211> LENGTH: 22
<212> TYPE: RNA
```

```
<213> ORGANISM: homo sapiens

<400> SEQUENCE: 192
uggcucaguu cagcaggaac ag                                          22

<210> SEQ ID NO 193
<211> LENGTH: 22
<212> TYPE: RNA
<213> ORGANISM: homo sapiens

<400> SEQUENCE: 193
uggcucaguu cagcaggaac ag                                          22

<210> SEQ ID NO 194
<211> LENGTH: 22
<212> TYPE: RNA
<213> ORGANISM: homo sapiens

<400> SEQUENCE: 194
cauugcacuu gucucggucu ga                                          22

<210> SEQ ID NO 195
<211> LENGTH: 22
<212> TYPE: RNA
<213> ORGANISM: homo sapiens

<400> SEQUENCE: 195
uucaaguaau ccaggauagg cu                                          22

<210> SEQ ID NO 196
<211> LENGTH: 22
<212> TYPE: RNA
<213> ORGANISM: homo sapiens

<400> SEQUENCE: 196
uucaaguaau ccaggauagg cu                                          22

<210> SEQ ID NO 197
<211> LENGTH: 21
<212> TYPE: RNA
<213> ORGANISM: homo sapiens

<400> SEQUENCE: 197
uucaaguaau ucaggauagg u                                           21

<210> SEQ ID NO 198
<211> LENGTH: 21
<212> TYPE: RNA
<213> ORGANISM: homo sapiens

<400> SEQUENCE: 198
uucacagugg cuaaguuccg c                                           21

<210> SEQ ID NO 199
<211> LENGTH: 21
<212> TYPE: RNA
<213> ORGANISM: homo sapiens

<400> SEQUENCE: 199
uucacagugg cuaaguucug c                                           21

<210> SEQ ID NO 200
<211> LENGTH: 22
```

<212> TYPE: RNA
<213> ORGANISM: homo sapiens

<400> SEQUENCE: 200
cacuagauug ugagcuccug ga                                              22

<210> SEQ ID NO 201
<211> LENGTH: 22
<212> TYPE: RNA
<213> ORGANISM: homo sapiens

<400> SEQUENCE: 201 gagguuggg uggaggcucu cc                                               22

<210> SEQ ID NO 202
<211> LENGTH: 22
<212> TYPE: RNA
<213> ORGANISM: homo sapiens

<400> SEQUENCE: 202
augguuuacc gucccacaua ca                                              22

<210> SEQ ID NO 203
<211> LENGTH: 22
<212> TYPE: RNA
<213> ORGANISM: homo sapiens

<400> SEQUENCE: 203
uagcaccauc ugaaaucggu ua                                              22

<210> SEQ ID NO 204
<211> LENGTH: 23
<212> TYPE: RNA
<213> ORGANISM: homo sapiens

<400> SEQUENCE: 204
uagcaccauu ugaaaucagu guu                                             23

<210> SEQ ID NO 205
<211> LENGTH: 23
<212> TYPE: RNA
<213> ORGANISM: homo sapiens

<400> SEQUENCE: 205
uagcaccauu ugaaaucagu guu                                             23

<210> SEQ ID NO 206
<211> LENGTH: 22
<212> TYPE: RNA
<213> ORGANISM: homo sapiens

<400> SEQUENCE: 206
uagcaccauu ugaaaucggu ua                                              22

<210> SEQ ID NO 207
<211> LENGTH: 23
<212> TYPE: RNA
<213> ORGANISM: homo sapiens

<400> SEQUENCE: 207
cagugcaaug auauugucaa agc                                             23

<210> SEQ ID NO 208

```
<211> LENGTH: 22
<212> TYPE: RNA
<213> ORGANISM: homo sapiens

<400> SEQUENCE: 208
uguaaacauc cucgacugga ag                                              22

<210> SEQ ID NO 209
<211> LENGTH: 22
<212> TYPE: RNA
<213> ORGANISM: homo sapiens

<400> SEQUENCE: 209
uguaaacauc cuacacucag cu                                              22

<210> SEQ ID NO 210
<211> LENGTH: 23
<212> TYPE: RNA
<213> ORGANISM: homo sapiens

<400> SEQUENCE: 210
uguaaacauc cuacacucuc agc                                             23

<210> SEQ ID NO 211
<211> LENGTH: 23
<212> TYPE: RNA
<213> ORGANISM: homo sapiens

<400> SEQUENCE: 211
uguaaacauc cuacacucuc agc                                             23

<210> SEQ ID NO 212
<211> LENGTH: 22
<212> TYPE: RNA
<213> ORGANISM: homo sapiens

<400> SEQUENCE: 212
uguaaacauc cccgacugga ag                                              22

<210> SEQ ID NO 213
<211> LENGTH: 22
<212> TYPE: RNA
<213> ORGANISM: homo sapiens

<400> SEQUENCE: 213
uguaaacauc cuugacugga ag                                              22

<210> SEQ ID NO 214
<211> LENGTH: 21
<212> TYPE: RNA
<213> ORGANISM: homo sapiens

<400> SEQUENCE: 214
aggcaagaug cuggcauagc u                                               21

<210> SEQ ID NO 215
<211> LENGTH: 22
<212> TYPE: RNA
<213> ORGANISM: homo sapiens

<400> SEQUENCE: 215
uauugcacau uacuaaguug ca                                              22
```

```
<210> SEQ ID NO 216
<211> LENGTH: 22
<212> TYPE: RNA
<213> ORGANISM: homo sapiens

<400> SEQUENCE: 216
aaaagcuggg uugagagggc ga                                              22

<210> SEQ ID NO 217
<211> LENGTH: 22
<212> TYPE: RNA
<213> ORGANISM: homo sapiens

<400> SEQUENCE: 217
aaaagcuggg uugagagggc aa                                              22

<210> SEQ ID NO 218
<211> LENGTH: 22
<212> TYPE: RNA
<213> ORGANISM: homo sapiens

<400> SEQUENCE: 218
aaaagcuggg uugagagggc aa                                              22

<210> SEQ ID NO 219
<211> LENGTH: 20
<212> TYPE: RNA
<213> ORGANISM: homo sapiens

<400> SEQUENCE: 219
aaaagcuggg uugagagggu                                                 20

<210> SEQ ID NO 220
<211> LENGTH: 20
<212> TYPE: RNA
<213> ORGANISM: homo sapiens

<400> SEQUENCE: 220
aaaagcuggg uugagagggu                                                 20

<210> SEQ ID NO 221
<211> LENGTH: 19
<212> TYPE: RNA
<213> ORGANISM: homo sapiens

<400> SEQUENCE: 221
aaaagcuggg uugagagga                                                  19

<210> SEQ ID NO 222
<211> LENGTH: 19
<212> TYPE: RNA
<213> ORGANISM: homo sapiens

<400> SEQUENCE: 222
aaaagcuggg uugagagga                                                  19

<210> SEQ ID NO 223
<211> LENGTH: 21
<212> TYPE: RNA
<213> ORGANISM: homo sapiens

<400> SEQUENCE: 223
cacauuacac ggucgaccuc u                                               21
```

```
<210> SEQ ID NO 224
<211> LENGTH: 23
<212> TYPE: RNA
<213> ORGANISM: homo sapiens

<400> SEQUENCE: 224
cgcauccccu agggcauugg ugu                                              23

<210> SEQ ID NO 225
<211> LENGTH: 22
<212> TYPE: RNA
<213> ORGANISM: homo sapiens

<400> SEQUENCE: 225
cuggcccucu cugcccuucc gu                                               22

<210> SEQ ID NO 226
<211> LENGTH: 23
<212> TYPE: RNA
<213> ORGANISM: homo sapiens

<400> SEQUENCE: 226
gcaaagcaca cggccugcag aga                                              23

<210> SEQ ID NO 227
<211> LENGTH: 21
<212> TYPE: RNA
<213> ORGANISM: homo sapiens

<400> SEQUENCE: 227
gccccugggc cuauccuaga a                                                21

<210> SEQ ID NO 228
<211> LENGTH: 23
<212> TYPE: RNA
<213> ORGANISM: homo sapiens

<400> SEQUENCE: 228
ucaagagcaa uaacgaaaaa ugu                                              23

<210> SEQ ID NO 229
<211> LENGTH: 22
<212> TYPE: RNA
<213> ORGANISM: homo sapiens

<400> SEQUENCE: 229
uccagcauca gugauuuugu ug                                               22

<210> SEQ ID NO 230
<211> LENGTH: 23
<212> TYPE: RNA
<213> ORGANISM: homo sapiens

<400> SEQUENCE: 230
ugagcgccuc gacgacagag ccg                                              23

<210> SEQ ID NO 231
<211> LENGTH: 21
<212> TYPE: RNA
<213> ORGANISM: homo sapiens

<400> SEQUENCE: 231
gugcauugua guugcauugc a                                                21
```

<210> SEQ ID NO 232
<211> LENGTH: 20
<212> TYPE: RNA
<213> ORGANISM: homo sapiens

<400> SEQUENCE: 232
gugcauugcu guugcauugc                                               20

<210> SEQ ID NO 233
<211> LENGTH: 22
<212> TYPE: RNA
<213> ORGANISM: homo sapiens

<400> SEQUENCE: 233
uuauaaagca augagacuga uu                                            22

<210> SEQ ID NO 234
<211> LENGTH: 21
<212> TYPE: RNA
<213> ORGANISM: homo sapiens

<400> SEQUENCE: 234
aggggugcua ucugugauug a                                             21

<210> SEQ ID NO 235
<211> LENGTH: 22
<212> TYPE: RNA
<213> ORGANISM: homo sapiens

<400> SEQUENCE: 235
gcugacuccu aguccagggc uc                                            22

<210> SEQ ID NO 236
<211> LENGTH: 22
<212> TYPE: RNA
<213> ORGANISM: homo sapiens

<400> SEQUENCE: 236
uggcaguguc uuagcugguu gu                                            22

<210> SEQ ID NO 237
<211> LENGTH: 22
<212> TYPE: RNA
<213> ORGANISM: homo sapiens

<400> SEQUENCE: 237
aggcaguguc auuagcugau ug                                            22

<210> SEQ ID NO 238
<211> LENGTH: 23
<212> TYPE: RNA
<213> ORGANISM: homo sapiens

<400> SEQUENCE: 238
aggcagugua guuagcugau ugc                                           23

<210> SEQ ID NO 239
<211> LENGTH: 22
<212> TYPE: RNA
<213> ORGANISM: homo sapiens

<400> SEQUENCE: 239
uuaucagaau cuccaggggu ac                                                    22

<210> SEQ ID NO 240
<211> LENGTH: 22
<212> TYPE: RNA
<213> ORGANISM: homo sapiens

<400> SEQUENCE: 240
aacacaccua uucaaggauu ca                                                    22

<210> SEQ ID NO 241
<211> LENGTH: 22
<212> TYPE: RNA
<213> ORGANISM: homo sapiens

<400> SEQUENCE: 241
aauugcacgg uauccaucug ua                                                    22

<210> SEQ ID NO 242
<211> LENGTH: 22
<212> TYPE: RNA
<213> ORGANISM: homo sapiens

<400> SEQUENCE: 242
uaaugccccu aaaaauccuu au                                                    22

<210> SEQ ID NO 243
<211> LENGTH: 21
<212> TYPE: RNA
<213> ORGANISM: homo sapiens

<400> SEQUENCE: 243
aauaauacau gguugaucuu u                                                     21

<210> SEQ ID NO 244
<211> LENGTH: 22
<212> TYPE: RNA
<213> ORGANISM: homo sapiens

<400> SEQUENCE: 244
gccugcuggg guggaaccug gu                                                    22

<210> SEQ ID NO 245
<211> LENGTH: 20
<212> TYPE: RNA
<213> ORGANISM: homo sapiens

<400> SEQUENCE: 245
acucaaacug uggggggcacu                                                      20

<210> SEQ ID NO 246
<211> LENGTH: 22
<212> TYPE: RNA
<213> ORGANISM: homo sapiens

<400> SEQUENCE: 246
uuauaauaca accugauaag ug                                                    22

<210> SEQ ID NO 247
<211> LENGTH: 22
<212> TYPE: RNA
<213> ORGANISM: homo sapiens

<400> SEQUENCE: 247
auauaauaca accugcuaag ug 22

<210> SEQ ID NO 248
<211> LENGTH: 22
<212> TYPE: RNA
<213> ORGANISM: homo sapiens

<400> SEQUENCE: 248
uuuguucguu cggcucgcgu ga 22

<210> SEQ ID NO 249
<211> LENGTH: 22
<212> TYPE: RNA
<213> ORGANISM: homo sapiens

<400> SEQUENCE: 249
agagguugcc cuuggugaau uc 22

<210> SEQ ID NO 250
<211> LENGTH: 21
<212> TYPE: RNA
<213> ORGANISM: homo sapiens

<400> SEQUENCE: 250
acuggacuug gagucagaag g 21

<210> SEQ ID NO 251
<211> LENGTH: 21
<212> TYPE: RNA
<213> ORGANISM: homo sapiens

<400> SEQUENCE: 251
ugguagacua uggaacguag g 21

<210> SEQ ID NO 252
<211> LENGTH: 22
<212> TYPE: RNA
<213> ORGANISM: homo sapiens

<400> SEQUENCE: 252
uauacaaggg caagcucucu gu 22

<210> SEQ ID NO 253
<211> LENGTH: 22
<212> TYPE: RNA
<213> ORGANISM: homo sapiens

<400> SEQUENCE: 253
gaaguuguuc gugguggauu cg 22

<210> SEQ ID NO 254
<211> LENGTH: 22
<212> TYPE: RNA
<213> ORGANISM: homo sapiens

<400> SEQUENCE: 254
agaucagaag gugauugugg cu 22

<210> SEQ ID NO 255
<211> LENGTH: 22
<212> TYPE: RNA
<213> ORGANISM: homo sapiens

```
<400> SEQUENCE: 255
cgaauguugc ucggugaacc cc                                              22

<210> SEQ ID NO 256
<211> LENGTH: 21
<212> TYPE: RNA
<213> ORGANISM: homo sapiens

<400> SEQUENCE: 256
aauauaacac agauggccug u                                               21

<210> SEQ ID NO 257
<211> LENGTH: 22
<212> TYPE: RNA
<213> ORGANISM: homo sapiens

<400> SEQUENCE: 257
auaguagacc guauagcgua cg                                              22

<210> SEQ ID NO 258
<211> LENGTH: 23
<212> TYPE: RNA
<213> ORGANISM: homo sapiens

<400> SEQUENCE: 258
aucaacagac auuaauuggg cgc                                             23

<210> SEQ ID NO 259
<211> LENGTH: 23
<212> TYPE: RNA
<213> ORGANISM: homo sapiens

<400> SEQUENCE: 259
ugaggggcag agagcgagac uuu                                             23

<210> SEQ ID NO 260
<211> LENGTH: 22
<212> TYPE: RNA
<213> ORGANISM: homo sapiens

<400> SEQUENCE: 260
cagcagcaau ucauguuuug aa                                              22

<210> SEQ ID NO 261
<211> LENGTH: 22
<212> TYPE: RNA
<213> ORGANISM: homo sapiens

<400> SEQUENCE: 261
uaauacuguc ugguaaaacc gu                                              22

<210> SEQ ID NO 262
<211> LENGTH: 23
<212> TYPE: RNA
<213> ORGANISM: homo sapiens

<400> SEQUENCE: 262
ucuuggagua ggucauuggg ugg                                             23

<210> SEQ ID NO 263
<211> LENGTH: 22
<212> TYPE: RNA
<213> ORGANISM: homo sapiens
```

```
<400> SEQUENCE: 263
aucaugaugg gcuccucggu gu                                          22

<210> SEQ ID NO 264
<211> LENGTH: 22
<212> TYPE: RNA
<213> ORGANISM: homo sapiens

<400> SEQUENCE: 264
uugcauaugu aggauguccc au                                          22

<210> SEQ ID NO 265
<211> LENGTH: 22
<212> TYPE: RNA
<213> ORGANISM: homo sapiens

<400> SEQUENCE: 265
uggcagugua uuguuagcug gu                                          22

<210> SEQ ID NO 266
<211> LENGTH: 22
<212> TYPE: RNA
<213> ORGANISM: homo sapiens

<400> SEQUENCE: 266
aggcagugua uuguuagcug gc                                          22

<210> SEQ ID NO 267
<211> LENGTH: 22
<212> TYPE: RNA
<213> ORGANISM: homo sapiens

<400> SEQUENCE: 267
uuuugcgaug uguuccuaau au                                          22

<210> SEQ ID NO 268
<211> LENGTH: 22
<212> TYPE: RNA
<213> ORGANISM: homo sapiens

<400> SEQUENCE: 268
uuuugcgaug uguuccuaau au                                          22

<210> SEQ ID NO 269
<211> LENGTH: 22
<212> TYPE: RNA
<213> ORGANISM: homo sapiens

<400> SEQUENCE: 269
uuuugcaaua uguuccugaa ua                                          22

<210> SEQ ID NO 270
<211> LENGTH: 22
<212> TYPE: RNA
<213> ORGANISM: homo sapiens

<400> SEQUENCE: 270
aacuguuugc agaggaaacu ga                                          22

<210> SEQ ID NO 271
<211> LENGTH: 23
<212> TYPE: RNA
```

<213> ORGANISM: homo sapiens

<400> SEQUENCE: 271
uagugcaaua uugcuuauag ggu					23

<210> SEQ ID NO 272
<211> LENGTH: 21
<212> TYPE: RNA
<213> ORGANISM: homo sapiens

<400> SEQUENCE: 272
gcaguccaug ggcauauaca c						21

<210> SEQ ID NO 273
<211> LENGTH: 22
<212> TYPE: RNA
<213> ORGANISM: homo sapiens

<400> SEQUENCE: 273
aagacgggag gaaagaaggg ag					22

<210> SEQ ID NO 274
<211> LENGTH: 22
<212> TYPE: RNA
<213> ORGANISM: homo sapiens

<400> SEQUENCE: 274
ucaggcucag uccccucccg au					22

<210> SEQ ID NO 275
<211> LENGTH: 22
<212> TYPE: RNA
<213> ORGANISM: homo sapiens

<400> SEQUENCE: 275
agaggcuggc cgugaugaau uc					22

<210> SEQ ID NO 276
<211> LENGTH: 22
<212> TYPE: RNA
<213> ORGANISM: homo sapiens

<400> SEQUENCE: 276
uccuguacug agcugccccg ag					22

<210> SEQ ID NO 277
<211> LENGTH: 22
<212> TYPE: RNA
<213> ORGANISM: homo sapiens

<400> SEQUENCE: 277
aaucguacag ggucauccac uu					22

<210> SEQ ID NO 278
<211> LENGTH: 21
<212> TYPE: RNA
<213> ORGANISM: homo sapiens

<400> SEQUENCE: 278
cccagauaau ggcacucuca a						21

<210> SEQ ID NO 279
<211> LENGTH: 22

```
<212> TYPE: RNA
<213> ORGANISM: homo sapiens

<400> SEQUENCE: 279
uuguacaugg uaggcuuuca uu                                              22

<210> SEQ ID NO 280
<211> LENGTH: 22
<212> TYPE: RNA
<213> ORGANISM: homo sapiens

<400> SEQUENCE: 280
ugaaacauac acgggaaacc uc                                              22

<210> SEQ ID NO 281
<211> LENGTH: 22
<212> TYPE: RNA
<213> ORGANISM: homo sapiens

<400> SEQUENCE: 281
aaacaaacau ggugcacuuc uu                                              22

<210> SEQ ID NO 282
<211> LENGTH: 21
<212> TYPE: RNA
<213> ORGANISM: homo sapiens

<400> SEQUENCE: 282
cagcagcaca cugugguuug u                                               21

<210> SEQ ID NO 283
<211> LENGTH: 21
<212> TYPE: RNA
<213> ORGANISM: homo sapiens

<400> SEQUENCE: 283
uuaagacuug cagugauguu u                                               21

<210> SEQ ID NO 284
<211> LENGTH: 22
<212> TYPE: RNA
<213> ORGANISM: homo sapiens

<400> SEQUENCE: 284
augcaccugg gcaaggauuc ug                                              22

<210> SEQ ID NO 285
<211> LENGTH: 22
<212> TYPE: RNA
<213> ORGANISM: homo sapiens

<400> SEQUENCE: 285
aaugcacccg ggcaaggauu cu                                              22

<210> SEQ ID NO 286
<211> LENGTH: 22
<212> TYPE: RNA
<213> ORGANISM: homo sapiens

<400> SEQUENCE: 286
aaugcaccug ggcaaggauu ca                                              22

<210> SEQ ID NO 287
```

```
<211> LENGTH: 23
<212> TYPE: RNA
<213> ORGANISM: homo sapiens

<400> SEQUENCE: 287
uagcagcggg aacaguucug cag                                              23

<210> SEQ ID NO 288
<211> LENGTH: 22
<212> TYPE: RNA
<213> ORGANISM: homo sapiens

<400> SEQUENCE: 288
agacccuggu cugcacucua uc                                               22

<210> SEQ ID NO 289
<211> LENGTH: 22
<212> TYPE: RNA
<213> ORGANISM: homo sapiens

<400> SEQUENCE: 289
gggagccagg aaguauugau gu                                               22

<210> SEQ ID NO 290
<211> LENGTH: 23
<212> TYPE: RNA
<213> ORGANISM: homo sapiens

<400> SEQUENCE: 290
ugauuguagc cuuuuggagu aga                                              23

<210> SEQ ID NO 291
<211> LENGTH: 22
<212> TYPE: RNA
<213> ORGANISM: homo sapiens

<400> SEQUENCE: 291
uacugcagac guggcaauca ug                                               22

<210> SEQ ID NO 292
<211> LENGTH: 18
<212> TYPE: RNA
<213> ORGANISM: homo sapiens

<400> SEQUENCE: 292
uucacaggga ggugucau                                                    18

<210> SEQ ID NO 293
<211> LENGTH: 18
<212> TYPE: RNA
<213> ORGANISM: homo sapiens

<400> SEQUENCE: 293
uucacaggga ggugucau                                                    18

<210> SEQ ID NO 294
<211> LENGTH: 22
<212> TYPE: RNA
<213> ORGANISM: homo sapiens

<400> SEQUENCE: 294
uucacaagga ggugucauuu au                                               22
```

-continued

```
<210> SEQ ID NO 295
<211> LENGTH: 22
<212> TYPE: RNA
<213> ORGANISM: homo sapiens

<400> SEQUENCE: 295
uucucaagga ggugucguuu au                                              22

<210> SEQ ID NO 296
<211> LENGTH: 22
<212> TYPE: RNA
<213> ORGANISM: homo sapiens

<400> SEQUENCE: 296
caugccuuga guguaggacc gu                                              22

<210> SEQ ID NO 297
<211> LENGTH: 22
<212> TYPE: RNA
<213> ORGANISM: homo sapiens

<400> SEQUENCE: 297
ugugacagau ugauaacuga aa                                              22

<210> SEQ ID NO 298
<211> LENGTH: 22
<212> TYPE: RNA
<213> ORGANISM: homo sapiens

<400> SEQUENCE: 298
aaacauucgc ggugcacuuc uu                                              22

<210> SEQ ID NO 299
<211> LENGTH: 22
<212> TYPE: RNA
<213> ORGANISM: homo sapiens

<400> SEQUENCE: 299
caaaacuggc aauuacuuuu gc                                              22

<210> SEQ ID NO 300
<211> LENGTH: 22
<212> TYPE: RNA
<213> ORGANISM: homo sapiens

<400> SEQUENCE: 300
caaaacuggc aauuacuuuu gc                                              22

<210> SEQ ID NO 301
<211> LENGTH: 22
<212> TYPE: RNA
<213> ORGANISM: homo sapiens

<400> SEQUENCE: 301
caaaacuggc aauuacuuuu gc                                              22

<210> SEQ ID NO 302
<211> LENGTH: 22
<212> TYPE: RNA
<213> ORGANISM: homo sapiens

<400> SEQUENCE: 302
caagaaccuc aguugcuuuu gu                                              22
```

```
<210> SEQ ID NO 303
<211> LENGTH: 22
<212> TYPE: RNA
<213> ORGANISM: homo sapiens

<400> SEQUENCE: 303
aaaaacugag acuacuuuug ca                                              22

<210> SEQ ID NO 304
<211> LENGTH: 22
<212> TYPE: RNA
<213> ORGANISM: homo sapiens

<400> SEQUENCE: 304
aaaaguaauc gcgguuuuug uc                                              22

<210> SEQ ID NO 305
<211> LENGTH: 22
<212> TYPE: RNA
<213> ORGANISM: homo sapiens

<400> SEQUENCE: 305
aaaaguaauc gcgguuuuug uc                                              22

<210> SEQ ID NO 306
<211> LENGTH: 22
<212> TYPE: RNA
<213> ORGANISM: homo sapiens

<400> SEQUENCE: 306
aaaaguaauc gcgguuuuug uc                                              22

<210> SEQ ID NO 307
<211> LENGTH: 22
<212> TYPE: RNA
<213> ORGANISM: homo sapiens

<400> SEQUENCE: 307
aaaaguaauc gcgguuuuug uc                                              22

<210> SEQ ID NO 308
<211> LENGTH: 22
<212> TYPE: RNA
<213> ORGANISM: homo sapiens

<400> SEQUENCE: 308
aaaaguaauu gcggucuuug gu                                              22

<210> SEQ ID NO 309
<211> LENGTH: 22
<212> TYPE: RNA
<213> ORGANISM: homo sapiens

<400> SEQUENCE: 309
aaaaguacuu gcggauuuug cu                                              22

<210> SEQ ID NO 310
<211> LENGTH: 22
<212> TYPE: RNA
<213> ORGANISM: homo sapiens

<400> SEQUENCE: 310
aaaaguauuu gcggguuuug uc                                              22
```

```
<210> SEQ ID NO 311
<211> LENGTH: 22
<212> TYPE: RNA
<213> ORGANISM: homo sapiens

<400> SEQUENCE: 311
caaaaguaau uguggauuuu gu                                              22

<210> SEQ ID NO 312
<211> LENGTH: 23
<212> TYPE: RNA
<213> ORGANISM: homo sapiens

<400> SEQUENCE: 312
agugccugag ggaguaagag ccc                                             23

<210> SEQ ID NO 313
<211> LENGTH: 23
<212> TYPE: RNA
<213> ORGANISM: homo sapiens

<400> SEQUENCE: 313
agugccugag ggaguaagag ccc                                             23

<210> SEQ ID NO 314
<211> LENGTH: 21
<212> TYPE: RNA
<213> ORGANISM: homo sapiens

<400> SEQUENCE: 314
gcgacccaua cuugguuuca g                                               21

<210> SEQ ID NO 315
<211> LENGTH: 22
<212> TYPE: RNA
<213> ORGANISM: homo sapiens

<400> SEQUENCE: 315
cacgcucaug cacacaccca ca                                              22

<210> SEQ ID NO 316
<211> LENGTH: 22
<212> TYPE: RNA
<213> ORGANISM: homo sapiens

<400> SEQUENCE: 316
aagaugugga aaaauuggaa uc                                              22

<210> SEQ ID NO 317
<211> LENGTH: 22
<212> TYPE: RNA
<213> ORGANISM: homo sapiens

<400> SEQUENCE: 317
guagauaaaa uauugguacc ug                                              22

<210> SEQ ID NO 318
<211> LENGTH: 22
<212> TYPE: RNA
<213> ORGANISM: homo sapiens

<400> SEQUENCE: 318
```

```
uaacugguug aacaacugaa cc                                              22
```

<210> SEQ ID NO 319
<211> LENGTH: 23
<212> TYPE: RNA
<213> ORGANISM: homo sapiens

<400> SEQUENCE: 319

```
uuacaguugu ucaaccaguu acu                                             23
```

<210> SEQ ID NO 320
<211> LENGTH: 22
<212> TYPE: RNA
<213> ORGANISM: homo sapiens

<400> SEQUENCE: 320

```
uuaugguuug ccugggacug ag                                              22
```

<210> SEQ ID NO 321
<211> LENGTH: 22
<212> TYPE: RNA
<213> ORGANISM: homo sapiens

<400> SEQUENCE: 321

```
ugagaaccac gucugcucug ag                                              22
```

<210> SEQ ID NO 322
<211> LENGTH: 21
<212> TYPE: RNA
<213> ORGANISM: homo sapiens

<400> SEQUENCE: 322

```
uaauuuuaug uauaagcuag u                                               21
```

<210> SEQ ID NO 323
<211> LENGTH: 22
<212> TYPE: RNA
<213> ORGANISM: homo sapiens

<400> SEQUENCE: 323

```
uacgucaucg uugucaucgu ca                                              22
```

<210> SEQ ID NO 324
<211> LENGTH: 22
<212> TYPE: RNA
<213> ORGANISM: homo sapiens

<400> SEQUENCE: 324

```
uccgagccug ggucucccuc uu                                              22
```

<210> SEQ ID NO 325
<211> LENGTH: 22
<212> TYPE: RNA
<213> ORGANISM: homo sapiens

<400> SEQUENCE: 325

```
aagucauugg aggguuugag ca                                              22
```

<210> SEQ ID NO 326
<211> LENGTH: 23
<212> TYPE: RNA
<213> ORGANISM: homo sapiens

<400> SEQUENCE: 326

```
aaacucuacu uguccuucug agu                                                23

<210> SEQ ID NO 327
<211> LENGTH: 21
<212> TYPE: RNA
<213> ORGANISM: homo sapiens

<400> SEQUENCE: 327 aggggggaaag uucuauaguc c                                                 21

<210> SEQ ID NO 328
<211> LENGTH: 22
<212> TYPE: RNA
<213> ORGANISM: homo sapiens

<400> SEQUENCE: 328
augcugacau auuuacuaga gg                                                 22

<210> SEQ ID NO 329
<211> LENGTH: 21
<212> TYPE: RNA
<213> ORGANISM: homo sapiens

<400> SEQUENCE: 329
uggguuuacg uugggagaac u                                                  21

<210> SEQ ID NO 330
<211> LENGTH: 24
<212> TYPE: RNA
<213> ORGANISM: homo sapiens

<400> SEQUENCE: 330
aaagacauag gauagaguca ccuc                                               24

<210> SEQ ID NO 331
<211> LENGTH: 22
<212> TYPE: RNA
<213> ORGANISM: homo sapiens

<400> SEQUENCE: 331
acacuuguau gcuagcucag gu                                                 22

<210> SEQ ID NO 332
<211> LENGTH: 22
<212> TYPE: RNA
<213> ORGANISM: homo sapiens

<400> SEQUENCE: 332
uuuaggauaa gcuugacuuu ug                                                 22

<210> SEQ ID NO 333
<211> LENGTH: 21
<212> TYPE: RNA
<213> ORGANISM: homo sapiens

<400> SEQUENCE: 333
aauggcgcca cuaggguugu g                                                  21

<210> SEQ ID NO 334
<211> LENGTH: 22
<212> TYPE: RNA
<213> ORGANISM: homo sapiens
```

```
<400> SEQUENCE: 334
uaugucugcu gaccaucacc uu                                        22

<210> SEQ ID NO 335
<211> LENGTH: 22
<212> TYPE: RNA
<213> ORGANISM: homo sapiens

<400> SEQUENCE: 335
uacccauugc auaucggagu ug                                        22

<210> SEQ ID NO 336
<211> LENGTH: 21
<212> TYPE: RNA
<213> ORGANISM: homo sapiens

<400> SEQUENCE: 336
uccgguucuc agggcuccac c                                         21

<210> SEQ ID NO 337
<211> LENGTH: 23
<212> TYPE: RNA
<213> ORGANISM: homo sapiens

<400> SEQUENCE: 337
aaggagcuua caaucuagcu ggg                                       23

<210> SEQ ID NO 338
<211> LENGTH: 23
<212> TYPE: RNA
<213> ORGANISM: homo sapiens

<400> SEQUENCE: 338
uggaagacua gugauuuugu ugu                                       23

<210> SEQ ID NO 339
<211> LENGTH: 23
<212> TYPE: RNA
<213> ORGANISM: homo sapiens

<400> SEQUENCE: 339
uggaagacua gugauuuugu ugu                                       23

<210> SEQ ID NO 340
<211> LENGTH: 23
<212> TYPE: RNA
<213> ORGANISM: homo sapiens

<400> SEQUENCE: 340
uggaagacua gugauuuugu ugu                                       23

<210> SEQ ID NO 341
<211> LENGTH: 20
<212> TYPE: RNA
<213> ORGANISM: homo sapiens

<400> SEQUENCE: 341
cggcucuggg ucugugggga                                           20

<210> SEQ ID NO 342
<211> LENGTH: 23
<212> TYPE: RNA
<213> ORGANISM: homo sapiens
```

```
<400> SEQUENCE: 342
ugcaccaugg uugucugagc aug                                               23

<210> SEQ ID NO 343
<211> LENGTH: 22
<212> TYPE: RNA
<213> ORGANISM: homo sapiens

<400> SEQUENCE: 343
ugagaccucu ggguucugag cu                                                22

<210> SEQ ID NO 344
<211> LENGTH: 21
<212> TYPE: RNA
<213> ORGANISM: homo sapiens

<400> SEQUENCE: 344
gcaggaacuu gugagucucc u                                                 21

<210> SEQ ID NO 345
<211> LENGTH: 22
<212> TYPE: RNA
<213> ORGANISM: homo sapiens

<400> SEQUENCE: 345
cugcccuggc ccgagggacc ga                                                22

<210> SEQ ID NO 346
<211> LENGTH: 20
<212> TYPE: RNA
<213> ORGANISM: homo sapiens

<400> SEQUENCE: 346
guagaggaga uggcgcaggg                                                   20

<210> SEQ ID NO 347
<211> LENGTH: 22
<212> TYPE: RNA
<213> ORGANISM: homo sapiens

<400> SEQUENCE: 347
gugaacgggc gccaucccga gg                                                22

<210> SEQ ID NO 348
<211> LENGTH: 21
<212> TYPE: RNA
<213> ORGANISM: homo sapiens

<400> SEQUENCE: 348
uuaauaucgg acaaccauug u                                                 21

<210> SEQ ID NO 349
<211> LENGTH: 22
<212> TYPE: RNA
<213> ORGANISM: homo sapiens

<400> SEQUENCE: 349
ugcaacgaac cugagccacu ga                                                22

<210> SEQ ID NO 350
<211> LENGTH: 21
<212> TYPE: RNA
```

```
<213> ORGANISM: homo sapiens

<400> SEQUENCE: 350
cacugugucc uuucugcgua g                                              21

<210> SEQ ID NO 351
<211> LENGTH: 23
<212> TYPE: RNA
<213> ORGANISM: homo sapiens

<400> SEQUENCE: 351
ucuuugguua ucuagcugua uga                                            23

<210> SEQ ID NO 352
<211> LENGTH: 23
<212> TYPE: RNA
<213> ORGANISM: homo sapiens

<400> SEQUENCE: 352
ucuuugguua ucuagcugua uga                                            23

<210> SEQ ID NO 353
<211> LENGTH: 22
<212> TYPE: RNA
<213> ORGANISM: homo sapiens

<400> SEQUENCE: 353
uauugcacuu gucccggccu gu                                             22

<210> SEQ ID NO 354
<211> LENGTH: 22
<212> TYPE: RNA
<213> ORGANISM: homo sapiens

<400> SEQUENCE: 354
uauugcacuu gucccggccu gu                                             22

<210> SEQ ID NO 355
<211> LENGTH: 22
<212> TYPE: RNA
<213> ORGANISM: homo sapiens

<400> SEQUENCE: 355
uauugcacuc gucccggccu cc                                             22

<210> SEQ ID NO 356
<211> LENGTH: 23
<212> TYPE: RNA
<213> ORGANISM: homo sapiens

<400> SEQUENCE: 356
caaagugcug uucgugcagg uag                                            23

<210> SEQ ID NO 357
<211> LENGTH: 23
<212> TYPE: RNA
<213> ORGANISM: homo sapiens

<400> SEQUENCE: 357
ucuuugguua ucuagcugua uga                                            23

<210> SEQ ID NO 358
<211> LENGTH: 21
```

```
<212> TYPE: RNA
<213> ORGANISM: homo sapiens

<400> SEQUENCE: 358
aaggcagggc ccccgcuccc c                                              21

<210> SEQ ID NO 359
<211> LENGTH: 22
<212> TYPE: RNA
<213> ORGANISM: homo sapiens

<400> SEQUENCE: 359
uucucuguuu uggccaugug ug                                             22

<210> SEQ ID NO 360
<211> LENGTH: 22
<212> TYPE: RNA
<213> ORGANISM: homo sapiens

<400> SEQUENCE: 360
aaauuauugu acaucggaug ag                                             22

<210> SEQ ID NO 361
<211> LENGTH: 22
<212> TYPE: RNA
<213> ORGANISM: homo sapiens

<400> SEQUENCE: 361
uucaacgggu auuuauugag ca                                             22

<210> SEQ ID NO 362
<211> LENGTH: 23
<212> TYPE: RNA
<213> ORGANISM: homo sapiens

<400> SEQUENCE: 362
uuuggcacua gcacauuuuu gcu                                            23

<210> SEQ ID NO 363
<211> LENGTH: 22
<212> TYPE: RNA
<213> ORGANISM: homo sapiens

<400> SEQUENCE: 363
ugagguagua aguuguauug uu                                             22

<210> SEQ ID NO 364
<211> LENGTH: 22
<212> TYPE: RNA
<213> ORGANISM: homo sapiens

<400> SEQUENCE: 364
aacccguaga uccgaucuug ug                                             22

<210> SEQ ID NO 365
<211> LENGTH: 22
<212> TYPE: RNA
<213> ORGANISM: homo sapiens

<400> SEQUENCE: 365
cacccguaga accgaccuug cg                                             22

<210> SEQ ID NO 366
```

-continued

<211> LENGTH: 21
<212> TYPE: RNA
<213> ORGANISM: homo sapiens

<400> SEQUENCE: 366
aacauagagg aaauuccacg u                                              21

<210> SEQ ID NO 367
<211> LENGTH: 22
<212> TYPE: RNA
<213> ORGANISM: homo sapiens

<400> SEQUENCE: 367
aucauagagg aaaauccaug uu                                             22

<210> SEQ ID NO 368
<211> LENGTH: 22
<212> TYPE: RNA
<213> ORGANISM: homo sapiens

<400> SEQUENCE: 368
uggugggccg cagaacaugu gc                                             22

<210> SEQ ID NO 369
<211> LENGTH: 21
<212> TYPE: RNA
<213> ORGANISM: homo sapiens

<400> SEQUENCE: 369
aucauagagg aaaauccacg u                                              21

<210> SEQ ID NO 370
<211> LENGTH: 21
<212> TYPE: RNA
<213> ORGANISM: homo sapiens

<400> SEQUENCE: 370
aucauagagg aaaauccacg u                                              21

<210> SEQ ID NO 371
<211> LENGTH: 22
<212> TYPE: RNA
<213> ORGANISM: homo sapiens

<400> SEQUENCE: 371
aaaaccgucu aguuacaguu gu                                             22

<210> SEQ ID NO 372
<211> LENGTH: 22
<212> TYPE: RNA
<213> ORGANISM: homo sapiens

<400> SEQUENCE: 372
auauacaggg ggagacucuc au                                             22

<210> SEQ ID NO 373
<211> LENGTH: 20
<212> TYPE: RNA
<213> ORGANISM: homo sapiens

<400> SEQUENCE: 373
ccuagaaugg ggauuguggg                                                20

```
<210> SEQ ID NO 374
<211> LENGTH: 22
<212> TYPE: RNA
<213> ORGANISM: homo sapiens

<400> SEQUENCE: 374
agcgagaccu caacucuaca au                                              22

<210> SEQ ID NO 375
<211> LENGTH: 22
<212> TYPE: RNA
<213> ORGANISM: homo sapiens

<400> SEQUENCE: 375
ucgaccggac cucgaccggc uc                                              22

<210> SEQ ID NO 376
<211> LENGTH: 22
<212> TYPE: RNA
<213> ORGANISM: homo sapiens

<400> SEQUENCE: 376
auguagggau ggaagccaug aa                                              22

<210> SEQ ID NO 377
<211> LENGTH: 21
<212> TYPE: RNA
<213> ORGANISM: homo sapiens

<400> SEQUENCE: 377
cucacugaac aaugaaugca a                                               21

<210> SEQ ID NO 378
<211> LENGTH: 22
<212> TYPE: RNA
<213> ORGANISM: homo sapiens

<400> SEQUENCE: 378
cggguagaga gggcaguggg ag                                              22

<210> SEQ ID NO 379
<211> LENGTH: 21
<212> TYPE: RNA
<213> ORGANISM: homo sapiens

<400> SEQUENCE: 379
gcugggaagg caaagggacg u                                               21

<210> SEQ ID NO 380
<211> LENGTH: 22
<212> TYPE: RNA
<213> ORGANISM: homo sapiens

<400> SEQUENCE: 380
accuuggcuc uagacugcuu ac                                              22

<210> SEQ ID NO 381
<211> LENGTH: 22
<212> TYPE: RNA
<213> ORGANISM: homo sapiens

<400> SEQUENCE: 381
gcucugacuu uauugcacua cu                                              22
```

<210> SEQ ID NO 382
<211> LENGTH: 22
<212> TYPE: RNA
<213> ORGANISM: homo sapiens

<400> SEQUENCE: 382
agggacuuuu gggggcagau gu                                              22

<210> SEQ ID NO 383
<211> LENGTH: 21
<212> TYPE: RNA
<213> ORGANISM: homo sapiens

<400> SEQUENCE: 383
uuggggacau uuugcauuca u                                               21

<210> SEQ ID NO 384
<211> LENGTH: 20
<212> TYPE: RNA
<213> ORGANISM: homo sapiens

<400> SEQUENCE: 384
aauguguagc aaaagacaga                                                 20

<210> SEQ ID NO 385
<211> LENGTH: 20
<212> TYPE: RNA
<213> ORGANISM: homo sapiens

<400> SEQUENCE: 385
aauguguagc aaaagacaga                                                 20

<210> SEQ ID NO 386
<211> LENGTH: 22
<212> TYPE: RNA
<213> ORGANISM: homo sapiens

<400> SEQUENCE: 386
aucauacaag gacaauuucu uu                                              22

<210> SEQ ID NO 387
<211> LENGTH: 22
<212> TYPE: RNA
<213> ORGANISM: homo sapiens

<400> SEQUENCE: 387
aaagguaauu gcaguuuuuc cc                                              22

<210> SEQ ID NO 388
<211> LENGTH: 22
<212> TYPE: RNA
<213> ORGANISM: homo sapiens

<400> SEQUENCE: 388
ucgcgguuug ugccagauga cg                                              22

<210> SEQ ID NO 389
<211> LENGTH: 22
<212> TYPE: RNA
<213> ORGANISM: homo sapiens

<400> SEQUENCE: 389
agaaggcacu augagauuua ga                                              22

<210> SEQ ID NO 390
<211> LENGTH: 22
<212> TYPE: RNA
<213> ORGANISM: homo sapiens

<400> SEQUENCE: 390
agacacauuu ggagagggaa cc                                            22

<210> SEQ ID NO 391
<211> LENGTH: 22
<212> TYPE: RNA
<213> ORGANISM: homo sapiens

<400> SEQUENCE: 391
aggaccuucc cugaaccaag ga                                            22

<210> SEQ ID NO 392
<211> LENGTH: 22
<212> TYPE: RNA
<213> ORGANISM: homo sapiens

<400> SEQUENCE: 392
auauacaggg ggagacucuu au                                            22

<210> SEQ ID NO 393
<211> LENGTH: 22
<212> TYPE: RNA
<213> ORGANISM: homo sapiens

<400> SEQUENCE: 393
cugcgcaagc uacugccuug cu                                            22

<210> SEQ ID NO 394
<211> LENGTH: 22
<212> TYPE: RNA
<213> ORGANISM: homo sapiens

<400> SEQUENCE: 394
acggauguuu gagcaugugc ua                                            22

<210> SEQ ID NO 395
<211> LENGTH: 22
<212> TYPE: RNA
<213> ORGANISM: homo sapiens

<400> SEQUENCE: 395
acggauguuu gagcaugugc ua                                            22

<210> SEQ ID NO 396
<211> LENGTH: 22
<212> TYPE: RNA
<213> ORGANISM: homo sapiens

<400> SEQUENCE: 396
cugcaaugua agcacuucuu ac                                            22

<210> SEQ ID NO 397
<211> LENGTH: 21
<212> TYPE: RNA
<213> ORGANISM: homo sapiens

<400> SEQUENCE: 397
cauuauuacu uuugguacgc g                                      21

<210> SEQ ID NO 398
<211> LENGTH: 22
<212> TYPE: RNA
<213> ORGANISM: homo sapiens

<400> SEQUENCE: 398
aagcccuuac cccaaaaagu au                                     22

<210> SEQ ID NO 399
<211> LENGTH: 22
<212> TYPE: RNA
<213> ORGANISM: homo sapiens

<400> SEQUENCE: 399
aagcccuuac cccaaaaagc au                                     22

<210> SEQ ID NO 400
<211> LENGTH: 22
<212> TYPE: RNA
<213> ORGANISM: homo sapiens

<400> SEQUENCE: 400
ucuacagugc acgugucucc ag                                     22

<210> SEQ ID NO 401
<211> LENGTH: 22
<212> TYPE: RNA
<213> ORGANISM: homo sapiens

<400> SEQUENCE: 401
cugguacagg ccuggggggac ag                                    22

<210> SEQ ID NO 402
<211> LENGTH: 22
<212> TYPE: RNA
<213> ORGANISM: homo sapiens

<400> SEQUENCE: 402
acugcaguga aggcacuugu ag                                     22

<210> SEQ ID NO 403
<211> LENGTH: 22
<212> TYPE: RNA
<213> ORGANISM: homo sapiens

<400> SEQUENCE: 403
gugaauuacc gaagggccau aa                                     22

<210> SEQ ID NO 404
<211> LENGTH: 22
<212> TYPE: RNA
<213> ORGANISM: homo sapiens

<400> SEQUENCE: 404
aggggcuggc uuuccucugg uc                                     22

<210> SEQ ID NO 405
<211> LENGTH: 23
<212> TYPE: RNA
<213> ORGANISM: homo sapiens

<400> SEQUENCE: 405
acugcccuaa gugcuccuuc ugg    23

<210> SEQ ID NO 406
<211> LENGTH: 22
<212> TYPE: RNA
<213> ORGANISM: homo sapiens

<400> SEQUENCE: 406
aacuggccua caaaguccca gu    22

<210> SEQ ID NO 407
<211> LENGTH: 22
<212> TYPE: RNA
<213> ORGANISM: homo sapiens

<400> SEQUENCE: 407 cggggиuuug agggcgagau ga    22

<210> SEQ ID NO 408
<211> LENGTH: 23
<212> TYPE: RNA
<213> ORGANISM: homo sapiens

<400> SEQUENCE: 408
cccaguguuc agacuaccug uuc    23

<210> SEQ ID NO 409
<211> LENGTH: 22
<212> TYPE: RNA
<213> ORGANISM: homo sapiens

<400> SEQUENCE: 409
aguuuugcau aguugcacua ca    22

<210> SEQ ID NO 410
<211> LENGTH: 23
<212> TYPE: RNA
<213> ORGANISM: homo sapiens

<400> SEQUENCE: 410
aguuuugcag guuugcaucc agc    23

<210> SEQ ID NO 411
<211> LENGTH: 22
<212> TYPE: RNA
<213> ORGANISM: homo sapiens

<400> SEQUENCE: 411
acuguaguau gggcacuucc ag    22

<210> SEQ ID NO 412
<211> LENGTH: 22
<212> TYPE: RNA
<213> ORGANISM: homo sapiens

<400> SEQUENCE: 412
accuggcaua caauguagau uu    22

<210> SEQ ID NO 413
<211> LENGTH: 22
<212> TYPE: RNA
<213> ORGANISM: homo sapiens

```
<400> SEQUENCE: 413
uggguuccug gcaugcugau uu                                          22

<210> SEQ ID NO 414
<211> LENGTH: 21
<212> TYPE: RNA
<213> ORGANISM: homo sapiens

<400> SEQUENCE: 414
aggcggagac uugggcaauu g                                           21

<210> SEQ ID NO 415
<211> LENGTH: 22
<212> TYPE: RNA
<213> ORGANISM: homo sapiens

<400> SEQUENCE: 415
agagcuuagc ugauugguga ac                                          22

<210> SEQ ID NO 416
<211> LENGTH: 22
<212> TYPE: RNA
<213> ORGANISM: homo sapiens

<400> SEQUENCE: 416
cugggaggug gauguuuacu uc                                          22

<210> SEQ ID NO 417
<211> LENGTH: 22
<212> TYPE: RNA
<213> ORGANISM: homo sapiens

<400> SEQUENCE: 417
cugggagagg guuguuuacu cc                                          22

<210> SEQ ID NO 418
<211> LENGTH: 22
<212> TYPE: RNA
<213> ORGANISM: homo sapiens

<400> SEQUENCE: 418
cugggagaag gcuguuuacu cu                                          22

<210> SEQ ID NO 419
<211> LENGTH: 22
<212> TYPE: RNA
<213> ORGANISM: homo sapiens

<400> SEQUENCE: 419
cuuucagucg gauguuuaca gc                                          22

<210> SEQ ID NO 420
<211> LENGTH: 23
<212> TYPE: RNA
<213> ORGANISM: homo sapiens

<400> SEQUENCE: 420
ucccuguccu ccaggagcuc acg                                         23

<210> SEQ ID NO 421
<211> LENGTH: 23
<212> TYPE: RNA
<213> ORGANISM: homo sapiens
```

```
<400> SEQUENCE: 421
ucucacacag aaaucgcacc cgu                                        23

<210> SEQ ID NO 422
<211> LENGTH: 22
<212> TYPE: RNA
<213> ORGANISM: homo sapiens

<400> SEQUENCE: 422
caaucagcaa guauacugcc cu                                         22

<210> SEQ ID NO 423
<211> LENGTH: 23
<212> TYPE: RNA
<213> ORGANISM: homo sapiens

<400> SEQUENCE: 423 uccccaggu gugauucuga uuu                                         23

<210> SEQ ID NO 424
<211> LENGTH: 24
<212> TYPE: RNA
<213> ORGANISM: homo sapiens

<400> SEQUENCE: 424
aauccuugga accaggugu gagu                                        24

<210> SEQ ID NO 425
<211> LENGTH: 22
<212> TYPE: RNA
<213> ORGANISM: homo sapiens

<400> SEQUENCE: 425
agggacuuuc aggggcagcu gu                                         22

<210> SEQ ID NO 426
<211> LENGTH: 22
<212> TYPE: RNA
<213> ORGANISM: homo sapiens

<400> SEQUENCE: 426
cuuaucagau uguauuguaa uu                                         22

<210> SEQ ID NO 427
<211> LENGTH: 22
<212> TYPE: RNA
<213> ORGANISM: homo sapiens

<400> SEQUENCE: 427
cuuagcaggu uguauuauca uu                                         22

<210> SEQ ID NO 428
<211> LENGTH: 23
<212> TYPE: RNA
<213> ORGANISM: homo sapiens

<400> SEQUENCE: 428
agguuacccg agcaacuuug cau                                        23

<210> SEQ ID NO 429
<211> LENGTH: 21
<212> TYPE: RNA
```

```
<213> ORGANISM: homo sapiens

<400> SEQUENCE: 429
caaaacguga ggcgcugcua u                                        21

<210> SEQ ID NO 430
<211> LENGTH: 22
<212> TYPE: RNA
<213> ORGANISM: homo sapiens

<400> SEQUENCE: 430
uaugugccuu uggacuacau cg                                       22

<210> SEQ ID NO 431
<211> LENGTH: 22
<212> TYPE: RNA
<213> ORGANISM: homo sapiens

<400> SEQUENCE: 431
gucauacacg gcucuccucu cu                                       22

<210> SEQ ID NO 432
<211> LENGTH: 22
<212> TYPE: RNA
<213> ORGANISM: homo sapiens

<400> SEQUENCE: 432
ugucuuacuc ccucaggcac au                                       22

<210> SEQ ID NO 433
<211> LENGTH: 22
<212> TYPE: RNA
<213> ORGANISM: homo sapiens

<400> SEQUENCE: 433
ugucuuacuc ccucaggcac au                                       22

<210> SEQ ID NO 434
<211> LENGTH: 22
<212> TYPE: RNA
<213> ORGANISM: homo sapiens

<400> SEQUENCE: 434
gaaaucaagc gugggugaga cc                                       22

<210> SEQ ID NO 435
<211> LENGTH: 22
<212> TYPE: RNA
<213> ORGANISM: homo sapiens

<400> SEQUENCE: 435
auucuaauuu cuccacgucu uu                                       22

<210> SEQ ID NO 436
<211> LENGTH: 24
<212> TYPE: RNA
<213> ORGANISM: homo sapiens

<400> SEQUENCE: 436
ucagaacaaa ugccgguucc caga                                     24

<210> SEQ ID NO 437
<211> LENGTH: 22
```

```
<212> TYPE: RNA
<213> ORGANISM: homo sapiens

<400> SEQUENCE: 437
gagcuuauuc auaaaagugc ag                                            22

<210> SEQ ID NO 438
<211> LENGTH: 22
<212> TYPE: RNA
<213> ORGANISM: homo sapiens

<400> SEQUENCE: 438
gggggucccc ggugcucgga uc                                            22

<210> SEQ ID NO 439
<211> LENGTH: 22
<212> TYPE: RNA
<213> ORGANISM: homo sapiens

<400> SEQUENCE: 439
gacuauagaa cuuuccccu ca                                             22

<210> SEQ ID NO 440
<211> LENGTH: 22
<212> TYPE: RNA
<213> ORGANISM: homo sapiens

<400> SEQUENCE: 440
uggugggccg cagaacaugu gc                                            22

<210> SEQ ID NO 441
<211> LENGTH: 23
<212> TYPE: RNA
<213> ORGANISM: homo sapiens

<400> SEQUENCE: 441
aggaagcccu ggaggggcug gag                                           23

<210> SEQ ID NO 442
<211> LENGTH: 22
<212> TYPE: RNA
<213> ORGANISM: homo sapiens

<400> SEQUENCE: 442
caacuagacu gugagcuucu ag                                            22

<210> SEQ ID NO 443
<211> LENGTH: 22
<212> TYPE: RNA
<213> ORGANISM: homo sapiens

<400> SEQUENCE: 443
caacaaauca cagucugcca ua                                            22

<210> SEQ ID NO 444
<211> LENGTH: 22
<212> TYPE: RNA
<213> ORGANISM: homo sapiens

<400> SEQUENCE: 444
auaaagcuag auaaccgaaa gu                                            22

<210> SEQ ID NO 445
```

```
<211> LENGTH: 22
<212> TYPE: RNA
<213> ORGANISM: homo sapiens

<400> SEQUENCE: 445
auaaagcuag auaaccgaaa gu                                              22

<210> SEQ ID NO 446
<211> LENGTH: 22
<212> TYPE: RNA
<213> ORGANISM: homo sapiens

<400> SEQUENCE: 446
agggacggga cgcggugcag ug                                              22

<210> SEQ ID NO 447
<211> LENGTH: 22
<212> TYPE: RNA
<213> ORGANISM: homo sapiens

<400> SEQUENCE: 447
auaaagcuag auaaccgaaa gu                                              22

<210> SEQ ID NO 448
<211> LENGTH: 22
<212> TYPE: RNA
<213> ORGANISM: homo sapiens

<400> SEQUENCE: 448
ugagguagua gguuguauag uu                                              22

<210> SEQ ID NO 449
<211> LENGTH: 22
<212> TYPE: RNA
<213> ORGANISM: homo sapiens

<400> SEQUENCE: 449
ugagguagua gguuguauag uu                                              22

<210> SEQ ID NO 450
<211> LENGTH: 22
<212> TYPE: RNA
<213> ORGANISM: homo sapiens

<400> SEQUENCE: 450
ugagguagua gguuguaugg uu                                              22

<210> SEQ ID NO 451
<211> LENGTH: 22
<212> TYPE: RNA
<213> ORGANISM: homo sapiens

<400> SEQUENCE: 451
ugagguagga gguuguauag uu                                              22

<210> SEQ ID NO 452
<211> LENGTH: 22
<212> TYPE: RNA
<213> ORGANISM: homo sapiens

<400> SEQUENCE: 452
ugagguagua gauuguauag uu                                              22
```

```
<210> SEQ ID NO 453
<211> LENGTH: 22
<212> TYPE: RNA
<213> ORGANISM: homo sapiens

<400> SEQUENCE: 453
ugagguagua guuuguacag uu                                              22

<210> SEQ ID NO 454
<211> LENGTH: 22
<212> TYPE: RNA
<213> ORGANISM: homo sapiens

<400> SEQUENCE: 454
ugagguagua guuugugcug uu                                              22

<210> SEQ ID NO 455
<211> LENGTH: 22
<212> TYPE: RNA
<213> ORGANISM: homo sapiens

<400> SEQUENCE: 455
aacccguaga uccgaacuug ug                                              22

<210> SEQ ID NO 456
<211> LENGTH: 21
<212> TYPE: RNA
<213> ORGANISM: homo sapiens

<400> SEQUENCE: 456
uacaguacug ugauaacuga a                                               21

<210> SEQ ID NO 457
<211> LENGTH: 21
<212> TYPE: RNA
<213> ORGANISM: homo sapiens

<400> SEQUENCE: 457
uacaguacug ugauaacuga a                                               21

<210> SEQ ID NO 458
<211> LENGTH: 23
<212> TYPE: RNA
<213> ORGANISM: homo sapiens

<400> SEQUENCE: 458
agcagcauug uacagggcua uga                                             23

<210> SEQ ID NO 459
<211> LENGTH: 23
<212> TYPE: RNA
<213> ORGANISM: homo sapiens

<400> SEQUENCE: 459
agcagcauug uacagggcua uga                                             23

<210> SEQ ID NO 460
<211> LENGTH: 23
<212> TYPE: RNA
<213> ORGANISM: homo sapiens

<400> SEQUENCE: 460
ucaaaugcuc agacuccugu ggu                                             23
```

```
<210> SEQ ID NO 461
<211> LENGTH: 23
<212> TYPE: RNA
<213> ORGANISM: homo sapiens

<400> SEQUENCE: 461
ucaaaugcuc agacuccugu ggu                                              23

<210> SEQ ID NO 462
<211> LENGTH: 23
<212> TYPE: RNA
<213> ORGANISM: homo sapiens

<400> SEQUENCE: 462
aaaagugcuu acagugcagg uag                                              23

<210> SEQ ID NO 463
<211> LENGTH: 21
<212> TYPE: RNA
<213> ORGANISM: homo sapiens

<400> SEQUENCE: 463
uaaagugcug acagugcaga u                                                21

<210> SEQ ID NO 464
<211> LENGTH: 23
<212> TYPE: RNA
<213> ORGANISM: homo sapiens

<400> SEQUENCE: 464
agcagcauug uacagggcua uca                                              23

<210> SEQ ID NO 465
<211> LENGTH: 23
<212> TYPE: RNA
<213> ORGANISM: homo sapiens

<400> SEQUENCE: 465
uacccuguag auccgaauuu gug                                              23

<210> SEQ ID NO 466
<211> LENGTH: 23
<212> TYPE: RNA
<213> ORGANISM: homo sapiens

<400> SEQUENCE: 466
uacccuguag aaccgaauuu gug                                              23

<210> SEQ ID NO 467
<211> LENGTH: 22
<212> TYPE: RNA
<213> ORGANISM: homo sapiens

<400> SEQUENCE: 467
uggaauguaa agaaguaugu au                                               22

<210> SEQ ID NO 468
<211> LENGTH: 22
<212> TYPE: RNA
<213> ORGANISM: homo sapiens

<400> SEQUENCE: 468
uggaauguaa agaaguaugu au                                               22
```

<210> SEQ ID NO 469
<211> LENGTH: 22
<212> TYPE: RNA
<213> ORGANISM: homo sapiens

<400> SEQUENCE: 469
uggaguguga caaugguguu ug					22

<210> SEQ ID NO 470
<211> LENGTH: 20
<212> TYPE: RNA
<213> ORGANISM: homo sapiens

<400> SEQUENCE: 470
uaaggcacgc ggugaaugcc					20

<210> SEQ ID NO 471
<211> LENGTH: 20
<212> TYPE: RNA
<213> ORGANISM: homo sapiens

<400> SEQUENCE: 471
uaaggcacgc ggugaaugcc					20

<210> SEQ ID NO 472
<211> LENGTH: 20
<212> TYPE: RNA
<213> ORGANISM: homo sapiens

<400> SEQUENCE: 472
uaaggcacgc ggugaaugcc					20

<210> SEQ ID NO 473
<211> LENGTH: 22
<212> TYPE: RNA
<213> ORGANISM: homo sapiens

<400> SEQUENCE: 473
acccgucccg uucguccccg ga					22

<210> SEQ ID NO 474
<211> LENGTH: 21
<212> TYPE: RNA
<213> ORGANISM: homo sapiens

<400> SEQUENCE: 474
acggugcugg auguggccuu u					21

<210> SEQ ID NO 475
<211> LENGTH: 22
<212> TYPE: RNA
<213> ORGANISM: homo sapiens

<400> SEQUENCE: 475
agaaggaaau ugaauucauu ua					22

<210> SEQ ID NO 476
<211> LENGTH: 24
<212> TYPE: RNA
<213> ORGANISM: homo sapiens

<400> SEQUENCE: 476
agccuggaag cuggagccug cagu                                          24

<210> SEQ ID NO 477
<211> LENGTH: 23
<212> TYPE: RNA
<213> ORGANISM: homo sapiens

<400> SEQUENCE: 477
aggaugagca aagaaaguag auu                                           23

<210> SEQ ID NO 478
<211> LENGTH: 22
<212> TYPE: RNA
<213> ORGANISM: homo sapiens

<400> SEQUENCE: 478
aggcauugac uucucacuag cu                                            22

<210> SEQ ID NO 479
<211> LENGTH: 22
<212> TYPE: RNA
<213> ORGANISM: homo sapiens

<400> SEQUENCE: 479
ucguaccgug aguaauaaug cg                                            22

<210> SEQ ID NO 480
<211> LENGTH: 22
<212> TYPE: RNA
<213> ORGANISM: homo sapiens

<400> SEQUENCE: 480
augggugaau uuguagaagg au                                            22

<210> SEQ ID NO 481
<211> LENGTH: 22
<212> TYPE: RNA
<213> ORGANISM: homo sapiens

<400> SEQUENCE: 481
augguacccu ggcauacuga gu                                            22

<210> SEQ ID NO 482
<211> LENGTH: 22
<212> TYPE: RNA
<213> ORGANISM: homo sapiens

<400> SEQUENCE: 482
caggaugugg ucaaguguug uu                                            22

<210> SEQ ID NO 483
<211> LENGTH: 23
<212> TYPE: RNA
<213> ORGANISM: homo sapiens

<400> SEQUENCE: 483
ccucagggcu guagaacagg gcu                                           23

<210> SEQ ID NO 484
<211> LENGTH: 22
<212> TYPE: RNA
<213> ORGANISM: homo sapiens

<400> SEQUENCE: 484
cuggacugag ccgugcuacu gg                                           22

<210> SEQ ID NO 485
<211> LENGTH: 23
<212> TYPE: RNA
<213> ORGANISM: homo sapiens

<400> SEQUENCE: 485
cuggagauau ggaagagcug ugu                                          23

<210> SEQ ID NO 486
<211> LENGTH: 22
<212> TYPE: RNA
<213> ORGANISM: homo sapiens

<400> SEQUENCE: 486
cuuggcaccu agcaagcacu ca                                           22

<210> SEQ ID NO 487
<211> LENGTH: 22
<212> TYPE: RNA
<213> ORGANISM: homo sapiens

<400> SEQUENCE: 487
ucggauccgu cugagcuugg cu                                           22

<210> SEQ ID NO 488
<211> LENGTH: 22
<212> TYPE: RNA
<213> ORGANISM: homo sapiens

<400> SEQUENCE: 488
uacguagaua uauauguauu uu                                           22

<210> SEQ ID NO 489
<211> LENGTH: 22
<212> TYPE: RNA
<213> ORGANISM: homo sapiens

<400> SEQUENCE: 489
uaguacugug cauaucaucu au                                           22

<210> SEQ ID NO 490
<211> LENGTH: 21
<212> TYPE: RNA
<213> ORGANISM: homo sapiens

<400> SEQUENCE: 490
ucacagugaa ccggucucuu u                                            21

<210> SEQ ID NO 491
<211> LENGTH: 21
<212> TYPE: RNA
<213> ORGANISM: homo sapiens

<400> SEQUENCE: 491
ucacagugaa ccggucucuu u                                            21

<210> SEQ ID NO 492
<211> LENGTH: 21
<212> TYPE: RNA
<213> ORGANISM: homo sapiens

```
<400> SEQUENCE: 492
cuuuuugcgg ucugggcuug c                                              21

<210> SEQ ID NO 493
<211> LENGTH: 21
<212> TYPE: RNA
<213> ORGANISM: homo sapiens

<400> SEQUENCE: 493
cuuuuugcgg ucugggcuug c                                              21

<210> SEQ ID NO 494
<211> LENGTH: 22
<212> TYPE: RNA
<213> ORGANISM: homo sapiens

<400> SEQUENCE: 494
ugugagguug gcauuguugu cu                                             22

<210> SEQ ID NO 495
<211> LENGTH: 21
<212> TYPE: RNA
<213> ORGANISM: homo sapiens

<400> SEQUENCE: 495
uuaggccgca gaucugggug a                                              21

<210> SEQ ID NO 496
<211> LENGTH: 22
<212> TYPE: RNA
<213> ORGANISM: homo sapiens

<400> SEQUENCE: 496
uucauucggc uguccagaug ua                                             22

<210> SEQ ID NO 497
<211> LENGTH: 24
<212> TYPE: RNA
<213> ORGANISM: homo sapiens

<400> SEQUENCE: 497
uugcagcugc cugggaguga cuuc                                           24

<210> SEQ ID NO 498
<211> LENGTH: 22
<212> TYPE: RNA
<213> ORGANISM: homo sapiens

<400> SEQUENCE: 498
uuugaggcua cagugagaug ug                                             22

<210> SEQ ID NO 499
<211> LENGTH: 18
<212> TYPE: RNA
<213> ORGANISM: homo sapiens

<400> SEQUENCE: 499
acguuggcuc ugguggug                                                  18

<210> SEQ ID NO 500
<211> LENGTH: 22
<212> TYPE: RNA
<213> ORGANISM: homo sapiens
```

```
<400> SEQUENCE: 500
acucggcgug gcgucggucg ug                                    22

<210> SEQ ID NO 501
<211> LENGTH: 22
<212> TYPE: RNA
<213> ORGANISM: homo sapiens

<400> SEQUENCE: 501
cagugcaaug uuaaaagggc au                                    22

<210> SEQ ID NO 502
<211> LENGTH: 22
<212> TYPE: RNA
<213> ORGANISM: homo sapiens

<400> SEQUENCE: 502
cagugcaaug augaaagggc au                                    22

<210> SEQ ID NO 503
<211> LENGTH: 22
<212> TYPE: RNA
<213> ORGANISM: homo sapiens

<400> SEQUENCE: 503
uaacagucua cagccauggu cg                                    22

<210> SEQ ID NO 504
<211> LENGTH: 22
<212> TYPE: RNA
<213> ORGANISM: homo sapiens

<400> SEQUENCE: 504
accguggcuu ucgauuguua cu                                    22

<210> SEQ ID NO 505
<211> LENGTH: 22
<212> TYPE: RNA
<213> ORGANISM: homo sapiens

<400> SEQUENCE: 505
ugugacuggu ugaccagagg gg                                    22

<210> SEQ ID NO 506
<211> LENGTH: 23
<212> TYPE: RNA
<213> ORGANISM: homo sapiens

<400> SEQUENCE: 506
uauggcuuuu cauuccuaug uga                                   23

<210> SEQ ID NO 507
<211> LENGTH: 23
<212> TYPE: RNA
<213> ORGANISM: homo sapiens

<400> SEQUENCE: 507
acuccauuug uuuugaugau gga                                   23

<210> SEQ ID NO 508
<211> LENGTH: 23
<212> TYPE: RNA
```

```
<213> ORGANISM: homo sapiens

<400> SEQUENCE: 508
agcugguguu gugaaucagg ccg                                    23

<210> SEQ ID NO 509
<211> LENGTH: 23
<212> TYPE: RNA
<213> ORGANISM: homo sapiens

<400> SEQUENCE: 509
agcugguguu gugaaucagg ccg                                    23

<210> SEQ ID NO 510
<211> LENGTH: 22
<212> TYPE: RNA
<213> ORGANISM: homo sapiens

<400> SEQUENCE: 510
ggagacgcgg cccuguugga gu                                     22

<210> SEQ ID NO 511
<211> LENGTH: 21
<212> TYPE: RNA
<213> ORGANISM: homo sapiens

<400> SEQUENCE: 511
uaccacaggg uagaaccacg g                                      21

<210> SEQ ID NO 512
<211> LENGTH: 22
<212> TYPE: RNA
<213> ORGANISM: homo sapiens

<400> SEQUENCE: 512
uaacacuguc ugguaaagau gg                                     22

<210> SEQ ID NO 513
<211> LENGTH: 21
<212> TYPE: RNA
<213> ORGANISM: homo sapiens

<400> SEQUENCE: 513
cauaaaguag aaagcacuac u                                      21

<210> SEQ ID NO 514
<211> LENGTH: 21
<212> TYPE: RNA
<213> ORGANISM: homo sapiens

<400> SEQUENCE: 514
ugagaugaag cacuguagcu c                                      21

<210> SEQ ID NO 515
<211> LENGTH: 22
<212> TYPE: RNA
<213> ORGANISM: homo sapiens

<400> SEQUENCE: 515
ggauaucauc auauacugua ag                                     22

<210> SEQ ID NO 516
<211> LENGTH: 23
```

```
<212> TYPE: RNA
<213> ORGANISM: homo sapiens

<400> SEQUENCE: 516
guccaguuuu cccaggaauc ccu                                           23

<210> SEQ ID NO 517
<211> LENGTH: 22
<212> TYPE: RNA
<213> ORGANISM: homo sapiens

<400> SEQUENCE: 517
ugagaacuga auccaugggg uu                                            22

<210> SEQ ID NO 518
<211> LENGTH: 22
<212> TYPE: RNA
<213> ORGANISM: homo sapiens

<400> SEQUENCE: 518
ugagaacuga auccauagg cu                                             22

<210> SEQ ID NO 519
<211> LENGTH: 22
<212> TYPE: RNA
<213> ORGANISM: homo sapiens

<400> SEQUENCE: 519
ucagugcacu acagaacuuu gu                                            22

<210> SEQ ID NO 520
<211> LENGTH: 22
<212> TYPE: RNA
<213> ORGANISM: homo sapiens

<400> SEQUENCE: 520
ucagugcauc acagaacuuu gu                                            22

<210> SEQ ID NO 521
<211> LENGTH: 22
<212> TYPE: RNA
<213> ORGANISM: homo sapiens

<400> SEQUENCE: 521
ucucccaacc cuuguaccag ug                                            22

<210> SEQ ID NO 522
<211> LENGTH: 21
<212> TYPE: RNA
<213> ORGANISM: homo sapiens

<400> SEQUENCE: 522
cuagacugaa gcuccuugag g                                             21

<210> SEQ ID NO 523
<211> LENGTH: 21
<212> TYPE: RNA
<213> ORGANISM: homo sapiens

<400> SEQUENCE: 523
ucagugcaug acagaacuug g                                             21

<210> SEQ ID NO 524
```

```
<210> SEQ ID NO 524
<211> LENGTH: 23
<212> TYPE: RNA
<213> ORGANISM: homo sapiens

<400> SEQUENCE: 524
uuaaugcuaa ucgugauagg ggu                                              23

<210> SEQ ID NO 525
<211> LENGTH: 22
<212> TYPE: RNA
<213> ORGANISM: homo sapiens

<400> SEQUENCE: 525
uagcagcaca uaaugguuug ug                                               22

<210> SEQ ID NO 526
<211> LENGTH: 22
<212> TYPE: RNA
<213> ORGANISM: homo sapiens

<400> SEQUENCE: 526
uagcagcaca ucaugguuua ca                                               22

<210> SEQ ID NO 527
<211> LENGTH: 22
<212> TYPE: RNA
<213> ORGANISM: homo sapiens

<400> SEQUENCE: 527
uagcagcacg uaaauauugg cg                                               22

<210> SEQ ID NO 528
<211> LENGTH: 22
<212> TYPE: RNA
<213> ORGANISM: homo sapiens

<400> SEQUENCE: 528
uagcagcacg uaaauauugg cg                                               22

<210> SEQ ID NO 529
<211> LENGTH: 23
<212> TYPE: RNA
<213> ORGANISM: homo sapiens

<400> SEQUENCE: 529
caaagugcuu acagugcagg uag                                              23

<210> SEQ ID NO 530
<211> LENGTH: 23
<212> TYPE: RNA
<213> ORGANISM: homo sapiens

<400> SEQUENCE: 530
aacauucaac gcugucggug agu                                              23

<210> SEQ ID NO 531
<211> LENGTH: 23
<212> TYPE: RNA
<213> ORGANISM: homo sapiens

<400> SEQUENCE: 531
aacauucaac gcugucggug agu                                              23
```

```
<210> SEQ ID NO 532
<211> LENGTH: 23
<212> TYPE: RNA
<213> ORGANISM: homo sapiens

<400> SEQUENCE: 532
aacauucauu gcugucggug ggu                                              23

<210> SEQ ID NO 533
<211> LENGTH: 23
<212> TYPE: RNA
<213> ORGANISM: homo sapiens

<400> SEQUENCE: 533
aacauucauu gcugucggug ggu                                              23

<210> SEQ ID NO 534
<211> LENGTH: 22
<212> TYPE: RNA
<213> ORGANISM: homo sapiens

<400> SEQUENCE: 534
aacauucaac cugucgguga gu                                               22

<210> SEQ ID NO 535
<211> LENGTH: 23
<212> TYPE: RNA
<213> ORGANISM: homo sapiens

<400> SEQUENCE: 535
aacauucauu guugucggug ggu                                              23

<210> SEQ ID NO 536
<211> LENGTH: 24
<212> TYPE: RNA
<213> ORGANISM: homo sapiens

<400> SEQUENCE: 536
uuuggcaaug guagaacuca cacu                                             24

<210> SEQ ID NO 537
<211> LENGTH: 22
<212> TYPE: RNA
<213> ORGANISM: homo sapiens

<400> SEQUENCE: 537
uauggcacug guagaauuca cu                                               22

<210> SEQ ID NO 538
<211> LENGTH: 22
<212> TYPE: RNA
<213> ORGANISM: homo sapiens

<400> SEQUENCE: 538
uggacggaga acugauaagg gu                                               22

<210> SEQ ID NO 539
<211> LENGTH: 22
<212> TYPE: RNA
<213> ORGANISM: homo sapiens

<400> SEQUENCE: 539
uggagagaaa ggcaguuccu ga                                               22
```

```
<210> SEQ ID NO 540
<211> LENGTH: 22
<212> TYPE: RNA
<213> ORGANISM: homo sapiens

<400> SEQUENCE: 540
caaagaauuc uccuuugggg cu                                              22

<210> SEQ ID NO 541
<211> LENGTH: 21
<212> TYPE: RNA
<213> ORGANISM: homo sapiens

<400> SEQUENCE: 541
caucccuugc augguggagg g                                               21

<210> SEQ ID NO 542
<211> LENGTH: 23
<212> TYPE: RNA
<213> ORGANISM: homo sapiens

<400> SEQUENCE: 542
uaaggugcau cuagugcaga uag                                             23

<210> SEQ ID NO 543
<211> LENGTH: 23
<212> TYPE: RNA
<213> ORGANISM: homo sapiens

<400> SEQUENCE: 543
caacggaauc ccaaaagcag cug                                             23

<210> SEQ ID NO 544
<211> LENGTH: 21
<212> TYPE: RNA
<213> ORGANISM: homo sapiens

<400> SEQUENCE: 544
cugaccuaug aauugacagc c                                               21

<210> SEQ ID NO 545
<211> LENGTH: 22
<212> TYPE: RNA
<213> ORGANISM: homo sapiens

<400> SEQUENCE: 545
ugggucuuug cgggcgagau ga                                              22

<210> SEQ ID NO 546
<211> LENGTH: 22
<212> TYPE: RNA
<213> ORGANISM: homo sapiens

<400> SEQUENCE: 546
aacuggcccu caaaguccccg cu                                             22

<210> SEQ ID NO 547
<211> LENGTH: 22
<212> TYPE: RNA
<213> ORGANISM: homo sapiens

<400> SEQUENCE: 547
uguaacagca acuccaugug ga                                              22
```

```
<210> SEQ ID NO 548
<211> LENGTH: 21
<212> TYPE: RNA
<213> ORGANISM: homo sapiens

<400> SEQUENCE: 548
uagcagcaca gaaauauugg c                                              21

<210> SEQ ID NO 549
<211> LENGTH: 22
<212> TYPE: RNA
<213> ORGANISM: homo sapiens

<400> SEQUENCE: 549
uagguaguuu cauguuguug gg                                             22

<210> SEQ ID NO 550
<211> LENGTH: 22
<212> TYPE: RNA
<213> ORGANISM: homo sapiens

<400> SEQUENCE: 550
uagguaguuu cauguuguug gg                                             22

<210> SEQ ID NO 551
<211> LENGTH: 22
<212> TYPE: RNA
<213> ORGANISM: homo sapiens

<400> SEQUENCE: 551
uagguaguuu ccuguuguug gg                                             22

<210> SEQ ID NO 552
<211> LENGTH: 22
<212> TYPE: RNA
<213> ORGANISM: homo sapiens

<400> SEQUENCE: 552
uucaccaccu ucuccaccca gc                                             22

<210> SEQ ID NO 553
<211> LENGTH: 22
<212> TYPE: RNA
<213> ORGANISM: homo sapiens

<400> SEQUENCE: 553
acaguagucu gcacauuggu ua                                             22

<210> SEQ ID NO 554
<211> LENGTH: 22
<212> TYPE: RNA
<213> ORGANISM: homo sapiens

<400> SEQUENCE: 554
acaguagucu gcacauuggu ua                                             22

<210> SEQ ID NO 555
<211> LENGTH: 22
<212> TYPE: RNA
<213> ORGANISM: homo sapiens

<400> SEQUENCE: 555
```
acaguagucu gcacauuggu ua                                           22

<210> SEQ ID NO 556
<211> LENGTH: 23
<212> TYPE: RNA
<213> ORGANISM: homo sapiens

<400> SEQUENCE: 556
ugugcaaauc uaugcaaaac uga                                          23

<210> SEQ ID NO 557
<211> LENGTH: 23
<212> TYPE: RNA
<213> ORGANISM: homo sapiens

<400> SEQUENCE: 557
ugugcaaauc caugcaaaac uga                                          23

<210> SEQ ID NO 558
<211> LENGTH: 23
<212> TYPE: RNA
<213> ORGANISM: homo sapiens

<400> SEQUENCE: 558
ugugcaaauc caugcaaaac uga                                          23

<210> SEQ ID NO 559
<211> LENGTH: 22
<212> TYPE: RNA
<213> ORGANISM: homo sapiens

<400> SEQUENCE: 559
uaacacuguc ugguaacgau gu                                           22

<210> SEQ ID NO 560
<211> LENGTH: 22
<212> TYPE: RNA
<213> ORGANISM: homo sapiens

<400> SEQUENCE: 560
uaauacugcc ugguaaugau ga                                           22

<210> SEQ ID NO 561
<211> LENGTH: 23
<212> TYPE: RNA
<213> ORGANISM: homo sapiens

<400> SEQUENCE: 561
uaauacugcc ggguaaugau gga                                          23

<210> SEQ ID NO 562
<211> LENGTH: 22
<212> TYPE: RNA
<213> ORGANISM: homo sapiens

<400> SEQUENCE: 562
uuccuaugca uauacuucuu ug                                           22

<210> SEQ ID NO 563
<211> LENGTH: 22
<212> TYPE: RNA
<213> ORGANISM: homo sapiens

<400> SEQUENCE: 563

| | |
|---|---|
| gugaaauguu uaggaccacu ag | 22 |

<210> SEQ ID NO 564
<211> LENGTH: 22
<212> TYPE: RNA
<213> ORGANISM: homo sapiens

<400> SEQUENCE: 564

| | |
|---|---|
| uucccuuugu cauccuaugc cu | 22 |

<210> SEQ ID NO 565
<211> LENGTH: 22
<212> TYPE: RNA
<213> ORGANISM: homo sapiens

<400> SEQUENCE: 565

| | |
|---|---|
| uccuucauuc caccggaguc ug | 22 |

<210> SEQ ID NO 566
<211> LENGTH: 22
<212> TYPE: RNA
<213> ORGANISM: homo sapiens

<400> SEQUENCE: 566

| | |
|---|---|
| uggaauguaa ggaagugugu gg | 22 |

<210> SEQ ID NO 567
<211> LENGTH: 23
<212> TYPE: RNA
<213> ORGANISM: homo sapiens

<400> SEQUENCE: 567

| | |
|---|---|
| uaaagugcuu auagugcagg uag | 23 |

<210> SEQ ID NO 568
<211> LENGTH: 23
<212> TYPE: RNA
<213> ORGANISM: homo sapiens

<400> SEQUENCE: 568

| | |
|---|---|
| caaagugcuc auagugcagg uag | 23 |

<210> SEQ ID NO 569
<211> LENGTH: 22
<212> TYPE: RNA
<213> ORGANISM: homo sapiens

<400> SEQUENCE: 569

| | |
|---|---|
| uagcuuauca gacugauguu ga | 22 |

<210> SEQ ID NO 570
<211> LENGTH: 22
<212> TYPE: RNA
<213> ORGANISM: homo sapiens

<400> SEQUENCE: 570

| | |
|---|---|
| cugugcgugu gacagcggcu ga | 22 |

<210> SEQ ID NO 571
<211> LENGTH: 21
<212> TYPE: RNA
<213> ORGANISM: homo sapiens

```
<400> SEQUENCE: 571
uaacagucuc cagucacggc c                                    21

<210> SEQ ID NO 572
<211> LENGTH: 22
<212> TYPE: RNA
<213> ORGANISM: homo sapiens

<400> SEQUENCE: 572
acagcaggca cagacaggca gu                                   22

<210> SEQ ID NO 573
<211> LENGTH: 21
<212> TYPE: RNA
<213> ORGANISM: homo sapiens

<400> SEQUENCE: 573
augaccuaug aauugacaga c                                    21

<210> SEQ ID NO 574
<211> LENGTH: 22
<212> TYPE: RNA
<213> ORGANISM: homo sapiens

<400> SEQUENCE: 574
aaaucucugc aggcaaaugu ga                                   22

<210> SEQ ID NO 575
<211> LENGTH: 23
<212> TYPE: RNA
<213> ORGANISM: homo sapiens

<400> SEQUENCE: 575
uacugcauca ggaacugauu gga                                  23

<210> SEQ ID NO 576
<211> LENGTH: 22
<212> TYPE: RNA
<213> ORGANISM: homo sapiens

<400> SEQUENCE: 576
agaguugagu cuggacgucc cg                                   22

<210> SEQ ID NO 577
<211> LENGTH: 22
<212> TYPE: RNA
<213> ORGANISM: homo sapiens

<400> SEQUENCE: 577
aagcugccag uugaagaacu gu                                   22

<210> SEQ ID NO 578
<211> LENGTH: 23
<212> TYPE: RNA
<213> ORGANISM: homo sapiens

<400> SEQUENCE: 578
agcuacauug ucugcugggu uuc                                  23

<210> SEQ ID NO 579
<211> LENGTH: 21
<212> TYPE: RNA
<213> ORGANISM: homo sapiens
```

<400> SEQUENCE: 579
agcuacaucu ggcuacuggg u                                              21

<210> SEQ ID NO 580
<211> LENGTH: 22
<212> TYPE: RNA
<213> ORGANISM: homo sapiens

<400> SEQUENCE: 580
cguguauuug acaagcugag uu                                             22

<210> SEQ ID NO 581
<211> LENGTH: 21
<212> TYPE: RNA
<213> ORGANISM: homo sapiens

<400> SEQUENCE: 581
caagucacua gugguuccgu u                                              21

<210> SEQ ID NO 582
<211> LENGTH: 21
<212> TYPE: RNA
<213> ORGANISM: homo sapiens

<400> SEQUENCE: 582
aucacauugc cagggauuuc c                                              21

<210> SEQ ID NO 583
<211> LENGTH: 21
<212> TYPE: RNA
<213> ORGANISM: homo sapiens

<400> SEQUENCE: 583
aucacauugc cagggauuac c                                              21

<210> SEQ ID NO 584
<211> LENGTH: 22
<212> TYPE: RNA
<213> ORGANISM: homo sapiens

<400> SEQUENCE: 584
uggcucaguu cagcaggaac ag                                             22

<210> SEQ ID NO 585
<211> LENGTH: 22
<212> TYPE: RNA
<213> ORGANISM: homo sapiens

<400> SEQUENCE: 585
uggcucaguu cagcaggaac ag                                             22

<210> SEQ ID NO 586
<211> LENGTH: 22
<212> TYPE: RNA
<213> ORGANISM: homo sapiens

<400> SEQUENCE: 586
cauugcacuu gucucggucu ga                                             22

<210> SEQ ID NO 587
<211> LENGTH: 22
<212> TYPE: RNA

<213> ORGANISM: homo sapiens

<400> SEQUENCE: 587
uucaaguaau ccaggauagg cu                                    22

<210> SEQ ID NO 588
<211> LENGTH: 22
<212> TYPE: RNA
<213> ORGANISM: homo sapiens

<400> SEQUENCE: 588
uucaaguaau ccaggauagg cu                                    22

<210> SEQ ID NO 589
<211> LENGTH: 21
<212> TYPE: RNA
<213> ORGANISM: homo sapiens

<400> SEQUENCE: 589
uucaaguaau ucaggauagg u                                     21

<210> SEQ ID NO 590
<211> LENGTH: 21
<212> TYPE: RNA
<213> ORGANISM: homo sapiens

<400> SEQUENCE: 590
uucacagugg cuaaguuccg c                                     21

<210> SEQ ID NO 591
<211> LENGTH: 21
<212> TYPE: RNA
<213> ORGANISM: homo sapiens

<400> SEQUENCE: 591
uucacagugg cuaaguucug c                                     21

<210> SEQ ID NO 592
<211> LENGTH: 22
<212> TYPE: RNA
<213> ORGANISM: homo sapiens

<400> SEQUENCE: 592
cacuagauug ugagcuccug ga                                    22

<210> SEQ ID NO 593
<211> LENGTH: 22
<212> TYPE: RNA
<213> ORGANISM: homo sapiens

<400> SEQUENCE: 593 gagguuggg uggaggcucu cc                                     22

<210> SEQ ID NO 594
<211> LENGTH: 22
<212> TYPE: RNA
<213> ORGANISM: homo sapiens

<400> SEQUENCE: 594
ugguuuaccg ucccacauac au                                    22

<210> SEQ ID NO 595
<211> LENGTH: 22

```
<212> TYPE: RNA
<213> ORGANISM: homo sapiens

<400> SEQUENCE: 595
uagcaccauc ugaaaucggu ua                                           22

<210> SEQ ID NO 596
<211> LENGTH: 23
<212> TYPE: RNA
<213> ORGANISM: homo sapiens

<400> SEQUENCE: 596
uagcaccauu ugaaaucagu guu                                          23

<210> SEQ ID NO 597
<211> LENGTH: 23
<212> TYPE: RNA
<213> ORGANISM: homo sapiens

<400> SEQUENCE: 597
uagcaccauu ugaaaucagu guu                                          23

<210> SEQ ID NO 598
<211> LENGTH: 22
<212> TYPE: RNA
<213> ORGANISM: homo sapiens

<400> SEQUENCE: 598
uagcaccauu ugaaaucggu ua                                           22

<210> SEQ ID NO 599
<211> LENGTH: 23
<212> TYPE: RNA
<213> ORGANISM: homo sapiens

<400> SEQUENCE: 599
cagugcaaug auauugucaa agc                                          23

<210> SEQ ID NO 600
<211> LENGTH: 22
<212> TYPE: RNA
<213> ORGANISM: homo sapiens

<400> SEQUENCE: 600
uguaaacauc cucgacugga ag                                           22

<210> SEQ ID NO 601
<211> LENGTH: 22
<212> TYPE: RNA
<213> ORGANISM: homo sapiens

<400> SEQUENCE: 601
uguaaacauc cuacacucag cu                                           22

<210> SEQ ID NO 602
<211> LENGTH: 23
<212> TYPE: RNA
<213> ORGANISM: homo sapiens

<400> SEQUENCE: 602
uguaaacauc cuacacucuc agc                                          23

<210> SEQ ID NO 603
```

```
<211> LENGTH: 23
<212> TYPE: RNA
<213> ORGANISM: homo sapiens

<400> SEQUENCE: 603
uguaaacauc cuacacucuc agc                                              23

<210> SEQ ID NO 604
<211> LENGTH: 22
<212> TYPE: RNA
<213> ORGANISM: homo sapiens

<400> SEQUENCE: 604
uguaaacauc cccgacugga ag                                               22

<210> SEQ ID NO 605
<211> LENGTH: 22
<212> TYPE: RNA
<213> ORGANISM: homo sapiens

<400> SEQUENCE: 605
uguaaacauc cuugacugga ag                                               22

<210> SEQ ID NO 606
<211> LENGTH: 21
<212> TYPE: RNA
<213> ORGANISM: homo sapiens

<400> SEQUENCE: 606
aggcaagaug cuggcauagc u                                                21

<210> SEQ ID NO 607
<211> LENGTH: 22
<212> TYPE: RNA
<213> ORGANISM: homo sapiens

<400> SEQUENCE: 607
uauugcacau uacuaaguug ca                                               22

<210> SEQ ID NO 608
<211> LENGTH: 22
<212> TYPE: RNA
<213> ORGANISM: homo sapiens

<400> SEQUENCE: 608
aaaagcuggg uugagagggc ga                                               22

<210> SEQ ID NO 609
<211> LENGTH: 22
<212> TYPE: RNA
<213> ORGANISM: homo sapiens

<400> SEQUENCE: 609
aaaagcuggg uugagagggc aa                                               22

<210> SEQ ID NO 610
<211> LENGTH: 22
<212> TYPE: RNA
<213> ORGANISM: homo sapiens

<400> SEQUENCE: 610
aaaagcuggg uugagagggc aa                                               22
```

```
<210> SEQ ID NO 611
<211> LENGTH: 20
<212> TYPE: RNA
<213> ORGANISM: homo sapiens

<400> SEQUENCE: 611
aaaagcuggg uugagagggu                                              20

<210> SEQ ID NO 612
<211> LENGTH: 20
<212> TYPE: RNA
<213> ORGANISM: homo sapiens

<400> SEQUENCE: 612
aaaagcuggg uugagagggu                                              20

<210> SEQ ID NO 613
<211> LENGTH: 19
<212> TYPE: RNA
<213> ORGANISM: homo sapiens

<400> SEQUENCE: 613
aaaagcuggg uugagagga                                               19

<210> SEQ ID NO 614
<211> LENGTH: 19
<212> TYPE: RNA
<213> ORGANISM: homo sapiens

<400> SEQUENCE: 614
aaaagcuggg uugagagga                                               19

<210> SEQ ID NO 615
<211> LENGTH: 21
<212> TYPE: RNA
<213> ORGANISM: homo sapiens

<400> SEQUENCE: 615
cacauuacac ggucgaccuc u                                            21

<210> SEQ ID NO 616
<211> LENGTH: 23
<212> TYPE: RNA
<213> ORGANISM: homo sapiens

<400> SEQUENCE: 616
cgcauccccu agggcauugg ugu                                          23

<210> SEQ ID NO 617
<211> LENGTH: 22
<212> TYPE: RNA
<213> ORGANISM: homo sapiens

<400> SEQUENCE: 617
cuggcccucu cugcccuucc gu                                           22

<210> SEQ ID NO 618
<211> LENGTH: 23
<212> TYPE: RNA
<213> ORGANISM: homo sapiens

<400> SEQUENCE: 618
gcaaagcaca cggccugcag aga                                          23
```

```
<210> SEQ ID NO 619
<211> LENGTH: 21
<212> TYPE: RNA
<213> ORGANISM: homo sapiens

<400> SEQUENCE: 619
gccccugggc cuauccuaga a                                             21

<210> SEQ ID NO 620
<211> LENGTH: 23
<212> TYPE: RNA
<213> ORGANISM: homo sapiens

<400> SEQUENCE: 620
ucaagagcaa uaacgaaaaa ugu                                           23

<210> SEQ ID NO 621
<211> LENGTH: 22
<212> TYPE: RNA
<213> ORGANISM: homo sapiens

<400> SEQUENCE: 621
uccagcauca gugauuuugu ug                                            22

<210> SEQ ID NO 622
<211> LENGTH: 23
<212> TYPE: RNA
<213> ORGANISM: homo sapiens

<400> SEQUENCE: 622
ugagcgccuc gacgacagag ccg                                           23

<210> SEQ ID NO 623
<211> LENGTH: 21
<212> TYPE: RNA
<213> ORGANISM: homo sapiens

<400> SEQUENCE: 623
gugcauugua guugcauugc a                                             21

<210> SEQ ID NO 624
<211> LENGTH: 20
<212> TYPE: RNA
<213> ORGANISM: homo sapiens

<400> SEQUENCE: 624
gugcauugcu guugcauugc                                               20

<210> SEQ ID NO 625
<211> LENGTH: 22
<212> TYPE: RNA
<213> ORGANISM: homo sapiens

<400> SEQUENCE: 625
uuauaaagca augagacuga uu                                            22

<210> SEQ ID NO 626
<211> LENGTH: 21
<212> TYPE: RNA
<213> ORGANISM: homo sapiens

<400> SEQUENCE: 626
aggggugcua ucugugauug a                                             21
```

```
<210> SEQ ID NO 627
<211> LENGTH: 22
<212> TYPE: RNA
<213> ORGANISM: homo sapiens

<400> SEQUENCE: 627
gcugacuccu aguccagggc uc                                              22

<210> SEQ ID NO 628
<211> LENGTH: 22
<212> TYPE: RNA
<213> ORGANISM: homo sapiens

<400> SEQUENCE: 628
uggcaguguc uuagcugguu gu                                              22

<210> SEQ ID NO 629
<211> LENGTH: 23
<212> TYPE: RNA
<213> ORGANISM: homo sapiens

<400> SEQUENCE: 629
uaggcagugu cauuagcuga uug                                             23

<210> SEQ ID NO 630
<211> LENGTH: 23
<212> TYPE: RNA
<213> ORGANISM: homo sapiens

<400> SEQUENCE: 630
aggcagugua guuagcugau ugc                                             23

<210> SEQ ID NO 631
<211> LENGTH: 22
<212> TYPE: RNA
<213> ORGANISM: homo sapiens

<400> SEQUENCE: 631
uuaucagaau cuccaggggu ac                                              22

<210> SEQ ID NO 632
<211> LENGTH: 22
<212> TYPE: RNA
<213> ORGANISM: homo sapiens

<400> SEQUENCE: 632
aacacaccua uucaaggauu ca                                              22

<210> SEQ ID NO 633
<211> LENGTH: 22
<212> TYPE: RNA
<213> ORGANISM: homo sapiens

<400> SEQUENCE: 633
aauugcacgg uauccaucug ua                                              22

<210> SEQ ID NO 634
<211> LENGTH: 22
<212> TYPE: RNA
<213> ORGANISM: homo sapiens

<400> SEQUENCE: 634
```
uaaugccccu aaaaauccuu au                                22

<210> SEQ ID NO 635
<211> LENGTH: 21
<212> TYPE: RNA
<213> ORGANISM: homo sapiens

<400> SEQUENCE: 635
aauaauacau gguugaucuu u                                 21

<210> SEQ ID NO 636
<211> LENGTH: 22
<212> TYPE: RNA
<213> ORGANISM: homo sapiens

<400> SEQUENCE: 636
gccugcuggg guggaaccug gu                                22

<210> SEQ ID NO 637
<211> LENGTH: 20
<212> TYPE: RNA
<213> ORGANISM: homo sapiens

<400> SEQUENCE: 637
acucaaacug uggggcacu                                    20

<210> SEQ ID NO 638
<211> LENGTH: 22
<212> TYPE: RNA
<213> ORGANISM: homo sapiens

<400> SEQUENCE: 638
uuauaauaca accugauaag ug                                22

<210> SEQ ID NO 639
<211> LENGTH: 22
<212> TYPE: RNA
<213> ORGANISM: homo sapiens

<400> SEQUENCE: 639
auauaauaca accugcuaag ug                                22

<210> SEQ ID NO 640
<211> LENGTH: 22
<212> TYPE: RNA
<213> ORGANISM: homo sapiens

<400> SEQUENCE: 640
uuuguucguu cggcucgcgu ga                                22

<210> SEQ ID NO 641
<211> LENGTH: 22
<212> TYPE: RNA
<213> ORGANISM: homo sapiens

<400> SEQUENCE: 641
agagguugcc cuuggugaau uc                                22

<210> SEQ ID NO 642
<211> LENGTH: 21
<212> TYPE: RNA
<213> ORGANISM: homo sapiens

<400> SEQUENCE: 642

```
acuggacuug gagucagaag g                                         21

<210> SEQ ID NO 643
<211> LENGTH: 21
<212> TYPE: RNA
<213> ORGANISM: homo sapiens

<400> SEQUENCE: 643
ugguagacua uggaacguag g                                         21

<210> SEQ ID NO 644
<211> LENGTH: 22
<212> TYPE: RNA
<213> ORGANISM: homo sapiens

<400> SEQUENCE: 644
uauacaaggg caagcucucu gu                                        22

<210> SEQ ID NO 645
<211> LENGTH: 22
<212> TYPE: RNA
<213> ORGANISM: homo sapiens

<400> SEQUENCE: 645
gaaguuguuc gugguggauu cg                                        22

<210> SEQ ID NO 646
<211> LENGTH: 22
<212> TYPE: RNA
<213> ORGANISM: homo sapiens

<400> SEQUENCE: 646
agaucagaag gugauugugg cu                                        22

<210> SEQ ID NO 647
<211> LENGTH: 22
<212> TYPE: RNA
<213> ORGANISM: homo sapiens

<400> SEQUENCE: 647
gaauguugcu cggugaaccc cu                                        22

<210> SEQ ID NO 648
<211> LENGTH: 21
<212> TYPE: RNA
<213> ORGANISM: homo sapiens

<400> SEQUENCE: 648
aauauaacac agauggccug u                                         21

<210> SEQ ID NO 649
<211> LENGTH: 21
<212> TYPE: RNA
<213> ORGANISM: homo sapiens

<400> SEQUENCE: 649
uaguagaccg uauagcguac g                                         21

<210> SEQ ID NO 650
<211> LENGTH: 23
<212> TYPE: RNA
<213> ORGANISM: homo sapiens
```

```
<400> SEQUENCE: 650
aucaacagac auuaauuggg cgc                                               23

<210> SEQ ID NO 651
<211> LENGTH: 23
<212> TYPE: RNA
<213> ORGANISM: homo sapiens

<400> SEQUENCE: 651
ugaggggcag agagcgagac uuu                                               23

<210> SEQ ID NO 652
<211> LENGTH: 22
<212> TYPE: RNA
<213> ORGANISM: homo sapiens

<400> SEQUENCE: 652
cagcagcaau ucauguuuug aa                                                22

<210> SEQ ID NO 653
<211> LENGTH: 22
<212> TYPE: RNA
<213> ORGANISM: homo sapiens

<400> SEQUENCE: 653
uaauacuguc ugguaaaacc gu                                                22

<210> SEQ ID NO 654
<211> LENGTH: 23
<212> TYPE: RNA
<213> ORGANISM: homo sapiens

<400> SEQUENCE: 654
ucuuggagua ggucauuggg ugg                                               23

<210> SEQ ID NO 655
<211> LENGTH: 22
<212> TYPE: RNA
<213> ORGANISM: homo sapiens

<400> SEQUENCE: 655
aucaugaugg gcuccucggu gu                                                22

<210> SEQ ID NO 656
<211> LENGTH: 22
<212> TYPE: RNA
<213> ORGANISM: homo sapiens

<400> SEQUENCE: 656
uugcauaugu aggauguccc au                                                22

<210> SEQ ID NO 657
<211> LENGTH: 22
<212> TYPE: RNA
<213> ORGANISM: homo sapiens

<400> SEQUENCE: 657
uggcagugua uuguuagcug gu                                                22

<210> SEQ ID NO 658
<211> LENGTH: 22
<212> TYPE: RNA
<213> ORGANISM: homo sapiens
```

```
<400> SEQUENCE: 658
aggcagugua uuguuagcug gc                                        22

<210> SEQ ID NO 659
<211> LENGTH: 22
<212> TYPE: RNA
<213> ORGANISM: homo sapiens

<400> SEQUENCE: 659
uuuugcgaug uguuccuaau au                                        22

<210> SEQ ID NO 660
<211> LENGTH: 22
<212> TYPE: RNA
<213> ORGANISM: homo sapiens

<400> SEQUENCE: 660
uuuugcgaug uguuccuaau au                                        22

<210> SEQ ID NO 661
<211> LENGTH: 22
<212> TYPE: RNA
<213> ORGANISM: homo sapiens

<400> SEQUENCE: 661
uuuugcaaua uguuccugaa ua                                        22

<210> SEQ ID NO 662
<211> LENGTH: 22
<212> TYPE: RNA
<213> ORGANISM: homo sapiens

<400> SEQUENCE: 662
aacuguuugc agaggaaacu ga                                        22

<210> SEQ ID NO 663
<211> LENGTH: 23
<212> TYPE: RNA
<213> ORGANISM: homo sapiens

<400> SEQUENCE: 663
uagugcaaua uugcuuauag ggu                                       23

<210> SEQ ID NO 664
<211> LENGTH: 21
<212> TYPE: RNA
<213> ORGANISM: homo sapiens

<400> SEQUENCE: 664
gcaguccaug ggcauauaca c                                         21

<210> SEQ ID NO 665
<211> LENGTH: 22
<212> TYPE: RNA
<213> ORGANISM: homo sapiens

<400> SEQUENCE: 665
aagacgggag gaaagaaggg ag                                        22

<210> SEQ ID NO 666
<211> LENGTH: 22
<212> TYPE: RNA
```

```
<213> ORGANISM: homo sapiens

<400> SEQUENCE: 666
ucaggcucag uccccucccg au                                              22

<210> SEQ ID NO 667
<211> LENGTH: 22
<212> TYPE: RNA
<213> ORGANISM: homo sapiens

<400> SEQUENCE: 667
agaggcuggc cgugaugaau uc                                              22

<210> SEQ ID NO 668
<211> LENGTH: 22
<212> TYPE: RNA
<213> ORGANISM: homo sapiens

<400> SEQUENCE: 668
uccuguacug agcugccccg ag                                              22

<210> SEQ ID NO 669
<211> LENGTH: 22
<212> TYPE: RNA
<213> ORGANISM: homo sapiens

<400> SEQUENCE: 669
aaucguacag ggucauccac uu                                              22

<210> SEQ ID NO 670
<211> LENGTH: 21
<212> TYPE: RNA
<213> ORGANISM: homo sapiens

<400> SEQUENCE: 670
cccagauaau ggcacucuca a                                               21

<210> SEQ ID NO 671
<211> LENGTH: 22
<212> TYPE: RNA
<213> ORGANISM: homo sapiens

<400> SEQUENCE: 671
uuguacaugg uaggcuuuca uu                                              22

<210> SEQ ID NO 672
<211> LENGTH: 22
<212> TYPE: RNA
<213> ORGANISM: homo sapiens

<400> SEQUENCE: 672
ugaaacauac acgggaaacc uc                                              22

<210> SEQ ID NO 673
<211> LENGTH: 22
<212> TYPE: RNA
<213> ORGANISM: homo sapiens

<400> SEQUENCE: 673
aaacaaacau ggugcacuuc uu                                              22

<210> SEQ ID NO 674
<211> LENGTH: 21
```

-continued

```
<212> TYPE: RNA
<213> ORGANISM: homo sapiens

<400> SEQUENCE: 674
cagcagcaca cuggguuug u                                              21

<210> SEQ ID NO 675
<211> LENGTH: 21
<212> TYPE: RNA
<213> ORGANISM: homo sapiens

<400> SEQUENCE: 675
uuaagacuug cagugauguu u                                             21

<210> SEQ ID NO 676
<211> LENGTH: 22
<212> TYPE: RNA
<213> ORGANISM: homo sapiens

<400> SEQUENCE: 676
augcaccugg gcaaggauuc ug                                            22

<210> SEQ ID NO 677
<211> LENGTH: 22
<212> TYPE: RNA
<213> ORGANISM: homo sapiens

<400> SEQUENCE: 677
aaugcacccg ggcaaggauu cu                                            22

<210> SEQ ID NO 678
<211> LENGTH: 22
<212> TYPE: RNA
<213> ORGANISM: homo sapiens

<400> SEQUENCE: 678
aaugcaccug ggcaaggauu ca                                            22

<210> SEQ ID NO 679
<211> LENGTH: 23
<212> TYPE: RNA
<213> ORGANISM: homo sapiens

<400> SEQUENCE: 679
uagcagcggg aacaguucug cag                                           23

<210> SEQ ID NO 680
<211> LENGTH: 22
<212> TYPE: RNA
<213> ORGANISM: homo sapiens

<400> SEQUENCE: 680
agacccuggu cugcacucua uc                                            22

<210> SEQ ID NO 681
<211> LENGTH: 22
<212> TYPE: RNA
<213> ORGANISM: homo sapiens

<400> SEQUENCE: 681
gggagccagg aaguauugau gu                                            22

<210> SEQ ID NO 682
```

-continued

```
<211> LENGTH: 23
<212> TYPE: RNA
<213> ORGANISM: homo sapiens

<400> SEQUENCE: 682
ugauuguagc cuuuuggagu aga                                              23

<210> SEQ ID NO 683
<211> LENGTH: 22
<212> TYPE: RNA
<213> ORGANISM: homo sapiens

<400> SEQUENCE: 683
uacugcagac guggcaauca ug                                               22

<210> SEQ ID NO 684
<211> LENGTH: 18
<212> TYPE: RNA
<213> ORGANISM: homo sapiens

<400> SEQUENCE: 684
uucacaggga ggugucau                                                    18

<210> SEQ ID NO 685
<211> LENGTH: 18
<212> TYPE: RNA
<213> ORGANISM: homo sapiens

<400> SEQUENCE: 685
uucacaggga ggugucau                                                    18

<210> SEQ ID NO 686
<211> LENGTH: 22
<212> TYPE: RNA
<213> ORGANISM: homo sapiens

<400> SEQUENCE: 686
uucacaagga ggugucauuu au                                               22

<210> SEQ ID NO 687
<211> LENGTH: 22
<212> TYPE: RNA
<213> ORGANISM: homo sapiens

<400> SEQUENCE: 687
uucucaagga ggugucguuu au                                               22

<210> SEQ ID NO 688
<211> LENGTH: 22
<212> TYPE: RNA
<213> ORGANISM: homo sapiens

<400> SEQUENCE: 688
caugccuuga guguaggacc gu                                               22

<210> SEQ ID NO 689
<211> LENGTH: 22
<212> TYPE: RNA
<213> ORGANISM: homo sapiens

<400> SEQUENCE: 689
ugugacagau ugauaacuga aa                                               22
```

```
<210> SEQ ID NO 690
<211> LENGTH: 22
<212> TYPE: RNA
<213> ORGANISM: homo sapiens

<400> SEQUENCE: 690
aaacauucgc ggugcacuuc uu                                              22

<210> SEQ ID NO 691
<211> LENGTH: 22
<212> TYPE: RNA
<213> ORGANISM: homo sapiens

<400> SEQUENCE: 691
caaaacuggc aauuacuuuu gc                                              22

<210> SEQ ID NO 692
<211> LENGTH: 22
<212> TYPE: RNA
<213> ORGANISM: homo sapiens

<400> SEQUENCE: 692
caaaacuggc aauuacuuuu gc                                              22

<210> SEQ ID NO 693
<211> LENGTH: 22
<212> TYPE: RNA
<213> ORGANISM: homo sapiens

<400> SEQUENCE: 693
caaaacuggc aauuacuuuu gc                                              22

<210> SEQ ID NO 694
<211> LENGTH: 22
<212> TYPE: RNA
<213> ORGANISM: homo sapiens

<400> SEQUENCE: 694
caagaaccuc aguugcuuuu gu                                              22

<210> SEQ ID NO 695
<211> LENGTH: 22
<212> TYPE: RNA
<213> ORGANISM: homo sapiens

<400> SEQUENCE: 695
aaaaacugag acuacuuuug ca                                              22

<210> SEQ ID NO 696
<211> LENGTH: 22
<212> TYPE: RNA
<213> ORGANISM: homo sapiens

<400> SEQUENCE: 696
aaaaguaauc gcgguuuuug uc                                              22

<210> SEQ ID NO 697
<211> LENGTH: 22
<212> TYPE: RNA
<213> ORGANISM: homo sapiens

<400> SEQUENCE: 697
aaaaguaauc gcgguuuuug uc                                              22
```

```
<210> SEQ ID NO 698
<211> LENGTH: 22
<212> TYPE: RNA
<213> ORGANISM: homo sapiens

<400> SEQUENCE: 698
aaaaguaauc gcgguuuuug uc                                            22

<210> SEQ ID NO 699
<211> LENGTH: 22
<212> TYPE: RNA
<213> ORGANISM: homo sapiens

<400> SEQUENCE: 699
aaaaguaauc gcgguuuuug uc                                            22

<210> SEQ ID NO 700
<211> LENGTH: 22
<212> TYPE: RNA
<213> ORGANISM: homo sapiens

<400> SEQUENCE: 700
aaaaguaauu gcggucuuug gu                                            22

<210> SEQ ID NO 701
<211> LENGTH: 22
<212> TYPE: RNA
<213> ORGANISM: homo sapiens

<400> SEQUENCE: 701
aaaaguacuu gcggauuuug cu                                            22

<210> SEQ ID NO 702
<211> LENGTH: 22
<212> TYPE: RNA
<213> ORGANISM: homo sapiens

<400> SEQUENCE: 702
aaaaguauuu gcggguuuug uc                                            22

<210> SEQ ID NO 703
<211> LENGTH: 22
<212> TYPE: RNA
<213> ORGANISM: homo sapiens

<400> SEQUENCE: 703
caaaaguaau uguggauuuu gu                                            22

<210> SEQ ID NO 704
<211> LENGTH: 23
<212> TYPE: RNA
<213> ORGANISM: homo sapiens

<400> SEQUENCE: 704
agugccugag ggaguaagag ccc                                           23

<210> SEQ ID NO 705
<211> LENGTH: 23
<212> TYPE: RNA
<213> ORGANISM: homo sapiens

<400> SEQUENCE: 705
agugccugag ggaguaagag ccc                                           23
```

<210> SEQ ID NO 706
<211> LENGTH: 21
<212> TYPE: RNA
<213> ORGANISM: homo sapiens

<400> SEQUENCE: 706
gcgacccaua cuugguuuca g          21

<210> SEQ ID NO 707
<211> LENGTH: 22
<212> TYPE: RNA
<213> ORGANISM: homo sapiens

<400> SEQUENCE: 707
cacgcucaug cacacaccca ca         22

<210> SEQ ID NO 708
<211> LENGTH: 22
<212> TYPE: RNA
<213> ORGANISM: homo sapiens

<400> SEQUENCE: 708
aagaugugga aaaauuggaa uc         22

<210> SEQ ID NO 709
<211> LENGTH: 21
<212> TYPE: RNA
<213> ORGANISM: homo sapiens

<400> SEQUENCE: 709
uagauaaaau auugguaccu g          21

<210> SEQ ID NO 710
<211> LENGTH: 22
<212> TYPE: RNA
<213> ORGANISM: homo sapiens

<400> SEQUENCE: 710
uaacugguug aacaacugaa cc         22

<210> SEQ ID NO 711
<211> LENGTH: 23
<212> TYPE: RNA
<213> ORGANISM: homo sapiens

<400> SEQUENCE: 711
uuacaguugu ucaaccaguu acu        23

<210> SEQ ID NO 712
<211> LENGTH: 22
<212> TYPE: RNA
<213> ORGANISM: homo sapiens

<400> SEQUENCE: 712
uuaugguuug ccugggacug ag         22

<210> SEQ ID NO 713
<211> LENGTH: 22
<212> TYPE: RNA
<213> ORGANISM: homo sapiens

<400> SEQUENCE: 713

```
ugagaaccac gucugcucug ag                                           22

<210> SEQ ID NO 714
<211> LENGTH: 21
<212> TYPE: RNA
<213> ORGANISM: homo sapiens

<400> SEQUENCE: 714
uaauuuuaug uauaagcuag u                                            21

<210> SEQ ID NO 715
<211> LENGTH: 22
<212> TYPE: RNA
<213> ORGANISM: homo sapiens

<400> SEQUENCE: 715
uacgucaucg uugucaucgu ca                                           22

<210> SEQ ID NO 716
<211> LENGTH: 22
<212> TYPE: RNA
<213> ORGANISM: homo sapiens

<400> SEQUENCE: 716
uccgagccug ggucucccuc uu                                           22

<210> SEQ ID NO 717
<211> LENGTH: 22
<212> TYPE: RNA
<213> ORGANISM: homo sapiens

<400> SEQUENCE: 717
agucauugga ggguuugagc ag                                           22

<210> SEQ ID NO 718
<211> LENGTH: 23
<212> TYPE: RNA
<213> ORGANISM: homo sapiens

<400> SEQUENCE: 718
aaacucuacu uguccuucug agu                                          23

<210> SEQ ID NO 719
<211> LENGTH: 21
<212> TYPE: RNA
<213> ORGANISM: homo sapiens

<400> SEQUENCE: 719 aggggggaaag uucuauaguc c                                           21

<210> SEQ ID NO 720
<211> LENGTH: 22
<212> TYPE: RNA
<213> ORGANISM: homo sapiens

<400> SEQUENCE: 720
augcugacau auuuacuaga gg                                           22

<210> SEQ ID NO 721
<211> LENGTH: 21
<212> TYPE: RNA
<213> ORGANISM: homo sapiens

<400> SEQUENCE: 721
```
ugggutuacg uugggagaac u                                        21

<210> SEQ ID NO 722
<211> LENGTH: 24
<212> TYPE: RNA
<213> ORGANISM: homo sapiens

<400> SEQUENCE: 722
aaagacauag gauagaguca ccuc                                     24

<210> SEQ ID NO 723
<211> LENGTH: 22
<212> TYPE: RNA
<213> ORGANISM: homo sapiens

<400> SEQUENCE: 723
acuuguaugc uagcucaggu ag                                       22

<210> SEQ ID NO 724
<211> LENGTH: 22
<212> TYPE: RNA
<213> ORGANISM: homo sapiens

<400> SEQUENCE: 724
uuuaggauaa gcuugacuuu ug                                       22

<210> SEQ ID NO 725
<211> LENGTH: 21
<212> TYPE: RNA
<213> ORGANISM: homo sapiens

<400> SEQUENCE: 725
aauggcgcca cuagggggu g                                         21

<210> SEQ ID NO 726
<211> LENGTH: 22
<212> TYPE: RNA
<213> ORGANISM: homo sapiens

<400> SEQUENCE: 726
uaugucugcu gaccaucacc uu                                       22

<210> SEQ ID NO 727
<211> LENGTH: 22
<212> TYPE: RNA
<213> ORGANISM: homo sapiens

<400> SEQUENCE: 727
uacccauugc auaucggagu ug                                       22

<210> SEQ ID NO 728
<211> LENGTH: 21
<212> TYPE: RNA
<213> ORGANISM: homo sapiens

<400> SEQUENCE: 728
uccgguucuc agggcuccac c                                        21

<210> SEQ ID NO 729
<211> LENGTH: 23
<212> TYPE: RNA
<213> ORGANISM: homo sapiens

```
<400> SEQUENCE: 729
aaggagcuua caaucuagcu ggg                                          23

<210> SEQ ID NO 730
<211> LENGTH: 23
<212> TYPE: RNA
<213> ORGANISM: homo sapiens

<400> SEQUENCE: 730
uggaagacua gugauuugu ugu                                           23

<210> SEQ ID NO 731
<211> LENGTH: 23
<212> TYPE: RNA
<213> ORGANISM: homo sapiens

<400> SEQUENCE: 731
uggaagacua gugauuugu ugu                                           23

<210> SEQ ID NO 732
<211> LENGTH: 23
<212> TYPE: RNA
<213> ORGANISM: homo sapiens

<400> SEQUENCE: 732
uggaagacua gugauuugu ugu                                           23

<210> SEQ ID NO 733
<211> LENGTH: 20
<212> TYPE: RNA
<213> ORGANISM: homo sapiens

<400> SEQUENCE: 733
cggcucuggg ucuguggga                                               20

<210> SEQ ID NO 734
<211> LENGTH: 23
<212> TYPE: RNA
<213> ORGANISM: homo sapiens

<400> SEQUENCE: 734
ugcaccaugg uugucugagc aug                                          23

<210> SEQ ID NO 735
<211> LENGTH: 22
<212> TYPE: RNA
<213> ORGANISM: homo sapiens

<400> SEQUENCE: 735
ugagaccucu ggguucugag cu                                           22

<210> SEQ ID NO 736
<211> LENGTH: 21
<212> TYPE: RNA
<213> ORGANISM: homo sapiens

<400> SEQUENCE: 736
gcaggaacuu gugagucucc u                                            21

<210> SEQ ID NO 737
<211> LENGTH: 22
<212> TYPE: RNA
<213> ORGANISM: homo sapiens
```

-continued

```
<400> SEQUENCE: 737
cugcccuggc ccgagggacc ga                                              22

<210> SEQ ID NO 738
<211> LENGTH: 20
<212> TYPE: RNA
<213> ORGANISM: homo sapiens

<400> SEQUENCE: 738
guagaggaga uggcgcaggg                                                 20

<210> SEQ ID NO 739
<211> LENGTH: 22
<212> TYPE: RNA
<213> ORGANISM: homo sapiens

<400> SEQUENCE: 739
gugaacgggc gccaucccga gg                                              22

<210> SEQ ID NO 740
<211> LENGTH: 21
<212> TYPE: RNA
<213> ORGANISM: homo sapiens

<400> SEQUENCE: 740
uuaauaucgg acaaccauug u                                               21

<210> SEQ ID NO 741
<211> LENGTH: 22
<212> TYPE: RNA
<213> ORGANISM: homo sapiens

<400> SEQUENCE: 741
ugcaacgaac cugagccacu ga                                              22

<210> SEQ ID NO 742
<211> LENGTH: 21
<212> TYPE: RNA
<213> ORGANISM: homo sapiens

<400> SEQUENCE: 742
cacugugucc uuucugcgua g                                               21

<210> SEQ ID NO 743
<211> LENGTH: 23
<212> TYPE: RNA
<213> ORGANISM: homo sapiens

<400> SEQUENCE: 743
ucuuugguua ucuagcugua uga                                             23

<210> SEQ ID NO 744
<211> LENGTH: 23
<212> TYPE: RNA
<213> ORGANISM: homo sapiens

<400> SEQUENCE: 744
ucuuugguua ucuagcugua uga                                             23

<210> SEQ ID NO 745
<211> LENGTH: 22
<212> TYPE: RNA
```

<213> ORGANISM: homo sapiens

<400> SEQUENCE: 745
uauugcacuu gucccggccu gu                                        22

<210> SEQ ID NO 746
<211> LENGTH: 22
<212> TYPE: RNA
<213> ORGANISM: homo sapiens

<400> SEQUENCE: 746
uauugcacuu gucccggccu gu                                        22

<210> SEQ ID NO 747
<211> LENGTH: 22
<212> TYPE: RNA
<213> ORGANISM: homo sapiens

<400> SEQUENCE: 747
uauugcacuc gucccggccu cc                                        22

<210> SEQ ID NO 748
<211> LENGTH: 23
<212> TYPE: RNA
<213> ORGANISM: homo sapiens

<400> SEQUENCE: 748
caaagugcug uucgugcagg uag                                       23

<210> SEQ ID NO 749
<211> LENGTH: 23
<212> TYPE: RNA
<213> ORGANISM: homo sapiens

<400> SEQUENCE: 749
ucuuugguua ucuagcugua uga                                       23

<210> SEQ ID NO 750
<211> LENGTH: 21
<212> TYPE: RNA
<213> ORGANISM: homo sapiens

<400> SEQUENCE: 750
aaggcagggc ccccgcuccc c                                         21

<210> SEQ ID NO 751
<211> LENGTH: 22
<212> TYPE: RNA
<213> ORGANISM: homo sapiens

<400> SEQUENCE: 751
ucuucucugu uuuggccaug ug                                        22

<210> SEQ ID NO 752
<211> LENGTH: 22
<212> TYPE: RNA
<213> ORGANISM: homo sapiens

<400> SEQUENCE: 752
aaauuauugu acaucggaug ag                                        22

<210> SEQ ID NO 753
<211> LENGTH: 22

```
<212> TYPE: RNA
<213> ORGANISM: homo sapiens

<400> SEQUENCE: 753
uucaacgggu auuuauugag ca                                        22

<210> SEQ ID NO 754
<211> LENGTH: 23
<212> TYPE: RNA
<213> ORGANISM: homo sapiens

<400> SEQUENCE: 754
uuuggcacua gcacauuuuu gcu                                       23

<210> SEQ ID NO 755
<211> LENGTH: 22
<212> TYPE: RNA
<213> ORGANISM: homo sapiens

<400> SEQUENCE: 755
ugagguagua aguuguauug uu                                        22

<210> SEQ ID NO 756
<211> LENGTH: 22
<212> TYPE: RNA
<213> ORGANISM: homo sapiens

<400> SEQUENCE: 756
aacccguaga uccgaucuug ug                                        22

<210> SEQ ID NO 757
<211> LENGTH: 22
<212> TYPE: RNA
<213> ORGANISM: homo sapiens

<400> SEQUENCE: 757
cacccguaga accgaccuug cg                                        22

<210> SEQ ID NO 758
<211> LENGTH: 21
<212> TYPE: RNA
<213> ORGANISM: homo sapiens

<400> SEQUENCE: 758
aacauagagg aaauuccacg u                                         21

<210> SEQ ID NO 759
<211> LENGTH: 22
<212> TYPE: RNA
<213> ORGANISM: homo sapiens

<400> SEQUENCE: 759
aucauagagg aaaauccaug uu                                        22

<210> SEQ ID NO 760
<211> LENGTH: 22
<212> TYPE: RNA
<213> ORGANISM: homo sapiens

<400> SEQUENCE: 760 ugugggccg cagaacaugu gc                                         22

<210> SEQ ID NO 761
```

```
<211> LENGTH: 21
<212> TYPE: RNA
<213> ORGANISM: homo sapiens

<400> SEQUENCE: 761
aucauagagg aaaauccacg u                                              21

<210> SEQ ID NO 762
<211> LENGTH: 21
<212> TYPE: RNA
<213> ORGANISM: homo sapiens

<400> SEQUENCE: 762
aucauagagg aaaauccacg u                                              21

<210> SEQ ID NO 763
<211> LENGTH: 21
<212> TYPE: RNA
<213> ORGANISM: homo sapiens

<400> SEQUENCE: 763
ccaaaacugc aguuacuuuu g                                              21

<210> SEQ ID NO 764
<211> LENGTH: 22
<212> TYPE: RNA
<213> ORGANISM: homo sapiens

<400> SEQUENCE: 764
gagccuggaa gcuggagccu gc                                             22

<210> SEQ ID NO 765
<211> LENGTH: 20
<212> TYPE: RNA
<213> ORGANISM: homo sapiens

<400> SEQUENCE: 765
cgggcguggu gguggggugug                                               20

<210> SEQ ID NO 766
<211> LENGTH: 21
<212> TYPE: RNA
<213> ORGANISM: homo sapiens

<400> SEQUENCE: 766
ucgaggagcu cacagucuag a                                              21

<210> SEQ ID NO 767
<211> LENGTH: 21
<212> TYPE: RNA
<213> ORGANISM: homo sapiens

<400> SEQUENCE: 767
uaaggugcau cuagugcagu u                                              21

<210> SEQ ID NO 768
<211> LENGTH: 17
<212> TYPE: RNA
<213> ORGANISM: homo sapiens

<400> SEQUENCE: 768
gaggguuggg uggaggc                                                   17
```

```
<210> SEQ ID NO 769
<211> LENGTH: 22
<212> TYPE: RNA
<213> ORGANISM: homo sapiens

<400> SEQUENCE: 769
aucauagagg aaaauccaug uu                                              22

<210> SEQ ID NO 770
<211> LENGTH: 21
<212> TYPE: RNA
<213> ORGANISM: homo sapiens

<400> SEQUENCE: 770
aacauagagg aaauuccacg u                                               21

<210> SEQ ID NO 771
<211> LENGTH: 20
<212> TYPE: RNA
<213> ORGANISM: homo sapiens

<400> SEQUENCE: 771
acuggacuug gagucagaaa                                                 20

<210> SEQ ID NO 772
<211> LENGTH: 20
<212> TYPE: RNA
<213> ORGANISM: homo sapiens

<400> SEQUENCE: 772
acuggacuug gagucagaaa                                                 20

<210> SEQ ID NO 773
<211> LENGTH: 19
<212> TYPE: RNA
<213> ORGANISM: homo sapiens

<400> SEQUENCE: 773
acuggacuug gagucagga                                                  19

<210> SEQ ID NO 774
<211> LENGTH: 22
<212> TYPE: RNA
<213> ORGANISM: homo sapiens

<400> SEQUENCE: 774
aggcagugua uugcuagcgg cu                                              22

<210> SEQ ID NO 775
<211> LENGTH: 22
<212> TYPE: RNA
<213> ORGANISM: homo sapiens

<400> SEQUENCE: 775
ugcacccagg caaggauucu gc                                              22

<210> SEQ ID NO 776
<211> LENGTH: 22
<212> TYPE: RNA
<213> ORGANISM: homo sapiens

<400> SEQUENCE: 776
uaauccuugc uaccugggug ag                                              22
```

```
<210> SEQ ID NO 777
<211> LENGTH: 22
<212> TYPE: RNA
<213> ORGANISM: homo sapiens

<400> SEQUENCE: 777
aaaaguaauc gcgguuuuug uc                                               22

<210> SEQ ID NO 778
<211> LENGTH: 22
<212> TYPE: RNA
<213> ORGANISM: homo sapiens

<400> SEQUENCE: 778
aaaaguaauu guggauuuug cu                                               22

<210> SEQ ID NO 779
<211> LENGTH: 22
<212> TYPE: RNA
<213> ORGANISM: homo sapiens

<400> SEQUENCE: 779
aaaaguaauu guggauuuug cu                                               22

<210> SEQ ID NO 780
<211> LENGTH: 22
<212> TYPE: RNA
<213> ORGANISM: homo sapiens

<400> SEQUENCE: 780
ugucuuacuc ccucaggcac au                                               22

<210> SEQ ID NO 781
<211> LENGTH: 18
<212> TYPE: RNA
<213> ORGANISM: homo sapiens

<400> SEQUENCE: 781
ggugggcuuc ccggaggg                                                    18

<210> SEQ ID NO 782
<211> LENGTH: 18
<212> TYPE: RNA
<213> ORGANISM: homo sapiens

<400> SEQUENCE: 782
gaagcggugg cugggcug                                                    18

<210> SEQ ID NO 783
<211> LENGTH: 18
<212> TYPE: RNA
<213> ORGANISM: homo sapiens

<400> SEQUENCE: 783
cacugcagga cucagcag                                                    18

<210> SEQ ID NO 784
<211> LENGTH: 17
<212> TYPE: RNA
<213> ORGANISM: homo sapiens

<400> SEQUENCE: 784
ugagggagga gacugca                                                     17
```

```
<210> SEQ ID NO 785
<211> LENGTH: 20
<212> TYPE: RNA
<213> ORGANISM: homo sapiens

<400> SEQUENCE: 785
acuggacuug gagccagaag                                                   20

<210> SEQ ID NO 786
<211> LENGTH: 22
<212> TYPE: RNA
<213> ORGANISM: homo sapiens

<400> SEQUENCE: 786
gucacugaug ucuguagcug ag                                                22

<210> SEQ ID NO 787
<211> LENGTH: 22
<212> TYPE: RNA
<213> ORGANISM: homo sapiens

<400> SEQUENCE: 787
gaugaggaug gauagcaagg aa                                                22

<210> SEQ ID NO 788
<211> LENGTH: 22
<212> TYPE: RNA
<213> ORGANISM: homo sapiens

<400> SEQUENCE: 788
accugucugu ggaaaggagc ua                                                22

<210> SEQ ID NO 789
<211> LENGTH: 21
<212> TYPE: RNA
<213> ORGANISM: homo sapiens

<400> SEQUENCE: 789
aaaagcauca ggaaguaccc a                                                 21

<210> SEQ ID NO 790
<211> LENGTH: 22
<212> TYPE: RNA
<213> ORGANISM: homo sapiens

<400> SEQUENCE: 790
ugccuggaac auaguaggga cu                                                22

<210> SEQ ID NO 791
<211> LENGTH: 22
<212> TYPE: RNA
<213> ORGANISM: homo sapiens

<400> SEQUENCE: 791
ugccuggaac auaguaggga cu                                                22

<210> SEQ ID NO 792
<211> LENGTH: 20
<212> TYPE: RNA
<213> ORGANISM: homo sapiens

<400> SEQUENCE: 792
```
uggauuaaaa acaauggagg                                              20

<210> SEQ ID NO 793
<211> LENGTH: 21
<212> TYPE: RNA
<213> ORGANISM: homo sapiens

<400> SEQUENCE: 793
auaggcacca aaaagcaaca a                                            21

<210> SEQ ID NO 794
<211> LENGTH: 20
<212> TYPE: RNA
<213> ORGANISM: homo sapiens

<400> SEQUENCE: 794
acugggcuug gagucagaag                                              20

<210> SEQ ID NO 795
<211> LENGTH: 22
<212> TYPE: RNA
<213> ORGANISM: homo sapiens

<400> SEQUENCE: 795
caaaaaccgg caauuacuuu ug                                           22

<210> SEQ ID NO 796
<211> LENGTH: 22
<212> TYPE: RNA
<213> ORGANISM: homo sapiens

<400> SEQUENCE: 796
gucaaaugaa gggcugauca cg                                           22

<210> SEQ ID NO 797
<211> LENGTH: 27
<212> TYPE: RNA
<213> ORGANISM: homo sapiens

<400> SEQUENCE: 797
aaagggagga uuugcuuaga aggaugg                                      27

<210> SEQ ID NO 798
<211> LENGTH: 22
<212> TYPE: RNA
<213> ORGANISM: homo sapiens

<400> SEQUENCE: 798
agaguuaacu caaaauggac ua                                           22

<210> SEQ ID NO 799
<211> LENGTH: 22
<212> TYPE: RNA
<213> ORGANISM: homo sapiens

<400> SEQUENCE: 799
uguugggauu cagcaggacc au                                           22

<210> SEQ ID NO 800
<211> LENGTH: 22
<212> TYPE: RNA
<213> ORGANISM: homo sapiens

<400> SEQUENCE: 800
uaaauagagu aggcaaagga ca                                         22

<210> SEQ ID NO 801
<211> LENGTH: 22
<212> TYPE: RNA
<213> ORGANISM: homo sapiens

<400> SEQUENCE: 801
agagucgaga gugggagaag ag                                         22

<210> SEQ ID NO 802
<211> LENGTH: 17
<212> TYPE: RNA
<213> ORGANISM: homo sapiens

<400> SEQUENCE: 802
gaagauggac guacuuu                                               17

<210> SEQ ID NO 803
<211> LENGTH: 21
<212> TYPE: RNA
<213> ORGANISM: homo sapiens

<400> SEQUENCE: 803
ucugaauaga gucugaagag u                                          21

<210> SEQ ID NO 804
<211> LENGTH: 22
<212> TYPE: RNA
<213> ORGANISM: homo sapiens

<400> SEQUENCE: 804
caaggagacg ggaacaugga gc                                         22

<210> SEQ ID NO 805
<211> LENGTH: 22
<212> TYPE: RNA
<213> ORGANISM: homo sapiens

<400> SEQUENCE: 805
aagaggaaga aauggcuggu uc                                         22

<210> SEQ ID NO 806
<211> LENGTH: 21
<212> TYPE: RNA
<213> ORGANISM: homo sapiens

<400> SEQUENCE: 806
uucgcgggcg aaggcaaagu c                                          21

<210> SEQ ID NO 807
<211> LENGTH: 20
<212> TYPE: RNA
<213> ORGANISM: homo sapiens

<400> SEQUENCE: 807
aaaagcuggg cugagaggcg                                            20

<210> SEQ ID NO 808
<211> LENGTH: 22
<212> TYPE: RNA
<213> ORGANISM: homo sapiens

```
<400> SEQUENCE: 808
auggccaaaa cugcaguuau uu                                              22

<210> SEQ ID NO 809
<211> LENGTH: 22
<212> TYPE: RNA
<213> ORGANISM: homo sapiens

<400> SEQUENCE: 809
uaguggauga ugcacucugu gc                                              22

<210> SEQ ID NO 810
<211> LENGTH: 18
<212> TYPE: RNA
<213> ORGANISM: homo sapiens

<400> SEQUENCE: 810
aggcuggagu gagcggag                                                   18

<210> SEQ ID NO 811
<211> LENGTH: 22
<212> TYPE: RNA
<213> ORGANISM: homo sapiens

<400> SEQUENCE: 811
gaaaacgaca augacuuuug ca                                              22

<210> SEQ ID NO 812
<211> LENGTH: 22
<212> TYPE: RNA
<213> ORGANISM: homo sapiens

<400> SEQUENCE: 812
gcgacucuga aaacuagaag gu                                              22

<210> SEQ ID NO 813
<211> LENGTH: 21
<212> TYPE: RNA
<213> ORGANISM: homo sapiens

<400> SEQUENCE: 813
agaaggcugg agcgcggcgg u                                               21

<210> SEQ ID NO 814
<211> LENGTH: 20
<212> TYPE: RNA
<213> ORGANISM: homo sapiens

<400> SEQUENCE: 814
aaagacucug caagaugccu                                                 20

<210> SEQ ID NO 815
<211> LENGTH: 21
<212> TYPE: RNA
<213> ORGANISM: homo sapiens

<400> SEQUENCE: 815
acaggagugg gggugggaca u                                               21

<210> SEQ ID NO 816
<211> LENGTH: 18
<212> TYPE: RNA
<213> ORGANISM: homo sapiens
```

```
<400> SEQUENCE: 816
aggagaagua aaguagaa                                                18

<210> SEQ ID NO 817
<211> LENGTH: 22
<212> TYPE: RNA
<213> ORGANISM: homo sapiens

<400> SEQUENCE: 817
auggccagag cucacacaga gg                                           22

<210> SEQ ID NO 818
<211> LENGTH: 21
<212> TYPE: RNA
<213> ORGANISM: homo sapiens

<400> SEQUENCE: 818
gcaggacagg cagaagugga u                                            21

<210> SEQ ID NO 819
<211> LENGTH: 22
<212> TYPE: RNA
<213> ORGANISM: homo sapiens

<400> SEQUENCE: 819
aucagggcuu guggaauggg aa                                           22

<210> SEQ ID NO 820
<211> LENGTH: 22
<212> TYPE: RNA
<213> ORGANISM: homo sapiens

<400> SEQUENCE: 820
auggccagag cucacacaga gg                                           22

<210> SEQ ID NO 821
<211> LENGTH: 22
<212> TYPE: RNA
<213> ORGANISM: homo sapiens

<400> SEQUENCE: 821
ugaggauaug gcagggaagg gg                                           22

<210> SEQ ID NO 822
<211> LENGTH: 18
<212> TYPE: RNA
<213> ORGANISM: homo sapiens

<400> SEQUENCE: 822
aggagguugg uguggauu                                                18

<210> SEQ ID NO 823
<211> LENGTH: 22
<212> TYPE: RNA
<213> ORGANISM: homo sapiens

<400> SEQUENCE: 823
uuggaagaca uggagcauga gg                                           22

<210> SEQ ID NO 824
<211> LENGTH: 22
<212> TYPE: RNA
```

```
<213> ORGANISM: homo sapiens

<400> SEQUENCE: 824
ucuggcaagu aaaaaacucu ca                                    22

<210> SEQ ID NO 825
<211> LENGTH: 21
<212> TYPE: RNA
<213> ORGANISM: homo sapiens

<400> SEQUENCE: 825
ugggcucagg guacaaaggu u                                     21

<210> SEQ ID NO 826
<211> LENGTH: 21
<212> TYPE: RNA
<213> ORGANISM: homo sapiens

<400> SEQUENCE: 826
caaaaacugc aauuacuuuc a                                     21

<210> SEQ ID NO 827
<211> LENGTH: 21
<212> TYPE: RNA
<213> ORGANISM: homo sapiens

<400> SEQUENCE: 827
caaaaacugc aauuacuuuc a                                     21

<210> SEQ ID NO 828
<211> LENGTH: 21
<212> TYPE: RNA
<213> ORGANISM: homo sapiens

<400> SEQUENCE: 828
gcugcaccgg agacugggua a                                     21

<210> SEQ ID NO 829
<211> LENGTH: 21
<212> TYPE: RNA
<213> ORGANISM: homo sapiens

<400> SEQUENCE: 829
gcugcaccgg agacugggua a                                     21

<210> SEQ ID NO 830
<211> LENGTH: 22
<212> TYPE: RNA
<213> ORGANISM: homo sapiens

<400> SEQUENCE: 830
auccccagau acaauggaca au                                    22

<210> SEQ ID NO 831
<211> LENGTH: 22
<212> TYPE: RNA
<213> ORGANISM: homo sapiens

<400> SEQUENCE: 831
auugaccuug cuguuuggag au                                    22

<210> SEQ ID NO 832
<211> LENGTH: 21
```

```
-continued

<212> TYPE: RNA
<213> ORGANISM: homo sapiens

<400> SEQUENCE: 832
cacaggcuua gaaaagacag u                                              21

<210> SEQ ID NO 833
<211> LENGTH: 22
<212> TYPE: RNA
<213> ORGANISM: homo sapiens

<400> SEQUENCE: 833
ucgaggacug guggaagggc cu                                             22

<210> SEQ ID NO 834
<211> LENGTH: 22
<212> TYPE: RNA
<213> ORGANISM: homo sapiens

<400> SEQUENCE: 834
gugacugaua ccuuggaggc au                                             22

<210> SEQ ID NO 835
<211> LENGTH: 22
<212> TYPE: RNA
<213> ORGANISM: homo sapiens

<400> SEQUENCE: 835
agggcuggac ucagcggcgg ag                                             22

<210> SEQ ID NO 836
<211> LENGTH: 22
<212> TYPE: RNA
<213> ORGANISM: homo sapiens

<400> SEQUENCE: 836
ugucgugggg cuugcuggcu ug                                             22

<210> SEQ ID NO 837
<211> LENGTH: 17
<212> TYPE: RNA
<213> ORGANISM: homo sapiens

<400> SEQUENCE: 837
acagggagga gauugua                                                   17

<210> SEQ ID NO 838
<211> LENGTH: 19
<212> TYPE: RNA
<213> ORGANISM: homo sapiens

<400> SEQUENCE: 838
acuggacuug gaggcagaa                                                 19

<210> SEQ ID NO 839
<211> LENGTH: 17
<212> TYPE: RNA
<213> ORGANISM: homo sapiens

<400> SEQUENCE: 839
gccggacaag agggagg                                                   17

<210> SEQ ID NO 840
```

-continued

```
<211> LENGTH: 22
<212> TYPE: RNA
<213> ORGANISM: homo sapiens

<400> SEQUENCE: 840
auacacauac acgcaacaca ca                                              22

<210> SEQ ID NO 841
<211> LENGTH: 17
<212> TYPE: RNA
<213> ORGANISM: homo sapiens

<400> SEQUENCE: 841
uuggaggcgu ggguuuu                                                    17

<210> SEQ ID NO 842
<211> LENGTH: 22
<212> TYPE: RNA
<213> ORGANISM: homo sapiens

<400> SEQUENCE: 842
aauucccuug uagauaaccc gg                                              22

<210> SEQ ID NO 843
<211> LENGTH: 22
<212> TYPE: RNA
<213> ORGANISM: homo sapiens

<400> SEQUENCE: 843
aagacuggag acaaaguggg ag                                              22

<210> SEQ ID NO 844
<211> LENGTH: 22
<212> TYPE: RNA
<213> ORGANISM: homo sapiens

<400> SEQUENCE: 844
cugacugaau agguaggguc au                                              22

<210> SEQ ID NO 845
<211> LENGTH: 18
<212> TYPE: RNA
<213> ORGANISM: homo sapiens

<400> SEQUENCE: 845
cucgaguugg aagaggcg                                                   18

<210> SEQ ID NO 846
<211> LENGTH: 22
<212> TYPE: RNA
<213> ORGANISM: homo sapiens

<400> SEQUENCE: 846
agauuguuuc uuuugccgug ca                                              22

<210> SEQ ID NO 847
<211> LENGTH: 21
<212> TYPE: RNA
<213> ORGANISM: homo sapiens

<400> SEQUENCE: 847
cacggcaaaa gaaacaaucc a                                               21
```

```
<210> SEQ ID NO 848
<211> LENGTH: 22
<212> TYPE: RNA
<213> ORGANISM: homo sapiens

<400> SEQUENCE: 848
cagggcuggc agugacaugg gu                                              22

<210> SEQ ID NO 849
<211> LENGTH: 17
<212> TYPE: RNA
<213> ORGANISM: homo sapiens

<400> SEQUENCE: 849 gguggggcu guuguuu                                                     17

<210> SEQ ID NO 850
<211> LENGTH: 22
<212> TYPE: RNA
<213> ORGANISM: homo sapiens

<400> SEQUENCE: 850 ugggaggug uggagucagc au                                               22

<210> SEQ ID NO 851
<211> LENGTH: 21
<212> TYPE: RNA
<213> ORGANISM: homo sapiens

<400> SEQUENCE: 851
gcagagaaca aaggacucag u                                               21

<210> SEQ ID NO 852
<211> LENGTH: 20
<212> TYPE: RNA
<213> ORGANISM: homo sapiens

<400> SEQUENCE: 852
ggcuccuugg ucuagggua                                                  20

<210> SEQ ID NO 853
<211> LENGTH: 22
<212> TYPE: RNA
<213> ORGANISM: homo sapiens

<400> SEQUENCE: 853
cgucccgggg cugcgcgagg ca                                              22

<210> SEQ ID NO 854
<211> LENGTH: 21
<212> TYPE: RNA
<213> ORGANISM: homo sapiens

<400> SEQUENCE: 854
aaagguaauu gugguuucug c                                               21

<210> SEQ ID NO 855
<211> LENGTH: 21
<212> TYPE: RNA
<213> ORGANISM: homo sapiens

<400> SEQUENCE: 855
aaagguaauu gugguuucug c                                               21
```

```
<210> SEQ ID NO 856
<211> LENGTH: 22
<212> TYPE: RNA
<213> ORGANISM: homo sapiens

<400> SEQUENCE: 856 ugggauuug gagaaguggu ga                                              22

<210> SEQ ID NO 857
<211> LENGTH: 20
<212> TYPE: RNA
<213> ORGANISM: homo sapiens

<400> SEQUENCE: 857
aaaagugauu gcaguguuug                                                20

<210> SEQ ID NO 858
<211> LENGTH: 17
<212> TYPE: RNA
<213> ORGANISM: homo sapiens

<400> SEQUENCE: 858
ugguagagcu gaggaca                                                   17

<210> SEQ ID NO 859
<211> LENGTH: 23
<212> TYPE: RNA
<213> ORGANISM: homo sapiens

<400> SEQUENCE: 859
uugaauucuu ggccuuaagu gau                                            23

<210> SEQ ID NO 860
<211> LENGTH: 22
<212> TYPE: RNA
<213> ORGANISM: homo sapiens

<400> SEQUENCE: 860
uaggagcuca acagaugccu gu                                             22

<210> SEQ ID NO 861
<211> LENGTH: 21
<212> TYPE: RNA
<213> ORGANISM: homo sapiens

<400> SEQUENCE: 861
agcuuuuggg aauucaggua g                                              21

<210> SEQ ID NO 862
<211> LENGTH: 20
<212> TYPE: RNA
<213> ORGANISM: homo sapiens

<400> SEQUENCE: 862
gagcuugguc uguagcgguu                                                20

<210> SEQ ID NO 863
<211> LENGTH: 20
<212> TYPE: RNA
<213> ORGANISM: homo sapiens

<400> SEQUENCE: 863
ggauccgagu cacggcacca                                                20
```

```
<210> SEQ ID NO 864
<211> LENGTH: 21
<212> TYPE: RNA
<213> ORGANISM: homo sapiens

<400> SEQUENCE: 864
caaaagugau cgugguuuuu g                                              21

<210> SEQ ID NO 865
<211> LENGTH: 17
<212> TYPE: RNA
<213> ORGANISM: homo sapiens

<400> SEQUENCE: 865
agggugugug uguuuuu                                                   17

<210> SEQ ID NO 866
<211> LENGTH: 17
<212> TYPE: RNA
<213> ORGANISM: homo sapiens

<400> SEQUENCE: 866
ccugguggcu uccuuuu                                                   17

<210> SEQ ID NO 867
<211> LENGTH: 22
<212> TYPE: RNA
<213> ORGANISM: homo sapiens

<400> SEQUENCE: 867
ucacaaggua uugacuggcg ua                                             22

<210> SEQ ID NO 868
<211> LENGTH: 19
<212> TYPE: RNA
<213> ORGANISM: homo sapiens

<400> SEQUENCE: 868
agagguaggu guggaagaa                                                 19

<210> SEQ ID NO 869
<211> LENGTH: 22
<212> TYPE: RNA
<213> ORGANISM: homo sapiens

<400> SEQUENCE: 869
ccaggaggcg gaggaggugg ag                                             22

<210> SEQ ID NO 870
<211> LENGTH: 21
<212> TYPE: RNA
<213> ORGANISM: homo sapiens

<400> SEQUENCE: 870
guggaggacu gagaagguga g                                              21

<210> SEQ ID NO 871
<211> LENGTH: 21
<212> TYPE: RNA
<213> ORGANISM: homo sapiens

<400> SEQUENCE: 871
```

```
acugacagga gagcauuuug a                                              21

<210> SEQ ID NO 872
<211> LENGTH: 22
<212> TYPE: RNA
<213> ORGANISM: homo sapiens

<400> SEQUENCE: 872
agcgcgggcu gagcgcugcc ag                                             22

<210> SEQ ID NO 873
<211> LENGTH: 21
<212> TYPE: RNA
<213> ORGANISM: homo sapiens

<400> SEQUENCE: 873
aagcucgggc gcuccggcug u                                              21

<210> SEQ ID NO 874
<211> LENGTH: 22
<212> TYPE: RNA
<213> ORGANISM: homo sapiens

<400> SEQUENCE: 874
auagugguug ugaauuuacc uu                                             22

<210> SEQ ID NO 875
<211> LENGTH: 23
<212> TYPE: RNA
<213> ORGANISM: homo sapiens

<400> SEQUENCE: 875
gauugagacu aguagggcua ggc                                            23

<210> SEQ ID NO 876
<211> LENGTH: 22
<212> TYPE: RNA
<213> ORGANISM: homo sapiens

<400> SEQUENCE: 876
cuaccccagg augccagcau ag                                             22

<210> SEQ ID NO 877
<211> LENGTH: 21
<212> TYPE: RNA
<213> ORGANISM: homo sapiens

<400> SEQUENCE: 877
acuggacuug gugucagaug g                                              21

<210> SEQ ID NO 878
<211> LENGTH: 22
<212> TYPE: RNA
<213> ORGANISM: homo sapiens

<400> SEQUENCE: 878
gacaaugaug agaagaccug ag                                             22

<210> SEQ ID NO 879
<211> LENGTH: 19
<212> TYPE: RNA
<213> ORGANISM: homo sapiens

<400> SEQUENCE: 879
```

-continued accgcucgau cuugggacc                                                19

<210> SEQ ID NO 880
<211> LENGTH: 22
<212> TYPE: RNA
<213> ORGANISM: homo sapiens

<400> SEQUENCE: 880
uaguggauga uggagacucg gu                                            22

<210> SEQ ID NO 881
<211> LENGTH: 21
<212> TYPE: RNA
<213> ORGANISM: homo sapiens

<400> SEQUENCE: 881
cucgggagcg uuagagaugg a                                             21

<210> SEQ ID NO 882
<211> LENGTH: 22
<212> TYPE: RNA
<213> ORGANISM: homo sapiens

<400> SEQUENCE: 882
ggcuggagcg agugcagugg ug                                            22

<210> SEQ ID NO 883
<211> LENGTH: 22
<212> TYPE: RNA
<213> ORGANISM: homo sapiens

<400> SEQUENCE: 883
ucaggugugg aaacugaggc ag                                            22

<210> SEQ ID NO 884
<211> LENGTH: 23
<212> TYPE: RNA
<213> ORGANISM: homo sapiens

<400> SEQUENCE: 884
ugacacggag gguggcuugg gaa                                           23

<210> SEQ ID NO 885
<211> LENGTH: 22
<212> TYPE: RNA
<213> ORGANISM: homo sapiens

<400> SEQUENCE: 885
gaagauggug cugugcugag ga                                            22

<210> SEQ ID NO 886
<211> LENGTH: 22
<212> TYPE: RNA
<213> ORGANISM: homo sapiens

<400> SEQUENCE: 886
aaagacugca auuacuuuug cg                                            22

<210> SEQ ID NO 887
<211> LENGTH: 17
<212> TYPE: RNA
<213> ORGANISM: homo sapiens

<400> SEQUENCE: 887 gagacuggggg uggggcc                                                17

<210> SEQ ID NO 888
<211> LENGTH: 21
<212> TYPE: RNA
<213> ORGANISM: homo sapiens

<400> SEQUENCE: 888
aagguuugga uagaugcaau a                                            21

<210> SEQ ID NO 889
<211> LENGTH: 22
<212> TYPE: RNA
<213> ORGANISM: homo sapiens

<400> SEQUENCE: 889
aaagguaauu gcaguuuuc cc                                            22

<210> SEQ ID NO 890
<211> LENGTH: 22
<212> TYPE: RNA
<213> ORGANISM: homo sapiens

<400> SEQUENCE: 890
aggggaccaa agagauauau ag                                           22

<210> SEQ ID NO 891
<211> LENGTH: 21
<212> TYPE: RNA
<213> ORGANISM: homo sapiens

<400> SEQUENCE: 891
uaaaaacugc aauuacuuuu a                                            21

<210> SEQ ID NO 892
<211> LENGTH: 21
<212> TYPE: RNA
<213> ORGANISM: homo sapiens

<400> SEQUENCE: 892
uaaaaacugc aauuacuuuu a                                            21

<210> SEQ ID NO 893
<211> LENGTH: 22
<212> TYPE: RNA
<213> ORGANISM: homo sapiens

<400> SEQUENCE: 893
cucaaguagu cugaccaggg ga                                           22

<210> SEQ ID NO 894
<211> LENGTH: 22
<212> TYPE: RNA
<213> ORGANISM: homo sapiens

<400> SEQUENCE: 894
ucuggcugag gaggaagugg ag                                           22

<210> SEQ ID NO 895
<211> LENGTH: 22
<212> TYPE: RNA
<213> ORGANISM: homo sapiens

```
<400> SEQUENCE: 895
ucuggcugag gaggaagugg ag                                              22

<210> SEQ ID NO 896
<211> LENGTH: 21
<212> TYPE: RNA
<213> ORGANISM: homo sapiens

<400> SEQUENCE: 896
ggcgacaaaa cgagacccug u                                               21

<210> SEQ ID NO 897
<211> LENGTH: 18
<212> TYPE: RNA
<213> ORGANISM: homo sapiens

<400> SEQUENCE: 897
gggugcgggc cggcgggg                                                   18

<210> SEQ ID NO 898
<211> LENGTH: 22
<212> TYPE: RNA
<213> ORGANISM: homo sapiens

<400> SEQUENCE: 898
ccugcugguc aggaguggau ac                                              22

<210> SEQ ID NO 899
<211> LENGTH: 22
<212> TYPE: RNA
<213> ORGANISM: homo sapiens

<400> SEQUENCE: 899
caugcuagga uagaaagaau gg                                              22

<210> SEQ ID NO 900
<211> LENGTH: 22
<212> TYPE: RNA
<213> ORGANISM: homo sapiens

<400> SEQUENCE: 900
aauguggaag uggucugagg ca                                              22

<210> SEQ ID NO 901
<211> LENGTH: 22
<212> TYPE: RNA
<213> ORGANISM: homo sapiens

<400> SEQUENCE: 901
gcaaagugau gaguaauacu gg                                              22

<210> SEQ ID NO 902
<211> LENGTH: 22
<212> TYPE: RNA
<213> ORGANISM: homo sapiens

<400> SEQUENCE: 902
uggcggcggu aguuaugggc uu                                              22

<210> SEQ ID NO 903
<211> LENGTH: 18
<212> TYPE: RNA
```

<213> ORGANISM: homo sapiens

<400> SEQUENCE: 903
agagcagaag gaugagau                                                 18

<210> SEQ ID NO 904
<211> LENGTH: 20
<212> TYPE: RNA
<213> ORGANISM: homo sapiens

<400> SEQUENCE: 904
uggaauggcc ugaaggugga                                               20

<210> SEQ ID NO 905
<211> LENGTH: 22
<212> TYPE: RNA
<213> ORGANISM: homo sapiens

<400> SEQUENCE: 905
gcucccucua gggucgcucg ga                                            22

<210> SEQ ID NO 906
<211> LENGTH: 21
<212> TYPE: RNA
<213> ORGANISM: homo sapiens

<400> SEQUENCE: 906
uggcaaacgu ggaagccgag a                                             21

<210> SEQ ID NO 907
<211> LENGTH: 22
<212> TYPE: RNA
<213> ORGANISM: homo sapiens

<400> SEQUENCE: 907
uuuguaugga uaugugugug ua                                            22

<210> SEQ ID NO 908
<211> LENGTH: 22
<212> TYPE: RNA
<213> ORGANISM: homo sapiens

<400> SEQUENCE: 908
ugaggagauc gucgagguug gc                                            22

<210> SEQ ID NO 909
<211> LENGTH: 22
<212> TYPE: RNA
<213> ORGANISM: homo sapiens

<400> SEQUENCE: 909
ugggaacuua guagagguuu aa                                            22

<210> SEQ ID NO 910
<211> LENGTH: 18
<212> TYPE: RNA
<213> ORGANISM: homo sapiens

<400> SEQUENCE: 910
gguggggggu guuguuuu                                                 18

<210> SEQ ID NO 911
<211> LENGTH: 18

<212> TYPE: RNA
<213> ORGANISM: homo sapiens

<400> SEQUENCE: 911
gguggggggu guuguuuu                                                     18

<210> SEQ ID NO 912
<211> LENGTH: 22
<212> TYPE: RNA
<213> ORGANISM: homo sapiens

<400> SEQUENCE: 912
cuagugcucu ccguuacaag ua                                                22

<210> SEQ ID NO 913
<211> LENGTH: 22
<212> TYPE: RNA
<213> ORGANISM: homo sapiens

<400> SEQUENCE: 913
cacuuguaau ggagaacacu aa                                                22

<210> SEQ ID NO 914
<211> LENGTH: 22
<212> TYPE: RNA
<213> ORGANISM: homo sapiens

<400> SEQUENCE: 914
uuguggcugg ucaugaggcu aa                                                22

<210> SEQ ID NO 915
<211> LENGTH: 21
<212> TYPE: RNA
<213> ORGANISM: homo sapiens

<400> SEQUENCE: 915
cccugggguu cugaggacau g                                                 21

<210> SEQ ID NO 916
<211> LENGTH: 22
<212> TYPE: RNA
<213> ORGANISM: homo sapiens

<400> SEQUENCE: 916
caagggacca agcauucauu au                                                22

<210> SEQ ID NO 917
<211> LENGTH: 22
<212> TYPE: RNA
<213> ORGANISM: homo sapiens

<400> SEQUENCE: 917
caggaaggau uuagggacag gc                                                22

<210> SEQ ID NO 918
<211> LENGTH: 22
<212> TYPE: RNA
<213> ORGANISM: homo sapiens

<400> SEQUENCE: 918
cuauuaagga cauuugugau uc                                                22

<210> SEQ ID NO 919

```
<211> LENGTH: 22
<212> TYPE: RNA
<213> ORGANISM: homo sapiens

<400> SEQUENCE: 919
auuaaggaca uuugugauug au                                           22

<210> SEQ ID NO 920
<211> LENGTH: 21
<212> TYPE: RNA
<213> ORGANISM: homo sapiens

<400> SEQUENCE: 920
aaaaggcaua aaaccaagac a                                            21

<210> SEQ ID NO 921
<211> LENGTH: 21
<212> TYPE: RNA
<213> ORGANISM: homo sapiens

<400> SEQUENCE: 921
aaaaggcaua aaaccaagac a                                            21

<210> SEQ ID NO 922
<211> LENGTH: 17
<212> TYPE: RNA
<213> ORGANISM: homo sapiens

<400> SEQUENCE: 922
gaggcugagc ugaggag                                                 17

<210> SEQ ID NO 923
<211> LENGTH: 22
<212> TYPE: RNA
<213> ORGANISM: homo sapiens

<400> SEQUENCE: 923
cugggaggug ugauauugug gu                                           22

<210> SEQ ID NO 924
<211> LENGTH: 20
<212> TYPE: RNA
<213> ORGANISM: homo sapiens

<400> SEQUENCE: 924
uaaaaacugc aauuacuuuc                                              20

<210> SEQ ID NO 925
<211> LENGTH: 20
<212> TYPE: RNA
<213> ORGANISM: homo sapiens

<400> SEQUENCE: 925
uaaaaacugc aauuacuuuc                                              20

<210> SEQ ID NO 926
<211> LENGTH: 22
<212> TYPE: RNA
<213> ORGANISM: homo sapiens

<400> SEQUENCE: 926
ugugauauca ugguuccugg ga                                           22
```

```
<210> SEQ ID NO 927
<211> LENGTH: 22
<212> TYPE: RNA
<213> ORGANISM: homo sapiens

<400> SEQUENCE: 927
gggaggugug aucucacacu cg                                              22

<210> SEQ ID NO 928
<211> LENGTH: 22
<212> TYPE: RNA
<213> ORGANISM: homo sapiens

<400> SEQUENCE: 928
cugggaggug ugauauugug gu                                              22

<210> SEQ ID NO 929
<211> LENGTH: 22
<212> TYPE: RNA
<213> ORGANISM: homo sapiens

<400> SEQUENCE: 929
ugugauauca ugguuccugg ga                                              22

<210> SEQ ID NO 930
<211> LENGTH: 22
<212> TYPE: RNA
<213> ORGANISM: homo sapiens

<400> SEQUENCE: 930
gggaggugug aucucacacu cg                                              22

<210> SEQ ID NO 931
<211> LENGTH: 22
<212> TYPE: RNA
<213> ORGANISM: homo sapiens

<400> SEQUENCE: 931
ugugauauca ugguuccugg ga                                              22

<210> SEQ ID NO 932
<211> LENGTH: 22
<212> TYPE: RNA
<213> ORGANISM: homo sapiens

<400> SEQUENCE: 932
ugugauaucg ugcuuccugg ga                                              22

<210> SEQ ID NO 933
<211> LENGTH: 22
<212> TYPE: RNA
<213> ORGANISM: homo sapiens

<400> SEQUENCE: 933
cgcgcggccg ugcucggagc ag                                              22

<210> SEQ ID NO 934
<211> LENGTH: 21
<212> TYPE: RNA
<213> ORGANISM: homo sapiens

<400> SEQUENCE: 934
ccaggcucug cagugggaac u                                               21
```

```
<210> SEQ ID NO 935
<211> LENGTH: 18
<212> TYPE: RNA
<213> ORGANISM: homo sapiens

<400> SEQUENCE: 935
ccaggcucug caguggga                                          18

<210> SEQ ID NO 936
<211> LENGTH: 21
<212> TYPE: RNA
<213> ORGANISM: homo sapiens

<400> SEQUENCE: 936
aaaaguaacu gcgguuuuug a                                      21

<210> SEQ ID NO 937
<211> LENGTH: 21
<212> TYPE: RNA
<213> ORGANISM: homo sapiens

<400> SEQUENCE: 937
agccaagugg aaguuacuuu a                                      21

<210> SEQ ID NO 938
<211> LENGTH: 17
<212> TYPE: RNA
<213> ORGANISM: homo sapiens

<400> SEQUENCE: 938
ggagugggcu ggugguu                                           17

<210> SEQ ID NO 939
<211> LENGTH: 18
<212> TYPE: RNA
<213> ORGANISM: homo sapiens

<400> SEQUENCE: 939
gagcgauccg agggacug                                          18

<210> SEQ ID NO 940
<211> LENGTH: 22
<212> TYPE: RNA
<213> ORGANISM: homo sapiens

<400> SEQUENCE: 940
aagggcuucc ucucugcagg ac                                     22

<210> SEQ ID NO 941
<211> LENGTH: 22
<212> TYPE: RNA
<213> ORGANISM: homo sapiens

<400> SEQUENCE: 941
aagggcuucc ucucugcagg ac                                     22

<210> SEQ ID NO 942
<211> LENGTH: 22
<212> TYPE: RNA
<213> ORGANISM: homo sapiens

<400> SEQUENCE: 942
aacccagugg gcuauggaaa ug                                     22
```

```
<210> SEQ ID NO 943
<211> LENGTH: 17
<212> TYPE: RNA
<213> ORGANISM: homo sapiens

<400> SEQUENCE: 943
gggguggucu guuguug                                                      17

<210> SEQ ID NO 944
<211> LENGTH: 20
<212> TYPE: RNA
<213> ORGANISM: homo sapiens

<400> SEQUENCE: 944
aaaaggcggg agaagcccca                                                   20

<210> SEQ ID NO 945
<211> LENGTH: 22
<212> TYPE: RNA
<213> ORGANISM: homo sapiens

<400> SEQUENCE: 945
uggcuguugg aggggggcagg cu                                               22

<210> SEQ ID NO 946
<211> LENGTH: 20
<212> TYPE: RNA
<213> ORGANISM: homo sapiens

<400> SEQUENCE: 946
uaacggccgc gguacccuaa                                                   20

<210> SEQ ID NO 947
<211> LENGTH: 22
<212> TYPE: RNA
<213> ORGANISM: homo sapiens

<400> SEQUENCE: 947
uaggauuaca agugucggcc ac                                                22

<210> SEQ ID NO 948
<211> LENGTH: 17
<212> TYPE: RNA
<213> ORGANISM: homo sapiens

<400> SEQUENCE: 948
gcugggcgag gcuggca                                                      17

<210> SEQ ID NO 949
<211> LENGTH: 19
<212> TYPE: RNA
<213> ORGANISM: homo sapiens

<400> SEQUENCE: 949
agagcuggcu gaagggcag                                                    19

<210> SEQ ID NO 950
<211> LENGTH: 18
<212> TYPE: RNA
<213> ORGANISM: homo sapiens

<400> SEQUENCE: 950
``` aggggcggg cuccggcg                                                      18

<210> SEQ ID NO 951
<211> LENGTH: 19
<212> TYPE: RNA
<213> ORGANISM: homo sapiens

<400> SEQUENCE: 951
gccgagaguc gucgggguu                                                    19

<210> SEQ ID NO 952
<211> LENGTH: 21
<212> TYPE: RNA
<213> ORGANISM: homo sapiens

<400> SEQUENCE: 952
uggggcuagu gaugcaggac g                                                 21

<210> SEQ ID NO 953
<211> LENGTH: 22
<212> TYPE: RNA
<213> ORGANISM: homo sapiens

<400> SEQUENCE: 953
ugugacuuua agggaaaugg cg                                                22

<210> SEQ ID NO 954
<211> LENGTH: 22
<212> TYPE: RNA
<213> ORGANISM: homo sapiens

<400> SEQUENCE: 954
ucucaggagu aaagacagag uu                                                22

<210> SEQ ID NO 955
<211> LENGTH: 22
<212> TYPE: RNA
<213> ORGANISM: homo sapiens

<400> SEQUENCE: 955
agguggaugc aaugugaccu ca                                                22

<210> SEQ ID NO 956
<211> LENGTH: 22
<212> TYPE: RNA
<213> ORGANISM: homo sapiens

<400> SEQUENCE: 956
aacggcaaug acuuuuguac ca                                                22

<210> SEQ ID NO 957
<211> LENGTH: 22
<212> TYPE: RNA
<213> ORGANISM: homo sapiens

<400> SEQUENCE: 957
ucugguaaga gauuugggca ua                                                22

<210> SEQ ID NO 958
<211> LENGTH: 22
<212> TYPE: RNA
<213> ORGANISM: homo sapiens

<400> SEQUENCE: 958

-continued aauguggacu ggugugacca aa                                          22

<210> SEQ ID NO 959
<211> LENGTH: 22
<212> TYPE: RNA
<213> ORGANISM: homo sapiens

<400> SEQUENCE: 959
aauguggacu ggugugacca aa                                          22

<210> SEQ ID NO 960
<211> LENGTH: 17
<212> TYPE: RNA
<213> ORGANISM: homo sapiens

<400> SEQUENCE: 960 ggggcuggc gcgcgcc                                                 17

<210> SEQ ID NO 961
<211> LENGTH: 21
<212> TYPE: RNA
<213> ORGANISM: homo sapiens

<400> SEQUENCE: 961
agaaggccuu uccaucucug u                                           21

<210> SEQ ID NO 962
<211> LENGTH: 22
<212> TYPE: RNA
<213> ORGANISM: homo sapiens

<400> SEQUENCE: 962
ccagacugug gcugaccaga gg                                          22

<210> SEQ ID NO 963
<211> LENGTH: 18
<212> TYPE: RNA
<213> ORGANISM: homo sapiens

<400> SEQUENCE: 963
aggagaagca ggagcugu                                               18

<210> SEQ ID NO 964
<211> LENGTH: 21
<212> TYPE: RNA
<213> ORGANISM: homo sapiens

<400> SEQUENCE: 964
aauguaaaca ggcuuuugc u                                            21

<210> SEQ ID NO 965
<211> LENGTH: 22
<212> TYPE: RNA
<213> ORGANISM: homo sapiens

<400> SEQUENCE: 965
gaggaaacug aagcugagag gg                                          22

<210> SEQ ID NO 966
<211> LENGTH: 17
<212> TYPE: RNA
<213> ORGANISM: homo sapiens
<210> SEQ ID NO 967
<211> LENGTH: 22
<212> TYPE: RNA
<213> ORGANISM: homo sapiens

<400> SEQUENCE: 966
cuccgggacg gcugggc                                                    17

<210> SEQ ID NO 967
<211> LENGTH: 22
<212> TYPE: RNA
<213> ORGANISM: homo sapiens

<400> SEQUENCE: 967
ugggcuggca gggcaagugc ug                                              22

<210> SEQ ID NO 968
<211> LENGTH: 18
<212> TYPE: RNA
<213> ORGANISM: homo sapiens

<400> SEQUENCE: 968
gaggcugaag gaagaugg                                                   18

<210> SEQ ID NO 969
<211> LENGTH: 17
<212> TYPE: RNA
<213> ORGANISM: homo sapiens

<400> SEQUENCE: 969
aagacugaga ggaggga                                                    17

<210> SEQ ID NO 970
<211> LENGTH: 17
<212> TYPE: RNA
<213> ORGANISM: homo sapiens

<400> SEQUENCE: 970
ugagguagua guuucuu                                                    17

<210> SEQ ID NO 971
<211> LENGTH: 22
<212> TYPE: RNA
<213> ORGANISM: homo sapiens

<400> SEQUENCE: 971
cggcugggag ccgaggcguc gg                                              22

<210> SEQ ID NO 972
<211> LENGTH: 21
<212> TYPE: RNA
<213> ORGANISM: homo sapiens

<400> SEQUENCE: 972
uaugugaccu cggaugaauc a                                               21

<210> SEQ ID NO 973
<211> LENGTH: 22
<212> TYPE: RNA
<213> ORGANISM: homo sapiens

<400> SEQUENCE: 973
gcugaugaug auggugcuga ag                                              22

<210> SEQ ID NO 974
<211> LENGTH: 21
<212> TYPE: RNA
<213> ORGANISM: homo sapiens

```
<400> SEQUENCE: 974
agauguaugg aaucuguaua u                                          21

<210> SEQ ID NO 975
<211> LENGTH: 22
<212> TYPE: RNA
<213> ORGANISM: homo sapiens

<400> SEQUENCE: 975
uuuaagcagg aaauagaauu ua                                         22

<210> SEQ ID NO 976
<211> LENGTH: 22
<212> TYPE: RNA
<213> ORGANISM: homo sapiens

<400> SEQUENCE: 976
ugugacaaua gagaugaaca ug                                         22

<210> SEQ ID NO 977
<211> LENGTH: 18
<212> TYPE: RNA
<213> ORGANISM: homo sapiens

<400> SEQUENCE: 977
aggcugggcu gggacgga                                              18

<210> SEQ ID NO 978
<211> LENGTH: 20
<212> TYPE: RNA
<213> ORGANISM: homo sapiens

<400> SEQUENCE: 978
aaaugggugg ucugaggcaa                                            20

<210> SEQ ID NO 979
<211> LENGTH: 20
<212> TYPE: RNA
<213> ORGANISM: homo sapiens

<400> SEQUENCE: 979
uaggaugggg gugagaggug                                            20

<210> SEQ ID NO 980
<211> LENGTH: 20
<212> TYPE: RNA
<213> ORGANISM: homo sapiens

<400> SEQUENCE: 980
cuggguuggg cugggcuggg                                            20

<210> SEQ ID NO 981
<211> LENGTH: 22
<212> TYPE: RNA
<213> ORGANISM: homo sapiens

<400> SEQUENCE: 981
aagggacugg aguggauugg gu                                         22

<210> SEQ ID NO 982
<211> LENGTH: 22
<212> TYPE: RNA
```

<213> ORGANISM: homo sapiens

<400> SEQUENCE: 982
aaggggcugg aguggauugg gg                                    22

<210> SEQ ID NO 983
<211> LENGTH: 17
<212> TYPE: RNA
<213> ORGANISM: homo sapiens

<400> SEQUENCE: 983
gcggggcugg gcgcgcg                                          17

<210> SEQ ID NO 984
<211> LENGTH: 22
<212> TYPE: RNA
<213> ORGANISM: homo sapiens

<400> SEQUENCE: 984
acuaaaggau auagaagguu uu                                    22

<210> SEQ ID NO 985
<211> LENGTH: 22
<212> TYPE: RNA
<213> ORGANISM: homo sapiens

<400> SEQUENCE: 985
acuaaaggau auagaagguu uu                                    22

<210> SEQ ID NO 986
<211> LENGTH: 22
<212> TYPE: RNA
<213> ORGANISM: homo sapiens

<400> SEQUENCE: 986
acuaaaggau auagaagguu uu                                    22

<210> SEQ ID NO 987
<211> LENGTH: 22
<212> TYPE: RNA
<213> ORGANISM: homo sapiens

<400> SEQUENCE: 987
aagcaauacu guuaccugaa au                                    22

<210> SEQ ID NO 988
<211> LENGTH: 22
<212> TYPE: RNA
<213> ORGANISM: homo sapiens

<400> SEQUENCE: 988
ugagggagua ggauguaugg uu                                    22

<210> SEQ ID NO 989
<211> LENGTH: 22
<212> TYPE: RNA
<213> ORGANISM: homo sapiens

<400> SEQUENCE: 989
gaagaacugu ugcauuugcc cu                                    22

<210> SEQ ID NO 990
<211> LENGTH: 22

<212> TYPE: RNA
<213> ORGANISM: homo sapiens

<400> SEQUENCE: 990
cagggccuca cuguaucgcc ca                                                22

<210> SEQ ID NO 991
<211> LENGTH: 22
<212> TYPE: RNA
<213> ORGANISM: homo sapiens

<400> SEQUENCE: 991
agacugacgg cuggaggccc au                                                22

<210> SEQ ID NO 992
<211> LENGTH: 18
<212> TYPE: RNA
<213> ORGANISM: homo sapiens

<400> SEQUENCE: 992
acaggcagga uuggggaa                                                     18

<210> SEQ ID NO 993
<211> LENGTH: 22
<212> TYPE: RNA
<213> ORGANISM: homo sapiens

<400> SEQUENCE: 993
aggacuggac ucccggcagc cc                                                22

<210> SEQ ID NO 994
<211> LENGTH: 22
<212> TYPE: RNA
<213> ORGANISM: homo sapiens

<400> SEQUENCE: 994
uagugaguua gagaugcaga gc                                                22

<210> SEQ ID NO 995
<211> LENGTH: 22
<212> TYPE: RNA
<213> ORGANISM: homo sapiens

<400> SEQUENCE: 995
acuggccugg gacuaccggg gg                                                22

<210> SEQ ID NO 996
<211> LENGTH: 17
<212> TYPE: RNA
<213> ORGANISM: homo sapiens

<400> SEQUENCE: 996
gggagaaggg ucggggc                                                      17

<210> SEQ ID NO 997
<211> LENGTH: 22
<212> TYPE: RNA
<213> ORGANISM: homo sapiens

<400> SEQUENCE: 997
uggggcggag cuuccggagg cc                                                22

<210> SEQ ID NO 998

```
<211> LENGTH: 22
<212> TYPE: RNA
<213> ORGANISM: homo sapiens

<400> SEQUENCE: 998 ugggggcggag cuuccggagg cc                                              22

<210> SEQ ID NO 999
<211> LENGTH: 22
<212> TYPE: RNA
<213> ORGANISM: homo sapiens

<400> SEQUENCE: 999 ugggggcggag cuuccggagg cc                                              22

<210> SEQ ID NO 1000
<211> LENGTH: 22
<212> TYPE: RNA
<213> ORGANISM: homo sapiens

<400> SEQUENCE: 1000 ugggggcggag cuuccggagg cc                                              22

<210> SEQ ID NO 1001
<211> LENGTH: 22
<212> TYPE: RNA
<213> ORGANISM: homo sapiens

<400> SEQUENCE: 1001 ugggggcggag cuuccggagg cc                                              22

<210> SEQ ID NO 1002
<211> LENGTH: 21
<212> TYPE: RNA
<213> ORGANISM: homo sapiens

<400> SEQUENCE: 1002
cucgugggcu cuggccacgg c                                                21

<210> SEQ ID NO 1003
<211> LENGTH: 22
<212> TYPE: RNA
<213> ORGANISM: homo sapiens

<400> SEQUENCE: 1003
agaaggggug aaauuuaaac gu                                               22

<210> SEQ ID NO 1004
<211> LENGTH: 22
<212> TYPE: RNA
<213> ORGANISM: homo sapiens

<400> SEQUENCE: 1004
agaaggggug aaauuuaaac gu                                               22

<210> SEQ ID NO 1005
<211> LENGTH: 22
<212> TYPE: RNA
<213> ORGANISM: homo sapiens

<400> SEQUENCE: 1005
agaaggggug aaauuuaaac gu                                               22
```

```
<210> SEQ ID NO 1006
<211> LENGTH: 25
<212> TYPE: RNA
<213> ORGANISM: homo sapiens

<400> SEQUENCE: 1006
aaauaugaug aaacucacag cugag                                          25

<210> SEQ ID NO 1007
<211> LENGTH: 26
<212> TYPE: RNA
<213> ORGANISM: homo sapiens

<400> SEQUENCE: 1007
gcucagggau gauaacugug cugaga                                         26

<210> SEQ ID NO 1008
<211> LENGTH: 18
<212> TYPE: RNA
<213> ORGANISM: homo sapiens

<400> SEQUENCE: 1008
cagcagugcg cagggcug                                                  18

<210> SEQ ID NO 1009
<211> LENGTH: 22
<212> TYPE: RNA
<213> ORGANISM: homo sapiens

<400> SEQUENCE: 1009
uuggacagaa aacacgcagg aa                                             22

<210> SEQ ID NO 1010
<211> LENGTH: 22
<212> TYPE: RNA
<213> ORGANISM: homo sapiens

<400> SEQUENCE: 1010
gcuaaggaag uccugugcuc ag                                             22

<210> SEQ ID NO 1011
<211> LENGTH: 22
<212> TYPE: RNA
<213> ORGANISM: homo sapiens

<400> SEQUENCE: 1011
cuggacugag ccaugcuacu gg                                             22

<210> SEQ ID NO 1012
<211> LENGTH: 21
<212> TYPE: RNA
<213> ORGANISM: homo sapiens

<400> SEQUENCE: 1012
ugacucugcc uguaggccgg u                                              21

<210> SEQ ID NO 1013
<211> LENGTH: 21
<212> TYPE: RNA
<213> ORGANISM: homo sapiens

<400> SEQUENCE: 1013
gaccgagagg gccucggcug u                                              21
```

```
<210> SEQ ID NO 1014
<211> LENGTH: 22
<212> TYPE: RNA
<213> ORGANISM: homo sapiens

<400> SEQUENCE: 1014
uagaggcugg aauagagauu cu                                              22

<210> SEQ ID NO 1015
<211> LENGTH: 22
<212> TYPE: RNA
<213> ORGANISM: homo sapiens

<400> SEQUENCE: 1015
uagccuucag aucuuggugu uu                                              22

<210> SEQ ID NO 1016
<211> LENGTH: 22
<212> TYPE: RNA
<213> ORGANISM: homo sapiens

<400> SEQUENCE: 1016
ccacuuggau cugaaggcug cc                                              22

<210> SEQ ID NO 1017
<211> LENGTH: 22
<212> TYPE: RNA
<213> ORGANISM: homo sapiens

<400> SEQUENCE: 1017
auagcagcau gaaccugucu ca                                              22

<210> SEQ ID NO 1018
<211> LENGTH: 22
<212> TYPE: RNA
<213> ORGANISM: homo sapiens

<400> SEQUENCE: 1018
ugagacaggc uuaugcugcu au                                              22

<210> SEQ ID NO 1019
<211> LENGTH: 21
<212> TYPE: RNA
<213> ORGANISM: homo sapiens

<400> SEQUENCE: 1019 gggggggaugu gcaugcuggu u                                              21

<210> SEQ ID NO 1020
<211> LENGTH: 22
<212> TYPE: RNA
<213> ORGANISM: homo sapiens

<400> SEQUENCE: 1020
cagggaggug aaugguucug uc                                              22

<210> SEQ ID NO 1021
<211> LENGTH: 22
<212> TYPE: RNA
<213> ORGANISM: homo sapiens

<400> SEQUENCE: 1021
gcugacagca gggcuggccg cu                                              22
```

-continued

<210> SEQ ID NO 1022
<211> LENGTH: 22
<212> TYPE: RNA
<213> ORGANISM: homo sapiens

<400> SEQUENCE: 1022
uggucugcaa agagaugacu gu                                           22

<210> SEQ ID NO 1023
<211> LENGTH: 22
<212> TYPE: RNA
<213> ORGANISM: homo sapiens

<400> SEQUENCE: 1023
ucauuauaug uaugaucugg ac                                           22

<210> SEQ ID NO 1024
<211> LENGTH: 21
<212> TYPE: RNA
<213> ORGANISM: homo sapiens

<400> SEQUENCE: 1024
auuggacugc ugauggcccg u                                            21

<210> SEQ ID NO 1025
<211> LENGTH: 21
<212> TYPE: RNA
<213> ORGANISM: homo sapiens

<400> SEQUENCE: 1025
uuggagggug uggaagacau c                                            21

<210> SEQ ID NO 1026
<211> LENGTH: 18
<212> TYPE: RNA
<213> ORGANISM: homo sapiens

<400> SEQUENCE: 1026
cccagcagga cgggagcg                                                18

<210> SEQ ID NO 1027
<211> LENGTH: 17
<212> TYPE: RNA
<213> ORGANISM: homo sapiens

<400> SEQUENCE: 1027
auggagaagg cuucuga                                                 17

<210> SEQ ID NO 1028
<211> LENGTH: 17
<212> TYPE: RNA
<213> ORGANISM: homo sapiens

<400> SEQUENCE: 1028
aaaagcuggg uugagaa                                                 17

<210> SEQ ID NO 1029
<211> LENGTH: 22
<212> TYPE: RNA
<213> ORGANISM: homo sapiens

<400> SEQUENCE: 1029

|  |  |
|---|---|
| uggaagguag acggccagag ag | 22 |

```
<210> SEQ ID NO 1030
<211> LENGTH: 22
<212> TYPE: RNA
<213> ORGANISM: homo sapiens

<400> SEQUENCE: 1030
```

|  |  |
|---|---|
| ucugggaggu uguagcagug ga | 22 |

```
<210> SEQ ID NO 1031
<211> LENGTH: 17
<212> TYPE: RNA
<213> ORGANISM: homo sapiens

<400> SEQUENCE: 1031
```

|  |  |
|---|---|
| ccccggggag cccggcg | 17 |

```
<210> SEQ ID NO 1032
<211> LENGTH: 22
<212> TYPE: RNA
<213> ORGANISM: homo sapiens

<400> SEQUENCE: 1032
```

|  |  |
|---|---|
| uggaaggagg uugccggacg cu | 22 |

```
<210> SEQ ID NO 1033
<211> LENGTH: 22
<212> TYPE: RNA
<213> ORGANISM: homo sapiens

<400> SEQUENCE: 1033
```

|  |  |
|---|---|
| caagaaccuc aauuaccuuu gc | 22 |

```
<210> SEQ ID NO 1034
<211> LENGTH: 22
<212> TYPE: RNA
<213> ORGANISM: homo sapiens

<400> SEQUENCE: 1034
```

|  |  |
|---|---|
| aaucugagaa ggcgcacaag gu | 22 |

```
<210> SEQ ID NO 1035
<211> LENGTH: 22
<212> TYPE: RNA
<213> ORGANISM: homo sapiens

<400> SEQUENCE: 1035
```

|  |  |
|---|---|
| caccuugcgc uacucagguc ug | 22 |

```
<210> SEQ ID NO 1036
<211> LENGTH: 22
<212> TYPE: RNA
<213> ORGANISM: homo sapiens

<400> SEQUENCE: 1036
```

|  |  |
|---|---|
| ggaggaaccu uggagcuucg gc | 22 |

```
<210> SEQ ID NO 1037
<211> LENGTH: 17
<212> TYPE: RNA
<213> ORGANISM: homo sapiens

<400> SEQUENCE: 1037
```

```
ggauggagga ggggucu                                              17

<210> SEQ ID NO 1038
<211> LENGTH: 21
<212> TYPE: RNA
<213> ORGANISM: homo sapiens

<400> SEQUENCE: 1038
acuggacuag gagucagaag g                                         21

<210> SEQ ID NO 1039
<211> LENGTH: 17
<212> TYPE: RNA
<213> ORGANISM: homo sapiens

<400> SEQUENCE: 1039
guggaccugg cugggac                                              17

<210> SEQ ID NO 1040
<211> LENGTH: 22
<212> TYPE: RNA
<213> ORGANISM: homo sapiens

<400> SEQUENCE: 1040
accuggaccc agcguagaca aa                                        22

<210> SEQ ID NO 1041
<211> LENGTH: 22
<212> TYPE: RNA
<213> ORGANISM: homo sapiens

<400> SEQUENCE: 1041
caaaaacugc aguuacuuuu gu                                        22

<210> SEQ ID NO 1042
<211> LENGTH: 20
<212> TYPE: RNA
<213> ORGANISM: homo sapiens

<400> SEQUENCE: 1042
uugggcuggg cugguuggg                                            20

<210> SEQ ID NO 1043
<211> LENGTH: 21
<212> TYPE: RNA
<213> ORGANISM: homo sapiens

<400> SEQUENCE: 1043
ugugguagau auaugcacga u                                         21

<210> SEQ ID NO 1044
<211> LENGTH: 19
<212> TYPE: RNA
<213> ORGANISM: homo sapiens

<400> SEQUENCE: 1044
agaagggaaa gaacaucaa                                            19

<210> SEQ ID NO 1045
<211> LENGTH: 21
<212> TYPE: RNA
<213> ORGANISM: homo sapiens
```

```
<400> SEQUENCE: 1045
cuguccuaag guuguugagu u                                    21

<210> SEQ ID NO 1046
<211> LENGTH: 20
<212> TYPE: RNA
<213> ORGANISM: homo sapiens

<400> SEQUENCE: 1046
aaaaggcauu gugguuuuug                                      20

<210> SEQ ID NO 1047
<211> LENGTH: 22
<212> TYPE: RNA
<213> ORGANISM: homo sapiens

<400> SEQUENCE: 1047
cgggcggcgg cuguuugcg ca                                    22

<210> SEQ ID NO 1048
<211> LENGTH: 22
<212> TYPE: RNA
<213> ORGANISM: homo sapiens

<400> SEQUENCE: 1048
uauggaaggg agaagagcuu ua                                   22

<210> SEQ ID NO 1049
<211> LENGTH: 20
<212> TYPE: RNA
<213> ORGANISM: homo sapiens

<400> SEQUENCE: 1049
cggcggggac ggcgauuggu                                      20

<210> SEQ ID NO 1050
<211> LENGTH: 22
<212> TYPE: RNA
<213> ORGANISM: homo sapiens

<400> SEQUENCE: 1050
ccuccugccc uccuugcugu ag                                   22

<210> SEQ ID NO 1051
<211> LENGTH: 22
<212> TYPE: RNA
<213> ORGANISM: homo sapiens

<400> SEQUENCE: 1051
ugagccgagc ugagcuuagc ug                                   22

<210> SEQ ID NO 1052
<211> LENGTH: 22
<212> TYPE: RNA
<213> ORGANISM: homo sapiens

<400> SEQUENCE: 1052
gagcuuggau gagcugggcu ga                                   22

<210> SEQ ID NO 1053
<211> LENGTH: 22
<212> TYPE: RNA
<213> ORGANISM: homo sapiens
```

```
<400> SEQUENCE: 1053
gcugaacugg cugagcugg gc                                              22

<210> SEQ ID NO 1054
<211> LENGTH: 23
<212> TYPE: RNA
<213> ORGANISM: homo sapiens

<400> SEQUENCE: 1054
cugggcugaa ugacagugau gag                                            23

<210> SEQ ID NO 1055
<211> LENGTH: 22
<212> TYPE: RNA
<213> ORGANISM: homo sapiens

<400> SEQUENCE: 1055
gggagccggg gcugugagag ga                                             22

<210> SEQ ID NO 1056
<211> LENGTH: 21
<212> TYPE: RNA
<213> ORGANISM: homo sapiens

<400> SEQUENCE: 1056
uuaguccugc cuguagguuu a                                              21

<210> SEQ ID NO 1057
<211> LENGTH: 70
<212> TYPE: RNA
<213> ORGANISM: homo sapiens

<400> SEQUENCE: 1057
uggugcaaaa guaauugcgg uuuuugccau uaaaaguaau gcggccaaaa cugcaguuac    60
uuuugcaccc                                                           70

<210> SEQ ID NO 1058
<211> LENGTH: 63
<212> TYPE: RNA
<213> ORGANISM: homo sapiens

<400> SEQUENCE: 1058
cugagccugg aagcuggagc cugcagugag cuaugaucau gucccuguac ucuagccugg    60
gca                                                                  63

<210> SEQ ID NO 1059
<211> LENGTH: 50
<212> TYPE: RNA
<213> ORGANISM: homo sapiens

<400> SEQUENCE: 1059
acccgggcgu gguguggggg gugggugccu guaauuccag cuaguuggga              50

<210> SEQ ID NO 1060
<211> LENGTH: 68
<212> TYPE: RNA
<213> ORGANISM: homo sapiens

<400> SEQUENCE: 1060
agucucucuu cagggcuccc gagacacaga aacagacacc ugcccucgag gagcucacag    60
``` ucuagaca                                                                    68

<210> SEQ ID NO 1061
<211> LENGTH: 79
<212> TYPE: RNA
<213> ORGANISM: homo sapiens

<400> SEQUENCE: 1061
ucuuguguua aggugcaucu agugcaguua gugaagcagc uuagaaucua cugcccuaaa           60
ugccccuucu ggcacaggc                                                        79

<210> SEQ ID NO 1062
<211> LENGTH: 60
<212> TYPE: RNA
<213> ORGANISM: homo sapiens

<400> SEQUENCE: 1062
cugccuccac cccgccuggc cugacccagc cagggcucua ggaggguugg guggaggcaa           60

<210> SEQ ID NO 1063
<211> LENGTH: 68
<212> TYPE: RNA
<213> ORGANISM: homo sapiens

<400> SEQUENCE: 1063
uaaaacgugg auauuccuuc uauguuuacg ugauuccugg uuaaucauag aggaaaaucc           60
auguuuuc                                                                    68

<210> SEQ ID NO 1064
<211> LENGTH: 68
<212> TYPE: RNA
<213> ORGANISM: homo sapiens

<400> SEQUENCE: 1064
uaaaaggugg auauuccuuc uauguuuaug uuauuuaugg uuaaacauag aggaaauucc           60
acguuuuc                                                                    68

<210> SEQ ID NO 1065
<211> LENGTH: 54
<212> TYPE: RNA
<213> ORGANISM: homo sapiens

<400> SEQUENCE: 1065
acuguuucug uccuuguucu uguuguuauu acuggacuug gagucagaaa cagg                 54

<210> SEQ ID NO 1066
<211> LENGTH: 76
<212> TYPE: RNA
<213> ORGANISM: homo sapiens

<400> SEQUENCE: 1066
aggagagaac acuggacuug gagucagaaa acuuucaucc aagucauucc cugcucuaag           60
ucccauuucu guucca                                                           76

<210> SEQ ID NO 1067
<211> LENGTH: 79
<212> TYPE: RNA
<213> ORGANISM: homo sapiens

<400> SEQUENCE: 1067
cugacuccag uguccaggcc aggggcagac aguggacaga gaacagugcc caagaccacu           60

```
ggacuuggag ucaggacau                                              79

<210> SEQ ID NO 1068
<211> LENGTH: 68
<212> TYPE: RNA
<213> ORGANISM: homo sapiens

<400> SEQUENCE: 1068
ucagguaggc aguguauugc uagcggcugu uaaugauuuu aacaguugcu aguugcacuc   60
cucucugu                                                          68

<210> SEQ ID NO 1069
<211> LENGTH: 84
<212> TYPE: RNA
<213> ORGANISM: homo sapiens

<400> SEQUENCE: 1069 guuccccuc ucuaauccuu gcuaccuggg ugagagugcu uucugaaugc agugcaccca   60
ggcaaggauu cugcaagggg gagu                                        84

<210> SEQ ID NO 1070
<211> LENGTH: 84
<212> TYPE: RNA
<213> ORGANISM: homo sapiens

<400> SEQUENCE: 1070 guuccccuc ucuaauccuu gcuaccuggg ugagagugcu uucugaaugc agugcaccca   60
ggcaaggauu cugcaagggg gagu                                        84

<210> SEQ ID NO 1071
<211> LENGTH: 60
<212> TYPE: RNA
<213> ORGANISM: homo sapiens

<400> SEQUENCE: 1071
acaaaaguaa ucgcgguuuu ugucauuacu uuuaacugua aaaccacgg uugcuuuugc   60

<210> SEQ ID NO 1072
<211> LENGTH: 84
<212> TYPE: RNA
<213> ORGANISM: homo sapiens

<400> SEQUENCE: 1072
auguuggugc aaaaguaauu guggauuuug cuauuacuug uauuuauuug uaaugcaaaa   60
cccgcaauua guuuugcacc aacc                                        84

<210> SEQ ID NO 1073
<211> LENGTH: 83
<212> TYPE: RNA
<213> ORGANISM: homo sapiens

<400> SEQUENCE: 1073
uguuggugca aaaguaauug uggauuuugc uauuacuugu auuuauuugu aaugcaaaac   60
ccgcaauuag uuuugcacca acc                                         83

<210> SEQ ID NO 1074
<211> LENGTH: 74
<212> TYPE: RNA
<213> ORGANISM: homo sapiens
```

```
<400> SEQUENCE: 1074
cuggugcagu gccugaggga guaagagucc uguuguugua agauaguguc uuacucccuc    60
aggcacaucu ccaa                                                      74

<210> SEQ ID NO 1075
<211> LENGTH: 73
<212> TYPE: RNA
<213> ORGANISM: homo sapiens

<400> SEQUENCE: 1075
gaaaacaacc agguggggcuu cccggagggc ggaacacccca gccccagcau ccagggcuca   60
ccuaccacgu uug                                                       73

<210> SEQ ID NO 1076
<211> LENGTH: 54
<212> TYPE: RNA
<213> ORGANISM: homo sapiens

<400> SEQUENCE: 1076
gaggcggccc uagcgccauu uuguggagc gaagcggugg cugggcugcg cuug            54

<210> SEQ ID NO 1077
<211> LENGTH: 62
<212> TYPE: RNA
<213> ORGANISM: homo sapiens

<400> SEQUENCE: 1077
ugguuuuugc ucugagugac cguggugguu gugggaguca cugcaggacu cagcaggaau    60
uc                                                                   62

<210> SEQ ID NO 1078
<211> LENGTH: 77
<212> TYPE: RNA
<213> ORGANISM: homo sapiens

<400> SEQUENCE: 1078 uggguggugug ugccuguagu cuuagcuacu cgggaggcug agggaggaga cugcagugag    60
uggaggucac gccacug                                                   77

<210> SEQ ID NO 1079
<211> LENGTH: 78
<212> TYPE: RNA
<213> ORGANISM: homo sapiens

<400> SEQUENCE: 1079
gucagguccu ggacucccau aguuuucagg cugcuaaaca acagaacgag cacuggacuu    60
ggagccagaa gucuuggg                                                  78

<210> SEQ ID NO 1080
<211> LENGTH: 77
<212> TYPE: RNA
<213> ORGANISM: homo sapiens

<400> SEQUENCE: 1080
cucuugguau gaacaucugu guguucaugu cucucugugc acagggacg agagucacug      60 augucuguag cugagac                                                   77

<210> SEQ ID NO 1081
<211> LENGTH: 65
```

```
<212> TYPE: RNA
<213> ORGANISM: homo sapiens

<400> SEQUENCE: 1081
cuggccucug ugccuggaua cuuuauacgu guaauuguga ugaggaugga uagcaaggaa    60
gccgc                                                                65

<210> SEQ ID NO 1082
<211> LENGTH: 69
<212> TYPE: RNA
<213> ORGANISM: homo sapiens

<400> SEQUENCE: 1082
cugggucucc uuucugcuga gaguugaaca cuuguuggga caaccugucu guggaaagga    60
gcuaccuac                                                            69

<210> SEQ ID NO 1083
<211> LENGTH: 83
<212> TYPE: RNA
<213> ORGANISM: homo sapiens

<400> SEQUENCE: 1083
aguucuucug cagacaaaag caucaggaag uacccaccau guaccagugg gcccuucuug    60
augcucuuga uugcagagga gcc                                            83

<210> SEQ ID NO 1084
<211> LENGTH: 77
<212> TYPE: RNA
<213> ORGANISM: homo sapiens

<400> SEQUENCE: 1084
uccuuuauug agucccuacu auguuccagg caccuacgau acccagugcc uggaacauag    60
uagggacuca auaaagu                                                   77

<210> SEQ ID NO 1085
<211> LENGTH: 76
<212> TYPE: RNA
<213> ORGANISM: homo sapiens

<400> SEQUENCE: 1085
ccuuuauuga gucccuacua uguuccaggc accuacgaua cccagugccu ggaacauagu    60
agggacucaa uaaagu                                                    76

<210> SEQ ID NO 1086
<211> LENGTH: 65
<212> TYPE: RNA
<213> ORGANISM: homo sapiens

<400> SEQUENCE: 1086
cgccuccaug uuucagcauc uaugucaugg gcuuggccu ggaguggauu aaaaacaaug    60
gaggu                                                                65

<210> SEQ ID NO 1087
<211> LENGTH: 80
<212> TYPE: RNA
<213> ORGANISM: homo sapiens

<400> SEQUENCE: 1087
aucauguacu gcaguugccu uuuuguuccc augcuguuua agccuagcau aggcaccaaa    60
```

```
aagcaacaac aguaugugaa                                              80

<210> SEQ ID NO 1088
<211> LENGTH: 41
<212> TYPE: RNA
<213> ORGANISM: homo sapiens

<400> SEQUENCE: 1088
cacugggcuu ggagucagaa gaccuggcuc cagcccagcu c                      41

<210> SEQ ID NO 1089
<211> LENGTH: 88
<212> TYPE: RNA
<213> ORGANISM: homo sapiens

<400> SEQUENCE: 1089
guauuagguu ggugcaaaag uuauguggu uuugcuauu uuuuuuaau ggcaaaaacc     60 ggcaauuacu uuugcacuaa ccuaguag                                     88

<210> SEQ ID NO 1090
<211> LENGTH: 60
<212> TYPE: RNA
<213> ORGANISM: homo sapiens

<400> SEQUENCE: 1090
aaagugucaa augaagggcu gaucacgaaa uagcgcauua gcucuuuuu ugaaaacuug   60

<210> SEQ ID NO 1091
<211> LENGTH: 70
<212> TYPE: RNA
<213> ORGANISM: homo sapiens

<400> SEQUENCE: 1091
gacuggcuac guaguucggg caaauccucc aaaagggaaa gggaggauuu gcuuagaagg  60
auggcgcucc                                                         70

<210> SEQ ID NO 1092
<211> LENGTH: 86
<212> TYPE: RNA
<213> ORGANISM: homo sapiens

<400> SEQUENCE: 1092
cuuacaucac acacagaguu aacucaaaau ggacuaauuu uuccacuagu uaguccauuu  60
caaguuaacu cuguguguga uguagu                                       86

<210> SEQ ID NO 1093
<211> LENGTH: 84
<212> TYPE: RNA
<213> ORGANISM: homo sapiens

<400> SEQUENCE: 1093
gugcuuuaca ugaauggucc cauugaaucc caacagcuuu gcgaaguguu guugggauuc  60
agcaggacca uucguguaaa guaa                                         84

<210> SEQ ID NO 1094
<211> LENGTH: 79
<212> TYPE: RNA
<213> ORGANISM: homo sapiens

<400> SEQUENCE: 1094
uaaaugguua uguccuuugc cuauucuauu uaagacaccc uguaccuuaa auagaguagg  60
```

| caaaggacag aaacauuuu | 79 |

<210> SEQ ID NO 1095
<211> LENGTH: 76
<212> TYPE: RNA
<213> ORGANISM: homo sapiens

<400> SEQUENCE: 1095

| gcagagucga gagugggaga agagcggagc gugugagcag uacugcggcc uccucuccuc | 60 |
| uccuaaccuc gcucuc | 76 |

<210> SEQ ID NO 1096
<211> LENGTH: 62
<212> TYPE: RNA
<213> ORGANISM: homo sapiens

<400> SEQUENCE: 1096

| aguugaagau ggacguacuu ugucugacua caauauucaa aaggagucua cucuucaucu | 60 |
| ug | 62 |

<210> SEQ ID NO 1097
<211> LENGTH: 68
<212> TYPE: RNA
<213> ORGANISM: homo sapiens

<400> SEQUENCE: 1097

| gaagccucuu ggggcuuauu uagacaaugg uuucaucauu ucgucugaau agagucugaa | 60 |
| gagucuuu | 68 |

<210> SEQ ID NO 1098
<211> LENGTH: 73
<212> TYPE: RNA
<213> ORGANISM: homo sapiens

<400> SEQUENCE: 1098

| uuggcaggug ccauguugcc ugcuccuuac uguacacgug gcuggcaagg agacgggaac | 60 |
| auggagccgc cau | 73 |

<210> SEQ ID NO 1099
<211> LENGTH: 73
<212> TYPE: RNA
<213> ORGANISM: homo sapiens

<400> SEQUENCE: 1099

| aggaagaaga ggaagaaaug gcugguucuc aggugaaugu gucugguuc aggggaugug | 60 |
| ucuccucuuu ucu | 73 |

<210> SEQ ID NO 1100
<211> LENGTH: 69
<212> TYPE: RNA
<213> ORGANISM: homo sapiens

<400> SEQUENCE: 1100

| ggcgggcuuc gcgggcgaag gcaaagucga uuccaaaag ugacuuuccu cacucccgug | 60 |
| aagucggcg | 69 |

<210> SEQ ID NO 1101
<211> LENGTH: 73
<212> TYPE: RNA

<213> ORGANISM: homo sapiens

<400> SEQUENCE: 1101
agggagaaaa gcugggcuga gaggcgacug gugucuaauu uguuugcuc uccaacucag      60 acugccuggc cca                                                       73

<210> SEQ ID NO 1102
<211> LENGTH: 76
<212> TYPE: RNA
<213> ORGANISM: homo sapiens

<400> SEQUENCE: 1102
cugcaaaaau aauugcaguu uuugccauua uuuuaauaa uuauaauaau ggccaaaacu      60
gcaguuauuu uugcac                                                    76

<210> SEQ ID NO 1103
<211> LENGTH: 76
<212> TYPE: RNA
<213> ORGANISM: homo sapiens

<400> SEQUENCE: 1103
cuacuuccag uaguggauga ugcacucugu gcagggccaa cugugcacac agugcuucau    60
ccacuacugg aagugu                                                    76

<210> SEQ ID NO 1104
<211> LENGTH: 49
<212> TYPE: RNA
<213> ORGANISM: homo sapiens

<400> SEQUENCE: 1104
gugaggcugg agugagcgga gaucguacca cugcacucca accugguga                49

<210> SEQ ID NO 1105
<211> LENGTH: 82
<212> TYPE: RNA
<213> ORGANISM: homo sapiens

<400> SEQUENCE: 1105
cuguuagguu ggugcaaaag uaauuguggu uuugaaagu aacuuggcga aaacgacaau     60
gacuuuugca ccaaucuaau ac                                             82

<210> SEQ ID NO 1106
<211> LENGTH: 94
<212> TYPE: RNA
<213> ORGANISM: homo sapiens

<400> SEQUENCE: 1106
ugguuugcga cucugaaaac uagaagguuu augacugggc auuucucacc caaugcccaa    60
uauugaacuu ucuaguuguc agagucauua accc                                94

<210> SEQ ID NO 1107
<211> LENGTH: 70
<212> TYPE: RNA
<213> ORGANISM: homo sapiens

<400> SEQUENCE: 1107
gcacugcggu ucugaggccg uuacuccggc uucuccauag agggcggaga aggcuggagc    60
gcggcgguga                                                           70

```
<210> SEQ ID NO 1108
<211> LENGTH: 84
<212> TYPE: RNA
<213> ORGANISM: homo sapiens

<400> SEQUENCE: 1108
gcaucuugca gagccguucc aaugcgacac cucuagagug ucaucccua gaaugucacc      60 uuggaaagac ucugcaagau gccu                                           84

<210> SEQ ID NO 1109
<211> LENGTH: 81
<212> TYPE: RNA
<213> ORGANISM: homo sapiens

<400> SEQUENCE: 1109
cauccuccuu acgucccacc ccccacuccu guuucggug aaauauucaa acaggagugg      60
gguggggaca uaaggaggau a                                              81

<210> SEQ ID NO 1110
<211> LENGTH: 53
<212> TYPE: RNA
<213> ORGANISM: homo sapiens

<400> SEQUENCE: 1110
ucacuuuagg agaaguaaag uagaacuuug guuucaacu uuccuacag ugu              53

<210> SEQ ID NO 1111
<211> LENGTH: 80
<212> TYPE: RNA
<213> ORGANISM: homo sapiens

<400> SEQUENCE: 1111
aggcagcaaa uggccagagc ucacacagag ggaugagugc acuucaccug cagugugacu     60
cagcaggcca acagaugcua                                                80

<210> SEQ ID NO 1112
<211> LENGTH: 85
<212> TYPE: RNA
<213> ORGANISM: homo sapiens

<400> SEQUENCE: 1112
gccucacuuu uccacuuaug ccugcccugc cccucgaauc ugcuccacga uuugggcagg     60
acaggcagaa guggauaagu gagga                                          85

<210> SEQ ID NO 1113
<211> LENGTH: 66
<212> TYPE: RNA
<213> ORGANISM: homo sapiens

<400> SEQUENCE: 1113
ggcccaucag ggcuugugga augggaagga gaagggacgc uccccuucu gcaggccugc      60 ugggug                                                               66

<210> SEQ ID NO 1114
<211> LENGTH: 74
<212> TYPE: RNA
<213> ORGANISM: homo sapiens

<400> SEQUENCE: 1114
gcaaauggcc agagcucaca cagagggaug agugcacuuc accugcagug ugacucagca     60
```

| | |
|---|---|
| ggccaacaga ugcu | 74 |

<210> SEQ ID NO 1115
<211> LENGTH: 70
<212> TYPE: RNA
<213> ORGANISM: homo sapiens

<400> SEQUENCE: 1115

| | |
|---|---|
| acguggugag gauauggcag ggaaggggag uuucccucua uucccuuccc cccaguaauc | 60 |
| uucaucaugc | 70 |

<210> SEQ ID NO 1116
<211> LENGTH: 60
<212> TYPE: RNA
<213> ORGANISM: homo sapiens

<400> SEQUENCE: 1116

| | |
|---|---|
| uaugaggagg uuggugugga uucuguugaa gaaaagaag gggaacacua auuuccauu | 60 |

<210> SEQ ID NO 1117
<211> LENGTH: 72
<212> TYPE: RNA
<213> ORGANISM: homo sapiens

<400> SEQUENCE: 1117

| | |
|---|---|
| uuuuggaaga cauggagcau gagguaagug ccuagauccu caaaccacuu gccuccaccu | 60 |
| augcuuccag gu | 72 |

<210> SEQ ID NO 1118
<211> LENGTH: 68
<212> TYPE: RNA
<213> ORGANISM: homo sapiens

<400> SEQUENCE: 1118

| | |
|---|---|
| cuuccucugg caaguaaaaa acucucauuu uccuuaaaaa augagaguuu uuacuugca | 60 |
| auaggaaa | 68 |

<210> SEQ ID NO 1119
<211> LENGTH: 60
<212> TYPE: RNA
<213> ORGANISM: homo sapiens

<400> SEQUENCE: 1119

| | |
|---|---|
| acuuugugca uuggguccac aaggagggga ugacccuugu gggcucaggg uacaagguu | 60 |

<210> SEQ ID NO 1120
<211> LENGTH: 70
<212> TYPE: RNA
<213> ORGANISM: homo sapiens

<400> SEQUENCE: 1120

| | |
|---|---|
| gcaguuuuug ccauuaaguu gcgguuuuug ccauuauaau ggcaaaaacu gcaauuacuu | 60 |
| ucacaccugc | 70 |

<210> SEQ ID NO 1121
<211> LENGTH: 67
<212> TYPE: RNA
<213> ORGANISM: homo sapiens

<400> SEQUENCE: 1121

| | |
|---|---|
| ugugcaaaag uaauuguggu uuuugucauu uaaaaguaau ggcaaaaacu gcaauuacuu | 60 | ucacacc 67

<210> SEQ ID NO 1122
<211> LENGTH: 77
<212> TYPE: RNA
<213> ORGANISM: homo sapiens

<400> SEQUENCE: 1122
acuugucaug ucuuacccag ucuccggugc agccuguugu caaggcugca ccggagacug   60
gguaagacau gacaagc                                                 77

<210> SEQ ID NO 1123
<211> LENGTH: 70
<212> TYPE: RNA
<213> ORGANISM: homo sapiens

<400> SEQUENCE: 1123
ugucuuaccc agucuccggu gcagccuuga caacaggcug caccggagac ugguaagac   60 augacaaguu                                                         70

<210> SEQ ID NO 1124
<211> LENGTH: 77
<212> TYPE: RNA
<213> ORGANISM: homo sapiens

<400> SEQUENCE: 1124
cgugucaucc ccagauacaa uggacaauau gcauuauaa ucguauggca uuguccuugc   60
uguuuggaga uaauacu                                                 77

<210> SEQ ID NO 1125
<211> LENGTH: 77
<212> TYPE: RNA
<213> ORGANISM: homo sapiens

<400> SEQUENCE: 1125
cgugucaucc ccagauacaa uggacaauau gcauuauaa ucguauggca uuguccuugc   60
uguuuggaga uaauacu                                                 77

<210> SEQ ID NO 1126
<211> LENGTH: 93
<212> TYPE: RNA
<213> ORGANISM: homo sapiens

<400> SEQUENCE: 1126
uaaguguaaa cuuaaggacu gucuuuucua agccugugcc uugccuuucc uuuggcacag   60
gcuuagaaaa gacagucuuu aaguuuacac uuc                                93

<210> SEQ ID NO 1127
<211> LENGTH: 73
<212> TYPE: RNA
<213> ORGANISM: homo sapiens

<400> SEQUENCE: 1127
ucucagaguc gaggacuggu ggaagggccu uuccccucag accaaggccc uggcccagc    60 uucuucucag agu                                                     73

<210> SEQ ID NO 1128
<211> LENGTH: 80
<212> TYPE: RNA

```
<213> ORGANISM: homo sapiens

<400> SEQUENCE: 1128
ccagugacug auaccuugga ggcauuuuau cuaagauaca cacaaagcaa augccucuaa    60
gguaucaguu uaccaggcca                                                80

<210> SEQ ID NO 1129
<211> LENGTH: 71
<212> TYPE: RNA
<213> ORGANISM: homo sapiens

<400> SEQUENCE: 1129
gcgcagaggg cuggacucag cggcggagcu ggcugcuggc cucaguucug ccucugucca    60
gguccuugug a                                                         71

<210> SEQ ID NO 1130
<211> LENGTH: 98
<212> TYPE: RNA
<213> ORGANISM: homo sapiens

<400> SEQUENCE: 1130
cucucaccaa gcaagugcag uggggcuugc uggcuugcac cgugacuccc ucucaccaag    60 caagugcgu ggggcuugcu ggcuugcacu gugaagau                             98

<210> SEQ ID NO 1131
<211> LENGTH: 100
<212> TYPE: RNA
<213> ORGANISM: homo sapiens

<400> SEQUENCE: 1131
cagagucucc uucguguaca gggaggagac uguacgugag agauagucag auccgcaugu    60
uagagcagag ucuccuucgu guacagggag gagauuguac                         100

<210> SEQ ID NO 1132
<211> LENGTH: 59
<212> TYPE: RNA
<213> ORGANISM: homo sapiens

<400> SEQUENCE: 1132
uggucauuga gucuucaagg cuaguggaaa gagcacugga cuuggaggca gaaagaccc     59

<210> SEQ ID NO 1133
<211> LENGTH: 67
<212> TYPE: RNA
<213> ORGANISM: homo sapiens

<400> SEQUENCE: 1133
gcgcccuccc ucucuccccg gugugcaaau guguguguge gguguuaugc cggacaagag    60
ggaggug                                                              67

<210> SEQ ID NO 1134
<211> LENGTH: 88
<212> TYPE: RNA
<213> ORGANISM: homo sapiens

<400> SEQUENCE: 1134
augugugugu auaugugugu ugcaugugug uauaugugug uauauaugua cacauacaca    60
uacacgcaac acacauauau acaugcac                                       88
```

```
<210> SEQ ID NO 1135
<211> LENGTH: 53
<212> TYPE: RNA
<213> ORGANISM: homo sapiens

<400> SEQUENCE: 1135
gguggggguu ggaggcgugg guuuuagaac cuaucccuuu cuagcccuga gca            53

<210> SEQ ID NO 1136
<211> LENGTH: 72
<212> TYPE: RNA
<213> ORGANISM: homo sapiens

<400> SEQUENCE: 1136
cgaucacuag auuaucuaca agggaauuuu uuuuuaauuu aaaaaauucc cuuguagaua    60
acccgguggu ca                                                         72

<210> SEQ ID NO 1137
<211> LENGTH: 77
<212> TYPE: RNA
<213> ORGANISM: homo sapiens

<400> SEQUENCE: 1137
caccaccaaa aucuccaggg gcaucguuga aaucguaagg gaugugcagc ucauuaagac    60
uggagacaaa gugggag                                                    77

<210> SEQ ID NO 1138
<211> LENGTH: 66
<212> TYPE: RNA
<213> ORGANISM: homo sapiens

<400> SEQUENCE: 1138
aaacugacug aauagguagg gucauuuuuc ugugacugca cauggcccaa ccuauucagu    60
uaguuc                                                                66

<210> SEQ ID NO 1139
<211> LENGTH: 74
<212> TYPE: RNA
<213> ORGANISM: homo sapiens

<400> SEQUENCE: 1139
gugacgacug gccccgccuc uuccucucgg ucccauauug aacucgaguu ggaagaggcg    60
aguccggucu caaa                                                       74

<210> SEQ ID NO 1140
<211> LENGTH: 70
<212> TYPE: RNA
<213> ORGANISM: homo sapiens

<400> SEQUENCE: 1140
uuccugcaga auguuucuuu ugccgugcaa guuuaaguuu uugcacggca aaagaaacaa    60
uccagagggu                                                            70

<210> SEQ ID NO 1141
<211> LENGTH: 70
<212> TYPE: RNA
<213> ORGANISM: homo sapiens

<400> SEQUENCE: 1141
uuccugcaga auguuucuuu ugccgugcaa guuuaaguuu uugcacggca aaagaaacaa    60
```
uccagagggu                                                              70

<210> SEQ ID NO 1142
<211> LENGTH: 67
<212> TYPE: RNA
<213> ORGANISM: homo sapiens

<400> SEQUENCE: 1142
cugguccauu ucccugccau ucccuuggcu ucaauuuacu cccagggcug gcagugacau       60
gggucaa                                                                 67

<210> SEQ ID NO 1143
<211> LENGTH: 91
<212> TYPE: RNA
<213> ORGANISM: homo sapiens

<400> SEQUENCE: 1143
guucuagagc augguuucuc aucauuugca cuacugauac uuggggucag auaauuguuu       60 guggugggg cuguuguuug cauuguagga u                                       91

<210> SEQ ID NO 1144
<211> LENGTH: 69
<212> TYPE: RNA
<213> ORGANISM: homo sapiens

<400> SEQUENCE: 1144 gggcauggg aggguggag ucagcauggg gcuaggaggc cccgcgcuga cccgccuucu        60
ccgcagcug                                                               69

<210> SEQ ID NO 1145
<211> LENGTH: 91
<212> TYPE: RNA
<213> ORGANISM: homo sapiens

<400> SEQUENCE: 1145
accugagcac cauuuacuga guccuuuguu cucuacuagu uuguaguagu ucguagcaga       60
gaacaaagga cucaguaaau ggugcucagg a                                      91

<210> SEQ ID NO 1146
<211> LENGTH: 86
<212> TYPE: RNA
<213> ORGANISM: homo sapiens

<400> SEQUENCE: 1146
aggagugacc aaaagacaag agugcgagcc uucuauuaug cccagacagg gccaccagag       60
ggcuccuugg ucuaggggua augcca                                            86

<210> SEQ ID NO 1147
<211> LENGTH: 66
<212> TYPE: RNA
<213> ORGANISM: homo sapiens

<400> SEQUENCE: 1147
agcagcccuc ggcggccggg ggcggggcg gcggugcccg ucccggggcu gcgcgaggca       60
caggcg                                                                  66

<210> SEQ ID NO 1148
<211> LENGTH: 66
<212> TYPE: RNA
<213> ORGANISM: homo sapiens

```
<400> SEQUENCE: 1148
gugcaaaggu aauugugguu ucugcuuuua aagguaaugg caaauauuac auuuacuuuu      60
gcacca                                                                66

<210> SEQ ID NO 1149
<211> LENGTH: 64
<212> TYPE: RNA
<213> ORGANISM: homo sapiens

<400> SEQUENCE: 1149
ugcaaaggua auugugguuu cugccauuga aaguaaaggc aagaaccuca auuaccuuug      60
cagc                                                                  64

<210> SEQ ID NO 1150
<211> LENGTH: 65
<212> TYPE: RNA
<213> ORGANISM: homo sapiens

<400> SEQUENCE: 1150
ugucugggga uuuggagaag uggugagcgc aggucuuugg caccaucucc ccuggucccu      60
uggcu                                                                 65

<210> SEQ ID NO 1151
<211> LENGTH: 76
<212> TYPE: RNA
<213> ORGANISM: homo sapiens

<400> SEQUENCE: 1151
agguuggugc aaaagugauu gcagguguuug ccaauaaaag uaaugacaaa aacugcaguu     60
acuuuugcac cagccc                                                     76

<210> SEQ ID NO 1152
<211> LENGTH: 66
<212> TYPE: RNA
<213> ORGANISM: homo sapiens

<400> SEQUENCE: 1152
ucuguaccuc agcuuugcuc ccaaccaacc acuuccacau guuuugcugg uagagcugag      60
gacagc                                                                66

<210> SEQ ID NO 1153
<211> LENGTH: 71
<212> TYPE: RNA
<213> ORGANISM: homo sapiens

<400> SEQUENCE: 1153
uggaucacuu gaggccaaga gugcaaggcu guagugugca cagccuugaa uucuuggccu      60
uaagugaucc c                                                          71

<210> SEQ ID NO 1154
<211> LENGTH: 70
<212> TYPE: RNA
<213> ORGANISM: homo sapiens

<400> SEQUENCE: 1154
ucagaguagg agcucaacag augccuguug acugaauaau aaacagguau cgcaggagcu      60
uuuguuaugu                                                            70
```

<210> SEQ ID NO 1155
<211> LENGTH: 96
<212> TYPE: RNA
<213> ORGANISM: homo sapiens

<400> SEQUENCE: 1155
uguccucuug agguaccuga auuaccaaaa gcuuuaugua uucugaaguu auugaaaaua     60
agagcuuuug ggaauucagg uaguucagga gugacu                              96

<210> SEQ ID NO 1156
<211> LENGTH: 88
<212> TYPE: RNA
<213> ORGANISM: homo sapiens

<400> SEQUENCE: 1156
uggagagcuu ggucuguagc gguuuccuug gggcaggugg ggacugcucc uuugggagga     60
aggaggaggc ccaggccgcg ucuucagg                                       88

<210> SEQ ID NO 1157
<211> LENGTH: 55
<212> TYPE: RNA
<213> ORGANISM: homo sapiens

<400> SEQUENCE: 1157
ccggauccga gucacggcac caaauuucau gcguguccgu gugaagagac cacca          55

<210> SEQ ID NO 1158
<211> LENGTH: 68
<212> TYPE: RNA
<213> ORGANISM: homo sapiens

<400> SEQUENCE: 1158
guggugcaaa agugaucgug guuuuugcaa uuuuuuaaug acaaaaacca caauuacuuu     60
ugcaccaa                                                             68

<210> SEQ ID NO 1159
<211> LENGTH: 58
<212> TYPE: RNA
<213> ORGANISM: homo sapiens

<400> SEQUENCE: 1159
agaagggugu guguguuuuu ccugagaaua agagaaggaa ggacagccaa auucuuca       58

<210> SEQ ID NO 1160
<211> LENGTH: 43
<212> TYPE: RNA
<213> ORGANISM: homo sapiens

<400> SEQUENCE: 1160
augaaccugg uggcuuccuu uucugggagg aaguuagggu uca                      43

<210> SEQ ID NO 1161
<211> LENGTH: 68
<212> TYPE: RNA
<213> ORGANISM: homo sapiens

<400> SEQUENCE: 1161
ggaguacucc agucaauacc gugugaguua gaaaagcuca auucacaagg uauugacugg     60
cguauuca                                                             68

```
<210> SEQ ID NO 1162
<211> LENGTH: 75
<212> TYPE: RNA
<213> ORGANISM: homo sapiens

<400> SEQUENCE: 1162
gagcgcacag agguaggugu ggaagaaagu gaaacacuau uuagguuuu aguuacacuc    60 ugcuguggug ugcug                                                   75

<210> SEQ ID NO 1163
<211> LENGTH: 66
<212> TYPE: RNA
<213> ORGANISM: homo sapiens

<400> SEQUENCE: 1163
acccaggagg cggaggaggu ggagguugca gugagccaag aucguggcac ugacuccagc    60
cugggg                                                             66

<210> SEQ ID NO 1164
<211> LENGTH: 75
<212> TYPE: RNA
<213> ORGANISM: homo sapiens

<400> SEQUENCE: 1164
augaugugga ggacugagaa ggugaggcag uuugccccg ugcugccuuc caccgguuaa    60
gaccuccaaa aucga                                                   75

<210> SEQ ID NO 1165
<211> LENGTH: 76
<212> TYPE: RNA
<213> ORGANISM: homo sapiens

<400> SEQUENCE: 1165
ggacaaaauu aaaaugcucu ucugucauug uaauaguuca uaugggcacu gacaggagag    60
cauuuugacu uuguca                                                  76

<210> SEQ ID NO 1166
<211> LENGTH: 57
<212> TYPE: RNA
<213> ORGANISM: homo sapiens

<400> SEQUENCE: 1166
gguucacugg ucgugcuucc ugcgggcuga gcgcgggcug agcgcugcca gucagcg       57

<210> SEQ ID NO 1167
<211> LENGTH: 66
<212> TYPE: RNA
<213> ORGANISM: homo sapiens

<400> SEQUENCE: 1167
gcucagucag cugggccgcc ucagcucucg gaguaggaag cucgggcgcu ccggcuguaa    60
ggagcc                                                             66

<210> SEQ ID NO 1168
<211> LENGTH: 86
<212> TYPE: RNA
<213> ORGANISM: homo sapiens

<400> SEQUENCE: 1168 guuuuugcc cauagugguu gugaauuuac cuucuccucu uugcagugau aaaggaggua    60
```
aauucacaac cacugugggc agaaac            86

<210> SEQ ID NO 1169
<211> LENGTH: 74
<212> TYPE: RNA
<213> ORGANISM: homo sapiens

<400> SEQUENCE: 1169
gaguaggcuu agguuaugua cguagucuag gccauacgug uuggagauug agacuaguag    60
ggcuaggccu acug            74

<210> SEQ ID NO 1170
<211> LENGTH: 74
<212> TYPE: RNA
<213> ORGANISM: homo sapiens

<400> SEQUENCE: 1170
auagcugguu ggcauucugg cccugguuca ugccaacucu uguuugacu accccaggau    60 gccagcauag uugc            74

<210> SEQ ID NO 1171
<211> LENGTH: 83
<212> TYPE: RNA
<213> ORGANISM: homo sapiens

<400> SEQUENCE: 1171
acaggaacac uggacuuggu gucagauggg augagcccug gcucuguuuc cuagcagcaa    60
ucugaucuug agcuagucac ugg            83

<210> SEQ ID NO 1172
<211> LENGTH: 80
<212> TYPE: RNA
<213> ORGANISM: homo sapiens

<400> SEQUENCE: 1172
ggggacaaug augagaagac cugaggauuu gcagccccca gcccuggguu caagucccag    60
cucuaccccu ucuuggcccc            80

<210> SEQ ID NO 1173
<211> LENGTH: 80
<212> TYPE: RNA
<213> ORGANISM: homo sapiens

<400> SEQUENCE: 1173
guuucaccgc ucgaucuugg dacccaccgc ugcccucagc uccgaguccar gggcgaggua    60 agggcuggag ucgggcagga            80

<210> SEQ ID NO 1174
<211> LENGTH: 92
<212> TYPE: RNA
<213> ORGANISM: homo sapiens

<400> SEQUENCE: 1174
auugaggcac ugguagugg augauggaga cucgguaccc acugcugagg gugggacca    60 agucugcguc auccucuccu cagugccuca aa            92

<210> SEQ ID NO 1175
<211> LENGTH: 77
<212> TYPE: RNA
<213> ORGANISM: homo sapiens

```
<400> SEQUENCE: 1175
gucucgggag cguuagagau ggagacuaac gucuuccaag ggagauugcg ucuccacuuu      60
cacccugguu cugagag                                                    77

<210> SEQ ID NO 1176
<211> LENGTH: 68
<212> TYPE: RNA
<213> ORGANISM: homo sapiens

<400> SEQUENCE: 1176
ugcccaggcu ggagcgagug cagguggugca gucaguccua gcucacugca gccucgaacu     60
ccugggcu                                                              68

<210> SEQ ID NO 1177
<211> LENGTH: 67
<212> TYPE: RNA
<213> ORGANISM: homo sapiens

<400> SEQUENCE: 1177
uuuucaggug uggaaacuga ggcaggaggc agugaaguaa cuugcucagg uugcacagcu      60
gggaagu                                                               67

<210> SEQ ID NO 1178
<211> LENGTH: 58
<212> TYPE: RNA
<213> ORGANISM: homo sapiens

<400> SEQUENCE: 1178
cuucccagcu gcccuaaguc aggagugggcu uuccugacac ggaggguggc uugggaaa       58

<210> SEQ ID NO 1179
<211> LENGTH: 66
<212> TYPE: RNA
<213> ORGANISM: homo sapiens

<400> SEQUENCE: 1179
ggugaagaug gugcugugcu gaggaaaggg gaugcagagc ccugcccagc accaccaccu      60
ccuaug                                                                66

<210> SEQ ID NO 1180
<211> LENGTH: 68
<212> TYPE: RNA
<213> ORGANISM: homo sapiens

<400> SEQUENCE: 1180
auggugcaaa aguaaugugg uuuuuuucuu uacuuuaau ggcaaagacu gcaauuacuu       60
uugcgcca                                                              68

<210> SEQ ID NO 1181
<211> LENGTH: 67
<212> TYPE: RNA
<213> ORGANISM: homo sapiens

<400> SEQUENCE: 1181
aauagauuau uggucaccac cuccaguuuc ugaauugug agacuggggu ggggccugag       60
aauuugc                                                               67

<210> SEQ ID NO 1182
```

```
<211> LENGTH: 92
<212> TYPE: RNA
<213> ORGANISM: homo sapiens

<400> SEQUENCE: 1182
ggaaccuuag uaagguuugg auagaugcaa uaaaguaugu ccacagcuga aaggacauac      60
uuuauugcau guauccaaac cuuacuaauu ca                                   92

<210> SEQ ID NO 1183
<211> LENGTH: 88
<212> TYPE: RNA
<213> ORGANISM: homo sapiens

<400> SEQUENCE: 1183
guauuagguu ggugcaaagg uaauugcagu uuuucccauu uaaaauaugg aaaaaaaaau     60
cacaauuacu uuugcaucaa ccuaauaa                                        88

<210> SEQ ID NO 1184
<211> LENGTH: 83
<212> TYPE: RNA
<213> ORGANISM: homo sapiens

<400> SEQUENCE: 1184
gaaacuacac uuuaagggga ccaaagagau auauagauau cagcuaccua uauaccuguu     60
cggucucuuu aaaguguagu uua                                             83

<210> SEQ ID NO 1185
<211> LENGTH: 72
<212> TYPE: RNA
<213> ORGANISM: homo sapiens

<400> SEQUENCE: 1185
auugguguaa aaguaauugc agguuaugcc auuaaaagua augguaaaaa cugcaauuac     60
uuuuacacua ac                                                         72

<210> SEQ ID NO 1186
<211> LENGTH: 92
<212> TYPE: RNA
<213> ORGANISM: homo sapiens

<400> SEQUENCE: 1186
aagguauuag guuggugcaa aaguaauugc aguuuuugcu auuacuuuua auggugaaaaa    60 cugcaauuac uuuuacacca accuaauauu ua                                   92

<210> SEQ ID NO 1187
<211> LENGTH: 70
<212> TYPE: RNA
<213> ORGANISM: homo sapiens

<400> SEQUENCE: 1187
cauguguccc cuggcacgcu auuugagguu uacuauggaa ccucaaguag ucugaccagg     60
ggacacauga                                                            70

<210> SEQ ID NO 1188
<211> LENGTH: 55
<212> TYPE: RNA
<213> ORGANISM: homo sapiens

<400> SEQUENCE: 1188
gcucuaguag ccacagccau ccccuagagg gaucuggcug aggaggaagu ggagg          55
```

<210> SEQ ID NO 1189
<211> LENGTH: 71
<212> TYPE: RNA
<213> ORGANISM: homo sapiens

<400> SEQUENCE: 1189
ccgccucagu ggcuuccucc acagccaccu ccggagggau cuggcugagg aggaagugga    60
ggugucacug g                                                         71

<210> SEQ ID NO 1190
<211> LENGTH: 65
<212> TYPE: RNA
<213> ORGANISM: homo sapiens

<400> SEQUENCE: 1190
cugggcgaca aaacgagacc cugucuuuuu uuuuucuga dacagagucu cguucuguug    60
cccaa                                                                65

<210> SEQ ID NO 1191
<211> LENGTH: 54
<212> TYPE: RNA
<213> ORGANISM: homo sapiens

<400> SEQUENCE: 1191
acgcgggugc gggccggcgg gguagaagcc acccggcccg gcccggcccg gcga          54

<210> SEQ ID NO 1192
<211> LENGTH: 71
<212> TYPE: RNA
<213> ORGANISM: homo sapiens

<400> SEQUENCE: 1192
gccauuccug cuggucagga guggauacug gagcaauaga uacaguucca cacugacacu    60
gcagaagugg a                                                         71

<210> SEQ ID NO 1193
<211> LENGTH: 98
<212> TYPE: RNA
<213> ORGANISM: homo sapiens

<400> SEQUENCE: 1193
auuuucuuug cuaagucccu ucuuucuauc cuaguauaac uugaagaauu caaauaguca    60
ugcuaggaua gaaagaaugg gacuuggcca gggaagaa                            98

<210> SEQ ID NO 1194
<211> LENGTH: 62
<212> TYPE: RNA
<213> ORGANISM: homo sapiens

<400> SEQUENCE: 1194
gaauagaaag aauguggaag uggucugagg cauauagagu auaugccaag aacacuacca    60
ua                                                                   62

<210> SEQ ID NO 1195
<211> LENGTH: 72
<212> TYPE: RNA
<213> ORGANISM: homo sapiens

<400> SEQUENCE: 1195

```
acaguaacuu uuauucucau uuccuuuuc ucuaccuugu agagaagcaa agugaugagu    60
aauacuggcu gg                                                      72

<210> SEQ ID NO 1196
<211> LENGTH: 63
<212> TYPE: RNA
<213> ORGANISM: homo sapiens

<400> SEQUENCE: 1196
ugguggcggc gguaguuaug ggcuucucuu ucucaccagc agccccuggg ccgccgccuc   60
ccu                                                                63

<210> SEQ ID NO 1197
<211> LENGTH: 64
<212> TYPE: RNA
<213> ORGANISM: homo sapiens

<400> SEQUENCE: 1197
agucuucucc uggggcuuug guggcuaugg uugacugggc cacucagagc agaaggauga   60
gaug                                                               64

<210> SEQ ID NO 1198
<211> LENGTH: 67
<212> TYPE: RNA
<213> ORGANISM: homo sapiens

<400> SEQUENCE: 1198
ccuggcagcc cucuggccua guucccacca cacaugaggu gguggaaugg ccugaaggug   60
gaacaga                                                            67

<210> SEQ ID NO 1199
<211> LENGTH: 79
<212> TYPE: RNA
<213> ORGANISM: homo sapiens

<400> SEQUENCE: 1199
ccgacgcgga gagcggcucu aggugggguuu ggcggcggcg aggacaccgc cgcucccucu   60
agggucgcuc ggagcguga                                                79

<210> SEQ ID NO 1200
<211> LENGTH: 72
<212> TYPE: RNA
<213> ORGANISM: homo sapiens

<400> SEQUENCE: 1200
cgagccucuu ucggcuuucc aguuugucuc gguccuuugg aacguggcaa acguggaagc   60
cgagagggcu cu                                                      72

<210> SEQ ID NO 1201
<211> LENGTH: 87
<212> TYPE: RNA
<213> ORGANISM: homo sapiens

<400> SEQUENCE: 1201
auauacauac auguacacac acaugucauc cacacacaua cauauauaua uguuuguaug   60
gauaugugug uguaugugug uguauac                                      87

<210> SEQ ID NO 1202
<211> LENGTH: 76
```

```
<212> TYPE: RNA
<213> ORGANISM: homo sapiens

<400> SEQUENCE: 1202
aaagcaggcc aaccucgagg aucuccccag ccuuggcguu caggugcuga ggagaucguc    60
gagguuggcc ugcuuc                                                   76

<210> SEQ ID NO 1203
<211> LENGTH: 83
<212> TYPE: RNA
<213> ORGANISM: homo sapiens

<400> SEQUENCE: 1203
ccaaauuuaa aacuuaaacc ucuacuaagu uccaugaaa agaacccaug ggaacuuagu     60
agagguuuaa guuuuaaauu uga                                           83

<210> SEQ ID NO 1204
<211> LENGTH: 80
<212> TYPE: RNA
<213> ORGANISM: homo sapiens

<400> SEQUENCE: 1204
uggcagaccc uugcucucuc acucucccua auggggcuga agacagcuca ggggcagggu    60
gggggguguu guuuuuguuu                                               80

<210> SEQ ID NO 1205
<211> LENGTH: 67
<212> TYPE: RNA
<213> ORGANISM: homo sapiens

<400> SEQUENCE: 1205
uggugggggu gggggguguu guuuuuguuu uugagacaga gucuugcucc gucgcccagg    60
ccggagu                                                             67

<210> SEQ ID NO 1206
<211> LENGTH: 91
<212> TYPE: RNA
<213> ORGANISM: homo sapiens

<400> SEQUENCE: 1206
aaggaacagg ggacacuugu aauggagaac acuaagcuau ggacugcuau ggacugcuag    60
ugcucuccgu uacaaguauc cccuguuacc u                                  91

<210> SEQ ID NO 1207
<211> LENGTH: 94
<212> TYPE: RNA
<213> ORGANISM: homo sapiens

<400> SEQUENCE: 1207
aaaggaacag gggacacuug uaauggagaa cacuaagcua uggacugcua uggacugcua    60
gugcucuccg uuacaaguau ccccuguuac cuug                               94

<210> SEQ ID NO 1208
<211> LENGTH: 78
<212> TYPE: RNA
<213> ORGANISM: homo sapiens

<400> SEQUENCE: 1208
uugccuaccu uguuagucuc augaucagac acaaauaugg cucuuugugg cuggucauga    60
```

```
ggcuaacaag guaggcac                                              78

<210> SEQ ID NO 1209
<211> LENGTH: 70
<212> TYPE: RNA
<213> ORGANISM: homo sapiens

<400> SEQUENCE: 1209
augcugcccu gggguucuga ggacaugcuc ugacuccccu gauguccucu guuccucagg   60
ugcugggcga                                                        70

<210> SEQ ID NO 1210
<211> LENGTH: 61
<212> TYPE: RNA
<213> ORGANISM: homo sapiens

<400> SEQUENCE: 1210
aucucaauga guguggguu cuaaaugacu cauagucaag ggaccaagca uucauuauga   60
a                                                                 61

<210> SEQ ID NO 1211
<211> LENGTH: 70
<212> TYPE: RNA
<213> ORGANISM: homo sapiens

<400> SEQUENCE: 1211
aaaagccugu cccuaaguuc cucccagccu uccagaguug gugccaggaa ggauuuaggg   60
acaggcuuug                                                        70

<210> SEQ ID NO 1212
<211> LENGTH: 81
<212> TYPE: RNA
<213> ORGANISM: homo sapiens

<400> SEQUENCE: 1212
uccuccuccc aucaaucaca aauguccuua auggcauuua aggauugcua uuaaggacau   60
uugugauuca cgggaggagg u                                           81

<210> SEQ ID NO 1213
<211> LENGTH: 81
<212> TYPE: RNA
<213> ORGANISM: homo sapiens

<400> SEQUENCE: 1213
accuccuccc gugaaucaca aauguccuua auagcaaucc uuaaaugcca uuaaggacau   60
uugugauuga ugggaggagg a                                           81

<210> SEQ ID NO 1214
<211> LENGTH: 84
<212> TYPE: RNA
<213> ORGANISM: homo sapiens

<400> SEQUENCE: 1214 cuuuuuugu ugcuugucuu gguuuaugc cuuuuaugug ccugauaua aaaggcauaa    60 aaccaagaca agcaacagaa aaac                                        84

<210> SEQ ID NO 1215
<211> LENGTH: 84
<212> TYPE: RNA
<213> ORGANISM: homo sapiens
```

```
<400> SEQUENCE: 1215
cugucaguuu uucuguugcu ugucuugguu uuaugccuuu uauaucaagg cacauaaaag    60
gcauaaaacc aagacaagca acaa                                          84

<210> SEQ ID NO 1216
<211> LENGTH: 86
<212> TYPE: RNA
<213> ORGANISM: homo sapiens

<400> SEQUENCE: 1216
ggccgaggcu gagcugagga gccuccaaac cuguagacag ggucaugcag uacuaggggc    60
gagccucauc cccugcagcc cuggcc                                        86

<210> SEQ ID NO 1217
<211> LENGTH: 72
<212> TYPE: RNA
<213> ORGANISM: homo sapiens

<400> SEQUENCE: 1217
gggaggugug auaucguggu uccugggagg ugugauaucg ugguuccugg gaggugugau    60
auugugguuc cu                                                       72

<210> SEQ ID NO 1218
<211> LENGTH: 100
<212> TYPE: RNA
<213> ORGANISM: homo sapiens

<400> SEQUENCE: 1218
augccaaaua uuagguuggc acaaaaguaa uuguggcuuu ugccauuaaa aguaauggua    60
aaaacugcaa uuacuuucgu gccaaccuaa uauuugugug                        100

<210> SEQ ID NO 1219
<211> LENGTH: 65
<212> TYPE: RNA
<213> ORGANISM: homo sapiens

<400> SEQUENCE: 1219
agugcaaaag uaauugcagu uuuugcguua cuuucaaucg uaaaaacugc aauuacuuuc    60
acacc                                                               65

<210> SEQ ID NO 1220
<211> LENGTH: 85
<212> TYPE: RNA
<213> ORGANISM: homo sapiens

<400> SEQUENCE: 1220
gcucccuggg aggugugaua ucaugguucc ugggaggugu gauccugugc uuccgggag    60 gugugauauc gugguuccug ggagg                                         85

<210> SEQ ID NO 1221
<211> LENGTH: 74
<212> TYPE: RNA
<213> ORGANISM: homo sapiens

<400> SEQUENCE: 1221
ugggaggugu gaucucacac ucgcugggag gugugcuauc gucuuccccg ggaggguguga    60 uccuguucuu ccug                                                     74
```

```
<210> SEQ ID NO 1222
<211> LENGTH: 72
<212> TYPE: RNA
<213> ORGANISM: homo sapiens

<400> SEQUENCE: 1222
gggaggugug auaucauggu uccugggagg ugugaucccg ugcuuccugg gaggugugau      60
auugugguuc cu                                                          72

<210> SEQ ID NO 1223
<211> LENGTH: 72
<212> TYPE: RNA
<213> ORGANISM: homo sapiens

<400> SEQUENCE: 1223
gggaggugug auaucauggu uccugggagg ugugaucccg ugcuuccugg gaggugugau      60
auugugguuc cu                                                          72

<210> SEQ ID NO 1224
<211> LENGTH: 80
<212> TYPE: RNA
<213> ORGANISM: homo sapiens

<400> SEQUENCE: 1224
acugggaggu gugaucucac acucgcuggg aggugugcua ucgucuuccc ugggaggugu      60
gauccuguuc uuccugagcg                                                  80

<210> SEQ ID NO 1225
<211> LENGTH: 72
<212> TYPE: RNA
<213> ORGANISM: homo sapiens

<400> SEQUENCE: 1225
gggaggugug auaucauggu uccugggagg uaugauaucg ugguuccugg gaggugugau      60
cccgugcucc cu                                                          72

<210> SEQ ID NO 1226
<211> LENGTH: 66
<212> TYPE: RNA
<213> ORGANISM: homo sapiens

<400> SEQUENCE: 1226
aggugugaua ucgugcuucc ugggacgugu gaugcugugc uuccugggag gugugauccc      60
acacuc                                                                 66

<210> SEQ ID NO 1227
<211> LENGTH: 71
<212> TYPE: RNA
<213> ORGANISM: homo sapiens

<400> SEQUENCE: 1227
gaaaccaagu ccgagcgugg cuggcgcggg aaaguucggg aacgcgcgcg gccgugcucg      60
gagcagcgcc a                                                           71

<210> SEQ ID NO 1228
<211> LENGTH: 92
<212> TYPE: RNA
<213> ORGANISM: homo sapiens

<400> SEQUENCE: 1228
```

```
ccuguuccgg gcaucaccuc ccacugcaga gccuggggag ccggacagcu cccuucccag    60
gcucugcagu gggaacugau gccuggaaca gu                                  92

<210> SEQ ID NO 1229
<211> LENGTH: 56
<212> TYPE: RNA
<213> ORGANISM: homo sapiens

<400> SEQUENCE: 1229
ccacugcaga gccugggaag ggagcugucc ggcucccccag gcucugcagu gggagu       56

<210> SEQ ID NO 1230
<211> LENGTH: 57
<212> TYPE: RNA
<213> ORGANISM: homo sapiens

<400> SEQUENCE: 1230
gugcaaaagu aacugcgguu uuugagaagu aauugaaaac cgcaauuacu uuugcag       57

<210> SEQ ID NO 1231
<211> LENGTH: 71
<212> TYPE: RNA
<213> ORGANISM: homo sapiens

<400> SEQUENCE: 1231
gcagagguga guugaccucc acagggccac ccagggagua aguagccaag uggaaguuac    60
uuuaccucug u                                                         71

<210> SEQ ID NO 1232
<211> LENGTH: 60
<212> TYPE: RNA
<213> ORGANISM: homo sapiens

<400> SEQUENCE: 1232
ggagugggcu ggugguuuuu uaagaggaag ggagaccuaa gcuagcacau gagcacgcuc    60

<210> SEQ ID NO 1233
<211> LENGTH: 56
<212> TYPE: RNA
<213> ORGANISM: homo sapiens

<400> SEQUENCE: 1233
cggcuucccg cggucccccgg ugcugaggag agagcgaucc gagggacugc gccgcc       56

<210> SEQ ID NO 1234
<211> LENGTH: 91
<212> TYPE: RNA
<213> ORGANISM: homo sapiens

<400> SEQUENCE: 1234
acauuauuca ggccgguccu gcagagagga agcccuucca auaccuguaa gcagaagggc    60
uuccucucug caggaccggc cugaauaaug a                                   91

<210> SEQ ID NO 1235
<211> LENGTH: 99
<212> TYPE: RNA
<213> ORGANISM: homo sapiens

<400> SEQUENCE: 1235
ggaucauuau ucaggccggu ccugcagaga ggaagcccuu cugcuuacag guauuggaag    60
```

```
ggcuuccucu cugcaggacc ggccugaaua auguaauca                                  99
```

<210> SEQ ID NO 1236
<211> LENGTH: 70
<212> TYPE: RNA
<213> ORGANISM: homo sapiens

<400> SEQUENCE: 1236

```
agugagcaac ccaguggggcu auggaaaugu guggaagaug gcauuucuau uucucagugg          60
ggcucuuacc                                                                 70
```

<210> SEQ ID NO 1237
<211> LENGTH: 62
<212> TYPE: RNA
<213> ORGANISM: homo sapiens

<400> SEQUENCE: 1237

```
aaaaaacaac auacuuagug cauacccaua uaauauuagg ggggucugu uguuguuuuu            60 cu                                                                         62
```

<210> SEQ ID NO 1238
<211> LENGTH: 83
<212> TYPE: RNA
<213> ORGANISM: homo sapiens

<400> SEQUENCE: 1238

```
ggguuccuc ugccuuuuuu uccaaugaaa auaacgaaac cuguuauuc ccaugaggg              60 ggaaaaaggc gggagaagcc cca                                                  83
```

<210> SEQ ID NO 1239
<211> LENGTH: 69
<212> TYPE: RNA
<213> ORGANISM: homo sapiens

<400> SEQUENCE: 1239

```
ggagccagcc cuccucccgc acccaaacuu ggagcacuug accuuuggcu guuggagggg          60
gcaggcucg                                                                  69
```

<210> SEQ ID NO 1240
<211> LENGTH: 57
<212> TYPE: RNA
<213> ORGANISM: homo sapiens

<400> SEQUENCE: 1240

```
agaggcaccg ccugcccagu gacaugcguu uaacggccgc gguacccuaa cugugca             57
```

<210> SEQ ID NO 1241
<211> LENGTH: 60
<212> TYPE: RNA
<213> ORGANISM: homo sapiens

<400> SEQUENCE: 1241

```
ccuaggauua caagugucgg ccacgggcug ggcacagugg cucacgccug uaaucccagc          60
```

<210> SEQ ID NO 1242
<211> LENGTH: 63
<212> TYPE: RNA
<213> ORGANISM: homo sapiens

<400> SEQUENCE: 1242

```
gcaugcuggg cgaggcuggc aucuagcaca ggcgguagau gcuugcucuu gccauugcaa          60
```

```
uga                                                                        63

<210> SEQ ID NO 1243
<211> LENGTH: 73
<212> TYPE: RNA
<213> ORGANISM: homo sapiens

<400> SEQUENCE: 1243
acuguccuuc agccagagcu ggcugaaggg cagaagggaa cuguccuuca gccagagcug         60
gcugaagggc aga                                                            73

<210> SEQ ID NO 1244
<211> LENGTH: 62
<212> TYPE: RNA
<213> ORGANISM: homo sapiens

<400> SEQUENCE: 1244 gguaggggc gggcuccggc gcuggacccc cacuagggug gcgccuuggc cccgcccgc           60 cc                                                                        62

<210> SEQ ID NO 1245
<211> LENGTH: 56
<212> TYPE: RNA
<213> ORGANISM: homo sapiens

<400> SEQUENCE: 1245
ucgccgagag ucgucggggu uccugcuuc aacagugcuu ggacggaacc cggcgc              56

<210> SEQ ID NO 1246
<211> LENGTH: 62
<212> TYPE: RNA
<213> ORGANISM: homo sapiens

<400> SEQUENCE: 1246
gggggugggg cuagugaugc aggacgcugg ggacuggaga aguccugccu gacccuguc          60 ca                                                                        62

<210> SEQ ID NO 1247
<211> LENGTH: 78
<212> TYPE: RNA
<213> ORGANISM: homo sapiens

<400> SEQUENCE: 1247
uggaaacugu gacuuuaagg gaaauggcgc acagcagacc cugcaaucau gccguuugc          60 uugaagucgc aguuccc                                                        78

<210> SEQ ID NO 1248
<211> LENGTH: 90
<212> TYPE: RNA
<213> ORGANISM: homo sapiens

<400> SEQUENCE: 1248
aacuugaagg uagggaacuc ugucuucacu caugaguacc uuccaacacg agcucucagg         60
aguaaagaca gaguucccua ccuucaaugu                                          90

<210> SEQ ID NO 1249
<211> LENGTH: 61
<212> TYPE: RNA
<213> ORGANISM: homo sapiens
```

-continued

<400> SEQUENCE: 1249
caagguggau gcaaugugac cucaacucuu gguccucuga ggucacauug uauccaccuu     60
a                                                                    61

<210> SEQ ID NO 1250
<211> LENGTH: 97
<212> TYPE: RNA
<213> ORGANISM: homo sapiens

<400> SEQUENCE: 1250
ggucggugca aaaguaauug cuguuuugc cauuaaaaau aauggcauua aaaguaaugg       60
caaaaacggc aaugacuuuu guaccaaucu aauaucu                             97

<210> SEQ ID NO 1251
<211> LENGTH: 84
<212> TYPE: RNA
<213> ORGANISM: homo sapiens

<400> SEQUENCE: 1251
auaguuucug caaugcucaa aucucuggcc aaagaccaga acuuaauggu cucugguaag     60
agauuugggc auauuagaaa cuaa                                           84

<210> SEQ ID NO 1252
<211> LENGTH: 68
<212> TYPE: RNA
<213> ORGANISM: homo sapiens

<400> SEQUENCE: 1252
acauuugguc acaccagucc acauuaacgu ggaccagaca auauuaaugu ggacuggugu     60
gaccaaaa                                                             68

<210> SEQ ID NO 1253
<211> LENGTH: 82
<212> TYPE: RNA
<213> ORGANISM: homo sapiens

<400> SEQUENCE: 1253
accuggacau uuggucacac caguccacau uaacguggac cagacaauau uaauguggac     60
uggugugacc aaaaguccag gc                                             82

<210> SEQ ID NO 1254
<211> LENGTH: 80
<212> TYPE: RNA
<213> ORGANISM: homo sapiens

<400> SEQUENCE: 1254
cugcagcgug cuucuccagg ccccgcgcgc ggacagacac acggacaagu cccgccaggg     60
gcugggcgcg cgccagccgg                                                80

<210> SEQ ID NO 1255
<211> LENGTH: 73
<212> TYPE: RNA
<213> ORGANISM: homo sapiens

<400> SEQUENCE: 1255
ccagagaugg gaaggccuuc cggugauuau cacagccaug ccuuuaccuc cagaaggccu     60
uuccaucucu guc                                                       73

<210> SEQ ID NO 1256
<211> LENGTH: 84
<212> TYPE: RNA
<213> ORGANISM: homo sapiens

<400> SEQUENCE: 1256
aguuuuaguu acccugguca ucugcagucu gaaaauacaa aauggaaaau uccagacugu    60
ggcugaccag agguaacuga aacc                                          84

<210> SEQ ID NO 1257
<211> LENGTH: 42
<212> TYPE: RNA
<213> ORGANISM: homo sapiens

<400> SEQUENCE: 1257
cugaggagaa gcaggagcug ucuugguaca uucaggucac ug                      42

<210> SEQ ID NO 1258
<211> LENGTH: 66
<212> TYPE: RNA
<213> ORGANISM: homo sapiens

<400> SEQUENCE: 1258
aagaaaugua aacaggcuuu uugcucagug gaguuauuuu gagcaaaaag cuuauuuaca    60
uuucug                                                              66

<210> SEQ ID NO 1259
<211> LENGTH: 61
<212> TYPE: RNA
<213> ORGANISM: homo sapiens

<400> SEQUENCE: 1259
acaucagcuc auauaauccu cgaagcugcc uuuagaaaug aggaaacuga agcugagagg    60
g                                                                   61

<210> SEQ ID NO 1260
<211> LENGTH: 89
<212> TYPE: RNA
<213> ORGANISM: homo sapiens

<400> SEQUENCE: 1260
accuccggga cggcugggcg ccggcggccg ggagauccgc gcuuccugaa ucccggccgg    60
cccgcccggc gcccguccgc ccgcgdgguc                                    89

<210> SEQ ID NO 1261
<211> LENGTH: 66
<212> TYPE: RNA
<213> ORGANISM: homo sapiens

<400> SEQUENCE: 1261 agggcuggge uggcagggca agugcugcag aucuuugucu aagcagcccc ugccuggau    60 cuccca                                                              66

<210> SEQ ID NO 1262
<211> LENGTH: 68
<212> TYPE: RNA
<213> ORGANISM: homo sapiens

<400> SEQUENCE: 1262
cucaggcuca guggugcaug cuuauagucc cagccacucu ggaggcugaa ggaagauggc    60

```
uugagccu                                                              68
```

<210> SEQ ID NO 1263
<211> LENGTH: 69
<212> TYPE: RNA
<213> ORGANISM: homo sapiens

<400> SEQUENCE: 1263

```
aagacugaga ggagggaacu ggugaguugu acauagaaau gcuuucuaac uccuugcuc      60 agucuguuu                                                             69
```

<210> SEQ ID NO 1264
<211> LENGTH: 76
<212> TYPE: RNA
<213> ORGANISM: homo sapiens

<400> SEQUENCE: 1264

```
caggagagaa aguacugccc agaagcuaaa guguagauca aacgcauaau ggcugaggua      60
guaguuucuu gaacuu                                                     76
```

<210> SEQ ID NO 1265
<211> LENGTH: 70
<212> TYPE: RNA
<213> ORGANISM: homo sapiens

<400> SEQUENCE: 1265

```
ggcggcuggg agccgaggcg ucggugcaga ccuggagacg ggcauggggg ggcugcggcu      60
gcuggcugug                                                            70
```

<210> SEQ ID NO 1266
<211> LENGTH: 64
<212> TYPE: RNA
<213> ORGANISM: homo sapiens

<400> SEQUENCE: 1266

```
uaugugaccu cggaugaauc acugaaauau gucugagcuu cuguuucauc agaugucaca      60
uuuu                                                                  64
```

<210> SEQ ID NO 1267
<211> LENGTH: 81
<212> TYPE: RNA
<213> ORGANISM: homo sapiens

<400> SEQUENCE: 1267

```
agccuuuagc aaguuguaau cuuuuugcug auggaggguc uugccuccau ggggauggcu      60
gaugaugaug gugcugaagg c                                               81
```

<210> SEQ ID NO 1268
<211> LENGTH: 60
<212> TYPE: RNA
<213> ORGANISM: homo sapiens

<400> SEQUENCE: 1268

```
gagauguaug gaaucuguau auaucuauau auauguguau auauagauuc cauaaaucua      60
```

<210> SEQ ID NO 1269
<211> LENGTH: 83
<212> TYPE: RNA
<213> ORGANISM: homo sapiens

<400> SEQUENCE: 1269

```
acaauguaga uauuuaagca ggaaauagaa uuuacauaua aauuucuauu uguuucuauu      60
uccugcuuaa auaucuacau ugc                                             83

<210> SEQ ID NO 1270
<211> LENGTH: 92
<212> TYPE: RNA
<213> ORGANISM: homo sapiens

<400> SEQUENCE: 1270
cuaagauaau guccuccagg uucaucucug uugucauuug uggcauggac cauuugugac      60
aauagagaug aacauggagg auauuaucuu aa                                   92

<210> SEQ ID NO 1271
<211> LENGTH: 73
<212> TYPE: RNA
<213> ORGANISM: homo sapiens

<400> SEQUENCE: 1271
ggaggcuggg cuggacggga cacccggccu ccacuuucug uggcagguac cuccuccaug      60
ucggcccgcc uug                                                        73

<210> SEQ ID NO 1272
<211> LENGTH: 77
<212> TYPE: RNA
<213> ORGANISM: homo sapiens

<400> SEQUENCE: 1272
uggccucugc caucagacca ucuggguuca aguuggcuc caucuuuaug aaaugggugg       60
ucugaggcaa guggucu                                                    77

<210> SEQ ID NO 1273
<211> LENGTH: 84
<212> TYPE: RNA
<213> ORGANISM: homo sapiens

<400> SEQUENCE: 1273
auggucccuc ccaauccagc cauuccucag accaggtggc ucccgagcca ccccaggcug      60
uaggaugggg gugagaggug cuag                                            84

<210> SEQ ID NO 1274
<211> LENGTH: 52
<212> TYPE: RNA
<213> ORGANISM: homo sapiens

<400> SEQUENCE: 1274
ucugggcuga gccgagcugg guuaagccga gcuggguugg gcugggcugg gu             52

<210> SEQ ID NO 1275
<211> LENGTH: 80
<212> TYPE: RNA
<213> ORGANISM: homo sapiens

<400> SEQUENCE: 1275
ggaagggacu ggaguggauu ggguacaucu auuauagugg gagcaccuac uacaacccgu      60
cccucaagag ucgagucacc                                                 80

<210> SEQ ID NO 1276
<211> LENGTH: 61
<212> TYPE: RNA
```

-continued

<213> ORGANISM: homo sapiens

<400> SEQUENCE: 1276
cuggugaauc uggguccgcc agcccccagg aaggggcug gaguggauug gggaaaucca     60
u                                                                   61

<210> SEQ ID NO 1277
<211> LENGTH: 70
<212> TYPE: RNA
<213> ORGANISM: homo sapiens

<400> SEQUENCE: 1277
aggacccagc ggggcugggc gcgcggagca gcgcugggug cagcgccugc gccggcagcu     60
gcaagggccg                                                           70

<210> SEQ ID NO 1278
<211> LENGTH: 94
<212> TYPE: RNA
<213> ORGANISM: homo sapiens

<400> SEQUENCE: 1278
cuuuaauacu aucucaaacu aaaggauaua gaagguuuuc ccuuucucuu gcccugaaac     60
cuucuguauc cuuuauuuug agauaguauu agaa                                94

<210> SEQ ID NO 1279
<211> LENGTH: 94
<212> TYPE: RNA
<213> ORGANISM: homo sapiens

<400> SEQUENCE: 1279
cuuuaauacu aucucaaacu aaaggauaua gaagguuuuc ccuuucucuu gcccugaaac     60
cuucuguauc cuuuauuuug agauaguauu agaa                                94

<210> SEQ ID NO 1280
<211> LENGTH: 94
<212> TYPE: RNA
<213> ORGANISM: homo sapiens

<400> SEQUENCE: 1280
cuuuaauacu aucucaaacu aaaggauaua gaagguuuuc ccuuucucuu gcccugaaac     60
cuucuguauc cuuuauuuug agauaguauu agaa                                94

<210> SEQ ID NO 1281
<211> LENGTH: 77
<212> TYPE: RNA
<213> ORGANISM: homo sapiens

<400> SEQUENCE: 1281
cucaaagaag caauacuguu accugaaaua ggcugcgaag auaacaguau uucagauaac     60
aguauuacau cuugaa                                                   77

<210> SEQ ID NO 1282
<211> LENGTH: 68
<212> TYPE: RNA
<213> ORGANISM: homo sapiens

<400> SEQUENCE: 1282
guguauguga gggaguagga uguaugguug uuagauagac aacuacaauc uuuucucaca     60
acagacag                                                            68

```
<210> SEQ ID NO 1283
<211> LENGTH: 87
<212> TYPE: RNA
<213> ORGANISM: homo sapiens

<400> SEQUENCE: 1283
aaaaaaaagg gaaagaagaa cguuugcauu ugcccugcac ucaguuugca caggguaaau      60
gcaauaguuc uucuuucccu uuuuua                                          87

<210> SEQ ID NO 1284
<211> LENGTH: 77
<212> TYPE: RNA
<213> ORGANISM: homo sapiens

<400> SEQUENCE: 1284
cucagcccgg gcaauauagu gagaccucgu cucuacaaaa aauugagaca gggccucacu      60
guaucgccca ggcugga                                                    77

<210> SEQ ID NO 1285
<211> LENGTH: 86
<212> TYPE: RNA
<213> ORGANISM: homo sapiens

<400> SEQUENCE: 1285
auucuaggug gggagacuga cggcuggagg cccauaagcu gucuaaaacu ucggccccca      60
gauuucuggu cucccacuu cagaac                                           86

<210> SEQ ID NO 1286
<211> LENGTH: 57
<212> TYPE: RNA
<213> ORGANISM: homo sapiens

<400> SEQUENCE: 1286
guugagacag gcaggauugg ggaaacaucu uuuaccucgu cucuugccug uuuuaga         57

<210> SEQ ID NO 1287
<211> LENGTH: 81
<212> TYPE: RNA
<213> ORGANISM: homo sapiens

<400> SEQUENCE: 1287
gcgggaggug uaacaggacu ggacucccgg cagccccagg gcaggggcgu ggggagcugg      60
uccuagcuca gcgcucccgg a                                               81

<210> SEQ ID NO 1288
<211> LENGTH: 67
<212> TYPE: RNA
<213> ORGANISM: homo sapiens

<400> SEQUENCE: 1288
agcguuaccu gguagugagu uagagaugca gagcccuggg cuccucagca aaccuacugg      60
aucugca                                                               67

<210> SEQ ID NO 1289
<211> LENGTH: 76
<212> TYPE: RNA
<213> ORGANISM: homo sapiens

<400> SEQUENCE: 1289
```

```
ucugcagcuc ccggcagccu cgggccacac ucccgggauc cccagggacu ggccugggac    60
uaccgggggu ggcggc                                                    76

<210> SEQ ID NO 1290
<211> LENGTH: 86
<212> TYPE: RNA
<213> ORGANISM: homo sapiens

<400> SEQUENCE: 1290
agggagaagg gucggggcag ggagggcagg gcaggcucug ggguggggggg ucugugaguc   60 agccacggcu cugcccacgu cucccc                                         86

<210> SEQ ID NO 1291
<211> LENGTH: 70
<212> TYPE: RNA
<213> ORGANISM: homo sapiens

<400> SEQUENCE: 1291
agcuuccaga cgcuccgccc cacgucgcau gcgccccggg aacgcguggg gcggagcuuc    60
cggaggcccc                                                           70

<210> SEQ ID NO 1292
<211> LENGTH: 70
<212> TYPE: RNA
<213> ORGANISM: homo sapiens

<400> SEQUENCE: 1292
agcuuccaga cgcuccgccc cacgucgcau gcgccccggg aacgcguggg gcggagcuuc    60
cggaggcccc                                                           70

<210> SEQ ID NO 1293
<211> LENGTH: 70
<212> TYPE: RNA
<213> ORGANISM: homo sapiens

<400> SEQUENCE: 1293
agcuuccaga cgcuccgccc cacgucgcau gcgccccggg aacgcguggg gcggagcuuc    60
cggaggcccc                                                           70

<210> SEQ ID NO 1294
<211> LENGTH: 70
<212> TYPE: RNA
<213> ORGANISM: homo sapiens

<400> SEQUENCE: 1294
agcuuccaga cgcuccgccc cacgucgcau gcgccccggg aacgcguggg gcggagcuuc    60
cggaggcccc                                                           70

<210> SEQ ID NO 1295
<211> LENGTH: 70
<212> TYPE: RNA
<213> ORGANISM: homo sapiens

<400> SEQUENCE: 1295
agcuuccaga cgcuccgccc cacgucgcau gcgccccggg aacgcguggg gcggagcuuc    60
cggaggcccc                                                           70

<210> SEQ ID NO 1296
<211> LENGTH: 84
```

```
<212> TYPE: RNA
<213> ORGANISM: homo sapiens

<400> SEQUENCE: 1296
uggagggcau uaggcagugg ccagagcccu gcagugcugg gcaugggcuu cucgugggcu     60
cuggccacgg cccugagcuc cucc                                            84

<210> SEQ ID NO 1297
<211> LENGTH: 88
<212> TYPE: RNA
<213> ORGANISM: homo sapiens

<400> SEQUENCE: 1297
gccaggauca cagacguuua aauuacacuc cuucugcugu gccuuacagc aguagaaggg     60
gugaaauuua aacgucugug auccuggg                                        88

<210> SEQ ID NO 1298
<211> LENGTH: 83
<212> TYPE: RNA
<213> ORGANISM: homo sapiens

<400> SEQUENCE: 1298
gaucacagac guuuaaauua cacuccuucu gcugugccuu acagcaguag aaggggugaa     60
auuuaaacgu cugugauccu ggg                                             83

<210> SEQ ID NO 1299
<211> LENGTH: 87
<212> TYPE: RNA
<213> ORGANISM: homo sapiens

<400> SEQUENCE: 1299
gccaggauca cagacguuua aauuacacuc cuucugcugu gccuuacagc aguagaaggg     60
gugaaauuua aacgucugug auccugg                                         87

<210> SEQ ID NO 1300
<211> LENGTH: 79
<212> TYPE: RNA
<213> ORGANISM: homo sapiens

<400> SEQUENCE: 1300
agguaaauau gaugaaacuc acagcugagg agcuuagcaa guagcuaagg ccagagcuug     60
uguuugggug guguggcug                                                  79

<210> SEQ ID NO 1301
<211> LENGTH: 83
<212> TYPE: RNA
<213> ORGANISM: homo sapiens

<400> SEQUENCE: 1301 uggggggaaaa gugcugggau ugauuaguga ugucugcugg ggaaccgggg cucagggaug    60
auaacugugc ugagaagccc ccu                                             83

<210> SEQ ID NO 1302
<211> LENGTH: 58
<212> TYPE: RNA
<213> ORGANISM: homo sapiens

<400> SEQUENCE: 1302
aaccucagca gugcgcaggg cugcacuguc uccgucugcg gccugcagua agcgggua       58
```

<210> SEQ ID NO 1303
<211> LENGTH: 70
<212> TYPE: RNA
<213> ORGANISM: homo sapiens

<400> SEQUENCE: 1303
gugugccacc ugcguguuuu cguccaaau cagaaaagga uuuggacaga aaacacgcag    60
gaagaaggaa                                                          70

<210> SEQ ID NO 1304
<211> LENGTH: 60
<212> TYPE: RNA
<213> ORGANISM: homo sapiens

<400> SEQUENCE: 1304
ucggcuaagg aaguccugug cucaguuuug uagcaucaaa acuaggauuu cucuuguuac    60

<210> SEQ ID NO 1305
<211> LENGTH: 75
<212> TYPE: RNA
<213> ORGANISM: homo sapiens

<400> SEQUENCE: 1305
ugagguuucu ggacugagcc augcuacugg cuucucuggu ucccagccuu acagauggcu    60
uaucauggga ccucu                                                    75

<210> SEQ ID NO 1306
<211> LENGTH: 87
<212> TYPE: RNA
<213> ORGANISM: homo sapiens

<400> SEQUENCE: 1306
gcgggcguug ccuggggggcc ucgcagggg agauccagcc caggcugguu ccgcugacuc    60
ugccuguagg ccgguggcgu cuucugg                                       87

<210> SEQ ID NO 1307
<211> LENGTH: 69
<212> TYPE: RNA
<213> ORGANISM: homo sapiens

<400> SEQUENCE: 1307 gcggggggacc gagagggccu cggcugugug aggacuagag gcggccgagg cccgggccgg    60
uucccccga                                                           69

<210> SEQ ID NO 1308
<211> LENGTH: 70
<212> TYPE: RNA
<213> ORGANISM: homo sapiens

<400> SEQUENCE: 1308
auuuuagagg cuggaauaga gauucuugag gcuuggaaga guaaggaucc cuuuaucugu    60
ccucuaggag                                                          70

<210> SEQ ID NO 1309
<211> LENGTH: 56
<212> TYPE: RNA
<213> ORGANISM: homo sapiens

<400> SEQUENCE: 1309
uggaucugaa ggcugcccu uugcucucug ggguagccuu cagaucuugg uguuuu        56

<210> SEQ ID NO 1310
<211> LENGTH: 65
<212> TYPE: RNA
<213> ORGANISM: homo sapiens

<400> SEQUENCE: 1310
ugggccacuu ggaucugaag gcugccccuu ugcucucugg gguagccuuc agaucuuggu    60
guuuu                                                                65

<210> SEQ ID NO 1311
<211> LENGTH: 69
<212> TYPE: RNA
<213> ORGANISM: homo sapiens

<400> SEQUENCE: 1311
gaacgauagc agcaugaacc ugucucacug cagaauuauu uugagacagg cuuaugcugc    60
uauccuuca                                                            69

<210> SEQ ID NO 1312
<211> LENGTH: 70
<212> TYPE: RNA
<213> ORGANISM: homo sapiens

<400> SEQUENCE: 1312
ggaacgauag cagcaugaac cugucucacu gcagaauuau uuugagacag gcuuaugcug    60
cuauccuuca                                                           70

<210> SEQ ID NO 1313
<211> LENGTH: 75
<212> TYPE: RNA
<213> ORGANISM: homo sapiens

<400> SEQUENCE: 1313
gucagagggg ggaugugcau gcugguuggg gugggcugcc uguggaccaa ucagcgugca    60
cuuccccacc cugaa                                                     75

<210> SEQ ID NO 1314
<211> LENGTH: 54
<212> TYPE: RNA
<213> ORGANISM: homo sapiens

<400> SEQUENCE: 1314
cuuagcuccc uggcuucagc ccuuuuucca gggaggugaa ugguucuguc ucgc          54

<210> SEQ ID NO 1315
<211> LENGTH: 87
<212> TYPE: RNA
<213> ORGANISM: homo sapiens

<400> SEQUENCE: 1315
ugcggugaca ucagggccca gucccugcug ucaugcccca ggugacgugc ugggcugaca    60
gcagggcugg ccgcuaacgu cacuguc                                        87

<210> SEQ ID NO 1316
<211> LENGTH: 70
<212> TYPE: RNA
<213> ORGANISM: homo sapiens

<400> SEQUENCE: 1316

```
ccagaagugg ucugcaaaga gaugacugug aauccaagau ccacaucagc ucugugcugc    60
cuacaucuga                                                           70
```

<210> SEQ ID NO 1317
<211> LENGTH: 90
<212> TYPE: RNA
<213> ORGANISM: homo sapiens

<400> SEQUENCE: 1317

```
uauucuacug agaguacaga ucuuuauaua uauguaucauu auauguauga ugagaucauu    60
auauguauga ucuggacacc caguagaauc                                     90
```

<210> SEQ ID NO 1318
<211> LENGTH: 78
<212> TYPE: RNA
<213> ORGANISM: homo sapiens

<400> SEQUENCE: 1318

```
augacaggcc aucagcaguc caaugaagac augaagaccc aaugucuuca uuggacugcu    60
gauggcccgu cacuggga                                                  78
```

<210> SEQ ID NO 1319
<211> LENGTH: 70
<212> TYPE: RNA
<213> ORGANISM: homo sapiens

<400> SEQUENCE: 1319

```
cuccacauug gaggguguqq aaqacaucug ggccaacucu gaucucuuca ucuacccccc    60
aggacuggga                                                           70
```

<210> SEQ ID NO 1320
<211> LENGTH: 56
<212> TYPE: RNA
<213> ORGANISM: homo sapiens

<400> SEQUENCE: 1320

```
cgaccgcacc cgcccgaagc uggqucaagg agcccagcag gacgggagcg cggcgc        56
```

<210> SEQ ID NO 1321
<211> LENGTH: 47
<212> TYPE: RNA
<213> ORGANISM: homo sapiens

<400> SEQUENCE: 1321

```
gccuaggagu ccuuggucag uggggacaug gagaaggcuu cugagga                  47
```

<210> SEQ ID NO 1322
<211> LENGTH: 60
<212> TYPE: RNA
<213> ORGANISM: homo sapiens

<400> SEQUENCE: 1322

```
gccuucucuu cccaguucuu ccuggagucg gggaaaagcu ggguugagaa ggugaaaaga    60
```

<210> SEQ ID NO 1323
<211> LENGTH: 73
<212> TYPE: RNA
<213> ORGANISM: homo sapiens

<400> SEQUENCE: 1323

```
ggucaccugu cuggccagcu acgucaccac ggcccuuguc agugugqaag guagacggcc    60
```

-continued agagagguga ccc                                                     73

<210> SEQ ID NO 1324
<211> LENGTH: 79
<212> TYPE: RNA
<213> ORGANISM: homo sapiens

<400> SEQUENCE: 1324
aggaagggau ucugggaggu uguagcagug gaaaaaguuc uuucuuccu cugaucgccc   60 ucucagcucu uccuucug                                                79

<210> SEQ ID NO 1325
<211> LENGTH: 51
<212> TYPE: RNA
<213> ORGANISM: homo sapiens

<400> SEQUENCE: 1325
acagaccccg gggagcccgg cggugaagcu ccugguaucc uggguguucug a          51

<210> SEQ ID NO 1326
<211> LENGTH: 71
<212> TYPE: RNA
<213> ORGANISM: homo sapiens

<400> SEQUENCE: 1326
ugagaaugug gaaggagguu gccggacgcu gcuggcugcc uuccagcguc cacuucccuu  60
ucucucucuc c                                                       71

<210> SEQ ID NO 1327
<211> LENGTH: 76
<212> TYPE: RNA
<213> ORGANISM: homo sapiens

<400> SEQUENCE: 1327
cgguuggugc aaagguaauu gugguuucug ccauugaaag uaaaggcaag aaccucaauu  60
accuuugcag cgaccu                                                  76

<210> SEQ ID NO 1328
<211> LENGTH: 76
<212> TYPE: RNA
<213> ORGANISM: homo sapiens

<400> SEQUENCE: 1328
ucgagggaau cugagaaggc gcacaagguu uguguccaau acaguccaca ccuugcgcua  60
cucaggucug cucgug                                                  76

<210> SEQ ID NO 1329
<211> LENGTH: 75
<212> TYPE: RNA
<213> ORGANISM: homo sapiens

<400> SEQUENCE: 1329
ucgagggaau cugagaaggc gcacaagguu uguguccaau acaguccaca ccuugcgcua  60
cucaggucug cucgu                                                   75

<210> SEQ ID NO 1330
<211> LENGTH: 60
<212> TYPE: RNA
<213> ORGANISM: homo sapiens

```
<400> SEQUENCE: 1330
ggcugaagcu cuaagguucc gccugcgggc aggaagcgga ggaaccuugg agcuucggca    60

<210> SEQ ID NO 1331
<211> LENGTH: 60
<212> TYPE: RNA
<213> ORGANISM: homo sapiens

<400> SEQUENCE: 1331
ugugaaugac ccccuuccag agccaaaauc accagggaug gaggaggggu cuuggguacu    60

<210> SEQ ID NO 1332
<211> LENGTH: 76
<212> TYPE: RNA
<213> ORGANISM: homo sapiens

<400> SEQUENCE: 1332
gggagcacug gacuaggagu cagaaggugg aguucgggu gcuguuucc cacucuuggg     60 cccugggcau guucug                                                  76

<210> SEQ ID NO 1333
<211> LENGTH: 59
<212> TYPE: RNA
<213> ORGANISM: homo sapiens

<400> SEQUENCE: 1333
aacugggucc cagucuucac aguugguuuc ugacacgugg accggcugg gacgaugug     59

<210> SEQ ID NO 1334
<211> LENGTH: 61
<212> TYPE: RNA
<213> ORGANISM: homo sapiens

<400> SEQUENCE: 1334
ccaccuggac ccagcguaga caaagaggug uuucuacucc auaucuaccu ggacccagug    60
u                                                                  61

<210> SEQ ID NO 1335
<211> LENGTH: 74
<212> TYPE: RNA
<213> ORGANISM: homo sapiens

<400> SEQUENCE: 1335
aguuggugca aaaguaauug cgguuuuugc cgucgaaaau aauggcaaaa acugcaguua    60
cuuuuguacc aaug                                                    74

<210> SEQ ID NO 1336
<211> LENGTH: 53
<212> TYPE: RNA
<213> ORGANISM: homo sapiens

<400> SEQUENCE: 1336
uuugggcugg gcugguugg gcaguucuuc ugcuggacuc accugugacc agc           53

<210> SEQ ID NO 1337
<211> LENGTH: 61
<212> TYPE: RNA
<213> ORGANISM: homo sapiens

<400> SEQUENCE: 1337 augugggua gauauaugca cuguauauaa acauaaugug guagauauau gcacgauaua    60
```

-continued

| | |
|---|---|
| g | 61 |

<210> SEQ ID NO 1338
<211> LENGTH: 84
<212> TYPE: RNA
<213> ORGANISM: homo sapiens

<400> SEQUENCE: 1338

| | |
|---|---|
| augguguuug ccuccuucau ccgcaaggca ucugaugccc acgaaguuag aagguccuu | 60 |
| ggggagaagg gaaagaacau caaa | 84 |

<210> SEQ ID NO 1339
<211> LENGTH: 69
<212> TYPE: RNA
<213> ORGANISM: homo sapiens

<400> SEQUENCE: 1339

| | |
|---|---|
| cgcaugacuc uucaaccuca ggacuugcag aauuaaugga augcuguccu aagguuguug | 60 |
| aguugugca | 69 |

<210> SEQ ID NO 1340
<211> LENGTH: 83
<212> TYPE: RNA
<213> ORGANISM: homo sapiens

<400> SEQUENCE: 1340

| | |
|---|---|
| cauuagguug gugcaaaagg cauugugguu uuugccuaua aaaguaaugg caaaaaccgc | 60 |
| aauuccuuuu gcaccaaccu aau | 83 |

<210> SEQ ID NO 1341
<211> LENGTH: 61
<212> TYPE: RNA
<213> ORGANISM: homo sapiens

<400> SEQUENCE: 1341

| | |
|---|---|
| cacucgcgcu gcggccagcg cccgggccug cgggcccggg cggcggcugu guugcgcagu | 60 |
| c | 61 |

<210> SEQ ID NO 1342
<211> LENGTH: 83
<212> TYPE: RNA
<213> ORGANISM: homo sapiens

<400> SEQUENCE: 1342

| | |
|---|---|
| uuauuaauau ggaagggaga agagcuuuaa ugauuggagu cauuuucaga gcauuaaagc | 60 |
| ucuucucccu uccauauuaa ugu | 83 |

<210> SEQ ID NO 1343
<211> LENGTH: 66
<212> TYPE: RNA
<213> ORGANISM: homo sapiens

<400> SEQUENCE: 1343

| | |
|---|---|
| ugccgcggcg gggacggcga uugguccgua uguguggugc caccggccgc cggcuccgcc | 60 |
| ccggcc | 66 |

<210> SEQ ID NO 1344
<211> LENGTH: 71
<212> TYPE: RNA

<213> ORGANISM: homo sapiens

<400> SEQUENCE: 1344
gcaaagggug gcagcaagga aggcaggggu ccuaaggugu guccuccugc ccuccuugcu    60
guagacuuug g                                                        71

<210> SEQ ID NO 1345
<211> LENGTH: 70
<212> TYPE: RNA
<213> ORGANISM: homo sapiens

<400> SEQUENCE: 1345
ugagccgagc ugagcuuagc ugggcugagc uaaccagggc ugggcugagc ugggcugagc    60
ugagcugagc                                                          70

<210> SEQ ID NO 1346
<211> LENGTH: 78
<212> TYPE: RNA
<213> ORGANISM: homo sapiens

<400> SEQUENCE: 1346
gagcuuggau gagcugggcu gaacugggcu ggguugagcu gggcugggcu gaguugagcc    60
aggcugaucu gggcugag                                                 78

<210> SEQ ID NO 1347
<211> LENGTH: 60
<212> TYPE: RNA
<213> ORGANISM: homo sapiens

<400> SEQUENCE: 1347
ugagcugggc ucugcugugc ugugcugagc agggcugagc ugaacgggc ugagcugggc     60

<210> SEQ ID NO 1348
<211> LENGTH: 61
<212> TYPE: RNA
<213> ORGANISM: homo sapiens

<400> SEQUENCE: 1348
gucaagucag aacagccagg uagagcccuu guccaaaccu gggcugaaug acagugauga    60
g                                                                   61

<210> SEQ ID NO 1349
<211> LENGTH: 104
<212> TYPE: RNA
<213> ORGANISM: homo sapiens

<400> SEQUENCE: 1349
cucuuugagc cuuggcugcc uuggugcagc agggucaucu guagggccac cccacagcuc    60
uuuccuuccc cuccucucuc cagggagccg gggcugugag agga                   104

<210> SEQ ID NO 1350
<211> LENGTH: 55
<212> TYPE: RNA
<213> ORGANISM: homo sapiens

<400> SEQUENCE: 1350
aagcugcaug gaccaggacu uggcaccuuu ggccuuaguc cugccuguag guuua         55

<210> SEQ ID NO 1351
<211> LENGTH: 22

-continued

<212> TYPE: DNA
<213> ORGANISM: Artificial
<220> FEATURE:
<223> OTHER INFORMATION: synthetic primer

<400> SEQUENCE: 1351
aagcccttac cccaaaaagc at                                              22

<210> SEQ ID NO 1352
<211> LENGTH: 21
<212> TYPE: DNA
<213> ORGANISM: Artificial
<220> FEATURE:
<223> OTHER INFORMATION: synthetic primer

<400> SEQUENCE: 1352
aggcggagac ttgggcaatt g                                               21

<210> SEQ ID NO 1353
<211> LENGTH: 22
<212> TYPE: DNA
<213> ORGANISM: Artificial
<220> FEATURE:
<223> OTHER INFORMATION: synthetic primer

<400> SEQUENCE: 1353
ctgggaggtg gatgtttact tc                                              22

<210> SEQ ID NO 1354
<211> LENGTH: 22
<212> TYPE: DNA
<213> ORGANISM: Artificial
<220> FEATURE:
<223> OTHER INFORMATION: synthetic primer

<400> SEQUENCE: 1354
ctgggagaag gctgtttact ct                                              22

<210> SEQ ID NO 1355
<211> LENGTH: 22
<212> TYPE: DNA
<213> ORGANISM: Artificial
<220> FEATURE:
<223> OTHER INFORMATION: synthetic primer

<400> SEQUENCE: 1355
ctttcagtcg gatgtttaca gc                                              22

<210> SEQ ID NO 1356
<211> LENGTH: 23
<212> TYPE: DNA
<213> ORGANISM: Artificial
<220> FEATURE:
<223> OTHER INFORMATION: synthetic primer

<400> SEQUENCE: 1356
tctcacacag aaatcgcacc cgt                                             23

<210> SEQ ID NO 1357
<211> LENGTH: 22
<212> TYPE: DNA
<213> ORGANISM: Artificial
<220> FEATURE:
<223> OTHER INFORMATION: synthetic primer

<400> SEQUENCE: 1357

-continued tgaggtagta ggttgtatag tt                                          22

<210> SEQ ID NO 1358
<211> LENGTH: 22
<212> TYPE: DNA
<213> ORGANISM: Artificial
<220> FEATURE:
<223> OTHER INFORMATION: synthetic primer

<400> SEQUENCE: 1358
tgaggtagta ggttgtatag tt                                          22

<210> SEQ ID NO 1359
<211> LENGTH: 22
<212> TYPE: DNA
<213> ORGANISM: Artificial
<220> FEATURE:
<223> OTHER INFORMATION: synthetic primer

<400> SEQUENCE: 1359
tgaggtagta ggttgtatgg tt                                          22

<210> SEQ ID NO 1360
<211> LENGTH: 22
<212> TYPE: DNA
<213> ORGANISM: Artificial
<220> FEATURE:
<223> OTHER INFORMATION: synthetic primer

<400> SEQUENCE: 1360
aacccgtaga tccgaacttg tg                                          22

<210> SEQ ID NO 1361
<211> LENGTH: 21
<212> TYPE: DNA
<213> ORGANISM: Artificial
<220> FEATURE:
<223> OTHER INFORMATION: synthetic primer

<400> SEQUENCE: 1361
tacagtactg tgataactga a                                           21

<210> SEQ ID NO 1362
<211> LENGTH: 21
<212> TYPE: DNA
<213> ORGANISM: Artificial
<220> FEATURE:
<223> OTHER INFORMATION: synthetic primer

<400> SEQUENCE: 1362
tacagtactg tgataactga a                                           21

<210> SEQ ID NO 1363
<211> LENGTH: 23
<212> TYPE: DNA
<213> ORGANISM: Artificial
<220> FEATURE:
<223> OTHER INFORMATION: synthetic primer

<400> SEQUENCE: 1363
agcagcattg tacagggcta tga                                         23

<210> SEQ ID NO 1364
<211> LENGTH: 23
<212> TYPE: DNA
<213> ORGANISM: Artificial

```
<220> FEATURE:
<223> OTHER INFORMATION: synthetic primer

<400> SEQUENCE: 1364
agcagcattg tacagggcta tga                                              23

<210> SEQ ID NO 1365
<211> LENGTH: 23
<212> TYPE: DNA
<213> ORGANISM: Artificial
<220> FEATURE:
<223> OTHER INFORMATION: synthetic primer

<400> SEQUENCE: 1365
aaaagtgctt acagtgcagg tag                                              23

<210> SEQ ID NO 1366
<211> LENGTH: 21
<212> TYPE: DNA
<213> ORGANISM: Artificial
<220> FEATURE:
<223> OTHER INFORMATION: synthetic primer

<400> SEQUENCE: 1366
taaagtgctg acagtgcaga t                                                21

<210> SEQ ID NO 1367
<211> LENGTH: 23
<212> TYPE: DNA
<213> ORGANISM: Artificial
<220> FEATURE:
<223> OTHER INFORMATION: synthetic primer

<400> SEQUENCE: 1367
agcagcattg tacagggcta tca                                              23

<210> SEQ ID NO 1368
<211> LENGTH: 23
<212> TYPE: DNA
<213> ORGANISM: Artificial
<220> FEATURE:
<223> OTHER INFORMATION: synthetic primer

<400> SEQUENCE: 1368
taccctgtag atccgaattt gtg                                              23

<210> SEQ ID NO 1369
<211> LENGTH: 23
<212> TYPE: DNA
<213> ORGANISM: Artificial
<220> FEATURE:
<223> OTHER INFORMATION: synthetic primer

<400> SEQUENCE: 1369
taccctgtag aaccgaattt gtg                                              23

<210> SEQ ID NO 1370
<211> LENGTH: 21
<212> TYPE: DNA
<213> ORGANISM: Artificial
<220> FEATURE:
<223> OTHER INFORMATION: synthetic primer

<400> SEQUENCE: 1370
tcacagtgaa ccggtctctt t                                                21
```

<210> SEQ ID NO 1371
<211> LENGTH: 21
<212> TYPE: DNA
<213> ORGANISM: Artificial
<220> FEATURE:
<223> OTHER INFORMATION: synthetic primer

<400> SEQUENCE: 1371
tcacagtgaa ccggtctctt t                                          21

<210> SEQ ID NO 1372
<211> LENGTH: 21
<212> TYPE: DNA
<213> ORGANISM: Artificial
<220> FEATURE:
<223> OTHER INFORMATION: synthetic primer

<400> SEQUENCE: 1372 cttttttgcgg tctgggcttg c                                         21

<210> SEQ ID NO 1373
<211> LENGTH: 21
<212> TYPE: DNA
<213> ORGANISM: Artificial
<220> FEATURE:
<223> OTHER INFORMATION: synthetic primer

<400> SEQUENCE: 1373 cttttttgcgg tctgggcttg c                                         21

<210> SEQ ID NO 1374
<211> LENGTH: 21
<212> TYPE: DNA
<213> ORGANISM: Artificial
<220> FEATURE:
<223> OTHER INFORMATION: synthetic primer

<400> SEQUENCE: 1374
ttaggccgca gatctgggtg a                                          21

<210> SEQ ID NO 1375
<211> LENGTH: 21
<212> TYPE: DNA
<213> ORGANISM: Artificial
<220> FEATURE:
<223> OTHER INFORMATION: synthetic primer

<400> SEQUENCE: 1375
taccacaggg tagaaccacg g                                          21

<210> SEQ ID NO 1376
<211> LENGTH: 21
<212> TYPE: DNA
<213> ORGANISM: Artificial
<220> FEATURE:
<223> OTHER INFORMATION: synthetic primer

<400> SEQUENCE: 1376
tgagatgaag cactgtagct c                                          21

<210> SEQ ID NO 1377
<211> LENGTH: 22
<212> TYPE: DNA
<213> ORGANISM: Artificial
<220> FEATURE:
<223> OTHER INFORMATION: synthetic primer

<400> SEQUENCE: 1377
tgagaactga attccatggg tt                                                22

<210> SEQ ID NO 1378
<211> LENGTH: 22
<212> TYPE: DNA
<213> ORGANISM: Artificial
<220> FEATURE:
<223> OTHER INFORMATION: synthetic primer

<400> SEQUENCE: 1378
tgagaactga attccatagg ct                                                22

<210> SEQ ID NO 1379
<211> LENGTH: 22
<212> TYPE: DNA
<213> ORGANISM: Artificial
<220> FEATURE:
<223> OTHER INFORMATION: synthetic primer

<400> SEQUENCE: 1379
tcagtgcact acagaactttt gt                                               22

<210> SEQ ID NO 1380
<211> LENGTH: 21
<212> TYPE: DNA
<213> ORGANISM: Artificial
<220> FEATURE:
<223> OTHER INFORMATION: synthetic primer

<400> SEQUENCE: 1380
ctagactgaa gctccttgag g                                                 21

<210> SEQ ID NO 1381
<211> LENGTH: 21
<212> TYPE: DNA
<213> ORGANISM: Artificial
<220> FEATURE:
<223> OTHER INFORMATION: synthetic primer

<400> SEQUENCE: 1381
tcagtgcatg acagaacttg g                                                 21

<210> SEQ ID NO 1382
<211> LENGTH: 23
<212> TYPE: DNA
<213> ORGANISM: Artificial
<220> FEATURE:
<223> OTHER INFORMATION: synthetic primer

<400> SEQUENCE: 1382
ttaatgctaa tcgtgatagg ggt                                               23

<210> SEQ ID NO 1383
<211> LENGTH: 22
<212> TYPE: DNA
<213> ORGANISM: Artificial
<220> FEATURE:
<223> OTHER INFORMATION: synthetic primer

<400> SEQUENCE: 1383
tagcagcaca taatggtttg tg                                                22

<210> SEQ ID NO 1384

```
<211> LENGTH: 22
<212> TYPE: DNA
<213> ORGANISM: Artificial
<220> FEATURE:
<223> OTHER INFORMATION: synthetic primer

<400> SEQUENCE: 1384
tagcagcaca tcatggttta ca                                              22

<210> SEQ ID NO 1385
<211> LENGTH: 22
<212> TYPE: DNA
<213> ORGANISM: Artificial
<220> FEATURE:
<223> OTHER INFORMATION: synthetic primer

<400> SEQUENCE: 1385
tagcagcacg taaatattgg cg                                              22

<210> SEQ ID NO 1386
<211> LENGTH: 22
<212> TYPE: DNA
<213> ORGANISM: Artificial
<220> FEATURE:
<223> OTHER INFORMATION: synthetic primer

<400> SEQUENCE: 1386
tagcagcacg taaatattgg cg                                              22

<210> SEQ ID NO 1387
<211> LENGTH: 23
<212> TYPE: DNA
<213> ORGANISM: Artificial
<220> FEATURE:
<223> OTHER INFORMATION: synthetic primer

<400> SEQUENCE: 1387
caaagtgctt acagtgcagg tag                                             23

<210> SEQ ID NO 1388
<211> LENGTH: 23
<212> TYPE: DNA
<213> ORGANISM: Artificial
<220> FEATURE:
<223> OTHER INFORMATION: synthetic primer

<400> SEQUENCE: 1388
aacattcaac gctgtcggtg agt                                             23

<210> SEQ ID NO 1389
<211> LENGTH: 23
<212> TYPE: DNA
<213> ORGANISM: Artificial
<220> FEATURE:
<223> OTHER INFORMATION: synthetic primer

<400> SEQUENCE: 1389
aacattcaac gctgtcggtg agt                                             23

<210> SEQ ID NO 1390
<211> LENGTH: 22
<212> TYPE: DNA
<213> ORGANISM: Artificial
<220> FEATURE:
<223> OTHER INFORMATION: synthetic primer

<400> SEQUENCE: 1390
```
aacattcatt gctgtcggtg gg                                              22

<210> SEQ ID NO 1391
<211> LENGTH: 22
<212> TYPE: DNA
<213> ORGANISM: Artificial
<220> FEATURE:
<223> OTHER INFORMATION: synthetic primer

<400> SEQUENCE: 1391
aacattcatt gctgtcggtg gg                                              22

<210> SEQ ID NO 1392
<211> LENGTH: 22
<212> TYPE: DNA
<213> ORGANISM: Artificial
<220> FEATURE:
<223> OTHER INFORMATION: synthetic primer

<400> SEQUENCE: 1392
aacattcaac ctgtcggtga gt                                              22

<210> SEQ ID NO 1393
<211> LENGTH: 24
<212> TYPE: DNA
<213> ORGANISM: Artificial
<220> FEATURE:
<223> OTHER INFORMATION: synthetic primer

<400> SEQUENCE: 1393
aacattcatt gttgtcggtg ggtt                                            24

<210> SEQ ID NO 1394
<211> LENGTH: 22
<212> TYPE: DNA
<213> ORGANISM: Artificial
<220> FEATURE:
<223> OTHER INFORMATION: synthetic primer

<400> SEQUENCE: 1394
tggagagaaa ggcagttcct ga                                              22

<210> SEQ ID NO 1395
<211> LENGTH: 23
<212> TYPE: DNA
<213> ORGANISM: Artificial
<220> FEATURE:
<223> OTHER INFORMATION: synthetic primer

<400> SEQUENCE: 1395
taaggtgcat ctagtgcaga tag                                             23

<210> SEQ ID NO 1396
<211> LENGTH: 23
<212> TYPE: DNA
<213> ORGANISM: Artificial
<220> FEATURE:
<223> OTHER INFORMATION: synthetic primer

<400> SEQUENCE: 1396
caacggaatc ccaaaagcag ctg                                             23

<210> SEQ ID NO 1397
<211> LENGTH: 21
<212> TYPE: DNA

```
<213> ORGANISM: Artificial
<220> FEATURE:
<223> OTHER INFORMATION: synthetic primer

<400> SEQUENCE: 1397
ctgacctatg aattgacagc c                                             21

<210> SEQ ID NO 1398
<211> LENGTH: 22
<212> TYPE: DNA
<213> ORGANISM: Artificial
<220> FEATURE:
<223> OTHER INFORMATION: synthetic primer

<400> SEQUENCE: 1398
tgggtctttg cgggcgagat ga                                            22

<210> SEQ ID NO 1399
<211> LENGTH: 22
<212> TYPE: DNA
<213> ORGANISM: Artificial
<220> FEATURE:
<223> OTHER INFORMATION: synthetic primer

<400> SEQUENCE: 1399
taggtagttt cctgttgttg gg                                            22

<210> SEQ ID NO 1400
<211> LENGTH: 22
<212> TYPE: DNA
<213> ORGANISM: Artificial
<220> FEATURE:
<223> OTHER INFORMATION: synthetic primer

<400> SEQUENCE: 1400
ttcaccacct tctccaccca gc                                            22

<210> SEQ ID NO 1401
<211> LENGTH: 22
<212> TYPE: DNA
<213> ORGANISM: Artificial
<220> FEATURE:
<223> OTHER INFORMATION: synthetic primer

<400> SEQUENCE: 1401
acagtagtct gcacattggt ta                                            22

<210> SEQ ID NO 1402
<211> LENGTH: 23
<212> TYPE: DNA
<213> ORGANISM: Artificial
<220> FEATURE:
<223> OTHER INFORMATION: synthetic primer

<400> SEQUENCE: 1402
tgtgcaaatc tatgcaaaac tga                                           23

<210> SEQ ID NO 1403
<211> LENGTH: 23
<212> TYPE: DNA
<213> ORGANISM: Artificial
<220> FEATURE:
<223> OTHER INFORMATION: synthetic primer

<400> SEQUENCE: 1403
taaagtgctt atagtgcagg tag                                           23
```

```
<210> SEQ ID NO 1404
<211> LENGTH: 23
<212> TYPE: DNA
<213> ORGANISM: Artificial
<220> FEATURE:
<223> OTHER INFORMATION: synthetic primer

<400> SEQUENCE: 1404
caaagtgctc atagtgcagg tag                                              23

<210> SEQ ID NO 1405
<211> LENGTH: 23
<212> TYPE: DNA
<213> ORGANISM: Artificial
<220> FEATURE:
<223> OTHER INFORMATION: synthetic primer

<400> SEQUENCE: 1405
agctacattg tctgctgggt ttc                                              23

<210> SEQ ID NO 1406
<211> LENGTH: 21
<212> TYPE: DNA
<213> ORGANISM: Artificial
<220> FEATURE:
<223> OTHER INFORMATION: synthetic primer

<400> SEQUENCE: 1406
agctacatct ggctactggg t                                                21

<210> SEQ ID NO 1407
<211> LENGTH: 21
<212> TYPE: DNA
<213> ORGANISM: Artificial
<220> FEATURE:
<223> OTHER INFORMATION: synthetic primer

<400> SEQUENCE: 1407
atcacattgc cagggatttc c                                                21

<210> SEQ ID NO 1408
<211> LENGTH: 22
<212> TYPE: DNA
<213> ORGANISM: Artificial
<220> FEATURE:
<223> OTHER INFORMATION: synthetic primer

<400> SEQUENCE: 1408
cattgcactt gtctcggtct ga                                               22

<210> SEQ ID NO 1409
<211> LENGTH: 22
<212> TYPE: DNA
<213> ORGANISM: Artificial
<220> FEATURE:
<223> OTHER INFORMATION: synthetic primer

<400> SEQUENCE: 1409
ttcaagtaat ccaggatagg ct                                               22

<210> SEQ ID NO 1410
<211> LENGTH: 22
<212> TYPE: DNA
<213> ORGANISM: Artificial
<220> FEATURE:
```

<223> OTHER INFORMATION: synthetic primer

<400> SEQUENCE: 1410
ttcaagtaat ccaggatagg ct                                             22

<210> SEQ ID NO 1411
<211> LENGTH: 21
<212> TYPE: DNA
<213> ORGANISM: Artificial
<220> FEATURE:
<223> OTHER INFORMATION: synthetic primer

<400> SEQUENCE: 1411
ttcaagtaat tcaggatagg t                                              21

<210> SEQ ID NO 1412
<211> LENGTH: 21
<212> TYPE: DNA
<213> ORGANISM: Artificial
<220> FEATURE:
<223> OTHER INFORMATION: synthetic primer

<400> SEQUENCE: 1412
ttcacagtgg ctaagttccg c                                              21

<210> SEQ ID NO 1413
<211> LENGTH: 22
<212> TYPE: DNA
<213> ORGANISM: Artificial
<220> FEATURE:
<223> OTHER INFORMATION: synthetic primer

<400> SEQUENCE: 1413
tagcaccatc tgaaatcggt ta                                             22

<210> SEQ ID NO 1414
<211> LENGTH: 22
<212> TYPE: DNA
<213> ORGANISM: Artificial
<220> FEATURE:
<223> OTHER INFORMATION: synthetic primer

<400> SEQUENCE: 1414
tgtaaacatc ctcgactgga ag                                             22

<210> SEQ ID NO 1415
<211> LENGTH: 22
<212> TYPE: DNA
<213> ORGANISM: Artificial
<220> FEATURE:
<223> OTHER INFORMATION: synthetic primer

<400> SEQUENCE: 1415
tgtaaacatc ctacactcag ct                                             22

<210> SEQ ID NO 1416
<211> LENGTH: 23
<212> TYPE: DNA
<213> ORGANISM: Artificial
<220> FEATURE:
<223> OTHER INFORMATION: synthetic primer

<400> SEQUENCE: 1416
tgtaaacatc ctacactctc agc                                            23

```
<210> SEQ ID NO 1417
<211> LENGTH: 23
<212> TYPE: DNA
<213> ORGANISM: Artificial
<220> FEATURE:
<223> OTHER INFORMATION: synthetic primer

<400> SEQUENCE: 1417
tgtaaacatc ctacactctc agc                                            23

<210> SEQ ID NO 1418
<211> LENGTH: 22
<212> TYPE: DNA
<213> ORGANISM: Artificial
<220> FEATURE:
<223> OTHER INFORMATION: synthetic primer

<400> SEQUENCE: 1418
tgtaaacatc cccgactgga ag                                             22

<210> SEQ ID NO 1419
<211> LENGTH: 22
<212> TYPE: DNA
<213> ORGANISM: Artificial
<220> FEATURE:
<223> OTHER INFORMATION: synthetic primer

<400> SEQUENCE: 1419
tgtaaacatc cttgactgga ag                                             22

<210> SEQ ID NO 1420
<211> LENGTH: 22
<212> TYPE: DNA
<213> ORGANISM: Artificial
<220> FEATURE:
<223> OTHER INFORMATION: synthetic primer

<400> SEQUENCE: 1420
aaaagctggg ttgagagggc ga                                             22

<210> SEQ ID NO 1421
<211> LENGTH: 22
<212> TYPE: DNA
<213> ORGANISM: Artificial
<220> FEATURE:
<223> OTHER INFORMATION: synthetic primer

<400> SEQUENCE: 1421
aaaagctggg ttgagagggc aa                                             22

<210> SEQ ID NO 1422
<211> LENGTH: 22
<212> TYPE: DNA
<213> ORGANISM: Artificial
<220> FEATURE:
<223> OTHER INFORMATION: synthetic primer

<400> SEQUENCE: 1422
aaaagctggg ttgagagggc aa                                             22

<210> SEQ ID NO 1423
<211> LENGTH: 21
<212> TYPE: DNA
<213> ORGANISM: Artificial
<220> FEATURE:
<223> OTHER INFORMATION: synthetic primer
```

<400> SEQUENCE: 1423
gcccctgggc ctatcctaga a                                              21

<210> SEQ ID NO 1424
<211> LENGTH: 21
<212> TYPE: DNA
<213> ORGANISM: Artificial
<220> FEATURE:
<223> OTHER INFORMATION: synthetic primer

<400> SEQUENCE: 1424
gtgcattgta gttgcattgc a                                              21

<210> SEQ ID NO 1425
<211> LENGTH: 22
<212> TYPE: DNA
<213> ORGANISM: Artificial
<220> FEATURE:
<223> OTHER INFORMATION: synthetic primer

<400> SEQUENCE: 1425
ttataaagca atgagactga tt                                             22

<210> SEQ ID NO 1426
<211> LENGTH: 22
<212> TYPE: DNA
<213> ORGANISM: Artificial
<220> FEATURE:
<223> OTHER INFORMATION: synthetic primer

<400> SEQUENCE: 1426
tggcagtgtc ttagctggtt gt                                             22

<210> SEQ ID NO 1427
<211> LENGTH: 22
<212> TYPE: DNA
<213> ORGANISM: Artificial
<220> FEATURE:
<223> OTHER INFORMATION: synthetic primer

<400> SEQUENCE: 1427
ttatcagaat ctccaggggt ac                                             22

<210> SEQ ID NO 1428
<211> LENGTH: 22
<212> TYPE: DNA
<213> ORGANISM: Artificial
<220> FEATURE:
<223> OTHER INFORMATION: synthetic primer

<400> SEQUENCE: 1428
aattgcacgg tatccatctg ta                                             22

<210> SEQ ID NO 1429
<211> LENGTH: 22
<212> TYPE: DNA
<213> ORGANISM: Artificial
<220> FEATURE:
<223> OTHER INFORMATION: synthetic primer

<400> SEQUENCE: 1429
taatgcccct aaaaatcctt at                                             22

<210> SEQ ID NO 1430
<211> LENGTH: 22

```
<212> TYPE: DNA
<213> ORGANISM: Artificial
<220> FEATURE:
<223> OTHER INFORMATION: synthetic primer

<400> SEQUENCE: 1430
ttataataca acctgataag tg                                                   22

<210> SEQ ID NO 1431
<211> LENGTH: 21
<212> TYPE: DNA
<213> ORGANISM: Artificial
<220> FEATURE:
<223> OTHER INFORMATION: synthetic primer

<400> SEQUENCE: 1431
actggacttg gagtcagaag g                                                    21

<210> SEQ ID NO 1432
<211> LENGTH: 23
<212> TYPE: DNA
<213> ORGANISM: Artificial
<220> FEATURE:
<223> OTHER INFORMATION: synthetic primer

<400> SEQUENCE: 1432 tgagggggcag agagcgagac ttt                                                 23

<210> SEQ ID NO 1433
<211> LENGTH: 22
<212> TYPE: DNA
<213> ORGANISM: Artificial
<220> FEATURE:
<223> OTHER INFORMATION: synthetic primer

<400> SEQUENCE: 1433
tggcagtgta ttgttagctg gt                                                   22

<210> SEQ ID NO 1434
<211> LENGTH: 23
<212> TYPE: DNA
<213> ORGANISM: Artificial
<220> FEATURE:
<223> OTHER INFORMATION: synthetic primer

<400> SEQUENCE: 1434
tagcagcggg aacagttctg cag                                                  23

<210> SEQ ID NO 1435
<211> LENGTH: 22
<212> TYPE: DNA
<213> ORGANISM: Artificial
<220> FEATURE:
<223> OTHER INFORMATION: synthetic primer

<400> SEQUENCE: 1435
catgccttga gtgtaggacc gt                                                   22

<210> SEQ ID NO 1436
<211> LENGTH: 22
<212> TYPE: DNA
<213> ORGANISM: Artificial
<220> FEATURE:
<223> OTHER INFORMATION: synthetic primer

<400> SEQUENCE: 1436
```
aagatgtgga aaaattggaa tc                                             22

<210> SEQ ID NO 1437
<211> LENGTH: 21
<212> TYPE: DNA
<213> ORGANISM: Artificial
<220> FEATURE:
<223> OTHER INFORMATION: synthetic primer

<400> SEQUENCE: 1437 aggggggaaag ttctatagtc c                                             21

<210> SEQ ID NO 1438
<211> LENGTH: 23
<212> TYPE: DNA
<213> ORGANISM: Artificial
<220> FEATURE:
<223> OTHER INFORMATION: synthetic primer

<400> SEQUENCE: 1438
tggaagacta gtgattttgt tgt                                            23

<210> SEQ ID NO 1439
<211> LENGTH: 23
<212> TYPE: DNA
<213> ORGANISM: Artificial
<220> FEATURE:
<223> OTHER INFORMATION: synthetic primer

<400> SEQUENCE: 1439
tggaagacta gtgattttgt tgt                                            23

<210> SEQ ID NO 1440
<211> LENGTH: 23
<212> TYPE: DNA
<213> ORGANISM: Artificial
<220> FEATURE:
<223> OTHER INFORMATION: synthetic primer

<400> SEQUENCE: 1440
tggaagacta gtgattttgt tgt                                            23

<210> SEQ ID NO 1441
<211> LENGTH: 22
<212> TYPE: DNA
<213> ORGANISM: Artificial
<220> FEATURE:
<223> OTHER INFORMATION: synthetic primer

<400> SEQUENCE: 1441
ctgccctggc ccgagggacc ga                                             22

<210> SEQ ID NO 1442
<211> LENGTH: 23
<212> TYPE: DNA
<213> ORGANISM: Artificial
<220> FEATURE:
<223> OTHER INFORMATION: synthetic primer

<400> SEQUENCE: 1442
tctttggtta tctagctgta tga                                            23

<210> SEQ ID NO 1443
<211> LENGTH: 23
<212> TYPE: DNA
<213> ORGANISM: Artificial

```
<220> FEATURE:
<223> OTHER INFORMATION: synthetic primer

<400> SEQUENCE: 1443
tctttggtta tctagctgta tga                                          23

<210> SEQ ID NO 1444
<211> LENGTH: 22
<212> TYPE: DNA
<213> ORGANISM: Artificial
<220> FEATURE:
<223> OTHER INFORMATION: synthetic primer

<400> SEQUENCE: 1444
tattgcactt gtcccggcct gt                                           22

<210> SEQ ID NO 1445
<211> LENGTH: 22
<212> TYPE: DNA
<213> ORGANISM: Artificial
<220> FEATURE:
<223> OTHER INFORMATION: synthetic primer

<400> SEQUENCE: 1445
tattgcactt gtcccggcct gt                                           22

<210> SEQ ID NO 1446
<211> LENGTH: 23
<212> TYPE: DNA
<213> ORGANISM: Artificial
<220> FEATURE:
<223> OTHER INFORMATION: synthetic primer

<400> SEQUENCE: 1446
caaagtgctg ttcgtgcagg tag                                          23

<210> SEQ ID NO 1447
<211> LENGTH: 23
<212> TYPE: DNA
<213> ORGANISM: Artificial
<220> FEATURE:
<223> OTHER INFORMATION: synthetic primer

<400> SEQUENCE: 1447
tctttggtta tctagctgta tga                                          23

<210> SEQ ID NO 1448
<211> LENGTH: 22
<212> TYPE: DNA
<213> ORGANISM: Artificial
<220> FEATURE:
<223> OTHER INFORMATION: synthetic primer

<400> SEQUENCE: 1448
aacccgtaga tccgatcttg tg                                           22

<210> SEQ ID NO 1449
<211> LENGTH: 23
<212> TYPE: DNA
<213> ORGANISM: Artificial
<220> FEATURE:
<223> OTHER INFORMATION: synthetic primer

<400> SEQUENCE: 1449
aaaggtaatt gcagttttc cca                                           23
```

<210> SEQ ID NO 1450
<211> LENGTH: 19
<212> TYPE: DNA
<213> ORGANISM: Artificial
<220> FEATURE:
<223> OTHER INFORMATION: synthetic primer

<400> SEQUENCE: 1450
actggacttg gagtcagga                                                  19

<210> SEQ ID NO 1451
<211> LENGTH: 24
<212> TYPE: DNA
<213> ORGANISM: Artificial
<220> FEATURE:
<223> OTHER INFORMATION: synthetic primer

<400> SEQUENCE: 1451
aggcagtgta ttgctagcgg ctgt                                            24

<210> SEQ ID NO 1452
<211> LENGTH: 22
<212> TYPE: DNA
<213> ORGANISM: Artificial
<220> FEATURE:
<223> OTHER INFORMATION: synthetic primer

<400> SEQUENCE: 1452
tgcacccagg caaggattct gc                                              22

<210> SEQ ID NO 1453
<211> LENGTH: 17
<212> TYPE: DNA
<213> ORGANISM: Artificial
<220> FEATURE:
<223> OTHER INFORMATION: synthetic primer

<400> SEQUENCE: 1453
tgagggagga gactgca                                                    17

<210> SEQ ID NO 1454
<211> LENGTH: 20
<212> TYPE: DNA
<213> ORGANISM: Artificial
<220> FEATURE:
<223> OTHER INFORMATION: synthetic primer

<400> SEQUENCE: 1454
actggacttg gagccagaag                                                 20

<210> SEQ ID NO 1455
<211> LENGTH: 26
<212> TYPE: DNA
<213> ORGANISM: Artificial
<220> FEATURE:
<223> OTHER INFORMATION: synthetic primer

<400> SEQUENCE: 1455
gtcactgatg tctgtagctg agacgg                                          26

<210> SEQ ID NO 1456
<211> LENGTH: 23
<212> TYPE: DNA
<213> ORGANISM: Artificial
<220> FEATURE:
<223> OTHER INFORMATION: synthetic primer

```
<400> SEQUENCE: 1456
gatgaggatg gatagcaagg aag                                    23

<210> SEQ ID NO 1457
<211> LENGTH: 21
<212> TYPE: DNA
<213> ORGANISM: Artificial
<220> FEATURE:
<223> OTHER INFORMATION: synthetic primer

<400> SEQUENCE: 1457
aaaagcatca ggaagtaccc a                                      21

<210> SEQ ID NO 1458
<211> LENGTH: 27
<212> TYPE: DNA
<213> ORGANISM: Artificial
<220> FEATURE:
<223> OTHER INFORMATION: synthetic primer

<400> SEQUENCE: 1458
gtcaaatgaa gggctgatca cgaaata                                27

<210> SEQ ID NO 1459
<211> LENGTH: 22
<212> TYPE: DNA
<213> ORGANISM: Artificial
<220> FEATURE:
<223> OTHER INFORMATION: synthetic primer

<400> SEQUENCE: 1459
agagttaact caaaatggac ta                                     22

<210> SEQ ID NO 1460
<211> LENGTH: 23
<212> TYPE: DNA
<213> ORGANISM: Artificial
<220> FEATURE:
<223> OTHER INFORMATION: synthetic primer

<400> SEQUENCE: 1460
tgttgggatt cagcaggacc att                                    23

<210> SEQ ID NO 1461
<211> LENGTH: 22
<212> TYPE: DNA
<213> ORGANISM: Artificial
<220> FEATURE:
<223> OTHER INFORMATION: synthetic primer

<400> SEQUENCE: 1461
taaatagagt aggcaaagga ca                                     22

<210> SEQ ID NO 1462
<211> LENGTH: 26
<212> TYPE: DNA
<213> ORGANISM: Artificial
<220> FEATURE:
<223> OTHER INFORMATION: synthetic primer

<400> SEQUENCE: 1462
aagaggaaga aatggctggt tctcag                                 26

<210> SEQ ID NO 1463
```

```
<211> LENGTH: 22
<212> TYPE: DNA
<213> ORGANISM: Artificial
<220> FEATURE:
<223> OTHER INFORMATION: synthetic primer

<400> SEQUENCE: 1463
tagtggatga tgcactctgt gc                                              22

<210> SEQ ID NO 1464
<211> LENGTH: 20
<212> TYPE: DNA
<213> ORGANISM: Artificial
<220> FEATURE:
<223> OTHER INFORMATION: synthetic primer

<400> SEQUENCE: 1464
aaagactctg caagatgcct                                                 20

<210> SEQ ID NO 1465
<211> LENGTH: 18
<212> TYPE: DNA
<213> ORGANISM: Artificial
<220> FEATURE:
<223> OTHER INFORMATION: synthetic primer

<400> SEQUENCE: 1465
aggagaagta aagtagaa                                                   18

<210> SEQ ID NO 1466
<211> LENGTH: 22
<212> TYPE: DNA
<213> ORGANISM: Artificial
<220> FEATURE:
<223> OTHER INFORMATION: synthetic primer

<400> SEQUENCE: 1466
atggccagag ctcacacaga gg                                              22

<210> SEQ ID NO 1467
<211> LENGTH: 23
<212> TYPE: DNA
<213> ORGANISM: Artificial
<220> FEATURE:
<223> OTHER INFORMATION: synthetic primer

<400> SEQUENCE: 1467
atcagggctt gtggaatggg aag                                             23

<210> SEQ ID NO 1468
<211> LENGTH: 22
<212> TYPE: DNA
<213> ORGANISM: Artificial
<220> FEATURE:
<223> OTHER INFORMATION: synthetic primer

<400> SEQUENCE: 1468
atggccagag ctcacacaga gg                                              22

<210> SEQ ID NO 1469
<211> LENGTH: 23
<212> TYPE: DNA
<213> ORGANISM: Artificial
<220> FEATURE:
<223> OTHER INFORMATION: synthetic primer

<400> SEQUENCE: 1469
```
tgaggatatg gcagggaagg gga                                       23

<210> SEQ ID NO 1470
<211> LENGTH: 22
<212> TYPE: DNA
<213> ORGANISM: Artificial
<220> FEATURE:
<223> OTHER INFORMATION: synthetic primer

<400> SEQUENCE: 1470
tgggctcagg gtacaaaggt tc                                        22

<210> SEQ ID NO 1471
<211> LENGTH: 21
<212> TYPE: DNA
<213> ORGANISM: Artificial
<220> FEATURE:
<223> OTHER INFORMATION: synthetic primer

<400> SEQUENCE: 1471
gctgcaccgg agactgggta a                                         21

<210> SEQ ID NO 1472
<211> LENGTH: 21
<212> TYPE: DNA
<213> ORGANISM: Artificial
<220> FEATURE:
<223> OTHER INFORMATION: synthetic primer

<400> SEQUENCE: 1472
gctgcaccgg agactgggta a                                         21

<210> SEQ ID NO 1473
<211> LENGTH: 22
<212> TYPE: DNA
<213> ORGANISM: Artificial
<220> FEATURE:
<223> OTHER INFORMATION: synthetic primer

<400> SEQUENCE: 1473
tgtcgtgggg cttgctggct tg                                        22

<210> SEQ ID NO 1474
<211> LENGTH: 19
<212> TYPE: DNA
<213> ORGANISM: Artificial
<220> FEATURE:
<223> OTHER INFORMATION: synthetic primer

<400> SEQUENCE: 1474
actggacttg gaggcagaa                                            19

<210> SEQ ID NO 1475
<211> LENGTH: 17
<212> TYPE: DNA
<213> ORGANISM: Artificial
<220> FEATURE:
<223> OTHER INFORMATION: synthetic primer

<400> SEQUENCE: 1475
ttggaggcgt gggtttt                                              17

<210> SEQ ID NO 1476
<211> LENGTH: 22
<212> TYPE: DNA

```
<213> ORGANISM: Artificial
<220> FEATURE:
<223> OTHER INFORMATION: synthetic primer

<400> SEQUENCE: 1476
ctgactgaat aggtagggtc at                                              22

<210> SEQ ID NO 1477
<211> LENGTH: 22
<212> TYPE: DNA
<213> ORGANISM: Artificial
<220> FEATURE:
<223> OTHER INFORMATION: synthetic primer

<400> SEQUENCE: 1477
agattgtttc ttttgccgtg ca                                              22

<210> SEQ ID NO 1478
<211> LENGTH: 21
<212> TYPE: DNA
<213> ORGANISM: Artificial
<220> FEATURE:
<223> OTHER INFORMATION: synthetic primer

<400> SEQUENCE: 1478
cacggcaaaa gaaacaatcc a                                               21

<210> SEQ ID NO 1479
<211> LENGTH: 22
<212> TYPE: DNA
<213> ORGANISM: Artificial
<220> FEATURE:
<223> OTHER INFORMATION: synthetic primer

<400> SEQUENCE: 1479
cagggctggc agtgacatgg gt                                              22

<210> SEQ ID NO 1480
<211> LENGTH: 17
<212> TYPE: DNA
<213> ORGANISM: Artificial
<220> FEATURE:
<223> OTHER INFORMATION: synthetic primer

<400> SEQUENCE: 1480
ggtgggggct gttgttt                                                    17

<210> SEQ ID NO 1481
<211> LENGTH: 23
<212> TYPE: DNA
<213> ORGANISM: Artificial
<220> FEATURE:
<223> OTHER INFORMATION: synthetic primer

<400> SEQUENCE: 1481
tggggaggtg tggagtcagc atg                                             23

<210> SEQ ID NO 1482
<211> LENGTH: 20
<212> TYPE: DNA
<213> ORGANISM: Artificial
<220> FEATURE:
<223> OTHER INFORMATION: synthetic primer

<400> SEQUENCE: 1482
ggctccttgg tctagggta                                                  20
```

<210> SEQ ID NO 1483
<211> LENGTH: 22
<212> TYPE: DNA
<213> ORGANISM: Artificial
<220> FEATURE:
<223> OTHER INFORMATION: synthetic primer

<400> SEQUENCE: 1483
tggggatttg gagaagtggt ga                                    22

<210> SEQ ID NO 1484
<211> LENGTH: 22
<212> TYPE: DNA
<213> ORGANISM: Artificial
<220> FEATURE:
<223> OTHER INFORMATION: synthetic primer

<400> SEQUENCE: 1484
aaaagtgatt gcagtgtttg cc                                    22

<210> SEQ ID NO 1485
<211> LENGTH: 22
<212> TYPE: DNA
<213> ORGANISM: Artificial
<220> FEATURE:
<223> OTHER INFORMATION: synthetic primer

<400> SEQUENCE: 1485
taggagctca acagatgcct gt                                    22

<210> SEQ ID NO 1486
<211> LENGTH: 21
<212> TYPE: DNA
<213> ORGANISM: Artificial
<220> FEATURE:
<223> OTHER INFORMATION: synthetic primer

<400> SEQUENCE: 1486
agcttttggg aattcaggta g                                     21

<210> SEQ ID NO 1487
<211> LENGTH: 21
<212> TYPE: DNA
<213> ORGANISM: Artificial
<220> FEATURE:
<223> OTHER INFORMATION: synthetic primer

<400> SEQUENCE: 1487
caaaagtgat cgtggttttt g                                     21

<210> SEQ ID NO 1488
<211> LENGTH: 17
<212> TYPE: DNA
<213> ORGANISM: Artificial
<220> FEATURE:
<223> OTHER INFORMATION: synthetic primer

<400> SEQUENCE: 1488
agggtgtgtg tgttttt                                          17

<210> SEQ ID NO 1489
<211> LENGTH: 21
<212> TYPE: DNA
<213> ORGANISM: Artificial
<220> FEATURE:

```
<223> OTHER INFORMATION: synthetic primer

<400> SEQUENCE: 1489
actgacagga gagcattttg a                                              21

<210> SEQ ID NO 1490
<211> LENGTH: 23
<212> TYPE: DNA
<213> ORGANISM: Artificial
<220> FEATURE:
<223> OTHER INFORMATION: synthetic primer

<400> SEQUENCE: 1490
atagtggttg tgaatttacc ttc                                            23

<210> SEQ ID NO 1491
<211> LENGTH: 24
<212> TYPE: DNA
<213> ORGANISM: Artificial
<220> FEATURE:
<223> OTHER INFORMATION: synthetic primer

<400> SEQUENCE: 1491
ctaccccagg atgccagcat agtt                                           24

<210> SEQ ID NO 1492
<211> LENGTH: 21
<212> TYPE: DNA
<213> ORGANISM: Artificial
<220> FEATURE:
<223> OTHER INFORMATION: synthetic primer

<400> SEQUENCE: 1492
actggacttg gtgtcagatg g                                              21

<210> SEQ ID NO 1493
<211> LENGTH: 22
<212> TYPE: DNA
<213> ORGANISM: Artificial
<220> FEATURE:
<223> OTHER INFORMATION: synthetic primer

<400> SEQUENCE: 1493
tagtggatga tggagactcg gt                                             22

<210> SEQ ID NO 1494
<211> LENGTH: 21
<212> TYPE: DNA
<213> ORGANISM: Artificial
<220> FEATURE:
<223> OTHER INFORMATION: synthetic primer

<400> SEQUENCE: 1494
aaggtttgga tagatgcaat a                                              21

<210> SEQ ID NO 1495
<211> LENGTH: 23
<212> TYPE: DNA
<213> ORGANISM: Artificial
<220> FEATURE:
<223> OTHER INFORMATION: synthetic primer

<400> SEQUENCE: 1495
aaaggtaatt gcagtttttc cca                                            23
```

```
<210> SEQ ID NO 1496
<211> LENGTH: 22
<212> TYPE: DNA
<213> ORGANISM: Artificial
<220> FEATURE:
<223> OTHER INFORMATION: synthetic primer

<400> SEQUENCE: 1496
aggggaccaa agagatatat ag                                              22

<210> SEQ ID NO 1497
<211> LENGTH: 22
<212> TYPE: DNA
<213> ORGANISM: Artificial
<220> FEATURE:
<223> OTHER INFORMATION: synthetic primer

<400> SEQUENCE: 1497
ggcgacaaaa cgagaccctg tc                                              22

<210> SEQ ID NO 1498
<211> LENGTH: 19
<212> TYPE: DNA
<213> ORGANISM: Artificial
<220> FEATURE:
<223> OTHER INFORMATION: synthetic primer

<400> SEQUENCE: 1498
gggtgcgggc cggcggggt                                                  19

<210> SEQ ID NO 1499
<211> LENGTH: 22
<212> TYPE: DNA
<213> ORGANISM: Artificial
<220> FEATURE:
<223> OTHER INFORMATION: synthetic primer

<400> SEQUENCE: 1499
catgctagga tagaaagaat gg                                              22

<210> SEQ ID NO 1500
<211> LENGTH: 22
<212> TYPE: DNA
<213> ORGANISM: Artificial
<220> FEATURE:
<223> OTHER INFORMATION: synthetic primer

<400> SEQUENCE: 1500
gcaaagtgat gagtaatact gg                                              22

<210> SEQ ID NO 1501
<211> LENGTH: 21
<212> TYPE: DNA
<213> ORGANISM: Artificial
<220> FEATURE:
<223> OTHER INFORMATION: synthetic primer

<400> SEQUENCE: 1501 ccctgggtt ctgaggacat g                                                21

<210> SEQ ID NO 1502
<211> LENGTH: 22
<212> TYPE: DNA
<213> ORGANISM: Artificial
<220> FEATURE:
<223> OTHER INFORMATION: synthetic primer
```

```
<400> SEQUENCE: 1502
caggaaggat ttagggacag gc                                             22

<210> SEQ ID NO 1503
<211> LENGTH: 22
<212> TYPE: DNA
<213> ORGANISM: Artificial
<220> FEATURE:
<223> OTHER INFORMATION: synthetic primer

<400> SEQUENCE: 1503
attaaggaca tttgtgattg at                                             22

<210> SEQ ID NO 1504
<211> LENGTH: 21
<212> TYPE: DNA
<213> ORGANISM: Artificial
<220> FEATURE:
<223> OTHER INFORMATION: synthetic primer

<400> SEQUENCE: 1504
aaaaggcata aaccaagac a                                               21

<210> SEQ ID NO 1505
<211> LENGTH: 21
<212> TYPE: DNA
<213> ORGANISM: Artificial
<220> FEATURE:
<223> OTHER INFORMATION: synthetic primer

<400> SEQUENCE: 1505
aaaaggcata aaccaagac a                                               21

<210> SEQ ID NO 1506
<211> LENGTH: 20
<212> TYPE: DNA
<213> ORGANISM: Artificial
<220> FEATURE:
<223> OTHER INFORMATION: synthetic primer

<400> SEQUENCE: 1506
taaaaactgc aattactttc                                                20

<210> SEQ ID NO 1507
<211> LENGTH: 22
<212> TYPE: DNA
<213> ORGANISM: Artificial
<220> FEATURE:
<223> OTHER INFORMATION: synthetic primer

<400> SEQUENCE: 1507
tgtgatatca tggttcctgg ga                                             22

<210> SEQ ID NO 1508
<211> LENGTH: 22
<212> TYPE: DNA
<213> ORGANISM: Artificial
<220> FEATURE:
<223> OTHER INFORMATION: synthetic primer

<400> SEQUENCE: 1508
tgtgatatca tggttcctgg ga                                             22

<210> SEQ ID NO 1509
<211> LENGTH: 22
```

```
<212> TYPE: DNA
<213> ORGANISM: Artificial
<220> FEATURE:
<223> OTHER INFORMATION: synthetic primer

<400> SEQUENCE: 1509
tgtgatatca tggttcctgg ga                                             22

<210> SEQ ID NO 1510
<211> LENGTH: 22
<212> TYPE: DNA
<213> ORGANISM: Artificial
<220> FEATURE:
<223> OTHER INFORMATION: synthetic primer

<400> SEQUENCE: 1510
tgtgatatcg tgcttcctgg ga                                             22

<210> SEQ ID NO 1511
<211> LENGTH: 21
<212> TYPE: DNA
<213> ORGANISM: Artificial
<220> FEATURE:
<223> OTHER INFORMATION: synthetic primer

<400> SEQUENCE: 1511
aaaagtaact gcggttttg a                                               21

<210> SEQ ID NO 1512
<211> LENGTH: 17
<212> TYPE: DNA
<213> ORGANISM: Artificial
<220> FEATURE:
<223> OTHER INFORMATION: synthetic primer

<400> SEQUENCE: 1512
ggagtgggct ggtggtt                                                   17

<210> SEQ ID NO 1513
<211> LENGTH: 22
<212> TYPE: DNA
<213> ORGANISM: Artificial
<220> FEATURE:
<223> OTHER INFORMATION: synthetic primer

<400> SEQUENCE: 1513
aagggcttcc tctctgcagg ac                                             22

<210> SEQ ID NO 1514
<211> LENGTH: 22
<212> TYPE: DNA
<213> ORGANISM: Artificial
<220> FEATURE:
<223> OTHER INFORMATION: synthetic primer

<400> SEQUENCE: 1514
aagggcttcc tctctgcagg ac                                             22

<210> SEQ ID NO 1515
<211> LENGTH: 19
<212> TYPE: DNA
<213> ORGANISM: Artificial
<220> FEATURE:
<223> OTHER INFORMATION: synthetic primer

<400> SEQUENCE: 1515
```
agagctggct gaagggcag					19

<210> SEQ ID NO 1516
<211> LENGTH: 22
<212> TYPE: DNA
<213> ORGANISM: Artificial
<220> FEATURE:
<223> OTHER INFORMATION: synthetic primer

<400> SEQUENCE: 1516
tgtgacttta agggaaatgg cg				22

<210> SEQ ID NO 1517
<211> LENGTH: 22
<212> TYPE: DNA
<213> ORGANISM: Artificial
<220> FEATURE:
<223> OTHER INFORMATION: synthetic primer

<400> SEQUENCE: 1517
tctcaggagt aaagacagag tt				22

<210> SEQ ID NO 1518
<211> LENGTH: 22
<212> TYPE: DNA
<213> ORGANISM: Artificial
<220> FEATURE:
<223> OTHER INFORMATION: synthetic primer

<400> SEQUENCE: 1518
aggtggatgc aatgtgacct ca				22

<210> SEQ ID NO 1519
<211> LENGTH: 18
<212> TYPE: DNA
<213> ORGANISM: Artificial
<220> FEATURE:
<223> OTHER INFORMATION: synthetic primer

<400> SEQUENCE: 1519
aggctgggct gggacgga					18

<210> SEQ ID NO 1520
<211> LENGTH: 20
<212> TYPE: DNA
<213> ORGANISM: Artificial
<220> FEATURE:
<223> OTHER INFORMATION: synthetic primer

<400> SEQUENCE: 1520
taggatgggg gtgagaggtg					20

<210> SEQ ID NO 1521
<211> LENGTH: 22
<212> TYPE: DNA
<213> ORGANISM: Artificial
<220> FEATURE:
<223> OTHER INFORMATION: synthetic primer

<400> SEQUENCE: 1521
tgagggagta ggatgtatgg tt				22

<210> SEQ ID NO 1522
<211> LENGTH: 22
<212> TYPE: DNA
<213> ORGANISM: Artificial

```
<220> FEATURE:
<223> OTHER INFORMATION: synthetic primer

<400> SEQUENCE: 1522
agactgacgg ctggaggccc at                                                22

<210> SEQ ID NO 1523
<211> LENGTH: 22
<212> TYPE: DNA
<213> ORGANISM: Artificial
<220> FEATURE:
<223> OTHER INFORMATION: synthetic primer

<400> SEQUENCE: 1523
tagtgagtta gagatgcaga gc                                                22

<210> SEQ ID NO 1524
<211> LENGTH: 17
<212> TYPE: DNA
<213> ORGANISM: Artificial
<220> FEATURE:
<223> OTHER INFORMATION: synthetic primer

<400> SEQUENCE: 1524
gggagaaggg tcggggc                                                      17

<210> SEQ ID NO 1525
<211> LENGTH: 22
<212> TYPE: DNA
<213> ORGANISM: Artificial
<220> FEATURE:
<223> OTHER INFORMATION: synthetic primer

<400> SEQUENCE: 1525
ctcgtgggct ctggccacgg cc                                                22

<210> SEQ ID NO 1526
<211> LENGTH: 22
<212> TYPE: DNA
<213> ORGANISM: Artificial
<220> FEATURE:
<223> OTHER INFORMATION: synthetic primer

<400> SEQUENCE: 1526 agaagggtg aaatttaaac gt                                                 22

<210> SEQ ID NO 1527
<211> LENGTH: 22
<212> TYPE: DNA
<213> ORGANISM: Artificial
<220> FEATURE:
<223> OTHER INFORMATION: synthetic primer

<400> SEQUENCE: 1527 agaagggtg aaatttaaac gt                                                 22

<210> SEQ ID NO 1528
<211> LENGTH: 22
<212> TYPE: DNA
<213> ORGANISM: Artificial
<220> FEATURE:
<223> OTHER INFORMATION: synthetic primer

<400> SEQUENCE: 1528 agaagggtg aaatttaaac gt                                                 22
```

<210> SEQ ID NO 1529
<211> LENGTH: 26
<212> TYPE: DNA
<213> ORGANISM: Artificial
<220> FEATURE:
<223> OTHER INFORMATION: synthetic primer

<400> SEQUENCE: 1529
gctcagggat gataactgtg ctgaga                                        26

<210> SEQ ID NO 1530
<211> LENGTH: 22
<212> TYPE: DNA
<213> ORGANISM: Artificial
<220> FEATURE:
<223> OTHER INFORMATION: synthetic primer

<400> SEQUENCE: 1530
ctggactgag ccatgctact gg                                            22

<210> SEQ ID NO 1531
<211> LENGTH: 22
<212> TYPE: DNA
<213> ORGANISM: Artificial
<220> FEATURE:
<223> OTHER INFORMATION: synthetic primer

<400> SEQUENCE: 1531
atagcagcat gaacctgtct ca                                            22

<210> SEQ ID NO 1532
<211> LENGTH: 22
<212> TYPE: DNA
<213> ORGANISM: Artificial
<220> FEATURE:
<223> OTHER INFORMATION: synthetic primer

<400> SEQUENCE: 1532
tgagacaggc ttatgctgct at                                            22

<210> SEQ ID NO 1533
<211> LENGTH: 23
<212> TYPE: DNA
<213> ORGANISM: Artificial
<220> FEATURE:
<223> OTHER INFORMATION: synthetic primer

<400> SEQUENCE: 1533
tggtctgcaa agagatgact gtg                                           23

<210> SEQ ID NO 1534
<211> LENGTH: 21
<212> TYPE: DNA
<213> ORGANISM: Artificial
<220> FEATURE:
<223> OTHER INFORMATION: synthetic primer

<400> SEQUENCE: 1534
ttggagggtg tggaagacat c                                             21

<210> SEQ ID NO 1535
<211> LENGTH: 17
<212> TYPE: DNA
<213> ORGANISM: Artificial
<220> FEATURE:
<223> OTHER INFORMATION: synthetic primer

```
<400> SEQUENCE: 1535
atggagaagg cttctga                                                  17

<210> SEQ ID NO 1536
<211> LENGTH: 18
<212> TYPE: DNA
<213> ORGANISM: Artificial
<220> FEATURE:
<223> OTHER INFORMATION: synthetic primer

<400> SEQUENCE: 1536
aaaagctggg ttgagaag                                                 18

<210> SEQ ID NO 1537
<211> LENGTH: 22
<212> TYPE: DNA
<213> ORGANISM: Artificial
<220> FEATURE:
<223> OTHER INFORMATION: synthetic primer

<400> SEQUENCE: 1537
tggaaggtag acggccagag ag                                            22

<210> SEQ ID NO 1538
<211> LENGTH: 22
<212> TYPE: DNA
<213> ORGANISM: Artificial
<220> FEATURE:
<223> OTHER INFORMATION: synthetic primer

<400> SEQUENCE: 1538
tctgggaggt tgtagcagtg ga                                            22

<210> SEQ ID NO 1539
<211> LENGTH: 23
<212> TYPE: DNA
<213> ORGANISM: Artificial
<220> FEATURE:
<223> OTHER INFORMATION: synthetic primer

<400> SEQUENCE: 1539
ggaggaacct tggagcttcg gca                                           23

<210> SEQ ID NO 1540
<211> LENGTH: 21
<212> TYPE: DNA
<213> ORGANISM: Artificial
<220> FEATURE:
<223> OTHER INFORMATION: synthetic primer

<400> SEQUENCE: 1540
actggactag gagtcagaag g                                             21

<210> SEQ ID NO 1541
<211> LENGTH: 22
<212> TYPE: DNA
<213> ORGANISM: Artificial
<220> FEATURE:
<223> OTHER INFORMATION: synthetic primer

<400> SEQUENCE: 1541
caaaaactgc agttactttt gt                                            22

<210> SEQ ID NO 1542
```

```
<211> LENGTH: 20
<212> TYPE: DNA
<213> ORGANISM: Artificial
<220> FEATURE:
<223> OTHER INFORMATION: synthetic primer

<400> SEQUENCE: 1542
aaaaggcatt gtggttttg                                                    20

<210> SEQ ID NO 1543
<211> LENGTH: 34
<212> TYPE: DNA
<213> ORGANISM: Artificial
<220> FEATURE:
<223> OTHER INFORMATION: synthetic primer

<400> SEQUENCE: 1543
atatctcgag gcccgagtcc ccgggcatct ttgg                                   34

<210> SEQ ID NO 1544
<211> LENGTH: 32
<212> TYPE: DNA
<213> ORGANISM: Artificial
<220> FEATURE:
<223> OTHER INFORMATION: synthetic primer

<400> SEQUENCE: 1544
atatatctag actacacacg acaaatactt tg                                     32

<210> SEQ ID NO 1545
<211> LENGTH: 41
<212> TYPE: DNA
<213> ORGANISM: Artificial
<220> FEATURE:
<223> OTHER INFORMATION: synthetic primer

<400> SEQUENCE: 1545
cagcccatcc atagtaacag tcatgattag cagaagaaag g                           41

<210> SEQ ID NO 1546
<211> LENGTH: 41
<212> TYPE: DNA
<213> ORGANISM: Artificial
<220> FEATURE:
<223> OTHER INFORMATION: synthetic primer

<400> SEQUENCE: 1546
cctttcttct gctaatcatg actgttacta tggatgggct g                           41

<210> SEQ ID NO 1547
<211> LENGTH: 32
<212> TYPE: DNA
<213> ORGANISM: Artificial
<220> FEATURE:
<223> OTHER INFORMATION: synthetic primer

<400> SEQUENCE: 1547
atatctcgag ggtcacatct cccaggaaga tc                                     32

<210> SEQ ID NO 1548
<211> LENGTH: 33
<212> TYPE: DNA
<213> ORGANISM: Artificial
<220> FEATURE:
<223> OTHER INFORMATION: synthetic primer

<400> SEQUENCE: 1548
```

```
atatatctag aagcactctc atggtgtgtg tag                                33
```

<210> SEQ ID NO 1549
<211> LENGTH: 33
<212> TYPE: DNA
<213> ORGANISM: Artificial
<220> FEATURE:
<223> OTHER INFORMATION: synthetic primer

<400> SEQUENCE: 1549

```
agagactcga ggattttcag aaaacactta ttt                                33
```

<210> SEQ ID NO 1550
<211> LENGTH: 21
<212> TYPE: DNA
<213> ORGANISM: Artificial
<220> FEATURE:
<223> OTHER INFORMATION: synthetic primer

<400> SEQUENCE: 1550

```
ttgcttctct agaggagaaa c                                             21
```

<210> SEQ ID NO 1551
<211> LENGTH: 21
<212> TYPE: DNA
<213> ORGANISM: Artificial
<220> FEATURE:
<223> OTHER INFORMATION: synthetic primer

<400> SEQUENCE: 1551

```
gtttctcctc tagagaagca a                                             21
```

<210> SEQ ID NO 1552
<211> LENGTH: 35
<212> TYPE: DNA
<213> ORGANISM: Artificial
<220> FEATURE:
<223> OTHER INFORMATION: synthetic primer

<400> SEQUENCE: 1552

```
agagagcggc cgcaggggag agacaaattg cattg                              35
```

<210> SEQ ID NO 1553
<211> LENGTH: 31
<212> TYPE: DNA
<213> ORGANISM: Artificial
<220> FEATURE:
<223> OTHER INFORMATION: synthetic primer

<400> SEQUENCE: 1553

```
agagactcga gataaaagga ggaatcttaa g                                  31
```

<210> SEQ ID NO 1554
<211> LENGTH: 35
<212> TYPE: DNA
<213> ORGANISM: Artificial
<220> FEATURE:
<223> OTHER INFORMATION: synthetic primer

<400> SEQUENCE: 1554

```
agagagcggc cgcgaaaaaa acaaaacaaa aacaa                              35
```

<210> SEQ ID NO 1555
<211> LENGTH: 33
<212> TYPE: DNA

```
<213> ORGANISM: Artificial
<220> FEATURE:
<223> OTHER INFORMATION: synthetic primer

<400> SEQUENCE: 1555
agagagcggc cgcccgattg agtcttgcct cat                              33

<210> SEQ ID NO 1556
<211> LENGTH: 31
<212> TYPE: DNA
<213> ORGANISM: Artificial
<220> FEATURE:
<223> OTHER INFORMATION: synthetic primer

<400> SEQUENCE: 1556
agagagaatt caatggtctc acatttccaa c                                31

<210> SEQ ID NO 1557
<211> LENGTH: 33
<212> TYPE: DNA
<213> ORGANISM: Artificial
<220> FEATURE:
<223> OTHER INFORMATION: synthetic primer

<400> SEQUENCE: 1557
agagagcggc cgcatgtcac agctattgtt cag                              33

<210> SEQ ID NO 1558
<211> LENGTH: 31
<212> TYPE: DNA
<213> ORGANISM: Artificial
<220> FEATURE:
<223> OTHER INFORMATION: synthetic primer

<400> SEQUENCE: 1558
agagagaatt cgcagtaaaa gaatgcagct a                                31

<210> SEQ ID NO 1559
<211> LENGTH: 40
<212> TYPE: DNA
<213> ORGANISM: Artificial
<220> FEATURE:
<223> OTHER INFORMATION: synthetic primer

<400> SEQUENCE: 1559
ggaagcgagt tgttatctat gcttatctag ctgtatgagt                       40

<210> SEQ ID NO 1560
<211> LENGTH: 40
<212> TYPE: DNA
<213> ORGANISM: Artificial
<220> FEATURE:
<223> OTHER INFORMATION: synthetic primer

<400> SEQUENCE: 1560
actcatacag ctagataagc atagataaca actcgcttcc                       40

<210> SEQ ID NO 1561
<211> LENGTH: 40
<212> TYPE: DNA
<213> ORGANISM: Artificial
<220> FEATURE:
<223> OTHER INFORMATION: synthetic primer

<400> SEQUENCE: 1561
accaagtttc agttcatgtt aagatcctac actcagctgt                       40
```

```
<210> SEQ ID NO 1562
<211> LENGTH: 40
<212> TYPE: DNA
<213> ORGANISM: Artificial
<220> FEATURE:
<223> OTHER INFORMATION: synthetic primer

<400> SEQUENCE: 1562
acagctgagt gtaggatctt aacatgaact gaaacttggt                                40

<210> SEQ ID NO 1563
<211> LENGTH: 40
<212> TYPE: DNA
<213> ORGANISM: Artificial
<220> FEATURE:
<223> OTHER INFORMATION: synthetic primer

<400> SEQUENCE: 1563
cagaaagtct gttgttgtta agatccccga ctggaagctg                                40

<210> SEQ ID NO 1564
<211> LENGTH: 40
<212> TYPE: DNA
<213> ORGANISM: Artificial
<220> FEATURE:
<223> OTHER INFORMATION: synthetic primer

<400> SEQUENCE: 1564
cagcttccag tcggggatct taacaacaac agactttctg                                40

<210> SEQ ID NO 1565
<211> LENGTH: 23
<212> TYPE: RNA
<213> ORGANISM: homo sapiens

<400> SEQUENCE: 1565
uggucugcaa agagaugacu gug                                                  23
```

MICRORNA AND USE THEREOF IN IDENTIFICATION OF B CELL MALIGNANCIES

CROSS REFERENCE TO RELATED APPLICATIONS

This patent application is a divisional of U.S. patent application Ser. No. 13/513,757, filed on Aug. 13, 2012, which is a national stage filing under 35 U.S.C. 371 of International Patent Application No. PCT/US2010/058952, filed Dec. 3, 2010, which claims the benefit of priority of U.S. Provisional Patent Application No. 61/266,733, filed Dec. 4, 2009, the contents of all of which are incorporated herein by reference. Priority to each application is hereby claimed.

STATEMENT OF GOVERNMENT SUPPORT

This invention was made with United States government support from the National Institutes of Health grant no. K12-CA-100639. The United States government has certain rights in this invention.

SEQUENCE LISTING

The sequence listing is filed with the application in electronic format only and is incorporated by reference herein. The sequence listing text file "WO_ASFILED_SequenceListing.txt" was created on Dec. 3, 2010, and is 262,254 bytes in size.

BACKGROUND

Naive B cells migrate through the circulation to lymphoid organs where they undergo the T cell-dependent germinal center reaction. Adaptive immunity is acquired as specific antigen-reactive germinal center B cells differentiate into the major effector B cells of the adaptive immune system: memory cells and plasma cells. See, e.g., FIG. 1A. Although the role of specific transcription factors in mature B cell differentiation has been examined (see Nutt et al. *Nature.* 1999; 401:556-562; Chang et al. *Proc Natl Acad Sci USA.* 1996; 93:6947-6952; Turner et al. *Cell.* 1994; 77:297-306; Shaffer et al., *Immunity.* 2004; 21:81-93; and Schebesta et al. *Curr Opin Immunol.* 2002; 14:216-223), mechanisms regulating such transcription factors during mature B cell differentiation are largely unknown.

Many malignancies derived from mature B cells are known and are believed to constitute the majority of leukemias and lymphomas. Such malignancies appear to reflect defined stages of normal B cell differentiation. Diagnosis of leukemias and lymphomas can be particularly difficult because of their shared lineage. These cancers frequently display overlapping morphologies, genetic abnormalities, and expression of surface markers, which can complicate the diagnosis. However, the distinction of these tumors is clinically important because there are important differences in the treatments and expected response to treatment. Thus methods that improve the accuracy of their diagnosis should provide to improved outcomes for these patients.

MicroRNAs are commonly 18-22 nucleotide-long RNA molecules that regulate expression of genes. There is an increasing recognition of the role of microRNAs in oncogenesis, lineage-selection, and immune cell function, including early B cell differentiation. See Calin et al. *N Engl J Med.* 2005; 353:1793-1801; O'Donnell et al. *Nature.* 2005; 435:839-843; Chen et al. *Science.* 2004; 303:83-86; Lim et al. *Nature.* 2005; 433:769-773; Li et al. *Cell.* 2007; 129:147-161; Xiao et al., *Nat Immunol.* 2008; 9:405-414; Baltimore et al. *Nat Immunol.* 2008; 9:839-845; and Ventura et al. *Cell.* 2008; 132:875-886. However, the full extent and function of microRNA expression during mature B cell differentiation and in B cell malignancies are not known.

Correct diagnosis of B cell malignancies is important from both a clinical standpoint and from the standpoint of setting appropriate patient expectations. A misdiagnosed B cell malignancy may lead to an inappropriate therapy, which can unnecessarily endanger the patient's life and/or be an ineffective treatment for the B cell malignancy. As an example, the diagnostic distinction of Burkitt lymphoma (BL) from diffuse large B cell lymphomas (DLBCLs) can be difficult because of overlapping morphology, immunophenotype and cytogenetics. Burkitt lymphoma tumors are molecularly distinct from DLBCL, however. The difficulty and importance of obtaining the correct diagnosis in BL was highlighted by the experience of a multicenter clinical trial, CALGB trial#925119, in which nearly half of the 100 patients with an assigned diagnosis of BL were found to have another diagnosis upon further pathology review.

If diagnosed and treated appropriately, nearly 80% of patients with BL can be cured with intensive (high dose) chemotherapy regimens. Thus, a misclassification of BL as DLBCL can result in a missed opportunity to cure the malignancy. On the other hand, misclassification of DLBCL as BL leads to unnecessarily morbidity from intensive chemotherapy regimens. Thus, methods that improve the diagnosis of BL, and other B cell malignancies, can provide better outcomes in patients.

DLBCLs can also be subclassified into two different B cell malignancies, activated B-cell (ABC) DLBCL and germinal center B cell like (GCB) DLBCL. There are at least two important clinical applications for the molecular subgrouping of DLBCL patients. First, the prognostic information could inform the choices and expectations of patients and their physicians. Second, the important molecular differences in these subgroups form the basis of testing different targeted therapies in these patients. The possibility of a differential response to therapy among ABC and GCB DLBCLs is supported by data that suggest that the benefit of receiving a proteosome inhibitor, bortozemib, is predominantly limited to those patients who have ABC DLBCL. However, the clinical distinction of the subgroups of DLBCL using immunohistochemistry is difficult with current methods distinguishing GCB DLBCL from non-GCB DLBCL with limited success.

Mature B cell differentiation is important for the development of adaptive immunity. The process is also of interest because B cell malignancies are common and retain a number of features derived from their normal counterpart B cell subsets. Unlike other maturation pathways in the hematopoietic and other cell lineages, successive stages of mature B cells do not simply signify progressive differentiation away from the stem cell stage. Rather, each stage represents a specialized state with specific functions. Thus, germinal center (GC) cells interact with CD4 T cells and dendritic cells and undergo somatic hypermutation and Ig-heavy chain class-switching. On the other hand, plasma cells secrete immunoglobulin, while memory cells are primed to proliferate and differentiate into plasma cells upon repeat contact with antigen. The specialized functions demand a finely tuned program of gene regulation.

MicroRNAs represent a novel class of biomarkers that provide new opportunities for clinical translation. First, intact microRNAs can be isolated from tissues preserved using standard methods, such as formalin fixed, paraffin embedded (FFPE) tissue. Thus, microRNA-based biomarkers could be easy to translate to clinical use. Second, microRNAs can be readily assayed using real-time PCR and other methods available in conventional pathology.

SUMMARY

In an aspect the disclosure provides an isolated nucleic acid molecule having at least 80% sequence identity to any one of SEQ ID NOs: 763-1350 or 1565 or a complementary sequence thereof. Embodiments provide for sequence identity of at least 90% or 95%.

In an aspect the disclosure provides an isolated nucleic acid molecule comprises any one of SEQ ID NOs: 763-1350 or 1565 or a complementary sequence thereof. Embodiments provide for isolated nucleic acid molecules comprising a primary miRNA, a precursor miRNA, a mature miRNA, or a DNA molecule coding therefore. Embodiments further provide for a cDNA molecule comprising sequence that corresponds to a miRNA sequence of any one of SEQ ID NOs: 763-1350 or 1565.

Aspects of the disclosure provide compositions, pharmaceutical compositions, vectors, host cells, and DNA libraries comprising at least one nucleic acid molecule described herein.

In an aspect the disclosure provides a method of determining the B cell stage of a B cell malignancy in a subject comprising determining the level of expression of at least one microRNA in a sample comprising a B cell taken from the subject relative the level of expression of the at least one microRNA in a control sample, wherein the at least one microRNA is selected from the microRNAs listed in Table 4.

In an aspect the disclosure provides a method of identifying a B cell malignancy in a subject comprising determining the level of expression of at least one microRNA in a sample comprising a B cell taken from the subject relative the level of expression of the at least one microRNA in a control sample, wherein the at least one microRNA is selected from the microRNAs listed in Table 4.

In an aspect the disclosure provides a method of diagnosing a B cell malignancy in a subject comprising determining the level of expression of at least one microRNA in a sample comprising a B cell taken from the subject relative the level of expression of the at least one microRNA in a control sample, wherein the at least one microRNA is selected from the microRNAs listed in Table 4.

In an aspect the disclosure provides a method of identifying a B cell malignancy in a subject comprising determining the level of expression of at least one microRNA in a sample comprising a B cell taken from the subject relative the level of expression of the at least one microRNA in a control sample, wherein the at least one microRNA is selected from the microRNAs listed in any one of Tables 7 to 35.

In an aspect the disclosure provides a method of diagnosing a B cell malignancy in a subject comprising determining the level of expression of at least one microRNA in a sample comprising a B cell taken from the subject relative to the level of expression of the at least one microRNA in a control sample, wherein the at least one microRNA is selected from the microRNAs listed in any one of Tables 7 to 35.

Embodiments of these aspects provide for identification or diagnosis of a B cell malignancy selected from chronic lymphocytic leukemia, follicular lymphoma, Hodgkin's lymphoma, activated B-cell diffuse large B cell lymphoma (DLBCL), germinal center-like DLBCL, and Burkitt lymphoma.

In an aspect the disclosure provides a method of determining whether a B cell malignancy in a sample is Burkitt lymphoma, activated B cell-like diffuse large B cell lymphoma (DLBCL), or germinal center-like DLBCL, comprising determining the level of expression of at least one microRNA in the sample relative to the level of expression of the at least one microRNA in a control sample, wherein the at least one microRNA is selected from the microRNAs listed in Table 10, column "BL miRNA list"; Table 14, column "BL High"; Table 11; Table 14, column "ABC High"; Table 10, column "GCB miRNA list"; Table 14, column "GCB High"; Table 32, or Table 35.

In an aspect the disclosure provides a method of determining whether a B cell malignancy in a sample is Burkitt lymphoma, activated B cell-like diffuse large B cell lymphoma (DLBCL), or germinal center-like DLBCL, comprising determining the level of expression of at least one microRNA in the sample relative to the level of expression of the at least one microRNA in a control sample, wherein the at least one microRNA is selected from the microRNAs listed in at least one column labeled "GCBvsBL" or "GCBvsABC" in Table 7 or "ABCvsBL" in Table 8.

In an aspect the disclosure provides a method of determining whether a B cell malignancy in a sample is activated B cell-like diffuse large B cell lymphoma (DLBCL), or germinal center-like DLBCL, comprising determining the level of expression of at least one microRNA in the sample relative to the level of expression of the at least one microRNA in a control sample, wherein the at least one microRNA is selected from the microRNAs listed in Table 35.

In an aspect the disclosure provides a microarray comprising miRNA-specific probe oligonucleotides wherein at least one miRNA-specific probe oligonucleotide is specific for a sequence of SEQ ID NOs: 763-1350 or 1565, or any combination thereof.

In an aspect the disclosure provides a kit comprising at least one primer sequence that can detect any one of SEQ ID NOs: 763-1350 or 1565, or a combination thereof.

In an aspect the disclosure provides a kit comprising at least one isolated nucleic acid molecule having a sequence of any one of SEQ ID NOs: 1351-1564.

In an aspect, the disclosure provides a method of identifying a B cell malignancy comprising determining the level of expression of at least one microRNA selected from the microRNAs listed in Table 4. In certain embodiments, a method comprises determining the level of expression of at least one microRNA selected from the microRNAs listed in Tables 7-35.

Other aspects and embodiments will be apparent to one of skill in the art in light of the following detailed description.

DESCRIPTION OF THE FIGURES

FIG. 1A is a diagram showing the overall schema of mature B cell differentiation. FIG. 1B shows selection of B cell subsets using flow cytometry. FIG. 1C shows the distinction between naive and memory B cells based on IgD and CD27 expression using flow cytometry. FIG. 1D shows relative expression of microRNA in the naive to germinal center B cell transition. FIG. 1E shows relative expression of mRNA in the naive to germinal center B cell transition. FIG. 1F shows relative expression of microRNA in the germinal center B cell to plasma cell transition. FIG. 1G shows relative expression of mRNA in the germinal center B cell to plasma cell transition. FIG. 1H shows relative expression of microRNA in the germinal center B cell to memory B cell transition. FIG. 1I shows relative expression of mRNA in the germinal center B cell to memory B cell transition. In FIGS. 1D, 1F, and 1H, miRNAs that were, on average, at least 2-fold differentially expressed at a false discovery rate of less than 5% are shown according to the color scale. In FIGS. and 1E, 1G, and 1I, mRNAs that were, on average, at least 2-fold differentially expressed at a false discovery rate of less than 1% are shown according to the color scale. FIG. 1J shows that expression of certain microRNA processing genes, DGCR8, DICER1, EIF2C2, DROSHA, and XP05 is unchanged among the B cell subsets (P>0.1 in all cases).

FIG. 2A shows base-pairing of the 3'UTR of the LM02 gene with nucleotides 1-8 of miR-223. This 8-mer is highly conserved across a number of species and serves as a potential binding site for miR-223. FIG. 2B shows the effects of over-expression of miR-223 in germinal center lymphoma-derived BJAB cells in 3 separate experiments. FIG. 2C shows the relative LM02 protein expression from a representative experiment (from 3 replicates) transfecting a scrambled control versus a precursor for miR-223 in BJAB cells. FIG. 2D shows average expression of LM02 relative to Actin over three Western blots of BJAB cells transfected with a scrambled control versus a precursor for miR-223. FIG. 2E shows luciferase activity in BJAB cells transfected with a vector comprising either a luciferase gene coupled to the 3'UTR of the LM02 gene or a luciferase gene coupled to the 3'UTR of the LM02 gene with the miR-223 binding site mutated, and cotransfected with miR-223.

FIG. 3A shows base-pairing of the 3'UTR of the PRDM1 gene with the 5' seed region of miR-9 and the miR-30 family. FIG. 3B shows the effects of over-expressing miR-9 and 2 members of the miR-30 family, miR-30b and miR-30d, in plasma cell myeloma-derived U266 cells in 3 separate experiments. FIG. 3C shows the relative PRDM1 protein expression from a representative experiment (from 3 replicates) transfecting a scrambled control versus a precursor for miR-9, miR-30b, or miR-30d in U266 cells. FIG. 3D shows the average expression of PRDM1 relative to Actin over three Western blots of U266 cells transfected with a scrambled control versus a precursor for miR-9, miR-30b, or miR-30d. (P<0.05 for miR-30b and miR-30d, P=0.08 for miR-9.) FIG. 3E shows repression of luciferase activity from the PRDM1 3'UTR construct by overexpression of miR-9, miR-30b, and miR-30d wild-type and mutant sequences.

FIG. 4A shows lineage prediction of both IgV mutated and unmutated chronic lymphocytic leukemia, germinal center B cell derived DLBCL, and Burkitt lymphoma based on differential expression of microRNAs in normal naïve B cells and germinal center B cells (microRNAs depicted in FIG. 1D). FIG. 4B shows miRNAs that were found to be differentially expressed (P<0.05) in malignant cells and normal cells as discussed in Example 5. FIG. 4C shows cloning frequency of miRNAs in unselected mature B cells (N=3) and certain B cell malignancies (N=42) from a previously published study ("sequencing data"), as discussed in Example 5. FIG. 4D shows differentially expressed miRNAs that distinguish Burkitt lymphoma, activated B cell-like (ABC) diffuse large B cell lymphoma (DLBCL), germinal center-like DLBCL (GCB DLBCL), and chronic lymphocytic leukemia. Predictor miRNAs from each pair-wise comparison that distinguish each entity are shown in the boxes.

FIG. 6A shows density plots of the expression frequency of predicted mRNA targets of miRNAs expressed highly in germinal center B cells compared to naive cells. FIG. 6B shows density plots of the expression frequency of predicted mRNA targets of miRNAs expressed highly in germinal center B cells compared to plasma cells. FIG. 6C shows density plots of the expression frequency of predicted mRNA targets of miRNAs expressed highly in the germinal center B cells compared to memory B cells.

In FIG. 7A, the left panel indicates the proportion of transcription factors that are differentially expressed in the naive to germinal center B-cell transition that are also predicted targets of differentially expressed miRNAs. The right panel indicates the proportion of transcription factors that are not differentially expressed and also are predicted targets of differentially expressed miRNA in that stage-transition. The p-value indicates the results of a chi-squared test for the enrichment of predicted miRNA targets among the differentially expressed transcription factors. FIG. 7B shows a similar analysis of the germinal center to plasma cell transition. FIG. 7C shows a similar analysis of the germinal center to memory cell transition.

FIG. 8A shows base-pairing of the 3'UTR of the MYBL1 gene with nucleotides 2-8 of miR-223. This 7-mer is highly conserved across a number of species and serves as a potential binding site for miR-223. FIG. 8B shows the effects of over-expression of miR-223 in germinal center lymphoma-derived BJAB cells in 3 separate experiments.

DETAILED DESCRIPTION

Figure 1:
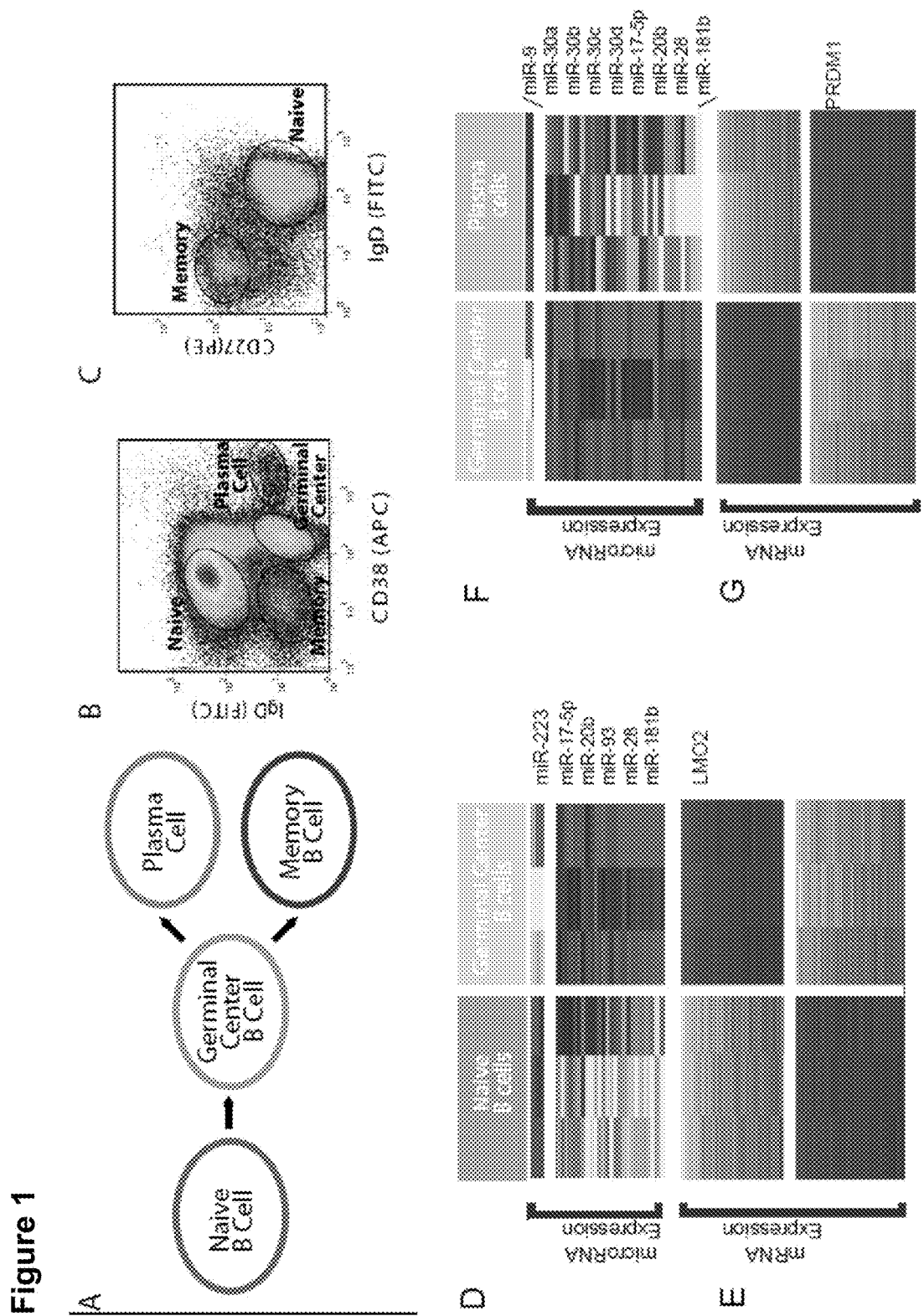
FIG. 1 shows that mature B cell subsets demonstrate distinct microRNA profiles.

All patent and non-patent literature references that are cited herein are incorporated herein by reference in their entirety.

In a general sense, the disclosure relates to nucleic acid sequences, such as microRNAs (miRNA), as well as to the identification and analysis of microRNA expression levels and/or patterns in B cells. Through concomitant microRNA and mRNA profiling, the inventors have identified regulatory roles for microRNAs at each stage in mature B cell differentiation. This provides methods identifying microRNA-mediated regulation of oncogenes and key transcription factors in B cell differentiation. This work establishes the landscape of normal microRNA expression in mature B cells and its role in regulating normal B cell differentiation. Further, our work demonstrates that in contrast to the described down-regulation in other malignancies, stage-specific microRNAs are retained in B cell malignancies. The lineage of common B cell malignancies can be predicted based upon miRNA profiles of normal B cells, pointing to a role for microRNAs in the maintenance of mature B cell phenotypes in normal and malignant B cells.

In an aspect, the disclosure relates to an isolated nucleic acid molecule comprising: (a) a nucleotide sequence as shown in Table 32; (b) a nucleotide sequence which is the complement of (a), (c) a nucleotide sequence comprising a sequence identity of at least 80%, (e.g., 80, 81, 82, 83, 84, 85, 86, 87, 88, 89, 90, 91, 92, 93, 94, 95, 96, 97, 98, or at least 99%), to a sequence of (a) or (b) and/or (d) a nucleotide sequence which hybridizes under stringent conditions to a sequence of (a), (b) and/or (c). In some embodiments, the identity of sequence (c) to a sequence of (a) or (b) is at least 90%. In other embodiments, the identity of sequence (c) to a sequence of (a) or (b) at least 95%. The percent identity can be calculated by any routine method used by one of skill in the art such as, for example, the methods described herein.

In embodiments, the isolated nucleic acid molecule relates to a miRNA molecule and analogs thereof, a miRNA precursor molecule, or a primary miRNA molecule, as well as to DNA molecules encoding miRNA, miRNA precursor, or primary miRNA molecules. Accordingly, in such embodiments, the isolated nucleic acid molecule can function as a miRNA molecule under suitable conditions. Suitable conditions include, but are not limited to, various buffer systems that approximate physiologically relevant ionic concentrations and pHs, as well as physiological conditions.

In some embodiments, the nucleic acid molecule comprises a sequence that hybridizes to a nucleotide sequence as shown in Table 32, a complementary sequence thereof or a nucleic acid molecule having at least 80% sequence identity under stringent hybridization conditions. The basic parameters affecting the choice of hybridization conditions and guidance for devising suitable conditions are set forth by Sambrook, et al. (See, 1989, Molecular Cloning: A Laboratory Manual, Cold Spring Harbor Laboratory Press, Cold Spring Harbor, N.Y.; and Current Protocols in Molecular Biology, 1995, Ausubel et al., eds., John Wiley & Sons, Inc.), and can be readily determined by those of ordinary skill in the art based on, for example, the length and/or base composition of the DNA. Generally, stringent salt concentration will ordinarily be less than about 750 mM NaCl and 75 mM trisodium citrate, or less than about 500 mM NaCl and 50 mM trisodium citrate, or even less than about 250 mM NaCl and 25 mM trisodium citrate. High stringency hybridization conditions can be obtained by adding an amount of organic solvent (e.g., at least about 35% to about 50% formamide). Stringent temperature conditions will ordinarily include temperatures of at least about 30° C., (e.g., at least about 37° C., 42° C., 45° C., 50° C., or 55° C.). Varying additional parameters, such as hybridization time, the concentration of detergent (e.g., 0.1-1.0% sodium dodecyl sulfate (SDS)), and the inclusion or exclusion of carrier DNA (e.g., about 100-200 µg/ml denatured salmon sperm DNA (ssDNA)), are well known to those skilled in the art.

Stringent hybridization conditions are known in the art and include non-limiting examples such as, washing for 1 hr in 300 mM NaCl, 30 mM trisodium citrate and 0.1% SDS at 45-50° C.; washing for 1 h in 300 mM NaCl, 30 mM trisodium citrate and 0.1% SDS at 45-50° C.; in 500 mM NaCl, 50 mM trisodium citrate, 1% SDS, 35% formamide, and 100 µg/ml denatured salmon sperm DNA (ssDNA) at 37° C.; or in 250 mM NaCl, 25 mM trisodium citrate, 1% SDS, 50% formamide, and 200 µg/ml ssDNA at 42° C. Useful variations on these conditions will be readily apparent to those skilled in the art.

The isolated nucleic acid molecules provided herein suitably have a length of from about 18 to about 100 nucleotides. In embodiments wherein the isolated nucleic acid molecules are miRNAs, the lengths of the miRNAs are suitably in an expected range for the particular type of miRNA molecule. For example, mature miRNAs are typically from about 15 to about 28 nucleotides in length, and suitably have a length of about 19 to about 24 nucleotides (e.g., 19, 20, 21, 22, 23, or 24 nucleotides). Precursor miRNAs typically comprise the mature miRNA sequence and contain a stem-loop structure, suitably of length of about 50 to about 90 nucleotides (e.g., 50, 55, 60, 65, 70, 75, 80, 85, or 90 nucleotides). Primary miRNAs (e.g., a primary transcript comprising a precursor miRNA) can suitably have a length of greater than 100 nucleotides.

The nucleic acid molecules can be provided in either a single-stranded or double-stranded form. Typically, a miRNA as such is identified as a single-stranded molecule, while the precursor miRNA is typically at least partially self-complementary and capable of forming double-stranded portions, e.g. stem- and loop-structures. DNA molecules encoding the miRNA and miRNA precursor molecules (e.g., expression vectors, cloning vectors, and the like) are typically double-stranded. The individual nucleic acids that comprise the isolated nucleic acid molecules can be selected from RNA, DNA, or nucleic acid analog molecules, such as chemically modified sugar (e.g., 2'-modified (2'-F, 2'-OMe, etc.) or backbone (e.g., phosphorothioates), or cap (e.g., 5'- and/or 3'-abasic groups) moieties of ribonucleotides or deoxyribonucleotides. Other nucleic acid analogs, such as peptide nucleic acids (PNA) or locked nucleic acids (LNA), are also suitable in various embodiments described herein. In some embodiments the nucleic acid molecules can comprise any combination of nucleic acid analog(s).

While many of the nucleic acid molecules in the Tables are identified as RNA sequences, e.g., miRNAs, the disclosure of those sequences should be understood to encompass the corresponding DNA (e.g., cDNA) sequences, wherein the uracil (U) nucleotides of the disclosed RNAs are substituted by thymidine (T) nucleotides in the corresponding DNA. One of skill in the art is able to generate such DNA sequences (e.g., cDNA) through routine microbiological techniques known in the art such as, for example, reverse transcription using methods that incorporate the reverse transcriptase enzyme.

In another aspect, the disclosure provides a recombinant expression vector comprising a recombinant nucleic acid sequence operatively linked to an expression control sequence, wherein expression of the recombinant nucleic acid sequence provides a miRNA sequence, a precursor miRNA sequence, or a primary miRNA sequence as described herein. The resulting sequence (e.g., primary or precursor miRNAs) can optionally be further processed to provide the miRNA sequence. In embodiments, the recombinant expression vector comprises at least one sequence in Table 32. Any suitable expression vector can be used such as, for example, a DNA vector (e.g., viral vector, plasmid, etc.). In some embodiments the expression vector is selected for expression in a eukaryotic cell such as, for example, a mammalian cell. One of skill in the art will be able to select an appropriate vector based on the particular application and/or expression system to be employed.

Thus, embodiments provide nucleic acid constructs in the form of plasmids, vectors, transcription or expression cassettes which comprise at least one nucleotide sequence encoding a miRNA described herein, or fragments thereof, and a suitable promoter region. Suitable vectors can be chosen or constructed, which contain appropriate regulatory sequences, such as promoter sequences, terminator sequences, polyadenylation sequences, enhancer sequences, marker genes and other sequences as desired. Vectors can be plasmids, phage (e.g. phage, or phagemid) or viral (e.g. lentivirus, adenovirus, AAV) or any other appropriate vector. For further details see, for example, Molecular Cloning: a Laboratory Manual: 2nd edition, Sambrook et al., 1989, Cold Spring Harbor Laboratory Press.

Relatedness of Nucleic Acid Molecules/Sequences

The term "identity" refers to a relationship between the sequences of two or more two or more nucleic acid molecules, as determined by comparing the sequences. In the art, "identity" also means the degree of sequence relatedness between amino acid or nucleic acid molecule sequences, as the case may be, as determined by the match between strings of nucleotide or amino acid sequences. "Identity" measures the percent of identical matches between two or more sequences with gap alignments addressed by a particular mathematical model or computer programs (i.e., "algorithms").

Identity of related nucleic acid molecules can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 19933; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M. Stockton Press, New York, 1991; and Carillo, H., and Lipman, D., SIAM J. Applied Math., 48:1073 (1988).

Non-limiting methods for determining identity are designed to give the largest match between the sequences tested. Methods to determine identity are codified in publicly available computer programs. Preferred computer program methods to determine identity between two sequences include, but are not limited to, the GCG program package, including GAP (Devereux, et al., Nucleic Acids Research 12:387 [1984]; Genetics Computer Group, University of Wisconsin, Madison, Wis.), BLASTN, and FASTA (Atschul et al., J. Molec. Biol. 215:403-410 [1990]). The BLAST X program is publicly available from the National Center for Biotechnology Information (NCBI) and other sources (BLAST Manual, Altschul] et al., NCB NLM NIH Bethesda, Md. 20894; Altschul et al., J. Mol. Biol. 215:403-410 [1990]). The well known Smith Waterman algorithm may also be used to determine identity.

Exemplary parameters for nucleic acid molecule sequence comparison include the following:
Algorithm: Needleman and Wunsch, J. Mol Biol. 48:443-453 (1970)
Comparison matrix: matches=+10, mismatch=0
Gap Penalty: 50
Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. can be used by those of skill in the art, including those set forth in the Program Manual, Wisconsin Package, Version 9, September 1997. The particular choices to be made will depend on the specific comparison to be made, such as DNA to DNA or RNA to DNA; and additionally, whether the comparison is between given pairs of sequences (in which case GAP or BestFit are generally preferred) or between one sequence and a large database of sequences (in which case FASTA or BLASTA are preferred).

In an aspect, the disclosure provides a vector comprising the isolated polynucleotide as described herein such as, for example one or more of SEQ ID NOs 773-1046 or 1450-1542. In embodiments, the vector can be any type of vector that finds use as a vehicle to transfer foreign genetic material into a cell. Non-limiting examples of vectors include plasmids, viral vectors (e.g., derived from lentivirus, adenovirus, adeno-associated virus (AAV), retrovirus, etc.), bacteriophage, cosmids, and artificial chromosomes. In embodiments, the vector can be an expression (or expression constructs) for driving expression of the polynucleotide in a target cell. Vectors and methods for inserting them into a target cell are known in the art [See, e.g., Sambrook et al., 1989].

In an aspect, the disclosure provides recombinant cells that comprise the vectors and/or polynucleotides described herein. The cells can be any cell suitable as a host for recombinant nucleic acid molecules, and selected based on well known techniques. Techniques for generating and maintaining recombinant cells are known in the art, such as those described in Sambrook et al., 1989.

The term "B cell malignancy," as used herein, refers to a malignancy derived from any stage of B cell, including, but not limited to, naïve cells, germinal center cells, memory B cells, and plasma cells. Examples of B cell malignancies include, but are not limited to, mantle cell lymphoma, follicular lymphoma, Hodgkin's lymphoma, Burkitt lymphoma, germinal center B-cell like diffuse large B cell lymphoma (DLBCL), chronic lymphocytic leukemia, small lymphocytic lymphoma, lymphoplasmacytic lymphoma, multiple myeloma, and activated B-cell like DLBCL.

In an aspect, the disclosure provides a method of distinguishing B cell malignancies on the basis of the B-cell origin. In certain embodiments, methods of diagnosing B cell malignancies on the basis of the B-cell origin are provided. In certain such embodiments, a B cell malignancy is determined to be derived from a particular B-cell stage. The B-cell origin of a B cell malignancy may be determined, in certain embodiments, by detecting one or more microRNAs that can be used to distinguish B-cell stages. Certain exemplary B-cell stages include, but are not limited to, naïve cells, germinal center cells, memory B cells, and plasma cells. Certain exemplary microRNAs that can be used to distinguish B-cell stages are shown in Table 4. In various embodiments, the method comprises detecting at least one, at least two, at least five, at least 10, at least 20, at least 30, at least 50, at least 75, or at least 100 microRNAs.

In certain embodiments, a panel of microRNAs is selected that will allow determination of the B cell stage from which a B cell malignancy is derived. For example, in certain embodiments, two or more microRNAs from Table 4 are selected such that detection of the levels of those microRNAs in a B cell malignancy will indicate whether the B cell malignancy is derived from naïve, germinal center, plasma, or memory B cells. In various embodiments, the panel of microRNAs comprises at least one, at least two, at least five, at least 10, at least 20, at least 30, at least 50, at least 75, or at least 100 microRNAs from Table 4. One skilled in the art can select a suitable panel of microRNAs, including one or more microRNAs from Table 4, according to the intended use of the panel.

As described throughout the disclosure, the methods herein can include detecting one or a plurality of miRNAs. When the term "at least" is used in association with a number (e.g., "at least 20") that term will be understood to include 20 as well as optionally any integer after 20 and up to and including the total number of microRNAs disclosed herein.

In some embodiments, a B cell malignancy derived from naïve cells is mantle cell lymphoma. In other embodiments, a B cell malignancy derived from germinal center cells includes, but is not limited to, follicular lymphoma, Hodgkin's lymphoma, Burkitt lymphoma, or germinal center B-cell like diffuse large B cell lymphoma (DLBCL). In other embodiments, a B cell malignancy derived from memory B cells includes, but is not limited to, chronic lymphocytic leukemia or small lymphocytic lymphoma. In some embodiments, a B cell malignancy derived from plasma cells includes, but is not limited to, multiple myeloma or activated B-cell DLBCL.

Certain B cell malignancies can be difficult to distinguish using current methodologies. In extreme cases, almost any B cell malignancy can be confused with another. As illustrative examples, Burkitt lymphoma and DLBCLs are often confused. Similarly, mantle cell lymphoma and small lymphocytic lymphoma can also be confused. Burkitt lymphoma and germinal center DLBCL are both derived from germinal center cells, while activated B-cell DLBCL is derived from plasma cells. Thus, if a B cell malignancy appears to be Burkitt lymphoma or a DLBCL, in certain embodiments, microRNA analysis can be used to narrow down the B cell malignancy to either a germinal center cell-derived B cell malignancy or a plasma cell-derived B cell malignancy. If the B cell malignancy is plasma-cell derived, then it may be activated B-cell DLBCL.

Thus, in certain embodiments, when the identity of a particular B cell malignancy has been narrowed down to two or more possible B cell malignancies, and at least two of those B cell malignancies are derived from different B cell stages, microRNAs that distinguish certain B cell stages can be used to further narrow down the identity of the B cell malignancy. In certain embodiments, microRNAs that distinguish certain B cell stages can be used to identify the B cell malignancy. One or more such microRNAs can be selected, in certain embodiments, from the microRNAs in Table 4. One skilled in the art can select a suitable set of microRNAs, including at least one microRNA from Table 4, for distinguishing particular B cell stages.

In an aspect, the disclosure provides a method of identifying a B cell malignancy comprising detecting one or a plurality of microRNAs. In certain embodiments, the method can provide a diagnosis of a B cell malignancy. In certain embodiments, one or more microRNAs that are characteristic of a particular B cell malignancy are used to identify the B cell malignancy. In certain embodiments, the identity of the B cell malignancy is first narrowed down to a list of two or more particular B cell malignancies using, for example, tumor morphology and/or immunohistochemistry and/or microRNA detection, e.g., to determine the B cell stage from which the tumor is derived. Certain exemplary microRNAs that can be used to identify B cell malignancies are shown in the Tables (e.g., Tables 7-35).

In certain embodiments, methods of identifying B cell malignancies comprise detecting one or more microRNAs from one or more of Tables 7 to 15, and Appendix B, Tables 16 to 30. That is, in certain embodiments, a panel of microRNAs is selected that will identify a B cell malignancy as being one of a particular selection of B cell malignancies. As a non-limiting example, a panel of microRNAs can be designed to identify a B cell malignancy as one of Burkitt lymphoma, ABC DLBCL, or GCB DLBCL. In certain such embodiments, the panel of microRNAs comprises at least one microRNA from Table 10, column "BL miRNA list" and/or Table 14, column "BL High"; at least one microRNA from Table 11 and/or Table 14, column "ABC High"; and at least one microRNA from Table 10, column "GCB miRNA list" and/or Table 14, column "GCB High".

When other methods indicate a particular identity for a B cell malignancy, in certain embodiments, microRNAs can be used to confirm that identification. Thus, for example, if a B cell malignancy is believed to be a Burkitt lymphoma, that identification can be confirmed by determining the expression level of one or more microRNAs listed in Table 10, column "BL miRNA list" and/or Table 14, column "BL High". Similarly, if a B cell malignancy is believed to be ABC DLBCL, that identification can be confirmed by determining the expression level of one or more microRNAs listed in Table 11 and/or Table 14, column "ABC High". If a B cell malignancy is believed to be GCB DLBCL, that identification can be confirmed by determining the expression level of one or more microRNAs listed in Table 10, column "GCB miRNA list" and/or Table 14, column "GCB High". If a B cell malignancy is believed to be chronic lymphocytic leukemia, that identification can be confirmed by determining the expression level of one or more microRNAs listed in Table 12 and/or Table 15, column "CLL High". If a B cell malignancy is believed to be Hodgkin's lymphoma, that identification can be confirmed by determining the expression level of one or more microRNAs listed in Table 13 and/or Table 15, column "HL High". If a B cell malignancy is believed to be follicular lymphoma, that identification can be confirmed by determining the expression level of one or more microRNAs listed in Table 10, column "FL miRNA list" and/or Table 15, column "FL High".

In certain embodiments, when the identity of a B cell malignancy has been narrowed down to two B cell malignancies selected from Burkitt lymphoma, GCB DLBCL, ABC DLBCL, chronic lymphocytic leukemia, follicular lymphoma, and Hodgkin's lymphoma, the identity of the B cell malignancy can be determined by detecting one or more microRNAs from Tables 16 to 30.

As discussed in the Examples, the miRNAs described herein as differentially expressed in a B cell malignancy have been identified with high confidence, and thus, identification of one miRNA is adequate to perform the methods of identification and diagnosis disclosed herein. Accordingly, in various embodiments, the methods can comprise detecting at least one, at least two, at least five, at least 10, at least 20, at least 30, or at least 50 microRNAs in order to narrow down the identity of, or identify, a B cell malignancy.

As noted above, the treatment regimens and prognoses for the various B cell malignancies can differ significantly. Thus, determining the correct identity and/or origin of a B cell malignancy can be important for selecting an effective therapy and/or setting appropriate patient expectations.

B cell malignancy samples may be obtained and prepared using methods known in the art. One skilled in the art can select an appropriate method of obtaining a B cell malignancy sample according to various parameters, such as the age, size, medical history, and/or identity of the patient. One skilled in the art can select an appropriate method of preparing a B cell malignancy sample for analysis according to the B cell malignancy sample source, size, quality, and/or intended use. For example, in certain embodiments, a B cell malignancy sample is prepared in a manner that preserves microRNAs in the sample as much as practicable under the circumstances.

MicroRNAs can be detected using any method known in the art. Exemplary methods of detecting microRNAs include, but are not limited to, hybridization-based methods and amplification-based methods. Certain exemplary detection methods include, but are not limited to, arrays (including microarrays and bead-based arrays), in situ hybridization, Northern blotting, TaqMan probes, RT-PCR, real-time PCR, and direct sequencing. One skilled in the art can select a suitable detection method according to the sample source, size, quality, and/or particular application.

In certain embodiments, real-time PCR is employed to determine the expression level of a microRNA. In some embodiments a miRNA is considered present in a subpopulation if the cycling time (CT) is less than 36 in all three biological replicates, and a CT greater than 36 is undetected.

In certain embodiments, the expression level of a microRNA in a sample is determined relative to a control sample. A control sample may be selected, in various embodiments, because it is expected to have either high or low expression of the microRNA.

In certain embodiments, the expression level of a microRNA may be normalized to the expression level of a polynucleotide that is expected to be expressed at similar levels in several different cell types and/or at constant levels in the cell type being analyzed.

In certain embodiments, an identified miRNA from Tables 7-35 is used to distinguish one of the six exemplified B cell malignancies from the other malignanicies. A "high" and a "low" in Tables 10 to 13 refer to at least a 2-fold difference in the expression of the identified miRNA when one lymphoma is compared to other lymphomas and benign lymph nodes.

In embodiments, mRNA levels can be profiled by using a microarray. In some embodiments, array elements with median signal intensities of less than 7 log 2 units across samples are removed from analysis. In embodiments, a gene is considered for further analysis if it is on-average 2-fold or higher differentially expressed in a binary comparison of B cell subsets and expressed in at least one of the two B cell subsets being compared.

In an embodiment, the level of at least one miRNA is measured by reverse transcribing RNA from a test sample obtained from a subject to provide a set of target oligodeoxynucleotides, hybridizing the target oligodeoxynucleotides to one or more miRNA-specific probe oligonucleotides (e.g., a microarray that comprises miRNA-specific probe oligonucleotides) to provide a hybridization profile for the test sample, and comparing the test sample hybridization profile to a hybridization profile generated from a control sample. An alteration in the signal of at least one miRNA in the test sample relative to the control sample is indicative of the subject either having, or being at risk for developing, a B-cell malignancy. In an embodiment, the signal of at least one miRNA is upregulated, relative to the signal generated from the control sample. In another embodiment, the signal of at least one miRNA is down-regulated, relative to the signal generated from the control sample. In some embodiments, the microarray comprises miRNA-specific probe oligonucleotides for a substantial portion of all known human miRNAs. In a further embodiment, the microarray comprises miRNA-specific probe oligonucleotides for one or more miRNAs selected from the group consisting of SEQ ID NOs: 763-1350, or 1565 and any combination thereof.

The microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs and other RNAs (e.g., rRNAs, mRNAs) from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems. Labeled cDNA corresponding to the target RNA sequence(s) is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under typical hybridizing conditions. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRNAs, in the patient sample.

In an aspect, the disclosure relates to kits. Such kits can be used in methods of identifying a miRNA or mRNA described herein; an expression level or expression pattern of one or more miRNA(s) or mRNA(s) described herein; and/or identifying a B-cell malignancy. In some embodiments the kit can provide a diagnosis of a B-cell type and or a B-cell malignancy. In some embodiments the kit can differentiate one B-cell malignancy from other B-cell malignancies (e.g., ABC-DLBCL from GBC-DLBCL), and can provide information useful to a medical professional regarding a preferred course of therapeutic treatment. Suitably, a kit can comprise an isolated nucleic acid molecule or a plurality of isolated nucleic acid molecules as described herein (e.g., a sequence complementary to any of the miRNAs disclosed in the Tables). In embodiments, the isolated nucleic acid molecule can comprise a sequence of one or more RT-PCR target sequences, primers directed thereto, or a sequence complementary thereto. The kit can also include adapter nucleic acid molecules (e.g., universal adapter molecules for attachment to expressed miRNAs/mRNAs for reverse transcription and amplification); appropriate buffer systems and reagents, detectable labels, an energy source (e.g., ATP), and other agents and components that can be used in performing analysis of miRNA expression (e.g., in RT-PCR, deep sequencing, or microarray-based methods). Kits also include instructions for use.

It will be understood that any numerical value recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between the lowest value and the highest value enumerated are to be considered to be expressly stated in this application.

In an aspect, the disclosure provides a DNA library comprising one or more miRNA sequences from Tables 4-5, or 6-33. In a related aspect, the disclosure provides a method for generating such a DNA library. In an embodiment the library comprises a cDNA library that includes sequences derived from a sample of the miRNAs or, in addition or alternatively, the mRNA purified from a particular source such as, for example, a collection of cells, a particular tissue, or an entire organism. In embodiments, the source of the cDNA library is a B cell, such as a B cell in any stage (e.g., naïve, germinal center, memory, activated, or plasma, etc.) or a B cell malignancy (e.g., mantle cell lymphoma, follicular lymphoma, Hodgkin's lymphoma, Burkitt lymphoma, germinal center B-cell like diffuse large B cell lymphoma (DLBCL), chronic lymphocytic leukemia, small lymphocytic lymphoma, lymphoplasmacytic lymphoma, multiple myeloma, and activated B-cell like DLBCL). Typically, the isolated miRNA (or mRNA) is converted to a DNA template by reverse transcription, and comprises the cDNA version of the expressed RNA (e.g., miRNA or mRNA). Thus, a library can represent the cDNA version of the active "transcriptome" in a particular source under the physiological, developmental, or environmental conditions that existed when the miRNA/mRNA was purified.

In an embodiment, the library comprises a miRNA sequence described in Tables 4-5; 7-33. In embodiments, the library comprises at least one of SEQ ID NOs 763-1350 or 1565, and any combination thereof. In an embodiment, the library comprises a collection of miRNA sequences comprising SEQ ID NOs 763-1350 or 1565. In embodiments the library can be used to identify and/or differentiate a B-cell malignancy from other B-cell malignancies. In such embodiments, the library comprises at least one miRNA sequence selected from those listed in any of Tables 4 or 7-35.

As used herein, a "library" is a collection of DNA sequences that is stored and propagated in a population of microorganisms through standard molecular cloning processes. A DNA library can be of any type such as, for example, a cDNA library (formed from reverse-transcribed RNA) or a genomic library (formed from genomic DNA). The DNA library can be used in any routine application or technique known in the art (e.g., gene discovery; cloning of full-length cDNAs to identify/study gene function; miRNA/mRNA expression in different cells or tissues; splice variants in different cells or tissues) and, in some embodiments, can depend on the source of the original DNA fragments. In embodiments, the library can be used to isolate, characterize, and/or quantify the actively expressed miRNA is a population of cells such as, for example, B-cells or B-cell malignancies. In some embodiments, the library can be used to study miRNA-protein interactions or miRNA-based regulation of protein expression or activity.

Any known method of library preparation can be used to make the library described herein, including the methods described in the detailed description and non-limiting Examples. Further general techniques can be based on the methods and techniques known in the art, (see, e.g., RNA Methodologies: A Laboratory Guide for Isolation and Characterization (R. E. Farrell, Academic Press, 1998); cDNA Library Protocols (Cowell & Austin, eds., Humana Press; Functional Genomics (Hunt & Livesey, eds., 2000); and the Annual Review of Genomics and Human Genetics (E. Lander, ed., yearly publications by Annual Reviews). Suitably, the nucleotide sequences of interest in a library are preserved as inserts in a plasmid or the genome of a bacteriophage that has been used to infect bacterial cells. There are differences in the cloning vectors and techniques used in library preparation, but in general each DNA fragment is uniquely inserted into a cloning vector and the pool of recombinant DNA molecules is then transferred into a population of bacteria or yeast such that each organism contains on average one construct (vector+insert). The DNA molecules are copied and propagated along with the population of organisms in culture (thus, effectively, "cloned"). Accordingly, in some embodiments, the term "library" can refer to a population of organisms, each of which carries a DNA molecule inserted into a cloning vector, or alternatively to the collection of all of the cloned vector molecules.

An "increased level" of expression, as used herein, refers to a level of expression that is at least 2-fold greater than the level of expression in a control cell type or tissue. In various embodiments, the level of expression is at least 2.5-fold, at least 3-fold, at least 5-fold, or at least 10-fold, greater than the level of expression in a control cell. Exemplary control cells and tissues include, but are not limited to, normal cells, benign lymph nodes, and other B cell malignancies. In certain embodiments, benign lymph nodes are used as a control tissue. Such benign lymph node tissue contains a variety of cell types.

A "decreased level" of expression, as used herein, refers to a level of expression that is less than 50% of the level of expression in a control cell.

The term "differentially expressed" or "differential expression" relates to a difference in the observed or detected level of expression of a biomolecule such as, for example, nucleic acids (e.g., a polynucleotide, mRNA, miRNA, etc.) or amino acid sequence (e.g., protein, polypeptide, etc.) in a test sample relative to the observed or detected level of expression of the same biomolecule in a control sample or other reference (e.g., a previously established reference level). The difference in expression can be either an increase or a decrease in the expression of the biomolecule in the test sample relative to the control sample.

The Examples that follow provide further illustration of certain aspects and embodiments described in the foregoing description. These illustrative Examples should not be interpreted as limiting the scope of the appended claims.

EXAMPLES

Example 1

Materials and Methods

Patient Sample Processing

B cell populations were obtained from young patients undergoing routine tonsillectomy using a protocol approved by the Clinical Center at the National Institutes of Health. Patient tonsils were disaggregated and separated by Ficoll. The mononuclear cell layer was harvested, washed in PBS, and resuspended in ACK lysing buffer to remove small numbers of red blood cells. After a wash and resuspension with 10 ml of PBS with 10% Bovine Serum Albumin, cells were counted and 200 million were stained with fluorochrome-tagged monoclonal antibodies to CDI9, IgD, CD38 and CD27. The specific monoclonal antibodies employed were anti-CDI9-PE-Cy5.5, anti-IgD-FITC, anti-CD27-PE, and anti-CD38-APC, all from BD Biosciences and BD Pharmingen (San Jose Calif.). Cells were sorted using the MoFlo Cell sorter (Dako Cytomation, Colorado Springs, Colo.) into naive B cells (CDI9+IgD+CD2TCD38+), germinal center B cells (CDI9+IgD-CD38++), memory B cells (CDI9+IgD-CD27+CD38dim) and plasma cells (CDI9dimIgD-CD27++CD38+++). Three replicates of each B cell subset were obtained from separate patients. The sample purity was verified by FACS and found to be over 90% in all cases.

Tumor specimens were obtained from patients who were examined under a protocol approved by the Duke University Medical Center Institutional Review Board. The pathologic diagnosis of the samples was verified prior to analysis. Samples from patients with diffuse large B cell lymphoma were further subclassified as described previously. See Hans et al. (2004) *Blood* 103: 275-282. Chronic lymphocytic leukemia samples were processed and purified as described previously. See Volkheimer et al. (2007) *Blood* 109: 1559-1567. Total RNA was extracted using the phenol-chloroform method to preserve miRNAs, using Ambion reagents.

microRNA Profiling Using Multiplexed Real-time PCR

MiRNA expression profiling was conducted using the Applied Biosystems 384-well multiplexed real-time PCR assay using 400 ng of total RNA. Eight reactions, each containing 50 ng of RNA and a multiplex looped primer pool with endogenous small nucleolar (sno)-RNA controls, were used to reverse-transcribe the miRNAs in parallel fashion. Each completed reaction was loaded onto the 384-well plate per manufacturer's instructions, and real-time PCR was run on the ABI 7900HT Prism. For each 384-well plate, we used the automatically determined cycle-threshold (CT) using the SDS 2.2.1 software (Applied Biosystems). Consistent with manufacturer recommendations, we considered CT greater than 36 as undetected. A miRNA was considered to be present in a subpopulation if the CT was less than 36 in all three biological replicates. The probes deemed to be present were normalized to the average expression of a sno-RNA control. The expression values were calculated as $2^{-\Delta CT}$, then median centered to 500 and log 2-transformed.

Gene Expression (mRNA) Profiling Using Microarrays

Gene expression profiling and normalization were performed using methods identical to those we have described previously. See Dave et al. (2004) *N. Engl. J. Med.* 351: 2159-2169. Array elements with median signal intensities of less than 7 log 2 units across the samples were removed from analysis, in order to exclude poorly measured genes and genes not appreciably expressed in the samples. Genes that were on-average 2-fold or higher differentially expressed in a binary comparison of B cell subsets, and appreciably expressed in at least one of the 2 B cell subsets being compared, were selected for further analysis as described below. The data have been deposited in the publicly available Gene Expression Omnibus database (GSE12366).

MiRNA Profiling Using Microarray

MiRNA expression profiling from human B cell malignancies was conducted using up to 1 μg of total RNA from sample and reference (normal lymph node), which were labeled with Cy3 or Cy5 fluorescent dyes, using the miRNA/LNA labeling kit (Exiqon, Denmark). The fluorescently labeled samples were combined and hybridized to a miRNA microarray (v. 10.0, Exiqon, Denmark), in a nitrogen atmosphere. The micro array slides were scanned with GenePix 4100 Scanner. The quantified signals were normalized using the global Lowess algorithm, using Genespring (Agilent) software. The intensity values for multiple spots were averaged and the normalized values were log 2-transformed. Missing values were replaced with the lowest value for analysis.

MiRNA Target Prediction

Annotated genes on the U133plus 2.0 array were matched to the miRNA target list downloaded from TargetScan (www.targetscan.org). For the purpose of this study, a target gene was defined by the presence of a seed sequence match (nucleotides 2-8) and conservation of the seed sequence and 3'UTR in humans, dog, rat, mouse and chicken. Additional conservation was examined in miRNA target genes selected for experimental validation. The distribution of the mRNA expression for these genes was plotted as a density plot using the Splus statistical software (Insightful Corporation). The difference in distribution between the B cell subsets was calculated using a two-sample, 1-sided Kolmogorov-Smirnov test to examine the hypothesis that being a miRNA target conferred repression in the appropriate population (consistent with the known biology of miRNA effects).

The 3'UTRs of LM02, MYBL1 and PRDM1 were aligned using Blastz alignment of Human, Chimp, Mouse, Rat, Dog, Chicken, Frog (*Xenopus*) and Zebrafish, and were displayed using the UCSC genome browser. The conservation of miR-223 seed sequence and the 3'UTRs of LM02 and MYBL1, as well as that of the miR-30 family and miR-9 on PRDM1, were thus verified.

Western Blot

RIPA Lysis buffer (1× phosphate-buffered saline [PBS], 1% Nonidet P-40, 0.5% sodium deoxycholate, 0.1% SDS, 10 mM phenylmethylsulfonyl fluoride, 1 μg/mL aprotinin, and 100 mM sodium orthovanadate) was added to 750,000 cells and incubated on ice for 30 minutes. The mixture was spun down and the supernatant was transferred to a new tube as the whole cell extract. A total of 20 μg of cell lysate was separated on a 4-18% Tris-Bis NuPAGE gel (Invitrogen) and transferred using the iBlot transfer device (Invitrogen) program 3 for 7 minutes (LM02 detection) or program 2 for 6 minutes (PRDM1). The blots were probed using 1:200 mouse-anti-LM02 (Santa Cruz Biotechnologies SC-65736), 1:750 mouse-anti-Blimp-1 (Santa Cruz Biotechnologies SC-66015) or 1:5000 goat-anti-B-actin (Santa Cruz Biotechnologies SC-47778) for 1 hour at room temperature. The antibodies were detected using 1:10,000 goat-anti-mouse horseradish peroxidase conjugated antibodies (Santa Cruz Biotechnologies). Western Blotting Luminol Reagent (Santa Cruz Biotechnologies) was used to visualize the bands corresponding to each antibody.

Single miRNA/mRNA Expression Using Real-time Polymerase Chain Reaction (RT-PCR)

With 10 ng of RNA per reaction, miRNAs of interest were reverse-transcribed with ABI individual stem-loop primers designed to detect only mature miRNA, and measured by Taqman real-time PCR normalized to the small nucleolar RNA, RNU48. In order to assess mRNA expression using RT-PCR, 1 μg of RNA was reverse-transcribed with the ABI High Capacity cDNA Reverse Transcription kit. Gene expression was measured with exon-spanning Taqman probes, and normalized to beta-2 micro globulin expression.

Cell Culture

BJAB and H929 were cultured in RPMI (Gibco) supplemented with 10% fetal bovine serum, and U266 was cultured in RPMI supplemented with 15% fetal bovine serum. 293T cells were grown in DMEM media (Gibco) with 10% FBS. All cell lines were grown in 37° C. humidified cell culture incubators with $CO_2$ maintained at 5%.

MiRNA Functional Analysis

MicroRNA Transfection miRNAs of interest were over-expressed in cell lines of interest by transfecting the appropriate miRNA precursors (Ambion) at 100 nanomoles using Amaxa's Nucleofector system. In particular, BJAB was transfected with Nucleofector solution T, program T-016, U266 with Nucleofector C, program X-005, and H929 with Nucleofector V, program T-001. 1.5 million cells were used per transfection and mixed with appropriate miRNA precursors (Ambion) for a concentration of 100 nM.

Statistical Analysis

Identifying Differentially Expressed miRNA and mRNA

MiRNAs were considered to be differentially expressed if the mean signal was changed at least 2-fold and a false discovery rate (q) was less than 5% using Significance Analysis of Microarrays (SAM) with 1000 permutations. See Tusher et al. *Proc Natl Acad Sci USA*. 2001; 98:5116-5121.

Differentially expressed genes (mRNA) in Naive versus Germinal Center, Germinal Center versus Plasma Cells, and Germinal Center versus Memory Cells comparisons were identified using SAM. Genes that were 2-fold differentially expressed at a false discovery rate (q) less than 1% with 1000 permutations were identified as significantly differentially expressed.

Transcription Factors and miRNA Target Genes

Transcription factors were identified based on the gene ontology (GO search term "transcription factor") and matched to the probes of the Affymetrix U133plus 2.0 microarray. Of the total of 938 transcription factor genes thus identified, we selected 364 genes that were differentially expressed in at least one of the B cell stage transitions. We evaluated the breakdown of the differentially expressed transcription factors among miRNA targets versus non targets. The p-values were computed using a chi-square test separately in each B cell stage-transition.

B Cell Malignancy Sample Classification

The top 50 most differentially expressed miRNAs (P<0.01) in each pair-wise B cell malignancy type comparison were chosen as the initial predictor. Singular value decomposition was applied to reduce the list to 20 most informative miRNAs in each pair-wise comparison. See West et al. *Proc Natl Acad Sci USA*. 2001; 98:11462-11467. A Bayesian logistic regression was performed in Matlab (Mathworks) using the 20-predictor miRNAs for each pair-wise comparison. Each sample was tested using the microRNA-based predictor in a leave-one-out fashion to determine the accuracy of each prediction. For a sample to be classified as a particular B cell malignancy (or normal) type, it had to be predicted as such in every pair-wise comparison.

Normal B Cell Stage Classification of B Cell Malignancies

We constructed a Bayesian predictor to distinguish normal naive from germinal center B cells based on the 32 miRNAs depicted in FIG. 1D. We then applied the predictor without optimization to the microarray data generated for GCB DLCBL, Burkitt lymphoma and chronic lymphocytic leukemia to render a Bayesian prediction of lineage; i.e. naive versus germinal center B cell.

Western Blot Quantitative Analysis

Western blot scans were quantified using NIH ImageJ software. For each experiment, the ratios of protein of interest (LM02, PRDM1) to Actin were determined and mean centered to 100 across the experiment. The average and standard deviation of these values across the three experiments were calculated and displayed relative to the scrambled control expression.

Luciferase Indicator Assay Quantitative Analysis

Firefly luciferase reporter constructs were created in the pL/SV40/GL3 vector for the LM02 3'UTR and the LM02 3'UTR with the predicted miR-223 binding site mutated, as described below. Mature microRNA expression of a pL/CMV/eGFP vector coding for pri-miR-223 from the 3'UTR of EGFP of the vector was confirmed by Taqman-real time PCR in transfected 293T cells. gl3 activity was normalized in dual luciferase assays to pL/SV40/RLuc, with which it was cotransfected. The PRDMI 3'UTR was also cloned into the pL/SV40/GL3 vector. microRNA expression vectors and their respective seed sequence mutants were created for miR-9-2, miR-30b, and miR-30d.

LM02

The LM02 3'UTR was PCR-amplified from BJAB cDNA using primers 1 and 2 (SEQ ID NOs: 1 and 2, respectively) and ligated into the XhoI and XbaI sites of the previously described lentiviral vector pL/SV40/GL3, which expresses firefly luciferase. See Tusher et al. *Proc Natl Acad Sci USA*. 2001; 98:5116-5121. As a control, an LM02 3'UTR mutant was created using mutant PCR primers 3 and 4 and then outer primers 1 and 2. The resulting fragment was also placed into the XhoI and XbaI sites of pL/SV40/GL3. In this LM02 3'UTR mutant, the seed match predicted to bind to nucleotides 2-8 of miR-223 is converted from 5'AACUGAC 3' to 5'AACAGUC 3'. To create a miR-223 expression vector, a ~350 nucleotide-long fragment of pri-miR-223, encompassing the pre-miRNA stem loop in its middle, was PCR-amplified from genomic BJAB DNA with primers 6 and 7 (SEQ ID NOs. 6 and 7) and ligated into the XhoI and XbaI sites of the pL/CMV/eGFP vector. This pL/CMV/eGFP vector was generated by ligating a fragment containing the CMV promoter and the EGFP ORF into the BamHI and XhoI sites of the previously described lentiviral backbone pL. See Tusher et al. *Proc Natl Acad Sci USA*. 2001; 98:5116-5121. The expression of miR-223 from the 3'UTR of EGFP in the resulting vector was confirmed by Taqman real time PCR in transfected 293T cells.

For luciferase indicator assays, 293T cells plated in 24 well plates were transfected using FUGENE6 as follows:

TABLE 1

| Luciferase indicator assay compositions | | |
|---|---|---|
| 2.5 ng pL/SV40/GL3 | 2.5 ng pL/SV40/GL3/ | 2.5 ng pL/SV40/GL3/ |
| 2.5 ng pL/SV40/RLuc | LMO2 UTR | LMO2 seed mut |
| 0.4 µg pL/CMV/ eGFP/miR-223 | 2.5 ng pL/SV40/RLuc | 2.5 ng pL/SV40/RLuc |
| 2.5 ng pL/SV40/GL3 | 0.4 µg pL/CMV/ eGFP/miR-223 | 0.4 µg pL/CMV/eGFP/ miR-223 |
| 2.5 ng pL/SV40/RLuc | 2.5 ng pL/SV40/ GL3/LMO2 UTR | 2.5 ng pL/SV40/GL3/ LMO2 seed mut |
| 0.4 µg pL/CMV/eGFP | 2.5 ng pL/SV40/RLuc | 2.5 ng pL/SV40/RLuc |
| | 0.4 µg pL/CMV/eGFP | 0.4 µg pL/CMV/eGFP |

Reporter expression was evaluated by dual luciferase assays (Promega) 48 hours post-transfection. Firefly Luciferase (GL3) to internal control *Renilla* Luciferase (RLuc) ratios from 293T cells transfected with pL/CMV/eGFP/miR-223 were divided by those obtained from 293T transfected with the pL/CMV/eGFP vector control. The average and standard deviation were taken across five experiments for the pL/SV40/gl3 empty, LM02, and LM02 mutant vectors.

Firefly Luciferase (GL3) activity readings of the PRDM1 3'UTR construct were divided by internal control *Renilla* Luciferase (RLuc) activity readings. The average and standard deviation of these ratios across three experiments were calculated and scaled relative to the empty vector (pL/CMV/eGFP) transfection.

TABLE 2

LM02 primer sequences

| Primer SEQ ID | description | Sequence (5'→3') |
|---|---|---|
| 1543 | LMO2 3'UTR, FW | ATATCTCGAGGCCCGAG TCCCCGGGCATCTTTGG |
| 1544 | LMO2 3'UTR, REV | ATATATCTAGACTACAC ACGACAAATACTTTG |
| 1545 | LMO2 3'UTR seed mutant, FW | CAGCCCATCCATAGTAA CAGTCATGATTAGCAGA AGAAAGG |
| 1546 | LMO2 3'UTR seed mutant, REV | CCTTTCTTCTGCTAATC ATGACTGTTACTATGGA TGGGCTG |
| 1547 | pri-mir-223, FW | ATATCTCGAGGGTCACA TCTCCCAGGAAGATC |
| 1548 | pri-mir-223, REV | ATATATCTAGAAGCACT CTCATGGTGTGTGTAG |

PRDM1

The PRDM1 3'UTR was PCR-amplified from BJAB genomic DNA in two reactions using primer pairs 7 and 8 in one reaction, and 9 and 10 in another (SEQ ID NOs: 7 to 10, respectively). The two fragments were then ligated together into the XhoI and NotI sites of pL/SV40/GL3 to generate the entire PRDM1 3'UTR. microRNA expression vectors were created as described above for mir-9-2, mir-30b, and mir-30d with the primers listed below. Again, over-expression from the 3'UTR of EGFP in the resulting vector was confirmed by Taqman real-time PCR in transfected 293T cells. For the PRDM1 luciferase assays, we used the sequences listed below to PCR-mutate the seed sequence of the microRNA expression vectors rather than the PRDM1 3'UTR, which had numerous seed sequence binding sites.

TABLE 3

PRDM1 primer sequences

| Primer SEQ ID | description | sequence |
|---|---|---|
| 1549 | PRDM1 3'UTR piece 1, FW | AGAGACTCGAGGATTTTCAGA AAACACTTATTT |
| 1550 | PRDM1 3'UTR piece 1, REV | TTGCTTCTCTAGAGGAGAAAC |
| 1551 | PRDM1 3'UTR piece 2, FW | GTTTCTCCTCTAGAGAAGCAA |
| 1552 | PRDM1 3'UTR piece 2, REV | AGAGAGCGGCCGCAGGGGAGA GACAAATTGCATTG |
| 1553 | pri-mir-9-2, FW | AGAGACTCGAGATAAAAGGAG GAATCTTAAG |
| 1554 | pri-mir-9-2, REV | AGAGAGCGGCCGCGAAAAAAA CAAAACAAAAACAA |
| 1555 | pri-mir-30b, FW | AGAGAGCGGCCGCCCGATTGA GTCTTGCCTCAT |
| 1556 | pri-mir-30b, REV | AGAGAGAATTCAATGGTCTCA CATTTCCAAC |
| 1557 | pri-mir-30d, FW | AGAGAGCGGCCGCATGTCACA GCTATTGTTCAG |
| 1558 | pri-mir-30d, REV | AGAGAGAATTCGCAGTAAAAG AATGCAGCTA |
| 1559 | pri-mir-9-2 seed mutant, FW | GGAAGCGAGTTGTTATCTATG CTTATCTAGCTGTATGAGT |
| 1560 | pri-mir-9-2 seed mutant, REV | ACTCATACAGCTAGATAAGCA TAGATAACAACTCGCTTCC |
| 1561 | pri-mir-30b seed mutant, FW | ACCAAGTTTCAGTTCATGTTA AGATCCTACACTCAGCTGT |
| 1562 | pri-mir-30b seed mutant, REV | ACAGCTGAGTGTAGGATCTTA ACATGAACTGAAACTTGGT |
| 1563 | pri-mir-30d seed mutant, FW | CAGAAAGTCTGTTGTTGTTAA GATCCCCGACTGGAAGCTG |
| 1564 | pri-mir-30d seed mutant, REV | CAGCTTCCAGTCGGGGATCTT AACAACAACAGACTTTCTG |

Luciferase assays were carried out in a manner similar to those described for LM02.

IgVH Mutation Status of Chronic Lymphocytic Leukemia Samples

IgVH mutation status was determined as described in Volkheimer et al. (*Blood.* 2007; 109:1559-1567) using genomic DNA. In brief, genomic DNA was isolated from purified CLL cells and isolated using the GenElute Mammalian DNA extraction Kit from Sigma (St. Louis, Mo.) according to the manufacturer's instructions. DNA was amplified using nested PCR primers. PCR products were electrophoresed, purified, and sequenced using an automated DNA sequencer (Applied Biosystems, Foster City, Calif.) with the BigDye Terminator kit (Perkin Elmer, Boston, Mass.). Forward and reverse sequences were aligned into a single resolved sequence using Sequencher 4.1 software (Gene Codes Corporation, Ann Arbor, Mich.), and then aligned with germline sequences derived from DNA Plot on the V BASE directory website (http://vbase.mrc-cpe.cam.ac.uk/). The percent sequence identity was calculated by dividing the number of mutations from FR1 to FR3 by the total number of nucleotides in this region. Samples were considered somatically mutated if they had greater than 2% mutations in this region.

Example 2

Mature B Cell Stages Display Characteristic Patterns of MicroRNA Expression

Mature B cell subsets can be defined by the expression of surface CD19, IgD, CD38, and CD27, and were obtained by fluorescence activated cell sorting of tonsils from young individuals undergoing routine tonsillectomy. See FIGS. 1B and 1C. Cells were previously gated on CD19 positive cells. Naive and memory B cells were distinguished from germinal center and plasma cells based on surface CD38 and IgD expression.

To determine whether mature B cell subsets had unique patterns of microRNA (miRNA) expression, we used a 384-well multiplexed real time polymerase chain reaction (RT-PCR) assay (Applied Biosystems) that allowed measurement of all 365 miRNAs in miRBase 9.2. See Chen et al. *Nucleic Acids Res.* 2005; 33:e179; and He et al. *Nature.* 2007; 447:1130-1134. We detected a total of 113 unique miRNAs in the B cell populations. See Table 4. This detection frequency compares favorably to the identification of 71 unique miRNAs (45 miRNAs with more than one clone) through the examination of 3101 sequences cloned from unselected CD19-positive mature B cells. See Landgraf et al. *Cell.* 2007; 129:1401-1414. We identified differentially expressed miRNAs in mature B cell subsets using a false discovery rate of less than 5%. See FIGS. 1D, 1F, and 1H. The complete list of assayed miRNAs found to be expressed in the B cell populations is shown in Tables 4 and 5.

In Table 4, normalized expression values for B-cell subsets are shown, along with significance analysis of microarrays q values. Empty microRNA expression cells indicate below-threshold values, defined as RT-QPCR Ct values greater than 36 or undetected. SAM q values greater than 5 were considered non-significant and not displayed.

TABLE 4

MicroRNAs detected in at least one B-cell subset

|  | Naive average | Germinal Center average | Plasma Cell average | Memory average | qNaive vs Germinal Center | qGerminal Center vs Plasma Cell | qGerminal Center vs Memory |
|---|---|---|---|---|---|---|---|
| hsa-let-7a | 11.7 | 9.2 |  | 11.2 |  |  | 1.4 |
| hsa-let-7b | 10.3 | 9.0 | 7.7 | 11.3 |  |  | 0.0 |
| hsa-let-7c | 7.3 |  |  | 7.2 |  |  |  |
| hsa-let-7d | 9.0 | 9.0 |  | 10.0 |  |  |  |
| hsa-let-7f | 10.3 | 7.6 | 8.4 | 10.2 |  |  | 0.0 |
| hsa-let-7g | 13.1 | 10.3 | 10.5 | 14.0 | 0.0 |  | 0.0 |
| hsa-miR-100 |  |  |  | 7.4 |  |  |  |
| hsa-miR-101 | 8.4 |  |  | 10.0 |  |  |  |
| hsa-miR-103 | 9.7 | 11.4 | 9.8 | 10.8 | 0.0 | 0.0 |  |
| hsa-miR-106b | 11.7 | 12.5 | 11.6 | 12.7 |  |  |  |
| hsa-miR-125a |  |  | 6.7 | 8.3 |  |  |  |
| hsa-miR-125b |  | 6.3 |  | 7.3 |  |  |  |
| hsa-miR-130b | 7.8 | 9.8 | 8.6 | 10.2 | 3.6 | 4.5 |  |
| hsa-miR-132 |  | 7.5 |  | 8.9 |  |  |  |
| hsa-miR-133b | 7.7 | 7.7 | 7.2 | 7.3 |  |  |  |
| hsa-miR-140 | 10.8 | 12.0 | 11.1 | 12.0 | 4.7 |  |  |
| hsa-miR-141 | 7.0 |  |  | 6.2 |  |  |  |
| hsa-miR-142-3p | 16.9 | 17.0 | 15.3 | 18.0 |  | 1.1 |  |
| hsa-miR-142-5p | 11.7 | 11.0 | 9.8 | 13.4 |  |  | 2.1 |
| hsa-miR-146a | 10.1 | 14.0 | 14.0 | 14.6 | 0.0 |  |  |
| hsa-miR-146b | 9.2 | 9.2 | 8.1 | 10.5 |  |  | 2.1 |
| hsa-miR-148a | 6.7 | 9.4 | 11.9 | 9.0 | 0.0 |  |  |
| hsa-miR-148b | 6.4 |  |  | 8.5 |  |  |  |
| hsa-miR-151 | 8.2 | 9.6 | 6.6 | 9.0 | 1.5 | 0.0 |  |
| hsa-miR-152 | 6.4 |  | 9.7 | 6.6 |  |  |  |
| hsa-miR-155 | 14.2 | 14.6 | 15.0 | 15.6 |  |  |  |
| hsa-miR-15a | 10.2 | 10.1 | 7.8 | 10.8 |  | 2.0 |  |
| hsa-miR-15b | 11.2 | 14.0 | 12.6 | 12.9 | 0.0 | 2.8 |  |
| hsa-miR-16 | 16.7 | 17.3 | 17.1 | 17.1 |  |  |  |
| hsa-miR-17-3p |  |  |  | 9.1 |  |  |  |
| hsa-miR-17-5p | 8.8 | 11.5 | 8.9 | 9.4 | 0.0 | 0.0 | 0.0 |
| hsa-miR-181b | 9.0 | 11.7 | 10.8 | 9.3 | 0.0 |  | 0.0 |
| hsa-miR-181d | 8.2 | 10.6 | 8.5 | 9.0 | 0.0 | 1.1 |  |
| hsa-miR-182 |  |  | 8.7 | 8.7 |  |  |  |
| hsa-miR-186 | 8.8 | 9.2 | 8.7 | 9.7 |  |  |  |
| hsa-miR-18a | 5.7 | 8.9 | 6.8 | 7.4 | 0.0 | 0.0 |  |
| hsa-miR-191 | 11.9 | 12.7 | 12.4 | 13.3 |  |  |  |
| hsa-miR-192 | 9.1 | 9.0 | 8.8 | 10.1 |  |  |  |
| hsa-miR-193b |  |  |  | 6.6 |  |  |  |
| hsa-miR-194 | 6.8 | 7.4 | 4.9 | 9.5 |  | 2.0 | 4.7 |
| hsa-miR-195 | 10.3 | 8.7 | 8.8 | 9.2 |  |  |  |
| hsa-miR-197 | 9.7 | 10.5 | 8.7 | 11.0 |  | 0.0 |  |
| hsa-miR-199a* |  |  |  | 7.0 |  |  |  |
| hsa-miR-19a | 9.7 | 12.8 | 11.9 | 11.1 | 0.0 |  |  |
| hsa-miR-19b | 14.0 | 15.6 | 14.9 | 15.0 | 0.8 |  |  |
| hsa-miR-200a | 6.5 |  |  | 6.8 |  |  |  |
| hsa-miR-200b |  |  |  | 7.5 |  |  |  |
| hsa-miR-200c | 9.0 | 9.6 |  | 9.7 |  |  |  |
| hsa-miR-203 | 7.9 |  |  | 7.6 |  |  |  |
| hsa-miR-20a | 12.5 | 14.9 | 12.2 | 13.8 | 0.0 | 0.0 |  |
| hsa-miR-20b | 8.4 | 11.0 | 8.0 | 8.5 | 0.0 | 1.1 | 0.0 |
| hsa-miR-21 | 12.6 | 13.0 | 11.2 | 15.1 |  | 2.8 | 2.1 |
| hsa-miR-210 | 9.2 | 11.1 | 10.7 | 10.2 | 0.8 |  |  |
| hsa-miR-214 |  |  |  | 7.6 |  |  |  |

TABLE 4-continued

MicroRNAs detected in at least one B-cell subset

| | Naive average | Germinal Center average | Plasma Cell average | Memory average | qNaive vs Germinal Center | qGerminal Center vs Plasma Cell | qGerminal Center vs Memory |
|---|---|---|---|---|---|---|---|
| hsa-miR-22 | | | 8.3 | 7.4 | | | |
| hsa-miR-221 | | | | 6.9 | | | |
| hsa-miR-222 | 11.4 | 11.6 | 7.8 | 12.7 | | 0.0 | 4.7 |
| hsa-miR-223 | 13.7 | 10.4 | 9.6 | 14.6 | 0.0 | | 0.0 |
| hsa-miR-23a | | | | 8.7 | | | |
| hsa-miR-23b | | | | 6.2 | | | |
| hsa-miR-24 | 11.7 | 11.8 | 12.8 | 13.4 | | | 2.1 |
| hsa-miR-25 | 9.7 | 10.8 | 8.8 | 11.2 | | 2.8 | |
| hsa-miR-26a | 14.7 | 13.6 | 14.2 | 16.3 | | | 0.0 |
| hsa-miR-26b | 12.6 | 12.1 | 12.0 | 14.1 | | | 3.4 |
| hsa-miR-27a | | 6.5 | | 11.1 | | | 0.0 |
| hsa-miR-27b | | | | 7.2 | | | |
| hsa-miR-28 | 9.4 | 13.3 | 8.4 | 10.3 | 0.0 | 0.0 | 0.0 |
| hsa-miR-296 | 6.9 | 8.1 | 6.6 | 7.9 | 0.0 | 2.0 | |
| hsa-miR-29a | 13.4 | 11.7 | 13.5 | 15.0 | | | 0.0 |
| hsa-miR-29c | 11.2 | 8.7 | 12.3 | 13.3 | 1.5 | 2.6 | 0.0 |
| hsa-miR-301 | 6.0 | 9.6 | 7.7 | 7.9 | 0.0 | 0.0 | |
| hsa-miR-30a-3p | | 8.2 | | | | | |
| hsa-miR-30a-5p | 11.9 | 12.6 | 11.3 | 13.0 | | 2.0 | |
| hsa-miR-30b | 11.7 | 12.6 | 11.2 | 13.0 | | 2.8 | |
| hsa-miR-30c | 13.0 | 13.9 | 12.7 | 14.3 | | 4.5 | |
| hsa-miR-30d | 10.8 | 11.9 | 10.1 | 12.1 | 3.8 | 0.0 | |
| hsa-miR-30e-3p | 8.3 | 9.0 | 6.8 | 9.9 | | 0.0 | |
| hsa-miR-30e-5p | 12.5 | 8.1 | 10.2 | 14.8 | | | 0.0 |
| hsa-miR-31 | | | | 9.0 | | | |
| hsa-miR-32 | 8.4 | | 7.0 | 10.5 | | | |
| hsa-miR-320 | 10.1 | 8.2 | 10.3 | 10.5 | 1.5 | 2.6 | 0.0 |
| hsa-miR-324-3p | 8.8 | 9.9 | 9.0 | 9.5 | | | |
| hsa-miR-324-5p | 8.0 | | | 7.8 | | | |
| hsa-miR-328 | 8.1 | 8.6 | 7.4 | 8.7 | | 2.8 | |
| hsa-miR-331 | 9.4 | 12.6 | 12.0 | 10.8 | 0.0 | | 2.6 |
| hsa-miR-335 | 6.3 | | | 6.9 | | | |
| hsa-miR-339 | 7.3 | | 5.7 | 8.9 | | | |
| hsa-miR-342 | 12.7 | 12.5 | 10.6 | 13.1 | | 0.0 | |
| hsa-miR-345 | 6.8 | 7.1 | 7.8 | 8.6 | | | 3.4 |
| hsa-miR-361 | | | | 8.3 | | | |
| hsa-miR-365 | 6.0 | 7.8 | 8.3 | 8.4 | 0.0 | | |
| hsa-miR-374 | 8.0 | 8.9 | 10.4 | 9.8 | | | |
| hsa-miR-423 | 8.0 | 9.7 | 7.6 | 8.7 | 0.0 | 0.0 | |
| hsa-miR-425 | | | | 6.9 | | | |
| hsa-miR-425-5p | 8.7 | 11.6 | 9.7 | 10.2 | 0.0 | 0.0 | |
| hsa-miR-484 | 11.5 | 12.3 | 12.9 | 12.0 | | | |
| hsa-miR-486 | 7.0 | 8.8 | 9.9 | 9.6 | 3.8 | | |
| hsa-miR-532 | 7.0 | | | 7.8 | | | |
| hsa-miR-545 | | | 5.5 | 6.3 | | | |
| hsa-miR-572 | | 7.7 | | 6.8 | | | |
| hsa-miR-629 | 6.7 | 7.3 | 7.2 | 9.0 | | | 1.4 |
| hsa-miR-646 | | 6.0 | | 7.3 | | | |
| hsa-miR-650 | | 8.8 | 11.4 | 8.0 | | | |
| hsa-miR-659 | | 7.6 | 6.0 | 6.8 | | | |
| hsa-miR-660 | 9.5 | | 8.6 | 10.1 | | | |
| hsa-miR-7 | 6.1 | | | 5.8 | | | |
| hsa-miR-9 | | 7.8 | 6.8 | 6.2 | | 2.8 | |
| hsa-miR-9* | | | 6.4 | 6.5 | | | |
| hsa-miR-92 | 14.5 | 15.8 | 14.2 | 15.5 | 3.6 | 0.0 | |
| hsa-miR-93 | 11.5 | 14.6 | 10.5 | 12.3 | 0.0 | 0.0 | 0.0 |
| hsa-miR-98 | 6.3 | 5.0 | 5.0 | 7.8 | | | 2.1 |
| hsa-miR-99a | | | | 7.3 | | | |
| hsa-miR-99b | | | | 6.8 | | | |

TABLE 5 miRNAs measured using the multiplex RT-PCR assay, but not consistently detected in any B-cell population

| | | | | | | | |
|---|---|---|---|---|---|---|---|
| hsa-let-7e | hsa-miR-383 | hsa-miR-376a | hsa-miR-566 | hsa-miR-34c | hsa-miR-432 | hsa-miR-432 | hsa-miR-586 |
| hsa-miR-I0a | hsa-miR-198 | hsa-miR-376b | hsa-miR-551b | hsa-miR-107 | hsa-miR-433 | hsa-miR-512-5p | hsa-miR-587 |
| hsa-miR-I0b | hsa-miR-224 | hsa-miR-380-5p | hsa-miR-569 | hsa-miR-181c | hsa-miR-485-5p | hsa-miR-199a | hsa-miR-548b |
| hsa-miR-34a | hsa-miR-299-5p | hsa-miR-410 | hsa-miR-570 | hsa-miR-215 | hsa-miR-489 | hsa-miR-199b | hsa-miR-588 |
| hsa-miR-34b | hsa-miR-409-5p | hsa-miR-412 | hsa-miR-548a | hsa-miR-218 | hsa-miR-494 | hsa-miR-219 | hsa-miR-589 |

TABLE 5-continued miRNAs measured using the multiplex RT-PCR assay, but
not consistently detected in any B-cell population

| | | | |
|---|---|---|---|
| hsa-miR-372 | hsa-miR-506 | hsa-miR-323 | hsa-miR-550 |
| hsa-miR-375 | hsa-miR-508 | hsa-miR-338 | hsa-miR-591 |
| hsa-miR-378 | hsa-miR-521 | hsa-miR-368 | hsa-miR-593 |
| hsa-miR-137 | hsa-miR-134 | hsa-miR-373 | hsa-miR-596 |
| hsa-miR-200a | hsa-miR-147 | hsa-miR-373 | hsa-miR-597 |
| hsa-miR-I | hsa-miR-149 | hsa-miR-382 | hsa-miR-622 |
| hsa-miR-183 | hsa-miR-153 | hsa-miR-424 | hsa-miR-599 |
| hsa-miR-302a | hsa-miR-187 | hsa-miR-448 | hsa-miR-600 |
| hsa-miR-302c | hsa-miR-190 | hsa-miR-450 | hsa-miR-624 |
| hsa-miR-302d | hsa-miR-193a | hsa-miR-451 | hsa-miR-601 |
| hsa-miR-367 | hsa-miR-196a | hsa-miR-452 | hsa-miR-626 |
| hsa-miR-369-5p | hsa-miR-196b | hsa-miR-452 | hsa-miR-548d |
| hsa-miR-449 | hsa-miR-205 | hsa-miR-453 | hsa-miR-639 |
| hsa-miR-497 | hsa-miR-208 | hsa-miR-485-3p | hsa-miR-613 |
| hsa-miR-501 | hsa-miR-213 | hsa-miR-488 | hsa-miR-614 |
| hsa-miR-509 | hsa-miR-220 | hsa-miR-490 | hsa-miR-615 |
| hsa-miR-510 | hsa-miR-325 | hsa-miR-492 | hsa-miR-616 |
| hsa-miR-511 | hsa-miR-326 | hsa-miR-493 | hsa-miR-548c |
| hsa-miR-514 | hsa-miR-337 | hsa-miR-503 | hsa-miR-617 |
| hsa-miR-515-3p | hsa-miR-340 | hsa-miR-504 | hsa-miR-642 |
| hsa-miR-515-5p | hsa-miR-380-3p | hsa-miR-505 | hsa-miR-618 |
| hsa-miR-517a | hsa-miR-422b | hsa-miR-507 | hsa-miR-644 |
| hsa-miR-517b | hsa-miR-422a | hsa-miR-513 | hsa-miR-647 |
| hsa-miR-517c | hsa-miR-429 | hsa-miR-516-5p | hsa-miR-649 |
| hsa-miR-518a | hsa-miR-491 | hsa-miR-517 | hsa-miR-661 |
| hsa-miR-518b | hsa-miR-496 | hsa-miR-518c | hsa-miR-662 |
| hsa-miR-518c | hsa-miR-500 | hsa-miR-518f | hsa-miR-449b |
| hsa-miR-518d | hsa-miR-502 | hsa-miR-519b | hsa-miR-653 |
| hsa-miR-518e | hsa-miR-105 | hsa-miR-519c | hsa-miR-411 |
| hsa-miR-520a | hsa-miR-122a | hsa-miR-519d | hsa-miR-654 |
| hsa-miR-520b | hsa-miR-124a | hsa-miR-51ge | hsa-miR-575 |
| hsa-miR-520c | hsa-miR-126 | hsa-miR-522 | hsa-miR-576 |
| hsa-miR-520d | hsa-miR-128b | hsa-miR-523 | hsa-miR-578 |
| hsa-miR-520e | hsa-miR-129 | hsa-miR-524 | hsa-miR-579 |
| hsa-miR-520f | hsa-miR-130a | hsa-miR-526b | hsa-miR-580 |
| hsa-miR-520g | hsa-miR-139 | hsa-miR-96 | hsa-miR-585 |
| hsa-miR-520h | hsa-miR-143 | hsa-miR-651 | hsa-miR-512-3p |
| hsa-miR-95 | hsa-miR-145 | hsa-miR-376a | hsa-miR-631 |
| hsa-miR-126 | hsa-miR-182 | hsa-miR-542-5p | hsa-miR-363 |
| hsa-miR-127 | hsa-miR-185 | hsa-miR-544 | hsa-miR-487b |
| hsa-miR-133a | hsa-miR-189 | hsa-miR-656 | hsa-miR-645 |
| hsa-miR-135a | hsa-miR-18b | hsa-miR-549 | hsa-miR-556 |
| hsa-miR-135b | hsa-miR-202 | hsa-miR-657 | hsa-miR-558 |
| hsa-miR-184 | hsa-miR-202 | hsa-miR-658 | hsa-miR-627 |
| hsa-miR-204 | hsa-miR-299-3p | hsa-miR-652 | hsa-miR-630 |
| hsa-miR-206 | hsa-miR-302a | hsa-miR-551a | hsa-miR-603 |
| hsa-miR-211 | hsa-miR-302b | hsa-miR-552 | hsa-miR-606 |
| hsa-miR-216 | hsa-miR-302b | hsa-miR-553 | hsa-miR-607 |
| hsa-miR-217 | hsa-miR-302c | hsa-miR-554 | hsa-miR-608 |
| hsa-miR-330 | hsa-miR-329 | hsa-miR-555 | hsa-miR-609 |
| hsa-miR-371 | hsa-miR-33 | hsa-miR-562 | hsa-miR-633 |
| hsa-miR-379 | hsa-miR-362 | hsa-miR-563 | hsa-miR-565* |
| hsa-miR-381 | hsa-miR-369-3p | hsa-miR-564 | hsa-miR-594* | miRNAs marked with * were not used in analyses because they have been reclassified as non-miRNAs.

The B cell subsets were profiled for gene expression at the whole genome level, as described previously. See Dave et al. *N Engl J Med.* 2004; 351:2159-2169. At each stage, we identified differentially expressed genes as those genes with a mean two-fold difference in expression and a false-discovery rate of less than 1%. See FIGS. 1E, 1G, and 1I. Genes that we found to be differentially expressed in each stage-transition were consistent with previous studies that examined gene expression in B cell subsets using microarrays with fewer probes, an overlap that was found to be highly statistically significant (P<0.001, chi-squared test). See, e.g., Klein et al. *Proc Natl Acad Sci USA.* 2003; 100:2639-2644; and Shaffer et al. *Immunity.* 2001; 15: 375-385.

In the naïve→germinal center (GC) B cell transition, we identified 32 miRNAs that were differentially expressed. Interestingly, all but 4 miRNAs were found to be expressed more highly in GC cells than in naive B cells. See FIG. 1D.

We confirmed the mRNA expression patterns of several genes that are known to be differentially expressed in the transition including BCL6, MME, MYBL1, as well as LM02. See FIG. 1E. LM02 was found to be expressed more highly in germinal center B cells compared to both naive B cells and memory B cells. See FIGS. 1E and 1I. In the GC→plasma cell transition, we found 33 miRNAs that were differentially expressed. Once again, we noted a striking asymmetry, with all but 2 miRNAs found to be expressed highly in GC cells, but down-regulated in plasma cells. See FIG. 1F. We also confirmed that the plasma cell-specific genes, PRDMI (FIG. 1G), XBPI and IRF4 were highly differentially expressed in our experiments. In the GC→memory B cell transition, there was a preponderance of the 27 significant miRNAs expressed at higher levels in memory cells. See FIG. 1H. Five miRNAs were expressed highly in GC cells compared to all the other B cell types. These included 3 members of the miR-17~92 cluster (miR-17-5p, miR-20b, miR-93), as well as miR-28 and miR-181b.

Figure 5:
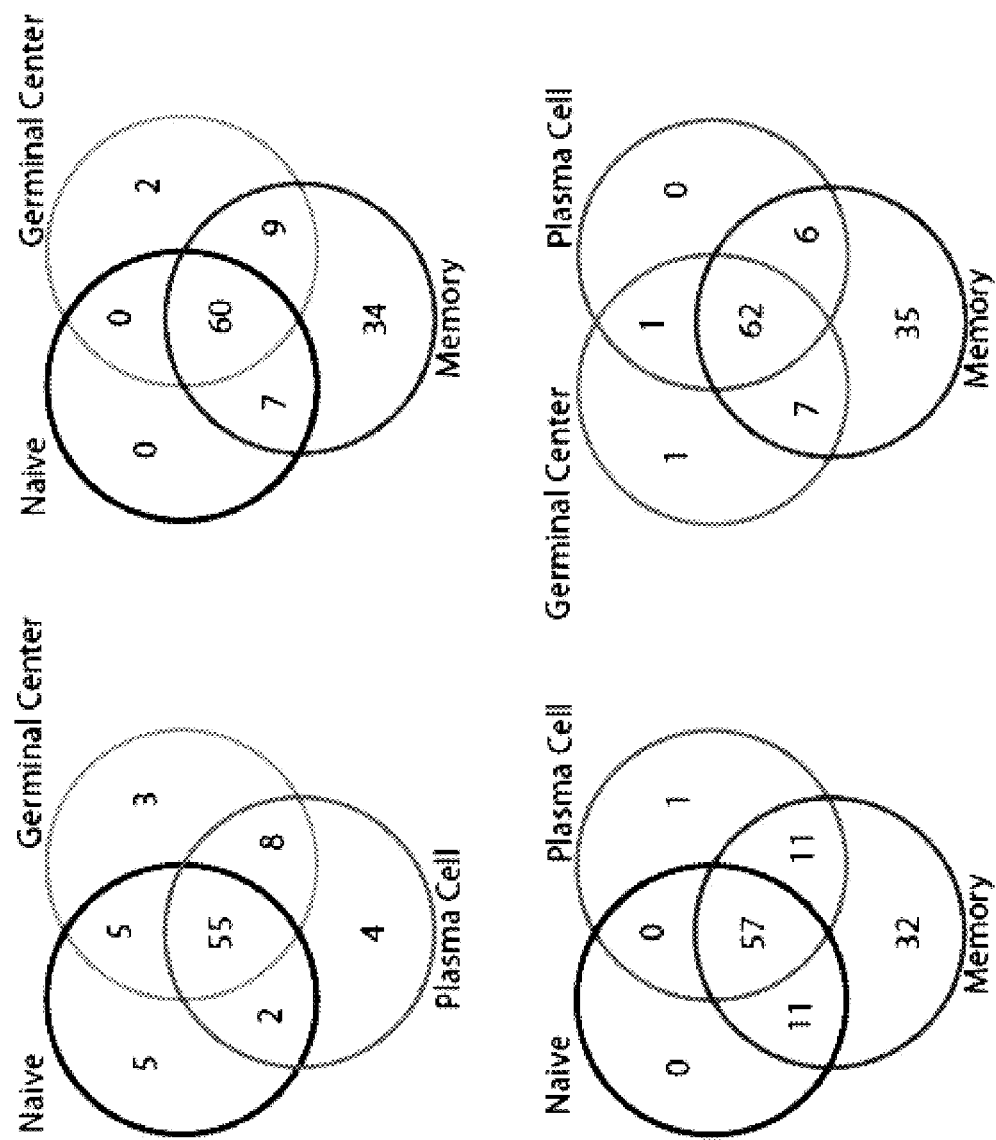
FIG. 5 shows the distribution of miRNAs present in B-cell subsets.

The expression pattern of all the miRNAs that were measurable in at least one of the B cell subsets is summarized in FIG. 5. Notably, there were no differences in the expression of genes involved in miRNA processing, including DICER1, DROSHA, XP05 (exportin5), EIF2C2 (ag02) and DGCR8, among the B cell subsets. See FIG. 1J.

Figure 6:
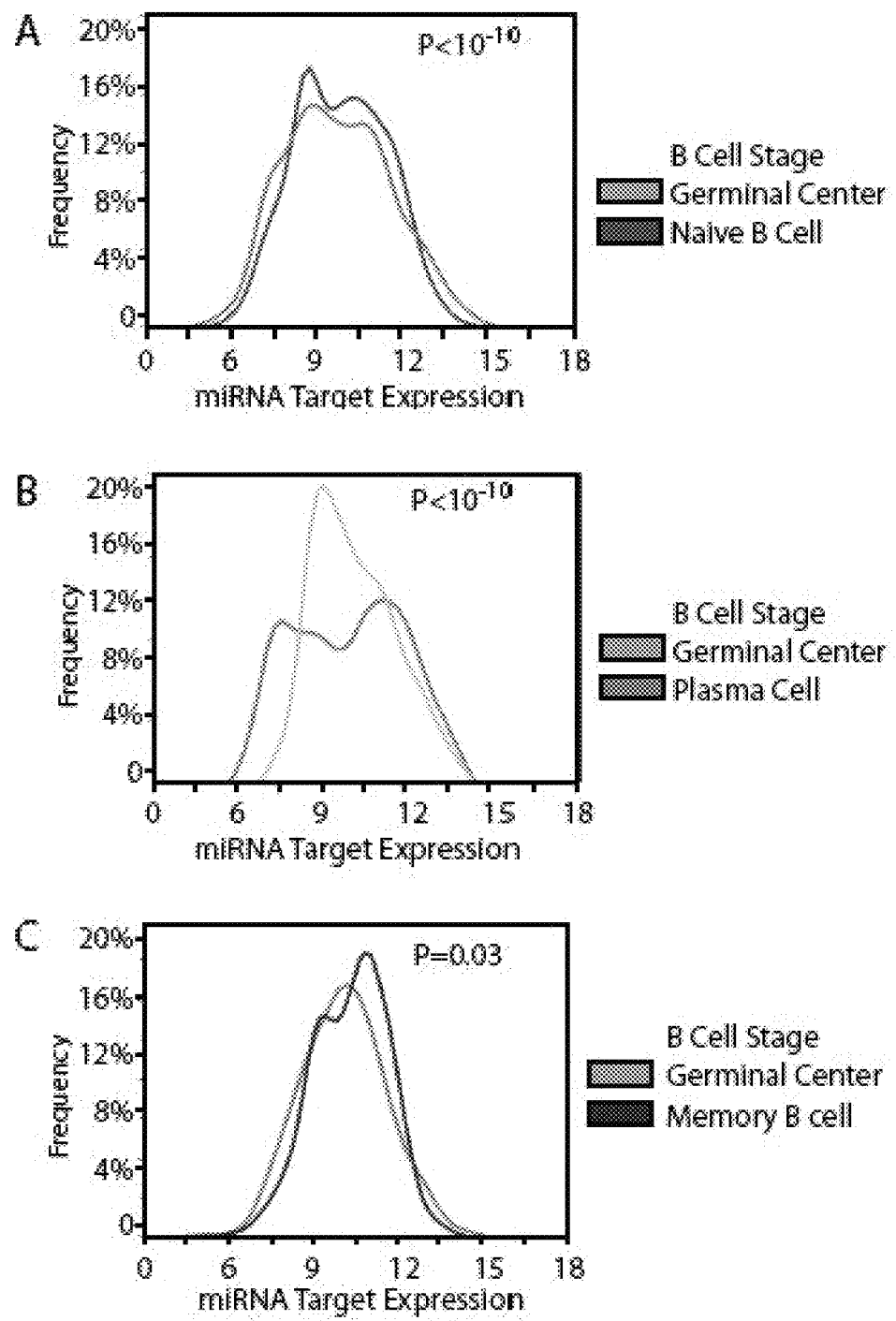
FIG. 6 shows that certain microRNA targets are expressed at lower levels.

Separately, we examined the expression of predicted target genes of differentially expressed microRNAs. We also found that predicted mRNA target genes of microRNAs expressed highly in GC cells were expressed at lower levels in GC cells compared to other stages. See FIG. 6 and Appendix A. FIG. 6A shows density plots of the expression frequency of predicted mRNA targets of microRNAs expressed highly in germinal center B cells compared to naive cells. mRNAs from FIG. 1E that were also predicted targets of the miRNAs (N=830) were plotted for both naive cells and germinal center B cells. The depicted p-value was calculated using a 1-sided Kolmogorov-Smirnov test. FIG. 6B shows density plots of the expression frequency of predicted mRNA targets of miRNAs expressed highly in germinal center B cells compared to plasma cells. mRNAs from FIG. 1G that were also predicted targets of the miR-NAs (N=1098) were plotted for both plasma cells and germinal center B cells. The depicted p-value was calculated using a 1-sided Kolmogorov-Smirnov test. FIG. 6C shows density plots of the expression frequency of predicted mRNA targets of miRNAs expressed highly in the germinal center B cells compared to memory B cells. mRNAs from FIG. 1I that were also predicted targets of the miRNAs (N=269) were plotted for both naive cells and germinal center B cells. The depicted p-value was calculated using a 1-sided Kolmogorov-Smirnov test.

In the naïve to germinal center transition (see FIG. 6A), genes with at least a two-fold change in expression were analyzed by SAM using a false discovery rate of less than 1% (Larsson et. al, *BMC Bioinformatics.* 2005; 6:129), depicted in FIG. 1E. From that list of significantly differentially expressed genes, we determined those that were predicted targets of miRNAs (defined as genes with 3'UTR sequence complementarity to microRNA nucleotides 2-7) that were expressed more highly in germinal center cells. The gene expression distribution of those mRNA targets was graphed for naïve B Cells (blue curve) and germinal center B cells (orange curve). Thus, in FIG. 6A, we show genes differentially expressed between naïve and germinal center B cells that are also predicted targets of miRNA expressed more highly in germinal center B cells. We observe that the expression of these microRNA target genes is lower in germinal center B cells compared to naïve B cells.

A similar analysis was carried out for the transitions from germinal center to plasma cell (FIG. 6B) and germinal center to memory cell (FIG. 6C). In all three cases examined, the distribution of germinal center miRNA target gene expression is statistically significantly lower (leftward shift of orange curve), which suggests a possible gene regulatory role for the miRNAs that are more highly expressed in germinal center cells. We note that the observed lower expression of the miRNA target genes could, however, also be caused by other factors such as downstream effects of particular transcription factors. The complete set of genes plotted in FIG. 6 is listed in Appendix A.

Figure 7:
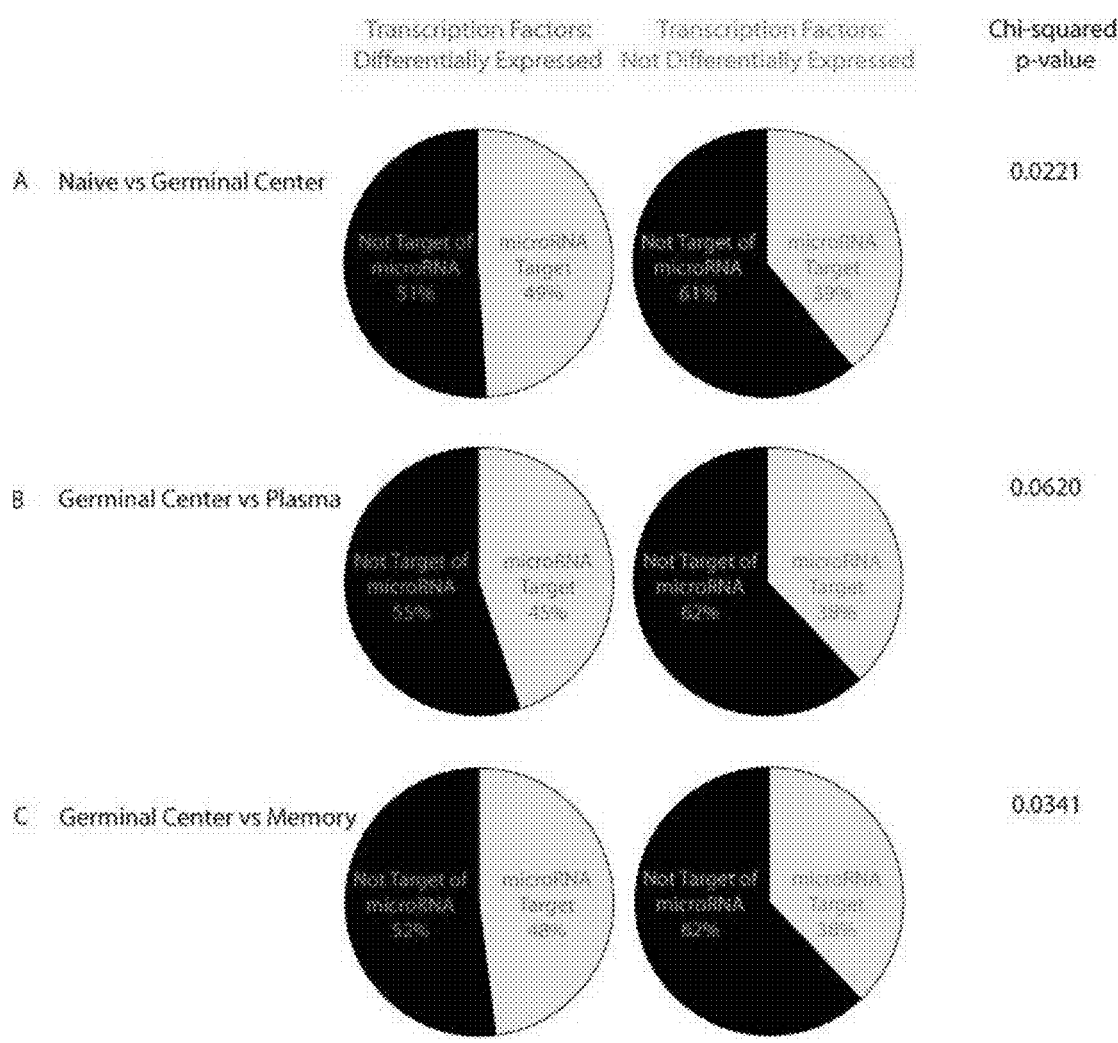
FIG. 7 shows that differentially expressed transcription factors are frequently microRNA targets.

Finally, we found that a higher proportion of differentially expressed transcription factors are predicted microRNA targets. See FIG. 7. Table 6 shows differentially expressed transcription factors, with the average level of expression for each in naïve, germinal center, plasma, and memory cells. Transcription factors for which the significance analysis showed a q value of 0 are indicated.

TABLE 6

Differentially-expressed transcription factors

| ID | NAME | Naive average | Germinal Center average | Plasma Cell average | Memory average | Naive vs GC: q value | GC vs PC: q value | GC vs Mem: q value |
|---|---|---|---|---|---|---|---|---|
| 1 | AHR | 8.9 | 10.33 | 8.36 | 10.38 | 0 | 0 | |
| 2 | APBB2 | 6.86 | 7.87 | 7.35 | 6.39 | 0 | | 0 |
| 3 | ARID1A | 12.3 | 12.22 | 11.11 | 12.17 | | 0 | |
| 4 | ARID3A | 8.03 | 6.9 | 9.81 | 8.76 | 0 | 0 | 0 |
| 5 | ARNTL | 9.47 | 8.4 | 8.23 | 9.7 | 0 | | 0 |
| 6 | ATF7 | 7.83 | 8.97 | 8.23 | 8.44 | 0 | | |
| 7 | BACH1 | 10.68 | 9.97 | 11.76 | 10.59 | | 0 | |
| 8 | BHLHB3 | 11.11 | 8.05 | 13.26 | 13.26 | 0 | 0 | 0 |
| 9 | BPTF | 12.23 | 12.46 | 11.34 | 11.86 | | 0 | |
| 10 | BTG1 | 15.88 | 14.95 | 13.94 | 15.28 | | 0 | |
| 11 | CASP8AP2 | 10.17 | 10.55 | 9.44 | 10.22 | | 0 | |
| 12 | CBL | 11.07 | 11.69 | 10.26 | 11.04 | | 0 | |
| 13 | CBX4 | 12.23 | 12.36 | 13.69 | 12.68 | | 0 | |
| 14 | CCNE1 | 7.86 | 9.18 | 8.87 | 7.66 | 0 | | 0 |
| 15 | CDH1 | 5.85 | 3.85 | 10.26 | 4.91 | | 0 | |
| 16 | CITED2 | 9.11 | 9.88 | 12.56 | 9.22 | | 0 | |
| 17 | CLOCK | 9.85 | 7.68 | 9.91 | 9.62 | 0 | 0 | 0 |
| 18 | CREB5 | 4.91 | 5.46 | 7.24 | 6.95 | | 0 | |
| 19 | CREBL1 | 7.53 | 6.97 | 8.06 | 8.09 | | | 0 |
| 20 | CREBL2 | 10.18 | 9.95 | 11.1 | 10.79 | | 0 | |
| 21 | CSDA | 12.12 | 8.59 | 10.1 | 8.98 | 0 | 0 | |
| 22 | DEK | 12.73 | 14.09 | 10.29 | 13.15 | 0 | 0 | |
| 23 | DLX2 | 6.08 | 4.66 | 7.04 | 7.08 | | 0 | 0 |
| 24 | DR1 | 11.83 | 11.97 | 10.65 | 12.1 | | 0 | |
| 25 | DTX1 | 10.98 | 11.6 | 10.55 | 9.62 | | 0 | 0 |
| 26 | DYRK1B | 6.32 | 5.92 | 7.61 | 4.96 | | 0 | |
| 27 | E2F1 | 7.01 | 8.37 | 7.95 | 7.21 | 0 | | 0 |
| 28 | EGR1 | 11.92 | 13.24 | 13.77 | 12.75 | 0 | | |
| 29 | EGR2 | 10.21 | 10.43 | 8.07 | 10.4 | | 0 | |
| 30 | EGR3 | 11.59 | 9.35 | 8.24 | 10.62 | 0 | 0 | 0 |
| 31 | ELF1 | 12.39 | 12.7 | 11.34 | 12.55 | | 0 | |
| 32 | ELL | 7.12 | 7.83 | 9.17 | 7.59 | | 0 | |
| 33 | ELL2 | 9.25 | 8.23 | 13.6 | 9.27 | | 0 | |
| 34 | EPAS1 | 7.1 | 7.02 | 8.39 | 7.5 | | 0 | |
| 35 | ETS1 | 14.25 | 14.4 | 12.62 | 14.17 | | 0 | |
| 36 | ETS2 | 6.37 | 7.5 | 5.66 | 4.9 | 0 | 0 | 0 |
| 37 | ETV1 | 8.19 | 6.9 | 7.38 | 7.06 | 0 | | |
| 38 | ETV4 | 5.99 | 5.42 | 7.15 | 6.09 | | 0 | |
| 39 | ETV6 | 10.36 | 7.14 | 8.89 | 10.43 | 0 | 0 | 0 |
| 40 | FHL2 | 4.82 | 7.77 | 6.82 | 5.65 | 0 | | 0 |
| 41 | FLNA | 9.95 | 9.2 | 8.57 | 11.03 | | | 0 |
| 42 | FOS | 12.35 | 11.25 | 13.34 | 11.23 | 0 | 0 | |
| 43 | FOSB | 10.13 | 7.21 | 11.05 | 10.79 | 0 | 0 | 0 |
| 44 | FOXC1 | 6.81 | 5.84 | 7.39 | 6.59 | | 0 | |
| 45 | FOXF2 | 7.05 | 4.83 | 6.37 | 5.84 | 0 | | |
| 46 | FOXJ2 | 10.01 | 8.38 | 9.97 | 9.85 | 0 | 0 | 0 |
| 47 | FOXK2 | 8.94 | 8.4 | 9.63 | 8.71 | | 0 | 0 |
| 48 | GATA3 | 8.05 | 7.76 | 8.51 | 9.6 | | | 0 |
| 49 | GATA6 | 7.08 | 5.41 | 7.59 | 6.26 | 0 | 0 | |
| 50 | GCN5L2 | 10.18 | 8.97 | 8.9 | 10.36 | 0 | | 0 |
| 51 | GLI2 | 6.93 | 7.26 | 7.52 | 6.09 | | | 0 |
| 52 | GPX3 | 6.72 | 5.92 | 7.61 | 5.58 | | 0 | |
| 53 | HCLS1 | 13.94 | 14.42 | 13.12 | 13.92 | | 0 | |
| 54 | HIPK2 | 9.36 | 8.66 | 11.04 | 10.85 | | 0 | 0 |
| 55 | HMGA1 | 11.26 | 12.47 | 10.36 | 10.86 | 0 | 0 | 0 |
| 56 | HMGB1 | 15.47 | 16.36 | 14.98 | 14.97 | | 0 | 0 |
| 57 | HMGB2 | 12.96 | 15.78 | 12.73 | 13.36 | 0 | 0 | 0 |
| 58 | HOXA1 | 5.36 | 7.7 | 7.23 | 7.64 | 0 | | |
| 59 | HOXA5 | 7.03 | 8.32 | 8.36 | 7.54 | 0 | | |

TABLE 6-continued

Differentially-expressed transcription factors

| ID | NAME | Naive average | Germinal Center average | Plasma Cell average | Memory average | Naive vs GC: q value | GC vs PC: q value | GC vs Mem: q value |
|---|---|---|---|---|---|---|---|---|
| 60 | HOXB4 | 8.2 | 7.58 | 9.27 | 8.01 | | 0 | |
| 61 | HOXB9 | 7.4 | 6.2 | 8.41 | 6.87 | | 0 | |
| 62 | HOXC11 | 6.6 | 6.4 | 7.88 | 6.21 | | 0 | |
| 63 | HOXC8 | 7.05 | 5.48 | 6.88 | 6.71 | 0 | | |
| 64 | ID4 | 6.49 | 5.93 | 7.79 | 6.41 | | 0 | |
| 65 | ILF3 | 11.26 | 11.94 | 10.71 | 10.99 | | 0 | |
| 66 | IRAK1 | 12.19 | 11.48 | 12.8 | 11.96 | | 0 | |
| 67 | IRF4 | 11.16 | 9.28 | 13.66 | 10.51 | 0 | 0 | 0 |
| 68 | ISL1 | 6.98 | 5.91 | 7.6 | 6.11 | | 0 | |
| 69 | JAZF1 | 11.93 | 10.65 | 7.49 | 11.31 | 0 | 0 | |
| 70 | JMJD1C | 12.34 | 12.34 | 11.11 | 12.56 | | 0 | |
| 71 | JUN | 12.14 | 9.34 | 12.7 | 12.16 | 0 | 0 | 0 |
| 72 | JUNB | 11.62 | 9.72 | 10.84 | 11.37 | 0 | | 0 |
| 73 | KLF11 | 8.08 | 5.94 | 6.88 | 8.39 | 0 | | 0 |
| 74 | KLF2 | 12.61 | 9.1 | 11.7 | 12.61 | 0 | 0 | 0 |
| 75 | KLF4 | 10.04 | 7.57 | 9.09 | 7.49 | 0 | 0 | |
| 76 | KLF5 | 7.08 | 5.26 | 6.14 | 5.07 | 0 | | |
| 77 | KLF6 | 12.06 | 11.33 | 9.24 | 12.40 | | 0 | 0 |
| 78 | KLF7 | 9.36 | 8.35 | 8.88 | 9.8 | 0 | | 0 |
| 79 | KLF9 | 9.47 | 7.34 | 6.64 | 9.27 | 0 | | 0 |
| 80 | LITAF | 12.52 | 10.18 | 11.82 | 12.49 | 0 | 0 | 0 |
| 81 | LMO1 | 6.86 | 4.75 | 7.16 | 6.88 | | 0 | |
| 82 | MAF | 8.05 | 9.95 | 8.25 | 10.83 | 0 | 0 | |
| 83 | MAFB | 6.58 | 7.3 | 8.56 | 7.29 | | 0 | |
| 84 | MAML3 | 8.05 | 10.85 | 9.07 | 7.04 | 0 | 0 | 0 |
| 85 | MDFIC | 12.06 | 13.67 | 13.6 | 13.08 | 0 | | |
| 86 | MEIS2 | 7.45 | 7.15 | 7.56 | 5.29 | | | 0 |
| 87 | MEN1 | 10.79 | 11.33 | 10.49 | 10.23 | | | 0 |
| 88 | MITF | 7.51 | 8.05 | 8.01 | 6.41 | | | 0 |
| 89 | MTF1 | 10.08 | 9.92 | 8.86 | 10.5 | | 0 | |
| 90 | MXD1 | 9.07 | 7.59 | 9.62 | 8.9 | 0 | 0 | 0 |
| 91 | MXI1 | 10.63 | 7.85 | 11.1 | 9.42 | 0 | 0 | 0 |
| 92 | MYB | 6.97 | 8.62 | 5.61 | 7.99 | 0 | 0 | |
| 93 | MYBL1 | 9.68 | 14.13 | 10.02 | 9.72 | 0 | 0 | 0 |
| 94 | MYBL2 | 9.07 | 12.41 | 9.12 | 8.52 | 0 | 0 | 0 |
| 95 | NAT14 | 6.62 | 7.66 | 7.33 | 7.63 | 0 | | |
| 96 | NF1 | 9.23 | 10.46 | 11.21 | 9.88 | 0 | | |
| 97 | NFAT5 | 11.71 | 12.09 | 10.72 | 11.77 | | 0 | |
| 98 | NFATC4 | 6.36 | 7.92 | 8.96 | 5.71 | 0 | | 0 |
| 99 | NFIX | 8.09 | 7.43 | 8.67 | 7.37 | | 0 | |
| 100 | NFKB1 | 11.91 | 11.9 | 10.7 | 11.55 | | 0 | |
| 101 | NFYC | 10.2 | 10.27 | 9.03 | 10.03 | | 0 | |
| 102 | NR3C2 | 8.85 | 5.58 | 4.91 | 8.41 | 0 | | 0 |
| 103 | NR6A1 | 9.1 | 6.03 | 6.42 | 7.62 | 0 | | 0 |
| 104 | NRIP1 | 11.79 | 10.3 | 10.33 | 11.20 | 0 | | |
| 105 | PAX3 | 7.01 | 5.55 | 5.01 | 5.96 | 0 | | |
| 106 | PHF1 | 11.85 | 10.69 | 12.26 | 11.45 | 0 | 0 | |
| 107 | POU3F1 | 6.08 | 7.52 | 6.86 | 7.52 | 0 | | |
| 108 | POU4F1 | 5.62 | 8.85 | 8.46 | 7.53 | 0 | | 0 |
| 109 | POU4F2 | 7.09 | 5.72 | 7.21 | 5.1 | 0 | 0 | |
| 110 | PPARD | 11.23 | 9.98 | 10.29 | 10.69 | 0 | | |
| 111 | PPARG | 7.79 | 7.22 | 6.74 | 5.47 | | | 0 |
| 112 | PPARGC1B | 6.89 | 6.09 | 6.51 | 7.91 | | | 0 |
| 113 | PRDM1 | 8.49 | 9.15 | 14.1 | 9.33 | | 0 | |
| 114 | PRDM4 | 10.48 | 9.81 | 9.76 | 10.83 | | | 0 |
| 115 | PROX1 | 7.18 | 6.38 | 7.89 | 5.54 | | 0 | |
| 116 | RAN | 13.46 | 14.57 | 12.39 | 13.78 | 0 | 0 | |
| 117 | RSF1 | 10.05 | 9.1 | 9.56 | 10.18 | | | 0 |
| 118 | RUNX1T1 | 7.37 | 5.95 | 6.63 | 6.34 | 0 | | |
| 119 | RUNX2 | 8.75 | 7.91 | 10.22 | 9.75 | | 0 | 0 |
| 120 | RUNX3 | 11.8 | 11.13 | 10.26 | 12.47 | | | 0 |
| 121 | RXRA | 9.07 | 7.15 | 8.81 | 8.32 | 0 | 0 | |
| 122 | SAP30 | 8.22 | 9.91 | 9.28 | 8.33 | 0 | | 0 |
| 123 | SCMH1 | 8.48 | 9.69 | 9.65 | 8.62 | 0 | | 0 |
| 124 | SCML1 | 10.32 | 8.48 | 7.81 | 7.91 | 0 | | |
| 125 | SCML2 | 10.33 | 8.76 | 9.27 | 8.96 | 0 | | |
| 126 | SF1 | 11.72 | 11.44 | 10.36 | 11.37 | | 0 | |
| 127 | SIAH2 | 10.35 | 12.34 | 10.57 | 9.90 | 0 | 0 | 0 |
| 128 | SLC2A4RG | 8.25 | 8.98 | 7.4 | 8.91 | | 0 | |
| 129 | SMAD1 | 5.91 | 8.1 | 6.34 | 7.33 | 0 | 0 | |
| 130 | SMAD2 | 10.45 | 11.57 | 10.8 | 10.98 | 0 | | |
| 131 | SMAD3 | 10.72 | 9.23 | 7.74 | 10.54 | 0 | 0 | 0 |
| 132 | SMARCA2 | 11.14 | 10.12 | 10.79 | 11.19 | 0 | | 0 |

TABLE 6-continued

Differentially-expressed transcription factors

| ID | NAME | Naive average | Germinal Center average | Plasma Cell average | Memory average | Naive vs GC: q value | GC vs PC: q value | GC vs Mem: q value |
|---|---|---|---|---|---|---|---|---|
| 133 | SOLH | 8.78 | 7.88 | 8.7 | 9.03 | | | 0 |
| 134 | SOX4 | 8.99 | 9.14 | 9.17 | 10.2 | | | 0 |
| 135 | SOX5 | 9.3 | 10.47 | 7.33 | 9.08 | 0 | 0 | 0 |
| 136 | SOX9 | 6.72 | 8.42 | 8.18 | 7.03 | 0 | | 0 |
| 137 | SP4 | 11.26 | 10.14 | 9.58 | 11.75 | 0 | | |
| 138 | SRCAP | 8.58 | 8.06 | 6.96 | 8.38 | | 0 | |
| 139 | SREBF1 | 8.23 | 8.36 | 6.56 | 5.89 | | 0 | 0 |
| 140 | STAT5B | 10.35 | 10.95 | 9.73 | 10.7 | | 0 | |
| 141 | SUFU | 7.12 | 6.03 | 7.84 | 7.62 | | 0 | 0 |
| 142 | SUPT16H | 11.12 | 11.35 | 9.6 | 10.71 | | 0 | |
| 143 | SUPT3H | 7.77 | 6.3 | 8.05 | 8.35 | 0 | 0 | 0 |
| 144 | TARDBP | 12.31 | 12.72 | 11.49 | 11.91 | | 0 | |
| 145 | TBP | 10.55 | 10.14 | 9.09 | 10.38 | | 0 | |
| 146 | TBX3 | 5.67 | 6.05 | 7.89 | 5.53 | | 0 | |
| 147 | TCEA1 | 13.31 | 15 | 14.05 | 13.6 | 0 | | 0 |
| 148 | TCERG1 | 12.29 | 12.5 | 11.46 | 12.04 | | 0 | |
| 149 | TCF7 | 10.21 | 10.82 | 9.97 | 12.61 | | | 0 |
| 150 | TFAP2A | 6.7 | 5.54 | 8.26 | 6.88 | | 0 | |
| 151 | TFAP4 | 7.28 | 5.29 | 5.42 | 5.13 | 0 | | |
| 152 | TFDP1 | 10.95 | 12.9 | 10.49 | 11.36 | 0 | 0 | 0 |
| 153 | TFEB | 11.56 | 11.15 | 9.49 | 11.77 | | 0 | |
| 154 | THRA | 7.41 | 7.26 | 8.48 | 7.05 | | 0 | |
| 155 | THRB | 7.45 | 7.51 | 6.11 | 6.29 | | 0 | 0 |
| 156 | TLE1 | 9.19 | 7.74 | 9.63 | 9.13 | 0 | 0 | |
| 157 | TMF1 | 10.76 | 9.68 | 10.71 | 10.42 | 0 | | |
| 158 | TSC22D3 | 13.22 | 11.26 | 12.67 | 13.4 | 0 | 0 | 0 |
| 159 | UHRF1 | 9.23 | 12.22 | 8.72 | 8.96 | 0 | 0 | |
| 160 | VEZF1 | 10.98 | 11.45 | 9.94 | 10.81 | | 0 | |
| 161 | XBP1 | 10.1 | 10.74 | 15.84 | 10.65 | | 0 | |
| 162 | YBX1 | 14.79 | 15.31 | 14.2 | 14.53 | | 0 | |
| 163 | YWHAH | 8.94 | 10.82 | 9.09 | 9.36 | 0 | | 0 |
| 164 | YWHAZ | 13.38 | 13.62 | 12.61 | 13.62 | | 0 | |
| 165 | ZFP36L1 | 14.07 | 12.89 | 10.09 | 13.87 | 0 | 0 | |
| 166 | ZHX3 | 8.29 | 7.76 | 7.47 | 6.66 | | | 0 |
| 167 | ZNF207 | 12.29 | 13.51 | 12.69 | 12.54 | 0 | | |
| 168 | ZNF217 | 11.68 | 10.77 | 9.73 | 11.61 | | 0 | |
| 169 | ZNF219 | 6.13 | 6.11 | 8.42 | 6.48 | | 0 | |
| 170 | ZNF238 | 13.05 | 11.27 | 10.08 | 12.54 | 0 | 0 | 0 |
| 171 | ZNF3 | 8.86 | 7.27 | 8.75 | 8.89 | 0 | 0 | 0 |
| 172 | ZNF367 | 7.97 | 10.99 | 8.04 | 8.22 | 0 | 0 | 0 |
| 173 | ZNF398 | 10.39 | 9.28 | 10.47 | 10.25 | 0 | 0 | |

Example 3

Figure 2:
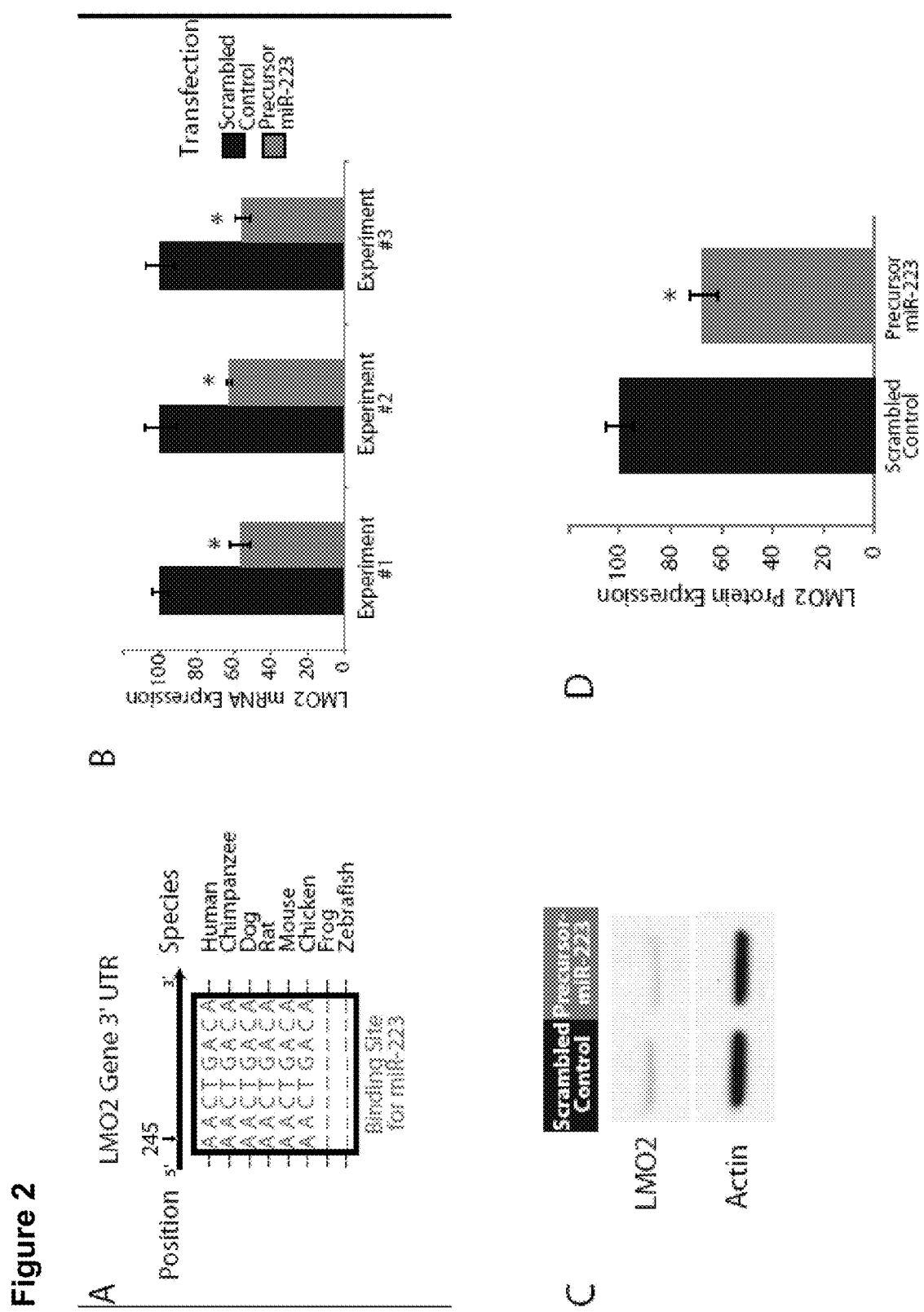
FIG. 2 shows experimental validation of the interaction of miR-223, which is expressed highly in naive and memory B cells compared to germinal center B cells, and targets the transcription factor LM02.
Figure 8:
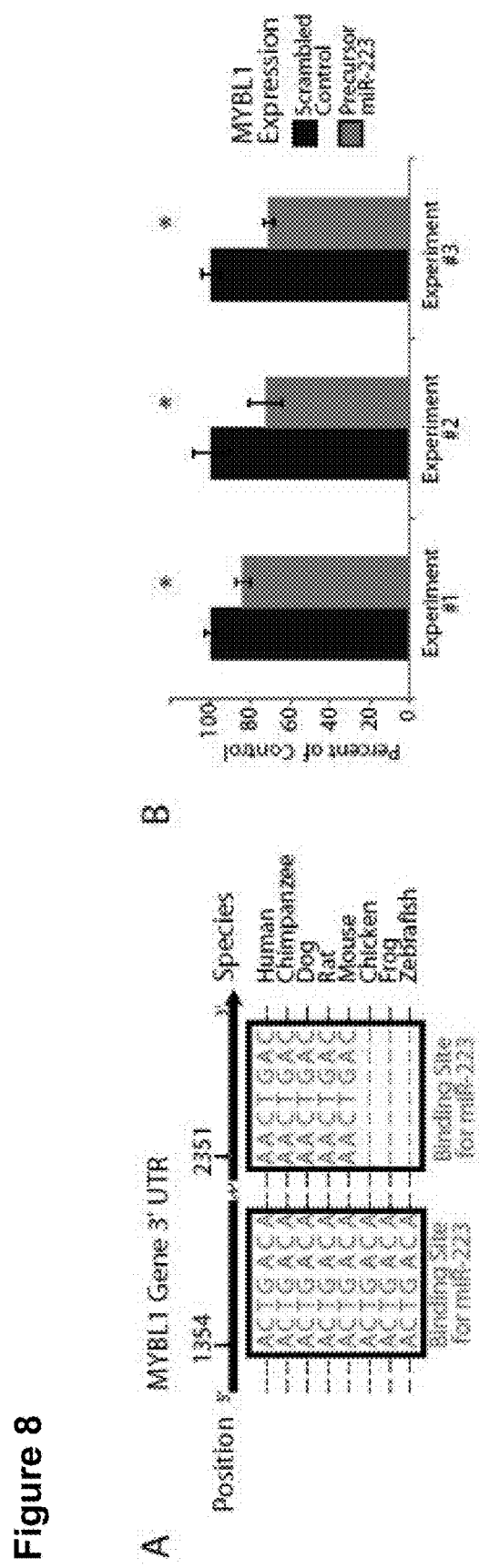
FIG. 8 shows that Mybl transcript levels decrease with miR-223 overexpression.

MiR-223 Regulates LM02 in the Naive~Germinal Center and Germinal Center~Memory Cell Transitions MiR-223 has previously been described as being important in the commitment to myeloid lineage. See Chen et al. *Science.* 2004; 303:83-86; Johnnidis et al. *Nature.* 2008; 451:1125-1129. We found miR-223 to be expressed at nearly 8-fold higher levels in both naive and memory cells compared to GC cells. This miRNA has a highly conserved sequence complementarity to the 3'UTR of 2 transcription factors that are expressed highly during GC cell differentiation: LM02 (FIG. 2A) and MYBL1 (FIG. 8A). Higher expression of miR-223 in the naive B cell stage could inhibit the untimely expression of these transcription factors until the cell is ready to undergo the germinal center reaction.

We evaluated the effects of miR-223 expression on its predicted target gene, LM02, by transfecting precursors of miR-223 into a cell line derived from GC cell lymphoma cells (BlAB). Over-expression of miR-223 resulted in a consistent down-regulation of LM02 at the transcript level compared to a transfection with a scrambled control with no sequence complementarity to the human genome. See FIG. 2B. In that figure, the blue bars depict expression of LM02 24 hours after transfection with a scrambled control that does not possess complementarity to the human genome. The orange bars depict the expression of LM02 24 hours after transfection with a precursor for miR-223. The expression of LM02 was consistently lower in the cells treated with the miR-223 precursor, and the results were statistically significant (P<0.05 in all cases, student's t-test). There was no effect on the expression of a non-target control, beta-2 micro globulin in these experiments (data not shown). Over-expression of miR-223 also resulted in a consistent down-regulation of LM02 at the protein level compared to a transfection with a scrambled control with no sequence complementarity to the human genome. See FIG. 2C. We quantified the results of 3 separate experiments examining LM02 protein expression and found consistent down-regulation of LM02 in cells treated with miR-223 compared to cells transfected with scrambled controls. See FIG. 2D. Those results that were statistically significant (P<0.05, student's t-test). The extent of down-regulation of LM02 mRNA and protein by miR-223 was comparable, suggesting that miR-223 regulation of LM02 occurs predominantly at the mRNA level. Similarly, over-expression of miR-223 resulted in a down-regulation of MYBL1 transcripts. See FIG. 8B. In that figure, the blue bars depict expression of MYBL1 mRNA 24 hours after transfection with a scrambled control that does not possess complementarity to the human genome. The orange bars depict the expression of Mybl1 24 hours after transfection with a precursor for miR-223. The expression of LM02 was consistently lower in the cells treated with the miR-223 precursor (P<0.05 in all cases).

As additional validation, we investigated whether the miR-223 had a direct effect on LM02 by cloning the 3'UTR sequence of LM02 3' to the firefly luciferase ORF (Flue). See Gottwein et al. *Nature.* 2007; 450:1096-1099. The resulting constructs and the unmodified vector were co-transfected into 293T cells along with a *Renilla* luciferase internal control and pL-CMV-eGFP constructs expressing either no miRNA or miR-223. Flue expression from constructs bearing LM02 3' UTR sequences were differentially down-regulated by miR-223 compared to those with mutated seed sequences; the seed sequence mutant construct had consistently diminished miR-223 repression compared to the wild-type construct in 5 separate experiments. See FIG. 2E. Those results were statistically significant (P<0.05, student's t-test). These observations provide evidence for an inhibitory role for miR-223 in regulating the transcription factor LM02.

Activation of LM02 has been associated with the development of leukemia in patients undergoing gene therapy. Hacein-Bey-Abina et al. *Science.* 2003; 302:415-419. On the other hand, higher expression of PRDM1 alone is sufficient to induce plasma cell-differentiation. Turner et al. *Cell.* 1994; 77:297-306. Inappropriate expression of such genes must be effectively turned off for a cell to maintain its state. This mode of regulation is reflected in the effects of miR-223, miR-9 and miR-30, which turn off the inappropriate expression of LM02 and PRDMI and might promote state maintenance and inhibition of lymphomagenesis.

On the other hand, our data also identify a number of instances in which miRNAs are co-expressed with their predicted targets. It is possible that such interactions within the cell help to stabilize a defined expression level by dampening fluctuations. For example, in GC cells, we found that miR-181b was strongly co-expressed with its predicted target, BCL6. Such interactions could also be important in B cell stage maintenance and curbing the oncogenic potential of genes involved in B cell differentiation. See Cattoretti et al. *Cancer Cell.* 2005; 7:445-455; Dorsett et al. *Immunity.* 2008; 28:630-638.

Example 4

Figure 9:
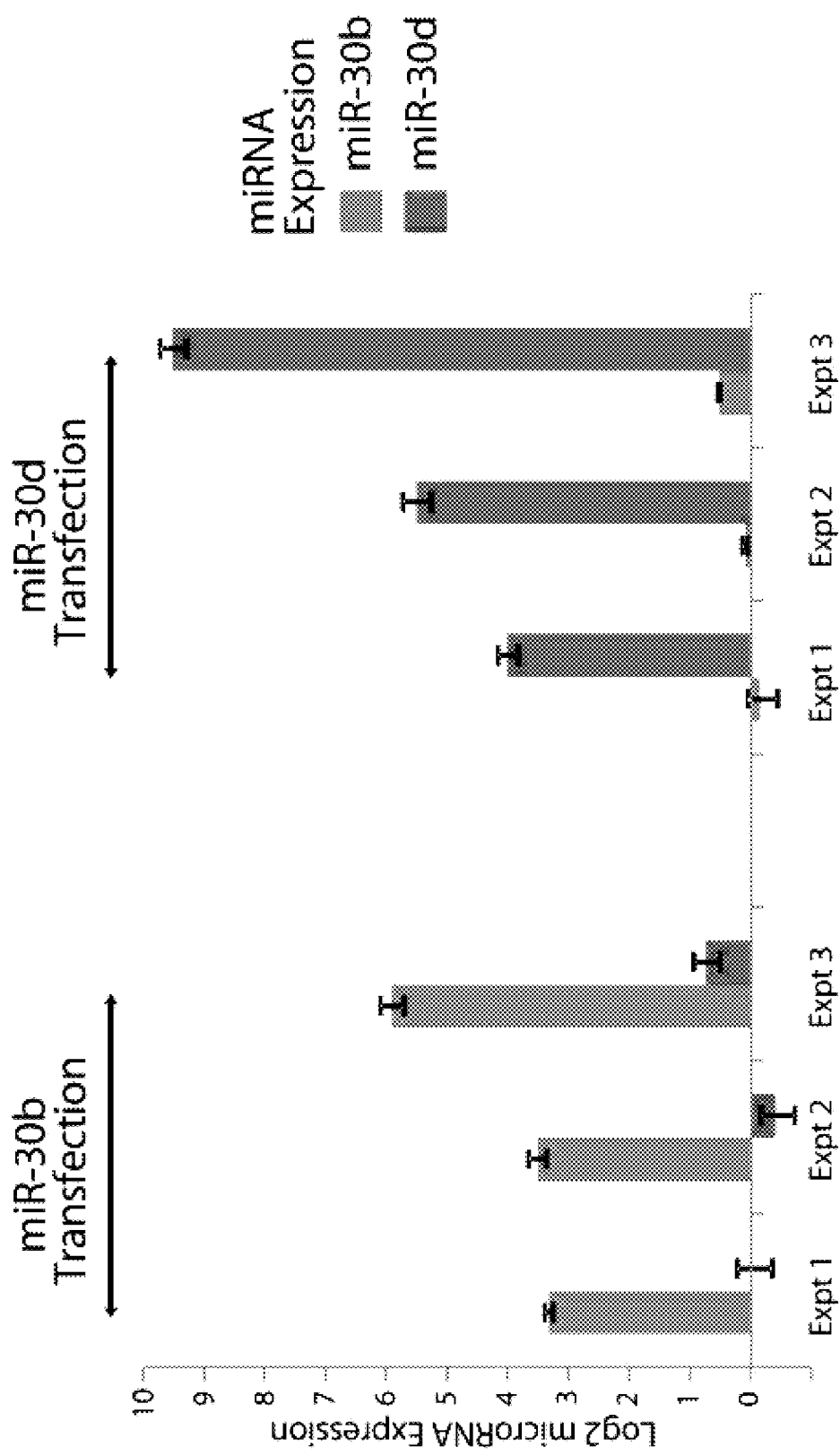
FIG. 9 shows the specificity of real-time PCR probes for members of the miR-30 family.

MiR-9 and the miR-30 Family Regulate PRDM1 (Blimp-1) in the Germinal Center →Plasma Cell Transition In the GC→plasma cell transition, we observed that several members of the miR-30 family were expressed at 2-fold or higher levels in GC cells. See FIG. 1F. The transcription factor PRDMI is an essential regulator of plasma cell differentiation. Martins et al. *Annu Rev Immunol.* 2008; 26:133-169. The miR-30 family comprises 5 members (miR-30a, 30b, 30c, 30d and 30e), of which 4 (all except 30e) were found to be expressed at higher levels in GC cells compared to plasma cells. Control transfection experiments documented good specificity of the RT-PCR probes for individual members of the miR-30 family with no discernible cross-hybridization. See FIG. 9. Three separate transfection experiments using high concentrations of miR-30b precursors are shown in the left panel with measurement of miR-30b and miR-30d. Similar experiments were performed with precursors for miR-30d (right panel).

Figure 3:
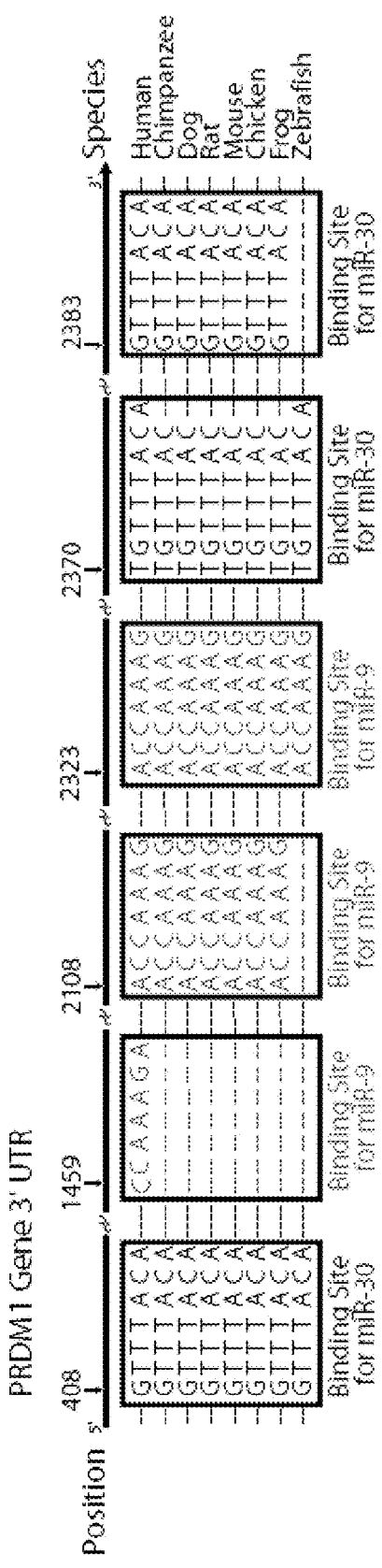
FIG. 3 shows experimental validation of the interaction of miR-9 and miR-30, which are expressed highly in germinal center B cells compared to plasma cells and target the transcription factor PRDM1.
Figure 3:
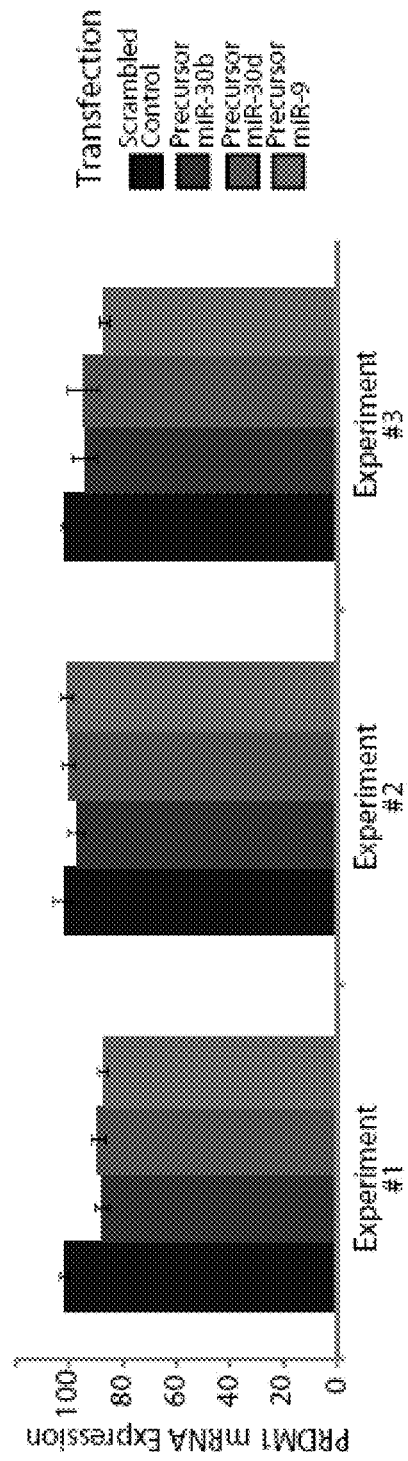

The 3'UTR of PRDM1 contains 3 highly conserved binding sites complementary to the seed sequence of members of the miR-30 family, as well as 3 binding sites for the seed sequence of miR-9, 2 of which are highly conserved across multiple species. See FIG. 3A. The 3'UTR region of PRDM1 complementary to miR-30 is shown in red. The 3 sites are complementary to nucleotides 2-8 (UTR position 408), nucleotides 1-8 (UTR position 2370) and nucleotides 2-8 (UTR position 2383) on the miRNA, respectively. The 3'UTR region of PRDM1 complementary to miR-9 is shown in green. The 3 sites are complementary to nucleotides 1-7 (UTR position 1459), nucleotides 2-8 (UTR position 2108) and nucleotides 2-8 (UTR position 2323) on the miRNA respectively. These sites are highly conserved across a number of species, with the exception of one miR-9 site (UTR position 1459) that is only present in humans.

To evaluate the effects of the miR-30 family and miR-9 on PRDM1 expression in plasma cells, we introduced precursors of miR-9, miR-30b and miR-30d into the U266 multiple myeloma (plasma cell) cell line. Overexpression of miR-30 family members miR-30b and miR-30d, as well as miR-9, had no effect on PRDM1 at the mRNA level. See FIG. 3B. In that figure, the blue bars depict expression of PRDM1 24 hours after transfection with a scrambled control with no complementarity to the human genome. The magenta bars depict the expression of PRDM1 24 hours after transfection with a hairpin precursor for miR-30b, while the red bars depict the expression of PRDM1 24 hours after transfection with a hairpin precursor for miR-30d. The green bars depict the expression of PRDM1 24 hours after transfection with a hairpin precursor for miR-9. By contrast, there was a consistent down-regulation of PRDM1 at the protein level. See FIGS. 3C and 3D. Those results were statistically significant in each case (P<0.05, student's t-test), except for the transfections with the precursor to miR-9 (P=0.08, student's t-test). Overexpression of each of those microRNAs had an average knockdown effect of around 40%. These exclusively post-transcriptional effects of miR-9 and miR-30 on PRDMI expression are consistent with one mechanism of miRNA regulation that has been described previously in other systems. See, e.g., O'Donnell et al. *Nature.* 2005; 435:839-843; Gottwein et al. *Nature.* 2007; 450:1096-1099; Selbach et al. *Nature.* 2008; 455:58-63; and Baek et al. *Nature.* 2008; 455:64-71. There was no effect on the expression of a non-target control (Actin).

Additionally, luciferase reporter activity of the PRDM1 3'UTR construct was decreased by overexpression of miR-9, miR-30b, and miR-30d, but not their respective seed sequence mutants. See FIG. 3E, which shows the average of three experiments. The down-regulation of the luciferase reporter signal and its restoration in the mutant constructs was found to be statistically significant in each of the 3 microRNAs: miR-9, miR-30b and miR-30d (P<0.05, student's t-test). The luciferase reporter activity level was rescued to the activity level of the empty vector control when the seed sequence of the microRNAs was mutated.

The combined effect of 5 different microRNA species (miR-30a, miR-30b, miR-30c, miR-30d and miR-9) is likely to be more potent than that of a single microRNA. The role of mutual repression of BCL6 and PRDMI in the germinal center to plasma cell differentiation as been described previously. See Martins et al. *Immunol.* 2008; 26:133-169. Our data suggest that microRNAs may bolster the effects of BCL6 in the inhibition of PRDM1.

Our data show that members of the miR-17~92 family are consistently expressed in GC cells and may play a role in mature B cell differentiation. Interestingly, the miR-17~92 family has been implicated in early B cell differentiation and mice lacking the loci that encode these miRNAs have arrested early B cell development. See Ventura et al. *Cell.* 2008; 132:875-886. The expression patterns of the miR-17~92 family suggest that the regulatory motifs embedded in the interaction of this miRNA family and its targets might have an additional function in regulating mature B cell differentiation.

A striking observation in this study is the high degree of asymmetry observed in relative expression of miRNAs in GC cells compared to naive and plasma cells. At least 2 hypotheses could account for these findings. First, miRNA expression may promote a highly regulated state that enables GC cells to interact with T cells and antigen presenting cells, and to leave the GC cells poised for differentiation into memory or plasma cells. Second, miRNAs expressed highly in naive and plasma cells may be underrepresented in current miRNA libraries. Such libraries are often constructed from lymph nodes, which are typically enriched in GC cells. High throughput sequencing of sorted populations of B cells could reveal novel miRNAs that are highly expressed in those populations. Interestingly, a larger number of miRNAs were highly expressed in memory cells compared to GC cells. This observation might stem from the fact that memory cells are known to be heterogeneous (Sanz et al. *Semin Immunol.* 2008; 20:67-82) and standard methods used to select memory cells may capture a diverse group of memory subpopulations.

Example 5

MiRNAs and B Cell Malignancies

To examine the expression of B cell stage-specific microRNAs in B cell malignancies, we undertook miRNA profiling of 75 tissue samples derived from normal lymph nodes (N=5) as well as patients with B cell malignancies including the molecular subsets of diffuse large B cell lymphoma (DLBCL; see Rosenwald et al. *N Engl J Med.* 2002; 346: 1937-1947), germinal center B cell-like (GCB) DLBCL (N=20) and activated B cell-like (ABC) DLBCL (N=20), as well as cases of IgV mutated and unmutated chronic lymphocytic leukemia (N=20) and Burkitt lymphoma (N=10).

Figure 4:
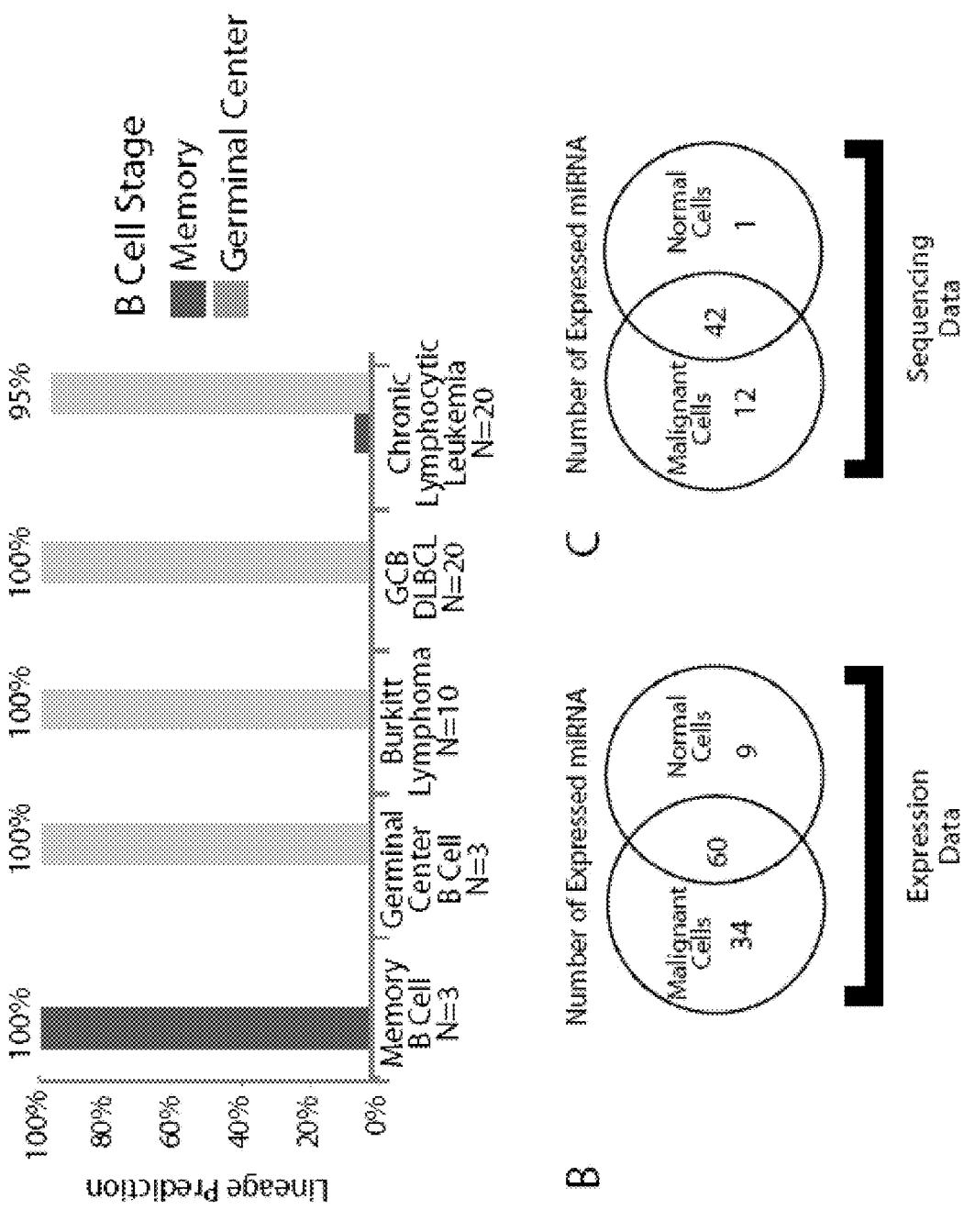
FIG. 4 shows that expression of microRNAs in normal B cells is conserved in certain B cell malignancies.

We constructed a Bayesian predictor from miRNAs that distinguished normal memory B cells from GC cells. See FIG. 1H. We tested the predictor in the B cell malignancies derived from germinal center B cells (Burkitt lymphoma and GCB DLBCL) along with chronic lymphocytic leukemia, which is thought to arise from memory B cells. See Klein et al. *J Exp Med.* 2001; 194:1625-1638. Using leave one out cross-validation, we found that the predictor constructed from miRNAs expressed in normal B cells was able to correctly identify the B cell specific stage of the B cell malignancy type in over 95% of the cases. See FIG. 4A.

An interesting aspect regarding the role of miRNAs in malignancies is their reported down-regulation in a number of malignancies compared to normal cells from the same lineage. See Lu et al. *Nature.* 2005; 435:834-838. To further examine this effect in B cell malignancies, we examined the expression of 113 miRNAs that we had identified in normal B cells. See Table 4, above. Of the 113 miRNAs, 103 were detected using the microarrays that we used to profile B cell malignancies and normal lymph nodes. We applied a 2-sided student's t-test to evaluate the relative expression of those 103 miRNAs in B cell malignancies (N=60) and normal lymph nodes (N=5). 34 miRNAs were differentially expressed (P<0.05) at higher levels in malignant cells and 9 miRNAs were expressed more highly in normal cells. 60 miRNAs were not differentially expressed. See FIG. 4B.

As additional validation, we examined miRNA cloning frequencies for sequences cloned from normal and malignant B cells. See Landgraf et al. *Cell.* 2007; 129:1401-1414. MiRNAs for which a sequence was identified in at least 2 of the 3 available normal B cell samples were used in the analysis. We applied a 2-sided student's t-test (P<0.05) to compare the differential cloning frequency of the miRNAs between normal B cells (N=3) and a variety of mature B cell malignancy patient samples and cell lines (N=42). In all, we found 56 miRNAs that were consistently expressed in normal B cells. We found 13 of those 56 miRNAs were differentially expressed (P<0.05) between normal and malignant B cells, of which 12 miRNAs were expressed more highly in malignant cells and 1 miRNA was expressed more highly in normal cells. See FIG. 4C. In order to avoid effects from tumor-infiltrating non-malignant cells, we repeated the analysis with 20 chronic lymphocytic leukemia samples in the malignant group. The results were similar to those obtained with the larger set of malignancies (data not shown).

These results demonstrate that miRNAs are not down-regulated in B cell malignancies compared to normal B cells and that normal B cell stage-specific miRNAs are maintained in B cell malignancies.

MicroRNA profiling also revealed that each B cell malignancy type had a distinctive pattern of miRNA expression. See FIG. 4D. In order to evaluate the ability of miRNA profiles to distinguish different B cell malignancy types, we constructed Bayesian predictors from the most highly differentially expressed miRNAs for each pair-wise comparison. See Tables 7, 8, and 9.

TABLE 7

Predictor microRNAs that distinguish germinal center B-cell (GCB) DLBCL from Burkitt Lymphoma, activated B-cell (ABC) DLBCL, and chronic lymphocytic leukemia

| GCBvsBL | GCBvsABC | GCBvsCLL |
|---|---|---|
| hsa-miR-146a | hsa-miR-142-3p | hsa-miR-126 |
| hsa-miR-154 | hsa-miR-16 | hsa-miR-130a |
| hsa-miR-155 | hsa-miR-184 | hsa-miR-I0b |
| hsa-miR-184 | hsa-miR-191 | hsa-miR-154 |
| hsa-miR-29b | hsa-miR-19a | hsa-miR-193b |
| hsa-miR-29c | hsa-miR-19b | hsa-miR-199a-3p |
| hsa-miR-363 | hsa-miR-299-5p | hsa-miR-365 |
| hsa-miR-503 | hsa-miR-32 | hsa-miR-99b |
| hsa-miR-519c-5p | hsa-miR-30e* | hsa-miR-143 |
| hsa-miR-301a | hsa-miR-151-5p | hsa-miR-585 |
| hsa-miR-152 | hsa-miR-583 | hsa-miR-193a-5p |
| hsa-miR-30b* | mghv-miR-MI-7-5p | hsa-miR-886-5p |
| hsa-miR-590-5p | hsa-miR-142-5p | hsa-miR-I00 |
| hsa-miR-149* | hsa-miR-106b | hsa-miR-768-5p |
| hsa-miR-300 | hsa-miR-30e | hsa-miR-145 |
| hsa-miR-625* | hsa-miR-140-3p | hsa-miR-943 |
| kshv-miR-K12-3 | hsa-miR-20a | hsa-miR-371-5p |
| hsa-miR-28-5p | hsa-miR-526b* | hsa-miR-675 |
| hsa-miR-25* | hsa-miR-28-5p | hsa-miR-150 |
| ebv-miR-BHRFI-2 | hsa-miR-30c | hsa-miR-181a |

BL = Burkitt lymphoma, ABC = activated B-cell DLBCL, CLL = chronic lymphocytic lymphoma

TABLE 8

Predictor microRNAs that distinguish activated B-cell (ABC)
DLBCL from Burkitt Lymphoma and chronic lymphocytic leukemia

| ABCvsBL | ABCvsCLL |
|---|---|
| hsa-miR-182 | hsa-miR-193b |
| hsa-miR-377 | hsa-miR-99b |
| hsa-miR-660 | hsa-miR-551a |
| hsa-miR-595 | mghv-miR-MI-7-3p |
| ebv-miR-BARTI0 | hsa-miR-585 |
| hsa-miR-532-5p | hsa-miR-617 |
| hsa-miR-200c* | hsa-miR-629* |
| hsa-miR-362-3p | hsa-miR-575 |
| hsa-miR-455-3p | kshv-miR-K12-6-5p |
| hsa-miR-128 | hsa-miR-193a-5p |
| hsa-miR-21* | hsa-miR-30e |
| hsa-miR-589 | hsa-miR-296-3p |
| hsa-miR-135a* | hsa-miR-518b |
| hsa-miR-532-3p | hsa-miR-492 |
| hsa-miR-548d-5p | hsa-miR-220c |
| hsa-miR-652 | hsa-miR-326 |
| hsa-miR-150* | hsa-miR-671-5p |
| hsa-miR-330-5p | hsa-miR-340* |
| hsa-miR-339-3p | hsa-miR-150 |
| hsa-miR-502-3p | hsa-miR-193b* |

BL = Burkitt lymphoma, CLL = chronic lymphocytic lymphoma.

TABLE 9

Predictor microRNAs that distinguish Burkitt
lymphoma from chronic lymphocytic leukemia BLvsCLL hsa-miR-130b
hsa-miR-154
hsa-miR-155
hsa-miR-29b
hsa-miR-29c
hsa-miR-637
hsa-miR-658
hsa-miR-193a-5p
hsa-miR-886-5p
hsa-miR-768-5p
hsa-miR-I0I
hsa-miR-933
hsa-miR-371-5p

TABLE 9-continued

Figure 10:
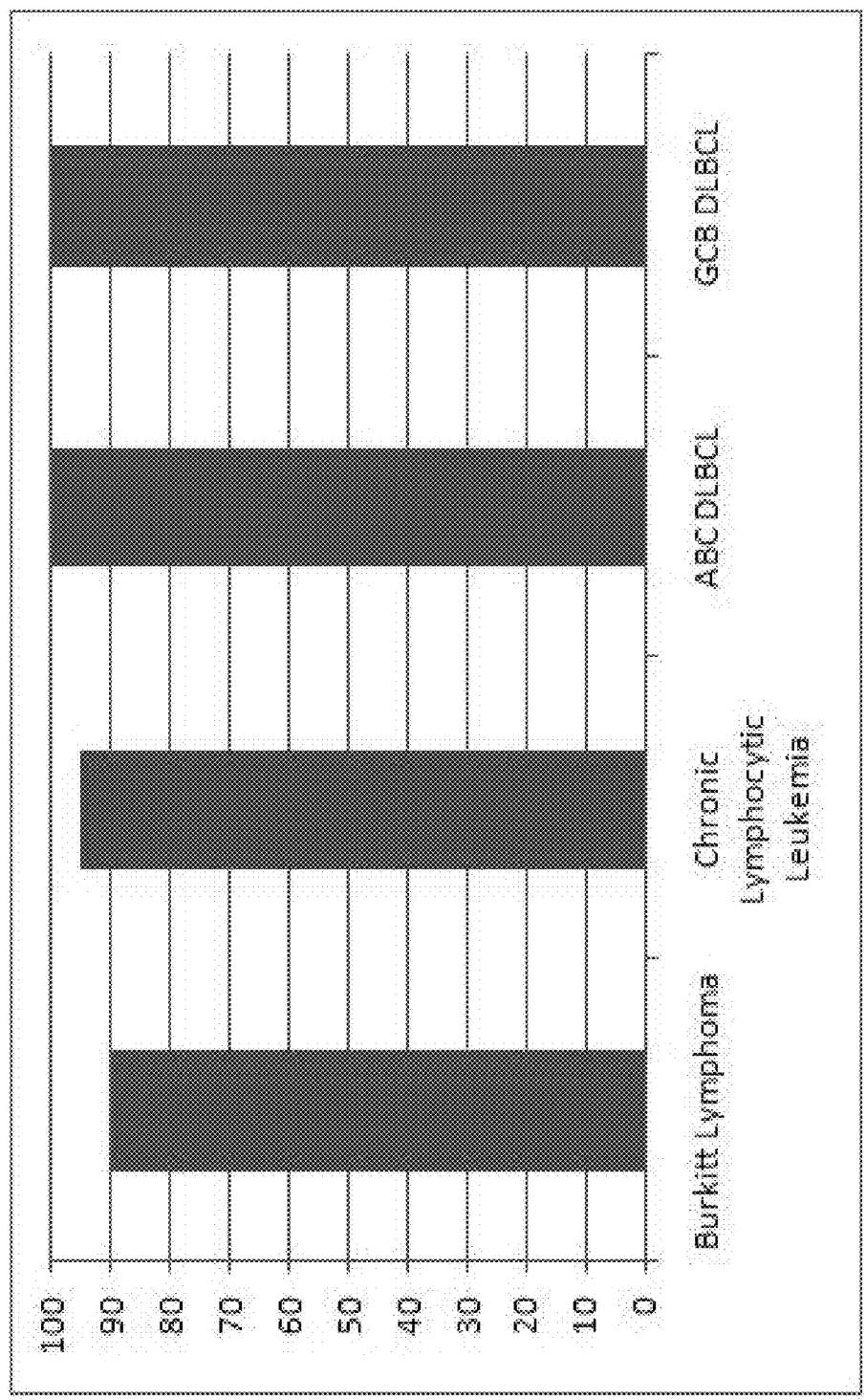
FIG. 10 shows the results of leave one out cross validation applied to the predictors for Burkitt lymphoma, chronic lymphocytic leukemia, activated B-cell diffuse large B-cell lymphoma, and germinal center B-cell DLBCL.

Predictor microRNAs that distinguish Burkitt
lymphoma from chronic lymphocytic leukemia BLvsCLL hsa-miR-675
hsa-miR-150
hsa-miR-874
hsa-miR-181a
hsa-miR-30c
ebv-miR-BHRFI-2
hsa-miR-628-3p CLL = chronic lymphocytic lymphoma We tested the performance of the predictor using leave-one-out cross-validation applied to the predictors for Burkitt lymphoma, chronic lymphocytic leukemia, activated B-cell diffuse large B-cell lymphoma, and germinal center B-cell DLBCL. For a sample prediction to be correct, it had to be classified correctly in each pair-wise comparison with all remaining entities. We found it to be over 90% accurate in the identification of each entity. See FIG. 10.

Figure 11:
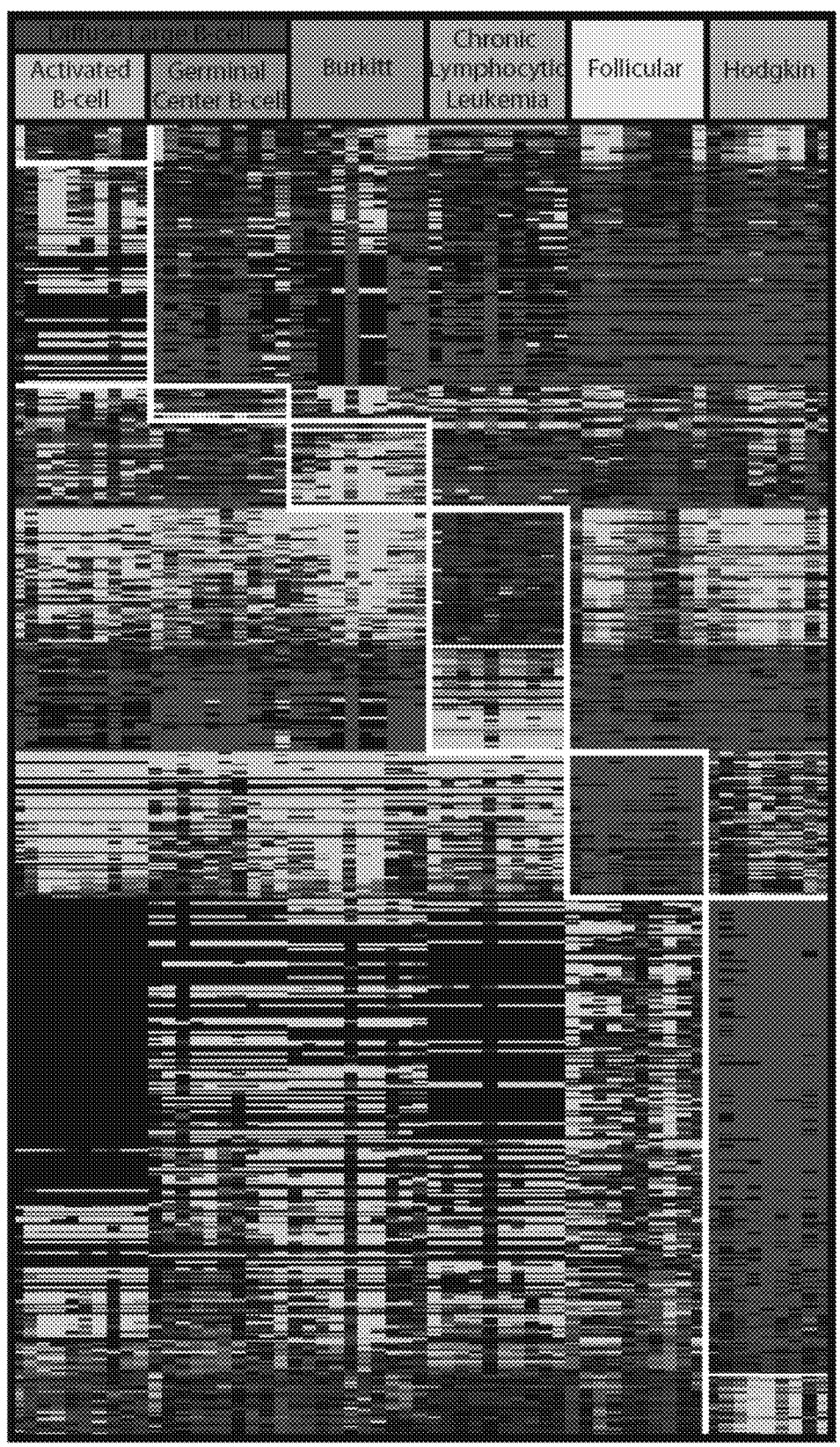
FIG. 11 shows differentially expressed miRNAs that distinguish activated B cell-like diffuse large B cell lymphoma (DLBCL), germinal center-like DLBCL (GCB DLBCL), Burkitt lymphoma, chronic lymphocytic leukemia, follicular lymphoma, and Hodgkin's lymphoma. Predictor miRNAs from each pair-wise comparison that distinguish each entity are shown in the boxes.

We next expanded the analysis to include follicular lymphoma and Hodgkin's lymphoma. We included the samples from the earlier study and we undertook miRNA profiling of the following additional samples: normal lymph nodes (N=5) and patients with germinal center B cell-like (GCB) DLBCL (N=10), activated B cell-like (ABC) DLBCL (N=10), chronic lymphocytic leukemia (N=10), Burkitt lymphoma (N=10), follicular lymphoma (N=10), and Hodgkin's lymphoma (N=9). As before, microRNA profiling revealed that each B cell malignancy type had a distinctive pattern of miRNA expression. See FIG. 11.

From that data, we identified microRNAs that can be used to distinguish each of the six B cell malignancies analyzed from the other five. Lists of those microRNAs, and whether they are expressed in high levels or low levels relative to the other 5 B cell malignancies, are shown in Tables 10 through 13. In certain embodiments, each of those microRNAs could be used to distinguish one of the six B cell malignancies from the other five. High and low in the table refer to at least a 2 fold difference when compared to other lymphomas and benign lymph nodes.

TABLE 10

Predictor microRNAs that distinguish Burkitt lymphoma, germinal center B-cell (GCB)
DLBCL, and follicular lymphoma from all other B cell malignancies in the study

| BL miRNA list | BL vs others | GCB miRNA list | GCB vs others | FL miRNA list | FL vs others |
|---|---|---|---|---|---|
| hsa-miR-106a | High | hsa-miR-93/mmu-miR-93/rno-miR-93 | High | hsa-miR-96/mmu-miR-96/rno-miR-96 | High |
| hsa-miR-17/mmu-miR-17/rno-miR-17-5p/rno-miR-17 | High | hsa-miR-886-3p | High | hsa-miR-138/mmu-miR-138/rno-miR-138 | High |
| hsa-miR-628-3p | High | hsa-miR-365/mmu-miR-365/rno-miR-365 | High | hsa-miR-342-5p/mmu-miR-342-5p/rno-miR-342-5p | High |
| hsa-miR-193a-5p | High | hsa-miR-378/mmu-miR-378/rno-miR-378 | High | | |
| hsa-miR-371-5p | High | hsa-miR-320/mmu-miR-320/rno-miR-320 | High | hsa-miR-337-3p | High |
| hsa-miR-20a/mmu-miR-20a/rno-miR-20a | High | hsa-miR-103/mmu-miR-103/rno-miR-103 | High | hsa-miR-301a/mmu-miR-301a/rno-miR-301a | High |
| hsa-miR-23a/mmu-miR-23a/rno-miR-23a | Low | hsa-miR-637 | High | hsa-miR-922 | High |
| hsa-miR-27a/mmu-miR-27a/rno-miR-27a | Low | hsa-miR-148a/mmu-miR-148a | High | hsa-miR-744/mmu-miR-744 | High |
| hsa-miR-34b/mmu-miR-34b-3p | Low | hsa-miR-199a-3p/hsa-miR-199b-3p/mmu-miR-199a-3p/mmu-miR-199b/rno-miR-199a-3p | High | hsa-miR-221* | High |
| hsa-miR-21/mmu-miR-21/rno-miR-21 | Low | | | hsa-miR-215 | High |
| hsa-miR-29a/mmu-miR-29a/rno-miR-29a | Low | hsa-miR-126*/mmu- | High | hsa-miR-197/mmu-miR-197 | High |
| | | | | hsa-miR-92b/mmu-miR-92b/rno-miR-92b | High |

TABLE 10-continued

Predictor microRNAs that distinguish Burkitt lymphoma, germinal center B-cell (GCB) DLBCL, and follicular lymphoma from all other B cell malignancies in the study

| BL miRNA list | BL vs others | GCB miRNA list | GCB vs others | FL miRNA list | FL vs others |
|---|---|---|---|---|---|
| hsa-let-7b/mmu-let-7b/rno-let-7b | Low | miR-126-5p/rno-miR-126* | | hsa-miR-218-2*/mmu-miR-218-2*/rno-miR-218* | High |
| hsa-let-7f/mmu-let-7f/rno-let-7f | Low | kshv-miR-K12-6-3p | High | | |
| hsa-miR-29b/mmu-miR-29b/rno-miR-29b | Low | hsa-miR-125a-5p/mmu-miR-125a-5p/rno-miR-125a-5p | High | hsa-miR-636 | High |
| | | | | hsa-miR-600 | High |
| | | | | kshv-miR-K12-7 | High |
| hsa-miR-549 | Low | hsa-miR-551b/mmu-miR-551b/rno-miR-551b | Low | hsa-miR-194/mmu-miR-194/rno-miR-194 | High |
| hsa-miR-374a | Low | hsa-miR-923 | Low | hsa-miR-524-5p | High |
| hsa-miR-513a-5p | | | | hsa-miR-22*/mmu-miR-22*/rno-miR-22* | High |
| hsa-miR-148a/mmu-miR-148a | Low | | | hsa-miR-34c-5p/mmu-miR-34c/rno-miR-34c | High |
| hsa-miR-223/mmu-miR-223/rno-miR-223 | Low | | | hsa-miR-151-3p | High |
| hsa-miR-138-1*/mmu-miR-138*/rno-miR-138* | Low | | | hsa-miR-425/mmu-miR-425/rno-miR-425 | High |
| | | | | ebv-miR-BART16 | High |
| hsa-miR-342-3p/mmu-miR-342-3p/rno-miR-342-3p | Low | | | hsa-miR-20b* | High |
| | | | | hsa-miR-574-3p/mmu-miR-574-3p | High |
| hsa-miR-146b-5p/mmu-miR-146b/rno-miR-146b | Low | | | hsa-miR-155* | High |
| | | | | hsa-miR-374b* | High |
| hsa-miR-195/mmu-miR-195/rno-miR-195 | Low | | | hsa-miR-497/mmu-miR-497/rno-miR-497 | High |
| hsa-miR-103/mmu-miR-103/rno-miR-103 | Low | | | hsa-miR-708/mmu-miR-708/rno-miR-708 | High |
| hsa-miR-888* | | | | hsa-miR-92a/mmu-miR-92a/rno-miR-92a | High |
| hsa-miR-363/mmu-miR-363/rno-miR-363 | Low | | | hsa-miR-361-3p | High |
| | | | | hsa-miR-513a-3p | High |
| hsa-miR-140-3p/mmu-miR-140*/rno-miR-140* | Low | | | hsa-miR-934 | High |
| | | | | hsa-miR-363*/rno-miR-363* | High |
| hsa-miR-191/mmu-miR-191/rno-miR-191 | Low | | | mghv-miR-M1-3 | High |
| | | | | hsa-miR-129* | High |
| hsa-miR-768-5p | Low | | | hsa-miR-148b/mmu-miR-148b/rno-miR-148b-3p | High |
| hsa-miR-222/mmu-miR-222/rno-miR-222 | Low | | | hsa-miR-493 | High |
| hsa-miR-668/mmu-miR-668 | Low | | | hsa-miR-151-5p/mmu-miR-151-5p/rno-miR-151 | High |
| hsa-miR-221/mmu-miR-221/rno-miR-221 | Low | | | hsa-miR-146b-3p | High |
| | | | | hsa-miR-886-5p | High |
| hsa-miR-24-1*/mmu-miR-24-1*/rno-miR-24-1* | Low | | | hsa-miR-331-3p/mmu-miR-331-3p/rno-miR-331 | High |
| | | | | hsa-miR-574-5p/mmu-miR-574-5p | High |
| hsa-miR-29c/mmu-miR-29c/rno-miR-29c | Low | | | hsa-miR-424 | High |
| hsa-miR-146a/mmu-miR-146a/rno-miR-146a | Low | | | hsa-miR-152/mmu-miR-152/rno-miR-152 | High |
| | | | | hsa-miR-302a/mmu-miR-302a | High |
| hsa-miR-154/mmu-miR-154/rno-miR-154 | Low | | | hsa-miR-181a/mmu-miR-181a/rno-miR-181a | High |
| hsa-miR-215 | Low | | | hsa-miR-509-5p | High |
| hsa-miR-487b/mmu-miR-487b/rno-miR-487b | Low | | | hsa-let-7d/mmu-let-7d/rno-let-7d | High |
| hsa-miR-155 | Low | | | hsa-miR-18b | High |
| | | | | hsa-miR-620 | High |
| | | | | hsa-miR-18a/mmu-miR-18a/rno-miR-18a | High |
| | | | | hsa-miR-298 | High |
| | | | | hsa-miR-98/mmu-miR-98/rno-miR-98 | High |
| | | | | hsa-miR-576-3p | High |
| | | | | hsa-miR-374b/mmu-miR-374b/rno-miR-374 | High |
| | | | | hsa-miR-32* | High |
| | | | | hsa-miR-302d* | High |
| | | | | ebv-miR-BART17-5p | High |

TABLE 10-continued

Predictor microRNAs that distinguish Burkitt lymphoma, germinal center B-cell (GCB) DLBCL, and follicular lymphoma from all other B cell malignancies in the study

| BL miRNA list | BL vs others | GCB miRNA list | GCB vs others | FL miRNA list | FL vs others |
|---|---|---|---|---|---|
| | | | | hsa-miR-620 | High |
| | | | | hsa-miR-665 | High |
| | | | | hsa-miR-185/mmu-miR-185/rno-miR-185 | High |
| | | | | hsa-miR-34b/mmu-miR-34b-3p | High |
| | | | | hsa-let-7e/mmu-let-7e/rno-let-7e | High |

TABLE 11

Predictor microRNAs that distinguish activated B-cell (ABC) DLBCL from all other B cell malignancies in the study

| ABC miRNA list | ABC vs others |
|---|---|
| hsa-miR-126/mmu-miR-126-3p/rno-miR-126 | High |
| hsa-miR-125b/mmu-miR-125b-5p/rno-miR-125b-5p | High |
| hsa-miR-145/mmu-miR-145/rno-miR-145 | High |
| hsa-miR-22/mmu-miR-22/rno-miR-22 | High |
| hsa-miR-21/mmu-miR-21/rno-miR-21 | High |
| hsa-miR-199a-3p/hsa-miR-199b-3p/mmu-miR-199a-3p/mmu-miR-199b/rno-miR-199a-3p | High |
| hsa-miR-24/mmu-miR-24/rno-miR-24 | High |
| hsa-miR-143/mmu-miR-143/rno-miR-143 | High |
| hsa-miR-23b/mmu-miR-23b/rno-miR-23b | High |
| hsa-miR-23a/mmu-miR-23a/rno-miR-23a | High |
| hsa-miR-142-3p/mmu-miR-142-3p/rno-miR-142-3p | High |
| hsa-let-7a/mmu-let-7a/rno-let-7a | High |
| hsa-miR-146b-5p/mmu-miR-146b/rno-miR-146b | High |
| hsa-miR-27a/mmu-miR-27a/rno-miR-27a | High |
| hsa-miR-30a/mmu-miR-30a/rno-miR-30a | High |
| hsa-miR-27b/mmu-miR-27b/rno-miR-27b | High |
| hsa-let-7c/mmu-let-7c/rno-let-7c | High |
| hsa-miR-921 | Low |
| ebv-miR-BHRF1-2 | Low |
| hsa-miR-199a-5p/mmu-miR-199a-5p/rno-miR-199a-5p | Low |
| hsa-miR-768-5p | Low |
| hsa-miR-491-3p | Low |
| hsa-miR-185/mmu-miR-185/rno-miR-185 | Low |
| ebv-miR-BART17-5p | Low |
| hsa-miR-32* | Low |
| hsa-miR-335/mmu-miR-335-5p/rno-miR-335 | Low |
| hsa-miR-149* | Low |
| hsa-miR-576-3p | Low |
| hsa-miR-214/mmu-miR-214/rno-miR-214 | Low |
| hsa-miR-184/mmu-miR-184/rno-miR-184 | Low |
| hsa-miR-520d-5p | Low |
| hsa-miR-518c* | Low |
| hsa-miR-801/mmu-miR-801 | Low |
| hsa-miR-298 | Low |
| hsa-miR-634 | Low |
| hsa-miR-583 | Low |
| hsa-miR-187* | Low |
| hsa-miR-30d/mmu-miR-30d/rno-miR-30d | Low |
| hsa-miR-129-5p/mmu-miR-129-5p/rno-miR-129 | Low |
| hsa-miR-300 | Low |
| hsa-miR-620 | Low |
| hsa-miR-130b*/mmu-miR-130b* | |
| hsa-miR-20b/mmu-miR-20b/rno-miR-20b-5p | Low |
| kshv-miR-K12-3 | Low |
| hsa-miR-28-3p/rno-miR-28* | Low |
| hsa-miR-557 | Low |
| hsa-miR-150/mmu-miR-150/rno-miR-150 | Low |
| hsa-miR-98/mmu-miR-98/rno-miR-98 | Low |
| hsa-miR-486-5p/mmu-miR-486 | Low |
| hsa-miR-518a-5p/hsa-miR-527 | Low |
| hsa-miR-302d* | Low |
| hsa-miR-516a-5p | Low |
| hsa-miR-148b/mmu-miR-148b/rno-miR-148b-3p | Low |
| hsa-miR-25* | Low |
| hsa-miR-374b/mmu-miR-374/rno-miR-374 | Low |
| hsa-miR-638 | Low |
| hsa-miR-302a/mmu-miR-302a | |
| hsa-miR-99b*/mmu-miR-99b*/rno-miR-99b* | Low |
| hsa-miR-29c*/mmu-miR-29c*/rno-miR-29c* | Low |
| hsa-miR-138/mmu-miR-138/rno-miR-138 | Low |

TABLE 11-continued

Predictor microRNAs that distinguish activated B-cell (ABC) DLBCL from all other B cell malignancies in the study

| ABC miRNA list | ABC vs others |
|---|---|
| hsa-miR-766 | Low |
| hsa-miR-488 | Low |
| hsa-miR-498 | Low |
| hsa-miR-339-5p/mmu-miR-339-5p/rno-miR-339-5p | Low |
| hsa-miR-193b* | Low |
| hsa-miR-299-5p/mmu-miR-299*/rno-miR-299 | Low |
| ebv-miR-BART8* | Low |
| hsa-miR-107/mmu-miR-107/rno-miR-107 | Low |
| hsa-miR-519e* | Low |
| hsa-miR-146b-3p | Low |
| hsa-miR-552 | Low |
| hsa-miR-509-5p | Low |
| hsa-miR-574-5p/mmu-miR-574-5p | Low |
| hsa-miR-524-5p | Low |
| mghv-miR-M1-7-5p | Low |
| hsa-miR-659 | Low |
| hcmv-miR-UL148D | Low |
| hsa-miR-92a/mmu-miR-92a/rno-miR-92a | Low |
| hsa-miR-30e*/mmu-miR-30e*/rno-miR-30e* | Low |
| hsa-miR-183*/mmu-miR-183* | Low |
| hsa-miR-144* | Low |
| hsa-miR-574-3p/mmu-miR-574-3p | Low |
| hsa-miR-889 | Low |
| hsa-miR-525-5p | Low |
| kshv-miR-K12-8 | Low |
| hsa-miR-32/mmu-miR-32/rno-miR-32 | Low |
| hsa-miR-938 | Low |
| hsa-miR-198 | Low |
| hsa-miR-186/mmu-miR-186/rno-miR-186 | Low |
| hsa-miR-18a/mmu-miR-18a/rno-miR-18a | Low |
| hsa-miR-516b | Low |
| hsa-miR-625* | Low |
| hsa-miR-551b* | Low |
| hsa-miR-885-5p | Low |
| hsa-miR-891a | Low |
| hsa-miR-340/mmu-miR-340-5p/rno-miR-340-5p | Low |
| hsa-let-7d/mmu-let-7d/rno-let-7d | Low |
| hsa-miR-151-5p/mmu-miR-151-5p/rno-miR-151 | Low |
| hsa-miR-18b | Low |
| ebv-miR-BHRF1-1 | Low |
| hsa-miR-510 | Low |
| hsa-miR-625 | Low |
| mghv-miR-M1-8 | Low |
| ebv-miR-BART19-3p | Low |
| hsa-miR-147 | Low |
| hsa-miR-28-5p/mmu-miR-28/rno-miR-28 | Low |
| ebv-miR-BART13 | Low |
| hsa-miR-25/mmu-miR-25/rno-miR-25 | Low |
| hsa-miR-519d | Low |
| hsa-miR-361-5p/mmu-miR-361/rno-miR-361 | Low |
| hsa-miR-331-3p/mmu-miR-331-3p/rno-miR-331 | Low |
| hsa-miR-423-3p/mmu-miR-423-3p/rno-miR-423 | Low |
| hsa-miR-93/mmu-miR-93/rno-miR-93 | Low |

TABLE 12

Predictor microRNAs that distinguish chronic lymphocytic leukemia from all other B cell malignancies in the study

| CLL miRNA list | CLL vs others |
|---|---|
| hsa-miR-30e*/mmu-miR-30e*/rno-miR-30e* | High |
| hsa-miR-32/mmu-miR-32/rno-miR-32 | High |
| hsa-let-7g/mmu-let-7g | High |
| hsa-miR-186/mmu-miR-186/rno-miR-186 | High |
| hsa-miR-140-5p/mmu-miR-140/rno-miR-140 | High |
| hsa-miR-196a*/mmu-miR-196a*/rno-miR-196a* | High |
| hsa-miR-487b/mmu-miR-487b/rno-miR-487b | High |
| hsa-miR-150/mmu-miR-150/rno-miR-150 | High |
| hsa-miR-147 | High |
| hsa-miR-486-5p/mmu-miR-486 | High |
| hsa-miR-144* | High |
| hsa-miR-154/mmu-miR-154/rno-miR-154 | High |
| hsa-miR-28-5p/mmu-miR-28/rno-miR-28 | High |
| hsa-miR-299-5p/mmu-miR-299*/rno-miR-299 | High |
| hsa-miR-33a/mmu-miR-33/rno-miR-33 | High |
| hsa-miR-363/mmu-miR-363/rno-miR-363 | High |

TABLE 12-continued

Predictor microRNAs that distinguish chronic lymphocytic leukemia from all other B cell malignancies in the study

| CLL miRNA list | CLL vs others |
|---|---|
| hsa-miR-891a | High |
| hsa-miR-768-5p | High |
| hsa-miR-361-5p/mmu-miR-361/rno-miR-361 | High |
| hsa-miR-519d | High |
| hsa-miR-335/mmu-miR-335-5p/rno-miR-335 | High |
| hsa-miR-668/mmu-miR-668 | High |
| hsa-let-7f/mmu-let-7f/rno-let-7f | High |
| hsa-miR-24-1*/mmu-miR-24-1*/rno-miR-24-1* | High |
| hsa-miR-223/mmu-miR-223/rno-miR-223 | High |
| hsa-miR-140-3p/mmu-miR-140*/rno-miR-140* | High |
| hsa-miR-144/mmu-miR-144/rno-miR-144 | High |
| hsa-miR-638 | High |
| hsa-miR-30d/mmu-miR-30d/rno-miR-30d | High |
| hsa-miR-423-3p/mmu-miR-423-3p/rno-miR-423 | High |
| hsa-miR-155 | High |
| hsa-miR-101/mmu-miR-101a/rno-miR-101a | High |
| hsa-miR-20b/mmu-miR-20b/rno-miR-20b-5p | High |
| hsa-miR-374a | High |
| hsa-miR-25/mmu-miR-25/rno-miR-25 | High |
| hsa-miR-199a-5p/mmu-miR-199a-5p/rno-miR-199a-5p | High |
| hsa-miR-649 | High |
| hsa-miR-191/mmu-miR-191/rno-miR-191 | High |
| hsa-miR-30e/mmu-miR-30e/rno-miR-30e | High |
| hsa-miR-107/mmu-miR-107/rno-miR-107 | High |
| hsa-miR-93/mmu-miR-93/rno-miR-93 | High |
| hsa-miR-29c/mmu-miR-29c/rno-miR-29c | High |
| hsa-miR-541* | High |
| hsa-miR-888* | High |
| hsa-miR-549 | High |
| hsa-miR-19a/rno-miR-19a | High |
| hsa-miR-342-3p/mmu-miR-342-3p/rno-miR-342-3p | High |
| hsa-miR-142-5p/mmu-miR-142-5p/rno-miR-142-5p | High |
| hsa-miR-801/mmu-miR-801 | High |
| hsa-let-7i/mmu-let-7i/rno-let-7i | High |
| hsa-miR-26a/mmu-miR-26a/rno-miR-26a | High |
| hsa-miR-15a/mmu-miR-15a | High |
| hsa-miR-195/mmu-miR-195/rno-miR-195 | High |
| hsa-miR-106b/mmu-miR-106b/rno-miR-106b | High |
| hsa-miR-26b/mmu-miR-26b/rno-miR-26b | High |
| hsa-miR-15b/mmu-miR-15b/rno-miR-15b | High |
| hsa-miR-222/mmu-miR-222/rno-miR-222 | High |
| hsa-miR-185/mmu-miR-185/rno-miR-185 | High |
| hsa-miR-550 | High |
| hsa-let-7e/mmu-let-7e/rno-let-7e | Low |
| hsa-miR-24/mmu-miR-24/rno-miR-24 | Low |
| hsa-miR-30c-2*/mmu-miR-30c-2*/rno-miR-30c-2* | Low |
| hsa-miR-765 | Low |
| mghv-miR-M1-4 | Low |
| hsa-miR-933 | Low |
| hsa-miR-620 | Low |
| hsa-miR-30b* | Low |
| hsa-miR-658 | Low |
| hsa-miR-10a/mmu-miR-10a/rno-miR-10a-5p | Low |
| hsa-miR-665 | Low |
| hsa-miR-185* | Low |
| hsa-miR-503 | Low |
| hsa-miR-126*/mmu-miR-126-5p/rno-miR-126* | Low |
| hsa-miR-10b/mmu-miR-10b/rno-miR-10b | Low |
| hsa-miR-628-3p | Low |
| hsa-miR-422a | Low |
| hsa-miR-193a-5p | Low |
| hsa-miR-143/mmu-miR-143/rno-miR-143 | Low |
| hsa-miR-371-5p | Low |
| hsa-miR-100/mmu-miR-100/rno-miR-100 | Low |
| hsa-miR-365/mmu-miR-365/rno-miR-365 | Low |
| hsa-miR-145/mmu-miR-145/rno-miR-145 | Low |
| kshv-miR-K12-6-3p | Low |
| ebv-miR-BART6-3p | Low |
| hsa-miR-220c | Low |
| hsa-miR-519c-5p/hsa-miR-519b-5p/hsa-miR-523*/hsa-miR-518e*/hsa-miR-522*/hsa-miR-519a* | Low |
| hsa-miR-130a/mmu-miR-130a/rno-miR-130a | Low |
| hsa-miR-424 | Low |
| hsa-miR-483-5p | Low |

TABLE 12-continued

Predictor microRNAs that distinguish chronic lymphocytic leukemia from all other B cell malignancies in the study

| CLL miRNA list | CLL vs others |
|---|---|
| hsa-miR-193b | Low |
| hsa-miR-637 | Low |
| hsa-miR-920 | Low |
| hsa-miR-488 | Low |
| ebv-miR-BHRF1-2 | Low |
| hsa-miR-526b | Low |
| hsa-miR-126/mmu-miR-126-3p/rno-miR-126 | Low |
| hsa-miR-943 | Low |
| hsa-miR-199a-3p/hsa-miR-199b-3p/mmu-miR-199a-3p/mmu-miR-199b/rno-miR-199a-3p | Low |
| mghv-miR-M1-3 | Low |
| hsa-miR-934 | Low |
| hsa-miR-886-5p | Low |
| hsa-miR-200b*/mmu-miR-200b* | Low |
| hsa-miR-485-3p/mmu-miR-485* | Low |
| hsa-miR-181a/mmu-miR-181a/rno-miR-181a | Low |
| hsa-miR-125b/mmu-miR-125b-5p/rno-miR-125b-5p | Low |

TABLE 13

Predictor microRNAs that distinguish Hodgkin's lympoma from all other B cell malignancies in the study

| HL miRNA list | HL vs others |
|---|---|
| hsa-miR-338-5p/mmu-miR-338-5p/rno-miR-338* | High |
| hsa-miR-433/mmu-miR-433/rno-miR-433 | High |
| hsa-miR-552 | High |
| hsa-miR-202 | High |
| hsa-miR-299-3p | High |
| hsa-miR-509-3-5p | High |
| hsa-miR-490-5p | High |
| hsa-miR-508-5p | High |
| hsa-miR-181a-2* | High |
| hsa-miR-663 | High |
| hsa-miR-326/mmu-miR-326/rno-miR-326 | High |
| hsa-miR-542-3p/mmu-miR-542-3p/rno-miR-542-3p | High |
| hsa-miR-492 | High |
| hsa-miR-584 | High |
| hsa-miR-654-5p | High |
| ebv-miR-BART20-3p | High |
| hsa-miR-542-5p/mmu-miR-542-5p/rno-miR-542-5p | High |
| ebv-miR-BART9* | High |
| hsa-miR-124/mmu-miR-124/rno-miR-124 | High |
| hsa-miR-551a | High |
| hsa-miR-208a/mmu-miR-208a/rno-miR-208 | High |
| hsa-miR-220b | High |
| hsa-miR-615-3p/mmu-miR-615-3p | High |
| hsa-miR-135a*/mmu-miR-135a* | High |
| hiv1-miR-H1 | High |
| hsa-miR-124*/mmu-miR-124*/rno-miR-124* | High |
| hsa-miR-502-5p | High |
| hsa-miR-92b* | High |
| hsa-miR-518a-3p | High |
| hsa-miR-377* | High |
| hsa-miR-125a-3p/mmu-miR-125a-3p/rno-miR-125a-3p | High |
| hsa-miR-30c-1*/mmu-miR-30c-1*/rno-miR-30c-1* | High |
| hsa-miR-650 | High |
| hsa-miR-629 | High |
| hsa-miR-296-3p/mmu-miR-296-3p/rno-miR-296 | High |
| hsa-miR-425*/mmu-miR-425* | High |
| hsa-miR-514 | High |
| hsa-miR-519e | High |
| hsa-miR-938 | High |
| hsa-miR-340*/mmu-miR-340-3p/rno-miR-340-3p | High |
| hsa-miR-657 | High |
| hsa-miR-9*/mmu-miR-9*/rno-miR-9* | High |
| ebv-miR-BART7* | High |
| hsa-miR-612 | High |
| hsa-miR-640 | High |
| hsa-miR-623 | High |
| hsa-miR-99b*/mmu-miR-99b*/rno-miR-99b* | High |
| hsa-miR-645 | High |
| hsa-miR-484/mmu-miR-484/rno-miR-484 | High |
| hsa-miR-376a* | High |
| hsa-miR-345 | High |
| hsa-miR-586 | High |
| hsa-miR-622 | High |
| hsa-miR-206/mmu-miR-206/rno-miR-206 | High |
| hcmv-miR-US25-1* | High |
| hsa-miR-302c* | High |
| hsa-miR-106b*/mmu-miR-106b*/rno-miR-106b* | High |
| hsa-miR-500 | High |
| hsa-miR-890 | High |
| hsa-miR-10a*/mmu-miR-10a*/rno-miR-10a-3p | High |
| kshv-miR-K12-1 | High |
| hsa-miR-629* | High |
| hsa-miR-193b* | High |
| ebv-miR-BHRF1-3 | High |
| hsa-miR-183/mmu-miR-183/rno-miR-183 | High |
| hsa-let-7b*/mmu-let-7b*/rno-let-7b* | High |
| hsa-miR-409-5p/mmu-miR-409-5p/rno-miR-409-5p | High |

TABLE 13-continued

Predictor microRNAs that distinguish Hodgkin's lympoma from all other B cell malignancies in the study

| HL miRNA list | HL vs others |
|---|---|
| hsa-miR-585 | High |
| hsa-miR-526b* | High |
| hsa-miR-337-3p | High |
| hsa-miR-212/mmu-miR-212/rno-miR-212 | High |
| hsa-miR-548b-3p | High |
| hcmv-miR-UL112 | High |
| hsa-miR-601 | High |
| hsa-let-7d*/mmu-let-7d*/rno-let-7d* | High |
| hsa-miR-181b/mmu-miR-181b/rno-miR-181b | High |
| hsa-miR-195* | High |
| kshv-miR-K12-5 | High |
| hsa-miR-500* | High |
| hsa-miR-24-2*/mmu-miR-24-2*/rno-miR-24-2* | High |
| hsa-miR-382/mmu-miR-382/rno-miR-382 | High |
| ebv-miR-BART8* | High |
| hsa-miR-125b-2*/rno-miR-125b* | High |
| hsa-miR-194* | High |
| hsa-miR-297/mmu-miR-297a | High |
| hsa-miR-610 | High |
| hsa-miR-575 | High |
| hsa-miR-21* | High |
| hsa-miR-936 | High |
| kshv-miR-K12-6-5p | High |
| hsa-miR-553 | High |
| hsa-miR-652/mmu-miR-652/rno-miR-652 | High |
| hsa-miR-877/mmu-miR-877/rno-miR-877 | High |
| hsa-miR-526a/hsa-miR-520c-5p/hsa-miR-518d-5p | High |
| hsa-miR-122* | High |
| hsa-miR-576-5p | High |
| mghv-miR-M1-6 | High |
| hsa-miR-551b* | High |
| hsa-miR-125b-1*/mmu-miR-125b-3p/rno-miR-125b-3p | High |
| hsa-miR-137/mmu-miR-137/rno-miR-137 | High |
| ebv-miR-BART18-3p | High |
| hsa-miR-452 | High |
| hsa-miR-23a*/rno-miR-23a* | High |
| hsa-miR-617 | High |
| hsa-miR-550* | High |
| hsa-miR-557 | High |
| hsa-miR-331-5p/mmu-miR-331-5p | High |
| hsa-miR-296-5p/mmu-miR-296-5p/rno-miR-296* | High |
| mghv-miR-M1-2 | High |
| ebv-miR-BART6-3p | High |
| hsa-miR-518b | High |
| hsa-miR-99b/mmu-miR-99b/rno-miR-99b | High |
| hsa-miR-525-5p | High |
| hsa-miR-589 | High |
| hsa-miR-7-2* | High |
| hsa-miR-490-3p/mmu-miR-490 | High |
| hsa-miR-150*/mmu-miR-150* | High |
| hsa-miR-17*/rno-miR-17-3p | High |
| hsa-miR-509-3p | High |
| ebv-miR-BHRF1-1 | High |
| hsa-miR-183*/mmu-miR-183* | High |
| hsa-miR-635 | High |
| hsa-miR-130b/mmu-miR-130b/rno-miR-130b | High |
| mghv-miR-M1-8 | High |
| hsa-miR-887 | High |
| hsa-miR-210/mmu-miR-210/rno-miR-210 | High |
| hsa-miR-766 | High |
| hsa-miR-671-5p/mmu-miR-671-5p | High |
| hsa-miR-659 | High |
| hsa-miR-330-5p/mmu-miR-330/rno-miR-330 | High |
| hsa-miR-323-3p/mmu-miR-323-3p/rno-miR-323 | High |
| ebv-miR-BART13 | High |
| ebv-miR-BART5 | High |
| hsa-miR-602 | High |
| hcmv-miR-UL148D | High |
| hsa-miR-373* | High |
| hsa-miR-526b | High |
| hsa-miR-328/mmu-miR-328/rno-miR-328 | High |
| hsa-miR-874/mmu-miR-874/rno-miR-874 | High |
| ebv-miR-BART19-3p | High |
| hsa-miR-595 | High |
| hsa-miR-889 | High |
| mghv-miR-M1-7-5p | High |
| hsa-miR-483-5p | High |
| hsa-miR-487b/mmu-miR-487b/rno-miR-487b | High |
| hsa-miR-675 | High |
| hsa-miR-220c | High |
| mghv-miR-M1-7-3p | High |
| hsa-miR-485-3p/mmu-miR-485* | High |
| hsa-miR-198 | High |
| hsa-miR-483-3p | High |
| hcmv-miR-UL70-3p | High |
| hsa-miR-149/mmu-miR-149 | High |
| hsa-miR-516a-5p | High |
| hsa-miR-145*/mmu-miR-145* | High |
| hsa-miR-656 | High |
| hsa-miR-502-3p | High |
| hsa-miR-29c*/mmu-miR-29c*/rno-miR-29c* | High |
| hsa-miR-937 | High |

TABLE 13-continued

Predictor microRNAs that distinguish Hodgkin's lympoma from all other B cell malignancies in the study

| HL miRNA list | HL vs others |
|---|---|
| hsa-miR-515-5p | High |
| hsa-miR-153/mmu-miR-153/rno-miR-153 | High |
| hsa-miR-519e* | High |
| hsa-miR-128/mmu-miR-128/rno-miR-128 | High |
| hsa-miR-516b | High |
| hsa-miR-532-5p/mmu-miR-532-5p/rno-miR-532-5p | High |
| kshv-miR-K12-8 | High |
| hsa-miR-455-3p | High |
| hsa-miR-27a*/mmu-miR-27a*/rno-miR-27a* | High |
| hsa-miR-510 | High |
| hsa-miR-505/rno-miR-505 | High |
| hsa-miR-187* | High |
| hsa-miR-498 | High |
| hsa-miR-625 | High |
| hsa-miR-129-5p/mmu-miR-129-5p/rno-miR-129 | High |
| ebv-miR-BHRF1-2 | High |
| hsa-miR-143* | High |
| kshv-miR-K12-3 | High |
| hsa-miR-660 | High |
| hsa-miR-25* | High |
| hsa-miR-29a*/mmu-miR-29a*/rno-miR-29a* | High |
| hsa-miR-422a | High |
| hsa-miR-518a-5p/hsa-miR-527 | High |
| hsa-miR-519c-5p/hsa-miR-519b-5p/hsa-miR-523*/hsa-miR-518e*/hsa-miR-522*/hsa-miR-519a* | High |
| hsa-miR-28-3p/rno-miR-28* | High |
| hsa-miR-300 | High |
| hsa-miR-130a/mmu-miR-130a/rno-miR-130a | High |
| hsa-miR-583 | High |
| hsa-miR-149* | High |
| hsa-miR-184/mmu-miR-184/rno-miR-184 | High |
| hsa-miR-625* | High |
| hsa-miR-99a/mmu-miR-99a/rno-miR-99a | High |
| hsa-miR-199b-5p | High |
| hsa-miR-513a-5p | High |
| hsa-miR-494/mmu-miR-494/rno-miR-494 | High |
| mghv-miR-M1-4 | High |
| hsa-miR-634 | High |
| hsa-miR-923 | High |
| hsa-miR-503 | High |
| ebv-miR-BART2-3p | High |
| hsa-miR-520d-5p | High |
| hsa-miR-30b* | High |
| hsa-miR-30c-2*/mmu-miR-30c-2*/rno-miR-30c-2* | High |
| hsa-miR-658 | High |
| hsa-miR-921 | High |
| hsa-miR-423-5p/mmu-miR-423-5p | High |
| hsa-miR-933 | High |
| hsa-miR-23b/mmu-miR-23b/rno-miR-23b | Low |
| hsa-miR-27b/mmu-miR-27b/rno-miR-27b | Low |
| hsa-miR-550 | Low |
| hsa-let-7a/mmu-let-7a/rno-let-7a | Low |
| hsa-miR-24/mmu-miR-24/rno-miR-24 | Low |
| hsa-miR-451/mmu-miR-451/rno-miR-451 | Low |
| hsa-miR-30a/mmu-miR-30a/rno-miR-30a | Low |
| hsa-miR-20b/mmu-miR-20b/rno-miR-20b-5p | Low |
| hsa-miR-26a/mmu-miR-26a/rno-miR-26a | Low |
| hsa-miR-26b/mmu-miR-26b/rno-miR-26b | Low |
| hsa-miR-101a/mmu-miR-101a/rno-miR-101a | Low |
| hsa-miR-106b/mmu-miR-106b/rno-miR-106b | Low |
| hsa-miR-16/mmu-miR-16/rno-miR-16 | Low |
| hsa-miR-29b/mmu-miR-29b/rno-miR-29b | Low |
| hsa-miR-768-3p | Low |
| hsa-miR-30e/mmu-miR-30e/rno-miR-30e | Low |
| hsa-miR-106a | Low |
| hsa-miR-142-5p/mmu-miR-142-5p/rno-miR-142-5p | Low |
| hsa-miR-144/mmu-miR-144/rno-miR-144 | Low |
| hsa-miR-17/mmu-miR-17/rno-miR-17-5p/rno-miR-17 | Low |
| hsa-miR-15b/mmu-miR-15b/rno-miR-15b | Low |
| hsa-miR-30c/mmu-miR-30c/rno-miR-30c | Low |
| hsa-miR-142-3p/mmu-miR-142-3p/rno-miR-142-3p | Low |
| hsa-miR-20a/mmu-miR-20a/rno-miR-20a | Low |
| hsa-miR-30b/mmu-miR-30b/rno-miR-30b-5p | Low |
| hsa-miR-19a/mmu-miR-19a/rno-miR-19a | Low |
| hsa-miR-19b/mmu-miR-19b/rno-miR-19b | Low |

From the data in Tables 10 through 13, we identified subsets of microRNAs that are sufficient to distinguish each of the six B cell malignancies from the other five. We selected only microRNAs that are expressed more highly in the selected B cell malignancy. Those microRNAs are listed in Tables 14 and 15. In certain embodiments, each of the microRNAs listed in Tables 14 and 15 can be used to distinguish one B cell malignancy from the other five.

TABLE 14

Predictor microRNAs that distinguish activated B-cell (ABC) DLBCL, germinal center B-cell like (GCB) DLBCL, and Burkitt lymphoma

| ABC High | GCB High | BL High |
|---|---|---|
| hsa-miR-22/mmu-miR-22/rno-miR-22 | hsa-miR-93/mmu-miR-93/rno-miR-93 | hsa-miR-628-3p |
| hsa-miR-21/mmu-miR-21/rno-miR-21 | hsa-miR-103/mmu-miR-103/rno-miR-103 | |

TABLE 14-continued

Predictor microRNAs that distinguish activated B-cell (ABC) DLBCL, germinal center B-cell like (GCB) DLBCL, and Burkitt lymphoma

| ABC High | GCB High | BL High |
|---|---|---|
| hsa-miR-24/mmu-miR-24/rno-miR-24 | hsa-miR-320/mmu-miR-320/rno-miR-320 | |
| hsa-miR-23b/mmu-miR-23b/rno-miR-23b | hsa-miR-125a-5p/mmu-miR-125a-5p/rno-miR-125a-5p | |
| hsa-miR-23a/mmu-miR-23a/rno-miR-23a | | |
| hsa-let-7a/mmu-let-7a/rno-let-7a | | |
| hsa-let-7c/mmu-let-7c/rno-let-7c | | |

TABLE 15

Predictor microRNAs that distinguish chronic lymphocytic leukemia, follicular lymphoma, and Hodgkin's lymphoma

| CLL High | FL High | HL High |
|---|---|---|
| hsa-miR-32/mmu-miR-32/rno-miR-32 | hsa-miR-152/mmu-miR-152/rno-miR-152 | hsa-miR-498 |
| hsa-miR-150/mmu-miR-150/rno-miR-150 | hsa-miR-885-5p | hsa-miR-525-5p |
| hsa-miR-140-5p/mmu-miR-140/rno-miR-140 | hsv1-miR-H1 | hsa-miR-551b* |
| hsa-let-7g/mmu-let-7g | hsa-miR-548d-5p | hsa-miR-340*/mmu-miR-340-3p/rno-miR-340-3p |
| hsa-miR-154/mmu-miR-154/rno-miR-154 | hsa-miR-488 | hsa-miR-494/mmu-miR-494/rno-miR-494 |
| hsa-miR-486-5p/mmu-miR-486 | ebv-miR-BART16 | hsa-miR-183*/mmu-miR-183* |
| hsa-miR-101/mmu-miR-101a/rno-miR-101a | hsa-miR-22*/mmu-miR-22*/rno-miR-22* | hsa-miR-659 |
| hsa-miR-30e/mmu-miR-30e/rno-miR-30e | hsa-miR-513a-3p | hsa-miR-193b* |
| hsa-miR-768-5p | hsa-miR-708/mmu-miR-708/rno-miR-708 | hsa-miR-766 |
| hsa-miR-363/mmu-miR-363/rno-miR-363 | hsa-miR-425/mmu-miR-425/rno-miR-425 | hsa-miR-516a-5p |
| hsa-miR-668/mmu-miR-668 | hsa-miR-337-3p | hsa-miR-125b-1*/mmu-miR-125b-3p/rno-miR-125b-3p |
| hsa-miR-147 | ebv-miR-BART17-5p | ebv-miR-BART6-3p |
| hsa-miR-196a*/mmu-miR-196a*/rno-miR-196a* | hsa-miR-221* | ebv-miR-BART8* |
| hsa-miR-142-5p/mmu-miR-142-5p/rno-miR-142-5p | hsa-miR-92b/mmu-miR-92b/rno-miR-92b | hsa-miR-509-3-5p |
| hsa-miR-199a-5p/mmu-miR-199a-5p/rno-miR-199a-5p | hsa-miR-197/mmu-miR-197 | hsa-miR-602 |
| hsa-miR-24-1*/mmu-miR-24-1*/rno-miR-24-1* | hsa-miR-32* | ebv-miR-BHRF1-1 |
| hsa-miR-891a | hsa-miR-342-5p/mmu-miR-342-5p/rno-miR-342-5p | mghv-miR-M1-2 |
| hsa-miR-550 | hsa-miR-524-5p | hsa-miR-145*/mmu-miR-145* |
| hsa-miR-801/mmu-miR-801 | hsa-miR-34c-5p/mmu-miR-34c/rno-miR-34c | hsa-miR-296-5p/mmu-miR-296-5p/rno-miR-296* |
| hsa-miR-549 | hsa-let-7e/mmu-let-7e/rno-let-7e | hsa-miR-17*/rno-miR-17-3p |
| hsa-miR-888* | hsa-miR-151-3p | hsa-miR-452 |
| | hsa-miR-744/mmu-miR-744 | hsa-miR-326/mmu-miR-326/rno-miR-326 |
| | hsa-miR-574-3p/mmu-miR-574-3p | hsa-miR-652/mmu-miR-652/rno-miR-652 |
| | hsa-miR-600 | hsa-miR-623 |
| | hsa-miR-20b* | hsa-miR-194* |
| | hsa-miR-194/mmu-miR-194/rno-miR-194 | hsa-miR-125a-3p/mmu-miR-125a-3p/rno-miR-125a-3p |
| | hsa-miR-363*/rno-miR-363* | hsa-miR-10a*/mmu-miR-10a*/rno-miR-10a-3p |
| | hsa-miR-155* | hsa-miR-519e |
| | hsa-miR-34b/mmu-miR-34b-3p | hsa-miR-502-5p |
| | hsa-miR-922 | hsa-miR-124*/mmu-miR-124*/rno-miR-124* |
| | hsa-miR-497/mmu-miR-497/rno-miR-497 | hsa-miR-345 |
| | hsa-miR-493 | hsa-miR-584 |
| | hsa-miR-138/mmu-miR-138/rno-miR-138 | hsa-miR-650 |
| | hsa-miR-215 | hsa-miR-202 |
| | hsa-miR-302a/mmu-miR-302a | hsa-miR-548b-3p |
| | hsa-miR-96/mmu-miR-96/rno-miR-96 | hsa-miR-492 |
| | hsa-miR-218-2*/mmu-miR-218-2*/rno-miR-218* | hsa-miR-135a*/mmu-miR-135a* |
| | kshv-miR-K12-7 | ebv-miR-BART20-3p |
| | | hsa-miR-586 |
| | | hsa-miR-338-5p/mmu-miR-338-5p/rno-miR-338* |
| | | hsa-miR-92b* |
| | | hiv1-miR-H1 |

TABLE 15-continued

Predictor microRNAs that distinguish chromic lymphocytic leukemia, follicular lymphoma, and Hodgkin's lymphoma

| CLL High | FL High | HL High |
|---|---|---|
| | hsa-miR-301a/mmu-miR-301a/rno-miR-301a | hsa-miR-508-5p<br>hsa-miR-542-5p/mmu-miR-542-5p/rno-miR-542-5p<br>hsa-miR-490-5p<br>hsa-miR-663<br>hsa-miR-433/mmu-miR-433/rno-miR-433 |

Finally, we identified sets of microRNAs that can distinguish between each pair of B cell malignancies in the study. Lists of those microRNAs are shown in Appendix B, Tables 16 to 30. In certain embodiments, each of the listed microRNAs is sufficient to distinguish between the two B cell malignancies listed in the table description.

The consistent expression of a number of miRNAs in a diverse set of B cell malignances suggests a role for miRNAs in the maintenance of tumor phenotype. Assays for stage-specific B cell markers such as BCL6, a marker for GC cells, are essential in the clinical diagnosis of B cell malignancies. Our data suggest that stage-specific biology in B cell malignancies is retained at the miRNA level. Recent work has demonstrated the utility of gene expression profiling in reliably distinguishing closely related B cell malignancies. See Hummel et al. *N Engl J Med.* 2006; 354:2419-2430; Dave et al. *N Engl J Med.* 2006; 354:2431-2442. However, clinical translation of gene expression profiling has proved to be difficult because of the need for freshly frozen tissue. Since intact miRNAs can be isolated from tissues preserved using standard methods (see, e.g., Doleshal et al. *J Mol Diagn.* 2008; 10:203-211; Xi et al. *Rna.* 2007; 13:1668-1674), diagnostic methods based upon miRNA profiles could be fairly easy to translate to clinical use.

Interestingly, in contrast to a previous study (Lu et al. *Nature* 2005; 435:834-838), we did not note a decrease in the expression of the total number or overall expression levels of miRNAs in B cell malignancies compared to normal lymph nodes. Although B cell malignancies maintain the expression of a number of stage-specific miRNAs, their miRNA expression patterns are clearly deranged compared to normal lymph nodes. The consequences of altered miRNA expression in B cell tumors would be important to explore in future studies.

In conclusion, our study demonstrates that mature B cell subsets have distinct patterns of microRNA expression, suggesting a role for miRNAs in B cell differentiation. We provide experimental evidence that transcription factors such as LM02 and PRDMI are direct targets of differentially expressed miRNAs. B cell malignancies demonstrate a distinct pattern of miRNA expression that could be useful in distinguishing morphologically identical subtypes of these tumors. The conserved expression of stage-specific microRNAs in normal and malignant B cells suggests a role for microRNAs in the maintenance of the mature B cell phenotype.

Example 6

Differential Expression of miRNAs in ABC DLBCL Vs. GBC DLBCL Malignancies

As discussed above, microRNAs have shown promise as biomarkers in a number of malignancies. Diffuse large B cell lymphoma (DLBCL) is the most common form of lymphoma and is known to comprise at least 2 molecularly distinct subgroups with different responses to standard therapy. These two distinct subgroups are typically identified as ABC DLBCL and GC (or GCB) DLBCL.

However, the current methods used to distinguish GCB from non GCB DLBCL are limited fashion and can yield inconsistent results. While gene expression profiling remains the gold standard for distinguishing these 2 molecular subgroups it is not routinely performed in clinical laboratories. In an effort to expand and improve the existing analytical options we sought to develop microRNA-based assays. We created RNA libraries from 31 different samples and performed deep sequencing analysis to identify the present miRNAs.

Small RNA Library Creation and Deep Sequencing

Total RNA was extracted from the 31 samples using the phenol-chloroform method to preserve microRNAs, using Ambion reagents. Total RNA (typically 5 µg) from each sample was run on denaturing polyacrylamide-urea gels. The ~17-25 nucleotide RNAs were excised from the gel, ligated to sequencing adaptors on both ends and reverse transcribed. The resulting cDNA library was PCR-amplified for 15 cycles and gel purified on 6% acrylamide gel. The gel-purified amplicon quality and quantity were analyzed on a 6% acrylamide gel relative to oligonucleotides of known concentration and size. 120 µl of 1-4 pM library were loaded on to the Illumina cluster station, where DNA molecules were attached to high-density universal adaptors in the flow cells and amplified. The DNA clusters generated via this process were sequenced with sequencing-by-synthesis technology, where successive high-resolution images of the four-color fluorescence excitation dependent on the base incorporated during each cycle were captured. Sequencing reads were generated for each of the 31 samples and base calls were rendered using Illumina software. All the primary sequencing data and gene expression data is publicly available through the GEO archive through accession GSE22898.

The small RNA libraries from the 31 samples which were subjected to massively parallel, high-throughput sequencing using the Illumina platform generated a total of 328 million separate reads. Our approach to analyzing the sequences and discovering microRNAs broadly follows a previously described method (see, Zheng, Q., et al. GOEAST: a web-based software toolkit for Gene Ontology enrichment analysis, *Nucleic acids Res.* 2008; 36 (Web Server issue: W358-363). All bioinformatics analyses were performed using a cluster of 1024 Linux computer nodes. Preprocessing was carried out using locally written Shell and Perl scripts.

From the raw sequences generated by high-throughput sequencing, the 3'- and 5'-adaptor sequences were trimmed. Low quality sequences were identified as those sequencing reads that contained stretches of consecutive identical bases or uncalled nucleotides (N) in the first 12 bases and sequencing reads shorter than 17 nucleotides. To minimize redundancy, reads were initially curtailed to the first 22 nucleotides and identical sequences were represented with a single fasta entry for analysis. Each unique sequence was mapped to the reference genome (Ensembl, build 50) and reads were filtered such that only perfect alignments (full length, 100% identity) were retained. Reads that aligned to more than five positions in the genome and reads that overlapped with the UCSC RNA genes were identified and excluded from microRNA analysis.

Identification and Analysis of the Captured miRNA Sequences

Sequences that occurred 20 or more times in at least one sample were consolidated and annotated for the 31 samples. Genomic loci that overlapped with microRNAs described in miRBase (version 13) were identified as known microRNAs (see Table 31). The remaining genomic loci were identified as encoding candidate novel microRNAs (see Table 32).

The vast majority (96%) of the candidate novel microRNAs were found in more than one sample, with only a small minority of microRNAs were expressed exclusively in a specific B cell subset or malignancy. Many of the microRNAs that we identified in normal and malignant B cells were expressed at ten-fold or higher levels in these non B cell cases. These findings suggest that the microRNAs we have identified are broadly expressed and may have roles in a number of diverse tissue types.

miRNA Profiling Using Real-time PCR miRNA expression profiling was conducted using the Applied Biosystems 384-well multiplexed real-time PCR assay using 400 ng of total RNA. Eight reactions, each containing 50 ng of RNA and a multiplex looped primer pool with endogenous small nucleolar (sno)-RNA controls, were used to reverse-transcribe the miRNAs in parallel fashion (see Tables 33 and 34 for primers). The completed reactions were loaded onto the 384-well plate per manufacturer's instructions, and real-time PCR was run on the ABI 7900HT Prism instrument. For each 384-well plate, we used the automatically determined cycle-threshold ($C_T$) using the SDS 2.2.1 software (Applied Biosystems). Consistent with manufacturer recommendations, a $C_T$ greater than 35 was treated as undetected. The probes deemed to be present were normalized to the average expression of a sno-RNA control. The expression values were calculated as $2^{-\Delta C_T}$, then median centered to 500 and log 2-transformed.

For further validation of the deep sequencing results, we selected candidate novel microRNAs (see Table 34) that were detectably measured in at the sequencing data from least one of four diffuse large B cell lymphoma (DLBCL) cases. Using stem-loop reverse transcription (Ashburner, M., et al., *Nat Genet*. (2000); 25(1):25-29) for quantitative PCR, we tested the expression of the candidate microRNAs in 101 primary tumors from patients with DLBCL and found that about 92% were detectably measured by real-time PCR in at least 10% of these cases, suggesting that real-time PCR reproducibly identifies microRNAs that are expressed in lymphomas. We also used real-time PCR to measure the expression of known microRNAs (see Table 33) in the same 101 samples and found that over 90% of these were also detected in at least 10% of the cases using real-time PCR. We found that six of the seven RT-PCR constructs that targeted RNA hairpins that had low probability of being a microRNA resulted in no detectable signal. These results suggest that our assays have high specificity for microRNAs and that the computational predictions based on our sequencing data correctly identified microRNAs.

Differentiating ABC DLBCL Vs. GCB DLBCL Malignancies

Gene expression profiling of patients with DLBCL has demonstrated that the tumors comprise at least two distinct diseases with different response rates to standard chemotherapy regimens (Chen, C., et al., *Nucleic Acids Res*. (2005); 33(20):e179). We hypothesized that microRNAs might be used to make this clinically important distinction for which gene expression profiling remains the gold standard. We performed gene expression profiling on 101 DLBCL cases and further subdivided these cases into the molecular subgroups.

Tumor samples from 101 patients with diffuse large B cell lymphoma were obtained at the time of diagnosis and freshly frozen. These cases were profiled using Affymetrix Gene 1.0 ST arrays. The molecular subgroups were distinguished using a Bayesian approach described previously (Ambros, V., et al., *RNA* (2003);9(3):277-279).

We found that 25 microRNAs with the highest t-statistic were equally efficacious as the gene expression profiling in differentiating the two groups of DLBCL with over 95% overlap between the classifications rendered by the two methods, using leave out one cross-validation (see Table 35). Interestingly, a subset of these 25 predictor microRNAs was candidate novel microRNAs, suggesting a biological and clinical relevance for these candidate novel microRNAs in DLBCL tumors.

Our work provides an exhaustive identification of the microRNAs in normal and malignant B cells; that is a prerequisite to the delineation of their role. Further, we have developed a comprehensive framework that spans the identification of microRNAs from deep sequencing data to measuring their expression using real-time PCR and validating their expression in primary human tumors.

It is also conceivable that some of the low-abundance microRNAs that we have identified in our study may be expressed at higher levels in other development stages or in other cell types. This notion is confirmed by our examination of the novel microRNAs in non B cell data. For instance, a number of the microRNAs that we discovered were also present at 10-fold or higher levels in cell lines derived from breast cancer and cervical cancer, suggesting that the microRNAs that we have discovered in B cells have broad biological significance.

Deep Sequencing Reveals a Novel miRNA Cluster that Regulates the TGF-β Pathway

Although microRNAs appear to be distributed throughout the genome, a number of microRNAs have been found in clusters such as miR-17-92 that are transcribed from a single primary transcript and cleaved into the individual microRNAs by the enzyme DROSHA. We found 2 separate clusters of candidate novel microRNAs on chromosome 9 and chromosome 14 (within the IgH locus), respectively. The first cluster was previously annotated as a hypothetical gene LOC100130622, and subsequently discarded from Refseq when no associated protein was identified. Our data demonstrate that this cluster (miR-2355), conserved only in primates, encodes 6 separate microRNAs: has-miR-2355a-1, has-miR-2356-1, has-miR-2355a-2, has-miR-2356-2, hsa-miR2355a—3, and hsa-miR-2355b (see Table 32 for sequence).

In order to evaluate whether the microRNAs encoded in these clusters originate from the same primary transcript, we took KMS12 multiple myeloma cells which express these microRNAs and used siRNA to knock-down the expression of the microRNA processing enzyme Drosha. This enzyme acts at the first step of microRNA processing by cleaving microRNA precursors from the primary transcript. We found that decreased Drosha expression was associated with increased accumulation of primary transcripts of both the miR-17-92 cluster as well as the novel miR-2355 cluster. MicroRNAs from miR-2355 cluster were found to be expressed more highly in normal germinal center (GC) B cells compared to memory cells.

The microRNAs of this cluster all share the same seed sequence, suggesting that they target the same genes. Among the computationally predicted targets of this microRNA cluster, we identified SMAD2 and SMAD3 which are well known mediators of the TGF-beta signaling pathway. We noted that gene expression of both SMAD2 and SMAD3 in our set of 101 DLBCLs were inversely correlated with this cluster (P<0.001, correlation test). Gene set enrichment analysis revealed that expression of the TGF-beta pathway in DLBCL samples varied inversely with the expression of the microRNA cluster, with a higher expression of the microRNA associated with a lower expression of the pathway ($P<10^{-6}$), which has been noted as a factor in the biology of these tumors.

TABLE 31 miRNAs identified by deep sequencing analysis.

| SEQ ID NO. | Mature Sequence Captured | Putative Mature/Minor miRNA ID | miRBase ID | miRBase Mature/Minor ID | miRBase Mature/Minor Accession Number | miRBase Mature/Minor Sequence | SEQ ID NO. |
|---|---|---|---|---|---|---|---|
| 1 | CUGCGCAAGCUA CUGCCUUGCU | hsa-let-7i* | hsa-let-7i | hsa-let-7i* | MIMAT0004585 | CUGCGCAAGCUA CUGCCUUGCU | 393 |
| 2 | CCACGGAUGUUU GAGCAUGUGC | hsa-mir-105-1* | hsa-mir-105-1 | hsa-miR-105* | MIMAT0004516 | ACGGAUGUUUGA GCAUGUGCUA | 394 |
| 3 | CCACGGAUGUUU GAGCAUGUGC | hsa-mir-105-2* | hsa-mir-105-2 | hsa-miR-105* | MIMAT0004516 | ACGGAUGUUUGA GCAUGUGCUA | 395 |
| 4 | UACUGCAAUGUA AGCACUUCUU | hsa-mir-106a* | hsa-mir-106a | hsa-miR-106a* | MIMAT0004517 | CUGCAAUGUAAG CACUUCUUAC | 396 |
| 5 | CAUUAUUACUUU UGGUACGCG | hsa-mir-126* | hsa-mir-126 | hsa-miR-126* | MIMAT0000444 | CAUUAUUACUUU UGGUACGCG | 397 |
| 6 | AAGCCCUUACCC CAAAAAGUAU | hsa-mir-129* | hsa-mir-129-1 | hsa-miR-129* | MIMAT0004548 | AAGCCCUUACCC CAAAAAGUAU | 398 |
| 7 | AAGCCCUUACCC CAAAAAGCAU | hsa-mir-129-2* | hsa-mir-129-2 | hsa-miR-129-3p | MIMAT0004605 | AAGCCCUUACCC CAAAAAGCAU | 399 |
| 8 | UCUACAGUGCAC GUGUCUCCAG | hsa-mir-139-5p | hsa-mir-139 | hsa-miR-139-5p | MIMAT0000250 | UCUACAGUGCAC GUGUCUCCAG | 400 |
| 9 | CUGGUACAGGCC UGGGGGACAG | hsa-mir-150* | hsa-mir-150 | hsa-miR-150* | MIMAT0004610 | CUGGUACAGGCC UGGGGGACAG | 401 |
| 10 | ACUGCAGUGAAG GCACUUGUAG | hsa-mir-17* | hsa-mir-17 | hsa-miR-17* | MIMAT0000071 | ACUGCAGUGAAG GCACUUGUAG | 402 |
| 11 | UGAAUUACCGAA GGGCCAUAA | hsa-mir-183* | hsa-mir-183 | hsa-miR-183* | MIMAT0004560 | GUGAAUUACCGA AGGGCCAUAA | 403 |
| 12 | AGGGGCUGGCUU UCCUCUGGUC | hsa-mir-185* | hsa-mir-185 | hsa-miR-185* | MIMAT0004611 | AGGGGCUGGCUU UCCUCUGGUC | 404 |
| 13 | ACUGCCCUAAGU GCUCCUUCUGG | hsa-mir-18a* | hsa-mir-18a | hsa-miR-18a* | MIMAT0002891 | ACUGCCCUAAGU GCUCCUUCUGG | 405 |
| 14 | AACUGGCCUACA AAGUCCCAGU | hsa-mir-193a-3p | hsa-mir-193a | hsa-miR-193a-3p | MIMAT0000459 | AACUGGCCUACA AAGUCCCAGU | 406 |
| 15 | CGGGGUUUUGAG GGCGAGAUGA | hsa-mir-193b* | hsa-mir-193b | hsa-miR-193b* | MIMAT0004767 | CGGGGUUUUGAG GGCGAGAUGA | 407 |
| 16 | CCCAGUGUUCAG ACUACCUGUUC | hsa-mir-199a-2* | hsa-mir-199a-2 | hsa-miR-199a-5p | MIMAT0000231 | CCCAGUGUUCAG ACUACCUGUUC | 408 |
| 17 | UAGUUUUGCAUA GUUGCACUAC | hsa-mir-19a* | hsa-mir-19a | hsa-miR-19a* | MIMAT0004490 | AGUUUUGCAUAG UUGCACUACA | 409 |
| 18 | AGUUUUGCAGGU UUGCAUCCAGC | hsa-mir-19b-1* | hsa-mir-19b-1 | hsa-miR-19b-1* | MIMAT0004491 | AGUUUUGCAGGU UUGCAUCCAGC | 410 |
| 19 | ACUGUAGUAUGG GCACUUCCAG | hsa-mir-20b* | hsa-mir-20b | hsa-miR-20b* | MIMAT0004752 | ACUGUAGUAUGG GCACUUCCAG | 411 |
| 20 | ACCUGGCAUACA AUGUAGAUUU | hsa-mir-221* | hsa-mir-221 | hsa-miR-221* | MIMAT0004568 | ACCUGGCAUACA AUGUAGAUUU | 412 |

TABLE 31-continued miRNAs identified by deep sequencing analysis.

| SEQ ID NO. | Mature Sequence Captured | Putative Mature/Minor miRNA ID | miRBase ID | miRBase Mature/Minor ID | miRBase Mature/Minor Accession Number | miRBase Mature/Minor Sequence | SEQ ID NO. |
|---|---|---|---|---|---|---|---|
| 21 | GGGUUCCUGGCAUGCUGAUUU | hsa-mir-23b* | hsa-mir-23b | hsa-miR-23b* | MIMAT0004587 | UGGGUUCCUGGCAUGCUGAUUU | 413 |
| 22 | AGGCGGAGACUUGGGCAAUUG | hsa-mir-25* | hsa-mir-25 | hsa-miR-25* | MIMAT0004498 | AGGCGGAGACUUGGGCAAUUG | 414 |
| 23 | AGAGCUUAGCUGAUUGGUGAAC | hsa-mir-27b* | hsa-mir-27b | hsa-miR-27b* | MIMAT0004588 | AGAGCUUAGCUGAUUGGUGAAC | 415 |
| 24 | CUGGGAGGUGGAUGUUUACUUC | hsa-mir-30b* | hsa-mir-30b | hsa-miR-30b* | MIMAT0004589 | CUGGGAGGUGGAUGUUUACUUC | 416 |
| 25 | CUGGGAGAGGGUUGUUUACUCC | hsa-mir-30c-1* | hsa-mir-30c-1 | hsa-miR-30c-1* | MIMAT0004674 | CUGGGAGAGGGUUGUUUACUCC | 417 |
| 26 | CUGGGAGAAGGCUGUUUACUCU | hsa-mir-30c-2* | hsa-mir-30c-2 | hsa-miR-30c-2* | MIMAT0004550 | CUGGGAGAAGGCUGUUUACUCU | 418 |
| 27 | CUUUCAGUCGGAUGUUUACAGC | hsa-mir-30e* | hsa-mir-30e | hsa-miR-30e* | MIMAT0000693 | CUUUCAGUCGGAUGUUUACAGC | 419 |
| 28 | UCCCUGUCCUCCAGGAGCUCACG | hsa-mir-339-5p | hsa-mir-339 | hsa-miR-339-5p | MIMAT0000764 | UCCCUGUCCUCCAGGAGCUCACG | 420 |
| 29 | UCUCACACAGAAAUCGCACCCGU | hsa-mir-342-3p | hsa-mir-342 | hsa-miR-342-3p | MIMAT0000753 | UCUCACACAGAAAUCGCACCCGU | 421 |
| 30 | AAUCAGCAAGUAUACUGCCCUA | hsa-mir-34a* | hsa-mir-34a | hsa-miR-34a* | MIMAT0004557 | CAAUCAGCAAGUAUACUGCCCU | 422 |
| 31 | UCCCCCAGGUGUGAUUCUGAUUU | hsa-mir-361-3p | hsa-mir-361 | hsa-miR-361-3p | MIMAT0004682 | UCCCCCAGGUGUGAUUCUGAUUU | 423 |
| 32 | AAUCCUUGGAACCUAGGUGUGAGU | hsa-mir-362-5p | hsa-mir-362 | hsa-miR-362-5p | MIMAT0000705 | AAUCCUUGGAACCUAGGUGUGAGU | 424 |
| 33 | AGGGACUUUCAGGGGCAGCUGU | hsa-mir-365-2* | hsa-mir-365-2 | hsa-miR-365* | MIMAT0009199 | AGGGACUUUCAGGGGCAGCUGU | 425 |
| 34 | CUUAUCAGAUUGUAUUGUAAUU | hsa-mir-374a* | hsa-mir-374a | hsa-miR-374a* | MIMAT0004688 | CUUAUCAGAUUGUAUUGUAAUU | 426 |
| 35 | CUUAGCAGGUUGUAUUAUCAUU | hsa-mir-374b* | hsa-mir-374b | hsa-miR-374b* | MIMAT0004956 | CUUAGCAGGUUGUAUUAUCAUU | 427 |
| 36 | AGGUUACCCGAGCAACUUUGCAU | hsa-mir-409-5p | hsa-mir-409 | hsa-miR-409-5p | MIMAT0001638 | AGGUUACCCGAGCAACUUUGCAU | 428 |
| 37 | CAAAACGUGAGGCGCUGCUAU | hsa-mir-424* | hsa-mir-424 | hsa-miR-424* | MIMAT0004749 | CAAAACGUGAGGCGCUGCUAU | 429 |
| 38 | UAUGUGCCUUUGGACUACAUCG | hsa-mir-455-5p | hsa-mir-455 | hsa-miR-455-5p | MIMAT0003150 | UAUGUGCCUUUGGACUACAUCG | 430 |
| 39 | GUCAUACACGGCUCUCCUCUCU | hsa-mir-485-3p | hsa-mir-485 | hsa-miR-485-3p | MIMAT0002176 | GUCAUACACGGCUCUCCUCUCU | 431 |
| 40 | UGUCUUACUCCCUCAGGCACAU | hsa-mir-550-1* | hsa-mir-550-1 | hsa-miR-550* | MIMAT0003257 | UGUCUUACUCCCUCAGGCACAU | 432 |
| 41 | UGUCUUACUCCCUCAGGCACAU | hsa-mir-550-2* | hsa-mir-550-2 | hsa-miR-550* | MIMAT0003257 | UGUCUUACUCCCUCAGGCACAU | 433 |
| 42 | GAAAUCAAGCGUGGGUGAGACC | hsa-mir-551b* | hsa-mir-551b | hsa-miR-551b* | MIMAT0004794 | GAAAUCAAGCGUGGGUGAGACC | 434 |
| 43 | AUUCUAAUUUCUCCACGUCUUU | hsa-mir-576-5p | hsa-mir-576 | hsa-miR-576-5p | MIMAT0003241 | AUUCUAAUUUCUCCACGUCUUU | 435 |
| 44 | UCAGAACAAAUGCCGGUUCCCAGA | hsa-mir-589* | hsa-mir-589 | hsa-miR-589* | MIMAT0003256 | UCAGAACAAAUGCCGGUUCCCAGA | 436 |

TABLE 31-continued miRNAs identified by deep sequencing analysis.

| SEQ ID NO. | Mature Sequence Captured | Putative Mature/Minor miRNA ID | miRBase ID | miRBase Mature/Minor ID | miRBase Mature/Minor Accession Number | miRBase Mature/Minor Sequence | SEQ ID NO. |
|---|---|---|---|---|---|---|---|
| 45 | GAGCUUAUUCAU AAAAGUGCAG | hsa-mir-590-5p | hsa-mir-590 | hsa-miR-590-5p | MIMAT0003258 | GAGCUUAUUCAU AAAAGUGCAG | 437 |
| 46 | GGGGGUCCCCGG UGCUCGGAUC | hsa-mir-615-5p | hsa-mir-615 | hsa-miR-615-5p | MIMAT0004804 | GGGGGUCCCCGG UGCUCGGAUC | 438 |
| 47 | GACUAUAGAACU UUCCCCCUCA | hsa-mir-625* | hsa-mir-625 | hsa-miR-625* | MIMAT0004808 | GACUAUAGAACU UUCCCCCUCA | 439 |
| 48 | UGGUGGGCCGCA GAACAUGUGC | hsa-mir-654-5p | hsa-mir-654 | hsa-miR-654-5p | MIMAT0003330 | UGGUGGGCCGCA GAACAUGUGC | 440 |
| 49 | AGGAAGCCCUGG AGGGGCUGGAG | hsa-mir-671-5p | hsa-mir-671 | hsa-miR-671-5p | MIMAT0003880 | AGGAAGCCCUGG AGGGGCUGGAG | 441 |
| 50 | AACUAGACUGUG AGCUUCUAGA | hsa-mir-708* | hsa-mir-708 | hsa-miR-708* | MIMAT0004927 | CAACUAGACUGU GAGCUUCUAG | 442 |
| 51 | CAACAAAUCACA GUCUGCCAUA | hsa-mir-7-1* | hsa-mir-7-1 | hsa-miR-7-1* | MIMAT0004553 | CAACAAAUCACA GUCUGCCAUA | 443 |
| 52 | AUAAAGCUAGAU AACCGAAAGU | hsa-mir-9-1* | hsa-mir-9-1 | hsa-miR-9* | MIMAT0000442 | AUAAAGCUAGAU AACCGAAAGU | 444 |
| 53 | AUAAAGCUAGAU AACCGAAAGU | hsa-mir-9-2* | hsa-mir-9-2 | hsa-miR-9* | MIMAT0000442 | AUAAAGCUAGAU AACCGAAAGU | 445 |
| 54 | AGGGACGGGACG CGGUGCAGUG | hsa-mir-92b* | hsa-mir-92b | hsa-miR-92b* | MIMAT0004792 | AGGGACGGGACG CGGUGCAGUG | 446 |
| 55 | AUAAAGCUAGAU AACCGAAAGU | hsa-mir-9-3* | hsa-mir-9-3 | hsa-miR-9* | MIMAT0000442 | AUAAAGCUAGAU AACCGAAAGU | 447 |
| 56 | UGAGGUAGUAGG UUGUAUAGUU | hsa-let-7a-2 | hsa-let-7a-2 | hsa-let-7a | MIMAT0000062 | UGAGGUAGUAGG UUGUAUAGUU | 448 |
| 57 | UGAGGUAGUAGG UUGUAUAGUU | hsa-let-7a-3 | hsa-let-7a-3 | hsa-let-7a | MIMAT0000062 | UGAGGUAGUAGG UUGUAUAGUU | 449 |
| 58 | UGAGGUAGUAGG UUGUAUGGUU | hsa-let-7c | hsa-let-7c | hsa-let-7c | MIMAT0000064 | UGAGGUAGUAGG UUGUAUGGUU | 450 |
| 59 | UGAGGUAGGAGG UUGUAUAGUU | hsa-let-7e | hsa-let-7e | hsa-let-7e | MIMAT0000066 | UGAGGUAGGAGG UUGUAUAGUU | 451 |
| 60 | UGAGGUAGUAGA UUGUAUAGUU | hsa-let-7f-1 | hsa-let-7f-1 | hsa-let-7f | MIMAT0000067 | UGAGGUAGUAGA UUGUAUAGUU | 452 |
| 61 | UGAGGUAGUAGU UUGUACAGUU | hsa-let-7g | hsa-let-7g | hsa-let-7g | MIMAT0000414 | UGAGGUAGUAGU UUGUACAGUU | 453 |
| 62 | UGAGGUAGUAGU UUGUGCUGUU | hsa-let-7i | hsa-let-7i | hsa-let-7i | MIMAT0000415 | UGAGGUAGUAGU UUGUGCUGUU | 454 |
| 63 | AACCCGUAGAUC CGAACUUGUG | hsa-mir-100 | hsa-mir-100 | hsa-miR-100 | MIMAT0000098 | AACCCGUAGAUC CGAACUUGUG | 455 |
| 64 | UACAGUACUGUG AUAACUGAA | hsa-mir-101-1 | hsa-mir-101-1 | hsa-miR-101 | MIMAT0000099 | UACAGUACUGUG AUAACUGAA | 456 |
| 65 | GUACAGUACUGU GAUAACUGAA | hsa-mir-101-2 | hsa-mir-101-2 | hsa-miR-101 | MIMAT0000099 | UACAGUACUGUG AUAACUGAA | 457 |
| 66 | AGCAGCAUUGUA CAGGGCUAUGA | hsa-mir-103-1 | hsa-mir-103-1 | hsa-miR-103 | MIMAT0000101 | AGCAGCAUUGUA CAGGGCUAUGA | 458 |
| 67 | AGCAGCAUUGUA CAGGGCUAUGA | hsa-mir-103-2 | hsa-mir-103-2 | hsa-miR-103 | MIMAT0000101 | AGCAGCAUUGUA CAGGGCUAUGA | 4589 |

TABLE 31-continued miRNAs identified by deep sequencing analysis.

| SEQ ID NO. | Mature Sequence Captured | Putative Mature/Minor miRNA ID | miRBase ID | miRBase Mature/Minor ID | miRBase Mature/Minor Accession Number | miRBase Mature/Minor Sequence | SEQ ID NO. |
|---|---|---|---|---|---|---|---|
| 68 | AAAUGCUCAGACUCCUGUGGUG | hsa-mir-105-1 | hsa-mir-105-1 | hsa-miR-105 | MIMAT0000102 | UCAAAUGCUCAGACUCCUGUGGU | 460 |
| 69 | AAAUGCUCAGACUCCUGUGGUG | hsa-mir-105-2 | hsa-mir-105-2 | hsa-miR-105 | MIMAT0000102 | UCAAAUGCUCAGACUCCUGUGGU | 461 |
| 70 | AAAAGUGCUUACAGUGCAGGUAG | hsa-mir-106a | hsa-mir-106a | hsa-miR-106a | MIMAT0000103 | AAAAGUGCUUACAGUGCAGGUAG | 462 |
| 71 | UAAAGUGCUGACAGUGCAGAU | hsa-mir-106b | hsa-mir-106b | hsa-miR-106b | MIMAT0000680 | UAAAGUGCUGACAGUGCAGAU | 463 |
| 72 | AGCAGCAUUGUACAGGGCUAUCA | hsa-mir-107 | hsa-mir-107 | hsa-miR-107 | MIMAT0000104 | AGCAGCAUUGUACAGGGCUAUCA | 464 |
| 73 | UACCCUGUAGAUCCGAAUUUGUG | hsa-mir-10a | hsa-mir-10a | hsa-miR-10a | MIMAT0000253 | UACCCUGUAGAUCCGAAUUUGUG | 465 |
| 74 | UACCCUGUAGAACCGAAUUUGUG | hsa-mir-10b | hsa-mir-10b | hsa-miR-10b | MIMAT0000254 | UACCCUGUAGAACCGAAUUUGUG | 466 |
| 75 | UGGAAUGUAAAGAAGUAUGUAU | hsa-mir-1-1 | hsa-mir-1-1 | hsa-miR-1 | MIMAT0000416 | UGGAAUGUAAAGAAGUAUGUAU | 467 |
| 76 | UGGAAUGUAAAGAAGUAUGUAU | hsa-mir-1-2 | hsa-mir-1-2 | hsa-miR-1 | MIMAT0000416 | UGGAAUGUAAAGAAGUAUGUAU | 468 |
| 77 | UGGAGUGUGACAAUGGUGUUUG | hsa-mir-122 | hsa-mir-122 | hsa-miR-122 | MIMAT0000421 | UGGAGUGUGACAAUGGUGUUUG | 469 |
| 78 | UAAGGCACGCGGUGAAUGCC | hsa-mir-124-1 | hsa-mir-124-1 | hsa-miR-124 | MIMAT0000422 | UAAGGCACGCGGUGAAUGCC | 470 |
| 79 | UAAGGCACGCGGUGAAUGCC | hsa-mir-124-2 | hsa-mir-124-2 | hsa-miR-124 | MIMAT0000422 | UAAGGCACGCGGUGAAUGCC | 471 |
| 80 | UAAGGCACGCGGUGAAUGCC | hsa-mir-124-3 | hsa-mir-124-3 | hsa-miR-124 | MIMAT0000422 | UAAGGCACGCGGUGAAUGCC | 472 |
| 81 | ACCCGUCCCGUUCGUCCCCGGA | hsa-mir-1247 | hsa-mir-1247 | hsa-miR-1247 | MIMAT0005899 | ACCCGUCCCGUUCGUCCCCGGA | 473 |
| 82 | ACGGUGCUGGAUGUGGCCUUU | hsa-mir-1250 | hsa-mir-1250 | hsa-miR-1250 | MIMAT0005902 | ACGGUGCUGGAUGUGGCCUUU | 474 |
| 83 | AGAAGGAAAUUGAAUUCAUUUA | hsa-mir-1252 | hsa-mir-1252 | hsa-miR-1252 | MIMAT0005944 | AGAAGGAAAUUGAAUUCAUUUA | 475 |
| 84 | AGCCUGGAAGCUGGAGCCUGCAGU | hsa-mir-1254 | hsa-mir-1254 | hsa-miR-1254 | MIMAT0005905 | AGCCUGGAAGCUGGAGCCUGCAGU | 476 |
| 85 | AGGAUGAGCAAAGAAAGUAGAUU | hsa-mir-1255a | hsa-mir-1255a | hsa-miR-1255a | MIMAT0005906 | AGGAUGAGCAAAGAAAGUAGAUU | 477 |
| 86 | AGGCAUUGACUUCUCACUAGCU | hsa-mir-1256 | hsa-mir-1256 | hsa-miR-1256 | MIMAT0005907 | AGGCAUUGACUUCUCACUAGCU | 478 |
| 87 | CGUACCGUGAGUAAUAAUGCG | hsa-mir-126 | hsa-mir-126 | hsa-miR-126 | MIMAT0000445 | UCGUACCGUGAGUAAUAAUGCG | 479 |
| 88 | AUGGGUGAAUUUGUAGAAGGAU | hsa-mir-1262 | hsa-mir-1262 | hsa-miR-1262 | MIMAT0005914 | AUGGGUGAAUUUGUAGAAGGAU | 480 |
| 89 | AUGGUACCCUGGCAUACUGAGU | hsa-mir-1263 | hsa-mir-1263 | hsa-miR-1263 | MIMAT0005915 | AUGGUACCCUGGCAUACUGAGU | 481 |
| 90 | CAGGAUGUGGUCAAGUGUUGUU | hsa-mir-1265 | hsa-mir-1265 | hsa-miR-1265 | MIMAT0005918 | CAGGAUGUGGUCAAGUGUUGUU | 482 |

TABLE 31-continued miRNAs identified by deep sequencing analysis.

| SEQ ID NO. | Mature Sequence Captured | Putative Mature/Minor miRNA ID | miRBase ID | miRBase Mature/Minor ID | miRBase Mature/Minor Accession Number | miRBase Mature/Minor Sequence | SEQ ID NO. |
|---|---|---|---|---|---|---|---|
| 91 | CCUCAGGGCUGU AGAACAGGGCU | hsa-mir-1266 | hsa-mir-1266 | hsa-miR-1266 | MIMAT0005920 | CCUCAGGGCUGU AGAACAGGGCU | 483 |
| 92 | CUGGACUGAGCC GUGCUACUGG | hsa-mir-1269 | hsa-mir-1269 | hsa-miR-1269 | MIMAT0005923 | CUGGACUGAGCC GUGCUACUGG | 484 |
| 93 | CUGGAGAUAUGG AAGAGCUGUGU | hsa-mir-1270 | hsa-mir-1270 | hsa-miR-1270 | MIMAT0005924 | CUGGAGAUAUGG AAGAGCUGUGU | 485 |
| 94 | CUUGGCACCUAG CAAGCACUCA | hsa-mir-1271 | hsa-mir-1271 | hsa-miR-1271 | MIMAT0005796 | CUUGGCACCUAG CAAGCACUCA | 486 |
| 95 | UCGGAUCCGUCU GAGCUUGGCU | hsa-mir-127-3p | hsa-mir-127 | hsa-miR-127-3p | MIMAT0000446 | UCGGAUCCGUCU GAGCUUGGCU | 487 |
| 96 | UACGUAGAUAUA UAUGUAUUUU | hsa-mir-1277 | hsa-mir-1277 | hsa-miR-1277 | MIMAT0005933 | UACGUAGAUAUA UAUGUAUUUU | 488 |
| 97 | UAGUACUGUGCA UAUCAUCUAU | hsa-mir-1278 | hsa-mir-1278 | hsa-miR-1278 | MIMAT0005936 | UAGUACUGUGCA UAUCAUCUAU | 489 |
| 98 | UCACAGUGAACC GGUCUCUUU | hsa-mir-128-1 | hsa-mir-128-1 | hsa-miR-128 | MIMAT0000424 | UCACAGUGAACC GGUCUCUUU | 490 |
| 99 | UCACAGUGAACC GGUCUCUUU | hsa-mir-128-2 | hsa-mir-128-2 | hsa-miR-128 | MIMAT0000424 | UCACAGUGAACC GGUCUCUUU | 491 |
| 100 | CUUUUUGCGGUC UGGGCUUGC | hsa-mir-129-1 | hsa-mir-129-1 | hsa-miR-129-5p | MIMAT0000242 | CUUUUUGCGGUC UGGGCUUGC | 492 |
| 101 | CUUUUUGCGGUC UGGGCUUGC | hsa-mir-129-2 | hsa-mir-129-2 | hsa-miR-129-5p | MIMAT0000242 | CUUUUUGCGGUC UGGGCUUGC | 493 |
| 102 | UGUGAGGUUGGC AUUGUUGUCU | hsa-mir-1294 | hsa-mir-1294 | hsa-miR-1294 | MIMAT0005884 | UGUGAGGUUGGC AUUGUUGUCU | 494 |
| 103 | UUAGGCCGCAGA UCUGGGUGA | hsa-mir-1295 | hsa-mir-1295 | hsa-miR-1295 | MIMAT0005885 | UUAGGCCGCAGA UCUGGGUGA | 495 |
| 104 | UUCAUUCGGCUG UCCAGAUGUA | hsa-mir-1298 | hsa-mir-1298 | hsa-miR-1298 | MIMAT0005800 | UUCAUUCGGCUG UCCAGAUGUA | 496 |
| 105 | UUGCAGCUGCCU GGGAGUGACUUC | hsa-mir-1301 | hsa-mir-1301 | hsa-miR-1301 | MIMAT0005797 | UUGCAGCUGCCU GGGAGUGACUUC | 497 |
| 106 | CGGUUUGAGGCU ACAGUGAGAU | hsa-mir-1304 | hsa-mir-1304 | hsa-miR-1304 | MIMAT0005892 | UUUGAGGCUACA GUGAGAUGUG | 498 |
| 107 | ACGUUGGCUCUG GUGGUG | hsa-mir-1306 | hsa-mir-1306 | hsa-miR-1306 | MIMAT0005950 | ACGUUGGCUCUG GUGGUG | 499 |
| 108 | ACUCGGCGUGGC GUCGGUCGUG | hsa-mir-1307 | hsa-mir-1307 | hsa-miR-1307 | MIMAT0005951 | ACUCGGCGUGGC GUCGGUCGUG | 500 |
| 109 | CAGUGCAAUGUU AAAAGGGCAU | hsa-mir-130a | hsa-mir-130a | hsa-miR-130a | MIMAT0000425 | CAGUGCAAUGUU AAAAGGGCAU | 501 |
| 110 | CAGUGCAAUGAU GAAAGGGCAU | hsa-mir-130b | hsa-mir-130b | hsa-miR-130b | MIMAT0000691 | CAGUGCAAUGAU GAAAGGGCAU | 502 |
| 111 | UAACAGUCUACA GCCAUGGUCG | hsa-mir-132 | hsa-mir-132 | hsa-miR-132 | MIMAT0000426 | UAACAGUCUACA GCCAUGGUCG | 503 |
| 112 | ACCGUGGCUUUC GAUUGUUACU | hsa-mir-132* | hsa-mir-132 | hsa-miR-132* | MIMAT0004594 | ACCGUGGCUUUC GAUUGUUACU | 504 |
| 113 | UGUGACUGGUUG ACCAGAGGGG | hsa-mir-134 | hsa-mir-134 | hsa-miR-134 | MIMAT0000447 | UGUGACUGGUUG ACCAGAGGGG | 505 |
| 114 | UAUGGCUUUUCA UUCCUAUGUGA | hsa-mir-135b | hsa-mir-135b | hsa-miR-135b | MIMAT0000758 | UAUGGCUUUUCA UUCCUAUGUGA | 506 |

TABLE 31-continued miRNAs identified by deep sequencing analysis.

| SEQ ID NO. | Mature Sequence Captured | Putative Mature/Minor miRNA ID | miRBase ID | miRBase Mature/Minor ID | miRBase Mature/Minor Accession Number | miRBase Mature/Minor Sequence | SEQ ID NO. |
|---|---|---|---|---|---|---|---|
| 115 | ACUCCAUUUGUUUUGAUGAUGGA | hsa-mir-136 | hsa-mir-136 | hsa-miR-136 | MIMAT0000448 | ACUCCAUUUGUUUUGAUGAUGGA | 507 |
| 116 | AGCUGGUGUUGUGAAUCAGGCCG | hsa-mir-138-1 | hsa-mir-138-1 | hsa-miR-138 | MIMAT0000430 | AGCUGGUGUUGUGAAUCAGGCCG | 508 |
| 117 | AGCUGGUGUUGUGAAUCAGGCCG | hsa-mir-138-2 | hsa-mir-138-2 | hsa-miR-138 | MIMAT0000430 | AGCUGGUGUUGUGAAUCAGGCCG | 509 |
| 118 | UGGAGACGCGGCCCUGUUGGAG | hsa-mir-139-3p | hsa-mir-139 | hsa-miR-139-3p | MIMAT0004552 | GGAGACGCGGCCCUGUUGGAGU | 510 |
| 119 | UACCACAGGGUAGAACCACGG | hsa-mir-140-3p | hsa-mir-140 | hsa-miR-140-3p | MIMAT0004597 | UACCACAGGGUAGAACCACGG | 511 |
| 120 | UAACACUGUCUGGUAAAGAUGG | hsa-mir-141 | hsa-mir-141 | hsa-miR-141 | MIMAT0000432 | UAACACUGUCUGGUAAAGAUGG | 512 |
| 121 | CCCAUAAAGUAGAAAGCACU | hsa-mir-142 | hsa-mir-142 | hsa-miR-142-5p | MIMAT0000433 | CAUAAAGUAGAAAGCACUACU | 513 |
| 122 | UGAGAUGAAGCACUGUAGCUC | hsa-mir-143 | hsa-mir-143 | hsa-miR-143 | MIMAT0000435 | UGAGAUGAAGCACUGUAGCUC | 514 |
| 123 | GGAUAUCAUCAUAUACUGUAAG | hsa-mir-144 | hsa-mir-144 | hsa-miR-144* | MIMAT0004600 | GGAUAUCAUCAUAUACUGUAAG | 515 |
| 124 | GUCCAGUUUUCCCAGGAAUCCCU | hsa-mir-145 | hsa-mir-145 | hsa-miR-145 | MIMAT0000437 | GUCCAGUUUUCCCAGGAAUCCCU | 516 |
| 125 | UGAGAACUGAAUUCCAUGGGUU | hsa-mir-146a | hsa-mir-146a | hsa-miR-146a | MIMAT0000449 | UGAGAACUGAAUUCCAUGGGUU | 517 |
| 126 | UGAGAACUGAAUUCCAUAGGCU | hsa-mir-146b | hsa-mir-146b | hsa-miR-146b-5p | MIMAT0002809 | UGAGAACUGAAUUCCAUAGGCU | 518 |
| 127 | UCAGUGCACUACAGAACUUUGU | hsa-mir-148a | hsa-mir-148a | hsa-miR-148a | MIMAT0000243 | UCAGUGCACUACAGAACUUUGU | 519 |
| 128 | UCAGUGCAUCACAGAACUUUGU | hsa-mir-148b | hsa-mir-148b | hsa-miR-148b | MIMAT0000759 | UCAGUGCAUCACAGAACUUUGU | 520 |
| 129 | UCUCCCAACCCUUGUACCAGUG | hsa-mir-150 | hsa-mir-150 | hsa-miR-150 | MIMAT0000451 | UCUCCCAACCCUUGUACCAGUG | 521 |
| 130 | CUAGACUGAAGCUCCUUGAGG | hsa-mir-151-3p | hsa-mir-151 | hsa-miR-151-3p | MIMAT0000757 | CUAGACUGAAGCUCCUUGAGG | 522 |
| 131 | UCAGUGCAUGACAGAACUUGG | hsa-mir-152 | hsa-mir-152 | hsa-miR-152 | MIMAT0000438 | UCAGUGCAUGACAGAACUUGG | 523 |
| 132 | UUAAUGCUAAUCGUGAUAGGGGU | hsa-mir-155 | hsa-mir-155 | hsa-miR-155 | MIMAT0000646 | UUAAUGCUAAUCGUGAUAGGGGU | 524 |
| 133 | UAGCAGCACAUAAUGGUUUGUG | hsa-mir-15a | hsa-mir-15a | hsa-miR-15a | MIMAT0000068 | UAGCAGCACAUAAUGGUUUGUG | 525 |
| 134 | UAGCAGCACAUCAUGGUUUACA | hsa-mir-15b | hsa-mir-15b | hsa-miR-15b | MIMAT0000417 | UAGCAGCACAUCAUGGUUUACA | 526 |
| 135 | UAGCAGCACGUAAAUAUUGGCG | hsa-mir-16-1 | hsa-mir-16-1 | hsa-miR-16 | MIMAT0000069 | UAGCAGCACGUAAAUAUUGGCG | 527 |
| 136 | UAGCAGCACGUAAAUAUUGGCG | hsa-mir-16-2 | hsa-mir-16-2 | hsa-miR-16 | MIMAT0000069 | UAGCAGCACGUAAAUAUUGGCG | 528 |
| 137 | CAAAGUGCUUACAGUGCAGGUAG | hsa-mir-17 | hsa-mir-17 | hsa-miR-17 | MIMAT0000070 | CAAAGUGCUUACAGUGCAGGUAG | 529 |
| 138 | AACAUUCAACGCUGUCGGUGAGU | hsa-mir-181a-1 | hsa-mir-181a-1 | hsa-miR-181a | MIMAT0000256 | AACAUUCAACGCUGUCGGUGAGU | 530 |

TABLE 31-continued miRNAs identified by deep sequencing analysis.

| SEQ ID NO. | Mature Sequence Captured | Putative Mature/Minor miRNA ID | miRBase ID | miRBase Mature/Minor ID | miRBase Mature/Minor Accession Number | miRBase Mature/Minor Sequence | SEQ ID NO. |
|---|---|---|---|---|---|---|---|
| 139 | AACAUUCAACGCUGUCGGUGAGU | hsa-mir-181a-2 | hsa-mir-181a-2 | hsa-miR-181a | MIMAT0000256 | AACAUUCAACGCUGUCGGUGAGU | 531 |
| 140 | AACAUUCAUUGCUGUCGGUGGGU | hsa-mir-181b-1 | hsa-mir-181b-1 | hsa-miR-181b | MIMAT0000257 | AACAUUCAUUGCUGUCGGUGGGU | 532 |
| 141 | AACAUUCAUUGCUGUCGGUGGGU | hsa-mir-181b-2 | hsa-mir-181b-2 | hsa-miR-181b | MIMAT0000257 | AACAUUCAUUGCUGUCGGUGGGU | 533 |
| 142 | AACAUUCAACCUGUCGGUGAGU | hsa-mir-181c | hsa-mir-181c | hsa-miR-181c | MIMAT0000258 | AACAUUCAACCUGUCGGUGAGU | 534 |
| 143 | AACAUUCAUUGUUGUCGGUGGGU | hsa-mir-181d | hsa-mir-181d | hsa-miR-181d | MIMAT0002821 | AACAUUCAUUGUUGUCGGUGGGU | 535 |
| 144 | UUUGGCAAUGGUAGAACUCACACU | hsa-mir-182 | hsa-mir-182 | hsa-miR-182 | MIMAT0000259 | UUUGGCAAUGGUAGAACUCACACU | 536 |
| 145 | UAUGGCACUGGUAGAAUUCACU | hsa-mir-183 | hsa-mir-183 | hsa-miR-183 | MIMAT0000261 | UAUGGCACUGGUAGAAUUCACU | 537 |
| 146 | UGGACGGAGAACUGAUAAGGGU | hsa-mir-184 | hsa-mir-184 | hsa-miR-184 | MIMAT0000454 | UGGACGGAGAACUGAUAAGGGU | 538 |
| 147 | UGGAGAGAAAGGCAGUUCCUGA | hsa-mir-185 | hsa-mir-185 | hsa-miR-185 | MIMAT0000455 | UGGAGAGAAAGGCAGUUCCUGA | 539 |
| 148 | CAAAGAAUUCUCCUUUUGGGCU | hsa-mir-186 | hsa-mir-186 | hsa-miR-186 | MIMAT0000456 | CAAAGAAUUCUCCUUUUGGGCU | 540 |
| 149 | CAUCCCUUGCAUGGUGGAGGG | hsa-mir-188-5p | hsa-mir-188 | hsa-miR-188-5p | MIMAT0000457 | CAUCCCUUGCAUGGUGGAGGG | 541 |
| 150 | UAAGGUGCAUCUAGUGCAGAUAG | hsa-mir-18a | hsa-mir-18a | hsa-miR-18a | MIMAT0000072 | UAAGGUGCAUCUAGUGCAGAUAG | 542 |
| 151 | CAACGGAAUCCCAAAAGCAGCUG | hsa-mir-191 | hsa-mir-191 | hsa-miR-191 | MIMAT0000440 | CAACGGAAUCCCAAAAGCAGCUG | 543 |
| 152 | CUGACCUAUGAAUUGACAGCC | hsa-mir-192 | hsa-mir-192 | hsa-miR-192 | MIMAT0000222 | CUGACCUAUGAAUUGACAGCC | 544 |
| 153 | UGGGUCUUUGCGGGCGAGAUGA | hsa-mir-193a-5p | hsa-mir-193a | hsa-miR-193a-5p | MIMAT0004614 | UGGGUCUUUGCGGGCGAGAUGA | 545 |
| 154 | AACUGGCCCUCAAAGUCCCGCU | hsa-mir-193b | hsa-mir-193b | hsa-miR-193b | MIMAT0002819 | AACUGGCCCUCAAAGUCCCGCU | 546 |
| 155 | UGUAACAGCAACUCCAUGUGGA | hsa-mir-194-1 | hsa-mir-194-1 | hsa-miR-194 | MIMAT0000460 | UGUAACAGCAACUCCAUGUGGA | 547 |
| 156 | UAGCAGCACAGAAAUAUUGGC | hsa-mir-195 | hsa-mir-195 | hsa-miR-195 | MIMAT0000461 | UAGCAGCACAGAAAUAUUGGC | 548 |
| 157 | UAGGUAGUUUCAUGUUGUUGGG | hsa-mir-196a-1 | hsa-mir-196a-1 | hsa-miR-196a | MIMAT0000226 | UAGGUAGUUUCAUGUUGUUGGG | 549 |
| 158 | UAGGUAGUUUCAUGUUGUUGGG | hsa-mir-196a-2 | hsa-mir-196a-2 | hsa-miR-196a | MIMAT0000226 | UAGGUAGUUUCAUGUUGUUGGG | 550 |
| 159 | UAGGUAGUUUCCUGUUGUUGGG | hsa-mir-196b | hsa-mir-196b | hsa-miR-196b | MIMAT0001080 | UAGGUAGUUUCCUGUUGUUGGG | 551 |
| 160 | UUCACCACCUUCUCCACCCAGC | hsa-mir-197 | hsa-mir-197 | hsa-miR-197 | MIMAT0000227 | UUCACCACCUUCUCCACCCAGC | 552 |
| 161 | ACAGUAGUCUGCACAUUGGUUA | hsa-mir-199a-1 | hsa-mir-199a-1 | hsa-miR-199a-3p | MIMAT0000232 | ACAGUAGUCUGCACAUUGGUUA | 553 |
| 162 | ACAGUAGUCUGCACAUUGGUUA | hsa-mir-199a-2 | hsa-mir-199a-2 | hsa-miR-199a-3p | MIMAT0000232 | ACAGUAGUCUGCACAUUGGUUA | 554 |

TABLE 31-continued miRNAs identified by deep sequencing analysis.

| SEQ ID NO. | Mature Sequence Captured | Putative Mature/Minor miRNA ID | miRBase ID | miRBase Mature/Minor ID | miRBase Mature/Minor Accession Number | miRBase Mature/Minor Sequence | SEQ ID NO. |
|---|---|---|---|---|---|---|---|
| 163 | ACAGUAGUCUGCACAUUGGUUA | hsa-mir-199b | hsa-mir-199b | hsa-miR-199b-3p | MIMAT0004563 | ACAGUAGUCUGCACAUUGGUUA | 555 |
| 164 | UGUGCAAAUCUAUGCAAAACUGA | hsa-mir-19a | hsa-mir-19a | hsa-miR-19a | MIMAT0000073 | UGUGCAAAUCUAUGCAAAACUGA | 556 |
| 165 | UGUGCAAAUCCAUGCAAAACUGA | hsa-mir-19b-1 | hsa-mir-19b-1 | hsa-miR-19b | MIMAT0000074 | UGUGCAAAUCCAUGCAAAACUGA | 557 |
| 166 | UGUGCAAAUCCAUGCAAAACUGA | hsa-mir-19b-2 | hsa-mir-19b-2 | hsa-miR-19b | MIMAT0000074 | UGUGCAAAUCCAUGCAAAACUGA | 558 |
| 167 | UAACACUGUCUGGUAACGAUGU | hsa-mir-200a | hsa-mir-200a | hsa-miR-200a | MIMAT0000682 | UAACACUGUCUGGUAACGAUGU | 559 |
| 168 | UAAUACUGCCUGGUAAUGAUGA | hsa-mir-200b | hsa-mir-200b | hsa-miR-200b | MIMAT0000318 | UAAUACUGCCUGGUAAUGAUGA | 560 |
| 169 | UAAUACUGCCGGGUAAUGAUGGA | hsa-mir-200c | hsa-mir-200c | hsa-miR-200c | MIMAT0000617 | UAAUACUGCCGGGUAAUGAUGGA | 561 |
| 170 | UUCCUAUGCAUAUACUUCUUUG | hsa-mir-202* | hsa-mir-202 | hsa-miR-202* | MIMAT0002810 | UUCCUAUGCAUAUACUUCUUUG | 562 |
| 171 | GUGAAAUGUUUAGGACCACUAG | hsa-mir-203 | hsa-mir-203 | hsa-miR-203 | MIMAT0000264 | GUGAAAUGUUUAGGACCACUAG | 563 |
| 172 | UUCCCUUUGUCAUCCUAUGCCU | hsa-mir-204 | hsa-mir-204 | hsa-miR-204 | MIMAT0000265 | UUCCCUUUGUCAUCCUAUGCCU | 564 |
| 173 | UCCUUCAUUCCACCGGAGUCUG | hsa-mir-205 | hsa-mir-205 | hsa-miR-205 | MIMAT0000266 | UCCUUCAUUCCACCGGAGUCUG | 565 |
| 174 | UGGAAUGUAAGGAAGUGUGUGG | hsa-mir-206 | hsa-mir-206 | hsa-miR-206 | MIMAT0000462 | UGGAAUGUAAGGAAGUGUGUGG | 566 |
| 175 | UAAAGUGCUUAUAGUGCAGGUAG | hsa-mir-20a | hsa-mir-20a | hsa-miR-20a | MIMAT0000075 | UAAAGUGCUUAUAGUGCAGGUAG | 567 |
| 176 | CAAAGUGCUCAUAGUGCAGGUAG | hsa-mir-20b | hsa-mir-20b | hsa-miR-20b | MIMAT0001413 | CAAAGUGCUCAUAGUGCAGGUAG | 568 |
| 177 | UAGCUUAUCAGACUGAUGUUGA | hsa-mir-21 | hsa-mir-21 | hsa-miR-21 | MIMAT0000076 | UAGCUUAUCAGACUGAUGUUGA | 569 |
| 178 | CUGUGCGUGUGACAGCGGCUGA | hsa-mir-210 | hsa-mir-210 | hsa-miR-210 | MIMAT0000267 | CUGUGCGUGUGACAGCGGCUGA | 570 |
| 179 | UAACAGUCUCCAGUCACGGCC | hsa-mir-212 | hsa-mir-212 | hsa-miR-212 | MIMAT0000269 | UAACAGUCUCCAGUCACGGCC | 571 |
| 180 | ACAGCAGGCACAGACAGGCAGU | hsa-mir-214 | hsa-mir-214 | hsa-miR-214 | MIMAT0000271 | ACAGCAGGCACAGACAGGCAGU | 572 |
| 181 | UGACCUAUGAAUUGACAG | hsa-mir-215 | hsa-mir-215 | hsa-miR-215 | MIMAT0000272 | AUGACCUAUGAAUUGACAGAC | 573 |
| 182 | AAAUCUCUGCAGGCAAAUGUGA | hsa-mir-216b | hsa-mir-216b | hsa-miR-216b | MIMAT0004959 | AAAUCUCUGCAGGCAAAUGUGA | 574 |
| 183 | AUACUGCAUCAGGAACUGAUUG | hsa-mir-217 | hsa-mir-217 | hsa-miR-217 | MIMAT0000274 | UACUGCAUCAGGAACUGAUUGGA | 575 |
| 184 | AGAGUUGAGUCUGGACGUCCCG | hsa-mir-219-1 | hsa-mir-219-1 | hsa-miR-219-1-3p | MIMAT0004567 | AGAGUUGAGUCUGGACGUCCCG | 576 |
| 185 | AAGCUGCCAGUUGAAGAACUGU | hsa-mir-22 | hsa-mir-22 | hsa-miR-22 | MIMAT0000077 | AAGCUGCCAGUUGAAGAACUGU | 577 |
| 186 | AGCUACAUUGUCUGCUGGGUUUC | hsa-mir-221 | hsa-mir-221 | hsa-miR-221 | MIMAT0000278 | AGCUACAUUGUCUGCUGGGUUUC | 578 |

TABLE 31-continued miRNAs identified by deep sequencing analysis.

| SEQ ID NO. | Mature Sequence Captured | Putative Mature/Minor miRNA ID | miRBase ID | miRBase Mature/Minor ID | miRBase Mature/Minor Accession Number | miRBase Mature/Minor Sequence | SEQ ID NO. |
|---|---|---|---|---|---|---|---|
| 187 | AGCUACAUCUGG CUACUGGGU | hsa-mir-222 | hsa-mir-222 | hsa-miR-222 | MIMAT0000279 | AGCUACAUCUGG CUACUGGGU | 579 |
| 188 | CGUGUAUUUGAC AAGCUGAGUU | hsa-mir-223* | hsa-mir-223 | hsa-miR-223* | MIMAT0004570 | CGUGUAUUUGAC AAGCUGAGUU | 580 |
| 189 | CAAGUCACUAGU GGUUCCGUU | hsa-mir-224 | hsa-mir-224 | hsa-miR-224 | MIMAT0000281 | CAAGUCACUAGU GGUUCCGUU | 581 |
| 190 | AUCACAUUGCCA GGGAUUUCC | hsa-mir-23a | hsa-mir-23a | hsa-miR-23a | MIMAT0000078 | AUCACAUUGCCA GGGAUUUCC | 582 |
| 191 | AUCACAUUGCCA GGGAUUACC | hsa-mir-23b | hsa-mir-23b | hsa-miR-23b | MIMAT0000418 | AUCACAUUGCCA GGGAUUACC | 583 |
| 192 | UGGCUCAGUUCA GCAGGAACAG | hsa-mir-24-1 | hsa-mir-24-1 | hsa-miR-24 | MIMAT0000080 | UGGCUCAGUUCA GCAGGAACAG | 584 |
| 193 | UGGCUCAGUUCA GCAGGAACAG | hsa-mir-24-2 | hsa-mir-24-2 | hsa-miR-24 | MIMAT0000080 | UGGCUCAGUUCA GCAGGAACAG | 585 |
| 194 | CAUUGCACUUGU CUCGGUCUGA | hsa-mir-25 | hsa-mir-25 | hsa-miR-25 | MIMAT0000081 | CAUUGCACUUGU CUCGGUCUGA | 586 |
| 195 | UUCAAGUAAUCC AGGAUAGGCU | hsa-mir-26a-1 | hsa-mir-26a-1 | hsa-miR-26a | MIMAT0000082 | UUCAAGUAAUCC AGGAUAGGCU | 587 |
| 196 | UUCAAGUAAUCC AGGAUAGGCU | hsa-mir-26a-2 | hsa-mir-26a-2 | hsa-miR-26a | MIMAT0000082 | UUCAAGUAAUCC AGGAUAGGCU | 588 |
| 197 | UUCAAGUAAUUC AGGAUAGGU | hsa-mir-26b | hsa-mir-26b | hsa-miR-26b | MIMAT0000083 | UUCAAGUAAUUC AGGAUAGGU | 589 |
| 198 | UUCACAGUGGCU AAGUUCCGC | hsa-mir-27a | hsa-mir-27a | hsa-miR-27a | MIMAT0000084 | UUCACAGUGGCU AAGUUCCGC | 590 |
| 199 | UUCACAGUGGCU AAGUUCUGC | hsa-mir-27b | hsa-mir-27b | hsa-miR-27b | MIMAT0000419 | UUCACAGUGGCU AAGUUCUGC | 591 |
| 200 | CACUAGAUUGUG AGCUCCUGGA | hsa-mir-28 | hsa-mir-28 | hsa-miR-28-3p | MIMAT0004502 | CACUAGAUUGUG AGCUCCUGGA | 592 |
| 201 | GAGGGUUGGGUG GAGGCUCUCC | hsa-mir-296-3p | hsa-mir-296 | hsa-miR-296-3p | MIMAT0004679 | GAGGGUUGGGUG GAGGCUCUCC | 593 |
| 202 | AUGGUUUACCGU CCCACAUACA | hsa-mir-299-5p | hsa-mir-299 | hsa-miR-299-5p | MIMAT0002890 | UGGUUUACCGUC CCACAUACAU | 594 |
| 203 | UAGCACCAUCUG AAAUCGGUUA | hsa-mir-29a | hsa-mir-29a | hsa-miR-29a | MIMAT0000086 | UAGCACCAUCUG AAAUCGGUUA | 595 |
| 204 | UAGCACCAUUUG AAAUCAGUGUU | hsa-mir-29b-1 | hsa-mir-29b-1 | hsa-miR-29b | MIMAT0000100 | UAGCACCAUUUG AAAUCAGUGUU | 596 |
| 205 | UAGCACCAUUUG AAAUCAGUGUU | hsa-mir-29b-2 | hsa-mir-29b-2 | hsa-miR-29b | MIMAT0000100 | UAGCACCAUUUG AAAUCAGUGUU | 597 |
| 206 | UAGCACCAUUUG AAAUCGGUUA | hsa-mir-29c | hsa-mir-29c | hsa-miR-29c | MIMAT0000681 | UAGCACCAUUUG AAAUCGGUUA | 598 |
| 207 | CAGUGCAAUGAU AUUGUCAAAGC | hsa-mir-301b | hsa-mir-301b | hsa-miR-301b | MIMAT0004958 | CAGUGCAAUGAU AUUGUCAAAGC | 599 |
| 208 | UGUAAACAUCCU CGACUGGAAG | hsa-mir-30a | hsa-mir-30a | hsa-miR-30a | MIMAT0000087 | UGUAAACAUCCU CGACUGGAAG | 600 |
| 209 | UGUAAACAUCCU ACACUCAGCU | hsa-mir-30b | hsa-mir-30b | hsa-miR-30b | MIMAT0000420 | UGUAAACAUCCU ACACUCAGCU | 601 |
| 210 | UGUAAACAUCCU ACACUCUCAGC | hsa-mir-30c-1 | hsa-mir-30c-1 | hsa-miR-30c | MIMAT0000244 | UGUAAACAUCCU ACACUCUCAGC | 602 |

TABLE 31-continued miRNAs identified by deep sequencing analysis.

| SEQ ID NO. | Mature Sequence Captured | Putative Mature/Minor miRNA ID | miRBase ID | miRBase Mature/Minor ID | miRBase Mature/Minor Accession Number | miRBase Mature/Minor Sequence | SEQ ID NO. |
|---|---|---|---|---|---|---|---|
| 211 | UGUAAACAUCCUACACUCUCAGC | hsa-mir-30c-2 | hsa-mir-30c-2 | hsa-miR-30c | MIMAT0000244 | UGUAAACAUCCUACACUCUCAGC | 603 |
| 212 | UGUAAACAUCCCCGACUGGAAG | hsa-mir-30d | hsa-mir-30d | hsa-miR-30d | MIMAT0000245 | UGUAAACAUCCCCGACUGGAAG | 604 |
| 213 | UGUAAACAUCCUUGACUGGAAG | hsa-mir-30e | hsa-mir-30e | hsa-miR-30e | MIMAT0000692 | UGUAAACAUCCUUGACUGGAAG | 605 |
| 214 | AGGCAAGAUGCUGGCAUAGCU | hsa-mir-31 | hsa-mir-31 | hsa-miR-31 | MIMAT0000089 | AGGCAAGAUGCUGGCAUAGCU | 606 |
| 215 | UAUUGCACAUUACUAAGUUGCA | hsa-mir-32 | hsa-mir-32 | hsa-miR-32 | MIMAT0000090 | UAUUGCACAUUACUAAGUUGCA | 607 |
| 216 | AAAAGCUGGGUUGAGAGGGCGA | hsa-mir-320a | hsa-mir-320a | hsa-miR-320a | MIMAT0000510 | AAAAGCUGGGUUGAGAGGGCGA | 608 |
| 217 | AAAAGCUGGGUUGAGAGGGCAA | hsa-mir-320b-1 | hsa-mir-320b-1 | hsa-miR-320b | MIMAT0005792 | AAAAGCUGGGUUGAGAGGGCAA | 609 |
| 218 | AAAAGCUGGGUUGAGAGGGCAA | hsa-mir-320b-2 | hsa-mir-320b-2 | hsa-miR-320b | MIMAT0005792 | AAAAGCUGGGUUGAGAGGGCAA | 610 |
| 219 | AAAAGCUGGGUUGAGAGGGU | hsa-mir-320c-1 | hsa-mir-320c-1 | hsa-miR-320c | MIMAT0005793 | AAAAGCUGGGUUGAGAGGGU | 611 |
| 220 | AAAAGCUGGGUUGAGAGGGU | hsa-mir-320c-2 | hsa-mir-320c-2 | hsa-miR-320c | MIMAT0005793 | AAAAGCUGGGUUGAGAGGGU | 612 |
| 221 | AAAAGCUGGGUUGAGAGGA | hsa-mir-320d-1 | hsa-mir-320d-1 | hsa-miR-320d | MIMAT0006764 | AAAAGCUGGGUUGAGAGGA | 613 |
| 222 | AAAAGCUGGGUUGAGAGGA | hsa-mir-320d-2 | hsa-mir-320d-2 | hsa-miR-320d | MIMAT0006764 | AAAAGCUGGGUUGAGAGGA | 614 |
| 223 | CACAUUACACGGUCGACCUCU | hsa-mir-323 | hsa-mir-323 | hsa-miR-323-3p | MIMAT0000755 | CACAUUACACGGUCGACCUCU | 615 |
| 224 | CGCAUCCCCUAGGGCAUUGGUGU | hsa-mir-324 | hsa-mir-324 | hsa-miR-324-5p | MIMAT0000761 | CGCAUCCCCUAGGGCAUUGGUGU | 616 |
| 225 | CUGGCCCUCUCUGCCCUUCCGU | hsa-mir-328 | hsa-mir-328 | hsa-miR-328 | MIMAT0000752 | CUGGCCCUCUCUGCCCUUCCGU | 617 |
| 226 | GCAAAGCACACGGCCUGCAGAGA | hsa-mir-330 | hsa-mir-330 | hsa-miR-330-3p | MIMAT0000751 | GCAAAGCACACGGCCUGCAGAGA | 618 |
| 227 | GCCCCUGGGCCUAUCCUAGAA | hsa-mir-331 | hsa-mir-331 | hsa-miR-331-3p | MIMAT0000760 | GCCCCUGGGCCUAUCCUAGAA | 619 |
| 228 | UCAAGAGCAAUAACGAAAAAUGU | hsa-mir-335 | hsa-mir-335 | hsa-miR-335 | MIMAT0000765 | UCAAGAGCAAUAACGAAAAAUGU | 620 |
| 229 | UCCAGCAUCAGUGAUUUUGUUG | hsa-mir-338 | hsa-mir-338 | hsa-miR-338-3p | MIMAT0000763 | UCCAGCAUCAGUGAUUUUGUUG | 621 |
| 230 | UGAGCGCCUCGACGACAGAGCCG | hsa-mir-339-3p | hsa-mir-339 | hsa-miR-339-3p | MIMAT0004702 | UGAGCGCCUCGACGACAGAGCCG | 622 |
| 231 | GUGCAUUGUAGUUGCAUUGCA | hsa-mir-33a | hsa-mir-33a | hsa-miR-33a | MIMAT0000091 | GUGCAUUGUAGUUGCAUUGCA | 623 |
| 232 | GUGCAUUGCUGUUGCAUUGC | hsa-mir-33b | hsa-mir-33b | hsa-miR-33b | MIMAT0003301 | GUGCAUUGCUGUUGCAUUGC | 624 |
| 233 | UUAUAAAGCAAUGAGACUGAUU | hsa-mir-340 | hsa-mir-340 | hsa-miR-340 | MIMAT0004692 | UUAUAAAGCAAUGAGACUGAUU | 625 |
| 234 | AGGGGUGCUAUCUGUGAUUGA | hsa-mir-342-5p | hsa-mir-342 | hsa-miR-342-5p | MIMAT0004694 | AGGGGUGCUAUCUGUGAUUGA | 626 |

TABLE 31-continued miRNAs identified by deep sequencing analysis.

| SEQ ID NO. | Mature Sequence Captured | Putative Mature/Minor miRNA ID | miRBase ID | miRBase Mature/Minor ID | miRBase Mature/Minor Accession Number | miRBase Mature/Minor Sequence | SEQ ID NO. |
|---|---|---|---|---|---|---|---|
| 235 | GCUGACUCCUAG UCCAGGGCUC | hsa-mir-345 | hsa-mir-345 | hsa-miR-345 | MIMAT0000772 | GCUGACUCCUAG UCCAGGGCUC | 627 |
| 236 | UGGCAGUGUCUU AGCUGGUUGU | hsa-mir-34a | hsa-mir-34a | hsa-miR-34a | MIMAT0000255 | UGGCAGUGUCUU AGCUGGUUGU | 628 |
| 237 | AGGCAGUGUCAU UAGCUGAUUG | hsa-mir-34b* | hsa-mir-34b | hsa-miR-34b* | MIMAT0000685 | UAGGCAGUGUCA UUAGCUGAUUG | 629 |
| 238 | AGGCAGUGUAGU UAGCUGAUUGC | hsa-mir-34c-5p | hsa-mir-34c | hsa-miR-34c-5p | MIMAT0000686 | AGGCAGUGUAGU UAGCUGAUUGC | 630 |
| 239 | UUAUCAGAAUCU CCAGGGGUAC | hsa-mir-361-5p | hsa-mir-361 | hsa-miR-361-5p | MIMAT0000703 | UUAUCAGAAUCU CCAGGGGUAC | 631 |
| 240 | AACACACCUAUU CAAGGAUUCA | hsa-mir-362-3p | hsa-mir-362 | hsa-miR-362-3p | MIMAT0004683 | AACACACCUAUU CAAGGAUUCA | 632 |
| 241 | AAUUGCACGGUA UCCAUCUGUA | hsa-mir-363 | hsa-mir-363 | hsa-miR-363 | MIMAT0000707 | AAUUGCACGGUA UCCAUCUGUA | 633 |
| 242 | UAAUGCCCCUAA AAAUCCUUAU | hsa-mir-365-2 | hsa-mir-365-2 | hsa-miR-365 | MIMAT0000710 | UAAUGCCCCUAA AAAUCCUUAU | 634 |
| 243 | AAUAAUACAUGG UUGAUCUUU | hsa-mir-369 | hsa-mir-369 | hsa-miR-369-3p | MIMAT0000721 | AAUAAUACAUGG UUGAUCUUU | 635 |
| 244 | GCCUGCUGGGGU GGAACCUGGU | hsa-mir-370 | hsa-mir-370 | hsa-miR-370 | MIMAT0000722 | GCCUGCUGGGGU GGAACCUGGU | 636 |
| 245 | ACUCAAACUGUG GGGGCACU | hsa-mir-371 | hsa-mir-371 | hsa-miR-371-5p | MIMAT0004687 | ACUCAAACUGUG GGGGCACU | 637 |
| 246 | UUAUAAUACAAC CUGAUAAGUG | hsa-mir-374a | hsa-mir-374a | hsa-miR-374a | MIMAT0000727 | UUAUAAUACAAC CUGAUAAGUG | 638 |
| 247 | AUAUAAUACAAC CUGCUAAGUG | hsa-mir-374b | hsa-mir-374b | hsa-miR-374b | MIMAT0004955 | AUAUAAUACAAC CUGCUAAGUG | 639 |
| 248 | UUUGUUCGUUCG GCUCGCGUGA | hsa-mir-375 | hsa-mir-375 | hsa-miR-375 | MIMAT0000728 | UUUGUUCGUUCG GCUCGCGUGA | 640 |
| 249 | AGAGGUUGCCCU UGGUGAAUUC | hsa-mir-377* | hsa-mir-377 | hsa-miR-377* | MIMAT0004689 | AGAGGUUGCCCU UGGUGAAUUC | 641 |
| 250 | ACUGGACUUGGA GUCAGAAGG | hsa-mir-378 | hsa-mir-378 | hsa-miR-378 | MIMAT0000732 | ACUGGACUUGGA GUCAGAAGG | 642 |
| 251 | UGGUAGACUAUG GAACGUAGG | hsa-mir-379 | hsa-mir-379 | hsa-miR-379 | MIMAT0000733 | UGGUAGACUAUG GAACGUAGG | 643 |
| 252 | UAUACAAGGGCA AGCUCUCUGU | hsa-mir-381 | hsa-mir-381 | hsa-miR-381 | MIMAT0000736 | UAUACAAGGGCA AGCUCUCUGU | 644 |
| 253 | GAAGUUGUUCGU GGUGGAUUCG | hsa-mir-382 | hsa-mir-382 | hsa-miR-382 | MIMAT0000737 | GAAGUUGUUCGU GGUGGAUUCG | 645 |
| 254 | AGAUCAGAAGGU GAUUGUGGCU | hsa-mir-383 | hsa-mir-383 | hsa-miR-383 | MIMAT0000738 | AGAUCAGAAGGU GAUUGUGGCU | 646 |
| 255 | CGAAUGUUGCUC GGUGAACCCC | hsa-mir-409-3p | hsa-mir-409 | hsa-miR-409-3p | MIMAT0001639 | GAAUGUUGCUCG GUGAACCCU | 647 |
| 256 | AAUAUAACACAG AUGGCCUGU | hsa-mir-410 | hsa-mir-410 | hsa-miR-410 | MIMAT0002171 | AAUAUAACACAG AUGGCCUGU | 648 |
| 257 | AUAGUAGACCGU AUAGCGUACG | hsa-mir-411 | hsa-mir-411 | hsa-miR-411 | MIMAT0003329 | UAGUAGACCGUA UAGCGUACG | 649 |
| 258 | AUCAACAGACAU UAAUUGGGCGC | hsa-mir-421 | hsa-mir-421 | hsa-miR-421 | MIMAT0003339 | AUCAACAGACAU UAAUUGGGCGC | 650 |

TABLE 31-continued miRNAs identified by deep sequencing analysis.

| SEQ ID NO. | Mature Sequence Captured | Putative Mature/Minor miRNA ID | miRBase ID | miRBase Mature/Minor ID | miRBase Mature/Minor Accession Number | miRBase Mature/Minor Sequence | SEQ ID NO. |
|---|---|---|---|---|---|---|---|
| 259 | UGAGGGGCAGAGAGCGAGACUUU | hsa-mir-423 | hsa-mir-423 | hsa-miR-423-5p | MIMAT0004748 | UGAGGGGCAGAGAGCGAGACUUU | 651 |
| 260 | CAGCAGCAAUUCAUGUUUUGAA | hsa-mir-424 | hsa-mir-424 | hsa-miR-424 | MIMAT0001341 | CAGCAGCAAUUCAUGUUUUGAA | 652 |
| 261 | UAAUACUGUCUGGUAAAACCGU | hsa-mir-429 | hsa-mir-429 | hsa-miR-429 | MIMAT0001536 | UAAUACUGUCUGGUAAAACCGU | 653 |
| 262 | UCUUGGAGUAGGUCAUUGGGUGG | hsa-mir-432 | hsa-mir-432 | hsa-miR-432 | MIMAT0002814 | UCUUGGAGUAGGUCAUUGGGUGG | 654 |
| 263 | AUCAUGAUGGGCUCCUCGGUGU | hsa-mir-433 | hsa-mir-433 | hsa-miR-433 | MIMAT0001627 | AUCAUGAUGGGCUCCUCGGUGU | 655 |
| 264 | UUGCAUAUGUAGGAUGUCCCAU | hsa-mir-448 | hsa-mir-448 | hsa-miR-448 | MIMAT0001532 | UUGCAUAUGUAGGAUGUCCCAU | 656 |
| 265 | UGGCAGUGUAUUGUUAGCUGGU | hsa-mir-449a | hsa-mir-449a | hsa-miR-449a | MIMAT0001541 | UGGCAGUGUAUUGUUAGCUGGU | 657 |
| 266 | AGGCAGUGUAUUGUUAGCUGGC | hsa-mir-449b | hsa-mir-449b | hsa-miR-449b | MIMAT0003327 | AGGCAGUGUAUUGUUAGCUGGC | 658 |
| 267 | UUUUGCGAUGUGUUCCUAAUAU | hsa-mir-450a-1 | hsa-mir-450a-1 | hsa-miR-450a | MIMAT0001545 | UUUUGCGAUGUGUUCCUAAUAU | 659 |
| 268 | UUUUGCGAUGUGUUCCUAAUAU | hsa-mir-450a-2 | hsa-mir-450a-2 | hsa-miR-450a | MIMAT0001545 | UUUUGCGAUGUGUUCCUAAUAU | 660 |
| 269 | UUUUGCAAUAUGUUCCUGAAUA | hsa-mir-450b-5p | hsa-mir-450b | hsa-miR-450b-5p | MIMAT0004909 | UUUUGCAAUAUGUUCCUGAAUA | 661 |
| 270 | AACUGUUUGCAGAGGAAACUGA | hsa-mir-452 | hsa-mir-452 | hsa-miR-452 | MIMAT0001635 | AACUGUUUGCAGAGGAAACUGA | 662 |
| 271 | UAGUGCAAUAUUGCUUAUAGGGU | hsa-mir-454 | hsa-mir-454 | hsa-miR-454 | MIMAT0003885 | UAGUGCAAUAUUGCUUAUAGGGU | 663 |
| 272 | GCAGUCCAUGGGCAUAUACAC | hsa-mir-455-3p | hsa-mir-455 | hsa-miR-455-3p | MIMAT0004784 | GCAGUCCAUGGGCAUAUACAC | 664 |
| 273 | AAGACGGGAGGAAAGAAGGGAG | hsa-mir-483-5p | hsa-mir-483 | hsa-miR-483-5p | MIMAT0004761 | AAGACGGGAGGAAAGAAGGGAG | 665 |
| 274 | UCAGGCUCAGUCCCCUCCCGAU | hsa-mir-484 | hsa-mir-484 | hsa-miR-484 | MIMAT0002174 | UCAGGCUCAGUCCCCUCCCGAU | 666 |
| 275 | AGAGGCUGGCCGUGAUGAAUUC | hsa-mir-485-5p | hsa-mir-485 | hsa-miR-485-5p | MIMAT0002175 | AGAGGCUGGCCGUGAUGAAUUC | 667 |
| 276 | UCCUGUACUGAGCUGCCCCGAG | hsa-mir-486-5p | hsa-mir-486 | hsa-miR-486-5p | MIMAT0002177 | UCCUGUACUGAGCUGCCCCGAG | 668 |
| 277 | AAUCGUACAGGGUCAUCCACUU | hsa-mir-487b | hsa-mir-487b | hsa-miR-487b | MIMAT0003180 | AAUCGUACAGGGUCAUCCACUU | 669 |
| 278 | CCCAGAUAAUGGCACUCUCAA | hsa-mir-488* | hsa-mir-488 | hsa-miR-488* | MIMAT0002804 | CCCAGAUAAUGGCACUCUCAA | 670 |
| 279 | UUGUACAUGGUAGGCUUUCAUU | hsa-mir-493* | hsa-mir-493 | hsa-miR-493* | MIMAT0002813 | UUGUACAUGGUAGGCUUUCAUU | 671 |
| 280 | UGAAACAUACACGGGAAACCUC | hsa-mir-494 | hsa-mir-494 | hsa-miR-494 | MIMAT0002816 | UGAAACAUACACGGGAAACCUC | 672 |
| 281 | AAACAAACAUGGUGCACUUCUU | hsa-mir-495 | hsa-mir-495 | hsa-miR-495 | MIMAT0002817 | AAACAAACAUGGUGCACUUCUU | 673 |
| 282 | CAGCAGCACACUGUGGUUUGU | hsa-mir-497 | hsa-mir-497 | hsa-miR-497 | MIMAT0002820 | CAGCAGCACACUGUGGUUUGU | 674 |

TABLE 31-continued miRNAs identified by deep sequencing analysis.

| SEQ ID NO. | Mature Sequence Captured | Putative Mature/Minor miRNA ID | miRBase ID | miRBase Mature/Minor ID | miRBase Mature/Minor Accession Number | miRBase Mature/Minor Sequence | SEQ ID NO. |
|---|---|---|---|---|---|---|---|
| 283 | UUAAGACUUGCAGUGAUGUUU | hsa-mir-499-5p | hsa-mir-499 | hsa-miR-499-5p | MIMAT0002870 | UUAAGACUUGCAGUGAUGUUU | 675 |
| 284 | AUGCACCUGGGCAAGGAUUCUG | hsa-mir-500* | hsa-mir-500 | hsa-miR-500* | MIMAT0002871 | AUGCACCUGGGCAAGGAUUCUG | 676 |
| 285 | AAUGCACCCGGGCAAGGAUUCU | hsa-mir-501-3p | hsa-mir-501 | hsa-miR-501-3p | MIMAT0004774 | AAUGCACCCGGGCAAGGAUUCU | 677 |
| 286 | AAUGCACCUGGGCAAGGAUUCA | hsa-mir-502-3p | hsa-mir-502 | hsa-miR-502-3p | MIMAT0004775 | AAUGCACCUGGGCAAGGAUUCA | 678 |
| 287 | UAGCAGCGGGAACAGUUCUGCAG | hsa-mir-503 | hsa-mir-503 | hsa-miR-503 | MIMAT0002874 | UAGCAGCGGGAACAGUUCUGCAG | 679 |
| 288 | AGACCCUGGUCUGCACUCUAUC | hsa-mir-504 | hsa-mir-504 | hsa-miR-504 | MIMAT0002875 | AGACCCUGGUCUGCACUCUAUC | 680 |
| 289 | GGGAGCCAGGAAGUAUUGAUGU | hsa-mir-505* | hsa-mir-505 | hsa-miR-505* | MIMAT0004776 | GGGAGCCAGGAAGUAUUGAUGU | 681 |
| 290 | UGAUUGUAGCCUUUUGGAGUAGA | hsa-mir-508-3p | hsa-mir-508 | hsa-miR-508-3p | MIMAT0002880 | UGAUUGUAGCCUUUUGGAGUAGA | 682 |
| 291 | UACUGCAGACGUGGCAAUCAUG | hsa-mir-509-3-5p | hsa-mir-509-3 | hsa-miR-509-3-5p | MIMAT0004975 | UACUGCAGACGUGGCAAUCAUG | 683 |
| 292 | UUCACAGGGAGGUGUCAU | hsa-mir-513a-1 | hsa-mir-513a-1 | hsa-miR-513a-5p | MIMAT0002877 | UUCACAGGGAGGUGUCAU | 684 |
| 293 | UUCACAGGGAGGUGUCAU | hsa-mir-513a-2 | hsa-mir-513a-2 | hsa-miR-513a-5p | MIMAT0002877 | UUCACAGGGAGGUGUCAU | 685 |
| 294 | UUCACAAGGAGGUGUCAUUUAU | hsa-mir-513b | hsa-mir-513b | hsa-miR-513b | MIMAT0005788 | UUCACAAGGAGGUGUCAUUUAU | 686 |
| 295 | UUCUCAAGGAGGUGUCGUUUAU | hsa-mir-513c | hsa-mir-513c | hsa-miR-513c | MIMAT0005789 | UUCUCAAGGAGGUGUCGUUUAU | 687 |
| 296 | CAUGCCUUGAGUGUAGGACCGU | hsa-mir-532 | hsa-mir-532 | hsa-miR-532-5p | MIMAT0002888 | CAUGCCUUGAGUGUAGGACCGU | 688 |
| 297 | UGUGACAGAUUGAUAACUGAAA | hsa-mir-542-3p | hsa-mir-542 | hsa-miR-542-3p | MIMAT0003389 | UGUGACAGAUUGAUAACUGAAA | 689 |
| 298 | AAACAUUCGCGGUGCACUUCUU | hsa-mir-543 | hsa-mir-543 | hsa-miR-543 | MIMAT0004954 | AAACAUUCGCGGUGCACUUCUU | 690 |
| 299 | CAAAACUGGCAAUUACUUUUGC | hsa-mir-548a-1 | hsa-mir-548a-1 | hsa-miR-548a-3p | MIMAT0003251 | CAAAACUGGCAAUUACUUUUGC | 691 |
| 300 | CAAAACUGGCAAUUACUUUUGC | hsa-mir-548a-2 | hsa-mir-548a-2 | hsa-miR-548a-3p | MIMAT0003251 | CAAAACUGGCAAUUACUUUUGC | 692 |
| 301 | CAAAACUGGCAAUUACUUUUGC | hsa-mir-548a-3 | hsa-mir-548a-3 | hsa-miR-548a-3p | MIMAT0003251 | CAAAACUGGCAAUUACUUUUGC | 693 |
| 302 | CAAGAACCUCAGUUGCUUUUGU | hsa-mir-548b-3p | hsa-mir-548b | hsa-miR-548b-3p | MIMAT0003254 | CAAGAACCUCAGUUGCUUUUGU | 694 |
| 303 | AAAAACUGAGACUACUUUUGCA | hsa-mir-548e | hsa-mir-548e | hsa-miR-548e | MIMAT0005874 | AAAAACUGAGACUACUUUUGCA | 695 |
| 304 | AAAAGUAAUCGCGGUUUUUGUC | hsa-mir-548h-1 | hsa-mir-548h-1 | hsa-miR-548h | MIMAT0005928 | AAAAGUAAUCGCGGUUUUUGUC | 696 |
| 305 | AAAAGUAAUCGCGGUUUUUGUC | hsa-mir-548h-2 | hsa-mir-548h-2 | hsa-miR-548h | MIMAT0005928 | AAAAGUAAUCGCGGUUUUUGUC | 697 |
| 306 | AAAAGUAAUCGCGGUUUUUGUC | hsa-mir-548h-3 | hsa-mir-548h-3 | hsa-miR-548h | MIMAT0005928 | AAAAGUAAUCGCGGUUUUUGUC | 698 |

TABLE 31-continued miRNAs identified by deep sequencing analysis.

| SEQ ID NO. | Mature Sequence Captured | Putative Mature/Minor miRNA ID | miRBase ID | miRBase Mature/Minor ID | miRBase Mature/Minor Accession Number | miRBase Mature/Minor Sequence | SEQ ID NO. |
|---|---|---|---|---|---|---|---|
| 307 | AAAAGUAAUCGCGGUUUUUGUC | hsa-mir-548h-4 | hsa-mir-548h-4 | hsa-miR-548h | MIMAT0005928 | AAAAGUAAUCGCGGUUUUUGUC | 699 |
| 308 | AAAAGUAAUUGCGGUCUUUGGU | hsa-mir-548j | hsa-mir-548j | hsa-miR-548j | MIMAT0005875 | AAAAGUAAUUGCGGUCUUUGGU | 700 |
| 309 | AAAAGUACUUGCGGAUUUUGCU | hsa-mir-548k | hsa-mir-548k | hsa-miR-548k | MIMAT0005882 | AAAAGUACUUGCGGAUUUUGCU | 701 |
| 310 | AAAAGUAUUUGCGGGUUUUGUC | hsa-mir-548l | hsa-mir-548l | hsa-miR-548l | MIMAT0005889 | AAAAGUAUUUGCGGGUUUUGUC | 702 |
| 311 | CAAAAGUAAUUGUGGAUUUUGU | hsa-mir-548n | hsa-mir-548n | hsa-miR-548n | MIMAT0005916 | CAAAAGUAAUUGUGGAUUUUGU | 703 |
| 312 | AGUGCCUGAGGGAGUAAGAGCCC | hsa-mir-550-1 | hsa-mir-550-1 | hsa-miR-550 | MIMAT0004800 | AGUGCCUGAGGGAGUAAGAGCCC | 704 |
| 313 | AGUGCCUGAGGGAGUAAGAGCCC | hsa-mir-550-2 | hsa-mir-550-2 | hsa-miR-550 | MIMAT0004800 | AGUGCCUGAGGGAGUAAGAGCCC | 705 |
| 314 | GCGACCCAUACUUGGUUUCAG | hsa-mir-551b | hsa-mir-551b | hsa-miR-551b | MIMAT0003233 | GCGACCCAUACUUGGUUUCAG | 706 |
| 315 | CACGCUCAUGCACACACCCACA | hsa-mir-574-3p | hsa-mir-574 | hsa-miR-574-3p | MIMAT0003239 | CACGCUCAUGCACACACCCACA | 707 |
| 316 | AAGAUGUGGAAAAAUUGGAAUC | hsa-mir-576-3p | hsa-mir-576 | hsa-miR-576-3p | MIMAT0004796 | AAGAUGUGGAAAAAUUGGAAUC | 708 |
| 317 | GUAGAUAAAAUAUUGGUACCUG | hsa-mir-577 | hsa-mir-577 | hsa-miR-577 | MIMAT0003242 | UAGAUAAAAUAUUGGUACCUG | 709 |
| 318 | UAACUGGUUGAACAACUGAACC | hsa-mir-582-3p | hsa-mir-582 | hsa-miR-582-3p | MIMAT0004797 | UAACUGGUUGAACAACUGAACC | 710 |
| 319 | UUACAGUUGUUCAACCAGUUACU | hsa-mir-582-5p | hsa-mir-582 | hsa-miR-582-5p | MIMAT0003247 | UUACAGUUGUUCAACCAGUUACU | 711 |
| 320 | UUAUGGUUUGCCUGGGACUGAG | hsa-mir-584 | hsa-mir-584 | hsa-miR-584 | MIMAT0003249 | UUAUGGUUUGCCUGGGACUGAG | 712 |
| 321 | UGAGAACCACGUCUGCUCUGAG | hsa-mir-589 | hsa-mir-589 | hsa-miR-589 | MIMAT0004799 | UGAGAACCACGUCUGCUCUGAG | 713 |
| 322 | UAAUUUUAUGUAUAAGCUAGU | hsa-mir-590-3p | hsa-mir-590 | hsa-miR-590-3p | MIMAT0004801 | UAAUUUUAUGUAUAAGCUAGU | 714 |
| 323 | UACGUCAUCGUUGUCAUCGUCA | hsa-mir-598 | hsa-mir-598 | hsa-miR-598 | MIMAT0003266 | UACGUCAUCGUUGUCAUCGUCA | 715 |
| 324 | UCCGAGCCUGGGUCUCCCUCUU | hsa-mir-615-3p | hsa-mir-615 | hsa-miR-615-3p | MIMAT0003283 | UCCGAGCCUGGGUCUCCCUCUU | 716 |
| 325 | AAGUCAUUGGAGGGUUUGAGCA | hsa-mir-616 | hsa-mir-616 | hsa-miR-616 | MIMAT0004805 | AGUCAUUGGAGGGUUUGAGCAG | 717 |
| 326 | AAACUCUACUUGUCCUUCUGAGU | hsa-mir-618 | hsa-mir-618 | hsa-miR-618 | MIMAT0003287 | AAACUCUACUUGUCCUUCUGAGU | 718 |
| 327 | AGGGGGAAAGUUCUAUAGUCC | hsa-mir-625 | hsa-mir-625 | hsa-miR-625 | MIMAT0003294 | AGGGGGAAAGUUCUAUAGUCC | 719 |
| 328 | AUGCUGACAUAUUUACUAGAGG | hsa-mir-628-5p | hsa-mir-628 | hsa-miR-628-5p | MIMAT0004809 | AUGCUGACAUAUUUACUAGAGG | 720 |
| 329 | UGGGUUUACGUUGGGAGAACU | hsa-mir-629 | hsa-mir-629 | hsa-miR-629 | MIMAT0004810 | UGGGUUUACGUUGGGAGAACU | 721 |
| 330 | AAAGACAUAGGAUAGAGUCACCUC | hsa-mir-641 | hsa-mir-641 | hsa-miR-641 | MIMAT0003311 | AAAGACAUAGGAUAGAGUCACCUC | 722 |

TABLE 31-continued miRNAs identified by deep sequencing analysis.

| SEQ ID NO. | Mature Sequence Captured | Putative Mature/Minor miRNA ID | miRBase ID | miRBase Mature/Minor ID | miRBase Mature/Minor Accession Number | miRBase Mature/Minor Sequence | SEQ ID NO. |
|---|---|---|---|---|---|---|---|
| 331 | ACACUUGUAUGC UAGCUCAGGU | hsa-mir-643 | hsa-mir-643 | hsa-miR-643 | MIMAT0003313 | ACUUGUAUGCUA GCUCAGGUAG | 723 |
| 332 | UUUAGGAUAAGC UUGACUUUUG | hsa-mir-651 | hsa-mir-651 | hsa-miR-651 | MIMAT0003321 | UUUAGGAUAAGC UUGACUUUUG | 724 |
| 333 | AAUGGCGCCACU AGGGUUGUG | hsa-mir-652 | hsa-mir-652 | hsa-miR-652 | MIMAT0003322 | AAUGGCGCCACU AGGGUUGUG | 725 |
| 334 | UAUGUCUGCUGA CCAUCACCUU | hsa-mir-654-3p | hsa-mir-654 | hsa-miR-654-3p | MIMAT0004814 | UAUGUCUGCUGA CCAUCACCUU | 726 |
| 335 | UACCCAUUGCAU AUCGGAGUUG | hsa-mir-660 | hsa-mir-660 | hsa-miR-660 | MIMAT0003338 | UACCCAUUGCAU AUCGGAGUUG | 727 |
| 336 | UCCGGUUCUCAG GGCUCCACC | hsa-mir-671-3p | hsa-mir-671 | hsa-miR-671-3p | MIMAT0004819 | UCCGGUUCUCAG GGCUCCACC | 728 |
| 337 | AAGGAGCUUACA AUCUAGCUGGG | hsa-mir-708 | hsa-mir-708 | hsa-miR-708 | MIMAT0004926 | AAGGAGCUUACA AUCUAGCUGGG | 729 |
| 338 | UGGAAGACUAGU GAUUUUGUUGU | hsa-mir-7-1 | hsa-mir-7-1 | hsa-miR-7 | MIMAT0000252 | UGGAAGACUAGU GAUUUUGUUGU | 730 |
| 339 | UGGAAGACUAGU GAUUUUGUUGU | hsa-mir-7-2 | hsa-mir-7-2 | hsa-miR-7 | MIMAT0000252 | UGGAAGACUAGU GAUUUUGUUGU | 731 |
| 340 | UGGAAGACUAGU GAUUUUGUUGU | hsa-mir-7-3 | hsa-mir-7-3 | hsa-miR-7 | MIMAT0000252 | UGGAAGACUAGU GAUUUUGUUGU | 732 |
| 341 | CGGCUCUGGGUC UGUGGGGA | hsa-mir-760 | hsa-mir-760 | hsa-miR-760 | MIMAT0004957 | CGGCUCUGGGUC UGUGGGGA | 733 |
| 342 | UGCACCAUGGUU GUCUGAGCAUG | hsa-mir-767-5p | hsa-mir-767 | hsa-miR-767-5p | MIMAT0003882 | UGCACCAUGGUU GUCUGAGCAUG | 734 |
| 343 | UGAGACCUCUGG GUUCUGAGCU | hsa-mir-769-5p | hsa-mir-769 | hsa-miR-769-5p | MIMAT0003886 | UGAGACCUCUGG GUUCUGAGCU | 735 |
| 344 | GCAGGAACUUGU GAGUCUCCU | hsa-mir-873 | hsa-mir-873 | hsa-miR-873 | MIMAT0004953 | GCAGGAACUUGU GAGUCUCCU | 736 |
| 345 | CUGCCCUGGCCC GAGGGACCGA | hsa-mir-874 | hsa-mir-874 | hsa-miR-874 | MIMAT0004911 | CUGCCCUGGCCC GAGGGACCGA | 737 |
| 346 | GUAGAGGAGAUG GCGCAGGG | hsa-mir-877 | hsa-mir-877 | hsa-miR-877 | MIMAT0004949 | GUAGAGGAGAUG GCGCAGGG | 738 |
| 347 | GUGAACGGGCGC CAUCCCGAGG | hsa-mir-887 | hsa-mir-887 | hsa-miR-887 | MIMAT0004951 | GUGAACGGGCGC CAUCCCGAGG | 739 |
| 348 | UUAAUAUCGGAC AACCAUUGU | hsa-mir-889 | hsa-mir-889 | hsa-miR-889 | MIMAT0004921 | UUAAUAUCGGAC AACCAUUGU | 740 |
| 349 | UGCAACGAACCU GAGCCACUGA | hsa-mir-891a | hsa-mir-891a | hsa-miR-891a | MIMAT0004902 | UGCAACGAACCU GAGCCACUGA | 741 |
| 350 | CACUGUGUCCUU UCUGCGUAG | hsa-mir-892a | hsa-mir-892a | hsa-miR-892a | MIMAT0004907 | CACUGUGUCCUU UCUGCGUAG | 742 |
| 351 | UCUUUGGUUAUC UAGCUGUAUGA | hsa-mir-9-1 | hsa-mir-9-1 | hsa-miR-9 | MIMAT0000441 | UCUUUGGUUAUC UAGCUGUAUGA | 743 |
| 352 | UCUUUGGUUAUC UAGCUGUAUGA | hsa-mir-9-2 | hsa-mir-9-2 | hsa-miR-9 | MIMAT0000441 | UCUUUGGUUAUC UAGCUGUAUGA | 744 |
| 353 | UAUUGCACUUGU CCCGGCCUGU | hsa-mir-92a-1 | hsa-mir-92a-1 | hsa-miR-92a | MIMAT0000092 | UAUUGCACUUGU CCCGGCCUGU | 745 |

TABLE 31-continued miRNAs identified by deep sequencing analysis.

| SEQ ID NO. | Mature Sequence Captured | Putative Mature/Minor miRNA ID | miRBase ID | miRBase Mature/Minor ID | miRBase Mature/Minor Accession Number | miRBase Mature/Minor Sequence | SEQ ID NO. |
|---|---|---|---|---|---|---|---|
| 354 | UAUUGCACUUGUCCCGGCCUGU | hsa-mir-92a-2 | hsa-mir-92a-2 | hsa-miR-92a | MIMAT0000092 | UAUUGCACUUGUCCCGGCCUGU | 746 |
| 355 | UAUUGCACUCGUCCCGGCCUCC | hsa-mir-92b | hsa-mir-92b | hsa-miR-92b | MIMAT0003218 | UAUUGCACUCGUCCCGGCCUCC | 747 |
| 356 | CAAAGUGCUGUUCGUGCAGGUAG | hsa-mir-93 | hsa-mir-93 | hsa-miR-93 | MIMAT0000093 | CAAAGUGCUGUUCGUGCAGGUAG | 748 |
| 357 | UCUUUGGUUAUCUAGCUGUAUGA | hsa-mir-9-3 | hsa-mir-9-3 | hsa-miR-9 | MIMAT0000441 | UCUUUGGUUAUCUAGCUGUAUGA | 749 |
| 358 | AAGGCAGGGCCCCCGCUCCCC | hsa-mir-940 | hsa-mir-940 | hsa-miR-940 | MIMAT0004983 | AAGGCAGGGCCCCCGCUCCCC | 750 |
| 359 | UUCUCUGUUUUGGCCAUGUGUG | hsa-mir-942 | hsa-mir-942 | hsa-miR-942 | MIMAT0004985 | UCUUCUCUGUUUUGGCCAUGUG | 751 |
| 360 | AAAUUAUUGUACAUCGGAUGAG | hsa-mir-944 | hsa-mir-944 | hsa-miR-944 | MIMAT0004987 | AAAUUAUUGUACAUCGGAUGAG | 752 |
| 361 | UUCAACGGGUAUUUAUUGAGCA | hsa-mir-95 | hsa-mir-95 | hsa-miR-95 | MIMAT0000094 | UUCAACGGGUAUUUAUUGAGCA | 753 |
| 362 | UUUGGCACUAGCACAUUUUUGCU | hsa-mir-96 | hsa-mir-96 | hsa-miR-96 | MIMAT0000095 | UUUGGCACUAGCACAUUUUUGCU | 754 |
| 363 | UGAGGUAGUAAGUUGUAUUGUU | hsa-mir-98 | hsa-mir-98 | hsa-miR-98 | MIMAT0000096 | UGAGGUAGUAAGUUGUAUUGUU | 755 |
| 364 | AACCCGUAGAUCCGAUCUUGUG | hsa-mir-99a | hsa-mir-99a | hsa-miR-99a | MIMAT0000097 | AACCCGUAGAUCCGAUCUUGUG | 756 |
| 365 | CACCCGUAGAACCGACCUUGCG | hsa-mir-99b | hsa-mir-99b | hsa-miR-99b | MIMAT0000689 | CACCCGUAGAACCGACCUUGCG | 757 |
| 366 | AACAUAGAGGAAAUUCCACGU | hsa-mir-376c | hsa-mir-376c | hsa-mir-376c | | AACAUAGAGGAAAUUCCACGU | 758 |
| 367 | AUCAUAGAGGAAAAUCCAUGUU | hsa-mir-376b | hsa-mir-376b | hsa-mir-376b | | AUCAUAGAGGAAAAUCCAUGUU | 759 |
| 368 | UGGUGGGCCGCAGAACAUGUGC | hsa-mir-654 | hsa-mir-654 | hsa-mir-654 | | UGGUGGGCCGCAGAACAUGUGC | 760 |
| 369 | AUCAUAGAGGAAAAUCCACGU | hsa-mir-376a-2 | hsa-mir-376a-2 | hsa-mir-376a-2 | | AUCAUAGAGGAAAAUCCACGU | 761 |
| 370 | AUCAUAGAGGAAAAUCCACGU | hsa-mir-376a-1 | hsa-mir-376a-1 | hsa-mir-376a-1 | | AUCAUAGAGGAAAAUCCACGU | 762 |
| 371 | AAAACCGUCUAGUUACAGUUGU | hsa-mir-1537 | | | | | |
| 372 | AUAUACAGGGGGAGACUCUCAU | hsa-mir-1185-2 | | | | | |
| 373 | CCUAGAAUGGGGAUUGUGGG | hsa-mir-1301* | | | | | |
| 374 | AGCGAGACCUCAACUCUACAAU | hsa-mir-1303 | | | | | |
| 375 | UCGACCGGACCUCGACCGGCUC | hsa-mir-1307* | | | | | |
| 376 | AUGUAGGGAUGGAAGCCAUGAA | hsa-mir-135a-2 | | | | | |
| 377 | CUCACUGAACAAUGAAUGCAA | hsa-mir-181b-1* | | | | | |

TABLE 31-continued miRNAs identified by deep sequencing analysis.

| SEQ ID NO. | Mature Sequence Captured | Putative Mature/Minor miRNA ID | miRBase ID | miRBase Mature/Minor ID | miRBase Mature/Minor Accession Number | miRBase Mature/Minor Sequence | SEQ ID NO. |
|---|---|---|---|---|---|---|---|
| 378 | CGGGUAGAGAGG GCAGUGGGAG | hsa-mir-197* | | | | | |
| 379 | GCUGGGAAGGCA AAGGGACGU | hsa-mir-204* | | | | | |
| 380 | ACCUUGGCUCUA GACUGCUUAC | hsa-mir-212* | | | | | |
| 381 | GCUCUGACUUUA UUGCACUACU | hsa-mir-301a | | | | | |
| 382 | AGGGACUUUUGG GGGCAGAUGU | hsa-mir-365-1 | | | | | |
| 383 | UUGGGGACAUUU UGCAUUCAU | hsa-mir-450a-2* | | | | | |
| 384 | AAUGUGUAGCAA AAGACAGA | hsa-mir-511-1-3p | | | | | |
| 385 | AAUGUGUAGCAA AAGACAGA | hsa-mir-511-2-3p | | | | | |
| 386 | AUCAUACAAGGA CAAUUUCUUU | hsa-mir-539 | | | | | |
| 387 | AAAGGUAAUUGC AGUUUUUCCC | hsa-mir-570 | | | | | |
| 388 | UCGCGGUUUGUG CCAGAUGACG | hsa-mir-579 | | | | | |
| 389 | AGAAGGCACUAU GAGAUUUAGA | hsa-mir-605 | | | | | |
| 390 | AGACACAUUUGG AGAGGGAACC | hsa-mir-642 | | | | | |
| 391 | AGGACCUUCCCU GAACCAAGGA | hsa-mir-659 | | | | | |
| 392 | AUAUACAGGGGG AGACUCUUAU | hsa-mir-1185-1 | | | | | |

TABLE 32

Novel miRNAs identified by deep sequencing analysis.

| SEQ ID NO. | Mature Sequence Captured | Temporary Assigned miRNA ID | miRBase ID | SEQ ID NO. | miRNA Precursor Sequence |
|---|---|---|---|---|---|
| 763 | CCAAAACUGCAGUUACUUUUG | has-mir-548o-2 | pending | 1057 | UggUgcaaaagUaaUUgcggUUUUUgcc aUUaaaagUaaUgcggCCAAAACUGCAG UUACUUUUGcaccc |
| 764 | GAGCCUGGAAGCUGGAGCCUGC | hsa-mir-1254-2 | hsa-mir-1254-2 | 1058 | cUGAGCCUGGAAGCUGGAGCCUGCagUg agcUaUgaUcaUgUcccUgUacUcUagc cUgggca |
| 765 | CGGGCGUGGUGGUGGGGGUG | hsa-mir-1268b | hsa-mir-1268b | 1059 | accCGGGCGUGGUGGUGGGGGUGggUgc cUgUaaUUccagcUagUUggga |
| 766 | UCGAGGAGCUCACAGUCUAGA | hsa-miR-151-5p-2 | hsa-mir-151b | 1060 | agUcUcUcUUcagggcUcccgagacaca gaaacagacaccUgcccUCGAGGAGCUC ACAGUCUAGAca |

TABLE 32-continued

Novel miRNAs identified by deep sequencing analysis.

| SEQ ID NO. | Mature Sequence Captured | Temporary Assigned miRNA ID | miRBase ID | SEQ ID NO. | miRNA Precursor Sequence |
|---|---|---|---|---|---|
| 767 | UAAGGUGCAUCUAGUGCAGUU | hsa-mir-18b-2 | hsa-mir-18b | 1061 | UcUUgUgUUAAGGUGCAUCUAGUGCAGU UagUgaagcagcUUagaaUcUacUgccc UaaaUgccccUUcUggcacaggc |
| 768 | GAGGGUUGGGUGGAGGC | hsa-miR-296-2 | hsa-miR-296-2 | 1062 | cUgccUccaccccgccUggccUgaccca gccagggcUcUagGAGGGUUGGGUGGAG GCaa |
| 769 | AUCAUAGAGGAAAAUCCAUGUU | hsa-mir-376b-2 | hsa-mir-376b | 1063 | UaaaacgUggaUaUUccUUcUaUgUUa cgUgaUUccUggUUaAUCAUAGAGGAAA AUCCAUGUUUUc |
| 770 | AACAUAGAGGAAAUUCCACGU | hsa-mir-376c-2 | hsa-mir-376c | 1064 | UaaaaggUggaUaUUccUUcUaUgUUa UgUUaUUaUggUUaAACAUAGAGGAAA UUCCACGUUUUc |
| 771 | ACUGGACUUGGAGUCAGAAA | hsa-mir-378b-1 | hsa-mir-378d-1 | 1065 | acUgUUUcUgUccUUgUUcUUgUUgUUa UUACUGGACUUGGAGUCAGAAAcagg |
| 772 | ACUGGACUUGGAGUCAGAAA | hsa-mir-378b-2 | hsa-mir-378d-2 | 1066 | aggagagaacACUGGACUUGGAGUCAGA AAacUUUcaUccaagUcaUUcccUgcUc UaagUcccaUUUcUgUUcca |
| 773 | ACUGGACUUGGAGUCAGGA | hsa-miR-378c | hsa-mir-378e | 1067 | cUgacUccagUgUccaggccaggggcag acagUggacagagaacagUgcccaagac cACUGGACUUGGAGUCAGGAcaU |
| 774 | AGGCAGUGUAUUGCUAGCGGCU | hsa-mir-449c | hsa-mir-449c | 1068 | UcaggUAGGCAGUGUAUUGCUAGCGGCU gUUaaUgaUUUUaacagUUgcUagUUgc acUccUcUcUgU |
| 775 | UGCACCCAGGCAAGGAUUCUGC | hsa-mir-500-2 | hsa-mir-500b | 1069 | gUUcccccUcUcUaaUccUUgcUaccUg ggUgagagUgcUUUcUgaaUgcagUGCA CCCAGGCAAGGAUUCUGCaaggggggagU |
| 776 | UAAUCCUUGCUACCUGGGUGAG | hsa-mir-500-2* | has-mir-500b | 1070 | gUUcccccUcUcUAAUCCUUGCUACCUG GGUGAGagUgcUUUcUgaaUgcagUgca cccaggcaaggaUUcUgcaaggggggagU |
| 777 | AAAAGUAAUCGCGGUUUUUGUC | hsa-mir-548h-5 | hsa-mir-548h-5 | 1071 | acAAAAGUAAUCGCGGUUUUUGUCaUUa cUUUUaacUgUaaaaaccacggUUgcUU UUgc |
| 778 | AAAAGUAAUUGUGGAUUUUGCU | hsa-mir-548r-1 | hsa-mir-548ab | 1072 | aUgUUggUgcAAAAGUAAUUGUGGAUUU UGCUaUUacUUgUaUUUaUUUgUaaUgc aaaacccgcaaUUagUUUUgcaccaacc |
| 779 | AAAAGUAAUUGUGGAUUUUGCU | hsa-mir-548r-2 | has-mir-548ab | 1073 | UgUUggUgcAAAAGUAAUUGUGGAUUUU GCUaUUacUUgUaUUUaUUUgUaaUgca aaacccgcaaUUagUUUUgcaccaacc |
| 780 | UGUCUUACUCCCUCAGGCACAU | hsa-miR-550-3* | pending | 1074 | cUggUgcagUgccUgagggagUaagagU ccUgUUgUUgUaagaUagUGUCUUACUC CCUCAGGCACAUcUccaa |
| 781 | GGUGGGCUUCCCGGAGGG | hsa-mir-2221 | hsa-mir-4417 | 1075 | gaaaacaaccaGGUGGGCUUCCCGGAGG GcggaacacccagccccagcaUccaggg cUcaccUaccacgUUUg |
| 782 | GAAGCGGUGGCUGGGCUG | hsa-mir-2222 | pending | 1076 | gaggcggcccUagcgccaUUUgUggga gcGAAGCGGUGGCUGGGCUGcgcUUg |
| 783 | CACUGCAGGACUCAGCAG | hsa-mir-2223 | hsa-mir-4418 | 1077 | UggUUUUUgcUcUgagUgaccgUggUgg UUgUgggagUCACUGCAGGACUCAGCAG gaaUUc |
| 784 | UGAGGGAGGAGACUGCA | hsa-mir-2224 | hsa-mir-4419a | 1078 | UggUggUgUgUgccUgUagUcUUagcUa cUcgggaggcUGAGGGAGGAGACUGCAg UgagUggaggUcacgccacUg |
| 785 | ACUGGACUUGGAGCCAGAAG | hsa-mir-2225 | hsa-mir-378f | 1079 | gUcaggUccUggacUcccaUagUUUUca ggcUgcUaaacaacagaacgagcACUGG ACUUGGAGCCAGAAGUcUUggg |

TABLE 32-continued

Novel miRNAs identified by deep sequencing analysis.

| SEQ ID NO. | Mature Sequence Captured | Temporary Assigned miRNA ID | miRBase ID | SEQ ID NO. | miRNA Precursor Sequence |
|---|---|---|---|---|---|
| 786 | GUCACUGAUGUCUGUAGCUGAG | hsa-mir-2226 | hsa-mir-4420 | 1080 | cUcUUggUaUgaacaUcUgUgUgUUcaUgUcUcUcUgUgcacaggggacgagaGUCACUGAUGUCUGUAGCUGAGac |
| 787 | GAUGAGGAUGGAUAGCAAGGAA | hsa-mir-2227 | hsa-mir-3605 | 1081 | cUggccUcUgUgccUggaUacUUUaUacgUgUaaUUgUGAUGAGGAUGGAUAGCAAGGAAgccgc |
| 788 | ACCUGUCUGUGGAAAGGAGCUA | hsa-mir-2228 | hsa-mir-4421 | 1082 | cUgggUcUccUUUcUgcUgagagUUgaacacUUgUUgggacaACCUGUCUGUGGAAAGGAGCUAccUac |
| 789 | AAAAGCAUCAGGAAGUACCCA | hsa-mir-2229 | hsa-mir-4422 | 1083 | agUUcUUcUgcagacAAAAGCAUCAGGAAGUACCCAccaUgUaccagUgggcccUUcUUgaUgcUcUUgaUUgcagaggagcc |
| 790 | UGCCUGGAACAUAGUAGGGACU | hsa-mir-2230-1 | hsa-mir-3116-2 | 1084 | UccUUUaUUgagUcccUacUaUgUUccaggcaccUacgaUacccagUGCCUGGAACAUAGUAGGGACUcaaUaaagU |
| 791 | UGCCUGGAACAUAGUAGGGACU | hsa-mir-2230-2 | hsa-mir-3116-1 | 1085 | ccUUUaUUgagUcccUacUaUgUUccaggcaccUacgaUacccagUGCCUGGAACAUAGUAGGGACUcaaUaaagU |
| 792 | UGGAUUAAAAACAAUGGAGG | hsa-mir-2231 | pending | 1086 | cgccUccaUgUUUcagcaUcUaUgUcaUgggcUUggUccUggagUGGAUUAAAAACAAUGGAGGU |
| 793 | AUAGGCACCAAAAAGCAACAA | hsa-mir-2232 | hsa-mir-4423 | 1087 | aUcaUgUacUgcagUUgccUUUUUgUUcccaUgcUgUUUaagccUagcAUAGGCACCAAAAAGCAACAAcagUaUgUgaa |
| 794 | ACUGGGCUUGGAGUCAGAAG | hsa-mir-2233 | hsa-mir-378g | 1088 | cACUGGGCUUGGAGUCAGAAGaccUggcUccagcccagcUc |
| 795 | CAAAAACCGGCAAUUACUUUUG | hsa-mir-2234 | hsa-mir-548ac | 1089 | gUaUUaggUUggUgcaaaagUUaUUgUggUUUUUgcUaUUUUUUUUaaUggCAAAAACCGGCAAUUACUUUUGcacUaaccUagUag |
| 796 | GUCAAAUGAAGGGCUGAUCACG | hsa-mir-2235 | pending | 1090 | aaagUGUCAAAUGAAGGGCUGAUCACGaaaUagcgcaUUagcUcUUUUUUUgaaaacUUg |
| 797 | AAAGGGAGGAUUUGCUUAGAAGGAUGG | hsa-mir-2236 | pending | 1091 | gacUggcUacgUagUUcgggcaaaUccUccaaaagggAAAGGGAGGAUUUGCUUAGAAGGAUGGcgcUcc |
| 798 | AGAGUUAACUCAAAAUGGACUA | hsa-mir-2237 | hsa-mir-4424 | 1092 | cUUacaUcacacacAGAGUUAACUCAAAAUGGACUAaUUUUUccacUagUUagUccaUUUcaagUUaacUcUgUgUgaUgUagU |
| 799 | UGUUGGGAUUCAGCAGGACCAU | hsa-mir-2238 | hsa-mir-4425 | 1093 | gUgcUUUacaUgaaUgaUUcccaUUgaaUcccaacagcUUUgcgaagUgUUGUUGGGAUUCAGCAGGACCAUUcgUgUaaagUaa |
| 800 | UAAAUAGAGUAGGCAAAGGACA | hsa-mir-2239 | hsa-mir-3121 | 1094 | UaaaUggUUaUgUccUUUgccUaUUcUaUUUaagacaccUgUaccUUAAAUAGAGUAGGCAAAGGACAgaaacaUUUU |
| 801 | AGAGUCGAGAGUGGGAGAAGAG | hsa-mir-2240 | pending | 1095 | gcAGAGUCGAGAGUGGGAGAAGAGcggagcgUgUgagcagUacUgcggccUUccUcUccUcccUaaccUcgcUcUc |
| 802 | GAAGAUGGACGUACUUU | hsa-mir-2241 | hsa-mir-4426 | 1096 | agUUGAAGAUGGACGUACUUUgUcUgacUacaaUaUUcaaaaggagUcUacUcUUcaUcUUg |
| 803 | UCUGAAUAGAGUCUGAAGAGU | hsa-mir-2242 | hsa-mir-4427 | 1097 | gaagccUcUUggggcUUaUUUagacaaUggUUUcaUcaUUUcgUCUGAAUAGAGUCUGAAGAGUcUUU |

TABLE 32-continued

Novel miRNAs identified by deep sequencing analysis.

| SEQ ID NO. | Mature Sequence Captured | Temporary Assigned miRNA ID | miRBase ID | SEQ ID NO. | miRNA Precursor Sequence |
|---|---|---|---|---|---|
| 804 | CAAGGAGACGGGAACAUGGAGC | hsa-mir-2243 | hsa-mir-4428 | 1098 | UUggcaggUgccaUgUUgccUgcUccUUacUgUacacgUggcUggCAAGGAGACGGGAACAUGGAGCCgccaU |
| 805 | AAGAGGAAGAAAUGGCUGGUUC | hsa-mir-2244 | hsa-mir-3916 | 1099 | aggaagAAGAGGAAGAAAUGGCUGGUUCUcaggUgaaUgUgUcUgggUUcaggggaUgUgUcUccUcUUUUcU |
| 806 | UUCGCGGGCGAAGGCAAAGUC | hsa-mir-2245 | hsa-mir-3124 | 1100 | ggcgggcUUCGCGGGCGAAGGCAAAGUCgaUUCcaaaagUgacUUUUccUcacUcccgUgaagUcggcg |
| 807 | AAAAGCUGGGCUGAGAGGCG | hsa-mir-2246 | hsa-mir-4429 | 1101 | agggagAAAAGCUGGGCUGAGAGGCGacUggUgUcUaaUUgUUUgUcUcUccaacUcagacUgccUggccca |
| 808 | AUGGCCAAAACUGCAGUUAUUU | hsa-mir-2247 | hsa-mir-548s | 1102 | cUgcaaaaaUaaUUgcagUUUUUgccaUUaUUUUUaaUaaUUaUaaUaAUGGCCAAAACUGCAGUUAUUUUgcac |
| 809 | UAGUGGAUGAUGCACUCUGUGC | hsa-mir-2248 | hsa-mir-3681 | 1103 | cUacUUccagUAGUGGAUGAUGCACUCUGUGCagggccaacUgUgcacacagUgcUUcaUccacUacUggaagUgU |
| 810 | AGGCUGGAGUGAGCGGAG | hsa-mir-2249 | hsa-mir-4430 | 1104 | gUgAGGCUGGAGUGAGCGGAGaUcgUaccacUgcacUccaaccUggUga |
| 811 | GAAAACGACAAUGACUUUUGCA | hsa-mir-2250 | hsa-mir-548ad | 1105 | cUgUUaggUUggUgcaaaagUaaUUgUggUUUUUgaaagUaacUUggcGAAAACGACAAUGACUUUUGCAccaaUcUaaUac |
| 812 | GCGACUCUGAAAACUAGAAGGU | hsa-mir-2251 | hsa-mir-4431 | 1106 | UggUUUGCGACUCUGAAAACUAGAAGGUUUaUgacUgggcaUUUcUcacccaaUgcccaaUaUUgaacUUUcUagUUgUcagagUcaUUaaccc |
| 813 | AGAAGGCUGGAGCGCGGCGGU | hsa-mir-2252 | pending | 1107 | gcacUgcggUUcUgaggccgUUacUccggcUUcUccaUagagggcggAGAAGGCUGGAGCGCGGCGGUga |
| 814 | AAAGACUCUGCAAGAUGCCU | hsa-mir-2253 | hsa-mir-4432 | 1108 | gcaUcUUgcagagccgUUccaaUgcgacaccUcUagagUgUcaUccccUagaaUgUcaccUUggAAAGACUCUGCAAGAUGCCU |
| 815 | ACAGGAGUGGGGUGGGACAU | hsa-mir-2254 | hsa-mir-4433 | 1109 | caUccUccUUacgUcccaccccccacUccUgUUUcUggUgaaaUaUUcaaACAGGAGUGGGGUGGGACAUaaggaggaUa |
| 816 | AGGAGAAGUAAAGUAGAA | hsa-mir-2255 | hsa-mir-4434 | 1110 | UcacUUUAGGAGAAGUAAAGUAGAAcUUUggUUUUcaacUUUUccUacagUgU |
| 817 | AUGGCCAGAGCUCACACAGAGG | hsa-mir-2256 | hsa-mir-4435-1 | 1111 | aggcagcaaAUGGCCAGAGCUCACACAGAGGgaUgagUgcacUUcaccUgcagUgUgacUcagcaggccaacagaUgcUa |
| 818 | GCAGGACAGGCAGAAGUGGAU | hsa-mir-2257 | hsa-mir-4436 | 1112 | gccUcacUUUUccacUUaUgccUgcccUgccccUcgaaUcUgcUccacgaUUUggGCAGGACAGGCAGAAGUGGAUaagUgagga |
| 819 | AUCAGGGCUUGUGGAAUGGGAA | hsa-mir-2258 | hsa-mir-3127 | 1113 | ggcccAUCAGGGCUUGUGGAAUGGGAAggagaagggacgcUUccccUUcUgcaggccUgcUgggUg |
| 820 | AUGGCCAGAGCUCACACAGAGG | hsa-mir-2259 | hsa-mir-4435-2 | 1114 | gcaaAUGGCCAGAGCUCACACAGAGGgaUgagUgcacUUcaccUgcagUgUgacUcagcaggccaacagaUgcU |
| 821 | UGAGGAUAUGGCAGGGAAGGGG | hsa-mir-2260 | hsa-mir-3679 | 1115 | acgUggUGAGGAUAUGGCAGGGAAGGGGagUUcccUcUaUUcccUUccccccagUaaUcUUcaUcaUgc |

TABLE 32-continued

Novel miRNAs identified by deep sequencing analysis.

| SEQ ID NO. | Mature Sequence Captured | Temporary Assigned miRNA ID | miRBase ID | SEQ ID NO. | miRNA Precursor Sequence |
|---|---|---|---|---|---|
| 822 | AGGAGGUUGGUGUGGAUU | hsa-mir-2261 | pending | 1116 | UaUgAGGAGGUUGGUGUGGAUUcUgUUg aagaaaaagaagggggaacacUaaUUUUUc caUU |
| 823 | UUGGAAGACAUGGAGCAUGAGG | hsa-mir-2262 | pending | 1117 | UUUUGGAAGACAUGGAGCAUGAGGUaag UgccUagaUccUcaaaccacUUgccUcc accUaUgcUUccaggU |
| 824 | UCUGGCAAGUAAAAACUCUCA | hsa-mir-2263 | hsa-mir-3128 | 1118 | cUUccUCUGGCAAGUAAAAACUCUCAU UUUccUUaaaaaaUgagagUUUUUUacU UgcaaUaggaaa |
| 825 | UGGGCUCAGGGUACAAAGGUU | hsa-mir-2264 | hsa-mir-4437 | 1119 | acUUUgUgcaUUgggUccacaaggaggg gaUgacccUUgUGGGCUCAGGGUACAAA GGUU |
| 826 | CAAAAACUGCAAUUACUUUCA | hsa-mir-2265-1 | hsa-mir-548ae-1 | 1120 | gcagUUUUUgccaUUaagUUgcggUUUU UgccaUUaUaaUggCAAAAACUGCAAUU ACUUUCAcaccUgc |
| 827 | CAAAAACUGCAAUUACUUUCA | hsa-mir-2265-2 | hsa-mir-548ae-2 | 1121 | UgUgcaaaagUaaUUgUggUUUUUgUca UUUaaaagUaaUggCAAAAACUGCAAUU ACUUUCAcacc |
| 828 | GCUGCACCGGAGACUGGGUAA | hsa-mir-2266-1 | hsa-mir-3130-1 | 1122 | acUUgUcaUgUcUUUacccagUcUccggU gcagccUgUUgUcaagGCUGCACCGGAG ACUGGGUAAgacaUgacaagc |
| 829 | GCUGCACCGGAGACUGGGUAA | hsa-mir-2266-2 | hsa-mir-3130-2 | 1123 | UgUcUUUacccagUcUccggUgcagccUU gacaacagGCUGCACCGGAGACUGGGUA AgacaUgacaagUU |
| 830 | AUCCCCAGAUACAAUGGACAAU | hsa-mir-2267 | hsa-mir-2355 | 1124 | cgUgUcAUCCCCAGAUACAAUGGACAAU aUgcUaUUaUaaUcgUaUggcaUUgUcc UUgcUgUUUggagaUaaUacU |
| 831 | AUUGUCCUUGCUGUUUGGAGAU | hsa-mir-2267* | pending | 1125 | cgUgUcaUcccccagaUacaaUggacaaU aUgcUaUUaUaaUcgUaUggcAUUGUCC UUGCUGUUUGGAGAUaaUacU |
| 832 | CACAGGCUUAGAAAAGACAGU | hsa-mir-2268 | hsa-mir-4438 | 1126 | UaagUgUaaacUUaaggacUgUcUUUUc UaagccUgUgccUUgccUUUccUUUggC ACAGGCUUAGAAAAGACAGUcUUUaagU UUacacUUc |
| 833 | UCGAGGACUGGUGGAAGGGCCU | hsa-mir-2269 | hsa-mir-3131 | 1127 | UcUcagagUCGAGGACUGGUGGAAGGGC CUUUccccUcagaccaaggcccUggccc cagcUUcUUcUcagagU |
| 834 | GUGACUGAUACCUUGGAGGCAU | hsa-mir-2270 | hsa-mir-4439 | 1128 | ccaGUGACUGAUACCUUGGAGGCAUUUU aUcUaagaUacacacaaagcaaaUgccU cUaaggUaUcagUUUaccaggcca |
| 835 | AGGGCUGGACUCAGCGGCGGAG | hsa-mir-2271 | pending | 1129 | gcgcagAGGGCUGGACUCAGCGGCGGAG cUggcUgcUggccUcagUUcUgccUcUg UccaggUccUUgUga |
| 836 | UGUCGUGGGGCUUGCUGGCUUG | hsa-mir-2272 | hsa-mir-4440 | 1130 | cUcUcaccaagcaagUgcagUggggcUU gcUggcUUgcaccgUgacUcccUcUcac caagcaagUGUCGUGGGGCUUGCUGGCU UGcacUgUgaagaU |
| 837 | ACAGGGAGGAGAUUGUA | hsa-mir-2273 | hsa-mir-4441 | 1131 | cagagUcUccUUcgUgUacagggaggag acUgUacgUgagagaUagUcagaUccgc aUgUUagagcagagUcUccUUcgUgUAC AGGGAGGAGAUUGUAc |
| 838 | ACUGGACUUGGAGGCAGAA | hsa-mir-2274 | hsa-mir-378b | 1132 | UggUcaUUgagUcUUcaaggcUagUgga aagagcACUGGACUUGGAGGCAGAAaga ccc |
| 839 | GCCGGACAAGAGGGAGG | hsa-mir-2275 | hsa-mir-4442 | 1133 | gcgcccUcccUcUcUccccggUgUgcaa aUgUgUgUgcggUgUUaUGCCGGACA AGAGGGAGGUg |

TABLE 32-continued

Novel miRNAs identified by deep sequencing analysis.

| SEQ ID NO. | Mature Sequence Captured | Temporary Assigned miRNA ID | miRBase ID | SEQ ID NO. | miRNA Precursor Sequence |
|---|---|---|---|---|---|
| 840 | AUACACAUACACGCAACACACA | hsa-mir-2276 | hsa-mir-466 | 1134 | aUgUgUgUgUaUaUgUgUgUUgcaUgUg UgUaUaUgUgUgUaUaUaUgUacacAUA CACAUACACGCAACACACAUaUaUacaU gcac |
| 841 | UUGGAGGCGUGGGUUUU | hsa-mir-2277 | hsa-mir-4443 | 1135 | ggUgggggUUGGAGGCGUGGGUUUUaga accUaUcccUUUcUagcccUgagca |
| 842 | AAUUCCCUUGUAGAUAACCCGG | hsa-mir-2278 | hsa-mir-3938 | 1136 | cgaUcacUagaUUaUcUacaagggaaUU UUUUUUaaUUUaaaaAAUUCCCUUGUA GAUAACCCGGUggUca |
| 843 | AAGACUGGAGACAAAGUGGGAG | hsa-mir-2279 | pending | 1137 | CACCACCAAAAUCUCCAGGGGCAUCGUU GAAAUCGUAAGGGAUGUGCAGCUCAUUA AGACUGGAGACAAAGUGGGAG |
| 844 | CUGACUGAAUAGGUAGGGUCAU | hsa-mir-2280 | hsa-mir-3136 | 1138 | aaaCUGACUGAAUAGGUAGGGUCAUUUU UcUgUgacUgcacaUggcccaaccUaUU cagUUagUUc |
| 845 | CUCGAGUUGGAAGAGGCG | hsa-mir-2281 | hsa-mir-4444 | 1139 | gUgacgacUggccccgccUcUUccUcUc ggUcccaUaUUgaaCUCGAGUUGGAAGA GGCGagUccggUcUcaaa |
| 846 | AGAUUGUUUCUUUUGCCGUGCA | hsa-mir-2282 | hsa-mir-4445 | 1140 | UUccUgcAGAUUGUUUCUUUUGCCGUGC AagUUUaagUUUUUgcacggcaaaagaa acaaUccagagggU |
| 847 | CACGGCAAAAGAAACAAUCCA | hsa-mir-2282* | has-mir-4445 | 1141 | UUccUgcagaUUgUUUcUUUUgccgUgc aagUUUaagUUUUUgCACGGCAAAAGAA ACAAUCCAgagggU |
| 848 | CAGGGCUGGCAGUGACAUGGGU | hsa-mir-2283 | hsa-mir-4446 | 1142 | cUggUccaUUUcccUgccaUUcccUUgg cUUcaaUUUacUccCAGGGCUGGCAGUG ACAUGGGUcaa |
| 849 | GGUGGGGCUGUUGUUU | hsa-mir-2284 | hsa-mir-4447 | 1143 | gUUcUagagcaUggUUUcUcaUcaUUUg cacUacUgaUacUUggggUcagaUaaUU gUUUgUGGUGGGGCUGUUGUUUgcaUU gUaggaU |
| 850 | UGGGGAGGUGUGGAGUCAGCAU | hsa-mir-2285 | pending | 1144 | gggcaUGGGGAGGUGUGGAGUCAGCAUg gggcUaggaggccccgcgcUgacccgcc UUcUccgcagcUg |
| 851 | GCAGAGAACAAAGGACUCAGU | hsa-mir-2286 | hsa-mir-3919 | 1145 | accUgagcaccaUUUacUgagUccUUUg UUcUcUacUagUUUgUagUagUUcgUaG CAGAGAACAAAGGACUCAGUaaaUggUg cUcagga |
| 852 | GGCUCCUUGGUCUAGGGGUA | hsa-mir-2287 | hsa-mir-4448 | 1146 | aggagUgaccaaaagacaagagUgcgag ccUUcUaUUaUgcccagacagggccacc agagGGCUCCUUGGUCUAGGGGUAaUgc ca |
| 853 | CGUCCCGGGGCUGCGCGAGGCA | hsa-mir-2288 | hsa-mir-4449 | 1147 | agcagcccUcggcggcccgggggcggg cggcggUgccCGUCCCGGGGCUGCGCGA GGCAcaggcg |
| 854 | AAAGGUAAUUGUGGUUUCUGC | hsa-mir-2289-1 | hsa-mir-548ag-1 | 1148 | gUgcAAAGGUAAUUGUGGUUUCUGCUUU UaaaggUaaUUgcaaaUaUUacaUUUac UUUUgcacca |
| 855 | AAAGGUAAUUGUGGUUUCUGC | hsa-mir-2289-2 | hsa-mir-548ag-2 | 1149 | UgcAAAGGUAAUUGUGGUUUCUGCcaUU gaaagUaaaggcaagaaccUcaaUUacc UUUgcagc |
| 856 | UGGGGAUUUGGAGAAGUGGUGA | hsa-mir-2290 | hsa-mir-4450 | 1150 | UgUcUGGGGAUUUGGAGAAGUGGUGAgc gcaggUcUUUggcaccaUcUccccUggU cccUUggcU |
| 857 | AAAAGUGAUUGCAGUGUUUG | hsa-mir-2291 | hsa-mir-548ah | 1151 | aggUUggUgcAAAAGUGAUUGCAGUGUU UGccaaUaaaagUaaUgacaaaaacUgc agUUacUUUUgcaccagccc |

TABLE 32-continued

Novel miRNAs identified by deep sequencing analysis.

| SEQ ID NO. | Mature Sequence Captured | Temporary Assigned miRNA ID | miRBase ID | SEQ ID NO. | miRNA Precursor Sequence |
|---|---|---|---|---|---|
| 858 | UGGUAGAGCUGAGGACA | hsa-mir-2292 | hsa-mir-4451 | 1152 | UcUgUaccUcagcUUUgcUcccaaccaa ccacUUccacaUgUUUUgcUGGUAGAGC UGAGGACAgc |
| 859 | UUGAAUUCUUGGCCUUAAGUGAU | hsa-mir-2293 | hsa-mir-4452 | 1153 | UggaUcacUUgaggccaagagUgcaagg cUgUagUgUgcacagccUUGAAUUCUUG GCCUUAAGUGAUccc |
| 860 | UAGGAGCUCAACAGAUGCCUGU | hsa-mir-2294 | hsa-mir-3139 | 1154 | UcagagUAGGAGCUCAACAGAUGCCUGU UgacUgaaUaaUaaacaggUaUcgcagg agcUUUUgUUaUgU |
| 861 | AGCUUUUGGGAAUUCAGGUAG | hsa-mir-2295 | hsa-mir-3140 | 1155 | UgUccUcUUgaggUaccUgaaUUaccaa aagcUUUaUgUaUUcUgaagUUaUUgaa aaUaagAGCUUUUGGGAAUUCAGGUAGU UcaggagUgacU |
| 862 | GAGCUUGGUCUGUAGCGGUU | hsa-mir-2296 | hsa-mir-4453 | 1156 | UggaGAGCUUGGUCUGUAGCGGUUUccU UggggcaggUggggacUgcUccUUUggg aggaaggaggaggcccaggccgcgUcUU cagg |
| 863 | GGAUCCGAGUCACGGCACCA | hsa-mir-2297 | hsa-mir-4454 | 1157 | ccGGAUCCGAGUCACGGCACCAaaUUUc aUgcgUgUccgUgUgaagagaccacca |
| 864 | CAAAAGUGAUCGUGGUUUUUG | hsa-mir-2298 | hsa-mir-548t | 1158 | gUggUgCAAAAGUGAUCGUGGUUUUUGc aaUUUUUUaaUgacaaaaaccacaaUUa cUUUUgcaccaa |
| 865 | AGGGUGUGUGUGUUUUU | hsa-mir-2299 | hsa-mir-4455 | 1159 | agaAGGGUGUGUGUGUUUUUccUgagaa UaagagaaggaaggacagccaaaUUcUU ca |
| 866 | CCUGGUGGCUUCCUUUU | hsa-mir-2300 | hsa-mir-4456 | 1160 | aUgaaCCUGGUGGCUUCCUUUUcUggga ggaagUUagggUUca |
| 867 | UCACAAGGUAUUGACUGGCGUA | hsa-mir-2301 | hsa-mir-4457 | 1161 | ggagUacUccagUcaaUaccgUgUgagU UagaaaagcUcaaUUCACAAGGUAUUGA CUGGCGUAUca |
| 868 | AGAGGUAGGUGUGGAAGAA | hsa-mir-2302 | hsa-mir-4458 | 1162 | gagcgcacAGAGGUAGGUGUGGAAGAAa gUgaaacacUaUUUUaggUUUUagUUac acUcUgcUgUgggUgUgcUg |
| 869 | CCAGGAGGCGGAGGAGGUGGAG | hsa-mir-2303 | hsa-mir-4459 | 1163 | acCCAGGAGGCGGAGGAGGUGGAGgUUg cagUgagccaagaUcgUggcacUgacUc cagccUgggg |
| 870 | GUGGAGGACUGAGAAGGUGAG | hsa-mir-2304 | pending | 1164 | aUgaUGUGGAGGACUGAGAAGGUGAGgc agUUUUgccccgUgcUgccUUccaccgg UUaagaccUccaaaaUcga |
| 871 | ACUGACAGGAGAGCAUUUUGA | hsa-mir-2305 | hsa-mir-3660 | 1165 | ggacaaaaUUaaaaUgcUcUUcUgUcaU UgUaaUagUUcUaUgggcACUGACAGG AGAGCAUUUUGAcUUUgUca |
| 872 | AGCGCGGGCUGAGCGCUGCCAG | hsa-mir-2306 | hsa-mir-2277 | 1166 | ggUUcacUggUcgUgcUUccUgcgggcU gAGCGCGGGCUGAGCGCUGCCAGUcagc g |
| 873 | AAGCUCGGGCGCUCCGGCUGU | hsa-mir-2307 | pending | 1167 | gcUcagUcagcUgggccgccUcagcUcU cggagUaggAAGCUCGGGCGCUCCGGCU GUaaggagcc |
| 874 | AUAGUGGUUGUGAAUUUACCUU | hsa-mir-2308 | hsa-mir-4460 | 1168 | gUUUUUUgcccAUAGUGGUUGUGAAUUU ACCUUcUccUcUUUgcagUgaUaaagga ggUaaaUUcacaaccacUgUgggcagaa ac |
| 875 | GAUUGAGACUAGUAGGGCUAGGC | hsa-mir-2309 | hsa-mir-4461 | 1169 | gagUaggcUUaggUUaUgUacgUagUcU aggccaUacUgUUggaGAUUGAGACUA GUAGGGCUAGGCcUacUg |

TABLE 32-continued

Novel miRNAs identified by deep sequencing analysis.

| SEQ ID NO. | Mature Sequence Captured | Temporary Assigned miRNA ID | miRBase ID | SEQ ID NO. | miRNA Precursor Sequence |
|---|---|---|---|---|---|
| 876 | CUACCCCAGGAUGCCAGCAUAG | hsa-mir-2310 | pending | 1171 | aUagcUggUUggcaUUcUggcccUggUU caUgccaacUcUUgUgUUgaCUACCCCA GGAUGCCAGCAUAGUUgc |
| 877 | ACUGGACUUGGUGUCAGAUGG | hsa-mir-2311 | hsa-mir-378h | 1171 | acaggaacACUGGACUUGGUGUCAGAUG GgaUgagcccUggcUcUgUUUccUagca gcaaUcUgaUcUUgagcUagUcacUgg |
| 878 | GACAAUGAUGAGAAGACCUGAG | hsa-mir-2312 | pending | 1172 | gggGACAAUGAUGAGAAGACCUGAGgaU UUgcagcccccagcccUgggUUcaagUc ccagcUcUaccccUUcUUggcccc |
| 879 | ACCGCUCGAUCUUGGGACC | hsa-mir-2313 | pending | 1173 | gUUUcACCGCUCGAUCUUGGGACCcacc gcUgcccUcagcUccgagUccagggcga ggUaagggcUggagUcgggcagga |
| 880 | UAGUGGAUGAUGGAGACUCGGU | hsa-mir-2314 | hsa-mir-3691 | 1174 | aUUgaggcacUgggUAGUGGAUGAUGGA GACUCGGUacccacUgcUgagggUgggg accaagUcUgcgUcaUccUcUccUcagU gccUcaaa |
| 881 | CUCGGGAGCGUUAGAGAUGGA | hsa-mir-2315 | pending | 1175 | gUCUCGGGAGCGUUAGAGAUGGAgacUa acgUcUUccaagggagaUUgcgUcUcca cUUUcacccUggUacUgagag |
| 882 | GGCUGGAGCGAGUGCAGUGGUG | hsa-mir-2316 | hsa-mir-3135b | 1176 | UgcccaGGCUGGAGCGAGUGCAGUGGUG cagUcagUccUagcUcacUgcagccUcg aacUccUgggcU |
| 883 | UCAGGUGUGGAAACUGAGGCAG | hsa-mir-2317 | hsa-mir-3934 | 1177 | UUUUCAGGUGUGGAAACUGAGGCAGgag gcagUgaagUaacUUgcUcaggUUgcac agcUgggaagU |
| 884 | UGACACGGAGGGUGGCUUGGGAA | hsa-mir-2318 | hsa-mir-4462 | 1178 | cUUcccagcUgcccUaagUcaggagUgg cUUUccUGACACGGAGGGUGGCUUGGGA Aa |
| 885 | GAAGAUGGUGCUGUGCUGAGGA | hsa-mir-2319 | pending | 1179 | ggUGAAGAUGGUGCUGUGCUGAGGAaag gggaUgcagagcccUgcccagcaccacc accUccUaUg |
| 886 | AAAGACUGCAAUUACUUUUGCG | hsa-mir-2320 | hsa-mir-548u | 1180 | aUggUgcaaaagUaaUgUggUUUUUUUc UUUacUUUUaaUggcAAAGACUGCAAUU ACUUUUGCGcca |
| 887 | GAGACUGGGGUGGGGCC | hsa-mir-2321 | hsa-mir-4463 | 1181 | aaUagaUUaUUggUcaccaccUccagUU UcUgaaUUUgUGAGACUGGGGUGGGGCC UgagaaUUUgc |
| 888 | AAGGUUUGGAUAGAUGCAAUA | hsa-mir-2322 | hsa-mir-4464 | 1182 | ggaaccUUagUAAGGUUUGGAUAGAUGC AAUAaagUaUgUccacagcUgaaaggac aUacUUUaUUgcaUgUaUccaaaccUUa cUaaUUca |
| 889 | AAAGGUAAUUGCAGUUUUUCCC | hsa-mir-2323 | hsa-mir-548ai | 1183 | gUaUUaggUUggUgcAAAGGUAAUUGCA GUUUUUCCCaUUUaaaaUaUggaaaaaa aaaUcacaaUUacUUUUgcaUcaaccUa aUaa |
| 890 | AGGGGACCAAAGAGAUAUAUAG | hsa-mir-2324 | hsa-mir-3144 | 1184 | gaaacUacacUUUaAGGGGACCAAAGAG AUAUAUAGaUaUcagcUaccUaUaUacc UgUUcggUcUcUUUaaagUgUagUUUa |
| 891 | UAAAACUGCAAUUACUUUUA | hsa-mir-2325-1 | hsa-mir-548aj-1 | 1185 | aUUggUgUaaaagUaaUUgcaggUUaUg ccaUUaaaagUaaUggUAAAAACUGCAA UUACUUUUAcacUaac |
| 892 | UAAAACUGCAAUUACUUUUA | hsa-mir-2325-2 | hsa-mir-548aj-2 | 1186 | aaggUaUUaggUUggUgcaaaagUaaUU gcagUUUUUgcUaUUacUUUUaaUggUA AAACUGCAAUUACUUUUAcaccaaccU aaUaUUUa |

TABLE 32-continued

Novel miRNAs identified by deep sequencing analysis.

| SEQ ID NO. | Mature Sequence Captured | Temporary Assigned miRNA ID | miRBase ID | SEQ ID NO. | miRNA Precursor Sequence |
|---|---|---|---|---|---|
| 893 | CUCAAGUAGUCUGACCAGGGGA | hsa-mir-2326 | hsa-mir-4465 | 1187 | caUgUgUccccUggcacgcUaUUUgagg UUUacUaUggaacCUCAAGUAGUCUGAC CAGGGGAacacaUga |
| 894 | UCUGGCUGAGGAGGAAGUGGAG | hsa-mir-2327-1 | pending | 1188 | gcUcUagUagccacagccaUccccUaga gggaUCUGGCUGAGGAGGAAGUGGAGg |
| 895 | UCUGGCUGAGGAGGAAGUGGAG | hsa-mir-2327-2 | pending | 1189 | ccgccUcagUggcUUccUccacagccac cUccggagggaUCUGGCUGAGGAGGAAG UGGAGgUgUcacUgg |
| 896 | GGCGACAAAACGAGACCCUGU | hsa-mir-2328 | hsa-mir-1273c | 1190 | cUgGGCGACAAAACGAGACCCUGUcUUU UUUUUUUcUgagacagagUcUcgUUcU gUUgcccaa |
| 897 | GGGUGCGGGCCGGCGGGG | hsa-mir-2329 | hsa-mir-4466 | 1191 | acgcGGGUGCGGGCCGGCGGGGUagaag ccacccggcccggcccggcccggcga |
| 898 | CCUGCUGGUCAGGAGUGGAUAC | hsa-mir-2330 | hsa-mir-3692 | 1192 | gccaUUCCUGCUGGUCAGGAGUGGAUAC UggagcaaUagaUacagUUccacacUga cacUgcagaagUgga |
| 899 | CAUGCUAGGAUAGAAAGAAUGG | hsa-mir-2331 | hsa-mir-3146 | 1193 | aUUUUcUUUgcUaagUcccUUcUUUcUa UccUagUaUaacUUgaagaaUUcaaaUa gUCAUGCUAGGAUAGAAAGAAUGGgacU Uggccagggaagaa |
| 900 | AAUGUGGAAGUGGUCUGAGGCA | hsa-mir-2332 | pending | 1194 | gaaUagaaagAAUGUGGAAGUGGUCUGA GGCAUaUagagUaUaUgccaagaacacU accaUa |
| 901 | GCAAAGUGAUGAGUAAUACUGG | hsa-mir-2333 | hsa-mir-3609 | 1195 | acagUaacUUUUaUUcUcaUUUUccUUU UcUcUaccUUgUagagaaGCAAAGUGAU GAGUAAUACUGGcUgg |
| 902 | UGGCGGCGGUAGUUAUGGGCUU | hsa-mir-2334 | hsa-mir-4467 | 1196 | UggUGGCGGCGGUAGUUAUGGGCUUcUc UUUcUcaccagcagccccUgggccgccg ccUcccU |
| 903 | AGAGCAGAAGGAUGAGAU | hsa-mir-2335 | hsa-mir-4468 | 1197 | agUcUUcUccUggggcUUUggUggcUaU ggUUgacUgggccacUcAGAGCAGAAGG AUGAGAUg |
| 904 | UGGAAUGGCCUGAAGGUGGA | hsa-mir-2336 | pending | 1198 | ccUggcagcccUcUggccUagUUcccac cacacaUgaggUggUGGAAUGGCCUGAA GGUGGAacaga |
| 905 | GCUCCCUCUAGGGUCGCUCGGA | hsa-mir-2337 | hsa-mir-4469 | 1199 | ccgacgcggagagcggcUcUaggUgggU UUggcggcggcgaggacaccgccGCUCC CUCUAGGGUCGCUCGGAgcgUga |
| 906 | UGGCAAACGUGGAAGCCGAGA | hsa-mir-2338 | hsa-mir-4470 | 1200 | cgagccUcUUUcggcUUUccagUUUgUc UcggUccUUUggaacgUGGCAAACGUGG AAGCCGAGAgggcUcU |
| 907 | UUUGUAUGGAUAUGUGUGUGUA | hsa-mir-2339 | hsa-mir-3149 | 1201 | aUaUacaUacaUgUacacacacaUgUca UccacacacaUacaUaUaUaUgUUUG UAUGGAUAUGUGUGUGUAUgUgUgUa Uac |
| 908 | UGAGGAGAUCGUCGAGGUUGGC | hsa-mir-2340 | hsa-mir-3150b | 1202 | aaagcaggccaaccUcgaggaUcUcccc agccUUggcgUUcaggUgcUGAGGAGAU CGUCGAGGUUGGCcUgcUUc |
| 909 | UGGGAACUUAGUAGAGGUUUAA | hsa-mir-2341 | hsa-mir-4471 | 1203 | ccaaaUUUaaaacUUaaaccUcUacUaa gUUUccaUgaaaagaacccaUGGGAACU UAGUAGAGGUUUAAgUUUUaaaUUUga |
| 910 | GGUGGGGGGUGUUGUUUU | hsa-mir-2342-1 | hsa-mir-4472-1 | 1204 | UggcagcccUUgcUcUcUcacUcUccc UaaUgggcUgaagacagcUcaggggca gGGUGGGGGGUGUUGUUUUUgUUU |

TABLE 32-continued

Novel miRNAs identified by deep sequencing analysis.

| SEQ ID NO. | Mature Sequence Captured | Temporary Assigned miRNA ID | miRBase ID | SEQ ID NO. | miRNA Precursor Sequence |
|---|---|---|---|---|---|
| 911 | GGUGGGGGUGUUGUUUU | hsa-mir-2342-2 | hsa-mir-4472-2 | 1205 | UggUgggGGUGGGGGUGUUGUUUUUgU UUUUgagacagagUcUUgcUccgUcgcc caggccggagU |
| 912 | CUAGUGCUCUCCGUUACAAGUA | hsa-mir-2343 | hsa-mir-4473 | 1206 | aaggaacaggggacacUUgUaaUggaga acacUaagcUaUggacUgcUaUggacUg CUAGUGCUCUCCGUUACAAGUAUccccU gUUaccU |
| 913 | CACUUGUAAUGGAGAACACUAA | hsa-mir-2344 | pending | 1207 | aaaggaacaggggaCACUUGUAAUGGAG AACACUAAgcUaUggacUgcUaUggacU gcUagUgcUcUccgUUacaagUaUcccc UgUUaccUUg |
| 914 | UUGUGGCUGGUCAUGAGGCUAA | hsa-mir-2345 | hsa-mir-4474 | 1208 | UUgccUaccUUgUUagUcUcaUgaUcag acacaaaUaUggcUcUUUUGUGGCUGGUC AUGAGGCUAAcaaggUaggcac |
| 915 | CCCUGGGGUUCUGAGGACAUG | hsa-mir-2346 | pending | 1209 | aUgcUgCCCUGGGGUUCUGAGGACAUGc UcUgacUccccUgaUgUccUcUgUUccU caggUgcUgggcga |
| 916 | CAAGGGACCAAGCAUUCAUUAU | hsa-mir-2347 | hsa-mir-4475 | 1210 | aUcUcaaUgagUgUgUggUUcUaaaUga cUcaUagUCAAGGGACCAAGCAUUCAUU AUgaa |
| 917 | CAGGAAGGAUUUAGGGACAGGC | hsa-mir-2348 | hsa-mir-4476 | 1211 | aaaagccUgUcccUaagUcccUcccagc cUUccagagUUggUgcCAGGAAGGAUUU AGGGACAGGCUUUg |
| 918 | CUAUUAAGGACAUUUGUGAUUC | hsa-mir-2349 | hsa-mir-4477a | 1212 | UccUccUcccaUcaaUcacaaaUgUccU UaaUggcaUUUaaggaUUgCUAUUAAGG ACAUUUGUGAUUCacgggaggaggU |
| 919 | AUUAAGGACAUUUGUGAUUGAU | hsa-mir-2350 | hsa-mir-4477b | 1213 | accUccUcccgUgaaUcacaaaUgUccU UaaUagcaaUccUUaaaUgccAUUAAGG ACAUUUGUGAUUGAUgggaggagga |
| 920 | AAAAGGCAUAAAACCAAGACA | hsa-mir-2351-1 | hsa-mir-3910-2 | 1214 | cUUUUUUgUUgcUUgUcUUggUUUUaU gccUUUUaUgUgccUUgaUaUAAAAGGC AUAAAACCAAGACAagcaacagaaaaac |
| 921 | AAAAGGCAUAAAACCAAGACA | hsa-mir-2351-2 | hsa-mir-3910-1 | 1215 | cUgUcagUUUUUUcUgUUgcUUgUcUUgg UUUUaUgccUUUUaUaUcaaggcacaUA AAAGGCAUAAAACCAAGACAagcaacaa |
| 922 | GAGGCUGAGCUGAGGAG | hsa-mir-2352 | hsa-mir-4478 | 1216 | ggccGAGGCUGAGCUGAGGAGccUccaa accUgUagacagggUcaUgcagUacUag gggcgagccUcaUccccUgcagcccUgg cc |
| 923 | CUGGGAGGUGUGAUAUUGUGGU | hsa-mir-2353 | hsa-mir-3689c | 1217 | gggaggUgUgaUaUcgUggUUccUggga ggUgUgaUaUcgUggUUcCUGGGAGGUG UGAUAUUGUGGUUccU |
| 924 | UAAAAACUGCAAUUACUUUC | hsa-mir-2354-1 | hsa-mir-548x-2 | 1218 | aUgccaaaUaUUaggUUggcacaaaagU aaUUgUggcUUUUgccaUUaaaagUaaU ggUAAAAACUGCAAUUACUUUCgUgcca accUaaUaUUUgUgUg |
| 925 | UAAAAACUGCAAUUACUUUC | hsa-mir-2354-2 | hsa-mir-548x-1 | 1219 | agUgcaaaagUaaUUgcagUUUUUgcgU UacUUUcaaUcgUAAAAACUGCAAUUAC UUUCacacc |
| 926 | UGUGAUAUCAUGGUUCCUGGGA | hsa-mir-2355-1 | hsa-mir-3689a | 1220 | gcUcccUggaggUGUGAUAUCAUGGUU CCUGGGAggUgUgaUccUgUgcUUccUg ggaggUgUgaUaUcgUggUUccUgggag g |
| 927 | GGGAGGUGUGAUCUCACACUCG | has-mir-2356-1 | hsa-mir-3689d-1 | 1221 | UGGGAGGUGUGAUCUCACACUCGcUggg aggUgUgcUaUcgUcUUccccgggaggU gUgaUccUgUUcUUUccUg |

TABLE 32-continued

Novel miRNAs identified by deep sequencing analysis.

| SEQ ID NO. | Mature Sequence Captured | Temporary Assigned miRNA ID | miRBase ID | SEQ ID NO. | miRNA Precursor Sequence |
|---|---|---|---|---|---|
| 928 | CUGGGAGGUGUGAUAUUGUGGU | mir-2355-2* | has-mir-3689b-1 | 1222 | gggaggUGUGAUAUCAUGGUUCCUGGGA ggUgUgaUcccgUgcUUcCUGGGAGGUG UGAUAUUGUGGUUccU |
| 929 | UGUGAUAUCAUGGUUCCUGGGA | hsa-mir-2355-2 | hsa-mir-3689b-1 | 1223 | gggaggUGUGAUAUCAUGGUUCCUGGGA ggUgUgaUcccgUgcUUcCUGGGAGGUG UGAUAUUGUGGUUccU |
| 930 | GGGAGGUGUGAUCUCACACUCG | has-mir-2356-2 | hsa-mir-3689d-2 | 1224 | acUGGGAGGUGUGAUCUCACACUCGcUg ggaggUgUgcUaUcgUcUUcccUgggag gUgUgaUccUgUUcUUccUgagcg |
| 931 | UGUGAUAUCAUGGUUCCUGGGA | hsa-mir-2355-3 | has-mir-3689b-2 | 1225 | gggaggUGUGAUAUCAUGGUUCCUGGGA ggUaUgaUaUcgUggUUccUgggaggUg UgaUcccgUgcUcccU |
| 932 | UGUGAUAUCGUGCUUCCUGGGA | hsa-mir-2355b | hsa-mir-3689f | 1226 | aggUGUGAUAUCGUGCUUCCUGGGAcgU gUgaUgcUgUgcUUccUgggaggUgUga UcccacacUc |
| 933 | CGCGCGGCCGUGCUCGGAGCAG | hsa-mir-2356 | hsa-mir-4479 | 1227 | gaaaccaagUccgagcgUggcUggcgcg ggaaagUUcgggaacgCGCGCGGCCGUG CUCGGAGCAGcgcca |
| 934 | CCAGGCUCUGCAGUGGGAACU | hsa-mir-2357a | hsa-mir-3155a | 1228 | ccUgUUccgggcaUcaccUcccacUgca gagccUggggagccggacagcUcccUUc CCAGGCUCUGCAGUGGGAACUgaUgccU ggaacagU |
| 935 | CCAGGCUCUGCAGUGGGA | hsa-mir-2357b | hsa-mir-3155b | 1229 | ccacUgcagagccUgggaagggagcUgU ccggcUccCCAGGCUCUGCAGUGGGAgU |
| 936 | AAAAGUAACUGCGGUUUUUGA | hsa-mir-2358 | hsa-mir-548ak | 1230 | gUgcAAAAGUAACUGCGGUUUUUGAgaa gUaaUUgaaaaccgcaaUUacUUUUgca g |
| 937 | AGCCAAGUGGAAGUUACUUUA | hsa-mir-2359 | hsa-mir-4480 | 1231 | gcagaggUgagUUgaccUccacagggcc acccaggagUaagUAGCCAAGUGGAAG UUACUUUAccUcUgU |
| 938 | GGAGUGGGCUGGUGGUU | hsa-mir-2360 | hsa-mir-4481 | 1232 | GGAGUGGGCUGGUGGUUUUUUaagagga agggagaccUaagcUagcacaUgagcac gcUc |
| 939 | GAGCGAUCCGAGGGACUG | hsa-mir-2361 | pending | 1233 | cggcUUcccgcggUccccggUgcUgagg agaGAGCGAUCCGAGGGACUGcgccgcc |
| 940 | AAGGGCUUCCUCUCUGCAGGAC | hsa-mir-2362-1 | hsa-mir-3158-2 | 1234 | acaUUaUUcaggccggUccUgcagagag gaagcccUUccaaUaccUgUaagcagAA GGGCUUCCUCUCUGCAGGACcggccUga aUaaUga |
| 941 | AAGGGCUUCCUCUCUGCAGGAC | hsa-mir-2362-2 | hsa-mir-3158-1 | 1235 | ggaUcaUUaUUcaggccggUccUgcaga gaggaagcccUUcUgcUUacaggUaUUg gAAGGGCUUCCUCUCUGCAGGACcggcc UgaaUaaUgUaaUca |
| 942 | AACCCAGUGGGCUAUGGAAAUG | hsa-mir-2363 | hsa-mir-4482 | 1236 | agUgagcAACCCAGUGGGCUAUGGAAAU GUgUggaagaUggcaUUcUaUUUcUca gUggggcUcUUacc |
| 943 | GGGGUGGUCUGUUGUUG | hsa-mir-2364 | hsa-mir-4483 | 1237 | aaaaaacaacaUacUUUagUgcaUaccca UaUaaUaUUaGGGGUGGUCUGUUGUUGU UUUUcU |
| 944 | AAAAGGCGGGAGAAGCCCCA | hsa-mir-2365 | hsa-mir-4484 | 1238 | gggUUUccUcUgccUUUUUUUccaaUga aaaUaacgaaaccUgUUaUUUcccaUUg aggggaAAAAGGCGGGAGAAGCCCCA |
| 945 | UGGCUGUUGGAGGGGCAGGCU | hsa-mir-2366 | pending | 1239 | ggagccagcccUccUcccgcacccaaac UUggagcacUUgaccUUUGGCUGUUGGA GGGGGCAGGCUcg |

TABLE 32-continued

Novel miRNAs identified by deep sequencing analysis.

| SEQ ID NO. | Mature Sequence Captured | Temporary Assigned miRNA ID | miRBase ID | SEQ ID NO. | miRNA Precursor Sequence |
|---|---|---|---|---|---|
| 946 | UAACGGCCGCGGUACCCUAA | hsa-mir-2367 | hsa-mir-4485 | 1240 | agaggcaccgccUgcccagUgacaUgcgUUUAACGGCCGCGGUACCCUAAcUgUgca |
| 947 | UAGGAUUACAAGUGUCGGCCAC | hsa-mir-2368 | hsa-mir-3159 | 1241 | ccUAGGAUUACAAGUGUCGGCCACgggcUgggcacagUggcUcacgccUgUaaUcccagc |
| 948 | GCUGGGCGAGGCUGGCA | hsa-mir-2369 | hsa-mir-4486 | 1242 | gcaUGCUGGGCGAGGCUGGCAUcUagcacaggcggUagaUgcUUgcUcUUgccaUUgcaaUga |
| 949 | AGAGCUGGCUGAAGGGCAG | hsa-mir-2370 | hsa-mir-4487 | 1243 | acUgUccUUcagccAGAGCUGGCUGAAGGGCAGaagggaacUgUccUUcagccagagcUggcUgaagggcaga |
| 950 | AGGGGGCGGGCUCCGGCG | hsa-mir-2371 | hsa-mir-4488 | 1244 | ggUAGGGGGCGGGCUCCGGCGcUgggacccacUagggUggcgccUUggccccgccccgccc |
| 951 | GCCGAGAGUCGUCGGGGUU | hsa-mir-2372 | pending | 1245 | UcGCCGAGAGUCGUCGGGGUUccUgcUUcaacagUgcUUggacggaacccggcgc |
| 952 | UGGGGCUAGUGAUGCAGGACG | hsa-mir-2373 | hsa-mir-4489 | 1246 | gggggUGGGGCUAGUGAUGCAGGACGcUggggacUggagaagUccUgccUgacccUgUccca |
| 953 | UGUGACUUUAAGGGAAAUGGCG | hsa-mir-2374 | hsa-mir-3164 | 1247 | UggaaacUGUGACUUUAAGGGAAAUGGCGcacagcagacccUgcaaUcaUgccgUUUUgcUUgaagUcgcagUUUccc |
| 954 | UCUCAGGAGUAAAGACAGAGUU | hsa-mir-2375 | hsa-mir-3664 | 1248 | aacUUgaaggUagggaacUcUgUcUUcacUcaUgagUaccUUccaacacgagcUCUCAGGAGUAAAGACAGAGUUcccUaccUUcaaUgU |
| 955 | AGGUGGAUGCAAUGUGACCUCA | hsa-mir-2376 | hsa-mir-3165 | 1249 | caAGGUGGAUGCAAUGUGACCUCAacUcUUggUccUcUgaggUcacaUUgUaUccaccUUa |
| 956 | AACGGCAAUGACUUUUGUACCA | hsa-mir-2377 | hsa-mir-548al | 1250 | ggUcggUgcaaaagUaaUUgcUgUUUUUgccaUUaaaaaUaaUggcaUUaaaagUaaUggcaaaAACGGCAAUGACUUUUGUACCAaUcUaaUaUcU |
| 957 | UCUGGUAAGAGAUUUGGGCAUA | hsa-mir-2378 | hsa-mir-4490 | 1251 | aUagUUUcUgcaaUgcUcaaaUcUcUggccaaagaccagaacUUaaUggUcUCUGGUAAGAGAUUUGGGCAUAUUagaaacUaa |
| 958 | AAUGUGGACUGGUGUGACCAAA | hsa-mir-2379-1 | hsa-mir-4491 | 1252 | acaUUUggUcacaccagUccacaUUaacgUggaccagacaaUaUUAAUGUGGACUGGUGUGACCAAAa |
| 959 | AAUGUGGACUGGUGUGACCAAA | hsa-mir-2379-2 | pending | 1253 | accUggacaUUUggUcacaccagUccacaUUaacgUggaccagacaaUaUUAAUGUGGACUGGUGUGACCAAAagUccaggc |
| 960 | GGGGCUGGGCGCGCGCC | hsa-mir-2380 | hsa-mir-4492 | 1254 | cUgcagcgUgcUUcUccaggccccgcgcgcggacagacacacggacaagUcccgccaGGGGCUGGGCGCGCGCCagccgg |
| 961 | AGAAGGCCUUUCCAUCUCUGU | hsa-mir-2381 | hsa-mir-4493 | 1255 | ccagagaUgggaaggccUUccggUgaUUaUcacagccaUgccUUUaccUccAGAAGGCCUUUCCAUCUCUGUc |
| 962 | CCAGACUGUGGCUGACCAGAGG | hsa-mir-2382 | hsa-mir-4494 | 1256 | agUUUUagUUacccUggUcaUcUgcagUcUgaaaaUacaaaaUggaaaaUUCCAGACUGUGGCUGACCAGAGGUaacUgaaacc |
| 963 | AGGAGAAGCAGGAGCUGU | hsa-mir-2383 | pending | 1257 | cUgAGGAGAAGCAGGAGCUGUcUUggUacaUUcaggUcacUg |

TABLE 32-continued

Novel miRNAs identified by deep sequencing analysis.

| SEQ ID NO. | Mature Sequence Captured | Temporary Assigned miRNA ID | miRBase ID | SEQ ID NO. | miRNA Precursor Sequence |
|---|---|---|---|---|---|
| 964 | AAUGUAAACAGGCUUUUUGCU | hsa-mir-2384 | hsa-mir-4495 | 1258 | aagaAAUGUAAACAGGCUUUUUGCUcag UggagUUaUUUUgagcaaaaagcUUaUU UacaUUUcUg |
| 965 | GAGGAAACUGAAGCUGAGAGGG | hsa-mir-2385 | hsa-mir-4496 | 1259 | ACAUCAGCUCAUAUAAUCCUCGAAGCUG CCUUUAGAAAUGAGGAAACUGAAGCUGA GAGGG |
| 966 | CUCCGGGACGGCUGGGC | hsa-mir-2386 | hsa-mir-4497 | 1260 | acCUCCGGGACGGCUGGGCgccggcggc cgggagaUccgcgcUUccUgaaUcccgg ccgccccgcccggcgcccgUccgcccgc gggUc |
| 967 | UGGGCUGGCAGGGCAAGUGCUG | hsa-mir-2387 | hsa-mir-4498 | 1261 | agggcUGGGCUGGCAGGGCAAGUGCUGc agaUcUUUgUcUaagcagccccUgccUU ggaUcUccca |
| 968 | GAGGCUGAAGGAAGAUGG | hsa-mir-2388 | hsa-mir-4419b | 1262 | cUcaggcUcagUggUgcaUgcUUaUagU cccagccacUcUgGAGGCUGAAGGAAGA UGGcUUgagccU |
| 969 | AAGACUGAGAGGAGGGA | hsa-mir-2389 | hsa-mir-4499 | 1263 | AAGACUGAGAGGAGGGAacUggUgagUU gUacaUagaaaUgcUUUcUaacUccUUg UcUcagUcUgUUU |
| 970 | UGAGGUAGUAGUUUCUU | hsa-mir-2390 | hsa-mir-4500 | 1264 | caggagagaaagUacUgcccagaagcUa aagUgUagaUcaaacgcaUaaUggcUGA GGUAGUAGUUUCUUgaacUU |
| 971 | CGGCUGGGAGCCGAGGCGUCGG | hsa-mir-2391 | pending | 1265 | ggCGGCUGGGAGCCGAGGCGUCGGUgca gaccUggagacgggcaUgggggggcUgc ggcUgcUggcUgUg |
| 972 | UAUGUGACCUCGGAUGAAUCA | hsa-mir-2392 | hsa-mir-4501 | 1266 | UAUGUGACCUCGGAUGAAUCAcUgaaaU aUgUcUgagcUUcUgUUUcaUcagaUgU cacaUUUU |
| 973 | GCUGAUGAUGAUGGUGCUGAAG | hsa-mir-2393 | hsa-mir-4502 | 1267 | agccUUUagcaagUUgUaaUcUUUUUgc UgaUggagggUcUUgccUccaUggggaU gGCUGAUGAUGAUGGUGCUGAAGgc |
| 974 | AGAUGUAUGGAAUCUGUAUAU | hsa-mir-2394 | hsa-mir-3171 | 1268 | gAGAUGUAUGGAAUCUGUAUAUaUcUaU aUaUaUgUaUaUaUagaUUccaUaaa UcUa |
| 975 | UUUAAGCAGGAAAUAGAAUUUA | hsa-mir-2395 | hsa-mir-4503 | 1269 | acaaUgUagaUaUUUAAGCAGGAAAUAG AAUUUAcaUaUaaaUUUcUaUUUgUUUc UaUUUccUgcUUaaaUaUcUacaUUgc |
| 976 | UGUGACAAUAGAGAUGAACAUG | hsa-mir-2396 | hsa-mir-4504 | 1270 | cUaagaUaaUgUccUccaggUUcaUcUc UgUUgUcaUUUgUggcaUggaccaUUUG UGACAAUAGAGAUGAACAUGgaggaUaU UaUcUUaa |
| 977 | AGGCUGGGCUGGGACGGA | hsa-mir-2397 | hsa-mir-4505 | 1271 | ggAGGCUGGGCUGGGACGGAcacccggc cUccacUUUcUgUggcaggUaccUccUc caUgUcggcccgccUUg |
| 978 | AAAUGGGUGGUCUGAGGCAA | hsa-mir-2398 | hsa-mir-4506 | 1272 | UggccUcUgccaUcagaccaUcUgggUU caagUUUggcUccaUcUUUaUgAAAUGG GUGGUCUGAGGCAAgUggUcU |
| 979 | UAGGAUGGGGUGAGAGGUG | hsa-mir-2399 | hsa-mir-2392 | 1273 | aUggUcccUcccaaUccagccaUUccUc agaccaggUggcUcccgagccaccccag gcUgUAGGAUGGGGUGAGAGGUGcag |
| 980 | CUGGGUUGGCUGGGCUGGG | hsa-mir-2400 | hsa-mir-4507 | 1274 | UcUgggcUgagccgagcUgggUUaagcc gagCUGGGUUGGCUGGGCUGGGU |
| 981 | AAGGGACUGGAGUGGAUUGGGU | hsa-mir-2401 | pending | 1275 | ggAAGGGACUGGAGUGGAUUGGGUacaU cUaUUaUagUgggagcaccUacUacaac ccgUcccUcaagagUcgagUcacc |

TABLE 32-continued

Novel miRNAs identified by deep sequencing analysis.

| SEQ ID NO. | Mature Sequence Captured | Temporary Assigned miRNA ID | miRBase ID | SEQ ID NO. | miRNA Precursor Sequence |
|---|---|---|---|---|---|
| 982 | AAGGGGCUGGAGUGGAUUGGGG | hsa-mir-2402 | pending | 1276 | cUggUgaaUcUgggUccgccagccccca gggAAGGGGCUGGAGUGGAUUGGGGaaa UccaU |
| 983 | GCGGGGCUGGGCGCGCG | hsa-mir-2403 | hsa-mir-4508 | 1277 | aggacccaGCGGGGCUGGGCGCGCGgag cagcgcUgggUgcagcgccUgcgccggc agcUgcaagggccg |
| 984 | ACUAAAGGAUAUAGAAGGUUUU | hsa-mir-2404-1 | hsa-mir-4509-1 | 1278 | cUUUaaUacUaUcUcaaACUAAAGGAUA UAGAAGGUUUUcccUUUcUcUUgcccUg aaaccUUcUgUaUccUUUaUUUUgagaU agUaUUagaa |
| 985 | ACUAAAGGAUAUAGAAGGUUUU | hsa-mir-2404-2 | hsa-mir-4509-2 | 1279 | cUUUaaUacUaUcUcaaACUAAAGGAUA UAGAAGGUUUUcccUUUcUcUUgcccUg aaaccUUcUgUaUccUUUaUUUUgagaU agUaUUagaa |
| 986 | ACUAAAGGAUAUAGAAGGUUUU | hsa-mir-2404-3 | hsa-mir-4509-3 | 1280 | cUUUaaUacUaUcUcaaACUAAAGGAUA UAGAAGGUUUUcccUUUcUcUUgcccUg aaaccUUcUgUaUccUUUaUUUUgagaU agUaUUagaa |
| 987 | AAGCAAUACUGUUACCUGAAAU | hsa-mir-2405 | hsa-mir-3942 | 1281 | cUcaaagAAGCAAUACUGUUACCUGAAA UaggcUgcgaagaUaacagUaUUUcaga UaacagUaUUacaUcUUUgaa |
| 988 | UGAGGGAGUAGGAUGUAUGGUU | hsa-mir-2406 | hsa-mir-4510 | 1282 | gUgUaUgUGAGGGAGUAGGAUGUAUGGU UgUUagaUagacaacUacaaUcUUUUcU cacaacagacag |
| 989 | GAAGAACUGUUGCAUUUGCCCU | hsa-mir-2407 | hsa-mir-4511 | 1283 | aaaaaaagggaaaGAAGAACUGUUGCA UUUGCCCUgcacUcagUUUgcacagggU aaaUgcaaUagUUcUUcUUUcccUUUUU UUa |
| 990 | CAGGGCCUCACUGUAUCGCCCA | hsa-mir-2408 | hsa-mir-4512 | 1284 | cUcagcccgggcaaUaUagUgagaccUc gUcUcUacaaaaaaUUgagaCAGGGCCU CACUGUAUCGCCCAggcUgga |
| 991 | AGACUGACGGCUGGAGGCCCAU | hsa-mir-2409 | hsa-mir-4513 | 1285 | aUUcUaggUggggAGACUGACGGCUGGA GGCCCAUaagcUgUcUaaaacUUcggcc cccagaUUUcUggUcUccccacUUcaga ac |
| 992 | ACAGGCAGGAUUGGGGAA | hsa-mir-2410 | hsa-mir-4514 | 1286 | gUUgagACAGGCAGGAUUGGGGAAacaU cUUUUaccUcgUcUcUUgccUgUUUUag a |
| 993 | AGGACUGGACUCCCGGCAGCCC | hsa-mir-2411 | hsa-mir-4515 | 1287 | gcgggaggUgUaacAGGACUGGACUCCC GGCAGCCCcagggcaggggcgUggggag cUggUccUagcUcagcgcUcccgga |
| 994 | UAGUGAGUUAGAGAUGCAGAGC | hsa-mir-2412 | hsa-mir-3174 | 1288 | agcgUUaccUggUAGUGAGUUAGAGAUG CAGAGCcccUgggcUccUcagcaaaccUa cUggaUcUgca |
| 995 | ACUGGCCUGGGACUACCGGGGG | hsa-mir-2413 | hsa-mir-3176 | 1289 | UcUgcagcUcccggcagccUcgggccac acUcccgggaUcccagggACUGGCCUG GGACUACCGGGGGUggcggc |
| 996 | GGGAGAAGGGUCGGGGC | hsa-mir-2414 | hsa-mir-4516 | 1290 | aGGGAGAAGGGUCGGGGCagggagggca gggcaggcUcUggggUggggggUcUgUg agUcagccacgUcUgcccacgUcUcc cc |
| 997 | UGGGGCGGAGCUUCCGGAGGCC | hsa-mir-2415-1 | hsa-mir-3180-1 | 1291 | agcUUccagacgcUccgccccacgUcgc aUgcgccccgggaacgcgUGGGGCGGAG CUUCCGGAGGCCcc |
| 998 | UGGGGCGGAGCUUCCGGAGGCC | hsa-mir-2415-2 | hsa-mir-3180-2 | 1292 | agcUUccagacgcUccgccccacgUcgc aUgcgccccgggaacgcgUGGGGCGGAG CUUCCGGAGGCCcc |

TABLE 32-continued

Novel miRNAs identified by deep sequencing analysis.

| SEQ ID NO. | Mature Sequence Captured | Temporary Assigned miRNA ID | miRBase ID | SEQ ID NO. | miRNA Precursor Sequence |
|---|---|---|---|---|---|
| 999 | UGGGGCGGAGCUUCCGGAGGCC | hsa-mir-2415-3 | hsa-mir-3180-3 | 1293 | agcUUccagacgcUccgccccacgUcgc aUgcgccccgggaacgcgUGGGGCGGAG CUUCCGGAGGCCcc |
| 1000 | UGGGGCGGAGCUUCCGGAGGCC | hsa-mir-2415-4 | hsa-mir-3180-4 | 1294 | agcUUccagacgcUccgccccacgUcgc aUgcgccccgggaacgcgUGGGGCGGAG CUUCCGGAGGCCcc |
| 1001 | UGGGGCGGAGCUUCCGGAGGCC | hsa-mir-2415-5 | hsa-mir-3180-5 | 1295 | agcUUccagacgcUccgccccacgUcgc aUgcgccccgggaacgcgUGGGGCGGAG CUUCCGGAGGCCcc |
| 1002 | CUCGUGGGCUCUGGCCACGGC | hsa-mir-2416 | hsa-mir-3677 | 1296 | UggagggcaUUaggcagUggccagagcc cUgcagUgcUgggcaUgggcUUCUCGUG GGCUCUGGCCACGGCccUgagcUccUcc |
| 1003 | AGAAGGGGUGAAAUUUAAACGU | hsa-mir-2417-1 | hsa-mir-3179-1 | 1297 | gccaggaUcacagacgUUUaaaUUacac UccUUcUgcUgUgccUUacagcagUAGA AGGGGUGAAAUUUAAACGUcUgUgaUcc Uggg |
| 1004 | AGAAGGGGUGAAAUUUAAACGU | hsa-mir-2417-2 | hsa-mir-3179-2 | 1298 | gaUcacagacgUUUaaaUUacacUccUU cUgcUgUgccUUacagcagUAGAAGGGG UGAAAUUUAAACGUcUgUgaUccUggg |
| 1005 | AGAAGGGGUGAAAUUUAAACGU | hsa-mir-2417-3 | hsa-mir-3179-3 | 1299 | gccaggaUcacagacgUUUaaaUUacac UccUUcUgcUgUgccUUacagcagUAGA AGGGGUGAAAUUUAAACGUcUgUgaUcc Ugg |
| 1006 | AAAUAUGAUGAAACUCACAGCUG AG | hsa-mir-2418 | hsa-mir-4517 | 1300 | aggUAAAUAUGAUGAAACUCACAGCUGA GgagcUUagcaagUagcUaaggccagag cUUgUgUUUgggUggUgUggcUg |
| 1007 | GCUCAGGGAUGAUAACUGUGCUG AGA | hsa-mir-2419 | hsa-mir-4518 | 1301 | UggggaaaagUgcUgggaUUgaUUagU gaUgUcUgcUggggaaccgggGCUCAGG GAUGAUAACUGUGCUGAGAagccccU |
| 1008 | CAGCAGUGCGCAGGGCUG | hsa-mir-2420 | hsa-mir-4519 | 1302 | aaccUCAGCAGUGCGCAGGGCUGcacUg UcUccgUcUgcggccUgcagUaagcggg Ua |
| 1009 | UUGGACAGAAAACACGCAGGAA | hsa-mir-2421 | hsa-mir-4520 | 1303 | gUgUgccaccUgcgUgUUUUcUgUccaa aUcagaaaaggaUUUGGACAGAAAACAC GCAGGAAgaaggaa |
| 1010 | GCUAAGGAAGUCCUGUGCUCAG | hsa-mir-2422 | hsa-mir-4521 | 1304 | UcgGCUAAGGAAGUCCUGUGCUCAGUUU UgUagcaUcaaaacUaggaUUUcUcUUg UUac |
| 1011 | CUGGACUGAGCCAUGCUACUGG | hsa-mir-2423 | hsa-mir-1269b | 1305 | UgaggUUUCUGGACUGAGCCAUGCUACU GGcUUcUcUggUUcUccagcUUacagaU ggcUUaUcaUgggaccUcU |
| 1012 | UGACUCUGCCUGUAGGCCGGU | hsa-mir-2424 | hsa-mir-4522 | 1306 | gcggggcgUUgccUggggggccUcgcaggg ggagaUccagcccaggcUggUUccgcUG ACUCUGCCUGUAGGCCGGUggcgUcUUc Ugg |
| 1013 | GACCGAGAGGGCCUCGGCUGU | hsa-mir-2425 | hsa-mir-4523 | 1307 | gcggggGACCGAGAGGGCCUCGGCUGUg UgaggacUagaggcggccgaggcccggg ccggUUccccga |
| 1014 | UAGAGGCUGGAAUAGAGAUUCU | hsa-mir-2426 | pending | 1308 | aUUUUAGAGGCUGGAAUAGAGAUUCUUg aggcUUggaagagUaaggaUcccUUUaU cUgUccUcUaggag |
| 1015 | UAGCCUUCAGAUCUUGGUGUUU | hsa-mir-2427 | hsa-mir-3614 | 1309 | UggaUcUgaaggcUgccccUUUgcUcUc UggggUAGCCUUCAGAUCUUGGUGUUU |
| 1016 | CCACUUGGAUCUGAAGGCUGCC | hsa-mir-2427* | has-mir-3614 | 1310 | UgggCCACUUGGAUCUGAAGGCUGCCcc UUUgcUcUcUggggUagccUUcagaUcU UggUgUUUU |

TABLE 32-continued

Novel miRNAs identified by deep sequencing analysis.

| SEQ ID NO. | Mature Sequence Captured | Temporary Assigned miRNA ID | miRBase ID | SEQ ID NO. | miRNA Precursor Sequence |
|---|---|---|---|---|---|
| 1017 | AUAGCAGCAUGAACCUGUCUCA | hsa-mir-2428 | hsa-mir-4524 | 1311 | gaacgAUAGCAGCAUGAACCUGUCUCAcUgcagaaUUaUUUUgagacaggcUUaUgcUgcUaUccUUca |
| 1018 | UGAGACAGGCUUAUGCUGCUAU | hsa-mir-2428* | has-mir-4524 | 1312 | ggaacgaUagcagcaUgaaccUgUcUcacUgcagaaUUaUUUUGAGACAGGCUUAUGCUGCUAUccUUca |
| 1019 | GGGGGGAUGUGCAUGCUGGUU | hsa-mir-2429 | hsa-mir-4525 | 1313 | gUcagaGGGGGGAUGUGCAUGCUGGUUggggUgggcUgccUgUggaccaaUcagcgUgcacUUccccacccUgaa |
| 1020 | CAGGGAGGUGAAUGGUUCUGUC | hsa-mir-2430 | pending | 1314 | cUUagcUcccUggcUUcagcccUUUUUcCAGGGAGGUGAAUGGUUCUGUCUcgc |
| 1021 | GCUGACAGCAGGGCUGGCCGCU | hsa-mir-2431 | hsa-mir-4526 | 1315 | UgcggUgacaUcagggcccagUcccUgcUgUcaUgccccaggUgacgUgcUggGCUGACAGCAGGGCUGGCCGCUaacgUcacUgUc |
| 1022 | UGGUCUGCAAAGAGAUGACUGU | hsa-mir-2432 | hsa-mir-4527 | 1316 | ccagaagUGGUCUGCAAAGAGAUGACUGUgaaUccaagaUccacaUcagcUcUgUgcUgccUacaUcUga |
| 1023 | UCAUUAUAUGUAUGAUCUGGAC | hsa-mir-2433 | hsa-mir-4528 | 1317 | UaUUcUacUgagagUacagaUcUUUaUaUaUaUgaUcaUUaUaUgUaUgaUgagaUCAUUAUAUGUAUGAUCUGGACacccagUagaaUc |
| 1024 | AUUGGACUGCUGAUGGCCCGU | hsa-mir-2434 | hsa-mir-4529 | 1318 | aUgacaggccaUcagcagUccaaUgaagacaUgaagacccaaUgUcUUcAUUGGACUGCUGAUGGCCCGUcacUggga |
| 1025 | UUGGAGGGUGUGGAAGACAUC | hsa-mir-2435 | pending | 1319 | cUccacaUUGGAGGGUGUGGAAGACAUCUgggccaacUcUgaUcUcUUcaUcUaccccccaggacUggga |
| 1026 | CCCAGCAGGACGGGAGCG | hsa-mir-2436 | hsa-mir-4530 | 1320 | cgaccgcacccgcccgaagcUgggUcaaggagCCCAGCAGGACGGGAGCGcggcgc |
| 1027 | AUGGAGAAGGCUUCUGA | hsa-mir-2437 | hsa-mir-4531 | 1321 | gccUaggagUccUUggUcagUggggacAUGGAGAAGGCUUCUGAgga |
| 1028 | AAAAGCUGGGUUGAGAA | hsa-mir-2438 | hsa-mir-320e | 1322 | gccUUcUcUUccccagUUcUUccUggagUcggggAAAAGCUGGGUUGAGAAggUgaaaaga |
| 1029 | UGGAAGGUAGACGGCCAGAGAG | hsa-mir-2439 | hsa-mir-3190 | 1323 | ggUcaccUgUcUggccagcUacgUccccacggcccUUgUcagUgUGGAAGGUAGACGGCCAGAGAGgUgaccc |
| 1030 | UCUGGGAGGUUGUAGCAGUGGA | hsa-mir-2440 | hsa-mir-3192 | 1324 | aggaagggaUUCUGGGAGGUUGUAGCAGUGGAaaaagUUcUUUUcUUccUcUgaUcgcccUcUcagcUcUUUUccUUcUg |
| 1031 | CCCCGGGGAGCCCGGCG | hsa-mir-2441 | hsa-mir-4532 | 1325 | acagaCCCCGGGGAGCCCGGCGgUgaagcUccUggUaUccUgggUgUcUga |
| 1032 | UGGAAGGAGGUUGCCGGACGCU | hsa-mir-2442 | hsa-mir-4533 | 1326 | UgagaaUgUGGAAGGAGGUUGCCGGACGCUgcUggcUgccUUccagcgUccacUUcccUUUcUcUcUcc |
| 1033 | CAAGAACCUCAAUUACCUUUGC | hsa-mir-2443 | pending | 1327 | cggUUggUgcaaaggUaaUUgUggUUUcUgccaUUgaaagUaaaggCAAGAACCUCAAUUACCUUUGCagcgaccU |
| 1034 | AAUCUGAGAAGGCGCACAAGGU | hsa-mir-2444 | has-mir-3200 | 1328 | UcgagggAAUCUGAGAAGGCGCACAAGGUUUUgUgUccaaUacagUccacaccUUgcgcUacUcaggUcUgcUcgUg |
| 1035 | CACCUUGCGCUACUCAGGUCUG | hsa-mir-2444* | hsa-mir-3200 | 1329 | UcgagggaaUcUgagaaggcgcacaaggUUUUgUgUccaaUacagUccaCACCUUGCGCUACUCAGGUCUGcUcgU |

TABLE 32-continued

Novel miRNAs identified by deep sequencing analysis.

| SEQ ID NO. | Mature Sequence Captured | Temporary Assigned miRNA ID | miRBase ID | SEQ ID NO. | miRNA Precursor Sequence |
|---|---|---|---|---|---|
| 1036 | GGAGGAACCUUGGAGCUUCGGC | hsa-mir-2445 | hsa-mir-3928 | 1330 | ggcUgaagcUcUaaggUUccgccUgcgg gcaggaagcGGAGGAACCUUGGAGCUUC GGCa |
| 1037 | GGAUGGAGGAGGGGUCU | hsa-mir-2446 | hsa-mir-4534 | 1331 | UgUgaaUgaccccUUccagagccaaaa UcaccagGGAUGGAGGAGGGGUCUUggg UacU |
| 1038 | ACUGGACUAGGAGUCAGAAGG | hsa-mir-2447 | hsa-mir-378i | 1332 | gggagcACUGGACUAGGAGUCAGAAGGU ggagUUcUgggUgcUgUUUUcccacUcU UgggcccUgggcaUgUUcUg |
| 1039 | GUGGACCUGGCUGGGAC | hsa-mir-2448 | hsa-mir-4535 | 1333 | aacUgggUcccagUcUUcacagUUggUU UcUgacacGUGGACCUGGCUGGGACgaU gUg |
| 1040 | ACCUGGACCCAGCGUAGACAAA | hsa-mir-2449 | hsa-mir-3690 | 1334 | ccACCUGGACCCAGCGUAGACAAAgagg UgUUUcUacUccaUaUcUaccUggccc agUgU |
| 1041 | CAAAAACUGCAGUUACUUUUGU | hsa-mir-2450 | hsa-mir-548am | 1335 | agUUggUgcaaaagUaaUUgcggUUUUU gccgUcgaaaaUaaUggCAAAAACUGCA GUUACUUUUGUaccaaUg |
| 1042 | UUGGGCUGGGCUGGGUUGGG | hsa-mir-2451 | hsa-mir-1587 | 1336 | UUUGGGCUGGGCUGGGUUGGGcagUUcU UcUgcUggacUcaccUgUgaccagc |
| 1043 | UGUGGUAGAUAUAUGCACGAU | hsa-mir-2452 | hsa-mir-4536 | 1337 | aUgUgUggUagaUaUaUgcacUgUaUaU aaacaUaaUGUGGUAGAUAUAUGCACGA UaUag |
| 1044 | AGAAGGGAAAGAACAUCAA | hsa-mir-2453 | pending | 1338 | aUggUgUUUgccUccUUcaUccgcaagg caUcUgaUgcccacgaagUUaggaaggU ccUUggggAGAAGGGAAAGAACAUCAAa |
| 1045 | CUGUCCUAAGGUUGUUGAGUU | hsa-mir-2454 | hsa-mir-676 | 1339 | cgcaUgacUcUUcaaccUcaggacUUgc agaaUUaaUggaaUgCUGUCCUAAGGUU GUUGAGUUgUgca |
| 1046 | AAAAGGCAUUGUGGUUUUUG | hsa-mir-2455 | hsa-mir-548an | 1340 | caUUaggUUggUgcAAAAGGCAUUGUGG UUUUUGccUaUaaaagUaaUggcaaaaa ccgcaaUUccUUUUgcaccaaccUaaU |
| 1047 | CGGGCGGCGGCUGUGUUGCGCA | hsa-mir-2456 | pending | 1341 | cacUcgcgcUgcggccagcgcccgggcc UgcgggccCGGGCGGCGGCUGUGUUGCG CAgUc |
| 1048 | UAUGGAAGGGAGAAGAGCUUUA | hsa-mir-2457 | hsa-mir-3202-1 | 1342 | UUaUUaaUAUGGAAGGGAGAAGAGCUUU AaUgaUUggagUcaUUUUcagagcaUUa aagcUcUUcUcccUUccaUaUUaaUgU |
| 1049 | CGGCGGGACGGCGAUUGGU | hsa-mir-1908 | hsa-mir-1908 | 1343 | UgccgCGGCGGGACGGCGAUUGGUccg UaUgUgUgggUgccaccggccgccggcUc cgccccggcc |
| 1050 | CCUCCUGCCCUCCUUGCUGUAG | hsa-mir-1976 | pending | 1344 | gcaaagggUggcagcaaggaaggcaggg gUccUaaggUgUgUCCUCCUGCCCUCCU UGCUGUAGacUUUgg |
| 1051 | UGAGCCGAGCUGAGCUUAGCUG | hsa-mir-2457 | hsa-mir-4537 | 1345 | UGAGCCGAGCUGAGCUUAGCUGggcUga gcUaaccagggcUgggcUgagcUgggcU gagcUgagcUgagc |
| 1052 | GAGCUUGGAUGAGCUGGGCUGA | hsa-mir-2458 | hsa-mir-4538 | 1346 | GAGCUUGGAUGAGCUGGGCUGAacUggg cUgggUUgagcUgggcUgggcUgagUUg agccaggcUgaUcUgggcUgag |
| 1053 | GCUGAACUGGGCUGAGCUGGGC | hsa-mir-2459 | hsa-mir-4539 | 1347 | UgagcUgggcUcUgcUgUgcUgUgcUga gcagggcUgaGCUGAACUGGGCUGAGCU GGGC |
| 1054 | CUGGGCUGAAUGACAGUGAUGAG | hsa-mir-2460 | pending | 1348 | gUcaagUcagaacagccaggUagagccc UUgUccaaacCUGGGCUGAAUGACAGUG AUGAG |

TABLE 32-continued

Novel miRNAs identified by deep sequencing analysis.

| SEQ ID NO. | Mature Sequence Captured | Temporary Assigned miRNA ID | miRBase ID | SEQ ID NO. | miRNA Precursor Sequence |
|---|---|---|---|---|---|
| 1055 | GGGAGCCGGGGCUGUGAGAGGA | hsa-mir-2461 | pending | 1349 | cUcUUUgagccUUggcUgccUUggUgca gcagggUcaUcUgUagggccacccaca gcUcUUUccUUccccUccUcUcUccaGG GAGCCGGGGCUGUGAGAGGA |
| 1056 | UUAGUCCUGCCUGUAGGUUUA | hsa-mir-2462 | hsa-mir-4540 | 1350 | aagcUgcaUggaccaggacUUggcaccU UUggccUUAGUCCUGCCUGUAGGUUUA |

TABLE 33

Primers for Reverse Transcription for a subset of the known miRNAs identified by deep sequencing analysis.

| SEQ ID NO. | Putative Major/Minor miRNA ID | Mature Sequence Captured | Primer for reverse transcription of miRNA | SEQ ID NO. |
|---|---|---|---|---|
| 7 | hsa-mir-129-2* | AAGCCCUUACCCCAAAAAGCAU | AAGCCCTTACCCCAAAAAGCAT | 1351 |
| 22 | hsa-mir-25* | AGGCGGAGACUUGGGCAAUUG | AGGCGGAGACTTGGGCAATTG | 1352 |
| 24 | hsa-mir-30b* | CUGGGAGGUGGAUGUUUACUUC | CTGGGAGGTGGATGTTTACTTC | 1353 |
| 26 | hsa-mir-30c-2* | CUGGGAGAAGGCUGUUUACUCU | CTGGGAGAAGGCTGTTTACTCT | 1354 |
| 27 | hsa-mir-30e* | CUUUCAGUCGGAUGUUUACAGC | CTTTCAGTCGGATGTTTACAGC | 1355 |
| 29 | hsa-mir-342-3p | UCUCACACAGAAAUCGCACCCGU | TCTCACACAGAAATCGCACCCGT | 1356 |
| 56 | hsa-let-7a-2 | UGAGGUAGUAGGUUGUAUAGUU | TGAGGTAGTAGGTTGTATAGTT | 1357 |
| 57 | hsa-let-7a-3 | UGAGGUAGUAGGUUGUAUAGUU | TGAGGTAGTAGGTTGTATAGTT | 1358 |
| 58 | hsa-let-7c | UGAGGUAGUAGGUUGUAUGGUU | TGAGGTAGTAGGTTGTATGGTT | 1359 |
| 63 | hsa-mir-100 | AACCCGUAGAUCCGAACUUGUG | AACCCGTAGATCCGAACTTGTG | 1360 |
| 64 | hsa-mir-101-1 | UACAGUACUGUGAUAACUGAA | TACAGTACTGTGATAACTGAA | 1361 |
| 65 | hsa-mir-101-2 | GUACAGUACUGUGAUAACUGAA | TACAGTACTGTGATAACTGAA | 1362 |
| 66 | hsa-mir-103-1 | AGCAGCAUUGUACAGGGCUAUGA | AGCAGCATTGTACAGGGCTATGA | 1363 |
| 67 | hsa-mir-103-2 | AGCAGCAUUGUACAGGGCUAUGA | AGCAGCATTGTACAGGGCTATGA | 1364 |
| 70 | hsa-mir-106a | AAAAGUGCUUACAGUGCAGGUAG | AAAAGTGCTTACAGTGCAGGTAG | 1365 |
| 71 | hsa-mir-106b | UAAAGUGCUGACAGUGCAGAU | TAAAGTGCTGACAGTGCAGAT | 1366 |
| 72 | hsa-mir-107 | AGCAGCAUUGUACAGGGCUAUCA | AGCAGCATTGTACAGGGCTATCA | 1367 |
| 73 | hsa-mir-10a | UACCCUGUAGAUCCGAAUUUGUG | TACCCTGTAGATCCGAATTTGTG | 1368 |
| 74 | hsa-mir-10b | UACCCUGUAGAACCGAAUUUGUG | TACCCTGTAGAACCGAATTTGTG | 1369 |
| 98 | hsa-mir-128-1 | UCACAGUGAACCGGUCUCUUU | TCACAGTGAACCGGTCTCTTT | 1370 |
| 99 | hsa-mir-128-2 | UCACAGUGAACCGGUCUCUUU | TCACAGTGAACCGGTCTCTTT | 1371 |
| 100 | hsa-mir-129-1 | CUUUUUGCGGUCUGGGCUUGC | CTTTTTGCGGTCTGGGCTTGC | 1372 |
| 101 | hsa-mir-129-2 | CUUUUUGCGGUCUGGGCUUGC | CTTTTTGCGGTCTGGGCTTGC | 1373 |
| 103 | hsa-mir-1295 | UUAGGCCGCAGAUCUGGGUGA | TTAGGCCGCAGATCTGGGTGA | 1374 |
| 119 | hsa-mir-140-3p | UACCACAGGGUAGAACCACGG | TACCACAGGGTAGAACCACGG | 1375 |
| 122 | hsa-mir-143 | UGAGAUGAAGCACUGUAGCUC | TGAGATGAAGCACTGTAGCTC | 1376 |
| 125 | hsa-mir-146a | UGAGAACUGAAUUCCAUGGGUU | TGAGAACTGAATTCCATGGGTT | 1377 |

TABLE 33-continued

Primers for Reverse Transcription for a subset of the
known miRNAs identified by deep sequencing analysis.

| SEQ ID NO. | Putative Major/Minor miRNA ID | Mature Sequence Captured | Primer for reverse transcription of miRNA | SEQ ID NO. |
|---|---|---|---|---|
| 126 | hsa-mir-146b | UGAGAACUGAAUUCCAUAGGCU | TGAGAACTGAATTCCATAGGCT | 1378 |
| 127 | hsa-mir-148a | UCAGUGCACUACAGAACUUUGU | TCAGTGCACTACAGAACTTTGT | 1379 |
| 130 | hsa-mir-151-3p | CUAGACUGAAGCUCCUUGAGG | CTAGACTGAAGCTCCTTGAGG | 1380 |
| 131 | hsa-mir-152 | UCAGUGCAUGACAGAACUUGG | TCAGTGCATGACAGAACTTGG | 1381 |
| 132 | hsa-mir-155 | UUAAUGCUAAUCGUGAUAGGGGU | TTAATGCTAATCGTGATAGGGGT | 1382 |
| 133 | hsa-mir-15a | UAGCAGCACAUAAUGGUUUGUG | TAGCAGCACATAATGGTTTGTG | 1383 |
| 134 | hsa-mir-15b | UAGCAGCACAUCAUGGUUUACA | TAGCAGCACATCATGGTTTACA | 1384 |
| 135 | hsa-mir-16-1 | UAGCAGCACGUAAAUAUUGGCG | TAGCAGCACGTAAATATTGGCG | 1385 |
| 136 | hsa-mir-16-2 | UAGCAGCACGUAAAUAUUGGCG | TAGCAGCACGTAAATATTGGCG | 1386 |
| 137 | hsa-mir-17 | CAAAGUGCUUACAGUGCAGGUAG | CAAAGTGCTTACAGTGCAGGTAG | 1387 |
| 138 | hsa-mir-181a-1 | AACAUUCAACGCUGUCGGUGAGU | AACATTCAACGCTGTCGGTGAGT | 1388 |
| 139 | hsa-mir-181a-2 | AACAUUCAACGCUGUCGGUGAGU | AACATTCAACGCTGTCGGTGAGT | 1389 |
| 140 | hsa-mir-181b-1 | AACAUUCAUUGCUGUCGGUGGGU | AACATTCATTGCTGTCGGTGGG | 1390 |
| 141 | hsa-mir-181b-2 | AACAUUCAUUGCUGUCGGUGGGU | AACATTCATTGCTGTCGGTGGG | 1391 |
| 142 | hsa-mir-181c | AACAUUCAACCUGUCGGUGAGU | AACATTCAACCTGTCGGTGAGT | 1392 |
| 143 | hsa-mir-181d | AACAUUCAUUGUUGUCGGUGGGU | AACATTCATTGTTGTCGGTGGGTT | 1393 |
| 147 | hsa-mir-185 | UGGAGAGAAAGGCAGUUCCUGA | TGGAGAGAAAGGCAGTTCCTGA | 1394 |
| 150 | hsa-mir-18a | UAAGGUGCAUCUAGUGCAGAUAG | TAAGGTGCATCTAGTGCAGATAG | 1395 |
| 151 | hsa-mir-191 | CAACGGAAUCCCAAAAGCAGCUG | CAACGGAATCCCAAAAGCAGCTG | 1396 |
| 152 | hsa-mir-192 | CUGACCUAUGAAUUGACAGCC | CTGACCTATGAATTGACAGCC | 1397 |
| 153 | hsa-mir-193a-5p | UGGGUCUUUGCGGGCGAGAUGA | TGGGTCTTTGCGGGCGAGATGA | 1398 |
| 159 | hsa-mir-196b | UAGGUAGUUUCCUGUUGUUGGG | TAGGTAGTTTCCTGTTGTTGGG | 1399 |
| 160 | hsa-mir-197 | UUCACCACCUUCUCCACCCAGC | TTCACCACCTTCTCCACCCAGC | 1400 |
| 163 | hsa-mir-199b | ACAGUAGUCUGCACAUUGGUUA | ACAGTAGTCTGCACATTGGTTA | 1401 |
| 164 | hsa-mir-19a | UGUGCAAAUCUAUGCAAAACUGA | TGTGCAAATCTATGCAAAACTGA | 1402 |
| 175 | hsa-mir-20a | UAAAGUGCUUAUAGUGCAGGUAG | TAAAGTGCTTATAGTGCAGGTAG | 1403 |
| 176 | hsa-mir-20b | CAAAGUGCUCAUAGUGCAGGUAG | CAAAGTGCTCATAGTGCAGGTAG | 1404 |
| 186 | hsa-mir-221 | AGCUACAUUGUCUGCUGGGUUUC | AGCTACATTGTCTGCTGGGTTTC | 1405 |
| 187 | hsa-mir-222 | AGCUACAUCUGGCUACUGGGU | AGCTACATCTGGCTACTGGGT | 1406 |
| 190 | hsa-mir-23a | AUCACAUUGCCAGGGAUUUCC | ATCACATTGCCAGGGATTTCC | 1407 |
| 194 | hsa-mir-25 | CAUUGCACUUGUCUCGGUCUGA | CATTGCACTTGTCTCGGTCTGA | 1408 |
| 195 | hsa-mir-26a-1 | UUCAAGUAAUCCAGGAUAGGCU | TTCAAGTAATCCAGGATAGGCT | 1409 |
| 196 | hsa-mir-26a-2 | UUCAAGUAAUCCAGGAUAGGCU | TTCAAGTAATCCAGGATAGGCT | 1410 |
| 197 | hsa-mir-26b | UUCAAGUAAUUCAGGAUAGGU | TTCAAGTAATTCAGGATAGGT | 1411 |
| 198 | hsa-mir-27a | UUCACAGUGGCUAAGUUCCGC | TTCACAGTGGCTAAGTTCCGC | 1412 |
| 203 | hsa-mir-29a | UAGCACCAUCUGAAAUCGGUUA | TAGCACCATCTGAAATCGGTTA | 1413 |

TABLE 33-continued

Primers for Reverse Transcription for a subset of the known miRNAs identified by deep sequencing analysis.

| SEQ ID NO. | Putative Major/Minor miRNA ID | Mature Sequence Captured | Primer for reverse transcription of miRNA | SEQ ID NO. |
|---|---|---|---|---|
| 208 | hsa-mir-30a | UGUAAACAUCCUCGACUGGAAG | TGTAAACATCCTCGACTGGAAG | 1414 |
| 209 | hsa-mir-30b | UGUAAACAUCCUACACUCAGCU | TGTAAACATCCTACACTCAGCT | 1415 |
| 210 | hsa-mir-30c-1 | UGUAAACAUCCUACACUCUCAGC | TGTAAACATCCTACACTCTCAGC | 1416 |
| 211 | hsa-mir-30c-2 | UGUAAACAUCCUACACUCUCAGC | TGTAAACATCCTACACTCTCAGC | 1417 |
| 212 | hsa-mir-30d | UGUAAACAUCCCCGACUGGAAG | TGTAAACATCCCCGACTGGAAG | 1418 |
| 213 | hsa-mir-30e | UGUAAACAUCCUUGACUGGAAG | TGTAAACATCCTTGACTGGAAG | 1419 |
| 216 | hsa-mir-320a | AAAAGCUGGGUUGAGAGGGCGA | AAAAGCTGGGTTGAGAGGGCGA | 1420 |
| 217 | hsa-mir-320b-1 | AAAAGCUGGGUUGAGAGGGCAA | AAAAGCTGGGTTGAGAGGGCAA | 1421 |
| 218 | hsa-mir-320b-2 | AAAAGCUGGGUUGAGAGGGCAA | AAAAGCTGGGTTGAGAGGGCAA | 1422 |
| 227 | hsa-mir-331 | GCCCCUGGGCCUAUCCUAGAA | GCCCCTGGGCCTATCCTAGAA | 1423 |
| 231 | hsa-mir-33a | GUGCAUUGUAGUUGCAUUGCA | GTGCATTGTAGTTGCATTGCA | 1424 |
| 233 | hsa-mir-340 | UUAUAAAGCAAUGAGACUGAUU | TTATAAAGCAATGAGACTGATT | 1425 |
| 236 | hsa-mir-34a | UGGCAGUGUCUUAGCUGGUUGU | TGGCAGTGTCTTAGCTGGTTGT | 1426 |
| 239 | hsa-mir-361-5p | UUAUCAGAAUCUCCAGGGGUAC | TTATCAGAATCTCCAGGGGTAC | 1427 |
| 241 | hsa-mir-363 | AAUUGCACGGUAUCCAUCUGUA | AATTGCACGGTATCCATCTGTA | 1428 |
| 242 | hsa-mir-365-2 | UAAUGCCCCUAAAAAUCCUUAU | TAATGCCCCTAAAAATCCTTAT | 1429 |
| 246 | hsa-mir-374a | UUAUAAUACAACCUGAUAAGUG | TTATAATACAACCTGATAAGTG | 1430 |
| 250 | hsa-mir-378 | ACUGGACUUGGAGUCAGAAGG | ACTGGACTTGGAGTCAGAAGG | 1431 |
| 259 | hsa-mir-423 | UGAGGGGCAGAGAGCGAGACUUU | TGAGGGGCAGAGAGCGAGACTTT | 1432 |
| 265 | hsa-mir-449a | UGGCAGUGUAUUGUUAGCUGGU | TGGCAGTGTATTGTTAGCTGGT | 1433 |
| 287 | hsa-mir-503 | UAGCAGCGGGAACAGUUCUGCAG | TAGCAGCGGGAACAGTTCTGCAG | 1434 |
| 296 | hsa-mir-532 | CAUGCCUUGAGUGUAGGACCGU | CATGCCTTGAGTGTAGGACCGT | 1435 |
| 316 | hsa-mir-576-3p | AAGAUGUGGAAAAAUUGGAAUC | AAGATGTGGAAAAATTGGAATC | 1436 |
| 327 | hsa-mir-625 | AGGGGGAAAGUUCUAUAGUCC | AGGGGGAAAGTTCTATAGTCC | 1437 |
| 338 | hsa-mir-7-1 | UGGAAGACUAGUGAUUUUGUUGU | TGGAAGACTAGTGATTTTGTTGT | 1438 |
| 339 | hsa-mir-7-2 | UGGAAGACUAGUGAUUUUGUUGU | TGGAAGACTAGTGATTTTGTTGT | 1439 |
| 340 | hsa-mir-7-3 | UGGAAGACUAGUGAUUUUGUUGU | TGGAAGACTAGTGATTTTGTTGT | 1440 |
| 345 | hsa-mir-874 | CUGCCCUGGCCCGAGGGACCGA | CTGCCCTGGCCCGAGGGACCGA | 1441 |
| 351 | hsa-mir-9-1 | UCUUUGGUUAUCUAGCUGUAUGA | TCTTTGGTTATCTAGCTGTATGA | 1442 |
| 352 | hsa-mir-9-2 | UCUUUGGUUAUCUAGCUGUAUGA | TCTTTGGTTATCTAGCTGTATGA | 1443 |
| 353 | hsa-mir-92a-1 | UAUUGCACUUGUCCCGGCCUGU | TATTGCACTTGTCCCGGCCTGT | 1444 |
| 354 | hsa-mir-92a-2 | UAUUGCACUUGUCCCGGCCUGU | TATTGCACTTGTCCCGGCCTGT | 1445 |
| 356 | hsa-mir-93 | CAAAGUGCUGUUCGUGCAGGUAG | CAAAGTGCTGTTCGTGCAGGTAG | 1446 |
| 357 | hsa-mir-9-3 | UCUUUGGUUAUCUAGCUGUAUGA | TCTTTGGTTATCTAGCTGTATGA | 1447 |
| 364 | hsa-mir-99a | AACCCGUAGAUCCGAUCUUGUG | AACCCGTAGATCCGATCTTGTG | 1448 |
| 387 | hsa-mir-570 | AAAGGUAAUUGCAGUUUUUCCC | AAAGGTAATTGCAGTTTTTCCCA | 1449 |

TABLE 34

Primers for Reverse Transcription of a subset of
novel miRNAs identified by deep sequencing analysis.

| SEQ ID NO. | Temporary Assigned miRNA ID | Mature Sequence Captured | Primer for Reverse Transcription of miRNA | SEQ ID NO. |
|---|---|---|---|---|
| 773 | hsa-miR-378c | ACUGGACUUGGAGUCAGGA | ACTGGACTTGGAGTCAGGA | 1450 |
| 774 | hsa-mir-449c | AGGCAGUGUAUUGCUAGCGGCU | AGGCAGTGTATTGCTAGCGGCTGT | 1451 |
| 775 | hsa-mir-500-2 | UGCACCCAGGCAAGGAUUCUGC | TGCACCCAGGCAAGGATTCTGC | 1452 |
| 784 | hsa-mir-2224 | UGAGGGAGGAGACUGCA | TGAGGGAGGAGACTGCA | 1453 |
| 785 | hsa-mir-2225 | ACUGGACUUGGAGCCAGAAG | ACTGGACTTGGAGCCAGAAG | 1454 |
| 786 | hsa-mir-2226 | GUCACUGAUGUCUGUAGCUGAG | GTCACTGATGTCTGTAGCTGAGACGG | 1455 |
| 787 | hsa-mir-2227 | GAUGAGGAUGGAUAGCAAGGAA | GATGAGGATGGATAGCAAGGAAG | 1456 |
| 789 | hsa-mir-2229 | AAAAGCAUCAGGAAGUACCCA | AAAAGCATCAGGAAGTACCCA | 1457 |
| 796 | hsa-mir-2235 | GUCAAAUGAAGGGCUGAUCACG | GTCAAATGAAGGGCTGATCACGAAATA | 1458 |
| 798 | hsa-mir-2237 | AGAGUUAACUCAAAAUGGACUA | AGAGTTAACTCAAAATGGACTA | 1459 |
| 799 | hsa-mir-2238 | UGUUGGGAUUCAGCAGGACCAU | TGTTGGGATTCAGCAGGACCATT | 1460 |
| 800 | hsa-mir-2239 | UAAAUAGAGUAGGCAAAGGACA | TAAATAGAGTAGGCAAAGGACA | 1461 |
| 805 | hsa-mir-2244 | AAGAGGAAGAAAUGGCUGGUUC | AAGAGGAAGAAATGGCTGGTTCTCAG | 1462 |
| 809 | hsa-mir-2248 | UAGUGGAUGAUGCACUCUGUGC | TAGTGGATGATGCACTCTGTGC | 1463 |
| 814 | hsa-mir-2253 | AAAGACUCUGCAAGAUGCCU | AAAGACTCTGCAAGATGCCT | 1464 |
| 816 | hsa-mir-2255 | AGGAGAAGUAAAGUAGAA | AGGAGAAGTAAAGTAGAA | 1465 |
| 817 | hsa-mir-2256 | AUGGCCAGAGCUCACACAGAGG | ATGGCCAGAGCTCACACAGAGG | 1466 |
| 819 | hsa-mir-2258 | AUCAGGGCUUGUGGAAUGGGAA | ATCAGGGCTTGTGGAATGGGAAG | 1467 |
| 820 | hsa-mir-2259 | AUGGCCAGAGCUCACACAGAGG | ATGGCCAGAGCTCACACAGAGG | 1468 |
| 821 | hsa-mir-2260 | UGAGGAUAUGGCAGGGAAGGGG | TGAGGATATGGCAGGGAAGGGGA | 1469 |
| 825 | hsa-mir-2264 | UGGGCUCAGGGUACAAAGGUU | TGGGCTCAGGGTACAAAGGTTC | 1470 |
| 828 | hsa-mir-2266-1 | GCUGCACCGGAGACUGGGUAA | GCTGCACCGGAGACTGGGTAA | 1471 |
| 829 | hsa-mir-2266-2 | GCUGCACCGGAGACUGGGUAA | GCTGCACCGGAGACTGGGTAA | 1472 |
| 836 | hsa-mir-2272 | UGUCGUGGGGCUUGCUGGCUUG | TGTCGTGGGGCTTGCTGGCTTG | 1473 |
| 838 | hsa-mir-2274 | ACUGGACUUGGAGGCAGAA | ACTGGACTTGGAGGCAGAA | 1474 |
| 841 | hsa-mir-2277 | UUGGAGGCGUGGGUUUU | TTGGAGGCGTGGGTTTT | 1475 |
| 844 | hsa-mir-2280 | CUGACUGAAUAGGUAGGGUCAU | CTGACTGAATAGGTAGGGTCAT | 1476 |
| 846 | hsa-mir-2282 | AGAUUGUUUCUUUUGCCGUGCA | AGATTGTTTCTTTTGCCGTGCA | 1477 |
| 847 | hsa-mir-2282* | CACGGCAAAAGAAACAAUCCA | CACGGCAAAAGAAACAATCCA | 1478 |
| 848 | hsa-mir-2283 | CAGGGCUGGCAGUGACAUGGGU | CAGGGCTGGCAGTGACATGGGT | 1479 |
| 849 | hsa-mir-2284 | GGUGGGGGCUGUUGUUU | GGTGGGGGCTGTTGTTT | 1480 |
| 850 | hsa-mir-2285 | UGGGGAGGUGUGGAGUCAGCAU | TGGGGAGGTGTGGAGTCAGCATG | 1481 |
| 852 | hsa-mir-2287 | GGCUCCUUGGUCUAGGGGUA | GGCTCCTTGGTCTAGGGGTA | 1482 |
| 856 | hsa-mir-2290 | UGGGGAUUUGGAGAAGUGGUGA | TGGGGATTTGGAGAAGTGGTGA | 1483 |
| 857 | hsa-mir-2291 | AAAAGUGAUUGCAGUGUUUG | AAAAGTGATTGCAGTGTTTGCC | 1484 |
| 860 | hsa-mir-2294 | UAGGAGCUCAACAGAUGCCUGU | TAGGAGCTCAACAGATGCCTGT | 1485 |
| 861 | hsa-mir-2295 | AGCUUUUGGGAAUUCAGGUAG | AGCTTTTGGGAATTCAGGTAG | 1486 |

TABLE 34-continued

Primers for Reverse Transcription of a subset of
novel miRNAs identified by deep sequencing analysis.

| SEQ ID NO. | Temporary Assigned miRNA ID | Mature Sequence Captured | Primer for Reverse Transcription of miRNA | SEQ ID NO. |
|---|---|---|---|---|
| 864 | hsa-mir-2298 | CAAAAGUGAUCGUGGUUUUUG | CAAAAGTGATCGTGGTTTTTG | 1487 |
| 865 | hsa-mir-2299 | AGGGUGUGUGUGUUUUU | AGGGTGTGTGTGTTTTT | 1488 |
| 871 | hsa-mir-2305 | ACUGACAGGAGAGCAUUUUGA | ACTGACAGGAGAGCATTTTGA | 1489 |
| 874 | hsa-mir-2308 | AUAGUGGUUGUGAAUUUACCUU | ATAGTGGTTGTGAATTTACCTTC | 1490 |
| 876 | hsa-mir-2310 | CUACCCCAGGAUGCCAGCAUAG | CTACCCCAGGATGCCAGCATAGTT | 1491 |
| 877 | hsa-mir-2311 | ACUGGACUUGGUGUCAGAUGG | ACTGGACTTGGTGTCAGATGG | 1492 |
| 880 | hsa-mir-2314 | UAGUGGAUGAUGGAGACUCGGU | TAGTGGATGATGGAGACTCGGT | 1493 |
| 888 | hsa-mir-2322 | AAGGUUUGGAUAGAUGCAAUA | AAGGTTTGGATAGATGCAATA | 1494 |
| 889 | hsa-mir-2323 | AAAGGUAAUUGCAGUUUUUCCC | AAAGGTAATTGCAGTTTTTCCCA | 1495 |
| 890 | hsa-mir-2324 | AGGGGACCAAAGAGAUAUAUAG | AGGGGACCAAAGAGATATATAG | 1496 |
| 896 | hsa-mir-2328 | GGCGACAAAACGAGACCCUGU | GGCGACAAAACGAGACCCTGTC | 1497 |
| 897 | hsa-mir-2329 | GGGUGCGGGCCGGCGGGG | GGGTGCGGGCCGGCGGGGT | 1498 |
| 899 | hsa-mir-2331 | CAUGCUAGGAUAGAAAGAAUGG | CATGCTAGGATAGAAAGAATGG | 1499 |
| 901 | hsa-mir-2333 | GCAAAGUGAUGAGUAAUACUGG | GCAAAGTGATGAGTAATACTGG | 1500 |
| 915 | hsa-mir-2346 | CCCUGGGGUUCUGAGGACAUG | CCCTGGGGTTCTGAGGACATG | 1501 |
| 917 | hsa-mir-2348 | CAGGAAGGAUUUAGGGACAGGC | CAGGAAGGATTTAGGGACAGGC | 1502 |
| 919 | hsa-mir-2350 | AUUAAGGACAUUUGUGAUUGAU | ATTAAGGACATTTGTGATTGAT | 1503 |
| 920 | hsa-mir-2351-1 | AAAAGGCAUAAAACCAAGACA | AAAAGGCATAAAACCAAGACA | 1504 |
| 921 | hsa-mir-2351-2 | AAAAGGCAUAAAACCAAGACA | AAAAGGCATAAAACCAAGACA | 1505 |
| 924 | hsa-mir-2354-1 | UAAAAACUGCAAUUACUUUC | TAAAAACTGCAATTACTTTC | 1506 |
| 926 | hsa-mir-2355-1 | UGUGAUAUCAUGGUUCCUGGGA | TGTGATATCATGGTTCCTGGGA | 1507 |
| 929 | hsa-mir-2355-2 | UGUGAUAUCAUGGUUCCUGGGA | TGTGATATCATGGTTCCTGGGA | 1508 |
| 931 | hsa-mir-2355-3 | UGUGAUAUCAUGGUUCCUGGGA | TGTGATATCATGGTTCCTGGGA | 1509 |
| 932 | hsa-mir-2355b | UGUGAUAUCGUGCUUCCUGGGA | TGTGATATCGTGCTTCCTGGGA | 1510 |
| 936 | hsa-mir-2358 | AAAAGUAACUGCGGUUUUUGA | AAAAGTAACTGCGGTTTTTGA | 1511 |
| 938 | hsa-mir-2360 | GGAGUGGGCUGGUGGUU | GGAGTGGGCTGGTGGTT | 1512 |
| 940 | hsa-mir-2362-1 | AAGGGCUUCCUCUCUGCAGGAC | AAGGGCTTCCTCTCTGCAGGAC | 1513 |
| 941 | hsa-mir-2362-2 | AAGGGCUUCCUCUCUGCAGGAC | AAGGGCTTCCTCTCTGCAGGAC | 1514 |
| 949 | hsa-mir-2370 | AGAGCUGGCUGAAGGGCAG | AGAGCTGGCTGAAGGGCAG | 1515 |
| 953 | hsa-mir-2374 | UGUGACUUUAAGGGAAAUGGCG | TGTGACTTTAAGGGAAATGGCG | 1516 |
| 954 | hsa-mir-2375 | UCUCAGGAGUAAAGACAGAGUU | TCTCAGGAGTAAAGACAGAGTT | 1517 |
| 955 | hsa-mir-2376 | AGGUGGAUGCAAUGUGACCUCA | AGGTGGATGCAATGTGACCTCA | 1518 |
| 977 | hsa-mir-2397 | AGGCUGGGCUGGGACGGA | AGGCTGGGCTGGGACGGA | 1519 |
| 979 | hsa-mir-2399 | UAGGAUGGGGGUGAGAGGUG | TAGGATGGGGGTGAGAGGTG | 1520 |
| 988 | hsa-mir-2406 | UGAGGGAGUAGGAUGUAUGGUU | TGAGGGAGTAGGATGTATGGTT | 1521 |
| 991 | hsa-mir-2409 | AGACUGACGGCUGGAGGCCCAU | AGACTGACGGCTGGAGGCCCAT | 1522 |

TABLE 34-continued

Primers for Reverse Transcription of a subset of novel miRNAs identified by deep sequencing analysis.

| SEQ ID NO. | Temporary Assigned miRNA ID | Mature Sequence Captured | Primer for Reverse Transcription of miRNA | SEQ ID NO. |
|---|---|---|---|---|
| 994 | hsa-mir-2412 | UAGUGAGUUAGAGAUGCAGAGC | TAGTGAGTTAGAGATGCAGAGC | 1523 |
| 996 | hsa-mir-2414 | GGGAGAAGGGUCGGGGC | GGGAGAAGGGTCGGGGC | 1524 |
| 1002 | hsa-mir-2416 | CUCGUGGGCUCUGGCCACGGC | CTCGTGGGCTCTGGCCACGGCC | 1525 |
| 1003 | hsa-mir-2417-1 | AGAAGGGGUGAAAUUUAAACGU | AGAAGGGGTGAAATTTAAACGT | 1526 |
| 1004 | hsa-mir-2417-2 | AGAAGGGGUGAAAUUUAAACGU | AGAAGGGGTGAAATTTAAACGT | 1527 |
| 1005 | hsa-mir-2417-3 | AGAAGGGGUGAAAUUUAAACGU | AGAAGGGGTGAAATTTAAACGT | 1528 |
| 1007 | hsa-mir-2419 | GCUCAGGGAUGAUAACUGUGCUGAGA | GCTCAGGGATGATAACTGTGCTGAGA | 1529 |
| 1011 | hsa-mir-2423 | CUGGACUGAGCCAUGCUACUGG | CTGGACTGAGCCATGCTACTGG | 1530 |
| 1017 | hsa-mir-2428 | AUAGCAGCAUGAACCUGUCUCA | ATAGCAGCATGAACCTGTCTCA | 1531 |
| 1018 | hsa-mir-2428* | UGAGACAGGCUUAUGCUGCUAU | TGAGACAGGCTTATGCTGCTAT | 1532 |
| 1022 | hsa-mir-2432 | UGGUCUGCAAAGAGAUGACUGU | TGGTCTGCAAAGAGATGACTGTG | 1533 |
| 1025 | hsa-mir-2435 | UUGGAGGGUGUGGAAGACAUC | TTGGAGGGTGTGGAAGACATC | 1534 |
| 1027 | hsa-mir-2437 | AUGGAGAAGGCUUCUGA | ATGGAGAAGGCTTCTGA | 1535 |
| 1028 | hsa-mir-2438 | AAAAGCUGGGUUGAGAA | AAAAGCTGGGTTGAGAAG | 1536 |
| 1029 | hsa-mir-2439 | UGGAAGGUAGACGGCCAGAGAG | TGGAAGGTAGACGGCCAGAGAG | 1537 |
| 1030 | hsa-mir-2440 | UCUGGGAGGUUGUAGCAGUGGA | TCTGGGAGGTTGTAGCAGTGGA | 1538 |
| 1036 | hsa-mir-2445 | GGAGGAACCUUGGAGCUUCGGC | GGAGGAACCTTGGAGCTTCGGCA | 1539 |
| 1038 | hsa-mir-2447 | ACUGGACUAGGAGUCAGAAGG | ACTGGACTAGGAGTCAGAAGG | 1540 |
| 1041 | hsa-mir-2450 | CAAAAACUGCAGUUACUUUUGU | CAAAAACTGCAGTTACTTTTGT | 1541 |
| 1046 | hsa-mir-2455 | AAAAGGCAUUGUGGUUUUUG | AAAAGGCATTGTGGTTTTTG | 1542 |

TABLE 35 miRNAs that differentiate ABC DLBCL vs. GCB DLBCL

| MicroRNA | FoldChange ABC vs. GCB | pVal ABC vs. GCB |
|---|---|---|
| UGGUCUGCAAAGAGAUGACUGUG (SEQ ID NO. 1565) | -4.30138 | 0.001335 |
| CAAAAACUGCAGUUACUUUUGU (SEQ ID NO. 1041) | -3.52085 | 0.022949 |
| UGGGGAUUUGGAGAAGUGGUGA (SEQ ID NO. 856) | -2.8374 | 0.000753 |
| hsa-miR-129-3p | -2.48708 | 7.39E-05 |
| ACUGGACUUGGUGUCAGAUGG (SEQ ID NO. 877) | -1.3712 | 0.01173 |
| hsa-miR-196b | -1.28463 | 0.032606 |
| hsa-miR-9 | -1.00737 | 0.003176 |
| hsa-miR-28-5p | -0.82319 | 0.00026 |
| hsa-miR-365 | -0.78573 | 0.032749 |
| hsa-miR-185 | -0.75345 | 0.044082 |
| hsa-miR-199b-3p | -0.74898 | 0.015518 |
| hsa-miR-152 | -0.67388 | 0.001282 |
| hsa-miR-23a | -0.65979 | 0.028732 |
| hsa-miR-193a-5p | -0.54233 | 0.031154 |
| hsa-miR-27a | -0.49729 | 0.027207 |
| hsa-miR-331-3p | -0.47573 | 0.0128 |
| hsa-miR-301a | -0.45261 | 0.014231 |
| hsa-miR-128 | -0.4224 | 0.024065 |
| AGAUUGUUUCUUUUGCCGUGCA (SEQ ID NO. 846) | 0.557435 | 0.02141 |

TABLE 35-continued miRNAs that differentiate ABC DLBCL vs. GCB DLBCL

| MicroRNA | FoldChange ABC vs. GCB | pVal ABC vs. GCB |
|---|---|---|
| hsa-miR-625 | 0.747299 | 0.01813 |
| hsa-miR-155 | 0.781901 | 0.024175 |
| hsa-miR-20b | 0.986918 | 0.000746 |
| GGCUCCUUGGUCUAGGGGUA (SEQ ID NO. 852) | 1.945372 | 0.002596 |
| UAGUGAGUUAGAGAUGCAGAGC (SEQ ID NO. 994) | 2.347695 | 0.009081 |
| CAGGAAGGAUUUAGGGACAGGC (SEQ ID NO. 917) | 2.519326 | 0.04483 |

*The 3'-end G of SEQ ID NO. 1565 is optionally omitted (providing SEQ ID NO. 1022).

APPENDIX A

Average expression of the genes depicted in FIG. 6*

| ID | Gene Name | Naive vs Germinal Center | | Germinal Center vs Plasma | | Germinal Center vs Memory | |
|---|---|---|---|---|---|---|---|
| | | Naive Average | GC Average | GC average | PC Average | GC Average | Memory Average |
| 1 | VPS37B | 10.60 | 4.58 | 4.58 | 9.71 | | |
| 2 | SCN3A | 9.50 | 3.98 | | | | |
| 3 | NT5E | 10.76 | 5.69 | | | | |
| 4 | TBC1D9 | 12.03 | 7.03 | 7.03 | 11.19 | 7.03 | 12.88 |
| 5 | MAP7 | | | | | 1.64 | 8.03 |
| 6 | SPRY1 | 10.40 | 5.72 | | | | |
| 7 | TNFSF12 | 8.11 | 3.54 | | | 3.54 | 7.55 |
| 8 | SOCS3 | 9.00 | 4.48 | 4.48 | 9.39 | | |
| 9 | EDG1 | 11.43 | 6.91 | | | 6.91 | 8.69 |
| 10 | CTGF | 7.62 | 3.30 | 3.30 | 9.65 | | |
| 11 | FAM46A | 10.65 | 6.46 | | | 6.46 | 8.29 |
| 12 | MOBKL2B | 11.63 | 7.45 | | | | |
| 13 | DNMT3A | 10.56 | 6.44 | 6.44 | 7.85 | | |
| 14 | BHLHB2 | 10.75 | 6.64 | | | 6.64 | 10.96 |
| 15 | LAMC1 | 9.85 | 5.80 | 5.80 | 9.67 | | |
| 16 | CD69 | 13.27 | 9.40 | | | 9.40 | 12.27 |
| 17 | PLEKHA1 | 10.95 | 7.20 | | | | |
| 18 | PTGDR | 7.20 | 3.46 | | | | |
| 19 | TXNIP | 14.89 | 11.20 | 11.20 | 13.39 | 11.20 | 15.10 |
| 20 | SIDT1 | 11.52 | 7.86 | 7.86 | 9.38 | | |
| 21 | LY6E | 8.57 | 4.92 | 4.92 | 7.39 | | |
| 22 | IGF1R | 8.73 | 5.13 | | | | |
| 23 | PRICKLE1 | 11.68 | 8.09 | 8.09 | 9.69 | | |
| 24 | CSDA | 12.12 | 8.59 | 8.59 | 10.10 | | |
| 25 | KLF2 | 12.61 | 9.10 | 9.10 | 11.70 | | |
| 26 | ELOVL2 | 7.32 | 3.86 | | | | |
| 27 | CCND2 | 12.06 | 8.61 | | | 8.61 | 11.53 |
| 28 | LASS6 | 10.29 | 6.86 | 6.86 | 9.42 | 6.86 | 9.48 |
| 29 | DUSP6 | 11.93 | 8.53 | | | 8.53 | 10.19 |
| 30 | CUGBP2 | 14.28 | 10.93 | | | 10.93 | 14.29 |
| 31 | PTPRO | 9.64 | 6.32 | | | 6.32 | 8.63 |
| 32 | PHF16 | 10.33 | 7.04 | | | | |
| 33 | NR3C2 | 8.85 | 5.58 | | | | |
| 34 | CRTC3 | 12.56 | 9.32 | 9.32 | 11.11 | | |
| 35 | ADAMTS6 | 7.68 | 4.45 | | | | |
| 36 | ETV6 | 10.36 | 7.14 | 7.14 | 8.89 | 7.14 | 10.43 |
| 37 | LRRC17 | | | 3.10 | 7.49 | | |
| 38 | FAM46C | 12.18 | 8.98 | 8.98 | 14.76 | 8.98 | 10.54 |
| 39 | SATB2 | 7.20 | 4.02 | 4.02 | 7.60 | | |
| 40 | RNF125 | 9.00 | 5.83 | | | | |
| 41 | ST6GALNAC3 | 8.12 | 4.96 | | | | |
| 42 | LARGE | 9.05 | 5.89 | 5.89 | 8.73 | | |
| 43 | ZNF276 | 9.39 | 6.25 | | | | |
| 44 | KCNA3 | | | 4.83 | 9.82 | | |
| 45 | BCL2 | 10.89 | 7.76 | | | 7.76 | 11.41 |
| 46 | MTSS1 | 12.92 | 9.82 | | | 9.82 | 12.05 |
| 47 | NR6A1 | 9.10 | 6.03 | | | 6.03 | 7.62 |
| 48 | BHLHB3 | 11.11 | 8.05 | 8.05 | 13.26 | 8.05 | 13.26 |
| 49 | MYO10 | 7.22 | 4.19 | | | | |
| 50 | ITM2C | | | 6.44 | 13.85 | | |
| 51 | C18orf1 | 9.49 | 6.47 | 6.47 | 8.63 | | |

APPENDIX A-continued

Average expression of the genes depicted in FIG. 6*

| ID | Gene Name | Naive vs Germinal Center | | Germinal Center vs Plasma | | Germinal Center vs Memory | |
|---|---|---|---|---|---|---|---|
| | | Naive Average | GC Average | GC average | PC Average | GC Average | Memory Average |
| 52 | FXYD7 | 7.36 | 4.35 | | | | |
| 53 | DUSP8 | 7.96 | 4.96 | 4.96 | 8.41 | 4.96 | 7.75 |
| 54 | BTBD3 | 7.41 | 4.42 | | | | |
| 55 | TMEPAI | 11.15 | 8.20 | 8.20 | 11.03 | | |
| 56 | ANTXR2 | 9.90 | 6.97 | | | | |
| 57 | FOSB | 10.13 | 7.21 | 7.21 | 11.05 | | |
| 58 | TMCC3 | 8.23 | 5.31 | 5.31 | 7.09 | 5.31 | 8.05 |
| 59 | ARL4C | 11.31 | 8.41 | | | 8.41 | 10.32 |
| 60 | ZMYND11 | 11.33 | 8.43 | 8.43 | 11.34 | 8.43 | 11.68 |
| 61 | RHOBTB1 | 7.33 | 4.48 | | | | |
| 62 | JUN | 12.14 | 9.34 | 9.34 | 12.70 | | |
| 63 | SKI | 10.46 | 7.67 | | | 7.67 | 10.68 |
| 64 | TMEM121 | 7.07 | 4.29 | | | | |
| 65 | IL13RA1 | 8.99 | 6.21 | | | | |
| 66 | KIF13B | | | 6.23 | 9.01 | | |
| 67 | BHLHB5 | | | 4.26 | 7.39 | | |
| 68 | PGM2L1 | 10.35 | 7.65 | | | | |
| 69 | C14orf4 | 12.11 | 9.47 | 9.47 | 11.01 | 9.47 | 11.65 |
| 70 | PDE4B | 12.38 | 9.74 | 9.74 | 11.60 | | |
| 71 | PDE7B | 8.64 | 6.03 | | | | |
| 72 | BCL9L | 9.37 | 6.77 | 6.77 | 8.61 | | |
| 73 | PCDH9 | 10.32 | 7.73 | | | | |
| 74 | ARHGAP5 | 10.44 | 7.86 | 7.86 | 9.11 | 7.86 | 9.85 |
| 75 | KIAA0802 | 9.18 | 6.61 | 6.61 | 7.91 | 6.61 | 7.89 |
| 76 | ITGB4 | 7.48 | 4.91 | | | | |
| 77 | NOTCH2NL | | | 7.17 | 8.95 | | |
| 78 | CDC42BPA | 7.32 | 4.77 | | | | |
| 79 | SPG20 | 9.25 | 6.73 | | | | |
| 80 | KLF4 | 10.04 | 7.57 | 7.57 | 9.09 | | |
| 81 | AHNAK | 9.34 | 6.87 | 6.87 | 9.56 | 6.87 | 11.51 |
| 82 | FCHSD1 | 9.15 | 6.69 | | | | |
| 83 | KIAA1622 | | | 3.94 | 7.67 | | |
| 84 | PLXNC1 | 10.92 | 8.48 | | | | |
| 85 | TMEM150 | 8.39 | 5.96 | | | | |
| 86 | ACVR2A | 7.81 | 5.38 | 5.38 | 8.63 | 5.38 | 7.40 |
| 87 | KALRN | | | 5.61 | 7.64 | | |
| 88 | ANK2 | 7.69 | 5.28 | 5.28 | 7.54 | 5.28 | 7.00 |
| 89 | FLJ14213 | 7.61 | 5.21 | 5.21 | 7.97 | | |
| 90 | CHPT1 | 10.92 | 8.52 | | | | |
| 91 | TCF2 | | | 5.69 | 7.82 | | |
| 92 | FGF5 | | | 5.41 | 7.52 | | |
| 93 | SLC12A6 | 12.18 | 9.80 | 9.80 | 11.09 | | |
| 94 | MGC17330 | 11.53 | 9.16 | | | | |
| 95 | NR4A2 | 10.21 | 7.85 | 7.85 | 9.21 | 7.85 | 10.54 |
| 96 | SLC39A10 | 11.06 | 8.70 | | | | |
| 97 | LITAF | 12.52 | 10.18 | 10.18 | 11.82 | | |
| 98 | AKT3 | 9.32 | 6.99 | | | 6.99 | 9.25 |
| 99 | PDCD4 | 12.89 | 10.57 | | | 10.57 | 13.33 |
| 100 | STMN3 | 10.03 | 7.72 | | | | |
| 101 | SIDT2 | 13.13 | 10.85 | | | | |
| 102 | GRIA3 | 7.04 | 4.77 | | | | |
| 103 | EML4 | 12.83 | 10.57 | | | | |
| 104 | DIP2B | 11.26 | 8.99 | | | 8.99 | 10.77 |
| 105 | FBN1 | | | 4.89 | 8.17 | | |
| 106 | FAM84B | 9.21 | 6.96 | | | | |
| 107 | EGR3 | 11.59 | 9.35 | 9.35 | 8.24 | 9.35 | 10.62 |
| 108 | CTHRC1 | | | 4.25 | 11.94 | | |
| 109 | RRAGD | 7.69 | 5.46 | | | | |
| 110 | MACF1 | 12.88 | 10.66 | | | | |
| 111 | FOXF2 | 7.05 | 4.83 | | | | |
| 112 | GAB1 | 8.01 | 5.81 | 5.81 | 10.91 | | |
| 113 | ST18 | | | 4.42 | 7.40 | | |
| 114 | ZFP36L2 | 13.78 | 11.59 | 11.59 | 13.43 | 11.59 | 14.05 |
| 115 | GAB2 | 8.29 | 6.12 | 6.12 | 9.02 | | |
| 116 | CHST11 | 11.17 | 8.99 | 8.99 | 10.28 | | |
| 117 | CLOCK | 9.85 | 7.68 | 7.68 | 9.91 | 7.68 | 9.62 |
| 118 | PREX1 | 10.07 | 7.90 | | | 7.90 | 11.16 |
| 119 | KLF11 | 8.08 | 5.94 | | | 5.94 | 8.39 |
| 120 | PTGER4 | 11.66 | 9.53 | | | | |
| 121 | KLF9 | 9.47 | 7.34 | | | 7.34 | 9.27 |
| 122 | FLJ37078 | 7.55 | 5.42 | 5.42 | 7.49 | | |
| 123 | ODZ2 | 7.20 | 5.08 | 5.08 | 7.25 | 5.08 | 7.22 |

APPENDIX A-continued

Average expression of the genes depicted in FIG. 6*

| | | Naive vs Germinal Center | | Germinal Center vs Plasma | | Germinal Center vs Memory | |
|---|---|---|---|---|---|---|---|
| ID | Gene Name | Naive Average | GC Average | GC average | PC Average | GC Average | Memory Average |
| 124 | SESN3 | 11.24 | 9.11 | 9.11 | 7.60 | | |
| 125 | PDK4 | 7.22 | 5.09 | | | | |
| 126 | CNTNAP3 | 7.35 | 5.23 | 5.23 | 7.10 | | |
| 127 | DUSP1 | 13.34 | 11.22 | | | | |
| 128 | MARCKS | 11.19 | 9.07 | 9.07 | 11.05 | 9.07 | 12.21 |
| 129 | SPRY4 | 7.02 | 4.91 | | | | |
| 130 | LMO1 | | | 4.75 | 7.16 | | |
| 131 | MTUS1 | 7.77 | 5.66 | 5.66 | 8.16 | | |
| 132 | ADCY9 | 8.01 | 5.91 | 5.91 | 7.74 | | |
| 133 | SLC17A6 | | | 3.80 | 7.06 | | |
| 134 | NOX4 | 7.45 | 5.37 | 5.37 | 7.22 | | |
| 135 | UTRN | | | 9.46 | 10.97 | | |
| 136 | ZBTB10 | 8.50 | 6.45 | | | | |
| 137 | SLC26A7 | 8.37 | 6.32 | 6.32 | 7.89 | | |
| 138 | PNRC1 | 13.14 | 11.09 | | | | |
| 139 | LLGL2 | | | 6.83 | 9.29 | | |
| 140 | CHST1 | 7.15 | 5.12 | | | | |
| 141 | CREB3L2 | 10.53 | 8.51 | 8.51 | 13.30 | | |
| 142 | DDIT4 | 12.69 | 10.68 | | | | |
| 143 | C20orf108 | 8.82 | 6.80 | 6.80 | 10.19 | | |
| 144 | CDH1 | | | 3.85 | 10.26 | | |
| 145 | TFAP4 | 7.28 | 5.29 | | | | |
| 146 | SLC38A2 | 13.57 | 11.58 | 11.58 | 13.74 | 11.58 | 13.17 |
| 147 | SESN1 | 9.84 | 7.87 | 7.87 | 9.13 | | |
| 148 | YPEL2 | 10.18 | 8.20 | | | 8.20 | 10.04 |
| 149 | GRASP | 8.47 | 6.50 | | | | |
| 150 | TSC22D3 | 13.22 | 11.26 | 11.26 | 12.67 | | |
| 151 | ATP11A | 9.70 | 7.75 | 7.75 | 9.50 | | |
| 152 | L3MBTL3 | 10.61 | 8.66 | | | 8.66 | 10.06 |
| 153 | SORT1 | 7.61 | 5.67 | 5.67 | 8.11 | | |
| 154 | CAV1 | | | 4.80 | 9.11 | | |
| 155 | RXRA | 9.07 | 7.15 | 7.15 | 8.81 | | |
| 156 | CRELD1 | 8.40 | 6.48 | 6.48 | 8.26 | | |
| 157 | RBMS1 | 12.40 | 10.49 | 10.49 | 8.80 | | |
| 158 | LYST | 10.90 | 8.99 | | | | |
| 159 | PIP5K1B | 9.61 | 7.70 | 7.70 | 9.97 | | |
| 160 | JUNB | 11.62 | 9.72 | | | | |
| 161 | MBOAT1 | | | | | 4.80 | 7.27 |
| 162 | IRF4 | 11.16 | 9.28 | 9.28 | 13.66 | | |
| 163 | LIFR | | | 4.62 | 7.08 | | |
| 164 | MORC3 | 11.25 | 9.37 | | | | |
| 165 | MBP | 11.91 | 10.05 | 10.05 | 8.61 | | |
| 166 | SRC | | | 4.98 | 7.98 | | |
| 167 | ALS2CR13 | 11.79 | 9.93 | 9.93 | 8.89 | 9.93 | 11.47 |
| 168 | MYH1 | | | 4.40 | 7.37 | | |
| 169 | DUSP3 | 9.36 | 7.50 | 7.50 | 9.16 | | |
| 170 | HLX1 | 7.14 | 5.28 | | | 5.28 | 7.65 |
| 171 | CDKN1A | 9.09 | 7.23 | 7.23 | 8.97 | 7.23 | 8.43 |
| 172 | SOCS5 | 10.00 | 8.15 | | | | |
| 173 | PPP1R9A | | | 5.14 | 7.35 | | |
| 174 | TGFBR2 | 12.81 | 10.99 | | | 10.99 | 12.63 |
| 175 | LRRC16 | 8.47 | 6.66 | | | | |
| 176 | ZNF629 | 8.17 | 6.35 | 6.35 | 8.58 | | |
| 177 | RPS6KA5 | 11.75 | 9.95 | | | 9.95 | 11.48 |
| 178 | SATB1 | 12.79 | 10.99 | 10.99 | 9.06 | | |
| 179 | SEMA4C | 7.38 | 5.59 | 5.59 | 8.49 | 5.59 | 7.14 |
| 180 | ULK1 | 7.79 | 5.99 | 5.99 | 8.72 | 5.99 | 8.06 |
| 181 | STX3 | 8.88 | 7.09 | 7.09 | 8.91 | | |
| 182 | BAMBI | | | | | 4.81 | 7.26 |
| 183 | MAP3K5 | 10.63 | 8.84 | 8.84 | 7.66 | 8.84 | 10.71 |
| 184 | KIAA1147 | 11.70 | 9.91 | | | 9.91 | 11.53 |
| 185 | SBK1 | | | 5.20 | 7.04 | | |
| 186 | RYR3 | 7.80 | 6.02 | 6.02 | 8.27 | | |
| 187 | ZNF238 | 13.05 | 11.27 | 11.27 | 10.08 | 11.27 | 12.54 |
| 188 | IL12A | | | 5.65 | 7.26 | | |
| 189 | SLC2A3 | 12.00 | 10.23 | | | 10.23 | 11.89 |
| 190 | GFPT2 | | | 3.39 | 7.18 | | |
| 191 | G0S2 | 7.72 | 5.96 | | | | |
| 192 | LYRM5 | 10.29 | 8.53 | 8.53 | 10.93 | | |
| 193 | SSH2 | 11.67 | 9.91 | | | 9.91 | 11.85 |
| 194 | NRP1 | 7.44 | 5.69 | 5.69 | 7.22 | | |
| 195 | LMLN | 8.92 | 7.19 | | | | |

APPENDIX A-continued

Average expression of the genes depicted in FIG. 6*

| | | Naive vs Germinal Center | | Germinal Center vs Plasma | | Germinal Center vs Memory | |
|---|---|---|---|---|---|---|---|
| ID | Gene Name | Naive Average | GC Average | GC average | PC Average | GC Average | Memory Average |
| 196 | UCP3 | 7.71 | 5.99 | | | | |
| 197 | TMEM166 | 7.31 | 5.60 | | | | |
| 198 | CACNA1I | 7.46 | 5.76 | 5.76 | 7.06 | | |
| 199 | PHOSPHO1 | | | 3.55 | 7.10 | | |
| 200 | CRIM1 | 9.79 | 8.11 | | | 8.11 | 9.32 |
| 201 | GATA6 | | | 5.41 | 7.59 | | |
| 202 | SACS | 10.06 | 8.39 | | | 8.39 | 10.54 |
| 203 | CDKN1B | 12.91 | 11.24 | 11.24 | 14.41 | | |
| 204 | CACNA2D2 | | | 5.25 | 7.57 | 5.25 | 7.93 |
| 205 | MKRN3 | | | 3.65 | 7.10 | | |
| 206 | MTFR1 | 10.40 | 8.74 | 8.74 | 7.34 | 8.74 | 10.15 |
| 207 | GALNT3 | 10.19 | 8.54 | | | | |
| 208 | RPS6KA3 | 12.07 | 10.42 | | | 10.42 | 11.48 |
| 209 | DTNA | | | 5.47 | 7.86 | | |
| 210 | MAGI2 | 7.04 | 5.40 | 5.40 | 7.42 | | |
| 211 | FOXJ2 | 10.01 | 8.38 | 8.38 | 9.97 | 8.38 | 9.85 |
| 212 | KIAA0513 | | | 5.29 | 8.44 | 5.29 | 7.36 |
| 213 | NDRG1 | | | 7.75 | 10.02 | | |
| 214 | AKAP7 | 10.16 | 8.54 | | | | |
| 215 | CD72 | 13.74 | 12.12 | | | | |
| 216 | IGFBP5 | 7.30 | 5.69 | 5.69 | 7.59 | | |
| 217 | REPS2 | 7.51 | 5.92 | 5.92 | 7.60 | | |
| 218 | PRDM12 | 7.17 | 5.57 | | | | |
| 219 | ZNF3 | 8.86 | 7.27 | 7.27 | 8.75 | | |
| 220 | TLL2 | | | 4.88 | 7.01 | | |
| 221 | PCNX | 9.77 | 8.19 | | | | |
| 222 | ARHGAP24 | 11.31 | 9.73 | 9.73 | 8.65 | 9.73 | 11.32 |
| 223 | THRAP2 | 11.31 | 9.73 | | | | |
| 224 | RNF11 | 9.72 | 8.15 | 8.15 | 11.08 | | |
| 225 | HOXC8 | 7.05 | 5.48 | | | | |
| 226 | SCML2 | 10.33 | 8.76 | | | | |
| 227 | BMPR2 | 9.70 | 8.14 | | | 8.14 | 10.06 |
| 228 | STAC | | | 5.27 | 7.20 | | |
| 229 | C10orf54 | 9.12 | 7.56 | 7.56 | 10.16 | | |
| 230 | FBXL17 | 9.51 | 7.95 | 7.95 | 9.36 | | |
| 231 | CBX7 | 10.87 | 9.32 | | | 9.32 | 10.96 |
| 232 | UBE2W | 9.80 | 8.25 | 8.25 | 9.76 | 8.25 | 9.38 |
| 233 | ProSAPiP1 | | | 4.12 | 7.54 | | |
| 234 | UBL3 | 10.73 | 9.18 | 9.18 | 11.27 | 9.18 | 11.03 |
| 235 | TTYH3 | 7.35 | 5.81 | 5.81 | 8.16 | | |
| 236 | PUNC | | | 5.39 | 8.85 | 5.39 | 7.30 |
| 237 | GDF11 | 7.01 | 5.47 | 5.47 | 7.70 | | |
| 238 | LMX1A | | | 5.25 | 7.43 | | |
| 239 | TIMP2 | 7.51 | 5.97 | 5.97 | 7.69 | 5.97 | 7.40 |
| 240 | NHLH2 | | | 3.93 | 7.35 | | |
| 241 | CLCF1 | 10.50 | 8.98 | | | | |
| 242 | ITGB3 | 7.66 | 6.14 | | | | |
| 243 | TMEM132E | | | 3.93 | 7.20 | | |
| 244 | KCTD17 | 7.45 | 5.94 | 5.94 | 7.33 | | |
| 245 | ChGn | 7.75 | 6.24 | 6.24 | 8.36 | | |
| 246 | DIP2C | 9.25 | 7.75 | | | | |
| 247 | DKFZp667G2110 | 8.79 | 7.28 | 7.28 | 9.25 | | |
| 248 | CSNK1G3 | 10.84 | 9.34 | | | 9.34 | 10.70 |
| 249 | NRIP1 | 11.79 | 10.30 | | | | |
| 250 | SMAD3 | 10.72 | 9.23 | 9.23 | 7.74 | 9.23 | 10.54 |
| 251 | SHOX2 | 7.05 | 5.57 | | | | |
| 252 | LDLRAP1 | | | 6.80 | 9.84 | 6.80 | 8.59 |
| 253 | SUPT3H | 7.77 | 6.30 | 6.30 | 8.05 | | |
| 254 | KCNN2 | 7.18 | 5.70 | | | | |
| 255 | DLL1 | 7.37 | 5.90 | | | | |
| 256 | CEND1 | 7.72 | 6.26 | | | | |
| 257 | NOTCH1 | 10.90 | 9.45 | | | | |
| 258 | TLE1 | | | 7.74 | 9.63 | | |
| 259 | FCHO2 | 8.75 | 7.30 | | | | |
| 260 | JPH4 | 7.12 | 5.67 | 5.67 | 7.60 | | |
| 261 | KCNMB2 | 7.16 | 5.72 | | | | |
| 262 | KHDRBS2 | 7.17 | 5.73 | | | | |
| 263 | LEFTY1 | | | 4.38 | 7.21 | | |
| 264 | ST3GAL5 | 10.59 | 9.15 | | | | |
| 265 | LGR4 | | | 5.30 | 7.29 | | |
| 266 | FNDC8 | | | 4.25 | 8.01 | | |
| 267 | NPTXR | | | 5.87 | 7.65 | | |

APPENDIX A-continued

| | | Naive vs Germinal Center | | Germinal Center vs Plasma | | Germinal Center vs Memory | |
|---|---|---|---|---|---|---|---|
| ID | Gene Name | Naive Average | GC Average | GC average | PC Average | GC Average | Memory Average |
| 268 | PRICKLE2 | | | 5.47 | 7.47 | | |
| 269 | GRIA4 | | | 5.19 | 7.04 | | |
| 270 | RHOB | 8.66 | 7.23 | 7.23 | 9.56 | | |
| 271 | ZADH2 | 8.65 | 7.22 | | | | |
| 272 | ZBTB41 | 9.73 | 8.31 | | | 8.31 | 9.42 |
| 273 | GPRASP2 | | | 6.00 | 7.35 | | |
| 274 | SYS1 | 10.79 | 9.36 | | | | |
| 275 | RUNX1T1 | 7.37 | 5.95 | | | | |
| 276 | DLX2 | | | 4.66 | 7.04 | | |
| 277 | SLC30A7 | 11.58 | 10.17 | | | | |
| 278 | PER1 | 8.82 | 7.40 | | | | |
| 279 | NT5C3 | 12.67 | 11.25 | | | | |
| 280 | PDE3A | 11.62 | 10.21 | | | | |
| 281 | OCRL | 8.07 | 6.66 | | | 6.66 | 8.04 |
| 282 | PSD3 | 7.99 | 6.60 | | | | |
| 283 | LPHN1 | 7.80 | 6.41 | | | | |
| 284 | TNRC6B | 11.87 | 10.48 | | | 10.48 | 11.77 |
| 285 | SNN | 12.03 | 10.64 | 10.64 | 8.91 | 10.64 | 12.10 |
| 286 | HERPUD2 | 11.56 | 10.18 | | | | |
| 287 | UBQLNL | 7.45 | 6.07 | | | | |
| 288 | HES7 | 7.37 | 5.99 | | | | |
| 289 | GALNT2 | 10.08 | 8.69 | 8.69 | 10.63 | | |
| 290 | CAMKK1 | 8.45 | 7.07 | | | | |
| 291 | ELN | | | 5.44 | 7.18 | | |
| 292 | ICK | 8.09 | 6.72 | 6.72 | 8.01 | | |
| 293 | POU4F2 | 7.09 | 5.72 | 5.72 | 7.21 | | |
| 294 | GAS2 | 7.13 | 5.76 | 5.76 | 7.81 | | |
| 295 | ARHGEF3 | 10.11 | 8.75 | | | 8.75 | 11.04 |
| 296 | ZBTB4 | 11.45 | 10.09 | | | 10.09 | 11.78 |
| 297 | CHD7 | 12.14 | 10.78 | | | 10.78 | 12.08 |
| 298 | TMEM45B | | | 5.97 | 7.61 | | |
| 299 | CLDN11 | | | 5.74 | 7.22 | | |
| 300 | PTPN1 | 10.85 | 9.51 | | | | |
| 301 | PHF20 | 12.00 | 10.67 | | | | |
| 302 | VAV3 | | | 10.44 | 7.84 | | |
| 303 | CARKL | 8.38 | 7.06 | 7.06 | 8.94 | | |
| 304 | TRIM36 | | | 5.43 | 7.77 | | |
| 305 | CTLA4 | | | 6.57 | 7.95 | | |
| 306 | POLK | 9.69 | 8.38 | 8.38 | 10.55 | | |
| 307 | WSB1 | 13.22 | 11.91 | | | 11.91 | 13.02 |
| 308 | ALS2CR2 | 9.87 | 8.57 | 8.57 | 10.14 | | |
| 309 | PLK2 | | | 4.94 | 7.13 | | |
| 310 | SRPK2 | 10.83 | 9.53 | | | 9.53 | 11.13 |
| 311 | ARRDC2 | 10.86 | 9.55 | | | | |
| 312 | IER5 | 13.10 | 11.80 | | | | |
| 313 | EPN1 | 8.95 | 7.66 | 7.66 | 9.07 | | |
| 314 | SLC20A2 | 9.45 | 8.16 | | | | |
| 315 | DLG4 | | | 4.23 | 7.22 | | |
| 316 | TMTC2 | | | 6.16 | 7.92 | | |
| 317 | ETV1 | 8.19 | 6.90 | | | | |
| 318 | JAZF1 | 11.93 | 10.65 | 10.65 | 7.49 | | |
| 319 | VAV2 | 10.22 | 8.94 | | | | |
| 320 | C15orf27 | 7.19 | 5.91 | | | | |
| 321 | FYCO1 | 9.75 | 8.47 | | | | |
| 322 | KIAA0789 | 7.27 | 6.00 | | | | |
| 323 | OBFC2A | 9.94 | 8.66 | | | 8.66 | 10.94 |
| 324 | MCF2 | 7.19 | 5.92 | | | | |
| 325 | KIAA2018 | 11.77 | 10.50 | 10.50 | 9.50 | | |
| 326 | MTMR10 | 10.75 | 9.48 | | | | |
| 327 | FAM63B | | | 6.03 | 7.83 | 6.03 | 7.95 |
| 328 | SNF1LK | 10.20 | 8.93 | | | 8.93 | 10.18 |
| 329 | ZNF385 | 8.89 | 7.63 | | | | |
| 330 | SESTD1 | 11.05 | 9.78 | | | | |
| 331 | SLC31A2 | | | 5.41 | 9.13 | | |
| 332 | PCMTD1 | 12.03 | 10.76 | 10.76 | 12.44 | | |
| 333 | NBEA | 8.06 | 6.81 | 6.81 | 8.02 | 6.81 | 8.35 |
| 334 | ZNF295 | | | 9.24 | 10.61 | | |
| 335 | SIPA1L3 | 10.81 | 9.57 | | | | |
| 336 | CC2D1B | 9.11 | 7.87 | | | | |
| 337 | PRKAG2 | | | 7.12 | 8.42 | | |
| 338 | PKD1 | 9.04 | 7.81 | | | | |
| 339 | CNTNAP2 | 7.54 | 6.32 | | | | |

APPENDIX A-continued

Average expression of the genes depicted in FIG. 6*

| ID | Gene Name | Naive vs Germinal Center | | Germinal Center vs Plasma | | Germinal Center vs Memory | |
|---|---|---|---|---|---|---|---|
| | | Naive Average | GC Average | GC average | PC Average | GC Average | Memory Average |
| 340 | FNBP1L | 7.90 | 6.67 | | | | |
| 341 | HEXIM1 | 10.27 | 9.05 | | | 9.05 | 10.24 |
| 342 | C19orf2 | 12.29 | 11.07 | | | | |
| 343 | MYLIP | 11.62 | 10.41 | | | 10.41 | 11.81 |
| 344 | SLC11A2 | 9.27 | 8.06 | | | | |
| 345 | CLU | 9.92 | 8.71 | | | | |
| 346 | GCN5L2 | 10.18 | 8.97 | | | | |
| 347 | DKFZP564J0863 | 10.85 | 9.65 | | | 9.65 | 11.11 |
| 348 | CNNM2 | 7.85 | 6.64 | 6.64 | 8.07 | | |
| 349 | CDC42SE1 | 12.07 | 10.87 | | | 10.87 | 12.18 |
| 350 | HOXB9 | | | 6.20 | 8.41 | | |
| 351 | NFATC3 | 11.39 | 10.19 | | | | |
| 352 | UNC84B | 11.12 | 9.93 | 9.93 | 8.59 | | |
| 353 | DUSP5 | | | 6.23 | 9.44 | | |
| 354 | ING1 | 11.35 | 10.17 | | | | |
| 355 | ITM2B | | | 11.23 | 13.62 | | |
| 356 | FAM53B | 11.67 | 10.49 | | | | |
| 357 | ZFP36L1 | 14.07 | 12.89 | 12.89 | 10.09 | | |
| 358 | NIPA1 | 9.75 | 8.57 | | | 8.57 | 10.07 |
| 359 | GALNT1 | 10.93 | 9.76 | 9.76 | 11.12 | | |
| 360 | MYPN | | | 4.25 | 7.32 | | |
| 361 | ITPK1 | 10.03 | 8.86 | | | | |
| 362 | TTYH2 | 7.90 | 6.73 | | | | |
| 363 | DOCK10 | 10.80 | 9.63 | | | 9.63 | 11.53 |
| 364 | C14orf28 | 9.18 | 8.01 | 8.01 | 9.58 | 8.01 | 9.50 |
| 365 | RP11-130N24.1 | | | 4.76 | 7.62 | | |
| 366 | FGF12 | | | 5.82 | 7.33 | | |
| 367 | ATP2B2 | 7.93 | 6.76 | | | | |
| 368 | PPP1R9B | 9.77 | 8.60 | | | | |
| 369 | PPP3CA | 13.50 | 12.33 | | | 12.33 | 13.86 |
| 370 | TFAP2A | | | 5.54 | 8.26 | | |
| 371 | CYLD | 10.91 | 9.75 | | | | |
| 372 | PHF1 | 11.85 | 10.69 | 10.69 | 12.26 | | |
| 373 | NEBL | 7.98 | 6.82 | 6.82 | 8.08 | | |
| 374 | ACIN1 | 12.04 | 10.89 | | | 10.89 | 11.99 |
| 375 | SPTBN1 | 12.28 | 11.14 | 11.14 | 12.53 | 11.14 | 12.42 |
| 376 | VAMP4 | 10.81 | 9.67 | 9.67 | 11.18 | | |
| 377 | DNAJB9 | 10.80 | 9.66 | 9.66 | 15.21 | 9.66 | 11.03 |
| 378 | ZDHHC2 | 11.55 | 10.42 | | | | |
| 379 | TRIO | 10.57 | 9.43 | | | | |
| 380 | TMEM25 | | | 6.24 | 8.57 | | |
| 381 | TAF9B | 10.82 | 9.69 | | | | |
| 382 | ARID3A | 8.03 | 6.90 | 6.90 | 9.81 | | |
| 383 | KIAA0182 | 10.68 | 9.55 | | | | |
| 384 | RPS6KA2 | 8.61 | 7.49 | | | | |
| 385 | C3orf58 | 11.47 | 10.34 | | | | |
| 386 | CAST | 11.94 | 10.82 | | | | |
| 387 | SH3PXD2A | 8.46 | 7.34 | | | | |
| 388 | RAB6B | | | 5.93 | 7.36 | | |
| 389 | RNF141 | 11.47 | 10.35 | | | | |
| 390 | SP4 | 11.26 | 10.14 | | | | |
| 391 | ARMCX2 | 9.44 | 8.32 | 8.32 | 9.54 | | |
| 392 | ZNF398 | 10.39 | 9.28 | | | | |
| 393 | PBX3 | 9.69 | 8.58 | 8.58 | 7.00 | | |
| 394 | FOS | 12.35 | 11.25 | 11.25 | 13.34 | | |
| 395 | FHOD3 | | | 6.40 | 7.94 | | |
| 396 | C20orf59 | 10.11 | 9.01 | 9.01 | 10.92 | | |
| 397 | FAM117A | 11.67 | 10.57 | 10.57 | 12.06 | 10.57 | 11.64 |
| 398 | ATP8B2 | 8.58 | 7.49 | 7.49 | 10.87 | 7.49 | 8.88 |
| 399 | UXS1 | 9.53 | 8.43 | | | | |
| 400 | GOLGA8A | 12.84 | 11.74 | 11.74 | 13.14 | 11.74 | 13.05 |
| 401 | SUFU | | | 6.03 | 7.84 | | |
| 402 | NAGPA | 9.32 | 8.23 | | | | |
| 403 | MLLT6 | 11.70 | 10.61 | | | | |
| 404 | CPEB4 | 9.46 | 8.36 | 8.36 | 12.21 | | |
| 405 | TMEM50B | 10.67 | 9.58 | 9.58 | 11.41 | 9.58 | 10.63 |
| 406 | AMPD3 | 11.65 | 10.56 | 10.56 | 8.76 | | |
| 407 | SIX5 | | | 5.19 | 7.53 | | |
| 408 | MMP16 | | | 5.66 | 7.47 | | |
| 409 | LBH | 11.87 | 10.79 | 10.79 | 8.83 | | |
| 410 | POM121 | | | | | 9.60 | 11.26 |
| 411 | ATP8B1 | 11.93 | 10.86 | 10.86 | 8.88 | | |

APPENDIX A-continued

Average expression of the genes depicted in FIG. 6*

| | | Naive vs Germinal Center | | Germinal Center vs Plasma | | Germinal Center vs Memory | |
|---|---|---|---|---|---|---|---|
| ID | Gene Name | Naive Average | GC Average | GC average | PC Average | GC Average | Memory Average |
| 412 | ARHGAP29 | | | 3.75 | 7.60 | | |
| 413 | ZNF395 | | | 11.78 | 10.76 | | |
| 414 | CRY2 | | | | | 6.50 | 8.01 |
| 415 | BIN1 | | | 10.68 | 9.67 | | |
| 416 | PSAP | | | 11.24 | 13.41 | 11.24 | 12.71 |
| 417 | ISL1 | | | 5.91 | 7.60 | | |
| 418 | DNAJB5 | 8.04 | 6.97 | | | | |
| 419 | KIAA0284 | | | 6.42 | 8.79 | | |
| 420 | RBM35B | 11.44 | 10.38 | | | | |
| 421 | ADCY7 | 11.53 | 10.47 | | | | |
| 422 | ARRDC3 | | | | | 9.46 | 10.68 |
| 423 | MICAL1 | 11.72 | 10.67 | | | | |
| 424 | MTHFR | 10.31 | 9.26 | | | | |
| 425 | HOOK3 | 8.57 | 7.53 | 7.53 | 6.52 | | |
| 426 | EFNB3 | | | 5.16 | 7.79 | | |
| 427 | ARHGAP12 | 9.86 | 8.82 | | | | |
| 428 | LMBR1L | 9.33 | 8.29 | | | | |
| 429 | FGF7 | | | 5.88 | 7.86 | | |
| 430 | USP2 | | | 5.50 | 7.52 | | |
| 431 | SMARCA2 | 11.14 | 10.12 | | | | |
| 432 | ELL2 | | | 8.23 | 13.60 | | |
| 433 | C1orf26 | | | 7.06 | 10.01 | | |
| 434 | CXCR4 | | | 14.61 | 13.45 | | |
| 435 | HDGFRP3 | | | 5.58 | 7.39 | | |
| 436 | BNC2 | | | 6.18 | 7.72 | | |
| 437 | YPEL3 | | | 10.16 | 11.81 | 10.16 | 11.47 |
| 438 | PPFIA3 | | | 4.58 | 8.06 | | |
| 439 | DLGAP4 | | | 9.34 | 10.68 | | |
| 440 | ZBTB7A | | | | | 9.84 | 11.10 |
| 441 | D4S234E | | | 5.90 | 7.38 | | |
| 442 | FNDC3A | | | 9.41 | 13.60 | | |
| 443 | FOXC1 | | | 5.84 | 7.39 | | |
| 444 | KIF26B | | | 5.55 | 7.30 | | |
| 445 | NAV2 | | | 6.26 | 7.90 | | |
| 446 | DDX3Y | | | 8.07 | 10.38 | | |
| 447 | FGD1 | | | 7.31 | 6.06 | | |
| 448 | HTR4 | | | 7.26 | 9.01 | 7.26 | 8.40 |
| 449 | C22orf31 | | | 5.67 | 8.10 | | |
| 450 | RNF44 | | | 11.48 | 10.14 | | |
| 451 | GALNAC4S-6ST | | | 10.43 | 12.71 | | |
| 452 | CCNT2 | | | | | 10.15 | 11.23 |
| 453 | CHIC1 | | | | | 8.91 | 10.02 |
| 454 | NNAT | | | 5.97 | 8.19 | 5.97 | 7.84 |
| 455 | CTDP1 | | | 6.81 | 8.26 | | |
| 456 | BTG1 | | | 14.95 | 13.94 | | |
| 457 | CMTM4 | | | 5.27 | 7.81 | | |
| 458 | GOLGA8B | | | | | 11.37 | 12.63 |
| 459 | HBP1 | | | 10.07 | 12.13 | | |
| 460 | GDPD1 | | | | | 6.35 | 7.61 |
| 461 | CDYL | | | 9.31 | 10.61 | 9.31 | 10.50 |
| 462 | ZNF217 | | | 10.77 | 9.73 | | |
| 463 | KIF5A | | | 6.13 | 7.75 | | |
| 464 | C1QL1 | | | 5.80 | 8.11 | | |
| 465 | SOLH | | | | | 7.88 | 9.03 |
| 466 | ZC3H6 | | | | | 9.81 | 10.96 |
| 467 | LATS2 | | | 7.61 | 10.19 | | |
| 468 | COL18A1 | | | 6.46 | 7.85 | | |
| 469 | C11orf24 | | | 9.89 | 11.07 | | |
| 470 | SCUBE3 | | | 6.14 | 7.88 | | |
| 471 | SEMA4G | | | 5.57 | 7.81 | | |
| 472 | FOXP1 | | | 12.31 | 10.84 | | |
| 473 | TRIB2 | | | 10.62 | 9.61 | | |
| 474 | LOC285382 | | | 5.35 | 7.20 | | |
| 475 | RUNX2 | | | 7.91 | 10.22 | | |
| 476 | LOC196463 | | | 4.16 | 7.52 | | |
| 477 | LPGAT1 | | | 10.57 | 7.99 | | |
| 478 | RASSF2 | | | 12.52 | 10.93 | | |
| 479 | IRF1 | | | 9.86 | 11.60 | | |
| 480 | RAB40B | | | 7.31 | 10.89 | | |
| 481 | CTDSPL | | | 6.37 | 7.83 | | |
| 482 | CLCN4 | | | | | 7.44 | 6.39 |
| 483 | CACNB1 | | | 6.41 | 8.20 | | |

APPENDIX A-continued

Average expression of the genes depicted in FIG. 6*

| | | Naive vs Germinal Center | | Germinal Center vs Plasma | | Germinal Center vs Memory | |
|---|---|---|---|---|---|---|---|
| ID | Gene Name | Naive Average | GC Average | GC average | PC Average | GC Average | Memory Average |
| 484 | SYNGR1 | | | 8.45 | 10.40 | | |
| 485 | ST8SLA4 | | | | | 10.67 | 11.81 |
| 486 | PLD3 | | | 7.63 | 10.59 | | |
| 487 | FOXO3A | | | 10.17 | 12.41 | | |
| 488 | TSPAN33 | | | 10.49 | 9.38 | | |
| 489 | HIST1H4F | | | 6.20 | 8.08 | | |
| 490 | LAPTM4A | | | | | 12.05 | 13.06 |
| 491 | PRKCB1 | | | 12.14 | 10.50 | | |
| 492 | PROX1 | | | 6.38 | 7.89 | | |
| 493 | CDK5R1 | | | 10.12 | 7.78 | | |
| 494 | MAP3K9 | | | 7.96 | 9.13 | | |
| 495 | GPX3 | | | 5.92 | 7.61 | | |
| 496 | GNS | | | 8.79 | 11.06 | | |
| 497 | ARL15 | | | 8.27 | 6.51 | | |
| 498 | OXR1 | | | 9.21 | 11.17 | 9.21 | 10.25 |
| 499 | AAK1 | | | 7.38 | 9.54 | 7.38 | 8.47 |
| 500 | SH3PX3 | | | 6.72 | 8.58 | | |
| 501 | MS4A7 | | | 10.55 | 8.35 | | |
| 502 | FLJ20273 | | | 5.96 | 11.23 | 5.96 | 8.65 |
| 503 | ISCU | | | 12.01 | 13.55 | | |
| 504 | ITGA2 | | | 5.70 | 7.60 | | |
| 505 | ME1 | | | 5.87 | 7.89 | | |
| 506 | LRP1 | | | 4.92 | 7.04 | | |
| 507 | ZNF652 | | | | | 9.66 | 10.81 |
| 508 | TRAK1 | | | 11.07 | 9.85 | | |
| 509 | SLC8A1 | | | 6.27 | 7.83 | | |
| 510 | C1orf119 | | | | | 10.76 | 11.98 |
| 511 | KLF6 | | | 11.33 | 9.24 | 11.33 | 12.40 |
| 512 | TRIM2 | | | 6.22 | 8.20 | | |
| 513 | USP3 | | | 11.11 | 12.51 | | |
| 514 | ARID5B | | | | | 11.02 | 12.48 |
| 515 | RASD1 | | | 6.15 | 9.32 | | |
| 516 | ZCCHC2 | | | 10.63 | 8.93 | | |
| 517 | LEFTY2 | | | | | 5.08 | 7.03 |
| 518 | BACH1 | | | 9.97 | 11.76 | | |
| 519 | IRAK1 | | | 11.48 | 12.80 | | |
| 520 | RP11-217H1.1 | | | 10.76 | 13.04 | | |
| 521 | HLCS | | | 6.54 | 8.45 | | |
| 522 | NAGK | | | 10.94 | 12.14 | | |
| 523 | CELSR2 | | | 6.26 | 7.89 | | |
| 524 | PCBP4 | | | 7.75 | 9.08 | | |
| 525 | FLJ25476 | | | | | 9.49 | 10.72 |
| 526 | TPP1 | | | 12.10 | 11.06 | | |
| 527 | ACVR1 | | | 7.95 | 9.31 | | |
| 528 | EHD3 | | | | | 8.99 | 10.35 |
| 529 | FAM80B | | | 9.35 | 8.02 | | |
| 530 | SPRYD3 | | | 8.19 | 9.51 | | |
| 531 | PRDM4 | | | | | 9.81 | 10.83 |
| 532 | C6orf134 | | | 7.92 | 5.60 | | |
| 533 | HSP90B1 | | | 12.04 | 16.36 | | |
| 534 | DYNC1I1 | | | 5.98 | 7.33 | | |
| 535 | NFLX | | | 7.43 | 8.67 | | |
| 536 | DOCK4 | | | | | 5.96 | 7.97 |
| 537 | ZNF287 | | | 7.09 | 8.47 | | |
| 538 | XRN1 | | | 10.92 | 12.37 | | |
| 539 | YES1 | | | 6.39 | 8.60 | | |
| 540 | RBM35A | | | 8.19 | 9.44 | | |
| 541 | HOXB4 | | | 7.58 | 9.27 | | |
| 542 | OTUD7B | | | 7.24 | 8.57 | | |
| 543 | CELSR3 | | | | | 6.83 | 8.39 |
| 544 | RHOC | | | | | 7.71 | 8.84 |
| 545 | ZNF607 | | | 8.10 | 6.95 | | |
| 546 | XYLT1 | | | 10.28 | 8.78 | 10.28 | 8.86 |
| 547 | FAM89B | | | 9.16 | 10.75 | | |
| 548 | OSBPL8 | | | 12.99 | 11.66 | | |
| 549 | SRCRB4D | | | 6.82 | 8.67 | | |
| 550 | RASL12 | | | 5.05 | 8.07 | | |
| 551 | NAG8 | | | 8.39 | 9.78 | | |
| 552 | MAN1A2 | | | 10.83 | 12.15 | | |
| 553 | PPARA | | | | | 8.59 | 9.65 |
| 554 | CLDN12 | | | 6.66 | 8.39 | | |
| 555 | ID4 | | | 5.93 | 7.79 | | |

APPENDIX A-continued

| | | Naive vs Germinal Center | | Germinal Center vs Plasma | | Germinal Center vs Memory | |
|---|---|---|---|---|---|---|---|
| ID | Gene Name | Naive Average | GC Average | GC average | PC Average | GC Average | Memory Average |
| 556 | HECTD2 | | | 7.98 | 6.80 | | |
| 557 | EFCAB4A | | | 5.93 | 8.96 | | |
| 558 | CREBL1 | | | | | 6.97 | 8.09 |
| 559 | SARM1 | | | | | 6.98 | 8.29 |
| 560 | MIDN | | | 8.48 | 7.29 | | |
| 561 | EMB | | | 10.48 | 8.65 | | |
| 562 | FOXK2 | | | 8.40 | 9.63 | | |
| 563 | INADL | | | 6.87 | 8.44 | | |
| 564 | KCNAB1 | | | 6.26 | 9.76 | | |
| 565 | MAP3K8 | | | 10.92 | 9.60 | | |
| 566 | C8orf58 | | | 7.89 | 5.62 | | |
| 567 | SLC4A7 | | | 9.82 | 8.52 | 9.82 | 10.90 |
| 568 | RAB8B | | | 12.46 | 10.92 | | |
| 569 | C10orf118 | | | 8.93 | 10.20 | | |
| 570 | CRTC2 | | | 9.37 | 7.94 | | |
| 571 | KLC2 | | | 7.31 | 9.19 | | |
| 572 | SRCAP | | | 8.06 | 6.96 | | |
| 573 | CNTFR | | | 7.15 | 8.67 | | |
| 574 | SPTBN2 | | | 4.75 | 7.11 | | |
| 575 | SMAD7 | | | | | 8.69 | 9.93 |
| 576 | NDFIP1 | | | 9.10 | 10.95 | | |
| 577 | BCL11A | | | 14.03 | 10.63 | | |
| 578 | SFXN5 | | | 7.26 | 8.87 | | |
| 579 | RIMBP2 | | | 5.93 | 8.33 | | |
| 580 | FUT8 | | | 8.62 | 11.08 | | |
| 581 | PSEN2 | | | 5.86 | 9.17 | | |
| 582 | MAP6 | | | 5.22 | 7.37 | | |
| 583 | FOXO1A | | | 11.53 | 10.14 | | |
| 584 | BTG2 | | | 11.81 | 13.82 | | |
| 585 | C10orf56 | | | 6.93 | 9.30 | | |
| 586 | MAPK1 | | | 12.06 | 10.36 | | |
| 587 | ZBTB47 | | | 6.63 | 8.12 | | |
| 588 | GOSR2 | | | 9.73 | 11.07 | | |
| 589 | ZFP90 | | | 10.15 | 8.92 | | |
| 590 | RALGPS1 | | | 8.02 | 9.38 | | |
| 591 | DGKI | | | 4.77 | 7.39 | | |
| 592 | RGL2 | | | 11.08 | 9.55 | | |
| 593 | PAK6 | | | 5.90 | 8.55 | | |
| 594 | DMXL1 | | | 11.85 | 10.31 | | |
| 595 | TMEM113 | | | 12.28 | 11.03 | | |
| 596 | SNX24 | | | 6.75 | 8.53 | | |
| 597 | HOXA3 | | | 5.99 | 8.27 | | |
| 598 | SAMD4A | | | 9.84 | 8.36 | | |
| 599 | WDR45 | | | 9.88 | 12.43 | | |
| 600 | TLOC1 | | | 12.91 | 14.52 | | |
| 601 | LARP2 | | | 7.64 | 11.50 | | |
| 602 | DTX2 | | | 7.60 | 6.20 | | |
| 603 | ITGA9 | | | | | 7.53 | 6.32 |
| 604 | FASTK | | | 10.04 | 11.22 | | |
| 605 | TAOK2 | | | 7.47 | 6.37 | | |
| 606 | CRTAP | | | | | 9.78 | 11.08 |
| 607 | SERTAD2 | | | 11.91 | 10.82 | | |
| 608 | TBP | | | 10.14 | 9.09 | | |
| 609 | IQGAP2 | | | 7.26 | 11.19 | 7.26 | 8.93 |
| 610 | RASGEF1B | | | 6.23 | 8.01 | | |
| 611 | PIP5K2B | | | 9.69 | 8.53 | | |
| 612 | PRRC1 | | | 10.32 | 11.92 | | |
| 613 | RHPN2 | | | 6.73 | 8.21 | | |
| 614 | DYRK1B | | | 5.92 | 7.61 | | |
| 615 | ADCY2 | | | 5.98 | 7.97 | | |
| 616 | C12orf34 | | | 5.61 | 7.09 | | |
| 617 | GMPR | | | 5.35 | 8.15 | | |
| 618 | PAK2 | | | 10.86 | 9.66 | | |
| 619 | KIAA1539 | | | 8.12 | 9.49 | | |
| 620 | PLAGL1 | | | 10.03 | 6.68 | | |
| 621 | LCORL | | | 9.74 | 11.29 | | |
| 622 | BCL9 | | | 7.21 | 9.16 | | |
| 623 | CPEB2 | | | | | 9.09 | 10.23 |
| 624 | TMEM59 | | | 12.10 | 14.75 | | |
| 625 | TRIP10 | | | 7.17 | 9.36 | | |
| 626 | CCPG1 | | | 8.38 | 11.86 | | |
| 627 | NDE1 | | | 10.71 | 9.30 | | |

APPENDIX A-continued

Average expression of the genes depicted in FIG. 6*

| ID | Gene Name | Naive vs Germinal Center | | Germinal Center vs Plasma | | Germinal Center vs Memory | |
|---|---|---|---|---|---|---|---|
| | | Naive Average | GC Average | GC average | PC Average | GC Average | Memory Average |
| 628 | ZDHHC21 | | | 9.38 | 8.11 | | |
| 629 | STOX2 | | | 5.87 | 7.66 | | |
| 630 | RAB4B | | | 10.63 | 8.66 | | |
| 631 | LRRFIP1 | | | 13.25 | 11.99 | | |
| 632 | OSBP | | | 10.10 | 11.39 | | |
| 633 | RAB6A | | | 10.76 | 12.27 | | |
| 634 | RHOV | | | 4.88 | 7.19 | | |
| 635 | SLC39A14 | | | 8.80 | 11.00 | | |
| 636 | ADARB1 | | | 10.05 | 7.69 | | |
| 637 | ESPN | | | 6.85 | 8.19 | | |
| 638 | SEC31A | | | 11.64 | 13.61 | | |
| 639 | PJA2 | | | 10.85 | 11.99 | | |
| 640 | SYNGR3 | | | 9.01 | 7.56 | | |
| 641 | LOC339745 | | | 11.94 | 10.54 | | |
| 642 | NEDD9 | | | 11.23 | 12.48 | | |
| 643 | COL23A1 | | | 5.41 | 7.02 | | |
| 644 | PIP5K3 | | | 11.93 | 10.79 | | |
| 645 | PTPRG | | | 7.30 | 8.49 | | |
| 646 | DAB2IP | | | 5.61 | 8.30 | | |
| 647 | MAPRE3 | | | 5.80 | 8.60 | | |
| 648 | SQSTM1 | | | 10.05 | 11.45 | | |
| 649 | RAB6C | | | 10.88 | 12.04 | | |
| 650 | FAM57A | | | 7.58 | 6.18 | | |
| 651 | YPEL5 | | | 12.41 | 13.78 | | |
| 652 | TTN | | | 9.61 | 7.03 | | |
| 653 | HTRA3 | | | 5.62 | 8.02 | | |
| 654 | CHST2 | | | 7.80 | 12.49 | | |
| 655 | BAZ1A | | | 11.43 | 10.06 | | |
| 656 | LRFN5 | | | | | 7.38 | 6.21 |
| 657 | MBNL1 | | | 14.10 | 12.62 | | |
| 658 | MLL2 | | | 10.93 | 9.89 | | |
| 659 | SF1 | | | 11.44 | 10.36 | | |
| 660 | FRMPD1 | | | 4.80 | 7.06 | | |
| 661 | PPP2R5B | | | 7.60 | 9.12 | | |
| 662 | RNF43 | | | 10.04 | 8.01 | | |
| 663 | GAP43 | | | 5.07 | 7.49 | | |
| 664 | NOMO1 | | | 11.11 | 14.31 | | |
| 665 | VEGFA | | | 7.79 | 9.36 | | |
| 666 | C22orf5 | | | 8.75 | 11.38 | | |
| 667 | AKAP11 | | | 11.79 | 10.64 | | |
| 668 | INSIG2 | | | 9.46 | 11.32 | | |
| 669 | PDIK1L | | | 9.11 | 10.72 | | |
| 670 | TMEM4 | | | 10.93 | 13.32 | | |
| 671 | LMNA | | | 7.80 | 9.75 | | |
| 672 | TP53INP1 | | | 11.84 | 14.14 | | |
| 673 | NAV1 | | | 6.96 | 8.31 | | |
| 674 | SPTY2D1 | | | 9.25 | 10.77 | | |
| 675 | CREBL2 | | | 9.95 | 11.10 | | |
| 676 | MFAP3L | | | 5.90 | 7.46 | | |
| 677 | REXO2 | | | 10.96 | 13.71 | | |
| 678 | SPTBN4 | | | 6.77 | 8.22 | | |
| 679 | NOMO2 | | | 9.74 | 12.94 | | |
| 680 | PTEN | | | 12.78 | 11.40 | | |
| 681 | FBXL16 | | | 6.86 | 9.56 | | |
| 682 | GPM6A | | | 7.87 | 6.15 | 7.87 | 6.67 |
| 683 | PRX | | | 6.76 | 8.91 | | |
| 684 | HOXC11 | | | 6.40 | 7.88 | | |
| 685 | KIAA0329 | | | 8.27 | 9.87 | | |
| 686 | PAFAH1B1 | | | 11.68 | 10.33 | | |
| 687 | C20orf174 | | | 9.58 | 7.27 | | |
| 688 | MTPN | | | 13.87 | 12.17 | | |
| 689 | TMED5 | | | 12.25 | 14.41 | | |
| 690 | FURIN | | | 8.03 | 9.54 | | |
| 691 | ELAVL3 | | | 4.66 | 8.01 | | |
| 692 | SH2B3 | | | 10.31 | 8.87 | | |
| 693 | LIN28B | | | 5.99 | 7.58 | | |
| 694 | KIAA1033 | | | 12.65 | 11.38 | | |
| 695 | TMEM28 | | | 4.95 | 7.14 | | |
| 696 | TBC1D15 | | | 10.30 | 11.52 | | |
| 697 | GOLGA4 | | | 10.11 | 11.71 | | |
| 698 | STX1A | | | 5.63 | 7.82 | | |
| 699 | SLC40A1 | | | | | 6.87 | 8.27 |

APPENDIX A-continued

Average expression of the genes depicted in FIG. 6*

| ID | Gene Name | Naive vs Germinal Center | | Germinal Center vs Plasma | | Germinal Center vs Memory | |
|---|---|---|---|---|---|---|---|
| | | Naive Average | GC Average | GC average | PC Average | GC Average | Memory Average |
| 700 | KIAA1815 | | | 9.18 | 7.93 | | |
| 701 | HNT | | | 5.53 | 7.09 | | |
| 702 | PDE11A | | | 5.72 | 7.82 | | |
| 703 | TGFBR3 | | | 7.84 | 9.52 | | |
| 704 | MTF1 | | | 9.92 | 8.86 | | |
| 705 | MAN1A1 | | | 9.99 | 13.65 | | |
| 706 | THRA | | | 7.26 | 8.48 | | |
| 707 | CBLB | | | 11.46 | 9.08 | | |
| 708 | SLC35F1 | | | 6.29 | 8.16 | | |
| 709 | FOXP4 | | | 8.52 | 7.30 | | |
| 710 | ELOVL5 | | | 13.83 | 12.78 | | |
| 711 | NMUR1 | | | 4.13 | 7.31 | | |
| 712 | ITPR1 | | | 12.06 | 9.69 | | |
| 713 | CDCA7L | | | 11.95 | 10.33 | | |
| 714 | RASSF1 | | | | | 9.35 | 10.69 |
| 715 | IL1RAPL1 | | | 6.42 | 8.18 | | |
| 716 | AUH | | | 9.37 | 11.19 | | |
| 717 | DIAPH1 | | | 11.52 | 9.74 | | |
| 718 | ENSA | | | 12.33 | 11.22 | | |
| 719 | FAM43A | | | 10.62 | 9.39 | | |
| 720 | CSMD3 | | | 4.79 | 7.58 | | |
| 721 | SLC25A37 | | | 10.10 | 8.69 | | |
| 722 | SLC33A1 | | | 9.78 | 12.19 | | |
| 723 | CNOT6 | | | 9.98 | 8.93 | | |
| 724 | GRID1 | | | 7.05 | 8.80 | | |
| 725 | C21orf91 | | | 11.51 | 10.18 | | |
| 726 | ITPKB | | | 11.28 | 8.91 | | |
| 727 | CP | | | 5.89 | 7.41 | | |
| 728 | HMBOX1 | | | 10.05 | 8.50 | | |
| 729 | ARID1A | | | 12.22 | 11.11 | | |
| 730 | C5orf5 | | | 11.86 | 10.38 | | |
| 731 | TMSB4X | | | 16.86 | 15.10 | | |
| 732 | EPAS1 | | | 7.02 | 8.39 | | |
| 733 | HPS3 | | | 11.65 | 10.16 | | |
| 734 | DKK1 | | | 6.16 | 7.86 | | |
| 735 | ZNF282 | | | 7.89 | 5.40 | | |
| 736 | AP3D1 | | | 11.29 | 12.84 | | |
| 737 | DERL1 | | | 11.69 | 13.43 | | |
| 738 | C5orf13 | | | 9.89 | 7.62 | | |
| 739 | CCNG2 | | | 13.32 | 11.64 | | |
| 740 | PGRMC2 | | | 9.44 | 11.38 | | |
| 741 | ARF6 | | | 13.60 | 12.55 | | |
| 742 | TMEM110 | | | 7.75 | 9.24 | | |
| 743 | FAM13A1 | | | 7.11 | 9.69 | | |
| 744 | BRMS1L | | | 8.58 | 10.18 | | |
| 745 | TRAM1 | | | 12.52 | 15.17 | | |
| 746 | CALU | | | 9.42 | 11.20 | | |
| 747 | GOLPH3 | | | 11.55 | 12.81 | | |
| 748 | MAP3K7 | | | 11.14 | 10.06 | | |
| 749 | ABCG4 | | | 6.90 | 8.22 | | |
| 750 | NELF | | | 8.75 | 7.70 | | |
| 751 | ADIPOR1 | | | 9.67 | 10.92 | | |
| 752 | INSR | | | 8.48 | 11.62 | | |
| 753 | GRM5 | | | | | 6.24 | 7.65 |
| 754 | TFG | | | 10.76 | 12.30 | | |
| 755 | USP48 | | | 11.91 | 13.09 | | |
| 756 | CLCN6 | | | 9.26 | 7.48 | | |
| 757 | ZNF219 | | | 6.11 | 8.42 | | |
| 758 | C7orf43 | | | | | 8.34 | 6.62 |
| 759 | NFKB1 | | | 11.90 | 10.70 | | |
| 760 | ARF3 | | | 11.11 | 9.87 | | |
| 761 | JMJD1C | | | 12.34 | 11.11 | | |
| 762 | ROD1 | | | 13.13 | 11.42 | | |
| 763 | OXSR1 | | | 10.69 | 9.15 | | |
| 764 | ERGIC2 | | | 10.86 | 12.81 | | |
| 765 | EIF4E3 | | | 7.61 | 9.87 | | |
| 766 | SEC24A | | | 10.05 | 12.85 | | |
| 767 | SPRED1 | | | 7.19 | 5.77 | | |
| 768 | HNRPH3 | | | 12.60 | 11.38 | | |
| 769 | ZDHHC7 | | | 10.34 | 9.05 | | |
| 770 | HNRPA1 | | | 16.14 | 15.14 | | |
| 771 | TMED2 | | | 12.01 | 14.26 | | |

APPENDIX A-continued

Average expression of the genes depicted in FIG. 6*

| ID | Gene Name | Naive vs Germinal Center | | Germinal Center vs Plasma | | Germinal Center vs Memory | |
|---|---|---|---|---|---|---|---|
| | | Naive Average | GC Average | GC average | PC Average | GC Average | Memory Average |
| 772 | VASP | | | 10.60 | 8.60 | | |
| 773 | CHD4 | | | 11.40 | 10.31 | | |
| 774 | RTN4RL1 | | | 5.48 | 8.36 | | |
| 775 | PPP1R12A | | | 12.03 | 10.97 | | |
| 776 | SGK3 | | | 9.58 | 11.68 | | |
| 777 | ARHGAP17 | | | 12.37 | 8.62 | | |
| 778 | GORASP2 | | | 11.28 | 13.30 | | |
| 779 | C2orf44 | | | 8.38 | 6.72 | | |
| 780 | FAM116A | | | 11.12 | 10.08 | | |
| 781 | SSR1 | | | 12.75 | 14.73 | | |
| 782 | MYH9 | | | 11.24 | 9.89 | | |
| 783 | PIK3CD | | | 12.99 | 10.03 | | |
| 784 | DAZAP2 | | | 14.26 | 13.23 | | |
| 785 | SEL1L | | | 10.74 | 14.04 | | |
| 786 | LOC388284 | | | 7.05 | 8.32 | | |
| 787 | THRB | | | 7.51 | 6.11 | 7.51 | 6.29 |
| 788 | MGAT2 | | | 11.91 | 14.44 | | |
| 789 | C8orf13 | | | 9.35 | 6.47 | | |
| 790 | PDZD2 | | | 7.00 | 4.39 | | |
| 791 | DERL2 | | | 10.74 | 12.75 | | |
| 792 | ZCCHC5 | | | | | 7.39 | 6.27 |
| 793 | NFYC | | | 10.27 | 9.03 | | |
| 794 | GLUD2 | | | 8.88 | 7.58 | | |
| 795 | ESR1 | | | 7.55 | 9.88 | | |
| 796 | NRP2 | | | 6.51 | 8.13 | | |
| 797 | NUS1 | | | 10.01 | 11.53 | | |
| 798 | BIRC6 | | | 12.15 | 10.94 | | |
| 799 | ARID3B | | | 7.83 | 9.22 | | |
| 800 | STCH | | | 10.16 | 13.88 | | |
| 801 | SLC7A11 | | | 6.32 | 8.00 | | |
| 802 | OSBPL5 | | | 7.91 | 9.22 | 7.91 | 6.62 |
| 803 | IGFBP3 | | | 5.60 | 7.61 | | |
| 804 | LNPEP | | | 13.72 | 11.05 | | |
| 805 | ZNRF1 | | | 8.18 | 9.68 | | |
| 806 | DDAH1 | | | 7.96 | 5.87 | | |
| 807 | ERG | | | 4.07 | 7.49 | | |
| 808 | APLP2 | | | | | 10.90 | 8.38 |
| 809 | ZNFX1 | | | 10.14 | 8.93 | | |
| 810 | GPM6B | | | 8.66 | 6.69 | | |
| 811 | BLCAP | | | 11.49 | 10.10 | | |
| 812 | SRP68 | | | 11.47 | 12.88 | | |
| 813 | PIK3AP1 | | | 14.12 | 11.74 | | |
| 814 | ANKRD28 | | | 11.00 | 12.46 | | |
| 815 | KCNH8 | | | 8.27 | 4.80 | | |
| 816 | KIAA0430 | | | 12.43 | 10.61 | | |
| 817 | PPP2R1B | | | 9.84 | 8.41 | | |
| 818 | TMED9 | | | 11.62 | 13.82 | | |
| 819 | CTNNBIP1 | | | 7.31 | 8.89 | | |
| 820 | PPP2R5D | | | 9.51 | 7.92 | | |
| 821 | CBX4 | | | 12.36 | 13.69 | | |
| 822 | AKAP6 | | | 7.38 | 5.55 | 7.38 | 4.93 |
| 823 | C2orf30 | | | 10.72 | 13.84 | | |
| 824 | DR1 | | | 11.97 | 10.65 | | |
| 825 | MTDH | | | 12.46 | 13.96 | | |
| 826 | ETS1 | | | 14.40 | 12.62 | | |
| 827 | EPHA8 | | | 6.12 | 8.10 | | |
| 828 | ANKRD13B | | | | | 7.23 | 5.85 |
| 829 | C4orf16 | | | 8.83 | 7.70 | | |
| 830 | SOX4 | | | | | 9.14 | 10.20 |
| 831 | SLC12A2 | | | 10.23 | 9.01 | | |
| 832 | IER3IP1 | | | 11.35 | 12.56 | | |
| 833 | DST | | | 7.02 | 8.34 | | |
| 834 | WRNIP1 | | | 11.03 | 9.49 | | |
| 835 | CLCC1 | | | 9.63 | 11.48 | | |
| 836 | B4GALT6 | | | 7.90 | 6.82 | | |
| 837 | BTBD10 | | | 10.12 | 8.07 | | |
| 838 | SDC1 | | | 7.05 | 12.14 | | |
| 839 | C10orf12 | | | 10.32 | 8.40 | | |
| 840 | ZDHHC3 | | | 9.80 | 8.78 | | |
| 841 | GNAI2 | | | 10.86 | 9.27 | | |
| 842 | HNRPU | | | 13.82 | 12.47 | | |
| 843 | GNAZ | | | | | 8.86 | 7.26 |

APPENDIX A-continued

Average expression of the genes depicted in FIG. 6*

| ID | Gene Name | Naive vs Germinal Center | | Germinal Center vs Plasma | | Germinal Center vs Memory | |
|---|---|---|---|---|---|---|---|
| | | Naive Average | GC Average | GC average | PC Average | GC Average | Memory Average |
| 844 | ALG9 | | | 8.93 | 10.97 | | |
| 845 | FBXL10 | | | 11.75 | 10.43 | | |
| 846 | ARID4B | | | 12.19 | 10.96 | | |
| 847 | PPP1R3F | | | 6.19 | 7.79 | | |
| 848 | EPB49 | | | 6.49 | 7.94 | | |
| 849 | PCNP | | | 12.91 | 11.74 | | |
| 850 | PCYT1B | | | 11.35 | 9.77 | | |
| 851 | RAB14 | | | 11.64 | 10.41 | | |
| 852 | TCERG1 | | | 12.50 | 11.46 | | |
| 853 | MKNK2 | | | 14.87 | 12.67 | | |
| 854 | COL4A3 | | | | | 8.78 | 12.23 |
| 855 | HNRPA0 | | | 12.50 | 11.36 | | |
| 856 | P2RX4 | | | 8.88 | 10.29 | | |
| 857 | JUP | | | 9.23 | 5.70 | | |
| 858 | EGR2 | | | 10.43 | 8.07 | | |
| 859 | SUPT16H | | | 11.35 | 9.60 | | |
| 860 | PNRC2 | | | 13.93 | 11.64 | | |
| 861 | SRPR | | | 11.87 | 13.89 | | |
| 862 | BPTF | | | 12.46 | 11.34 | | |
| 863 | RBM16 | | | 12.05 | 10.52 | | |
| 864 | YWHAZ | | | 13.62 | 12.61 | | |
| 865 | EDEM3 | | | 11.01 | 12.76 | | |
| 866 | C12orf23 | | | 11.18 | 12.40 | | |
| 867 | DOC2A | | | 3.96 | 7.21 | | |
| 868 | SETD2 | | | 11.54 | 10.39 | | |
| 869 | FAM98A | | | 10.91 | 12.10 | | |
| 870 | C13orf18 | | | 13.25 | 9.86 | | |
| 871 | BRP44L | | | 10.48 | 11.91 | | |
| 872 | CCDC6 | | | 11.25 | 9.82 | | |
| 873 | GLCCI1 | | | 12.22 | 15.19 | | |
| 874 | PLEKHH1 | | | 7.03 | 9.25 | | |
| 875 | SMEK1 | | | 11.38 | 10.37 | | |
| 876 | ANKRD9 | | | 4.70 | 8.61 | | |
| 877 | CSNK1E | | | 8.86 | 11.48 | | |
| 878 | DCUN1D3 | | | 7.48 | 5.95 | | |
| 879 | LTB | | | 14.66 | 9.91 | | |
| 880 | EOMES | | | 7.30 | 6.14 | | |
| 881 | PARP8 | | | 10.81 | 8.69 | | |
| 882 | ABCD1 | | | 7.12 | 8.49 | | |
| 883 | HOXA10 | | | 5.56 | 7.32 | | |
| 884 | RNPS1 | | | 12.60 | 11.25 | | |
| 885 | AYTL2 | | | 12.08 | 10.79 | | |
| 886 | FLJ20699 | | | 5.74 | 8.80 | | |
| 887 | SAPS1 | | | 11.43 | 9.76 | | |
| 888 | SYNJ1 | | | 8.36 | 9.64 | | |
| 889 | ZNF403 | | | 12.06 | 10.91 | | |
| 890 | KPNB1 | | | 13.37 | 12.26 | | |
| 891 | ISOC1 | | | 9.67 | 10.98 | | |
| 892 | HYOU1 | | | 9.95 | 11.85 | | |
| 893 | ZNF706 | | | 12.83 | 14.30 | | |
| 894 | HDLBP | | | 10.60 | 13.37 | | |
| 895 | ELF1 | | | 12.70 | 11.34 | | |
| 896 | TM9SF4 | | | 8.66 | 10.55 | | |
| 897 | RAB8A | | | 11.94 | 10.88 | | |
| 898 | MORF4L2 | | | 12.94 | 14.69 | | |
| 899 | SERP1 | | | 13.31 | 15.16 | | |
| 900 | ADAMTS5 | | | 5.71 | 7.31 | | |
| 901 | TRIOBP | | | 11.23 | 10.18 | | |
| 902 | ZNF664 | | | 11.32 | 12.57 | | |
| 903 | RAB11FIP1 | | | 11.78 | 9.03 | | |
| 904 | MYO18A | | | 8.06 | 6.19 | | |
| 905 | DUSP10 | | | 10.13 | 8.70 | | |
| 906 | ATXN1 | | | 6.66 | 10.65 | 6.66 | 10.25 |
| 907 | EPB41L4B | | | 6.12 | 7.95 | | |
| 908 | CNTNAP1 | | | 6.51 | 9.06 | | |
| 909 | SLC17A7 | | | 6.47 | 8.01 | | |
| 910 | SPCS2 | | | 13.75 | 15.53 | | |
| 911 | CCNC | | | 12.68 | 14.10 | | |
| 912 | WDR77 | | | 10.67 | 8.83 | | |
| 913 | GMFB | | | 12.03 | 10.70 | | |
| 914 | ITGA6 | | | 6.72 | 10.51 | | |
| 915 | CASP8AP2 | | | 10.55 | 9.44 | | |

APPENDIX A-continued

| | | Naive vs Germinal Center | | Germinal Center vs Plasma | | Germinal Center vs Memory | |
|---|---|---|---|---|---|---|---|
| ID | Gene Name | Naive Average | GC Average | GC average | PC Average | GC Average | Memory Average |
| 916 | SEC24D | | | 8.79 | 11.88 | | |
| 917 | CBX1 | | | 12.16 | 10.96 | | |
| 918 | TBX3 | | | 6.05 | 7.89 | | |
| 919 | NFAT5 | | | 12.09 | 10.72 | | |
| 920 | ATP6V1B2 | | | 10.73 | 9.53 | | |
| 921 | ACTG1 | | | 16.72 | 14.81 | | |
| 922 | RND3 | | | 7.31 | 5.65 | | |
| 923 | HNRPUL1 | | | 11.97 | 10.58 | | |
| 924 | TJP1 | | | 7.18 | 10.59 | | |
| 925 | RAPGEF4 | | | 5.25 | 8.09 | | |
| 926 | RGMA | | | 5.65 | 7.42 | | |
| 927 | NAP1L1 | | | 14.70 | 12.60 | | |
| 928 | TARDBP | | | 12.72 | 11.49 | | |
| 929 | DAZAP1 | | | 12.74 | 11.30 | | |
| 930 | ZNF609 | | | 8.26 | 6.94 | 8.26 | 9.52 |
| 931 | ARL1 | | | 10.44 | 12.41 | | |
| 932 | ERC2 | | | 7.03 | 5.97 | | |
| 933 | PDE4A | | | 7.65 | 9.22 | | |
| 934 | CSK | | | 12.83 | 10.59 | | |
| 935 | IMPAD1 | | | 8.44 | 10.05 | | |
| 936 | PNN | | | 13.75 | 12.48 | | |
| 937 | DCP2 | | | 13.06 | 10.74 | | |
| 938 | PIK3R3 | | | 6.34 | 7.82 | | |
| 939 | RAB1A | | | 13.59 | 14.83 | | |
| 940 | CENTB2 | | | 12.39 | 10.97 | | |
| 941 | SPTAN1 | | | 11.48 | 9.79 | | |
| 942 | DNAJC8 | | | 12.25 | 11.00 | | |
| 943 | UNC13B | | | 6.70 | 8.35 | | |
| 944 | DHX15 | | | 14.19 | 12.99 | | |
| 945 | VEZF1 | | | 11.45 | 9.94 | | |
| 946 | DHDDS | | | 8.74 | 10.05 | | |
| 947 | FAM55C | | | 8.19 | 9.74 | | |
| 948 | USP37 | | | 8.89 | 7.60 | | |
| 949 | MMD | | | 11.68 | 10.32 | | |
| 950 | HCLS1 | | | 14.42 | 13.12 | | |
| 951 | KIAA1370 | | | 13.30 | 14.72 | | |
| 952 | GANC | | | 8.31 | 6.12 | | |
| 953 | SSRP1 | | | 11.34 | 10.27 | | |
| 954 | G3BP1 | | | 12.24 | 10.55 | | |
| 955 | BAAT | | | 4.91 | 7.24 | | |
| 956 | FNDC3B | | | 8.27 | 14.34 | | |
| 957 | FBXW7 | | | 10.21 | 12.19 | | |
| 958 | SPECC1L | | | 10.27 | 7.66 | | |
| 959 | YBX1 | | | 15.31 | 14.20 | | |
| 960 | YAP1 | | | 7.23 | 5.61 | | |
| 961 | ARF4 | | | 12.09 | 14.23 | | |
| 962 | PNKD | | | 10.86 | 9.79 | | |
| 963 | CLEC2D | | | 11.96 | 10.90 | | |
| 964 | XPO1 | | | 13.81 | 11.82 | | |
| 965 | TRAM2 | | | 9.38 | 12.80 | | |
| 966 | MITF | | | | | 8.05 | 6.41 |
| 967 | CFL1 | | | 16.37 | 14.09 | | |
| 968 | CREB5 | | | 5.46 | 7.24 | | |
| 969 | GREM1 | | | 4.48 | 7.14 | | |
| 970 | LONRF1 | | | 11.26 | 10.00 | | |
| 971 | NME7 | | | 9.37 | 8.30 | | |
| 972 | PMAIP1 | | | 12.26 | 10.75 | | |
| 973 | KLHL14 | | | 11.89 | 10.84 | | |
| 974 | AOF1 | | | 9.33 | 7.96 | 9.33 | 8.28 |
| 975 | SMPD3 | | | 5.90 | 7.83 | | |
| 976 | RGL1 | | | 6.66 | 8.04 | | |
| 977 | LYPD6 | | | 5.38 | 7.39 | | |
| 978 | STAT5B | | | 10.95 | 9.73 | | |
| 979 | C10orf6 | | | 10.04 | 8.44 | | |
| 980 | CLDND1 | | | 10.72 | 12.01 | | |
| 981 | DUSP9 | | | 5.59 | 7.70 | | |
| 982 | SLC36A1 | | | 8.53 | 7.23 | | |
| 983 | PAM | | | 8.90 | 10.86 | | |
| 984 | GHR | | | 5.87 | 7.56 | | |
| 985 | CBL | | | 11.69 | 10.26 | | |
| 986 | CENTG2 | | | 5.96 | 7.39 | | |
| 987 | BACH2 | | | 13.68 | 9.35 | 13.68 | 11.88 |

APPENDIX A-continued

Average expression of the genes depicted in FIG. 6*

| ID | Gene Name | Naive vs Germinal Center | | Germinal Center vs Plasma | | Germinal Center vs Memory | |
|---|---|---|---|---|---|---|---|
| | | Naive Average | GC Average | GC average | PC Average | GC Average | Memory Average |
| 988 | NUP153 | | | 12.33 | 10.55 | | |
| 989 | CPD | | | 8.37 | 9.72 | | |
| 990 | APLN | | | 8.58 | 6.47 | | |
| 991 | RFXDC2 | | | 11.67 | 10.00 | | |
| 992 | GABRB2 | | | 5.58 | 8.10 | | |
| 993 | NOMO3 | | | 5.39 | 7.39 | | |
| 994 | RHOJ | | | 6.41 | 7.75 | | |
| 995 | PRDM1 | | | 9.15 | 14.10 | | |
| 996 | IGSF3 | | | 7.62 | 5.91 | | |
| 997 | UBE2A | | | 12.47 | 11.47 | | |
| 998 | KBTBD8 | | | 12.82 | 9.73 | 12.82 | 11.71 |
| 999 | PRR15 | | | 7.27 | 5.94 | 7.27 | 4.67 |
| 1000 | ILF3 | | | 11.94 | 10.71 | | |
| 1001 | WIPF1 | | | 13.81 | 12.41 | | |
| 1002 | GCNT2 | | | 11.01 | 8.49 | | |
| 1003 | DBNL | | | 10.43 | 8.48 | | |
| 1004 | C14orf43 | | | 10.14 | 8.01 | | |
| 1005 | MID1IP1 | | | 9.16 | 8.11 | | |
| 1006 | LIMD2 | | | 10.43 | 8.88 | | |
| 1007 | HNRPK | | | 14.49 | 12.95 | 14.49 | 13.46 |
| 1008 | ZNF697 | | | 5.74 | 8.07 | | |
| 1009 | TSHZ3 | | | 7.31 | 5.32 | | |
| 1010 | MBNL2 | | | 11.88 | 13.47 | | |
| 1011 | ELL | | | 7.83 | 9.17 | | |
| 1012 | MAFB | | | 7.30 | 8.56 | | |
| 1013 | GGA2 | | | 13.25 | 10.77 | | |
| 1014 | C20orf121 | | | 10.01 | 8.93 | | |
| 1015 | CDC2L6 | | | 11.52 | 9.69 | | |
| 1016 | TOB2 | | | 11.39 | 9.58 | | |
| 1017 | MAP4K4 | | | 12.04 | 10.41 | | |
| 1018 | FAM102A | | | 11.41 | 10.18 | | |
| 1019 | ITGB3BP | | | 11.86 | 10.76 | | |
| 1020 | HIVEP1 | | | 10.35 | 9.05 | | |
| 1021 | NUDT21 | | | 12.51 | 11.11 | | |
| 1022 | EIF4A1 | | | | | 14.02 | 12.98 |
| 1023 | TSPAN14 | | | 8.38 | 6.31 | | |
| 1024 | SLC2A4RG | | | 8.98 | 7.40 | | |
| 1025 | DGKZ | | | 9.74 | 7.85 | | |
| 1026 | PTPN9 | | | 9.30 | 7.85 | | |
| 1027 | BCL7A | | | 11.33 | 10.10 | | |
| 1028 | LSM14A | | | 12.74 | 11.19 | | |
| 1029 | GNB2 | | | 11.50 | 10.12 | | |
| 1030 | SLC6A6 | | | 11.35 | 8.51 | | |
| 1031 | TACC1 | | | 13.21 | 11.62 | | |
| 1032 | LIMK2 | | | 9.80 | 8.12 | | |
| 1033 | ACVR2B | | | 6.69 | 8.33 | | |
| 1034 | SCC-112 | | | 12.25 | 10.55 | | |
| 1035 | PTBP1 | | | 13.38 | 12.19 | 13.38 | 12.21 |
| 1036 | CITED2 | | | 9.88 | 12.56 | | |
| 1037 | SNX5 | | | 14.17 | 13.16 | | |
| 1038 | ACTR2 | | | 15.12 | 13.32 | | |
| 1039 | OSBPL3 | | | 10.59 | 12.84 | | |
| 1040 | SFRS1 | | | 14.60 | 13.24 | | |
| 1041 | ADM | | | 7.24 | 11.10 | | |
| 1042 | PFKFB3 | | | 11.91 | 10.01 | | |
| 1043 | FNBP1 | | | 13.61 | 12.25 | | |
| 1044 | MTMR2 | | | 10.53 | 9.06 | | |
| 1045 | DDHD1 | | | | | 10.18 | 8.74 |
| 1046 | HSPA5 | | | 13.70 | 16.32 | | |
| 1047 | PTK2 | | | 12.12 | 8.33 | | |
| 1048 | UBE2I | | | 13.17 | 11.22 | | |
| 1049 | SNAP23 | | | 13.78 | 12.23 | | |
| 1050 | MTERFD2 | | | 10.53 | 8.59 | | |
| 1051 | COTL1 | | | 13.89 | 10.14 | | |
| 1052 | PHACTR2 | | | 8.65 | 6.86 | | |
| 1053 | GLRA2 | | | 5.93 | 7.69 | | |
| 1054 | NUTF2 | | | 10.39 | 9.26 | | |
| 1055 | TSGA14 | | | 9.52 | 8.03 | | |
| 1056 | FKBP1A | | | 12.16 | 10.89 | 12.16 | 10.82 |
| 1057 | LRRC1 | | | 8.82 | 7.68 | | |
| 1058 | PDIA6 | | | 13.07 | 14.91 | | |
| 1059 | YWHAQ | | | 14.50 | 12.99 | | |

APPENDIX A-continued

Average expression of the genes depicted in FIG. 6*

| ID | Gene Name | Naive vs Germinal Center | | Germinal Center vs Plasma | | Germinal Center vs Memory | |
|---|---|---|---|---|---|---|---|
| | | Naive Average | GC Average | GC average | PC Average | GC Average | Memory Average |
| 1060 | ACHE | | | 5.59 | 8.29 | | |
| 1061 | KRAS | | | 12.36 | 10.49 | | |
| 1062 | FAM107B | | | 13.87 | 12.55 | | |
| 1063 | CCDC117 | | | | | 11.03 | 9.56 |
| 1064 | WDR1 | | | 13.38 | 11.36 | | |
| 1065 | HMGB1 | | | 16.36 | 14.98 | 16.36 | 14.97 |
| 1066 | CCND3 | | | 12.69 | 9.79 | | |
| 1067 | SUV39H1 | | | | | 9.28 | 8.07 |
| 1068 | RANBP5 | | | | | 11.94 | 10.87 |
| 1069 | SLC25A33 | | | 10.24 | 9.00 | | |
| 1070 | EDNRA | | | 5.94 | 7.12 | | |
| 1071 | RAB11A | | | 12.94 | 11.73 | | |
| 1072 | DDEF1 | | | 11.98 | 10.54 | | |
| 1073 | CXorf15 | | | 11.84 | 10.47 | | |
| 1074 | C4orf34 | | | 13.65 | 10.16 | | |
| 1075 | SLC44A1 | | | 11.10 | 13.50 | | |
| 1076 | EIF2AK3 | | | 12.29 | 13.83 | | |
| 1077 | RAP1B | | | 14.21 | 13.21 | | |
| 1078 | CDK2 | | | 10.20 | 8.73 | 10.20 | 9.01 |
| 1079 | JDP2 | | | 7.94 | 5.97 | | |
| 1080 | GSTCD | | | 8.86 | 7.85 | | |
| 1081 | TNKS2 | | | 10.95 | 9.62 | 10.95 | 9.62 |
| 1082 | FUZ | | | 7.15 | 8.96 | 7.15 | 8.19 |
| 1083 | SYPL1 | | | 13.56 | 10.87 | | |
| 1084 | EIF4H | | | | | 13.07 | 12.02 |
| 1085 | PIP5K2A | | | 9.65 | 8.06 | | |
| 1086 | RGS2 | | | 11.61 | 14.48 | | |
| 1087 | ARF5 | | | | | 10.35 | 9.13 |
| 1088 | JAKMIP2 | | | 8.57 | 6.96 | | |
| 1089 | RABGAP1 | | | 12.19 | 9.65 | 12.19 | 10.85 |
| 1090 | LRIG1 | 9.76 | 10.77 | | | 10.77 | 9.16 |
| 1091 | CLTA | | | 13.08 | 11.71 | | |
| 1092 | APBB2 | | | | | 7.87 | 6.39 |
| 1093 | SMC1A | | | 12.88 | 11.33 | | |
| 1094 | CDC27 | 9.86 | 10.88 | | | | |
| 1095 | STT3A | 8.64 | 9.66 | | | | |
| 1096 | ZFAND6 | 12.01 | 13.04 | 13.04 | 11.95 | | |
| 1097 | BZRAP1 | | | 8.43 | 7.15 | | |
| 1098 | DPP3 | 9.41 | 10.44 | 10.44 | 8.39 | | |
| 1099 | CNIH | 11.94 | 12.98 | | | | |
| 1100 | TMEM16F | 9.42 | 10.46 | | | | |
| 1101 | ARHGEF7 | 11.99 | 13.03 | 13.03 | 11.18 | 13.03 | 11.60 |
| 1102 | CAMTA1 | 10.60 | 11.64 | | | | |
| 1103 | PFN1 | 14.03 | 15.08 | | | | |
| 1104 | USP12 | 10.18 | 11.23 | | | | |
| 1105 | AZIN1 | 11.24 | 12.29 | | | | |
| 1106 | GNA13 | 13.89 | 14.94 | 14.94 | 13.37 | | |
| 1107 | RCOR1 | 10.46 | 11.51 | 11.51 | 9.96 | | |
| 1108 | USP1 | | | 13.36 | 11.52 | | |
| 1109 | VANGL1 | | | 7.47 | 9.15 | | |
| 1110 | CAPZB | 11.85 | 12.91 | | | | |
| 1111 | CDV3 | 13.86 | 14.91 | | | | |
| 1112 | ABI1 | 11.61 | 12.67 | 12.67 | 10.96 | | |
| 1113 | ST5 | 7.21 | 8.28 | | | | |
| 1114 | TTL | 8.63 | 9.69 | 9.69 | 8.03 | | |
| 1115 | ANP32E | 12.76 | 13.82 | 13.82 | 12.19 | | |
| 1116 | USP7 | 12.27 | 13.34 | | | | |
| 1117 | BCL11B | 7.20 | 8.27 | | | 8.27 | 9.68 |
| 1118 | OAZ2 | 8.98 | 10.06 | | | | |
| 1119 | PPP2CA | 12.04 | 13.12 | | | 13.12 | 11.89 |
| 1120 | TSC1 | 10.58 | 11.66 | | | | |
| 1121 | CTDSPL2 | 9.81 | 10.90 | 10.90 | 9.51 | 10.90 | 9.68 |
| 1122 | NEDD4L | 7.81 | 8.90 | | | | |
| 1123 | NAT13 | 12.06 | 13.16 | | | | |
| 1124 | ASF1A | 9.54 | 10.64 | | | | |
| 1125 | DPF1 | | | 7.18 | 8.50 | 7.18 | 5.84 |
| 1126 | RAN | 13.46 | 14.57 | 14.57 | 12.39 | | |
| 1127 | ELAVL1 | 11.66 | 12.77 | 12.77 | 11.43 | | |
| 1128 | GRHL1 | | | 5.76 | 7.24 | | |
| 1129 | SMAD2 | 10.45 | 11.57 | | | | |
| 1130 | IQWD1 | 9.70 | 10.83 | | | 10.83 | 9.73 |
| 1131 | ETS2 | | | 7.50 | 5.66 | | |

APPENDIX A-continued

Average expression of the genes depicted in FIG. 6*

| ID | Gene Name | Naive vs Germinal Center | | Germinal Center vs Plasma | | Germinal Center vs Memory | |
|---|---|---|---|---|---|---|---|
| | | Naive Average | GC Average | GC average | PC Average | GC Average | Memory Average |
| 1132 | CDC25B | 10.04 | 11.18 | | | | |
| 1133 | USP32 | 10.65 | 11.78 | | | 11.78 | 10.75 |
| 1134 | EED | 11.76 | 12.90 | 12.90 | 11.50 | | |
| 1135 | CTNND2 | | | 5.93 | 7.81 | | |
| 1136 | SHROOM3 | 7.86 | 9.01 | | | 9.01 | 6.05 |
| 1137 | PSCD3 | 6.43 | 7.57 | | | | |
| 1138 | ATF7 | 7.83 | 8.97 | | | | |
| 1139 | CDK6 | 10.31 | 11.46 | | | | |
| 1140 | GCH1 | | | 12.59 | 10.17 | | |
| 1141 | AP3S1 | 11.95 | 13.12 | | | | |
| 1142 | ARL6IP1 | 12.03 | 13.20 | 13.20 | 11.51 | | |
| 1143 | TBC1D1 | 11.00 | 12.17 | | | 12.17 | 10.01 |
| 1144 | ATP2A2 | 10.75 | 11.92 | | | 11.92 | 10.76 |
| 1145 | SORL1 | 12.49 | 13.67 | 13.67 | 10.58 | | |
| 1146 | SOX5 | 9.30 | 10.47 | 10.47 | 7.33 | 10.47 | 9.08 |
| 1147 | KIAA1411 | 8.65 | 9.83 | | | | |
| 1148 | KIAA0922 | 12.43 | 13.61 | 13.61 | 10.86 | 13.61 | 12.35 |
| 1149 | SSX2IP | 7.82 | 9.00 | | | 9.00 | 7.49 |
| 1150 | SNRPD1 | 11.85 | 13.04 | | | | |
| 1151 | EDD1 | 11.23 | 12.42 | | | | |
| 1152 | BLMH | 9.01 | 10.21 | | | | |
| 1153 | PTPLB | 11.32 | 12.52 | | | | |
| 1154 | SLC25A27 | | | | | 7.44 | 3.28 |
| 1155 | PGAM1 | 12.40 | 13.61 | 13.61 | 12.55 | | |
| 1156 | HMGA1 | 11.26 | 12.47 | 12.47 | 10.36 | | |
| 1157 | EDEM1 | 11.34 | 12.55 | | | | |
| 1158 | PRPF38A | 10.27 | 11.48 | 11.48 | 10.00 | | |
| 1159 | DCUN1D1 | 9.82 | 11.03 | | | | |
| 1160 | ROBO1 | 7.43 | 8.64 | | | | |
| 1161 | LRRC59 | | | 11.26 | 12.65 | | |
| 1162 | ZNF207 | 12.29 | 13.51 | | | | |
| 1163 | GTDC1 | 9.19 | 10.42 | 10.42 | 9.35 | | |
| 1164 | C1orf121 | 10.47 | 11.70 | | | | |
| 1165 | NF1 | 9.23 | 10.46 | | | | |
| 1166 | CUL3 | 12.98 | 14.21 | 14.21 | 12.80 | 14.21 | 12.99 |
| 1167 | B4GALT5 | 8.74 | 9.97 | 9.97 | 8.08 | 9.97 | 8.71 |
| 1168 | GADD45A | 8.14 | 9.37 | 9.37 | 11.74 | | |
| 1169 | RASD2 | | | 5.53 | 7.35 | | |
| 1170 | CD4 | 6.76 | 8.01 | 8.01 | 6.11 | | |
| 1171 | WWC1 | | | 6.16 | 7.88 | | |
| 1172 | DUSP2 | 9.43 | 10.69 | 10.69 | 9.18 | | |
| 1173 | TP53INP2 | 8.44 | 9.70 | 9.70 | 8.53 | 9.70 | 8.00 |
| 1174 | NRAS | 8.89 | 10.16 | | | | |
| 1175 | TFRC | 12.12 | 13.39 | 13.39 | 11.88 | | |
| 1176 | MASTL | 8.76 | 10.03 | 10.03 | 8.23 | 10.03 | 8.64 |
| 1177 | USP6 | 9.12 | 10.39 | | | 10.39 | 9.25 |
| 1178 | VGLL4 | 10.30 | 11.57 | 11.57 | 10.16 | | |
| 1179 | C10orf78 | 8.93 | 10.21 | | | | |
| 1180 | BTG3 | 9.87 | 11.16 | | | | |
| 1181 | TMOD2 | 8.64 | 9.93 | 9.93 | 6.94 | | |
| 1182 | HOXA5 | 7.03 | 8.32 | | | | |
| 1183 | AK2 | 10.33 | 11.62 | | | | |
| 1184 | MAP2K1 | 10.41 | 11.71 | 11.71 | 10.69 | 11.71 | 10.61 |
| 1185 | CASP3 | 10.16 | 11.47 | | | | |
| 1186 | STK40 | 9.30 | 10.60 | 10.60 | 8.13 | | |
| 1187 | GRHL3 | | | 5.20 | 7.46 | | |
| 1188 | SLC25A4 | 8.65 | 9.96 | | | | |
| 1189 | KLHDC5 | 9.52 | 10.83 | | | | |
| 1190 | SAMHD1 | 9.72 | 11.03 | | | | |
| 1191 | PHLPP | 7.93 | 9.24 | | | 9.24 | 7.58 |
| 1192 | CCNE1 | 7.86 | 9.18 | | | | |
| 1193 | EGR1 | 11.92 | 13.24 | | | | |
| 1194 | PIM1 | 9.44 | 10.76 | | | 10.76 | 8.87 |
| 1195 | HECW1 | 6.49 | 7.81 | | | | |
| 1196 | CHAC1 | | | 6.73 | 8.76 | | |
| 1197 | P4HA2 | 6.84 | 8.18 | | | | |
| 1198 | PPM1E | 6.59 | 7.92 | | | | |
| 1199 | KIAA0746 | 13.65 | 14.98 | | | | |
| 1200 | LOC401720 | | | 6.33 | 7.63 | | |
| 1201 | CAPN5 | 5.90 | 7.24 | | | | |
| 1202 | DYNLL1 | 12.69 | 14.03 | | | | |
| 1203 | EHMT1 | 10.40 | 11.75 | | | | |

APPENDIX A-continued

Average expression of the genes depicted in FIG. 6*

| ID | Gene Name | Naive vs Germinal Center | | Germinal Center vs Plasma | | Germinal Center vs Memory | |
|---|---|---|---|---|---|---|---|
| | | Naive Average | GC Average | GC average | PC Average | GC Average | Memory Average |
| 1204 | RIC8B | 7.54 | 8.89 | | | | |
| 1205 | GRIN1 | | | 7.40 | 8.93 | | |
| 1206 | DEK | 12.73 | 14.09 | 14.09 | 10.29 | | |
| 1207 | E2F1 | 7.01 | 8.37 | | | 8.37 | 7.21 |
| 1208 | FAM45A | 10.66 | 12.02 | | | | |
| 1209 | VAMP1 | 11.10 | 12.47 | | | | |
| 1210 | LTBP1 | 7.23 | 8.61 | | | | |
| 1211 | SOCS1 | 9.18 | 10.56 | 10.56 | 9.25 | | |
| 1212 | ZCCHC14 | 6.98 | 8.36 | | | | |
| 1213 | KLHL3 | 8.04 | 9.43 | | | | |
| 1214 | RET | 5.90 | 7.29 | 7.29 | 5.99 | | |
| 1215 | CUTL1 | 10.33 | 11.72 | 11.72 | 10.67 | 11.72 | 10.50 |
| 1216 | RBL1 | 7.58 | 8.98 | 8.98 | 7.52 | 8.98 | 7.97 |
| 1217 | TOP1 | 11.47 | 12.87 | | | | |
| 1218 | GPD1L | 7.94 | 9.35 | | | | |
| 1219 | SAR1B | 9.03 | 10.46 | 10.46 | 12.55 | | |
| 1220 | MTF2 | 11.84 | 13.27 | 13.27 | 11.18 | | |
| 1221 | ANP32B | | | 15.53 | 14.21 | | |
| 1222 | CIT | 8.19 | 9.63 | 9.63 | 7.43 | 9.63 | 7.77 |
| 1223 | POU3F1 | 6.08 | 7.52 | | | | |
| 1224 | MTMR12 | 11.44 | 12.89 | 12.89 | 11.13 | 12.89 | 11.60 |
| 1225 | MBOAT2 | 6.73 | 8.17 | | | 8.17 | 6.25 |
| 1226 | DOCK9 | 9.28 | 10.73 | | | | |
| 1227 | ZAK | 8.60 | 10.05 | 10.05 | 8.21 | | |
| 1228 | LOC152485 | 11.05 | 12.51 | 12.51 | 10.56 | | |
| 1229 | HNRPA3 | | | 14.33 | 12.26 | | |
| 1230 | LMNB1 | | | 10.63 | 8.78 | | |
| 1231 | ZFYVE21 | 8.42 | 9.90 | | | | |
| 1232 | TXNDC5 | | | 12.47 | 16.40 | | |
| 1233 | UBE2G1 | 11.36 | 12.84 | | | | |
| 1234 | KIF23 | 7.44 | 8.93 | 8.93 | 5.57 | 8.93 | 6.64 |
| 1235 | DPYSL2 | 9.98 | 11.46 | 11.46 | 9.03 | | |
| 1236 | ATP5G3 | 12.15 | 13.64 | | | | |
| 1237 | GLRX5 | 10.08 | 11.57 | | | | |
| 1238 | NLK | 10.41 | 11.92 | | | | |
| 1239 | ARL6IP6 | 10.51 | 12.02 | 12.02 | 10.43 | | |
| 1240 | CNNM4 | 6.17 | 7.68 | 7.68 | 5.21 | | |
| 1241 | TBC1D4 | 9.12 | 10.64 | 10.64 | 8.94 | | |
| 1242 | CD163 | | | 5.49 | 7.00 | | |
| 1243 | PKD2 | 8.17 | 9.71 | | | 9.71 | 7.48 |
| 1244 | DIAPH3 | 8.23 | 9.77 | 9.77 | 8.34 | | |
| 1245 | RAD23B | 10.65 | 12.20 | | | 12.20 | 10.54 |
| 1246 | DCAMKL2 | 5.53 | 7.08 | 7.08 | 5.88 | | |
| 1247 | LMBR1 | 7.22 | 8.77 | | | | |
| 1248 | RRAS2 | 11.24 | 12.79 | 12.79 | 11.03 | | |
| 1249 | MYO1D | 6.31 | 7.88 | 7.88 | 10.07 | | |
| 1250 | KLHL5 | 10.57 | 12.15 | 12.15 | 10.43 | 12.15 | 10.80 |
| 1251 | EPS15 | 12.32 | 13.91 | | | 13.91 | 12.70 |
| 1252 | FASLG | 5.47 | 7.06 | | | | |
| 1253 | H2AFY | 12.56 | 14.16 | | | | |
| 1254 | LIMA1 | 8.47 | 10.07 | 10.07 | 9.06 | | |
| 1255 | CDCA4 | 8.92 | 10.52 | 10.52 | 9.16 | | |
| 1256 | HAS3 | 5.70 | 7.31 | 7.31 | 6.15 | | |
| 1257 | HRBL | 5.96 | 7.57 | 7.57 | 6.35 | 7.57 | 5.97 |
| 1258 | SYAP1 | 9.71 | 11.32 | | | 11.32 | 9.76 |
| 1259 | MDFIC | 12.06 | 13.67 | | | | |
| 1260 | FAM76B | 11.27 | 12.89 | 12.89 | 10.52 | | |
| 1261 | SNTB2 | 8.22 | 9.85 | 9.85 | 8.64 | | |
| 1262 | ARL3 | 8.92 | 10.55 | | | | |
| 1263 | GPR124 | 5.50 | 7.14 | | | | |
| 1264 | BCL2L11 | 10.79 | 12.43 | | | 12.43 | 11.14 |
| 1265 | RNF103 | | | 12.03 | 13.23 | | |
| 1266 | MYB | 6.97 | 8.62 | 8.62 | 5.61 | | |
| 1267 | PKM2 | 11.21 | 12.87 | | | | |
| 1268 | VCL | 8.92 | 10.57 | 10.57 | 8.25 | | |
| 1269 | RBBP7 | 12.45 | 14.11 | 14.11 | 12.96 | 14.11 | 12.70 |
| 1270 | LBR | 12.86 | 14.53 | 14.53 | 12.16 | 14.53 | 12.50 |
| 1271 | RRBP1 | 6.97 | 8.64 | 8.64 | 11.94 | | |
| 1272 | GABRB3 | 5.33 | 7.00 | | | | |
| 1273 | SGCB | 7.78 | 9.45 | 9.45 | 8.22 | | |
| 1274 | FAM81A | 6.61 | 8.30 | 8.30 | 5.44 | | |
| 1275 | RAB15 | 5.75 | 7.44 | | | | |

APPENDIX A-continued

Average expression of the genes depicted in FIG. 6*

| | | Naive vs Germinal Center | | Germinal Center vs Plasma | | Germinal Center vs Memory | |
|---|---|---|---|---|---|---|---|
| ID | Gene Name | Naive Average | GC Average | GC average | PC Average | GC Average | Memory Average |
| 1276 | SOX9 | 6.72 | 8.42 | | | | |
| 1277 | SAP30 | 8.22 | 9.91 | | | | |
| 1278 | BRWD1 | 8.60 | 10.30 | 10.30 | 8.72 | 10.30 | 9.04 |
| 1279 | KCNMA1 | 7.47 | 9.17 | 9.17 | 10.42 | | |
| 1280 | WHSC1 | 9.67 | 11.37 | 11.37 | 9.60 | | |
| 1281 | CCDC126 | 9.36 | 11.09 | | | | |
| 1282 | GRAMD1C | 7.83 | 9.57 | | | | |
| 1283 | PHF19 | 8.98 | 10.73 | 10.73 | 9.18 | | |
| 1284 | ADAM23 | 7.02 | 8.77 | 8.77 | 7.00 | | |
| 1285 | C9orf150 | 5.38 | 7.13 | | | | |
| 1286 | ZNF572 | 6.52 | 8.30 | 8.30 | 6.82 | | |
| 1287 | STK39 | 9.38 | 11.15 | 11.15 | 9.40 | | |
| 1288 | SMS | 9.73 | 11.54 | | | | |
| 1289 | DMD | 8.96 | 10.77 | 10.77 | 9.32 | | |
| 1290 | C1orf83 | 6.15 | 7.96 | | | | |
| 1291 | MFHAS1 | 9.80 | 11.61 | 11.61 | 9.36 | | |
| 1292 | STXBP1 | | | 6.57 | 7.79 | | |
| 1293 | CPNE2 | 5.44 | 7.27 | 7.27 | 4.84 | | |
| 1294 | MYH10 | 7.07 | 8.90 | | | 8.90 | 7.85 |
| 1295 | CALM3 | 9.63 | 11.46 | 11.46 | 10.30 | | |
| 1296 | EFNB2 | 7.01 | 8.85 | | | | |
| 1297 | ACTN1 | 5.89 | 7.74 | | | | |
| 1298 | RBMS3 | 5.67 | 7.51 | | | | |
| 1299 | ACOT7 | | | 9.70 | 7.83 | | |
| 1300 | RKHD1 | | | 5.92 | 7.77 | | |
| 1301 | LRRK1 | 9.74 | 11.62 | | | 11.62 | 10.12 |
| 1302 | PTCH1 | 7.70 | 9.58 | | | | |
| 1303 | MGLL | 7.30 | 9.18 | 9.18 | 10.57 | 9.18 | 8.06 |
| 1304 | YWHAH | 8.94 | 10.82 | 10.82 | 9.09 | | |
| 1305 | PDE4D | 6.78 | 8.66 | | | | |
| 1306 | MAF | 8.05 | 9.95 | 9.95 | 8.25 | | |
| 1307 | PTGER3 | 5.18 | 7.09 | | | 7.09 | 6.06 |
| 1308 | PRKCD | 9.49 | 11.40 | | | | |
| 1309 | CCDC64 | 8.15 | 10.07 | 10.07 | 7.55 | | |
| 1310 | RASL11A | | | 7.89 | 6.65 | | |
| 1311 | KPNA2 | 11.18 | 13.09 | 13.09 | 11.78 | 13.09 | 11.55 |
| 1312 | GPR137B | 8.65 | 10.58 | | | 10.58 | 9.36 |
| 1313 | TIAM1 | 6.97 | 8.90 | | | | |
| 1314 | TFDP1 | 10.95 | 12.90 | 12.90 | 10.49 | | |
| 1315 | SSBP2 | 10.47 | 12.42 | 12.42 | 10.32 | | |
| 1316 | REEP1 | 5.64 | 7.61 | | | | |
| 1317 | MAP2 | 7.85 | 9.83 | | | 9.83 | 7.75 |
| 1318 | HOXA9 | 5.15 | 7.12 | | | | |
| 1319 | SCRN1 | | | 11.81 | 9.54 | | |
| 1320 | LOC129607 | 8.79 | 10.78 | 10.78 | 9.33 | 10.78 | 9.45 |
| 1321 | SIAH2 | 10.35 | 12.34 | 12.34 | 10.57 | | |
| 1322 | DKFZP564O0823 | 6.96 | 8.95 | | | | |
| 1323 | POLQ | 8.30 | 10.30 | 10.30 | 8.98 | 10.30 | 7.83 |
| 1324 | KLF15 | 5.88 | 7.88 | 7.88 | 9.36 | 7.88 | 6.74 |
| 1325 | PXDN | 8.36 | 10.37 | | | | |
| 1326 | BTBD12 | 8.06 | 10.08 | 10.08 | 8.56 | | |
| 1327 | PHF6 | 11.19 | 13.21 | 13.21 | 11.96 | 13.21 | 12.09 |
| 1328 | SLC41A2 | 5.67 | 7.68 | | | | |
| 1329 | HN1 | 9.87 | 11.92 | 11.92 | 9.85 | 11.92 | 10.58 |
| 1330 | ZNF608 | 8.98 | 11.07 | 11.07 | 9.74 | | |
| 1331 | RNGTT | 10.32 | 12.45 | | | | |
| 1332 | RAP2A | 10.35 | 12.47 | | | | |
| 1333 | LIMK1 | 5.18 | 7.36 | | | 7.36 | 5.05 |
| 1334 | SMAD1 | 5.91 | 8.10 | 8.10 | 6.34 | | |
| 1335 | NCOA7 | 10.39 | 12.58 | | | | |
| 1336 | PRDM15 | 10.29 | 12.49 | | | | |
| 1337 | PELI1 | 10.67 | 12.88 | | | | |
| 1338 | PLS1 | 5.43 | 7.65 | | | 7.65 | 4.53 |
| 1339 | RAB23 | 6.14 | 8.36 | | | | |
| 1340 | NAP1L5 | 7.40 | 9.63 | 9.63 | 8.30 | 9.63 | 8.34 |
| 1341 | DNER | 6.90 | 9.14 | | | | |
| 1342 | LRRC42 | 7.58 | 9.83 | | | | |
| 1343 | ID2 | 7.74 | 9.99 | | | | |
| 1344 | IBRDC2 | 9.98 | 12.24 | 12.24 | 8.84 | 12.24 | 9.94 |
| 1345 | DNMT1 | 11.21 | 13.50 | | | | |
| 1346 | STAC3 | 5.74 | 8.02 | 8.02 | 7.01 | | |
| 1347 | HMGB3 | 8.20 | 10.50 | 10.50 | 8.80 | 10.50 | 8.08 |

APPENDIX A-continued

Average expression of the genes depicted in FIG. 6*

| | | Naive vs Germinal Center | | Germinal Center vs Plasma | | Germinal Center vs Memory | |
|---|---|---|---|---|---|---|---|
| ID | Gene Name | Naive Average | GC Average | GC average | PC Average | GC Average | Memory Average |
| 1348 | BMPR1A | 6.75 | 9.06 | | | | |
| 1349 | SGK | 10.06 | 12.37 | | | | |
| 1350 | CBX2 | 6.06 | 8.37 | 8.37 | 6.38 | | |
| 1351 | LRRC20 | 5.69 | 8.03 | | | | |
| 1352 | LRRC4 | 4.81 | 7.15 | 7.15 | 5.05 | | |
| 1353 | HOXA1 | 5.36 | 7.70 | | | | |
| 1354 | LRRC62 | 4.95 | 7.30 | | | | |
| 1355 | ATAD2 | 9.00 | 11.34 | 11.34 | 8.44 | 11.34 | 9.37 |
| 1356 | MOBKL1A | 9.73 | 12.08 | 12.08 | 9.13 | 12.08 | 10.12 |
| 1357 | LOC220594 | 10.06 | 12.41 | | | 12.41 | 10.07 |
| 1358 | ZNF804A | 6.14 | 8.51 | | | | |
| 1359 | C1orf113 | 5.99 | 8.36 | | | 8.36 | 5.74 |
| 1360 | FMNL2 | 6.58 | 8.96 | | | | |
| 1361 | H2AFX | | | 12.49 | 10.60 | | |
| 1362 | ATP1B1 | 5.60 | 8.03 | | | | |
| 1363 | GPT2 | 6.54 | 8.97 | | | | |
| 1364 | PSRC1 | | | 9.89 | 7.46 | | |
| 1365 | SLC25A35 | 5.23 | 7.68 | | | | |
| 1366 | LHFPL2 | 8.94 | 11.41 | | | | |
| 1367 | UBE2J1 | 11.34 | 13.81 | | | 13.81 | 12.22 |
| 1368 | TBC1D8B | 5.43 | 7.91 | 7.91 | 6.89 | | |
| 1369 | SGPP1 | 10.96 | 13.46 | 13.46 | 11.28 | | |
| 1370 | C11orf9 | 4.74 | 7.24 | | | | |
| 1371 | BCL6 | 12.29 | 14.82 | 14.82 | 10.60 | 14.82 | 11.78 |
| 1372 | ANUBL1 | 8.12 | 10.66 | | | 10.66 | 8.78 |
| 1373 | MTA3 | 8.37 | 10.92 | | | | |
| 1374 | PGBD5 | 4.87 | 7.45 | | | 7.45 | 5.87 |
| 1375 | LPP | 11.00 | 13.59 | 13.59 | 10.07 | 13.59 | 10.89 |
| 1376 | NDFIP2 | 7.39 | 9.99 | | | | |
| 1377 | STMN1 | | | 11.76 | 9.03 | | |
| 1378 | PITPNC1 | 8.77 | 11.42 | 11.42 | 10.00 | | |
| 1379 | SH3RF1 | 7.37 | 10.05 | 10.05 | 8.10 | | |
| 1380 | ASF1B | 8.56 | 11.25 | 11.25 | 7.91 | 11.25 | 8.27 |
| 1381 | FLJ20186 | 12.06 | 14.82 | 14.82 | 12.05 | | |
| 1382 | SLC16A2 | | | 8.08 | 5.17 | | |
| 1383 | PEX5 | 9.12 | 11.90 | 11.90 | 9.50 | | |
| 1384 | ECT2 | 7.45 | 10.23 | 10.23 | 7.70 | 10.23 | 7.63 |
| 1385 | MAML3 | 8.05 | 10.85 | | | | |
| 1386 | TEAD1 | 4.42 | 7.24 | | | | |
| 1387 | HMGB2 | 12.96 | 15.78 | 15.78 | 12.73 | 15.78 | 13.36 |
| 1388 | NCALD | 5.15 | 7.97 | | | | |
| 1389 | RGC32 | 7.75 | 10.62 | | | | |
| 1390 | PPP1R3C | 4.18 | 7.06 | | | | |
| 1391 | DEPDC1B | | | 9.96 | 7.11 | | |
| 1392 | WEE1 | 10.11 | 13.01 | 13.01 | 10.32 | 13.01 | 11.84 |
| 1393 | FHL2 | 4.82 | 7.77 | | | | |
| 1394 | ITGB8 | 4.70 | 7.66 | | | | |
| 1395 | SLC1A1 | | | 10.86 | 8.88 | | |
| 1396 | FAM83D | 7.36 | 10.32 | | | | |
| 1397 | UHRF1 | | | 12.22 | 8.72 | | |
| 1398 | C7orf41 | 4.94 | 7.95 | 7.95 | 6.29 | | |
| 1399 | ZBTB8 | 5.58 | 8.59 | 8.59 | 11.07 | | |
| 1400 | ZNF367 | 7.97 | 10.99 | 10.99 | 8.04 | 10.99 | 8.22 |
| 1401 | CDC25A | 6.03 | 9.09 | 9.09 | 6.81 | | |
| 1402 | CHEK1 | 7.59 | 10.68 | 10.68 | 7.72 | | |
| 1403 | CDCA7 | 10.61 | 13.76 | 13.76 | 10.16 | 13.76 | 11.06 |
| 1404 | FGF13 | 4.55 | 7.69 | | | | |
| 1405 | SSBP3 | 6.20 | 9.35 | | | | |
| 1406 | EZH2 | 9.40 | 12.57 | 12.57 | 10.22 | | |
| 1407 | TNFSF11 | 5.18 | 8.36 | 8.36 | 5.91 | 8.36 | 9.78 |
| 1408 | PACSIN1 | 5.16 | 8.35 | | | | |
| 1409 | RRM2 | 10.59 | 13.82 | 13.82 | 9.47 | 13.82 | 10.79 |
| 1410 | POU4F1 | 5.62 | 8.85 | | | | |
| 1411 | MYBL2 | 9.07 | 12.41 | 12.41 | 9.12 | | |
| 1412 | KIAA1212 | 8.46 | 11.81 | | | 11.81 | 8.55 |
| 1413 | CCNE2 | 7.30 | 10.66 | 10.66 | 8.02 | 10.66 | 8.03 |
| 1414 | IGF2BP3 | 7.92 | 11.34 | 11.34 | 9.93 | 11.34 | 9.55 |
| 1415 | PRKAR2B | 6.17 | 9.66 | 9.66 | 8.16 | | |
| 1416 | CADPS | 5.04 | 8.58 | 8.58 | 6.18 | | |
| 1417 | ANKRD15 | 6.97 | 10.52 | | | 10.52 | 7.58 |
| 1418 | DAAM1 | 9.33 | 12.92 | | | | |
| 1419 | MAP1B | 4.05 | 7.68 | 7.68 | 5.03 | 7.68 | 6.23 |

APPENDIX A-continued

Average expression of the genes depicted in FIG. 6*

| ID | Gene Name | Naive vs Germinal Center | | Germinal Center vs Plasma | | Germinal Center vs Memory | |
|---|---|---|---|---|---|---|---|
| | | Naive Average | GC Average | GC average | PC Average | GC Average | Memory Average |
| 1420 | AFF2 | 6.32 | 10.00 | | | | |
| 1421 | E2F7 | 5.66 | 9.37 | 9.37 | 6.53 | 9.37 | 6.89 |
| 1422 | PRC1 | 8.37 | 12.08 | | | | |
| 1423 | ENPP5 | 3.54 | 7.26 | 7.26 | 4.97 | | |
| 1424 | E2F8 | 7.68 | 11.41 | | | | |
| 1425 | MED12L | 7.82 | 11.59 | 11.59 | 7.46 | 11.59 | 10.57 |
| 1426 | LOC162073 | 6.30 | 10.08 | | | | |
| 1427 | LRRC32 | 4.14 | 7.93 | 7.93 | 6.61 | 7.93 | 4.95 |
| 1428 | DMXL2 | 6.57 | 10.38 | 10.38 | 6.61 | 10.38 | 7.76 |
| 1429 | FLJ20366 | 7.86 | 11.68 | 11.68 | 7.62 | 11.68 | 9.86 |
| 1430 | TOX | 9.05 | 12.88 | 12.88 | 11.27 | | |
| 1431 | MME | | | 11.56 | 10.33 | | |
| 1432 | FGD6 | 7.63 | 11.73 | 11.73 | 9.12 | | |
| 1433 | MYBL1 | 9.68 | 14.13 | 14.13 | 10.02 | 14.13 | 9.72 |

*Empty cells indicate values not appreciably measured.

TABLE 16

Predictor microRNAs that distinguish activated B-cell (ABC) DLBCL from germinal center B-cell (GCB) DLBC

| ABC vs GCB | Higher in |
|---|---|
| hsa-miR-93/mmu-miR-93/rno-miR-93 | GCB |
| hsa-miR-331-3p/mmu-miR-331-3p/rno-miR-331 | GCB |
| hsa-miR-129* | GCB |
| hsa-miR-423-3p/mmu-miR-423-3p/rno-miR-423 | GCB |
| hsa-miR-28-5p/mmu-miR-28/rno-miR-28 | GCB |
| mghv-miR-M1-7-3p | GCB |
| hsa-miR-518b | GCB |
| ebv-miR-BHRF1-1 | GCB |
| hsa-miR-140-5p/mmu-miR-140/rno-miR-140 | GCB |
| hsa-miR-505* | GCB |
| hsa-miR-675 | GCB |
| hsa-miR-198 | GCB |
| hsa-miR-125b-1*/mmu-miR-125b-3p/rno-miR-125b-3p | GCB |
| hsa-miR-361-5p/mmu-miR-361/rno-miR-361 | GCB |
| ebv-miR-BART8* | GCB |

TABLE 17

Predictor microRNAs that distinguish activated B-cell (ABC) DLBCL from Burkitt lymphoma

| ABC vs BL | Higher in |
|---|---|
| hsa-miR-155 | ABC |
| hsa-miR-29c/mmu-miR-29c/rno-miR-29c | ABC |
| hsa-miR-146b-5p/mmu-miR-146b/rno-miR-146b | ABC |
| hsa-miR-29b/mmu-miR-29b/rno-miR-29b | ABC |
| hsa-miR-22/mmu-miR-22/rno-miR-22 | ABC |
| hsa-miR-21/mmu-miR-21/rno-miR-21 | ABC |
| hsa-miR-768-3p | ABC |
| hsa-miR-145/mmu-miR-145/rno-miR-145 | ABC |
| hsa-miR-29a/mmu-miR-29a/rno-miR-29a | ABC |
| hsa-miR-30e/mmu-miR-30e/rno-miR-30e | ABC |
| hsa-miR-26a/mmu-miR-26a/rno-miR-26a | ABC |
| hsa-miR-101/mmu-miR-101a/rno-miR-101a | ABC |
| hsa-miR-24/mmu-miR-24/rno-miR-24 | ABC |
| hsa-miR-26b/mmu-miR-26b/rno-miR-26b | ABC |
| hsa-miR-27a/mmu-miR-27a/rno-miR-27a | ABC |
| hsa-miR-27b/mmu-miR-27b/rno-miR-27b | ABC |
| hsa-miR-23b/mmu-miR-23b/rno-miR-23b | ABC |
| hsa-miR-23a/mmu-miR-23a/rno-miR-23a | ABC |
| hsa-miR-125b/mmu-miR-125b-5p/rno-miR-125b-5p | ABC |
| hsa-miR-30a/mmu-miR-30a/rno-miR-30a | ABC |
| hsa-miR-142-3p/mmu-miR-142-3p/rno-miR-142-3p | ABC |
| hsa-let-7a/mmu-let-7a/rno-let-7a | ABC |
| hsa-miR-30b/mmu-miR-30b/rno-miR-30b-5p | ABC |
| hsa-miR-142-5p/mmu-miR-142-5p/rno-miR-142-5p | ABC |
| hsa-miR-34b/mmu-miR-34b-3p | ABC |
| hsa-miR-16/mmu-miR-16/rno-miR-16 | ABC |
| hsa-miR-30c/mmu-miR-30c/rno-miR-30c | ABC |
| hsa-let-7c/mmu-let-7c/rno-let-7c | ABC |
| hsa-miR-550 | ABC |
| hsa-miR-921 | BL |
| hsa-miR-30c-2*/mmu-miR-30c-2*/rno-miR-30c-2* | BL |
| hsa-miR-933 | BL |
| hsa-miR-658 | BL |
| hsa-miR-628-3p | BL |
| hsa-miR-503 | BL |
| hsa-miR-193a-5p | BL |
| hsa-miR-30b* | BL |

TABLE 17-continued

Predictor microRNAs that distinguish activated B-cell (ABC) DLBCL from Burkitt lymphoma

| ABC vs BL | Higher in |
|---|---|
| hsa-miR-93/mmu-miR-93/rno-miR-93 | BL |
| hsa-miR-18b | BL |
| hsa-miR-18a/mmu-miR-18a/rno-miR-18a | BL |
| hsa-miR-874/mmu-miR-874/rno-miR-874 | BL |

TABLE 18

Predictor microRNAs that distinguish activated B-cell (ABC) DLBCL from chronic lymphocytic leukemia

| ABC vs CLL | Higher in | ABC vs CLL (con't) | Higher in | ABC vs CLL (con't) | Higher in |
|---|---|---|---|---|---|
| hsa-miR-125b/mmu-miR-125b-5p/rno-miR-125b-5p | ABC | hsa-miR-142-5p/mmu-miR-142-5p/rno-miR-142-5p | CLL | hsa-miR-340/mmu-miR-340-5p/rno-miR-340-5p | CLL |
| hsa-miR-126/mmu-miR-126-3p/rno-miR-126 | ABC | hsa-miR-101/mmu-miR-101a/rno-miR-101a | CLL | hsa-miR-331-3p/mmu-miR-331-3p/rno-miR-331 | CLL |
| hsa-miR-199a-3p/hsa-miR-199b-3p/mmu-miR-199a-3p/mmu-miR-199b/rno-miR-199a-3p | ABC | hsa-miR-185/mmu-miR-185/rno-miR-185 | CLL | hsa-miR-151-5p/mmu-miR-151-5p/rno-miR-151 | CLL |
| hsa-miR-145/mmu-miR-145/rno-miR-145 | ABC | hsa-miR-888* | CLL | hsa-miR-636 | CLL |
| hsa-miR-143/mmu-miR-143/rno-miR-143 | ABC | hsa-miR-199a-5p/mmu-miR-199a-5p/rno-miR-199a-5p | CLL | hsa-miR-33a/mmu-miR-33/rno-miR-33 | CLL |
| hsa-miR-637 | ABC | hsa-miR-668/mmu-miR-668 | CLL | hsa-miR-486-5p/mmu-miR-486 | CLL |
| hsa-miR-371-5p | ABC | hsa-miR-549 | CLL | hsa-miR-150/mmu-miR-150/rno-miR-150 | CLL |
| kshv-miR-K12-6-3p | ABC | hsa-miR-801/mmu-miR-801 | CLL | | |
| hsa-miR-628-3p | ABC | hsa-miR-649 | CLL | hsa-miR-25/mmu-miR-25/rno-miR-25 | CLL |
| hsa-miR-126*/mmu-miR-126-5p/rno-miR-126* | ABC | hsa-miR-625* | CLL | hsa-miR-331-5p/mmu-miR-331-5p | CLL |
| hsa-miR-193a-5p | ABC | hsa-miR-140-3p/mmu-miR-140*/rno-miR-140* | CLL | hsa-miR-299-5p/mmu-miR-299*/rno-miR-299 | CLL |
| hsa-miR-21/mmu-miR-21/rno-miR-21 | ABC | hsa-let-7f/mmu-let-7f/rno-let-7f | CLL | | |
| hsa-miR-24/mmu-miR-24/rno-miR-24 | ABC | hsa-miR-768-5p | CLL | hsa-miR-891a | CLL |
| hsa-miR-503 | ABC | hsa-miR-24-1*/mmu-miR-24-1*/rno-miR-24-1* | CLL | hsa-miR-144* | CLL |
| hsa-miR-23a/mmu-miR-23a/rno-miR-23a | ABC | | | hsa-miR-363*/rno-miR-363* | CLL |
| hsa-miR-23b/mmu-miR-23b/rno-miR-23b | ABC | ebv-miR-BART13 | CLL | hsa-miR-93/mmu-miR-93/rno-miR-93 | CLL |
| hsa-miR-22/mmu-miR-22/rno-miR-22 | ABC | hsa-miR-339-5p/mmu-miR-339-5p/rno-miR-339-5p | CLL | hsa-miR-423-3p/mmu-miR-423-3p/rno-miR-423 | CLL |
| hsa-miR-665 | ABC | | | | |
| hsa-let-7c/mmu-let-7c/rno-let-7c | ABC | hsa-miR-20b/mmu-miR-20b/rno-miR-20b-5p | CLL | hsa-let-7g/mmu-let-7g | CLL |
| hsa-miR-658 | ABC | | | | |
| hsa-let-7a/mmu-let-7a/rno-let-7a | ABC | hsa-miR-335/mmu-miR-335-5p/rno-miR-335 | CLL | hsa-miR-28-5p/mmu-miR-28/rno-miR-28 | CLL |
| mghv-miR-M1-4 | ABC | | | | |
| hsa-miR-933 | ABC | mghv-miR-M1-8 | CLL | hsa-miR-20b* | CLL |
| hsa-miR-550 | CLL | hsa-miR-30d/mmu-miR-30d/rno-miR-30d | CLL | hsa-miR-140-5p/mmu-miR-140/rno-miR-140 | CLL |
| hsa-miR-30e/mmu-miR-30e/rno-miR-30e | CLL | hsa-miR-363/mmu-miR-363/rno-miR-363 | CLL | hsa-miR-519d | CLL |
| | | | | hsa-miR-147 | CLL |
| | | hsa-miR-361-3p | CLL | hsa-miR-487b/mmu-miR-487b/rno-miR-487b | CLL |
| | | hsa-miR-107/mmu-miR-107/rno-miR-107 | CLL | | |
| | | hsa-miR-154/mmu-miR-154/rno-miR-154 | CLL | hsa-miR-361-5p/mmu-miR-361/rno-miR-361 | CLL |
| | | hsa-miR-638 | CLL | hsa-miR-186/mmu-miR-186/rno-miR-186 | CLL |

TABLE 18-continued

Predictor microRNAs that distinguish activated B-cell (ABC) DLBCL from chronic lymphocytic leukemia

| ABC vs CLL | Higher in | ABC vs CLL (con't) | Higher in | ABC vs CLL (con't) | Higher in |
|---|---|---|---|---|---|
| | | | | hsa-miR-32/mmu-miR-32/rno-miR-32 | CLL |
| | | | | hsa-miR-129* | CLL |
| | | | | hsa-miR-30e*/mmu-miR-30e*/rno-miR-30e* | CLL |
| | | | | hsa-miR-196a*/mmu-miR-196a*/rno-miR-196a* | CLL |

TABLE 19

Predictor microRNAs that distinguish activated B-cell (ABC) DLBCL from follicular lymphoma

| ABC vs FL | Higher in | ABC vs FL (con't) | Higher in | ABC vs FL (con't) | Higher in |
|---|---|---|---|---|---|
| hsa-miR-938 | ABC | hsa-miR-518b | FL | hsa-miR-98/mmu-miR-98/rno-miR-98 | FL |
| hsa-miR-183*/mmu-miR-183* | ABC | hsa-miR-194/mmu-miR-194/rno-miR-194 | FL | hsa-let-7g/mmu-let-7g | FL |
| hsa-miR-197/mmu-miR-197 | ABC | hsa-miR-647 | FL | hsa-miR-302a/mmu-miR-302a | FL |
| hsa-miR-382/mmu-miR-382/rno-miR-382 | ABC | kshv-miR-K12-6-5p | FL | hsa-miR-625* | FL |
| hsa-miR-20b* | ABC | hsa-miR-622 | FL | hsa-miR-30b* | FL |
| hsa-miR-524-5p | ABC | hsa-miR-516b | FL | hsa-miR-30b/mmu-miR-30b/rno-miR-30b-5p | FL |
| hsa-miR-337-3p | ABC | hsa-miR-675 | FL | | |
| hsa-miR-600 | ABC | hsa-miR-526b | FL | | |
| hsa-miR-96/mmu-miR-96/rno-miR-96 | ABC | hsa-miR-671-5p/mmu-miR-671-5p | FL | hsa-miR-377* | FL |
| mghv-miR-M1-8 | ABC | hsa-miR-18a/mmu-miR-18a/rno-miR-18a | FL | hsa-miR-106b*/mmu-miR-106b*/rno-miR-106b* | FL |
| hsa-miR-29c*/mmu-miR-29c*/rno-miR-29c* | ABC | hsa-miR-18b | FL | hsa-miR-181a-2* | FL |
| hsa-miR-575 | ABC | hsa-miR-181b/mmu-miR-181b/rno-miR-181b | FL | hsa-miR-887 | FL |
| hsa-miR-518a-3p | ABC | | | hsa-miR-208a/mmu-miR-208a/rno-miR-208 | FL |
| hsa-miR-361-5p/mmu-miR-361/rno-miR-361 | ABC | hsa-miR-215 | FL | ebv-miR-BART7* | FL |
| hsa-miR-193b* | ABC | hsa-miR-153/mmu-miR-153/rno-miR-153 | FL | hsa-miR-7-2* | FL |
| hsa-miR-340*/mmu-miR-340-3p/rno-miR-340-3p | ABC | | | hsa-miR-155* | FL |
| | | hsa-miR-625 | FL | hsa-miR-513a-3p | FL |
| hsa-miR-708/mmu-miR-708/rno-miR-708 | ABC | hsa-miR-510 | FL | kshv-miR-K12-7 | FL |
| hsa-miR-129* | ABC | hsa-miR-519d | FL | hsa-miR-299-3p | FL |
| hsa-miR-525-5p | ABC | mghv-miR-M1-7-3p | FL | hsa-miR-218-2*/mmu-miR-218-2*/rno-miR-218* | FL |
| hsa-miR-497/mmu-miR-497/rno-miR-497 | FL | hsa-miR-485-3p/mmu-miR-485* | FL | | |
| hsa-miR-22*/mmu-miR-22*/rno-miR-22* | FL | hsa-miR-483-5p | FL | hsa-miR-130b*/mmu-miR-130b* | FL |
| hsa-miR-130b/mmu-miR-130b/rno-miR-130b | FL | hsa-miR-140-5p/mmu-miR-140/rno-miR-140 | FL | hsa-miR-620 | FL |
| | | | | hsa-miR-33a/mmu-miR-33/rno-miR-33 | FL |
| hsa-miR-551b* | FL | hsa-miR-921 | FL | hsa-miR-7/mmu-miR-7a/rno-miR-7a | FL |
| hsa-miR-331-3p/mmu-miR-331-3p/rno-miR-331 | FL | hsa-miR-186/mmu-miR-186/rno-miR-186 | FL | ebv-miR-BART6-3p | FL |
| ebv-miR-BART13 | FL | hsa-miR-196a*/mmu-miR-196a*/rno-miR-196a* | FL | hsa-miR-22/mmu-miR-22/rno-miR-22 | FL |
| hsa-miR-877/mmu-miR-877/rno-miR-877 | FL | | | hsa-miR-199b-5p | FL |
| hsa-miR-636 | FL | hsa-miR-381/mmu-miR-381/rno-miR-381 | FL | hsa-miR-768-3p | FL |
| hsa-miR-922 | FL | | | hsa-miR-494/mmu-miR-494/rno-miR-494 | FL |
| hsa-miR-198 | FL | | | | |
| hsa-miR-342-5p/mmu-miR-342-5p/rno-miR-342-5p | FL | hsa-miR-620 | FL | hsa-miR-602 | FL |
| | | hsa-miR-152/mmu-miR-152/rno-miR-152 | FL | hsa-miR-125b-2*/rno-miR-125b* | FL |
| hsa-miR-585 | FL | | | hsa-miR-300 | FL |
| ebv-miR-BART8* | FL | | | hsa-let-7e/mmu-let-7e/rno-let-7e | FL |
| hsa-miR-617 | FL | hsa-miR-766 | FL | | |
| hsa-miR-221* | FL | mghv-miR-M1-7-5p | FL | hsa-miR-298 | FL |
| hsa-miR-125b-1*/mmu-miR-125b-3p/rno-miR-125b-3p | FL | hsa-miR-374b/mmu-miR-374/rno-miR-374 | FL | hsa-miR-576-3p | FL |
| | | | | hsa-miR-187* | FL |
| hsa-miR-93/mmu-miR-93/rno-miR-93 | FL | hsa-let-7c/mmu-let- | FL | hsa-miR-365/mmu-miR-365/rno-miR-365 | FL |

TABLE 19-continued

Predictor microRNAs that distinguish activated B-cell (ABC) DLBCL from follicular lymphoma

| ABC vs FL | Higher in | ABC vs FL (con't) | Higher in | ABC vs FL (con't) | Higher in |
|---|---|---|---|---|---|
| hsa-miR-363*/rno-miR-363* | FL | 7c/rno-let-7c | | hsa-miR-518a-5p/hsa-miR-527 | FL |
| hsa-miR-744/mmu-miR-744 | FL | kshv-miR-K12-8 | FL | hsa-miR-302d* | FL |
| hsa-miR-659 | FL | mghv-miR-M1-3 | FL | hsa-miR-105 | FL |
| hsa-miR-490-3p/mmu-miR-490 | FL | hsa-miR-920 | FL | hsa-miR-126/mmu-miR-126-3p/rno-miR-126 | FL |
| hsa-let-7d/mmu-let-7d/rno-let-7d | FL | hsa-miR-519e* | FL | hsa-miR-107/mmu-miR-107/rno-miR-107 | FL |
| hsa-miR-361-3p | FL | hsa-miR-147 | FL | hsa-miR-299-5p/mmu-miR-299*/rno-miR-299 | FL |
| ebv-miR-BHRF1-1 | FL | hsa-miR-424 | FL | | |
| hsa-miR-92b/mmu-miR-92b/rno-miR-92b | FL | hsa-miR-193b | FL | hsa-miR-28-3p/rno-miR-28* | FL |
| hsa-miR-151-5p/mmu-miR-151-5p/rno-miR-151 | FL | ebv-miR-BART19-3p | FL | hsa-miR-21/mmu-miR-21/rno-miR-21 | FL |
| hsa-miR-144* | FL | hsa-miR-146b-3p | FL | hsa-miR-27b/mmu-miR-27b/rno-miR-27b | FL |
| hsa-miR-425/mmu-miR-425/rno-miR-425 | FL | hsa-miR-30c/mmu-miR-30c/rno-miR-30c | FL | hsa-miR-516a-5p | FL |
| hsa-miR-138/mmu-miR-138/rno-miR-138 | FL | hsa-miR-30a/mmu-miR-30a/rno-miR-30a | FL | hsa-miR-129-5p/mmu-miR-129-5p/rno-miR-129 | FL |
| hsa-miR-92a/mmu-miR-92a/rno-miR-92a | FL | hsa-miR-939 | FL | hsa-miR-583 | FL |
| hsa-miR-151-3p | FL | hsa-let-7a/mmu-let-7a/rno-let-7a | FL | hsa-miR-483-3p | FL |
| hsa-miR-25/mmu-miR-25/rno-miR-25 | FL | hsa-miR-122* | FL | hsa-miR-326/mmu-miR-326/rno-miR-326 | FL |
| hsa-miR-509-3-5p | FL | hsa-miR-206/mmu-miR-206/rno-miR-206 | FL | hsa-miR-548d-5p | FL |
| hsa-miR-30e*/mmu-miR-30e*/rno-miR-30e* | FL | ebv-miR-BART18-3p | FL | hsa-miR-629 | FL |
| hsa-miR-28-5p/mmu-miR-28/rno-miR-28 | FL | hsa-miR-183/mmu-miR-183/rno-miR-183 | FL | ebv-miR-BART5 | FL |
| hsa-miR-200b*/mmu-miR-200b* | FL | hsa-miR-9*/mmu-miR-9*/rno-miR-9* | FL | hsa-miR-665 | FL |
| hsa-miR-148b/mmu-miR-148b/rno-miR-148b-3p | FL | kshv-miR-K12-1 | FL | hsa-miR-493 | FL |
| hsa-miR-488 | FL | hsa-miR-34c-5p/mmu-miR-34c/rno-miR-34c | FL | hsa-miR-484/mmu-miR-484/rno-miR-484 | FL |
| hsa-miR-99b/mmu-miR-99b/rno-miR-99b | FL | hsa-miR-934 | FL | hsa-miR-645 | FL |
| hsa-miR-339-5p/mmu-miR-339-5p/rno-miR-339-5p | FL | hsa-miR-890 | FL | hsa-miR-452 | FL |
| hsv1-miR-H1 | FL | hsa-miR-514 | FL | hsa-miR-518c* | FL |
| hsa-miR-32/mmu-miR-32/rno-miR-32 | FL | hsa-miR-297/mmu-miR-297a | FL | hsa-miR-24-2*/mmu-miR-24-2*/rno-miR-24-2* | FL |
| hsa-miR-885-5p | FL | hsa-miR-553 | FL | hsa-miR-124/mmu-miR-124/rno-miR-124 | FL |
| hsa-miR-630 | FL | hsa-miR-765 | FL | hsa-miR-184/mmu-miR-184/rno-miR-184 | FL |
| ebv-miR-BART16 | FL | hsa-let-7b*/mmu-let-7b*/rno-let-7b* | FL | hsa-miR-27a*/mmu-miR-27a* | FL |
| hsa-miR-505* | FL | hsa-miR-500* | FL | | |
| hsa-miR-374b* | FL | hsa-miR-601 | FL | hsa-miR-25* | FL |
| hsa-miR-574-3p/mmu-miR-574-3p | FL | ebv-miR-BHRF1-3 | FL | hsa-miR-34b/mmu-miR-34b-3p | FL |
| hsa-miR-874/mmu-miR-874/rno-miR-874 | FL | hsa-miR-296-3p/mmu-miR-296-3p/rno-miR-296 | FL | ebv-miR-BART17-5p | FL |
| hsa-miR-423-3p/mmu-miR-423-3p/rno-miR-423 | FL | hsa-miR-574-5p/mmu-miR-574-5p | FL | hsa-miR-658 | FL |
| hsa-miR-889 | FL | hsa-miR-409-5p/mmu-miR-409-5p/rno-miR-409-5p | FL | hsa-miR-212/mmu-miR-212/rno-miR-212 | FL |
| hcmv-miR-UL148D | FL | hsa-miR-195* | FL | hsa-miR-99a/mmu-miR-99a/rno-miR-99a | FL |
| hsa-miR-487b/mmu-miR-487b/rno-miR-487b | FL | hsa-miR-635 | FL | hsa-miR-801/mmu-miR-801 | FL |
| hsa-miR-552 | FL | hsa-miR-542-3p/mmu-miR-542-3p/rno-miR-542-3p | FL | hsa-miR-491-3p | FL |
| hsa-miR-220b | FL | hcmv-miR-US25-1* | FL | hsa-miR-551b/mmu-miR-551b/rno-miR-551b | FL |
| hsa-miR-551a | FL | mghv-miR-M1-2 | FL | | |
| hsa-let-7d*/mmu-let-7d*/rno-let-7d* | FL | hsa-miR-509-5p | FL | hsa-miR-214/mmu-miR-214/rno-miR-214 | FL |
| kshv-miR-K12-5 | FL | hsa-miR-340/mmu-miR-340-5p/rno-miR-340-5p | FL | hsa-miR-30e/mmu-miR-30e/rno-miR-30e | FL |
| hsa-miR-629* | FL | hsa-miR-891a | FL | hsa-miR-888* | FL |
| hsa-miR-99b*/mmu-miR-99b*/rno-miR-99b* | FL | hsa-miR-23a/mmu-miR-23a/rno-miR-23a | FL | hsa-miR-505/rno-miR-505 | FL |
| hsa-miR-615-3p/mmu-miR-615-3p | FL | hsa-miR-19b/mmu-miR-19b/rno-miR-19b | FL | hsa-miR-27a/mmu-miR-27a/rno-miR-27a | FL |
| hsa-miR-657 | FL | hsa-miR-515-5p | FL | hsa-miR-15a/mmu-miR-15a | FL |
| hsa-miR-301a/mmu-miR-301a/rno-miR-301a | FL | hsa-miR-23b/mmu-miR-23b/rno-miR-23b | | hsa-miR-20a/mmu-miR-20a/rno-miR-20a | FL |

TABLE 19-continued

Predictor microRNAs that distinguish activated B-cell (ABC) DLBCL from follicular lymphoma

| ABC vs FL | Higher in | ABC vs FL (con't) | Higher in | ABC vs FL (con't) | Higher in |
|---|---|---|---|---|---|
| | | 23b | | kshv-miR-K12-3 | FL |
| | | hsa-miR-498 | FL | hsa-miR-455-3p | FL |
| | | hsa-miR-886-5p | FL | hsa-miR-486-5p/mmu-miR-486 | FL |
| | | hsa-miR-220c | FL | | |
| | | hsa-miR-10a/mmu-miR-10a/rno-miR-10a-5p | FL | | |
| | | hsa-miR-32* | FL | | |
| | | hsa-miR-24/mmu-miR-24/rno-miR-24 | FL | | |

TABLE 20

Predictor microRNAs that distinguish activated B-cell (ABC) DLBCL from Hodgkin's lymphoma

| ABC vs HL | Higher in | ABC vs HL (con't) | Higher in | ABC vs HL (con't) | Higher in |
|---|---|---|---|---|---|
| hsa-miR-19b/mmu-miR-19b/rno-miR-19b | ABC | hsa-miR-934 | HL | hsa-miR-488 | HL |
| hsa-miR-30b/mmu-miR-30b/rno-miR-30b-5p | ABC | hsa-miR-328/mmu-miR-328/rno-miR-328 | HL | hsa-miR-125a-3p/mmu-miR-125a-3p/rno-miR-125a-3p | HL |
| hsa-miR-142-3p/mmu-miR-142-3p/rno-miR-142-3p | ABC | hsa-miR-187* | HL | hsa-miR-24-2*/mmu-miR-24-2*/rno-miR-24-2* | HL |
| hsa-miR-768-3p | ABC | kshv-miR-K12-3 | HL | | |
| hsa-miR-30c/mmu-miR-30c/rno-miR-30c | ABC | hsa-miR-373* | HL | hsa-miR-484/mmu-miR-484/rno-miR-484 | HL |
| hsa-miR-29b/mmu-miR-29b/rno-miR-29b | ABC | hsa-miR-96/mmu-miR-96/rno-miR-96 | HL | hsa-miR-106b*/mmu-miR-106b*/rno-miR-106b* | HL |
| hsa-miR-24/mmu-miR-24/rno-miR-24 | ABC | hsa-miR-186/mmu-miR-186/rno-miR-186 | HL | | |
| hsa-miR-22/mmu-miR-22/rno-miR-22 | ABC | hsa-miR-886-5p | HL | hsa-miR-600 | HL |
| hsa-miR-30e/mmu-miR-30e/rno-miR-30e | ABC | hsa-miR-424 | HL | hsa-let-7b*/mmu-let-7b*/rno-let-7b* | HL |
| hsa-miR-30a/mmu-miR-30a/rno-miR-30a | ABC | hsa-miR-147 | HL | hsa-miR-302c* | HL |
| hsa-miR-26b/mmu-miR-26b/rno-miR-26b | ABC | hsa-miR-340/mmu-miR-340-5p/rno-miR-340-5p | HL | hsa-miR-20b* | HL |
| hsa-miR-26a/mmu-miR-26a/rno-miR-26a | ABC | hsa-miR-129-5p/mmu-miR-129-5p/rno-miR-129 | HL | hsa-miR-524-5p | HL |
| hsa-miR-15a/mmu-miR-15a | ABC | hsa-miR-25* | HL | hsa-miR-505* | HL |
| hsa-miR-16/mmu-miR-16/rno-miR-16 | ABC | hsa-miR-193b | HL | hsa-miR-542-5p/mmu-miR-542-5p/rno-miR-542-5p | HL |
| hsa-miR-142-5p/mmu-miR-142-5p/rno-miR-142-5p | ABC | hsa-miR-574-5p/mmu-miR-574-5p | HL | hsa-miR-557 | HL |
| hsa-miR-29a/mmu-miR-29a/rno-miR-29a | ABC | hsa-miR-589 | HL | hsa-miR-183/mmu-miR-183/rno-miR-183 | HL |
| hsa-miR-101/mmu-miR-101a/rno-miR-101a | ABC | hsa-miR-339-5p/mmu-miR-339-5p/rno-miR-339-5p | HL | hsa-miR-122* | HL |
| hsa-miR-126/mmu-miR-126-3p/rno-miR-126 | ABC | hsa-miR-34c-5p/mmu-miR-34c/rno-miR-34c | HL | hsa-miR-675 | HL |
| hsa-miR-451/mmu-miR-451/rno-miR-451 | ABC | hsa-miR-891a | HL | hsv1-miR-H1 | HL |
| hsa-let-7a/mmu-let-7a/rno-let-7a | ABC | hsa-miR-18a/mmu-miR-18a/rno-miR-18a | HL | hsa-miR-99b/mmu-miR-99b/rno-miR-99b | HL |
| hsa-miR-23b/mmu-miR-23b/rno-miR-23b | ABC | hsa-miR-196a*/mmu-miR-196a*/rno-miR-196a* | HL | hsa-miR-766 | HL |
| hsa-miR-21/mmu-miR-21/rno-miR-21 | ABC | hsa-miR-17*/rno-miR-17-3p | HL | hsa-miR-409-5p/mmu-miR-409-5p/rno-miR-409-5p | HL |
| hsa-miR-29c/mmu-miR-29c/rno-miR-29c | ABC | hsa-miR-296-5p/mmu-miR-296-5p/rno-miR-296* | HL | ebv-miR-BART20-3p | HL |
| hsa-miR-20a/mmu-miR-20a/rno-miR-20a | ABC | hsa-miR-25/mmu-miR-25/rno-miR-25 | HL | hsa-miR-129* | HL |
| hsa-miR-27b/mmu-miR-27b/rno-miR-27b | ABC | hsa-miR-509-5p | HL | mghv-miR-M1-7-5p | HL |
| hsa-miR-23a/mmu-miR- | ABC | hsa-miR-550* | HL | hsa-miR-671-5p/mmu-miR-671-5p | HL |
| | | hsa-miR-708/mmu-miR-708/rno-miR-708 | HL | hsa-miR-629 | HL |
| | | hsa-miR-146b-3p | HL | hsa-miR-553 | HL |
| | | hsa-miR-625* | HL | hsa-let-7d*/mmu-let-7d*/rno-let-7d* | HL |
| | | hsa-miR-210/mmu-miR-210/rno-miR-210 | HL | hsa-miR-601 | HL |
| | | hsa-miR-93/mmu-miR-93/rno-miR-93 | HL | hsa-miR-645 | HL |
| | | hsa-miR-548b-3p | HL | hsa-miR-221* | HL |
| | | hsa-miR-652/mmu-miR- | HL | hsa-miR-874/mmu-miR-874/rno-miR-874 | HL |

TABLE 20-continued

Predictor microRNAs that distinguish activated B-cell (ABC) DLBCL from Hodgkin's lymphoma

| ABC vs HL | Higher in | ABC vs HL (con't) | Higher in | ABC vs HL (con't) | Higher in |
|---|---|---|---|---|---|
| 23a/rno-miR-23a | | 652/rno-miR-652 | | hsa-miR-890 | HL |
| hsa-miR-27a/mmu-miR-27a/rno-miR-27a | ABC | hsa-miR-153/mmu-miR-153/rno-miR-153 | HL | hsa-miR-492 | HL |
| hsa-miR-550 | ABC | mghv-miR-M1-3 | HL | hsa-miR-629* | HL |
| hsa-let-7c/mmu-let-7c/rno-let-7c | ABC | hsa-miR-194* | HL | hsa-miR-635 | HL |
| hsa-miR-34b/mmu-miR-34b-3p | ABC | hsa-miR-23a*/rno-miR-23a* | HL | hsa-miR-130b/mmu-miR-130b/rno-miR-130b | HL |
| hsa-miR-933 | HL | hsa-miR-943 | HL | hsa-miR-197/mmu-miR-197 | HL |
| hsa-miR-30c-2*/mmu-miR-30c-2*/rno-miR-30c-2* | HL | hsa-let-7d/mmu-let-7d/rno-let-7d | HL | hsa-miR-654-5p | HL |
| | | hsa-miR-498 | HL | hsa-miR-518b | HL |
| hsa-miR-503 | HL | hsa-miR-381/mmu-miR-381/rno-miR-381 | HL | hsa-miR-889 | HL |
| hsa-miR-765 | HL | | | hsa-miR-584 | HL |
| hsa-miR-658 | HL | hsa-miR-586 | HL | hsa-miR-198 | HL |
| hsa-miR-620 | HL | hsa-miR-137/mmu-miR-137/rno-miR-137 | HL | hsa-miR-636 | HL |
| hsa-miR-921 | HL | hsa-miR-610 | HL | hsa-miR-630 | HL |
| hsa-miR-30b* | HL | hsa-miR-920 | HL | hsa-miR-490-5p | HL |
| mghv-miR-M1-4 | HL | hsa-miR-936 | HL | hsa-miR-663 | HL |
| hsa-miR-939 | HL | hsa-miR-744/mmu-miR-744 | HL | hcmv-miR-UL148D | HL |
| hsa-miR-494/mmu-miR-494/rno-miR-494 | HL | | | hsa-miR-337-3p | HL |
| | | ebv-miR-BART5 | HL | hsa-miR-9*/mmu-miR-9*/rno-miR-9* | HL |
| hsa-miR-32* | HL | hsa-miR-21* | HL | hsa-miR-200b*/mmu-miR-200b* | HL |
| hsa-miR-491-3p | HL | hsa-miR-516a-5p | HL | | |
| hsa-miR-10a/mmu-miR-10a/rno-miR-10a-5p | HL | hsa-miR-576-5p | HL | ebv-miR-BART9* | HL |
| | | mghv-miR-M1-6 | HL | hsa-miR-342-5p/mmu-miR-342-5p/rno-miR-342-5p | HL |
| hsa-miR-33a/mmu-miR-33/rno-miR-33 | HL | hsa-miR-425/mmu-miR-425/rno-miR-425 | HL | | |
| hsa-miR-99a/mmu-miR-99a/rno-miR-99a | HL | hsa-miR-220c | HL | hsa-miR-206/mmu-miR-206/rno-miR-206 | HL |
| hsa-miR-199b-5p | HL | hsa-miR-10a*/mmu-miR-10a*/rno-miR-10a-3p | HL | | |
| hsa-miR-365/mmu-miR-365/rno-miR-365 | HL | hsa-miR-452 | HL | hcmv-miR-US25-1* | HL |
| | | hsa-miR-345 | HL | hsa-miR-659 | HL |
| hsa-miR-520d-5p | HL | hsa-miR-29c*/mmu-miR-29c*/rno-miR-29c* | HL | hsa-miR-514 | HL |
| hsa-miR-518c* | HL | | | kshv-miR-K12-6-5p | HL |
| hsa-miR-32/mmu-miR-32/rno-miR-32 | HL | hsa-miR-887 | HL | hsa-miR-508-5p | HL |
| | | hsa-miR-7-2* | HL | hsa-miR-377* | HL |
| hsa-miR-214/mmu-miR-214/rno-miR-214 | HL | hsa-miR-363*/rno-miR-363* | HL | ebv-miR-BART16 | HL |
| hsa-miR-98/mmu-miR-98/rno-miR-98 | HL | hsa-miR-22*/mmu-miR-22*/rno-miR-22* | HL | hsa-miR-181b/mmu-miR-181b/rno-miR-181b | HL |
| hsa-miR-302d* | HL | hsa-miR-922 | HL | hsa-miR-622 | HL |
| hsa-miR-30e*/mmu-miR-30e*/rno-miR-30e* | HL | hsa-miR-92b* | HL | kshv-miR-K12-1 | HL |
| | | hsa-miR-526a/hsa-miR-520c-5p/hsa-miR-518d-5p | HL | hsa-miR-490-3p/mmu-miR-490 | HL |
| hsa-miR-374b/mmu-miR-374/rno-miR-374 | HL | | | | |
| hsa-miR-29a*/mmu-miR-29a*/rno-miR-29a* | HL | hsa-miR-574-3p/mmu-miR-574-3p | HL | hsa-miR-125b-1*/mmu-miR-125b-3p/rno-miR-125b-3p | HL |
| hsa-miR-532-5p/mmu-miR-532-5p/rno-miR-532-5p | HL | hsa-miR-92a/mmu-miR-92a/rno-miR-92a | HL | hsa-miR-124/mmu-miR-124/rno-miR-124 | HL |
| | | hsa-miR-423-3p/mmu-miR-423-3p/rno-miR-423 | HL | | |
| hsa-miR-149* | HL | | | hsa-miR-657 | HL |
| hsa-miR-422a | HL | hsa-miR-526b | HL | ebv-miR-BHRF1-3 | HL |
| ebv-miR-BHRF1-2 | HL | hsa-miR-526b* | HL | kshv-miR-K12-5 | HL |
| hsa-miR-634 | HL | ebv-miR-BART6-3p | HL | hsa-miR-487b/mmu-miR-487b/rno-miR-487b | HL |
| hsa-miR-143* | HL | hsa-miR-92b/mmu-miR-92b/rno-miR-92b | HL | | |
| hsa-miR-620 | HL | | | | |
| hsa-miR-660 | HL | hsa-miR-519e* | HL | hsa-miR-183*/mmu-miR-183* | HL |
| hsa-miR-140-5p/mmu-miR-140/rno-miR-140 | HL | hiv1-miR-H1 | HL | | |
| | | hsa-miR-623 | HL | hsa-miR-297/mmu-miR-297a | HL |
| hsa-miR-28-5p/mmu-miR-28/rno-miR-28 | HL | hsa-miR-483-5p | HL | hsa-miR-885-5p | HL |
| | | mghv-miR-M1-2 | HL | hsa-miR-296-3p/mmu-miR-296-3p/rno-miR-296 | HL |
| hsa-miR-519c-5p/hsa-miR-519b-5p/hsa-miR-523*/hsa-miR-518e*/hsa-miR-522*/hsa-miR-519a* | HL | mghv-miR-M1-7-3p | HL | | |
| | | hsa-miR-519e | HL | | |
| | | hsa-miR-361-5p/mmu-miR-361/rno-miR-361 | HL | ebv-miR-BART19-3p | HL |
| hsa-miR-505/rno-miR-505 | HL | hsa-miR-650 | HL | hsa-miR-617 | HL |
| hsa-miR-184/mmu-miR-184/rno-miR-184 | HL | hsa-miR-361-3p | HL | hsa-miR-519d | HL |
| | | hsa-miR-374b* | HL | hsa-miR-195* | HL |
| hsa-miR-107/mmu-miR-107/rno-miR-107 | HL | kshv-miR-K12-8 | HL | hsa-miR-575 | HL |
| hsa-miR-298 | HL | hsa-miR-150*/mmu-miR-150* | HL | hsa-miR-208a/mmu-miR-208a/rno-miR-208 | HL |
| hsa-miR-455-3p | HL | | | | |
| hsa-miR-638 | HL | hsa-miR-425*/mmu-miR-425* | HL | hsa-miR-647 | HL |

TABLE 20-continued

Predictor microRNAs that distinguish activated B-cell (ABC) DLBCL from Hodgkin's lymphoma

| ABC vs HL | Higher in | ABC vs HL (con't) | Higher in | ABC vs HL (con't) | Higher in |
|---|---|---|---|---|---|
| hsa-miR-502-3p | HL | hsa-miR-135a*/mmu-miR-135a* | HL | hsa-miR-525-5p | HL |
| hsa-miR-149/mmu-miR-149 | HL | hsa-miR-612 | HL | ebv-miR-BART8* | HL |
| hsa-miR-583 | HL | hsa-miR-212/mmu-miR-212/rno-miR-212 | HL | hsa-miR-340*/mmu-miR-340-3p/rno-miR-340-3p | HL |
| hsa-miR-105 | HL | | | | |
| hsa-miR-128/mmu-miR-128/rno-miR-128 | HL | hsa-miR-125b-2*/rno-miR-125b* | HL | hsa-miR-220b | HL |
| hsa-miR-656 | HL | hcmv-miR-UL112 | HL | hsa-miR-382/mmu-miR-382/rno-miR-382 | HL |
| hsa-miR-497/mmu-miR-497/rno-miR-497 | HL | hsa-miR-500 | HL | | |
| | | hsa-miR-502-5p | HL | hsa-miR-585 | HL |
| hsa-miR-152/mmu-miR-152/rno-miR-152 | HL | ebv-miR-BART18-3p | HL | hsa-miR-877/mmu-miR-877/rno-miR-877 | HL |
| | | hsa-miR-625 | HL | | |
| hsa-miR-151-5p/mmu-miR-151-5p/rno-miR-151 | | hsa-miR-138/mmu-miR-138/rno-miR-138 | HL | | |
| hsa-miR-148b/mmu-miR-148b/rno-miR-148b-3p | HL | hsa-miR-500* | HL | hsa-miR-99b*/mmu-miR-99b*/rno-miR-99b* | HL |
| hsa-miR-300 | HL | hsa-miR-124*/mmu-miR-124*/rno-miR-124* | HL | | |
| hsa-miR-144* | HL | | | ebv-miR-BHRF1-1 | HL |
| hsa-miR-145*/mmu-miR-145* | HL | hsa-miR-516b | HL | hsa-miR-326/mmu-miR-326/rno-miR-326 | HL |
| | | hsa-miR-30c-1*/mmu-miR-30c-1*/rno-miR-30c-1* | HL | | |
| hcmv-miR-UL70-3p | HL | | | ebv-miR-BART7* | HL |
| hsa-miR-28-3p/rno-miR-28* | HL | hsa-miR-331-5p/mmu-miR-331-5p | HL | hsa-miR-615-3p/mmu-miR-615-3p | HL |
| hsa-miR-27a*/mmu-miR-27a*/rno-miR-27a* | HL | hsa-miR-510 | HL | mghv-miR-M1-8 | HL |
| | | hsa-miR-376a* | HL | hsa-miR-193b* | HL |
| hsa-miR-194/mmu-miR-194/rno-miR-194 | HL | hsa-miR-640 | HL | ebv-miR-BART13 | HL |
| | | hsa-miR-331-3p/mmu-miR-331-3p/rno-miR-331 | HL | hsa-miR-433/mmu-miR-433/rno-miR-433 | HL |
| hsa-miR-130b*/mmu-miR-130b* | HL | hsa-miR-602 | HL | | |
| hsa-miR-548d-5p | HL | hsa-miR-485-3p/mmu-miR-485* | HL | hsa-miR-202 | HL |
| hsa-miR-937 | HL | | | hsa-miR-551b* | HL |
| hsa-miR-7/mmu-miR-7a/rno-miR-7a | HL | | | hsa-miR-551a | HL |
| hsa-miR-518a-5p/hsa-miR-527 | HL | | | hsa-miR-542-3p/mmu-miR-542-3p/rno-miR-542-3p | HL |
| hsa-miR-323-3p/mmu-miR-323-3p/rno-miR-323 | HL | | | hsa-miR-338-5p/mmu-miR-338-5p/rno-miR-338* | HL |
| hsa-miR-215 | HL | | | | |
| hsa-miR-513a-3p | HL | | | hsa-miR-299-3p | HL |
| hsa-miR-595 | HL | | | hsa-miR-518a-3p | HL |
| hsa-miR-515-5p | HL | | | hsa-miR-181a-2* | HL |
| hsa-miR-483-3p | HL | | | hsa-miR-938 | HL |
| hsa-miR-330-5p/mmu-miR-330/rno-miR-330 | HL | | | hsa-miR-509-3-5p | HL |
| hsa-miR-18b | HL | | | hsa-miR-552 | HL |
| hsa-miR-509-3p | HL | | | | |
| hsa-miR-151-3p | HL | | | | |

TABLE 21

Predictor microRNAs that distinguish germinal center B-cell like (GCB) DLBCL from Burkitt lymphoma

| GCBvsBL | Higher in | GCB vs BL (con't) | Higher in |
|---|---|---|---|
| hsa-miR-129* | GCB | hsa-miR-140-3p/mmu-miR-140*/rno-miR-140* | GCB |
| hsa-miR-28-5p/mmu-miR-28/rno-miR-28 | GCB | | |
| | | hsa-miR-148a/mmu-miR-148a | GCB |
| hsa-miR-155 | GCB | hsa-miR-365/mmu-miR-365/rno-miR-365 | GCB |
| hsa-miR-196a*/mmu-miR-196a*/rno-miR-196a* | GCB | | |
| | | hsa-miR-29c/mmu-miR-29c/rno-miR-29c | GCB |
| hsa-miR-146a/mmu-miR-146a/rno-miR-146a | GCB | | |
| | | hsa-miR-30d/mmu-miR-30d/rno-miR-30d | GCB |
| hsa-miR-331-3p/mmu-miR-331-3p/rno-miR-331 | GCB | | |
| | | hsa-miR-214/mmu-miR-214/rno-miR-214 | GCB |
| hsa-miR-215 | GCB | | |
| hsa-miR-600 | GCB | hsa-miR-146b-5p/mmu-miR-146b/rno-miR-146b | GCB |
| mghv-miR-M1-7-3p | GCB | | |
| hsa-miR-107/mmu-miR-107/rno-miR-107 | GCB | hsa-miR-342-3p/mmu-miR-342-3p/rno-miR-342-3p | GCB |

TABLE 21-continued

Predictor microRNAs that distinguish germinal center B-cell like (GCB) DLBCL from Burkitt lymphoma

| GCBvsBL | Higher in | GCB vs BL (con't) | Higher in |
|---|---|---|---|
| hsa-miR-886-3p | GCB | hsa-miR-374a | GCB |
| hsa-miR-140-5p/mmu-miR-140/rno-miR-140 | GCB | hsa-miR-223/mmu-miR-223/rno-miR-223 | GCB |
| hsa-miR-154/mmu-miR-154/rno-miR-154 | GCB | hsa-miR-29b/mmu-miR-29b/rno-miR-29b | GCB |
| hsa-miR-103/mmu-miR-103/rno-miR-103 | GCB | hsa-miR-21/mmu-miR-21/rno-miR-21 | GCB |
| hsa-let-7g/mmu-let-7g | GCB | hsa-miR-29a/mmu-miR-29a/rno-miR-29a | GCB |
| hsa-miR-222/mmu-miR-222/rno-miR-222 | GCB | hsa-miR-23b/mmu-miR-23b/rno-miR-23b | GCB |
| hsa-miR-221/mmu-miR-221/rno-miR-221 | GCB | hsa-miR-24/mmu-miR-24/rno-miR-24 | GCB |
| hsa-miR-320/mmu-miR-320/rno-miR-320 | GCB | hsa-miR-26a/mmu-miR-26a/rno-miR-26a | GCB |
|  |  | hsa-miR-26b/mmu-miR-26b/rno-miR-26b | GCB |
|  |  | hsa-miR-34b/mmu-miR-34b-3p | GCB |
|  |  | hsa-miR-503 | BL |
|  |  | hsa-miR-30b* | BL |

TABLE 22

Predictor microRNAs that distinguish germinal center B-cell like (GCB) DLBCL from chronic lymphocytic leukemia

| GCB vs CLL | Higher in | GCB vs CLL (con't) | Higher in | GCB vs CLL (con't) | Higher in |
|---|---|---|---|---|---|
| hsa-miR-181a/mmu-miR-181a/rno-miR-181a | GCB | hsa-miR-100/mmu-miR-100/rno-miR-100 | GCB | hsa-miR-374a | CLL |
| hsa-miR-886-5p | GCB | hsa-miR-371-5p | GCB | hsa-miR-142-5p/mmu-miR-142-5p/rno-miR-142-5p | CLL |
| mghv-miR-M1-7-3p | GCB | hsa-miR-193a-5p | GCB | hsa-miR-29c/mmu-miR-29c/rno-miR-29c | CLL |
| hsa-miR-934 | GCB | hsa-miR-628-3p | GCB | | |
| mghv-miR-M1-3 | GCB | hsa-miR-185* | GCB | hsa-miR-140-3p/mmu-miR-140*/rno-miR-140* | CLL |
| hsa-miR-485-3p/mmu-miR-485* | GCB | hsa-miR-10b/mmu-miR-10b/rno-miR-10b | GCB | | |
|  |  | hsa-miR-665 | GCB | | |
| hsa-miR-125b/mmu-miR-125b-5p/rno-miR-125b-5p | GCB | hsa-miR-503 | GCB | hsa-miR-30e/mmu-miR-30e/rno-miR-30e | CLL |
|  |  | hsa-miR-642 | GCB | | |
|  |  | hsa-miR-658 | GCB | hsa-miR-801/mmu-miR-801 | CLL |
| hsa-miR-637 | GCB | hsa-miR-21/mmu-miR-21/rno-miR-21 | GCB | | |
| hsa-miR-365/mmu-miR-365/rno-miR-365 | GCB |  |  | hsa-miR-768-3p | CLL |
|  |  | hsa-miR-23a/mmu-miR-23a/rno-miR-23a | GCB | hsa-miR-549 | CLL |
|  |  |  |  | hsa-miR-199a-5p/mmu-miR-199a-5p/rno-miR-199a-5p | CLL |
| hsa-miR-505* | GCB | hsa-miR-125a-5p/mmu-miR-125a-5p/rno-miR-125a-5p | GCB | | |
| hsa-miR-199a-3p/hsa-miR-199b-3p/mmu-miR-199a-3p/mmu-miR-199b/rno-miR-199a-3p | GCB | hsa-miR-24/mmu-miR-24/rno-miR-24 | GCB | hsa-miR-223/mmu-miR-223 | CLL |
|  |  | hsa-miR-23b/mmu-miR-23b/rno-miR-23b | GCB | hsa-miR-101/mmu-miR-101a/rno-miR-101a | CLL |
| hsa-miR-675 | GCB | hsa-miR-620 | GCB | hsa-miR-888* | CLL |
| hsa-miR-424 | GCB | hsa-miR-933 | GCB | hsa-miR-24-1*/mmu-miR-24-1*/rno-miR-24-1* | CLL |
| ebv-miR-BHRF1-2 | GCB | hsa-miR-30b* | GCB | | |
| hsa-miR-519c-5p/hsa-miR-519b-5p/hsa-miR-523*/hsa-miR-518e*/hsa-miR-522*/hsa-miR-519a* | GCB | hsa-miR-22/mmu-miR-22/rno-miR-22 | GCB | hsa-miR-519d | CLL |
|  |  | hsa-let-7e/mmu-let-7e/rno-let-7e | GCB | hsa-miR-154/mmu-miR-154/rno-miR-154 | CLL |
|  |  | mghv-miR-M1-4 | GCB | hsa-miR-638 | CLL |
|  |  | hsa-miR-149* | GCB | hsa-miR-668/mmu-miR-668 | CLL |
|  |  | hsa-miR-765 | GCB | | |
| hsa-miR-130a/mmu-miR-130a/rno-miR-130a | GCB | hsa-let-7c/mmu-let-7c/rno-let-7c | GCB | hsa-miR-891a | CLL |
|  |  |  |  | hsa-miR-768-5p | CLL |
| hsa-miR-943 | GCB | hsa-miR-423-5p/mmu-miR-423-5p |  | hsa-miR-140-5p/mmu-miR-140/rno-miR-140 | CLL |
| hsa-miR-126/mmu-miR-126-3p/rno-miR-126 | GCB | hsa-miR-32* | CLL | hsa-miR-196a*/mmu-miR-196a*/rno-miR-196a* | CLL |
|  |  | hsa-miR-34b/mmu-miR-34b-3p | CLL | | |
| hsa-miR-193b | GCB | hsa-miR-551b/mmu-miR-551b/rno-miR-551b | CLL | hsa-miR-150/mmu-miR-150/rno-miR-150 | CLL |
| hsa-miR-198 | GCB |  |  | hsa-let-7g/mmu-let-7g | CLL |
| hsa-miR-200b*/mmu-miR-200b* | GCB | hsa-let-7i/mmu-let-7i/rno-let-7i | CLL | hsa-miR-363/mmu-miR-363/rno-miR-363 | CLL |

TABLE 22-continued

Predictor microRNAs that distinguish germinal center B-cell like (GCB) DLBCL from chronic lymphocytic leukemia

| GCB vs CLL | Higher in | GCB vs CLL (con't) | Higher in | GCB vs CLL (con't) | Higher in |
|---|---|---|---|---|---|
| kshv-miR-K12-6-3p | GCB | hsa-miR-29a/mmu-miR-29a/rno-miR-29a | CLL | hsa-miR-486-5p/mmu-miR-486 | CLL |
| hsa-miR-220c | GCB | | | | |
| hsa-miR-374b* | GCB | hsa-miR-138-1*/mmu-miR-138*/rno-miR-138* | CLL | hsa-miR-32/mmu-miR-32/rno-miR-32 | CLL |
| hsa-miR-518b | GCB | | | | |
| hsa-miR-920 | GCB | | | hsa-miR-147 | CLL |
| hsa-miR-125b-1*/mmu-miR-125b-3p/rno-miR-125b-3p | GCB | hsa-miR-29b/mmu-miR-29b/rno-miR-29b | CLL | hsa-miR-20b* | CLL |
| | | hsa-miR-191/mmu-miR-191/rno-miR-191 | CLL | hsa-miR-487b/mmu-miR-487b/rno-miR-487b | CLL |
| ebv-miR-BART8* | GCB | | | | |
| ebv-miR-BART16 | GCB | hsa-miR-26b/mmu-miR-26b/rno-miR-26b | CLL | hsa-miR-636 | CLL |
| hsa-miR-630 | GCB | | | hsa-miR-144* | CLL |
| hsa-miR-483-5p | GCB | hsa-miR-26a/mmu-miR-26a/rno-miR-26a | CLL | hsa-miR-186/mmu-miR-186/rno-miR-186 | CLL |
| hsa-miR-422a | GCB | | | | |
| hsa-miR-526b | GCB | hsa-miR-550 | CLL | hsa-miR-30e*/mmu-miR-30e*/rno-miR-30e* | CLL |
| hsa-miR-145/mmu-miR-145/rno-miR-145 | GCB | | | | |
| | | | | hsa-miR-331-5p/mmu-miR-331-5p | CLL |
| hsa-miR-126*/mmu-miR-126-5p/rno-miR-126* | GCB | | | | |
| hsa-miR-143/mmu-miR-143/rno-miR-143 | GCB | | | | |

TABLE 23

Predictor microRNAs that distinguish germinal center B-cell like (GCB) DLBCL from follicular lymphoma

| GCB vs FL | Higher in | GCB vs FL (con't) | Higher in | GCB vs FL (con't) | Higher in |
|---|---|---|---|---|---|
| hsa-miR-378/mmu-miR-378/rno-miR-378 | GCB | hcmv-miR-UL148D | FL | hsa-miR-425/mmu-miR-425/rno-miR-425 | FL |
| hsa-miR-20b/mmu-miR-20b/rno-miR-20b-5p | GCB | hsa-miR-497/mmu-miR-497/rno-miR-497 | FL | hsa-miR-99b*/mmu-miR-99b*/rno-miR-99b* | FL |
| | | ebv-miR-BART13 | FL | | |
| | | ebv-miR-BART16 | FL | | |
| hsa-miR-19b/mmu-miR-19b/rno-miR-19b | GCB | hsa-miR-125b-2*/rno-miR-125b* | FL | hsa-miR-513a-3p | FL |
| hsa-miR-106a | GCB | hsa-miR-490-3p/mmu-miR-490 | FL | hsa-miR-206/mmu-miR-206/rno-miR-206 | FL |
| hsa-miR-17/mmu-miR-17/rno-miR-17-5p/rno-miR-17 | GCB | hsa-miR-99b/mmu-miR-99b/rno-miR-99b | FL | hsa-miR-155* | FL |
| hsa-miR-93/mmu-miR-93/rno-miR-93 | GCB | hsa-miR-339-5p/mmu-miR-339-5p/rno-miR-339-5p | FL | hsa-miR-181b/mmu-miR-181b/rno-miR-181b | FL |
| hsa-miR-20a/mmu-miR-20a/rno-miR-20a | GCB | | | hsa-miR-299-3p | FL |
| hsa-miR-23b/mmu-miR-23b/rno-miR-23b | GCB | hsa-miR-574-3p/mmu-miR-574-3p | FL | hsa-miR-218-2*/mmu-miR-218-2*/rno-miR-218* | FL |
| | | hsa-miR-515-5p | FL | mghv-miR-M1-8 | FL |
| hsa-miR-23a/mmu-miR-23a/rno-miR-23a | GCB | hsa-miR-877/mmu-miR-877/rno-miR-877 | FL | ebv-miR-BART18-3p | FL |
| hsa-miR-22/mmu-miR-22/rno-miR-22 | GCB | hsa-miR-208a/mmu-miR-208a/rno-miR-208 | FL | hsa-miR-708/mmu-miR-708/rno-miR-708 | FL |
| hsa-miR-19a/mmu-miR-19a/rno-miR-19a | GCB | hcmv-miR-US25-1* | FL | hsa-miR-409-5p/mmu-miR-409-5p/rno-miR-409-5p | FL |
| hsa-miR-320/mmu-miR-320/rno-miR-320 | GCB | hsa-miR-326/mmu-miR-326/rno-miR-326 | FL | hsa-miR-553 | FL |
| | | hsa-miR-488 | FL | hsa-miR-361-3p | FL |
| hsa-miR-106b/mmu-miR-106b/rno-miR-106b | GCB | hsa-miR-629 | FL | hsa-miR-296-3p/mmu-miR-296-3p/rno-miR-296 | FL |
| | | hsa-miR-24-2*/mmu-miR-24-2*/rno-miR-24-2* | FL | | |
| hsa-miR-103/mmu-miR-103/rno-miR-103 | GCB | | | ebv-miR-BHRF1-3 | FL |
| | | hsa-miR-124/mmu-miR-124/rno-miR-124 | FL | hsa-miR-34c-5p/mmu-miR-34c/rno-miR-34c | FL |
| hsa-miR-30c/mmu-miR-30c/rno-miR-30c | GCB | hsa-miR-493 | FL | hsa-let-7b*/mmu-let-7b*/rno-let-7b* | FL |
| ebv-miR-BHRF1-2 | GCB | hsv1-miR-H1 | FL | | |
| hsa-miR-125a-5p/mmu-miR-125a-5p/rno-miR-125a-5p | GCB | hsa-miR-484/mmu-miR-484/rno-miR-484 | FL | hsa-miR-301a/mmu-miR-301a/rno-miR-301a | FL |
| | | hsa-miR-483-3p | FL | | |
| hsa-let-7a/mmu-let-7a/rno-let-7a | GCB | hsa-miR-27*/mmu-miR-27*/rno-miR-27a* | FL | hsa-miR-122* | FL |
| hsa-miR-628-3p | GCB | hsa-miR-144* | FL | hsa-miR-183/mmu-miR-183/rno-miR-183 | |

TABLE 23-continued

Predictor microRNAs that distinguish germinal center B-cell like (GCB) DLBCL from follicular lymphoma

| GCB vs FL | Higher in | GCB vs FL (con't) | Higher in | GCB vs FL (con't) | Higher in |
|---|---|---|---|---|---|
| hsa-let-7c/mmu-let-7c/rno-let-7c | GCB | hsa-miR-617 | FL | kshv-miR-K12-5 | FL |
|  |  | hsa-miR-377* | FL | kshv-miR-K12-7 | FL |
| hsa-miR-423-5p/mmu-miR-423-5p | FL | hsa-miR-363*/rno-miR-363* | FL | hsa-miR-552 | FL |
|  |  |  |  | hsa-miR-151-3p | FL |
| hsa-miR-24-1*/mmu-miR-24-1*/rno-miR-24-1* | FL | hsa-miR-148b/mmu-miR-148b/rno-miR-148b-3p | FL | hsa-miR-194/mmu-miR-194/rno-miR-194 | FL |
| ebv-miR-BART2-3p | FL | kshv-miR-K12-1 | FL | hsa-miR-585 | FL |
| hsa-miR-138-1*/mmu-miR-138*/rno-miR-138* | FL | hsa-miR-7/mmu-miR-7a/rno-miR-7a | FL | hsa-miR-340*/mmu-miR-340-3p/rno-miR-340-3p | FL |
|  |  | hsa-miR-193b* | FL |  |  |
|  |  | hsa-miR-542-3p/mmu-miR-542-3p/rno-miR-542-3p | FL | hsa-let-7d*/mmu-let-7d*/rno-let-7d* | FL |
| hsa-miR-768-5p | FL |  |  | hsa-miR-622 | FL |
| hsa-miR-30b* | FL |  |  | hsa-miR-575 | FL |
| hsa-miR-494/mmu-miR-494/rno-miR-494 | FL | hsa-miR-601 | FL | hsa-miR-514 | FL |
|  |  | hsa-miR-106b*/mmu-miR-106b*/rno-miR-106b* | FL | hsa-miR-92b/mmu-miR-92b/rno-miR-92b | FL |
| hsa-miR-583 | FL |  |  |  |  |
| hsa-miR-185/mmu-miR-185/rno-miR-185 | FL | hsa-miR-7-2* | FL | hsa-miR-551a | FL |
| hsa-miR-765 | FL | kshv-miR-K12-6-5p | FL | hsa-miR-221* | FL |
| hsa-miR-34b/mmu-miR-34b-3p | FL | hsa-miR-645 | FL | hsa-miR-922 | FL |
| hsa-miR-921 | FL | hsa-miR-524-5p | FL | hsa-miR-938 | FL |
| hsa-miR-551b/mmu-miR-551b/rno-miR-551b | FL | hsa-miR-548d-5p | FL | hsa-miR-615-3p/mmu-miR-615-3p | FL |
|  |  | hsa-miR-9*/mmu-miR-9*/rno-miR-9* | FL | hsa-miR-220b | FL |
| hsa-miR-549 | FL | hsa-miR-92a/mmu-miR-92a/rno-miR-92a | FL | hsa-miR-744/mmu-miR-744 | FL |
| hsa-miR-939 | FL | hsa-miR-22*/mmu-miR-22*/rno-miR-22* | FL | hsa-miR-657 | FL |
| hsa-miR-302d* | FL |  |  | hsa-miR-382/mmu-miR-382/rno-miR-382 | FL |
| ebv-miR-BART17-5p | FL | hsa-miR-500* | FL |  |  |
| hsa-miR-801/mmu-miR-801 | FL | hsa-miR-890 | FL | hsa-miR-518a-3p | FL |
|  |  | hsa-miR-297/mmu-miR-297a | FL | hsa-miR-138/mmu-miR-138/rno-miR-138 | FL |
| hsa-miR-888* | FL |  |  |  |  |
| hsa-miR-620 | FL | hsa-miR-197/mmu-miR-197 | FL | hsa-miR-636 | FL |
| hsa-miR-576-3p | FL |  |  | hsa-miR-96/mmu-miR-96/rno-miR-96 | FL |
| hsa-miR-32* | FL | hsa-miR-20b* | FL |  |  |
| hsa-miR-574-5p/mmu-miR-574-5p | FL | hsa-miR-629* | FL | hsa-miR-509-3-5p | FL |
|  |  | hsa-miR-887 | FL | hsa-miR-337-3p | FL |
| hsa-miR-505/rno-miR-505 | FL |  |  | hsa-miR-342-5p/mmu-miR-342-5p/rno-miR-342-5p | FL |
| hsa-miR-885-5p | FL |  |  |  |  |
| hsa-miR-455-3p | FL |  |  |  |  |
| hsa-miR-152/mmu-miR-152/rno-miR-152 | FL |  |  |  |  |
| hsa-miR-200b*/mmu-miR-200b* | FL |  |  |  |  |
| mghv-miR-M1-2 | FL |  |  |  |  |

TABLE 24

Predictor microRNAs that distinguish germinal center B-cell like (GCB) DLBCL from Hodgkin's lymphoma

| GCB vs HL | Higher in | GCB vs HL (con't) | Higher in | GCB vs HL (con't) | Higher in |
|---|---|---|---|---|---|
| hsa-miR-19b/mmu-miR-19b/rno-miR-19b | GCB | hsa-miR-130b/mmu-miR-130b/rno-miR-130b | HL | hsa-miR-744/mmu-miR-744 | HL |
| hsa-miR-19a/mmu-miR-19a/rno-miR-19a | GCB | hsa-miR-671-5p/mmu-miR-671-5p | HL | kshv-miR-K12-6-5p | HL |
|  |  |  |  | hcmv-miR-US25-1* | HL |
| hsa-miR-106a | GCB | hsa-miR-525-5p | HL | hsa-miR-21* | HL |
| hsa-miR-20b/mmu-miR-20b/rno-miR-20b-5p | GCB | hsa-miR-505/rno-miR-505 | HL | mghv-miR-M1-6 | HL |
|  |  |  |  | mghv-miR-M1-8 | HL |
| hsa-miR-17/mmu-miR-17/rno-miR-17-5p/rno-miR-17 | GCB | hsa-miR-488 | HL | hsa-miR-10a*/mmu-miR-10a*/rno-miR-10a-3p | HL |
|  |  | hsa-miR-766 | HL |  |  |
|  |  | hsa-miR-20b* | HL |  |  |
| hsa-miR-15b/mmu-miR-15b/rno-miR-15b | GCB | hsa-miR-339-5p/mmu-miR-339-5p/rno-miR-339-5p | HL | hsa-miR-345 | HL |
|  |  |  |  | hsa-miR-887 | HL |
| hsa-miR-20a/mmu-miR-20a/rno-miR-20a | GCB |  |  | hsa-miR-193b* | HL |
|  |  | hsa-miR-524-5p | HL | hsa-miR-122* | HL |
| hsa-miR-30b/mmu-miR-30b/rno-miR-30b-5p | GCB | hsa-miR-455-3p | HL | kshv-miR-K12-5 | HL |
|  |  | hsa-miR-92a/mmu-miR- | HL | hsa-miR-92b* | HL |

TABLE 24-continued

Predictor microRNAs that distinguish germinal center B-cell like (GCB) DLBCL from Hodgkin's lymphoma

| GCB vs HL | Higher in | GCB vs HL (con't) | Higher in | GCB vs HL (con't) | Higher in |
|---|---|---|---|---|---|
| hsa-miR-142-3p/mmu-miR-142-3p/rno-miR-142-3p | GCB | 92a/rno-miR-92a | | hsa-miR-526b* | HL |
| | | hsa-miR-502-3p | HL | hsa-miR-553 | HL |
| hsa-miR-30c/mmu-miR-30c/rno-miR-30c | GCB | hsa-miR-210/mmu-miR-210/rno-miR-210 | HL | hsa-miR-601 | HL |
| | | hsv1-miR-H1 | HL | hiv1-miR-H1 | HL |
| hsa-miR-378/mmu-miR-378/rno-miR-378 | GCB | ebv-miR-BART6-3p | HL | hsa-miR-623 | HL |
| hsa-miR-93/mmu-miR-93/rno-miR-93 | GCB | hsa-miR-490-3p/mmu-miR-490 | HL | hsa-miR-519e | HL |
| | | | | hsa-miR-650 | HL |
| hsa-miR-106b/mmu-miR-106b/rno-miR-106b | GCB | hsa-miR-149/mmu-miR-149 | HL | hsa-miR-575 | HL |
| | | | | hsa-miR-629* | HL |
| hsa-miR-374a | GCB | hsa-miR-128/mmu-miR-128/rno-miR-128 | HL | hsa-miR-890 | HL |
| hsa-miR-24/mmu-miR-24/rno-miR-24 | GCB | | | hsa-miR-150*/mmu-miR-150* | HL |
| | | hsa-miR-635 | HL | | |
| hsa-miR-29b/mmu-miR-29b/rno-miR-29b | GCB | hcmv-miR-UL148D | HL | hsa-miR-425*/mmu-miR-425* | HL |
| | | hsa-miR-373* | HL | | |
| hsa-miR-22/mmu-miR-22/rno-miR-22 | GCB | hsa-miR-647 | HL | hsa-miR-135a*/mmu-miR-135a* | HL |
| | | hsa-miR-197/mmu-miR-197 | HL | | |
| hsa-miR-142-5p/mmu-miR-142-5p/rno-miR-142-5p | GCB | hsa-miR-602 | HL | hsa-miR-612 | HL |
| | | hsa-miR-656 | HL | hsa-miR-636 | HL |
| hsa-miR-30e/mmu-miR-30e/rno-miR-30e | GCB | hsa-miR-874/mmu-miR-874/rno-miR-874 | HL | hsa-miR-500 | HL |
| hsa-miR-30a/mmu-miR-30a/rno-miR-30a | GCB | ebv-miR-BART19-3p | HL | hsa-miR-502-5p | HL |
| | | hsa-miR-551b* | HL | hsa-miR-9*/mmu-miR-9*/rno-miR-9* | HL |
| hsa-miR-30d/mmu-miR-30d/rno-miR-30d | GCB | hsa-miR-96/mmu-miR-96/rno-miR-96 | HL | hsa-miR-500* | HL |
| hsa-miR-23b/mmu-miR-23b/rno-miR-23b | GCB | hsa-miR-889 | HL | hsa-miR-124*/mmu-miR-124*/rno-miR-124* | HL |
| hsa-miR-16/mmu-miR-16/rno-miR-16 | GCB | hsa-miR-425/mmu-miR-425/rno-miR-425 | HL | | |
| hsa-miR-191/mmu-miR-191/rno-miR-191 | GCB | hsa-miR-34c-5p/mmu-miR-34c/rno-miR-34c | HL | hsa-miR-30c-1*/mmu-miR-30c-1*/rno-miR-30c-1* | HL |
| hsa-miR-15a/mmu-miR-15a | GCB | hcmv-miR-UL70-3p | HL | hsa-miR-99b*/mmu-miR-99b*/rno-miR-99b* | HL |
| | | hsa-miR-27a*/mmu-miR-27a*/rno-miR-27a* | HL | | |
| hsa-miR-26b/mmu-miR-26b/rno-miR-26b | GCB | hsa-miR-194/mmu-miR-194/rno-miR-194 | HL | hsa-miR-331-5p/mmu-miR-331-5p | HL |
| hsa-miR-23a/mmu-miR-23a/rno-miR-23a | GCB | hsa-miR-17*/rno-miR-17-3p | HL | | |
| hsa-let-7a/mmu-let-7a/rno-let-7a | GCB | hsa-miR-548d-5p | HL | hsa-miR-206/mmu-miR-206/rno-miR-206 | HL |
| hsa-miR-103/mmu-miR-103/rno-miR-103 | GCB | hsa-miR-7/mmu-miR-7a/rno-miR-7a | HL | | |
| hsa-miR-140-3p/mmu-miR-140*/rno-miR-140* | GCB | hsa-miR-877/mmu-miR-877/rno-miR-877 | HL | hsa-miR-376a* | HL |
| | | | | hsa-miR-585 | HL |
| hsa-miR-154/mmu-miR-154/rno-miR-154 | GCB | hsa-miR-22*/mmu-miR-22* | HL | hsa-miR-640 | HL |
| | | | | hsa-miR-377* | HL |
| hsa-miR-320/mmu-miR-320/rno-miR-320 | GCB | hsa-miR-323-3p/mmu-miR-323-3p/rno-miR-323 | HL | hsa-miR-125a-3p/mmu-miR-125a-3p/rno-miR-125a-3p | HL |
| hsa-miR-550 | GCB | | | | |
| hsa-miR-125a-5p/mmu-miR-125a-5p/rno-miR-125a-5p | GCB | hsa-miR-708/mmu-miR-708/rno-miR-708 | HL | hsa-miR-24-2*/mmu-miR-24-2*/rno-miR-24-2* | HL |
| | | hsa-miR-513a-3p | HL | | |
| hsa-let-7c/mmu-let-7c/rno-let-7c | GCB | hsa-miR-595 | HL | hsa-miR-484/mmu-miR-484/rno-miR-484 | HL |
| | | hsa-miR-922 | HL | | |
| hsa-miR-185/mmu-miR-185/rno-miR-185 | HL | hsa-miR-515-5p | HL | hsa-miR-106b*/mmu-miR-106b*/rno-miR-106b* | HL |
| | | hsa-miR-99b/mmu-miR-99b/rno-miR-99b | HL | | |
| hsa-miR-658 | HL | | | | |
| hsa-miR-549 | HL | hsa-miR-483-3p | HL | hsa-let-7b*/mmu-let-7b*/rno-let-7b* | HL |
| hsa-miR-634 | HL | hsa-miR-330-5p/mmu-miR-330/rno-miR-330 | HL | | |
| hsa-miR-551b/mmu-miR-551b/rno-miR-551b | HL | | | hsa-miR-302c* | HL |
| | | hsa-miR-509-3p | HL | | |
| hsa-miR-518c* | HL | hsa-miR-151-3p | HL | hsa-miR-542-5p/mmu-miR-542-5p/rno-miR-542-5p | HL |
| hsa-miR-888* | HL | ebv-miR-BART13 | HL | | |
| hsa-miR-765 | HL | hsa-miR-617 | HL | | |
| hsa-miR-423-5p/mmu-miR-423-5p | HL | hsa-miR-328/mmu-miR-328/rno-miR-328 | HL | hsa-miR-622 | HL |
| hsa-miR-30c-2*/mmu-miR-30c-2*/rno-miR-30c-2* | HL | hsa-miR-361-3p | HL | ebv-miR-BHRF1-3 | HL |
| | | hsa-miR-138/mmu-miR-138/rno-miR-138 | HL | hsa-miR-181a-2* | HL |
| hsa-miR-503 | HL | | | hsa-miR-183/mmu-miR-183/rno-miR-183 | HL |
| hsa-miR-921 | HL | ebv-miR-BART7* | HL | | |
| hsa-miR-520d-5p | HL | hsa-miR-589 | HL | | |
| hsa-miR-574-5p/mmu-miR-574-5p | HL | hsa-miR-576-5p | HL | hsa-miR-409-5p/mmu-miR-409-5p/rno-miR-409-5p | HL |
| | | hsa-miR-452 | HL | | |
| hsa-miR-32* | HL | hsa-miR-7-2* | HL | | |

TABLE 24-continued

Predictor microRNAs that distinguish germinal center B-cell like (GCB) DLBCL from Hodgkin's lymphoma

| GCB vs HL | Higher in | GCB vs HL (con't) | Higher in | GCB vs HL (con't) | Higher in |
|---|---|---|---|---|---|
| hsa-miR-939 | HL | hsa-miR-296-5p/mmu-miR-296-5p/rno-miR-296* | HL | ebv-miR-BART20-3p | HL |
| ebv-miR-BART2-3p | HL | | | hsa-miR-629 | HL |
| ebv-miR-BHRF1-2 | HL | | | hsa-let-7d*/mmu-let-7d*/rno-let-7d* | HL |
| hsa-miR-583 | HL | hsa-miR-550* | HL | | |
| hsa-miR-30b* | HL | hsa-miR-92b/mmu-miR-92b/rno-miR-92b | HL | hsa-miR-645 | HL |
| hsa-miR-149* | HL | | | hsa-miR-492 | HL |
| mghv-miR-M1-4 | HL | kshv-miR-K12-1 | HL | hsa-miR-654-5p | HL |
| hsa-miR-513a-5p | HL | hsa-miR-526a/hsa-miR-520c-5p/hsa-miR-518d-5p | HL | hsa-miR-208a/mmu-miR-208a/rno-miR-208 | HL |
| hsa-miR-494/mmu-miR-494/rno-miR-494 | HL | | | | |
| hsa-miR-498 | HL | mghv-miR-M1-2 | HL | hsa-miR-584 | HL |
| hsa-miR-485-3p/mmu-miR-485* | HL | hsa-miR-548b-3p | HL | hsa-miR-382/mmu-miR-382/rno-miR-382 | HL |
| hsa-miR-129-5p/mmu-miR-129-5p/rno-miR-129 | HL | hsa-miR-297/mmu-miR-297a | HL | | |
| hsa-miR-25* | HL | hsa-miR-195* | HL | hsa-miR-340*/mmu-miR-340-3p/rno-miR-340-3p | HL |
| hsa-miR-923 | HL | hsa-miR-652/mmu-miR-652/rno-miR-652 | HL | | |
| hsa-miR-519d | HL | hsa-miR-221* | HL | hsa-miR-490-5p | HL |
| hsa-miR-516a-5p | HL | hsa-miR-194* | HL | hsa-miR-663 | HL |
| hsa-miR-99a/mmu-miR-99a/rno-miR-99a | HL | hsa-miR-23a*/rno-miR-23a* | HL | hsa-miR-337-3p | HL |
| hsa-miR-943 | HL | hsa-miR-125b-2*/rno-miR-125b* | HL | hsa-miR-518a-3p | HL |
| hsa-miR-885-5p | HL | | | ebv-miR-BART9* | HL |
| ebv-miR-BHRF1-1 | HL | hsa-miR-212/mmu-miR-212/rno-miR-212 | HL | hsa-miR-342-5p/mmu-miR-342-5p/rno-miR-342-5p | HL |
| hsa-miR-152/mmu-miR-152/rno-miR-152 | HL | | | | |
| ebv-miR-BART8* | HL | ebv-miR-BART18-3p | HL | hsa-miR-514 | HL |
| hsa-miR-200b*/mmu-miR-200b* | HL | hsa-miR-586 | HL | hsa-miR-508-5p | HL |
| | | hsa-miR-137/mmu-miR-137/rno-miR-137 | HL | hsa-miR-124/mmu-miR-124/rno-miR-124 | HL |
| hsa-miR-125b-1*/mmu-miR-125b-3p/rno-miR-125b-3p | HL | hsa-miR-610 | HL | | |
| | | hcmv-miR-UL112 | HL | hsa-miR-657 | HL |
| hsa-miR-526b | HL | hsa-miR-181b/mmu-miR-181b/rno-miR-181b | HL | hsa-miR-938 | HL |
| hsa-miR-29a*/mmu-miR-29a*/rno-miR-29a* | HL | hsa-miR-936 | HL | hsa-miR-296-3p/mmu-miR-296-3p/rno-miR-296 | HL |
| hsa-miR-532-5p/mmu-miR-532-5p/rno-miR-532-5p | HL | | | | |
| hsa-miR-183*/mmu-miR-183* | HL | | | hsa-miR-551a | HL |
| hsa-miR-659 | HL | | | hsa-miR-542-3p/mmu-miR-542-3p/rno-miR-542-3p | HL |
| hsa-miR-145*/mmu-miR-145* | HL | | | hsa-miR-220b | HL |
| mghv-miR-M1-7-5p | HL | | | hsa-miR-326/mmu-miR-326/rno-miR-326 | HL |
| hsa-miR-143* | HL | | | | |
| hsa-miR-660 | HL | | | hsa-miR-615-3p/mmu-miR-615-3p | HL |
| | | | | hsa-miR-433/mmu-miR-433/rno-miR-433 | HL |
| | | | | hsa-miR-202 | HL |
| | | | | hsa-miR-338-5p/mmu-miR-338-5p/rno-miR-338* | HL |
| | | | | hsa-miR-552 | HL |
| | | | | hsa-miR-299-3p | HL |
| | | | | hsa-miR-509-3-5p | HL |

TABLE 25

Predictor microRNAs that distinguish Burkitt lymphoma from chromic lymphocytic leukemia

| BL vs CLL | Higher in |
|---|---|
| hsa-miR-874/mmu-miR-874/rno-miR-874 | BL |
| hsa-miR-125b/mmu-miR-125b-5p/rno-miR-125b-5p | BL |
| hsa-miR-126/mmu-miR-126-3p/rno-miR-126 | BL |
| ebv-miR-BHRF1-2 | BL |
| hsa-miR-193b | BL |

TABLE 25-continued

Predictor microRNAs that distinguish Burkitt lymphoma from chromic lymphocytic leukemia

| BL vs CLL | Higher in |
|---|---|
| hsa-miR-371-5p | BL |
| hsa-miR-193a-5p | BL |
| hsa-miR-628-3p | BL |
| hsa-miR-185* | BL |
| hsa-miR-503 | BL |
| hsa-miR-199a-3p/hsa-miR-199b-3p/mmu-miR-199a-3p/mmu-miR-199b/rno-miR-199a-3p | BL |
| hsa-miR-143/mmu-miR-143/rno-miR-143 | BL |
| hsa-miR-130a/mmu-miR-130a/rno-miR-130a | BL |
| hsa-miR-145/mmu-miR-145/rno-miR-145 | BL |
| hsa-miR-30b* | BL |
| hsa-miR-665 | BL |
| hsa-miR-658 | BL |
| hsa-miR-933 | BL |
| hsa-miR-30c-2*/mmu-miR-30c-2*/rno-miR-30c-2* | BL |
| hsa-miR-765 | BL |
| hsa-miR-620 | BL |
| hsa-miR-520d-5p | BL |
| hsa-miR-494/mmu-miR-494/rno-miR-494 | BL |
| hsa-miR-551b/mmu-miR-551b/rno-miR-551b | CLL |
| hsa-miR-106b/mmu-miR-106b/rno-miR-106b | CLL |
| hsa-miR-30c/mmu-miR-30c/rno-miR-30c | CLL |
| hsa-miR-16/mmu-miR-16/rno-miR-16 | CLL |
| hsa-miR-27a/mmu-miR-27a/rno-miR-27a | CLL |
| hsa-miR-27b/mmu-miR-27b/rno-miR-27b | CLL |
| hsa-miR-550 | CLL |
| hsa-miR-30a/mmu-miR-30a/rno-miR-30a | CLL |
| hsa-miR-30b/mmu-miR-30b/rno-miR-30b-5p | CLL |
| hsa-miR-34b/mmu-miR-34b-3p | CLL |
| hsa-miR-801/mmu-miR-801 | CLL |
| hsa-miR-26b/mmu-miR-26b/rno-miR-26b | CLL |
| hsa-let-7b/mmu-let-7b/rno-let-7b | CLL |
| hsa-miR-142-5p/mmu-miR-142-5p/rno-miR-142-5p | CLL |
| hsa-miR-26a/mmu-miR-26a/rno-miR-26a | CLL |
| hsa-miR-29a/mmu-miR-29a/rno-miR-29a | CLL |
| hsa-miR-768-3p | CLL |
| hsa-miR-199a-5p/mmu-miR-199a-5p/rno-miR-199a-5p | CLL |
| hsa-miR-30e/mmu-miR-30e/rno-miR-30e | CLL |
| hsa-miR-29b/mmu-miR-29b/rno-miR-29b | CLL |
| hsa-miR-101/mmu-miR-101a/rno-miR-101a | CLL |
| hsa-miR-138-1*/mmu-miR-138*/rno-miR-138* | CLL |
| hsa-miR-195/mmu-miR-195/rno-miR-195 | CLL |
| hsa-miR-549 | CLL |
| hsa-miR-103/mmu-miR-103/rno-miR-103 | CLL |
| hsa-miR-649 | CLL |
| hsa-miR-335/mmu-miR-335-5p/rno-miR-335 | CLL |
| hsa-miR-342-3p/mmu-miR-342-3p/rno-miR-342-3p | CLL |
| hsa-miR-423-3p/mmu-miR-423-3p/rno-miR-423 | CLL |
| hsa-miR-222/mmu-miR-222/rno-miR-222 | CLL |
| hsa-miR-374a | CLL |
| hsa-miR-888* | CLL |
| hsa-miR-30d/mmu-miR-30d/rno-miR-30d | CLL |
| hsa-miR-299-5p/mmu-miR-299*/rno-miR-299 | CLL |
| hsa-miR-107/mmu-miR-107/rno-miR-107 | CLL |
| hsa-miR-105 | CLL |
| hsa-let-7f/mmu-let-7f/rno-let-7f | CLL |
| hsa-miR-191/mmu-miR-191/rno-miR-191 | CLL |
| hsa-miR-223/mmu-miR-223/rno-miR-223 | CLL |
| hsa-miR-361-5p/mmu-miR-361/rno-miR-361 | CLL |
| hsa-miR-29c/mmu-miR-29c/rno-miR-29c | CLL |
| hsa-miR-147 | CLL |
| hsa-miR-361-3p | CLL |
| hsa-miR-140-3p/mmu-miR-140*/rno-miR-140* | CLL |
| hsa-miR-486-5p/mmu-miR-486 | CLL |
| hsa-miR-33a/mmu-miR-33/rno-miR-33 | CLL |
| hsa-miR-636 | CLL |
| hsa-miR-24-1*/mmu-miR-24-1*/rno-miR-24-1* | CLL |
| hsa-miR-144* | CLL |
| hsa-miR-668/mmu-miR-668 | CLL |
| hsa-miR-768-5p | CLL |
| hsa-miR-363/mmu-miR-363/rno-miR-363 | CLL |
| hsa-miR-150/mmu-miR-150/rno-miR-150 | CLL |
| hsa-miR-519d | CLL |
| hsa-miR-891a | CLL |
| hsa-miR-186/mmu-miR-186/rno-miR-186 | CLL |
| hsa-miR-331-5p/mmu-miR-331-5p | CLL |
| hsa-miR-28-5p/mmu-miR-28/rno-miR-28 | CLL |
| hsa-miR-154/mmu-miR-154/rno-miR-154 | CLL |
| hsa-miR-155 | CLL |
| hsa-miR-363*/rno-miR-363* | CLL |
| hsa-miR-32/mmu-miR-32/rno-miR-32 | CLL |
| hsa-miR-30e*/mmu-miR-30e*/rno-miR-30e* | CLL |

TABLE 25-continued

Predictor microRNAs that distinguish Burkitt lymphoma from chronic lymphocytic leukemia

| BL vs CLL | Higher in |
|---|---|
| hsa-miR-140-5p/mmu-miR-140/rno-miR-140 | CLL |
| hsa-let-7g/mmu-let-7g | CLL |
| hsa-miR-20b* | CLL |
| hsa-miR-129* | CLL |
| hsa-miR-196a*/mmu-miR-196a*/rno-miR-196a* | CLL |
| hsa-miR-487b/mmu-miR-487b/rno-miR-487b | CLL |

TABLE 26

Predictor microRNAs that distinguish Burkitt lymphoma from follicular lymphoma

| BL vs FL | Higher in |
|---|---|
| hsa-miR-17/mmu-miR-17/rno-miR-17-5p/rno-miR-17 | BL |
| hsa-miR-106a | BL |
| hsa-miR-19b/mmu-miR-19b/rno-miR-19b | BL |
| hsa-miR-20a/mmu-miR-20a/rno-miR-20a | BL |
| hsa-miR-19a/mmu-miR-19a/rno-miR-19a | BL |
| hsa-miR-628-3p | BL |
| hsa-miR-503 | BL |
| hsa-miR-371-5p | BL |
| hsa-miR-106b/mmu-miR-106b/rno-miR-106b | BL |
| hsa-miR-30c-2*/mmu-miR-30c-2*/rno-miR-30c-2* | BL |
| ebv-miR-BART2-3p | FL |
| hsa-let-7e/mmu-let-7e/rno-let-7e | FL |
| hsa-miR-551b/mmu-miR-551b/rno-miR-551b | FL |
| hsa-miR-26b/mmu-miR-26b/rno-miR-26b | FL |
| hsa-miR-26a/mmu-miR-26a/rno-miR-26a | FL |
| hsa-miR-620 | FL |
| hsa-miR-801/mmu-miR-801 | FL |
| ebv-miR-BART17-5p | FL |
| hsa-miR-29a/mmu-miR-29a/rno-miR-29a | FL |
| hsa-miR-34b/mmu-miR-34b-3p | FL |
| hsa-miR-32* | FL |
| hsa-miR-29b/mmu-miR-29b/rno-miR-29b | FL |
| hsa-miR-649 | FL |
| hsa-miR-576-3p | FL |
| hsa-miR-302a/mmu-miR-302a | FL |
| hsa-miR-365/mmu-miR-365/rno-miR-365 | FL |
| hsa-miR-148a/mmu-miR-148a | FL |
| hsa-miR-146b-5p/mmu-miR-146b/rno-miR-146b | FL |
| hsa-miR-505/rno-miR-505 | FL |
| hsa-miR-33a/mmu-miR-33/rno-miR-33 | FL |
| hsa-miR-455-3p | FL |

TABLE 26-continued

Predictor microRNAs that distinguish Burkitt lymphoma from follicular lymphoma

| BL vs FL | Higher in |
|---|---|
| hsa-miR-374b/mmu-miR-374/rno-miR-374 | FL |
| hsa-miR-214/mmu-miR-214/rno-miR-214 | FL |
| hsa-miR-138-1*/mmu-miR-138*/rno-miR-138* | FL |
| hsa-miR-140-3p/mmu-miR-140*/rno-miR-140* | FL |
| hsa-miR-212/mmu-miR-212/rno-miR-212 | FL |
| hsa-miR-29c/mmu-miR-29c/rno-miR-29c | FL |
| hsa-miR-888* | FL |
| hsa-miR-222/mmu-miR-222/rno-miR-222 | FL |
| hsa-miR-152/mmu-miR-152/rno-miR-152 | FL |
| hsa-miR-183*/mmu-miR-183* | FL |
| hsa-miR-768-5p | FL |
| hsa-miR-107/mmu-miR-107/rno-miR-107 | FL |
| hsa-miR-574-5p/mmu-miR-574-5p | FL |
| hsa-miR-154/mmu-miR-154/rno-miR-154 | FL |
| hsa-miR-620 | FL |
| hsa-miR-886-5p | FL |
| hsa-miR-208a/mmu-miR-208a/rno-miR-208 | FL |
| hsa-miR-374b* | FL |
| hsa-miR-525-5p | FL |
| hsa-miR-363/mmu-miR-363/rno-miR-363 | FL |
| hsa-miR-99b/mmu-miR-99b/rno-miR-99b | FL |
| hsa-miR-148b/mmu-miR-148b/rno-miR-148b-3p | FL |
| kshv-miR-K12-6-5p | FL |
| hsa-miR-125b-1*/mmu-miR-125b-3p/rno-miR-125b-3p | FL |
| hsa-miR-526b | FL |
| hsa-miR-629 | FL |
| hsa-miR-617 | FL |
| hsa-miR-124/mmu-miR-124/rno-miR-124 | FL |
| hsa-miR-493 | FL |
| hsa-miR-24-1*/mmu-miR-24-1*/rno-miR-24-1* | FL |
| hsa-miR-200b*/mmu-miR-200b* | FL |
| hsa-miR-484/mmu-miR-484/rno-miR-484 | FL |
| hsa-miR-483-3p | FL |
| hsa-miR-516b | FL |
| hsa-miR-125b-2*/rno-miR-125b* | FL |
| hsa-miR-490-3p/mmu-miR-490 | FL |
| hsa-miR-140-5p/mmu-miR-140/rno-miR-140 | FL |
| hsa-miR-877/mmu-miR-877/rno-miR-877 | FL |
| hsa-miR-381/mmu-miR-381/rno-miR-381 | FL |
| hsa-miR-193b* | FL |
| hsa-miR-635 | FL |
| hsa-miR-542-3p/mmu-miR-542-3p/rno-miR-542-3p | FL |

TABLE 26-continued

Predictor microRNAs that distinguish Burkitt lymphoma from follicular lymphoma

| BL vs FL | Higher in |
|---|---|
| hsa-miR-181a-2* | FL |
| hsa-miR-32/mmu-miR-32/rno-miR-32 | FL |
| hsa-miR-105 | FL |
| hsa-miR-488 | FL |
| hsa-miR-505* | FL |
| ebv-miR-BART16 | FL |
| hsa-miR-891a | FL |
| hsa-miR-221/mmu-miR-221/rno-miR-221 | FL |
| hsa-miR-7/mmu-miR-7a/rno-miR-7a | FL |
| hsa-miR-299-3p | FL |
| hsa-miR-575 | FL |
| hsa-miR-585 | FL |
| hsa-miR-30e*/mmu-miR-30e*/rno-miR-30e* | FL |
| hcmv-miR-US25-1* | FL |
| hsa-miR-708/mmu-miR-708/rno-miR-708 | FL |
| hsv1-miR-H1 | FL |
| hsa-let-7g/mmu-let-7g | FL |
| hsa-miR-146a/mmu-miR-146a/rno-miR-146a | FL |
| ebv-miR-BART8* | FL |
| hsa-miR-106b*/mmu-miR-106b*/rno-miR-106b* | FL |
| hsa-miR-601 | FL |
| hsa-miR-553 | FL |
| hsa-miR-518b | FL |
| hsa-miR-548d-5p | FL |
| hsa-miR-382/mmu-miR-382/rno-miR-382 | FL |
| hsa-miR-630 | FL |
| hsa-miR-144* | FL |
| hsa-miR-519d | FL |
| mghv-miR-M1-3 | FL |
| hsa-miR-497/mmu-miR-497/rno-miR-497 | FL |
| hsa-miR-524-5p | FL |
| hsa-miR-500* | FL |
| hsa-miR-920 | FL |
| hsa-miR-297/mmu-miR-297a | FL |
| hsa-miR-509-3-5p | FL |
| hsa-miR-340*/mmu-miR-340-3p/rno-miR-340-3p | FL |
| hsa-miR-99b*/mmu-miR-99b*/rno-miR-99b* | FL |
| hsa-miR-887 | FL |
| hsa-miR-331-3p/mmu-miR-331-3p/rno-miR-331 | FL |
| hsa-miR-206/mmu-miR-206/rno-miR-206 | FL |
| hsa-miR-377* | FL |
| mghv-miR-M1-8 | FL |
| hsa-miR-513a-3p | FL |
| hsa-miR-146b-3p | FL |
| hsa-miR-155* | FL |
| hsa-miR-574-3p/mmu-miR-574-3p | FL |
| hsa-miR-615-3p/mmu-miR-615-3p | FL |
| hsa-miR-28-5p/mmu-miR-28/rno-miR-28 | FL |
| hsa-miR-934 | FL |
| hsa-miR-151-5p/mmu-miR-151-5p/rno-miR-151 | FL |
| hsa-miR-885-5p | FL |
| hsa-miR-409-5p/mmu-miR-409-5p/rno-miR-409-5p | FL |
| hsa-let-7d*/mmu-let-7d*/rno-let-7d* | FL |
| hsa-miR-155 | FL |
| hsa-let-7b*/mmu-let-7b*/rno-let-7b* | FL |
| hsa-miR-7-2* | FL |
| hsa-miR-221* | FL |
| hsa-miR-9*/mmu-miR-9*/rno-miR-9* | FL |
| hsa-miR-122* | FL |
| hsa-miR-130b/mmu-miR-130b/rno-miR-130b | FL |
| hsa-miR-183/mmu-miR-183/rno-miR-183 | FL |
| hsa-miR-92a/mmu-miR-92a/rno-miR-92a | FL |
| hsa-miR-890 | FL |
| hsa-miR-938 | FL |
| kshv-miR-K12-7 | FL |
| hsa-miR-629* | FL |
| hsa-miR-922 | FL |
| kshv-miR-K12-5 | FL |
| hsa-miR-197/mmu-miR-197 | FL |
| hsa-miR-552 | FL |
| hsa-miR-151-3p | FL |
| hsa-miR-194/mmu-miR-194/rno-miR-194 | FL |
| hsa-miR-218-2*/mmu-miR-218-2*/rno-miR-218* | FL |
| hsa-miR-181b/mmu-miR-181b/rno-miR-181b | FL |
| ebv-miR-BART18-3p | FL |
| hsa-miR-34c-5p/mmu-miR-34c/rno-miR-34c | FL |
| hsa-miR-622 | FL |
| hsa-miR-514 | FL |
| hsa-miR-657 | FL |
| hsa-miR-518a-3p | FL |
| hsa-miR-647 | FL |
| hsa-miR-22*/mmu-miR-22*/rno-miR-22* | FL |
| hsa-miR-196a*/mmu-miR-196a*/rno-miR-196a* | FL |
| kshv-miR-K12-1 | FL |
| hsa-miR-425/mmu-miR-425/rno-miR-425 | FL |
| hsa-miR-361-3p | FL |
| hsa-miR-220b | FL |
| hsa-miR-744/mmu-miR-744 | FL |
| hsa-miR-551a | FL |
| hsa-miR-301a/mmu-miR-301a/rno-miR-301a | FL |
| hsa-miR-92b/mmu-miR-92b/rno-miR-92b | FL |
| hsa-miR-487b/mmu-miR-487b/rno-miR-487b | FL |
| hsa-miR-363*/rno-miR-363* | FL |
| hsa-miR-337-3p | FL |
| hsa-miR-636 | FL |
| hsa-miR-600 | FL |
| hsa-miR-138/mmu-miR-138/rno-miR-138 | FL |

TABLE 26-continued

Predictor microRNAs that distinguish Burkitt lymphoma from follicular lymphoma

| BL vs FL | Higher in |
|---|---|
| hsa-miR-96/mmu-miR-96/rno-miR-96 | FL |
| hsa-miR-20b* | FL |
| hsa-miR-342-5p/mmu-miR-342-5p/rno-miR-342-5p | FL |
| hsa-miR-215 | FL |
| hsa-miR-129* | FL |

TABLE 27

Predictor microRNAs that distinguish Burkitt lymphoma from Hodgkin's lymphoma

| BL vs HL | Higher in |
|---|---|
| hsa-miR-19b/mmu-miR-19b/rno-miR-19b | BL |
| hsa-miR-19a/mmu-miR-19a/rno-miR-19a | BL |
| hsa-miR-17/mmu-miR-17/rno-miR-17-5p/rno-miR-17 | BL |
| hsa-miR-106a | BL |
| hsa-miR-20a/mmu-miR-20a/rno-miR-20a | BL |
| hsa-miR-106b/mmu-miR-106b/rno-miR-106b | BL |
| hsa-miR-30c/mmu-miR-30c/rno-miR-30c | BL |
| hsa-miR-551b/mmu-miR-551b/rno-miR-551b | HL |
| hsa-miR-921 | HL |
| ebv-miR-BART2-3p | HL |
| hsa-miR-32* | HL |
| hsa-miR-494/mmu-miR-494/rno-miR-494 | HL |
| hsa-miR-29c/mmu-miR-29c/rno-miR-29c | HL |
| hsa-miR-923 | HL |
| hsa-miR-199b-5p | HL |
| hsa-miR-148a/mmu-miR-148a | HL |
| hsa-miR-130a/mmu-miR-130a/rno-miR-130a | HL |
| hsa-miR-154/mmu-miR-154/rno-miR-154 | HL |
| hsa-miR-151-5p/mmu-miR-151-5p/rno-miR-151 | HL |
| hsa-miR-28-5p/mmu-miR-28/rno-miR-28 | HL |
| hsa-miR-365/mmu-miR-365/rno-miR-365 | HL |
| hsa-miR-602 | HL |
| hsa-miR-222/mmu-miR-222/rno-miR-222 | HL |
| hsa-miR-214/mmu-miR-214/rno-miR-214 | HL |
| hsa-miR-144* | HL |
| hsa-miR-107/mmu-miR-107/rno-miR-107 | HL |
| hsa-miR-497/mmu-miR-497/rno-miR-497 | HL |
| hsa-let-7g/mmu-let-7g | HL |
| hsa-miR-146a/mmu-miR-146a/rno-miR-146a | HL |
| hsa-miR-186/mmu-miR-186/rno-miR-186 | HL |
| hsa-miR-886-5p | HL |
| hsa-miR-152/mmu-miR-152/rno-miR-152 | HL |

TABLE 27-continued

Predictor microRNAs that distinguish Burkitt lymphoma from Hodgkin's lymphoma

| BL vs HL | Higher in |
|---|---|
| hsa-miR-29a*/mmu-miR-29a*/rno-miR-29a* | HL |
| hsa-miR-140-5p/mmu-miR-140/rno-miR-140 | HL |
| hsa-miR-532-5p/mmu-miR-532-5p/rno-miR-532-5p | HL |
| hsa-miR-145*/mmu-miR-145* | HL |
| hsa-miR-515-5p | HL |
| hsa-miR-153/mmu-miR-153/rno-miR-153 | HL |
| hsa-miR-513a-5p | HL |
| hsa-miR-516a-5p | HL |
| hsa-miR-660 | HL |
| hsa-miR-29c*/mmu-miR-29c*/rno-miR-29c* | HL |
| hsa-miR-505/rno-miR-505 | HL |
| hsa-miR-455-3p | HL |
| hsa-miR-519e* | HL |
| hsa-miR-502-3p | HL |
| hsa-miR-922 | HL |
| hsa-miR-524-5p | HL |
| hsa-miR-483-5p | HL |
| hsa-miR-708/mmu-miR-708/rno-miR-708 | HL |
| hsa-miR-498 | HL |
| ebv-miR-BART19-3p | HL |
| hsa-miR-149/mmu-miR-149 | HL |
| hsa-miR-574-3p/mmu-miR-574-3p | HL |
| hsa-miR-659 | HL |
| hsa-miR-331-3p/mmu-miR-331-3p/rno-miR-331 | HL |
| hsa-miR-105 | HL |
| hsa-miR-128/mmu-miR-128/rno-miR-128 | HL |
| hsa-miR-200b*/mmu-miR-200b* | HL |
| hsa-miR-381/mmu-miR-381/rno-miR-381 | HL |
| hsa-miR-766 | HL |
| hsa-miR-557 | HL |
| ebv-miR-BART16 | HL |
| hsa-miR-488 | HL |
| hsa-miR-516b | HL |
| mghv-miR-M1-2 | HL |
| hsa-miR-891a | HL |
| hsa-miR-221/mmu-miR-221/rno-miR-221 | HL |
| hsa-miR-146b-3p | HL |
| hsa-miR-526b | HL |
| mghv-miR-M1-3 | HL |
| hsa-miR-505* | HL |
| hsv1-miR-H1 | HL |
| hcmv-miR-UL70-3p | HL |
| hsa-miR-24-2*/mmu-miR-24-2*/rno-miR-24-2* | HL |
| hsa-miR-617 | HL |
| hsa-miR-194/mmu-miR-194/rno-miR-194 | HL |
| hsa-miR-934 | HL |
| hsa-miR-220c | HL |
| hsa-miR-548d-5p | HL |
| hsa-miR-937 | HL |
| ebv-miR-BART13 | HL |
| hsa-miR-7/mmu-miR-7a/rno-miR-7a | HL |
| hsa-miR-210/mmu-miR-210/rno-miR-210 | HL |
| hsa-miR-490-3p/mmu-miR-490 | HL |

TABLE 27-continued

Predictor microRNAs that distinguish Burkitt lymphoma from Hodgkin's lymphoma

| BL vs HL | Higher in |
|---|---|
| hsa-miR-221* | HL |
| hsa-miR-92a/mmu-miR-92a/rno-miR-92a | HL |
| hsa-miR-183*/mmu-miR-183* | HL |
| hsa-miR-513a-3p | HL |
| hsa-miR-575 | HL |
| hsa-miR-595 | HL |
| hsa-miR-920 | HL |
| hsa-miR-483-3p | HL |
| hsa-miR-330-5p/mmu-miR-330/rno-miR-330 | HL |
| hsa-miR-525-5p | HL |
| hsa-miR-99b/mmu-miR-99b/rno-miR-99b | HL |
| hsa-miR-509-3p | HL |
| hsa-miR-151-3p | HL |
| ebv-miR-BHRF1-1 | HL |
| hsa-miR-630 | HL |
| mghv-miR-M1-7-3p | HL |
| hsa-miR-328/mmu-miR-328/rno-miR-328 | HL |
| hsa-miR-452 | HL |
| hsa-miR-635 | HL |
| ebv-miR-BART5 | HL |
| hsa-miR-373* | HL |
| hsa-miR-96/mmu-miR-96/rno-miR-96 | HL |
| hsa-miR-382/mmu-miR-382/rno-miR-382 | HL |
| hsa-miR-155 | HL |
| hsa-miR-197/mmu-miR-197 | HL |
| kshv-miR-K12-6-5p | HL |
| hcmv-miR-UL112 | HL |
| hsa-miR-551b* | HL |
| hsa-miR-877/mmu-miR-877/rno-miR-877 | HL |
| hsa-miR-589 | HL |
| hsa-miR-936 | HL |
| hsa-miR-34c-5p/mmu-miR-34c/rno-miR-34c | HL |
| hsa-miR-885-5p | HL |
| ebv-miR-BART6-3p | HL |
| hsa-miR-585 | HL |
| hsa-miR-302c* | HL |
| hsa-miR-196a*/mmu-miR-196a*/rno-miR-196a* | HL |
| hsa-miR-195* | HL |
| hsa-miR-17*/rno-miR-17-3p | HL |
| hsa-miR-296-5p/mmu-miR-296-5p/rno-miR-296* | HL |
| hsa-miR-550* | HL |
| ebv-miR-BHRF1-3 | HL |
| hsa-miR-296-3p/mmu-miR-296-3p/rno-miR-296 | HL |
| hsa-miR-526b* | HL |
| hsa-miR-548b-3p | HL |
| hsa-miR-652/mmu-miR-652/rno-miR-652 | HL |
| hsa-miR-297/mmu-miR-297a | HL |
| hsa-miR-553 | HL |
| hsa-miR-194* | HL |
| hsa-miR-23a*/rno-miR-23a* | HL |
| hsa-miR-130b/mmu-miR-130b/rno-miR-130b | HL |
| hsa-miR-586 | HL |
| hsa-miR-137/mmu-miR-137/rno-miR-137 | HL |
| hsa-miR-610 | HL |
| mghv-miR-M1-8 | HL |
| hsa-miR-193b* | HL |
| hsa-miR-519d | HL |
| hsa-miR-125b-1*/mmu-miR-125b-3p/rno-miR-125b-3p | HL |
| hsa-miR-744/mmu-miR-744 | HL |
| hsa-miR-138/mmu-miR-138/rno-miR-138 | HL |
| hsa-miR-21* | HL |
| hsa-miR-576-5p | HL |
| hsa-miR-125a-3p/mmu-miR-125a-3p/rno-miR-125a-3p | HL |
| mghv-miR-M1-6 | HL |
| hsa-miR-425/mmu-miR-425/rno-miR-425 | HL |
| hsa-miR-10a*/mmu-miR-10a*/rno-miR-10a-3p | HL |
| hsa-miR-215 | HL |
| hsa-miR-345 | HL |
| hsa-miR-887 | HL |
| hsa-miR-7-2* | HL |
| hsa-miR-122* | HL |
| hsa-miR-363*/rno-miR-363* | HL |
| hsa-miR-22*/mmu-miR-22*/rno-miR-22* | HL |
| hsa-miR-542-5p/mmu-miR-542-5p/rno-miR-542-5p | HL |
| hsa-miR-92b* | HL |
| hsa-miR-526a/hsa-miR-520c-5p/hsa-miR-518d-5p | HL |
| kshv-miR-K12-5 | HL |
| hsa-miR-340*/mmu-miR-340-3p/rno-miR-340-3p | HL |
| hsa-let-7d*/mmu-let-7d*/rno-let-7d* | HL |
| hsa-miR-92b/mmu-miR-92b/rno-miR-92b | HL |
| hsa-miR-518b | HL |
| hiv1-miR-H1 | HL |
| hsa-miR-623 | HL |
| hsa-miR-645 | HL |
| hsa-miR-601 | HL |
| hsa-miR-519e | HL |
| hsa-miR-650 | HL |
| hsa-miR-361-3p | HL |
| hsa-miR-150*/mmu-miR-150* | HL |
| hsa-miR-425*/mmu-miR-425* | HL |
| hsa-miR-135a*/mmu-miR-135a* | HL |
| hsa-miR-518a-3p | HL |
| hsa-miR-612 | HL |
| hsa-miR-212/mmu-miR-212/rno-miR-212 | HL |
| hsa-miR-125b-2*/rno-miR-125b* | HL |
| hsa-miR-500 | HL |
| hsa-miR-663 | HL |
| hsa-miR-647 | HL |
| hsa-miR-502-5p | HL |

TABLE 27-continued

Predictor microRNAs that distinguish Burkitt lymphoma from Hodgkin's lymphoma

| BL vs HL | Higher in |
|---|---|
| ebv-miR-BART18-3p | HL |
| hsa-miR-99b*/mmu-miR-99b*/rno-miR-99b* | HL |
| ebv-miR-BART7* | HL |
| hsa-miR-500* | HL |
| hsa-miR-124*/mmu-miR-124*/rno-miR-124* | HL |
| hsa-miR-206/mmu-miR-206/rno-miR-206 | HL |
| hsa-miR-615-3p/mmu-miR-615-3p | HL |
| hsa-miR-30c-1*/mmu-miR-30c-1*/rno-miR-30c-1* | HL |
| hsa-miR-331-5p/mmu-miR-331-5p | HL |
| hcmv-miR-US25-1* | HL |
| hsa-miR-326/mmu-miR-326/rno-miR-326 | HL |
| hsa-miR-181b/mmu-miR-181b/rno-miR-181b | HL |
| hsa-miR-376a* | HL |
| hsa-miR-433/mmu-miR-433/rno-miR-433 | HL |
| hsa-miR-640 | HL |
| hsa-miR-938 | HL |
| hsa-miR-508-5p | HL |
| hsa-miR-484/mmu-miR-484/rno-miR-484 | HL |
| hsa-miR-106b*/mmu-miR-106b*/rno-miR-106b* | HL |
| hsa-miR-600 | HL |
| hsa-let-7b*/mmu-let-7b*/rno-let-7b* | HL |
| hsa-miR-20b* | HL |
| hsa-miR-622 | HL |
| hsa-miR-657 | HL |
| hsa-miR-183/mmu-miR-183/rno-miR-183 | HL |
| hsa-miR-409-5p/mmu-miR-409-5p/rno-miR-409-5p | HL |
| ebv-miR-BART20-3p | HL |
| ebv-miR-BART8* | HL |
| hsa-miR-129* | HL |
| hsa-miR-629 | HL |
| hsa-miR-890 | HL |
| hsa-miR-208a/mmu-miR-208a/rno-miR-208 | HL |
| hsa-miR-492 | HL |
| hsa-miR-629* | HL |
| hsa-miR-654-5p | HL |
| hsa-miR-584 | HL |
| hsa-miR-636 | HL |
| hsa-miR-490-5p | HL |
| hsa-miR-337-3p | HL |
| hsa-miR-9*/mmu-miR-9*/rno-miR-9* | HL |
| ebv-miR-BART9* | HL |
| hsa-miR-509-3-5p | HL |
| hsa-miR-342-5p/mmu-miR-342-5p/rno-miR-342-5p | HL |
| hsa-miR-514 | HL |
| hsa-miR-377* | HL |
| kshv-miR-K12-1 | HL |
| hsa-miR-124/mmu-miR-124/rno-miR-124 | HL |
| hsa-miR-542-3p/mmu-miR-542-3p/rno-miR-542-3p | HL |
| hsa-miR-220b | HL |
| hsa-miR-299-3p | HL |
| hsa-miR-181a-2* | HL |
| hsa-miR-202 | HL |
| hsa-miR-487b/mmu-miR-487b/rno-miR-487b | HL |
| hsa-miR-551a | HL |
| hsa-miR-338-5p/mmu-miR-338-5p/rno-miR-338* | HL |
| hsa-miR-552 | HL |

TABLE 28

Predictor microRNAs that distinguish chronic lymphocytic leukemia from follicular lymphoma

| CLL vs FL | Higher in |
|---|---|
| hsa-miR-331-5p/mmu-miR-331-5p | CLL |
| hsa-miR-144/mmu-miR-144/rno-miR-144 | CLL |
| hsa-miR-150/mmu-miR-150/rno-miR-150 | CLL |
| hsa-miR-140-5p/mmu-miR-140/rno-miR-140 | CLL |
| hsa-miR-335/mmu-miR-335-5p/rno-miR-335 | CLL |
| hsa-miR-186/mmu-miR-186/rno-miR-186 | CLL |
| hsa-miR-486-5p/mmu-miR-486 | CLL |
| hsa-miR-154/mmu-miR-154/rno-miR-154 | CLL |
| hsa-miR-223/mmu-miR-223/rno-miR-223 | CLL |
| hsa-miR-299-5p/mmu-miR-299*/rno-miR-299 | CLL |
| hsa-let-7g/mmu-let-7g | CLL |
| hsa-miR-32/mmu-miR-32/rno-miR-32 | CLL |
| hsa-miR-30e*/mmu-miR-30e*/rno-miR-30e* | CLL |
| hsa-miR-147 | CLL |
| hsa-miR-20b/mmu-miR-20b/rno-miR-20b-5p | CLL |
| hsa-miR-101/mmu-miR-101a/rno-miR-101a | CLL |
| hsa-let-7f/mmu-let-7f/rno-let-7f | CLL |
| hsa-miR-30e/mmu-miR-30e/rno-miR-30e | CLL |
| hsa-miR-668/mmu-miR-668 | CLL |
| hsa-miR-768-5p | CLL |
| hsa-miR-19a/mmu-miR-19a/rno-miR-19a | CLL |

TABLE 28-continued

Predictor microRNAs that distinguish chronic lymphocytic leukemia from follicular lymphoma

| CLL vs FL | Higher in |
|---|---|
| hsa-miR-199a-5p/mmu-miR-199a-5p/rno-miR-199a-5p | CLL |
| hsa-miR-638 | CLL |
| hsa-miR-196a*/mmu-miR-196a*/rno-miR-196a* | CLL |
| hsa-miR-19b/mmu-miR-19b/rno-miR-19b | CLL |
| hsa-miR-30d/mmu-miR-30d/rno-miR-30d | CLL |
| hsa-miR-363/mmu-miR-363/rno-miR-363 | CLL |
| hsa-miR-374a | CLL |
| hsa-miR-140-3p/mmu-miR-140*/rno-miR-140* | CLL |
| hsa-miR-185/mmu-miR-185/rno-miR-185 | CLL |
| hsa-miR-106b/mmu-miR-106b/rno-miR-106b | CLL |
| hsa-miR-106a | CLL |
| hsa-miR-191/mmu-miR-191/rno-miR-191 | CLL |
| hsa-miR-17/mmu-miR-17/rno-miR-17-5p/rno-miR-17 | CLL |
| hsa-let-7i/mmu-let-7i/rno-let-7i | CLL |
| hsa-miR-20a/mmu-miR-20a/rno-miR-20a | CLL |
| hsa-miR-142-5p/mmu-miR-142-5p/rno-miR-142-5p | CLL |
| hsa-miR-768-3p | CLL |
| hsa-miR-30b/mmu-miR-30b/rno-miR-30b-5p | CLL |
| hsa-miR-891a | CLL |
| hsa-miR-24-1*/mmu-miR-24-1*/rno-miR-24-1* | CLL |
| hsa-miR-29c/mmu-miR-29c/rno-miR-29c | CLL |
| hsa-miR-28-5p/mmu-miR-28/rno-miR-28 | CLL |
| hsa-miR-30a/mmu-miR-30a/rno-miR-30a | CLL |
| hsa-miR-155 | CLL |
| hsa-miR-361-5p/mmu-miR-361/rno-miR-361 | CLL |
| hsa-miR-15a/mmu-miR-15a | CLL |
| hsa-miR-26a/mmu-miR-26a/rno-miR-26a | CLL |
| hsa-miR-30c/mmu-miR-30c/rno-miR-30c | CLL |
| hsa-miR-541* | CLL |
| hsa-miR-26b/mmu-miR-26b/rno-miR-26b | CLL |
| hsa-miR-519d | CLL |
| hsa-miR-15b/mmu-miR-15b/rno-miR-15b | CLL |
| hsa-miR-550 | CLL |
| hsa-miR-29b/mmu-miR-29b/rno-miR-29b | CLL |
| hsa-miR-29a/mmu-miR-29a/rno-miR-29a | CLL |
| hsa-miR-103/mmu-miR-103/rno-miR-103 | CLL |
| hsa-miR-423-3p/mmu-miR-423-3p/rno-miR-423 | CLL |
| hsa-miR-549 | CLL |
| hsa-miR-107/mmu-miR-107/rno-miR-107 | CLL |
| hsa-miR-888* | CLL |
| hsa-miR-801/mmu-miR-801 | CLL |
| hsa-miR-149* | FL |
| hsa-miR-634 | FL |
| ebv-miR-BART2-3p | FL |
| hsa-miR-921 | FL |
| hsa-miR-494/mmu-miR-494/rno-miR-494 | FL |
| hsa-miR-933 | FL |
| mghv-miR-M1-4 | FL |
| hsa-let-7e/mmu-let-7e/rno-let-7e | FL |
| hsa-miR-939 | FL |
| hsa-miR-518c* | FL |
| hsa-miR-32* | FL |
| hsa-miR-491-3p | FL |
| hsa-miR-185/mmu-miR-185/rno-miR-185 | FL |
| hsa-miR-765 | FL |
| ebv-miR-BART17-5p | FL |
| hsa-miR-576-3p | FL |
| hsa-miR-658 | FL |
| hsa-miR-503 | FL |
| hsa-miR-30b* | FL |
| hsa-miR-302a/mmu-miR-302a | FL |
| hsa-miR-628-3p | FL |
| hsa-miR-642 | FL |
| hsa-miR-620 | FL |
| hsa-miR-99a/mmu-miR-99a/rno-miR-99a | FL |
| hsa-miR-371-5p | FL |
| hsa-miR-452 | FL |
| hsa-miR-126*/mmu-miR-126-5p/rno-miR-126* | FL |
| hsa-miR-298 | FL |
| hsa-miR-193a-5p | FL |
| hsa-miR-583 | FL |
| hsa-miR-143/mmu-miR-143/rno-miR-143 | FL |
| hsa-miR-665 | FL |
| hsa-miR-505/rno-miR-505 | FL |
| hsa-miR-199b-5p | FL |
| hsa-miR-28-3p/rno-miR-28* | FL |
| hsa-miR-422a | FL |
| hsa-miR-515-5p | FL |
| hsa-miR-455-3p | FL |
| hsa-miR-10a/mmu-miR-10a/rno-miR-10a-5p | FL |
| hsa-miR-300 | FL |
| ebv-miR-BART5 | FL |
| hsa-miR-10b/mmu-miR-10b/rno-miR-10b | FL |
| hsa-miR-212/mmu-miR-212/rno-miR-212 | FL |
| hsa-miR-145/mmu-miR-145/rno-miR-145 | FL |
| hsa-miR-187* | FL |
| ebv-miR-BHRF1-1 | FL |
| ebv-miR-BHRF1-2 | FL |
| hsa-miR-126/mmu-miR-126-3p/rno-miR-126 | FL |
| hsa-miR-130b*/mmu-miR-130b* | FL |
| hsa-miR-326/mmu-miR-326/rno-miR-326 | FL |

TABLE 28-continued

Predictor microRNAs that distinguish chronic lymphocytic leukemia from follicular lymphoma

| CLL vs FL | Higher in |
|---|---|
| mghv-miR-M1-2 | FL |
| kshv-miR-K12-6-3p | FL |
| hsa-miR-516b | FL |
| hsa-miR-519e* | FL |
| mghv-miR-M1-7-3p | FL |
| hsa-miR-629 | FL |
| hsa-miR-24-2*/mmu-miR-24-2*/rno-miR-24-2* | FL |
| hsa-miR-943 | FL |
| hsa-miR-124/mmu-miR-124/rno-miR-124 | FL |
| hsa-miR-365/mmu-miR-365/rno-miR-365 | FL |
| hsa-miR-493 | FL |
| hsa-miR-29c*/mmu-miR-29c*/rno-miR-29c* | FL |
| hsa-miR-602 | FL |
| hsa-miR-484/mmu-miR-484/rno-miR-484 | FL |
| hsa-miR-483-3p | FL |
| hsa-miR-125b-2*/rno-miR-125b* | FL |
| hsa-miR-675 | FL |
| mghv-miR-M1-7-5p | FL |
| hsa-miR-152/mmu-miR-152/rno-miR-152 | FL |
| hsa-miR-27a*/mmu-miR-27a*/rno-miR-27a* | FL |
| hsa-miR-542-3p/mmu-miR-542-3p/rno-miR-542-3p | FL |
| hsa-miR-100/mmu-miR-100/rno-miR-100 | FL |
| hsa-miR-208a/mmu-miR-208a/rno-miR-208 | FL |
| hsa-miR-766 | FL |
| hsa-miR-637 | FL |
| hsa-miR-519c-5p/hsa-miR-519b-5p/hsa-miR-523*/hsa-miR-518e/hsa-miR-522*/hsa-miR-519a* | FL |
| hsa-miR-409-5p/mmu-miR-409-5p/rno-miR-409-5p | FL |
| hsa-miR-199a-3p/hsa-miR-199b-3p/mmu-miR-199a-3p/mmu-miR-199b/rno-miR-199a-3p | FL |
| hsa-miR-106b*/mmu-miR-106b*/rno-miR-106b* | FL |
| hsa-miR-130a/mmu-miR-130a/rno-miR-130a | FL |
| hsa-miR-645 | FL |
| hsa-miR-548d-5p | FL |
| hsa-miR-671-5p/mmu-miR-671-5p | FL |
| hsa-miR-574-3p/mmu-miR-574-3p | FL |
| hsa-miR-125b/mmu-miR-125b-5p/rno-miR-125b-5p | FL |
| hsa-miR-500* | FL |
| hsa-miR-425/mmu-miR-425/rno-miR-425 | FL |
| ebv-miR-BART8* | FL |
| hsa-miR-377* | FL |
| hsa-miR-513a-3p | FL |
| hsa-miR-181a-2* | FL |
| hsa-miR-938 | FL |
| hsa-miR-155* | FL |
| hsa-miR-218-2*/mmu-miR-218-2*/rno-miR-218* | FL |
| hsa-miR-198 | FL |
| hsa-miR-151-3p | FL |
| hsa-miR-299-3p | FL |
| hcmv-miR-US25-1* | FL |
| hsa-miR-708/mmu-miR-708/rno-miR-708 | FL |
| hsa-miR-659 | FL |
| hsa-miR-600 | FL |
| hsa-miR-601 | FL |
| hsa-miR-296-3p/mmu-miR-296-3p/rno-miR-296 | FL |
| hsa-let-7b*/mmu-let-7b*/rno-let-7b* | FL |
| ebv-miR-BART6-3p | FL |
| hsa-miR-7-2* | FL |
| hsa-miR-9*/mmu-miR-9*/rno-miR-9* | FL |
| hsa-miR-509-3-5p | FL |
| hsa-miR-518b | FL |
| hsa-miR-183*/mmu-miR-183* | FL |
| hsa-miR-125b-1*/mmu-miR-125b-3p/rno-miR-125b-3p | FL |
| hsa-miR-183/mmu-miR-183/rno-miR-183 | FL |
| hsa-miR-890 | FL |
| hsa-miR-153/mmu-miR-153/rno-miR-153 | FL |
| hsa-miR-874/mmu-miR-874/rno-miR-874 | FL |
| hsa-miR-220c | FL |
| hsa-miR-99b*/mmu-miR-99b*/rno-miR-99b* | FL |
| hsa-miR-193b* | FL |
| hsa-miR-629* | FL |
| hcmv-miR-UL148D | FL |
| ebv-miR-BART7* | FL |
| hsa-miR-99b/mmu-miR-99b/rno-miR-99b | FL |
| hsa-miR-206/mmu-miR-206/rno-miR-206 | FL |
| hsa-miR-381/mmu-miR-381/rno-miR-381 | FL |
| hsa-miR-194/mmu-miR-194/rno-miR-194 | FL |

TABLE 28-continued

Predictor microRNAs that distinguish chronic lymphocytic leukemia from follicular lymphoma

| CLL vs FL | Higher in |
|---|---|
| hsa-miR-525-5p | FL |
| hsa-miR-193b | FL |
| hsa-miR-497/mmu-miR-497/rno-miR-497 | FL |
| ebv-miR-BART18-3p | FL |
| hsa-miR-424 | FL |
| hsa-miR-553 | FL |
| hsa-let-7d*/mmu-let-7d*/rno-let-7d* | FL |
| hsa-miR-34c-5p/mmu-miR-34c/rno-miR-34c | FL |
| ebv-miR-BHRF1-3 | FL |
| kshv-miR-K12-6-5p | FL |
| hsa-miR-551a | FL |
| hsa-miR-195* | FL |
| hsa-miR-551b* | FL |
| hsa-miR-514 | FL |
| hsa-miR-552 | FL |
| hsa-miR-122* | FL |
| hsa-miR-92b/mmu-miR-92b/rno-miR-92b | FL |
| hsa-miR-22*/mmu-miR-22*/rno-miR-22* | FL |
| hsa-miR-635 | FL |
| kshv-miR-K12-1 | FL |
| hsa-miR-483-5p | FL |
| hsa-miR-340*/mmu-miR-340-3p/rno-miR-340-3p | FL |
| hsa-miR-615-3p/mmu-miR-615-3p | FL |
| hsa-miR-505* | FL |
| hsa-miR-622 | FL |
| hsa-miR-181b/mmu-miR-181b/rno-miR-181b | FL |
| hsa-miR-886-5p | FL |
| hsa-miR-885-5p | FL |
| hsa-miR-220b | FL |
| hsa-miR-524-5p | FL |
| hsa-miR-382/mmu-miR-382/rno-miR-382 | FL |
| hsa-miR-744/mmu-miR-744 | FL |
| hsv1-miR-H1 | FL |
| hsa-miR-526b | FL |
| hsa-miR-657 | FL |
| hsa-miR-130b/mmu-miR-130b/rno-miR-130b | FL |
| hsa-miR-181a/mmu-miR-181a/rno-miR-181a | FL |
| hsa-miR-301a/mmu-miR-301a/rno-miR-301a | FL |
| hsa-miR-490-3p/mmu-miR-490 | FL |
| hsa-miR-485-3p/mmu-miR-485* | FL |
| hsa-miR-297/mmu-miR-297a | FL |
| hsa-miR-630 | FL |
| hsa-miR-877/mmu-miR-877/rno-miR-877 | FL |
| kshv-miR-K12-5 | FL |
| hsa-miR-617 | FL |
| mghv-miR-M1-3 | FL |
| hsa-miR-920 | FL |
| hsa-miR-585 | FL |
| hsa-miR-374b* | FL |
| hsa-miR-215 | FL |
| hsa-miR-342-5p/mmu-miR-342-5p/rno-miR-342-5p | FL |
| hsa-miR-934 | FL |
| hsa-miR-575 | FL |
| hsa-miR-488 | FL |
| ebv-miR-BART16 | FL |
| hsa-miR-647 | FL |
| hsa-miR-138/mmu-miR-138/rno-miR-138 | FL |
| hsa-miR-221* | FL |
| hsa-miR-200b*/mmu-miR-200b* | FL |
| hsa-miR-337-3p | FL |
| hsa-miR-922 | FL |
| hsa-miR-197/mmu-miR-197 | FL |
| hsa-miR-96/mmu-miR-96/rno-miR-96 | FL |
| hsa-miR-518a-3p | FL |

TABLE 29

Predictor microRNAs that distinguish Burkitt lymphoma from Hodgkin's lymphoma

| CLL vs HL | Higher in |
|---|---|
| hsa-miR-32/mmu-miR-32/rno-miR-32 | CLL |
| hsa-miR-30e*/mmu-miR-30e*/rno-miR-30e* | CLL |
| hsa-let-7g/mmu-let-7g | CLL |
| hsa-miR-144/mmu-miR-144/rno-miR-144 | CLL |
| hsa-miR-140-5p/mmu-miR-140/rno-miR-140 | CLL |
| hsa-miR-19a/mmu-miR-19a/rno-miR-19a | CLL |
| hsa-miR-154/mmu-miR-154/rno-miR-154 | CLL |
| hsa-miR-150/mmu-miR-150/rno-miR-150 | CLL |
| hsa-miR-28-5p/mmu-miR-28/rno-miR-28 | CLL |
| hsa-miR-363/mmu-miR-363/rno-miR-363 | CLL |
| hsa-miR-101/mmu-miR-101a/rno-miR-101a | CLL |
| hsa-miR-299-5p/mmu-miR-299*/rno-miR-299 | CLL |
| hsa-miR-768-5p | CLL |
| hsa-miR-19b/mmu-miR-19b/rno-miR-19b | CLL |
| hsa-miR-30e/mmu-miR-30e/rno-miR-30e | CLL |
| hsa-miR-20b/mmu-miR-20b/rno-miR-20b-5p | CLL |
| hsa-miR-374a | CLL |
| hsa-let-7f/mmu-let-7f/rno-let-7f | CLL |
| hsa-miR-335/mmu-miR-335-5p/rno-miR-335 | CLL |
| hsa-miR-142-5p/mmu-miR-142-5p/rno-miR-142-5p | CLL |

TABLE 29-continued

Predictor microRNAs that distinguish Burkitt lymphoma from Hodgkin's lymphoma

| CLL vs HL | Higher in |
|---|---|
| hsa-miR-486-5p/mmu-miR-486 | CLL |
| hsa-miR-33a/mmu-miR-33/rno-miR-33 | CLL |
| hsa-miR-30b/mmu-miR-30b/rno-miR-30b-5p | CLL |
| hsa-miR-768-3p | CLL |
| hsa-miR-668/mmu-miR-668 | CLL |
| hsa-miR-15b/mmu-miR-15b/rno-miR-15b | CLL |
| hsa-miR-196a*/mmu-miR-196a*/rno-miR-196a* | CLL |
| hsa-miR-140-3p/mmu-miR-140*/rno-miR-140* | CLL |
| hsa-miR-29b/mmu-miR-29b/rno-miR-29b | CLL |
| hsa-miR-29c/mmu-miR-29c/rno-miR-29c | CLL |
| hsa-miR-186/mmu-miR-186/rno-miR-186 | CLL |
| hsa-miR-106a | CLL |
| hsa-miR-26a/mmu-miR-26a/rno-miR-26a | CLL |
| hsa-miR-106b/mmu-miR-106b/rno-miR-106b | CLL |
| hsa-miR-17/mmu-miR-17/rno-miR-17-5p/rno-miR-17 | CLL |
| hsa-miR-191/mmu-miR-191/rno-miR-191 | CLL |
| hsa-miR-20a/mmu-miR-20a/rno-miR-20a | CLL |
| hsa-miR-30c/mmu-miR-30c/rno-miR-30c | CLL |
| hsa-miR-26b/mmu-miR-26b/rno-miR-26b | CLL |
| hsa-miR-147 | CLL |
| hsa-miR-15a/mmu-miR-15a | CLL |
| hsa-miR-30d/mmu-miR-30d/rno-miR-30d | CLL |
| hsa-miR-199a-5p/mmu-miR-199a-5p/rno-miR-199a-5p | CLL |
| hsa-miR-29a/mmu-miR-29a/rno-miR-29a | CLL |
| hsa-miR-223/mmu-miR-223/rno-miR-223 | CLL |
| hsa-miR-30a/mmu-miR-30a/rno-miR-30a | CLL |
| hsa-miR-16/mmu-miR-16/rno-miR-16 | CLL |
| hsa-miR-451/mmu-miR-451/rno-miR-451 | CLL |
| hsa-miR-24-1*/mmu-miR-24-1*/rno-miR-24-1* | CLL |
| hsa-miR-550 | CLL |
| hsa-miR-342-3p/mmu-miR-342-3p/rno-miR-342-3p | CLL |
| hsa-miR-195/mmu-miR-195/rno-miR-195 | CLL |
| hsa-miR-801/mmu-miR-801 | CLL |
| hsa-miR-541* | CLL |
| hsa-let-7i/mmu-let-7i/rno-let-7i | CLL |
| hsa-miR-155 | CLL |
| hsa-miR-185/mmu-miR-185/rno-miR-185 | CLL |
| hsa-miR-891a | CLL |
| hsa-miR-138-1*/mmu-miR-138*/rno-miR-138* | CLL |
| hsa-miR-27b/mmu-miR-27b/rno-miR-27b | CLL |
| hsa-miR-361-5p/mmu-miR-361/rno-miR-361 | CLL |
| hsa-miR-129* | CLL |
| hsa-miR-638 | CLL |
| hsa-miR-34b/mmu-miR-34b-3p | CLL |
| hsa-miR-107/mmu-miR-107/rno-miR-107 | CLL |
| hsa-miR-549 | CLL |
| hsa-miR-888* | CLL |
| hsa-miR-423-3p/mmu-miR-423-3p/rno-miR-423 | CLL |
| hsa-let-7e/mmu-let-7e/rno-let-7e | HL |
| hsa-miR-125a-5p/mmu-miR-125a-5p/rno-miR-125a-5p | HL |
| hsa-miR-576-3p | HL |
| hsa-miR-513a-5p | HL |
| ebv-miR-BART17-5p | HL |
| hsa-miR-185/mmu-miR-185/rno-miR-185 | HL |
| hsa-miR-921 | HL |
| hsa-miR-518c* | HL |
| hsa-miR-520d-5p | HL |
| hsa-miR-939 | HL |
| hsa-miR-634 | HL |
| hsa-miR-491-3p | HL |
| ebv-miR-BART2-3p | HL |
| hsa-miR-30c-2*/mmu-miR-30c-2*/rno-miR-30c-2* | HL |
| hsa-miR-765 | HL |
| hsa-miR-923 | HL |
| hsa-miR-620 | HL |
| hsa-miR-933 | HL |
| hsa-miR-143/mmu-miR-143/rno-miR-143 | HL |
| hsa-miR-494/mmu-miR-494/rno-miR-494 | HL |
| hsa-miR-665 | HL |
| hsa-miR-642 | HL |
| hsa-miR-126*/mmu-miR-126-5p/rno-miR-126* | HL |
| hsa-miR-658 | HL |
| hsa-miR-149* | HL |
| hsa-miR-30b* | HL |
| mghv-miR-M1-4 | HL |
| hsa-miR-99a/mmu-miR-99a/rno-miR-99a | HL |
| hsa-miR-193a-5p | HL |
| hsa-miR-498 | HL |
| hsa-miR-628-3p | HL |
| hsa-miR-185* | HL |
| hsa-miR-371-5p | HL |
| hsa-miR-199b-5p | HL |
| hsa-miR-126/mmu-miR-126-3p/rno-miR-126 | HL |
| hsa-miR-503 | HL |
| hsa-miR-10a/mmu-miR-10a/rno-miR-10a-5p | HL |
| hsa-miR-300 | HL |
| hsa-miR-583 | HL |
| hsa-miR-518a-5p/hsa-miR-527 | HL |
| hsa-miR-10b/mmu-miR-10b/rno-miR-10b | HL |
| hsa-miR-145/mmu-miR-145/rno-miR-145 | HL |
| hsa-miR-128/mmu-miR-128/rno-miR-128 | HL |

TABLE 29-continued

Predictor microRNAs that distinguish Burkitt lymphoma from Hodgkin's lymphoma

| CLL vs HL | Higher in |
|---|---|
| hsa-miR-532-5p/mmu-miR-532-5p/rno-miR-532-5p | HL |
| hsa-miR-143* | HL |
| hsa-miR-28-3p/rno-miR-28* | HL |
| hsa-miR-130b*/mmu-miR-130b* | HL |
| hsa-miR-505/rno-miR-505 | HL |
| hsa-miR-25* | HL |
| hsa-miR-574-3p/mmu-miR-574-3p | HL |
| hsa-miR-455-3p | HL |
| kshv-miR-K12-3 | HL |
| hsa-miR-516b | HL |
| kshv-miR-K12-8 | HL |
| hsa-miR-502-3p | HL |
| kshv-miR-K12-6-3p | HL |
| hsa-miR-129-5p/mmu-miR-129-5p/rno-miR-129 | HL |
| hsa-miR-515-5p | HL |
| hsa-miR-199a-3p/hsa-miR-199b-3p/mmu-miR-199a-3p/mmu-miR-199b/rno-miR-199a-3p | HL |
| hsa-miR-149/mmu-miR-149 | HL |
| hsa-miR-889 | HL |
| hsa-miR-637 | HL |
| hsa-miR-600 | HL |
| hsa-miR-151-3p | HL |
| hsa-miR-656 | HL |
| hsa-miR-497/mmu-miR-497/rno-miR-497 | HL |
| hsa-miR-152/mmu-miR-152/rno-miR-152 | HL |
| hsa-miR-100/mmu-miR-100/rno-miR-100 | HL |
| hsa-miR-425/mmu-miR-425/rno-miR-425 | HL |
| hsa-miR-145*/mmu-miR-145* | HL |
| hsa-miR-365/mmu-miR-365/rno-miR-365 | HL |
| hsa-miR-422a | HL |
| hcmv-miR-UL70-3p | HL |
| hsa-miR-27a*/mmu-miR-27a*/rno-miR-27a* | HL |
| hsa-miR-194/mmu-miR-194/rno-miR-194 | HL |
| hsa-miR-548d-5p | HL |
| hsa-miR-187* | HL |
| hsa-miR-323-3p/mmu-miR-323-3p/rno-miR-323 | HL |
| hsa-miR-708/mmu-miR-708/rno-miR-708 | HL |
| hsa-miR-29c*/mmu-miR-29c*/rno-miR-29c* | HL |
| hsa-miR-513a-3p | HL |
| hsa-miR-595 | HL |
| hsa-miR-483-3p | HL |
| hsa-miR-330-5p/mmu-miR-330/rno-miR-330 | HL |
| hsa-miR-519e* | HL |
| hsa-miR-509-3p | HL |
| hsa-miR-328/mmu-miR-328/rno-miR-328 | HL |
| hsa-miR-373* | HL |
| hsa-miR-96/mmu-miR-96/rno-miR-96 | HL |
| hsa-miR-215 | HL |
| hsa-miR-589 | HL |
| hsa-miR-34c-5p/mmu-miR-34c/rno-miR-34c | HL |
| hsa-miR-125b/mmu-miR-125b-5p/rno-miR-125b-5p | HL |
| hsa-miR-130a/mmu-miR-130a/rno-miR-130a | HL |
| hsa-miR-519c-5p/hsa-miR-519b-5p/hsa-miR-523*/hsa-miR-518e*/hsa-miR-522*/hsa-miR-519a* | HL |
| mghv-miR-M1-7-5p | HL |
| hsa-miR-516a-5p | HL |
| hsa-miR-424 | HL |
| hsa-miR-17*/rno-miR-17-3p | HL |
| hsa-miR-296-5p/mmu-miR-296-5p/rno-miR-296* | HL |
| hsa-miR-550* | HL |
| hsa-miR-210/mmu-miR-210/rno-miR-210 | HL |
| hsa-miR-92b/mmu-miR-92b/rno-miR-92b | HL |
| hsa-miR-548b-3p | HL |
| hsa-miR-652/mmu-miR-652/rno-miR-652 | HL |
| hsa-miR-138/mmu-miR-138/rno-miR-138 | HL |
| hsa-miR-194* | HL |
| hsa-miR-23a*/rno-miR-23a* | HL |
| hsa-miR-153/mmu-miR-153/rno-miR-153 | HL |
| hsa-miR-586 | HL |
| hsa-miR-137/mmu-miR-137/rno-miR-137 | HL |
| hsa-miR-610 | HL |
| hsa-miR-381/mmu-miR-381/rno-miR-381 | HL |
| hsa-miR-936 | HL |
| hsa-miR-744/mmu-miR-744 | HL |
| ebv-miR-BART5 | HL |
| ebv-miR-BHRF1-1 | HL |
| hsa-miR-21* | HL |
| hsa-miR-576-5p | HL |
| mghv-miR-M1-6 | HL |

TABLE 29-continued

Predictor microRNAs that distinguish Burkitt lymphoma from Hodgkin's lymphoma

| CLL vs HL | Higher in |
|---|---|
| hsa-miR-193b | HL |
| hsa-miR-10a*/mmu-miR-10a*/rno-miR-10a-3p | HL |
| hsa-miR-524-5p | HL |
| hsa-miR-452 | HL |
| hsa-miR-345 | HL |
| hsa-miR-7-2* | HL |
| hsa-miR-409-5p/mmu-miR-409-5p/rno-miR-409-5p | HL |
| hsa-miR-557 | HL |
| hsa-miR-181a/mmu-miR-181a/rno-miR-181a | HL |
| hsa-miR-22*/mmu-miR-22*/rno-miR-22* | HL |
| hsa-miR-922 | HL |
| hsa-miR-92b* | HL |
| hsa-miR-938 | HL |
| hsa-miR-526a/hsa-miR-520c-5p/hsa-miR-518d-5p | HL |
| hsa-miR-526b* | HL |
| ebv-miR-BHRF1-2 | HL |
| hiv1-miR-H1 | HL |
| hsa-miR-623 | HL |
| mghv-miR-M1-2 | HL |
| mghv-miR-M1-7-3p | HL |
| hsa-miR-519e | HL |
| hsa-miR-650 | HL |
| hsa-miR-766 | HL |
| hsa-miR-602 | HL |
| hsa-miR-425*/mmu-miR-425* | HL |
| hsa-miR-135a*/mmu-miR-135a* | HL |
| hsa-miR-612 | HL |
| hsa-miR-212/mmu-miR-212/rno-miR-212 | HL |
| hsa-miR-125b-2*/rno-miR-125b* | HL |
| hcmv-miR-UL112 | HL |
| hsa-miR-374b* | HL |
| hsa-miR-886-5p | HL |
| hsa-miR-500 | HL |
| hsa-miR-502-5p | HL |
| ebv-miR-BART18-3p | HL |
| hsa-miR-198 | HL |
| hsa-miR-500* | HL |
| hsa-miR-342-5p/mmu-miR-342-5p/rno-miR-342-5p | HL |
| hsa-miR-124*/mmu-miR-124*/rno-miR-124* | HL |
| hsa-miR-30c-1*/mmu-miR-30c-1*/rno-miR-30c-1* | HL |
| hsa-miR-220c | HL |
| hsa-miR-376a* | HL |
| hsa-miR-640 | HL |
| hcmv-miR-UL148D | HL |
| hsa-miR-659 | HL |
| hsa-miR-934 | HL |
| hsa-miR-125a-3p/mmu-miR-125a-3p/rno-miR-125a-3p | HL |
| hsa-miR-885-5p | HL |
| hsa-miR-24-2*/mmu-miR-24-2*/rno-miR-24-2* | HL |
| hsa-miR-484/mmu-miR-484/rno-miR-484 | HL |
| hsa-miR-106b*/mmu-miR-106b*/rno-miR-106b* | HL |
| hsa-miR-505* | HL |
| hsa-let-7b*/mmu-let-7b*/rno-let-7b* | HL |
| hsa-miR-302c* | HL |
| hsa-miR-542-5p/mmu-miR-542-5p/rno-miR-542-5p | HL |
| hsv1-miR-H1 | HL |
| mghv-miR-M1-3 | HL |
| hsa-miR-183/mmu-miR-183/rno-miR-183 | HL |
| hsa-miR-122* | HL |
| hsa-miR-183*/mmu-miR-183* | HL |
| hsa-miR-675 | HL |
| hsa-miR-99b/mmu-miR-99b/rno-miR-99b | HL |
| hsa-miR-874/mmu-miR-874/rno-miR-874 | HL |
| ebv-miR-BART20-3p | HL |
| hsa-miR-483-5p | HL |
| hsa-miR-671-5p/mmu-miR-671-5p | HL |
| hsa-miR-629 | HL |
| hsa-miR-553 | HL |
| hsa-let-7d*/mmu-let-7d*/rno-let-7d* | HL |
| hsa-miR-601 | HL |
| hsa-miR-645 | HL |
| hsa-miR-920 | HL |
| hsa-miR-525-5p | HL |
| hsa-miR-221* | HL |
| hsa-miR-890 | HL |
| hsa-miR-492 | HL |
| hsa-miR-629* | HL |
| hsa-miR-635 | HL |
| hsa-miR-130b/mmu-miR-130b/rno-miR-130b | HL |
| hsa-miR-197/mmu-miR-197 | HL |
| hsa-miR-654-5p | HL |
| hsa-miR-518b | HL |
| hsa-miR-382/mmu-miR-382/rno-miR-382 | HL |
| hsa-miR-584 | HL |
| hsa-miR-99b*/mmu-miR-99b*/rno-miR-99b* | HL |
| hsa-miR-630 | HL |
| hsa-miR-490-5p | HL |
| hsa-miR-663 | HL |
| hsa-miR-337-3p | HL |
| hsa-miR-9*/mmu-miR-9*/rno-miR-9* | HL |
| hsa-miR-202 | HL |
| ebv-miR-BART16 | HL |
| ebv-miR-BART9* | HL |
| hsa-miR-193b* | HL |
| ebv-miR-BART8* | HL |
| hsa-miR-206/mmu-miR-206/rno-miR-206 | HL |

TABLE 29-continued

Predictor microRNAs that distinguish Burkitt lymphoma from Hodgkin's lymphoma

| CLL vs HL | Higher in |
|---|---|
| hcmv-miR-US25-1* | HL |
| hsa-miR-514 | HL |
| kshv-miR-K12-6-5p | HL |
| hsa-miR-488 | HL |
| hsa-miR-508-5p | HL |
| hsa-miR-551b* | HL |
| hsa-miR-377* | HL |
| ebv-miR-BART6-3p | HL |
| hsa-miR-181b/mmu-miR-181b/rno-miR-181b | HL |
| hsa-miR-526b | HL |
| hsa-miR-622 | HL |
| kshv-miR-K12-1 | HL |
| hsa-miR-485-3p/mmu-miR-485* | HL |
| hsa-miR-490-3p/mmu-miR-490 | HL |
| hsa-miR-125b-1*/mmu-miR-125b-3p/rno-miR-125b-3p | HL |
| hsa-miR-124/mmu-miR-124/rno-miR-124 | HL |
| hsa-miR-657 | HL |
| ebv-miR-BHRF1-3 | HL |
| hsa-miR-542-3p/mmu-miR-542-3p/rno-miR-542-3p | HL |
| kshv-miR-K12-5 | HL |
| hsa-miR-943 | HL |
| hsa-miR-551a | HL |
| hsa-miR-297/mmu-miR-297a | HL |
| hsa-miR-296-3p/mmu-miR-296-3p/rno-miR-296 | HL |
| hsa-miR-617 | HL |
| hsa-miR-195* | HL |
| hsa-miR-575 | HL |
| hsa-miR-208a/mmu-miR-208a/rno-miR-208 | HL |
| hsa-miR-647 | HL |
| hsa-miR-509-3-5p | HL |
| hsa-miR-340*/mmu-miR-340-3p/rno-miR-340-3p | HL |
| hsa-miR-220b | HL |
| hsa-miR-200b*/mmu-miR-200b* | HL |
| hsa-miR-585 | HL |
| hsa-miR-877/mmu-miR-877/rno-miR-877 | HL |
| hsa-miR-326/mmu-miR-326/rno-miR-326 | HL |
| ebv-miR-BART7* | HL |
| hsa-miR-615-3p/mmu-miR-615-3p | HL |
| hsa-miR-433/mmu-miR-433/rno-miR-433 | HL |
| hsa-miR-338-5p/mmu-miR-338-5p/rno-miR-338* | HL |
| hsa-miR-299-3p | HL |
| hsa-miR-518a-3p | HL |
| hsa-miR-181a-2* | HL |
| hsa-miR-552 | HL |

TABLE 30

Predictor microRNAs that distinguish follicular lymphoma from Hodgkin's lymphoma

| FL vs HL | Higher in |
|---|---|
| hsa-miR-301a/mmu-miR-301a/rno-miR-301a | FL |
| kshv-miR-K12-7 | FL |
| hsa-miR-96/mmu-miR-96/rno-miR-96 | FL |
| hsa-miR-151-5p/mmu-miR-151-5p/rno-miR-151 | FL |
| hsa-miR-28-5p/mmu-miR-28/rno-miR-28 | FL |
| hsa-miR-302a/mmu-miR-302a | FL |
| hsa-miR-215 | FL |
| hsa-miR-15b/mmu-miR-15b/rno-miR-15b | FL |
| hsa-miR-29b/mmu-miR-29b/rno-miR-29b | FL |
| hsa-miR-138/mmu-miR-138/rno-miR-138 | FL |
| hsa-miR-363/mmu-miR-363/rno-miR-363 | FL |
| hsa-miR-142-5p/mmu-miR-142-5p/rno-miR-142-5p | FL |
| hsa-miR-19a/mmu-miR-19a/rno-miR-19a | FL |
| hsa-miR-497/mmu-miR-497/rno-miR-497 | FL |
| hsa-miR-144* | FL |
| hsa-miR-16/mmu-miR-16/rno-miR-16 | FL |
| hsa-miR-138-1*/mmu-miR-138*/rno-miR-138* | FL |
| hsa-miR-768-5p | FL |
| hsa-miR-30c/mmu-miR-30c/rno-miR-30c | FL |
| hsa-miR-129* | FL |
| hsa-miR-801/mmu-miR-801 | FL |
| hsa-miR-34b/mmu-miR-34b-3p | FL |
| hsa-miR-363*/rno-miR-363* | FL |
| hsa-miR-20b* | FL |
| hsa-miR-550 | FL |
| hsa-miR-600 | FL |
| hsa-miR-196a*/mmu-miR-196a*/rno-miR-196a* | FL |
| hsa-miR-574-3p/mmu-miR-574-3p | FL |
| hsa-miR-620 | FL |
| hsa-miR-331-3p/mmu-miR-331-3p/rno-miR-331 | FL |
| hsa-let-7e/mmu-let-7e/rno-let-7e | FL |
| hsa-miR-524-5p | FL |
| hsa-miR-197/mmu-miR-197 | FL |
| hsa-miR-24-1*/mmu-miR-24-1*/rno-miR-24-1* | FL |
| hsa-miR-519e* | HL |
| hsa-miR-628-3p | HL |
| mghv-miR-M1-7-5p | HL |
| hsa-miR-498 | HL |
| hsa-miR-525-5p | HL |
| hsa-miR-520d-5p | HL |
| hsa-miR-551b* | HL |
| hsa-miR-340*/mmu-miR-340-3p/rno-miR-340-3p | HL |
| hsa-miR-889 | HL |
| hsa-miR-494/mmu-miR-494/rno-miR-494 | HL |

TABLE 30-continued

Predictor microRNAs that distinguish follicular lymphoma from Hodgkin's lymphoma

| FL vs HL | Higher in |
|---|---|
| hsa-miR-874/mmu-miR-874/rno-miR-874 | HL |
| hsa-miR-30c-2*/mmu-miR-30c-2*/rno-miR-30c-2* | |
| hsa-miR-183*/mmu-miR-183* | HL |
| hsa-miR-25* | HL |
| hsa-miR-513a-5p | HL |
| hsa-miR-198 | HL |
| hsa-miR-659 | HL |
| mghv-miR-M1-4 | HL |
| hsa-miR-129-5p/mmu-miR-129-5p/rno-miR-129 | HL |
| ebv-miR-BART13 | HL |
| hsa-miR-193b* | HL |
| hsa-miR-422a | HL |
| hsa-miR-503 | HL |
| kshv-miR-K12-3 | HL |
| hsa-miR-766 | HL |
| hsa-miR-516a-5p | HL |
| hsa-miR-125b-1*/mmu-miR-125b-3p/rno-miR-125b-3p | HL |
| hsa-miR-149* | HL |
| ebv-miR-BART6-3p | HL |
| ebv-miR-BART19-3p | HL |
| hsa-miR-671-5p/mmu-miR-671-5p | HL |
| ebv-miR-BART8* | HL |
| hsa-miR-509-3-5p | HL |
| hsa-miR-602 | HL |
| ebv-miR-BHRF1-1 | HL |
| mghv-miR-M1-7-3p | HL |
| mghv-miR-M1-2 | HL |
| hsa-miR-675 | HL |
| ebv-miR-BHRF1-2 | HL |
| hsa-miR-145*/mmu-miR-145* | HL |
| hsa-miR-296-5p/mmu-miR-296-5p/rno-miR-296* | HL |
| hsa-miR-17*/rno-miR-17-3p | HL |
| hsa-miR-452 | HL |
| hsa-miR-943 | HL |
| hsa-miR-326/mmu-miR-326/rno-miR-326 | HL |
| hsa-miR-652/mmu-miR-652/rno-miR-652 | HL |
| hsa-miR-623 | HL |
| hsa-miR-194* | HL |
| hsa-miR-557 | HL |
| hsa-miR-125a-3p/mmu-miR-125a-3p/rno-miR-125a-3p | HL |
| hsa-miR-425*/mmu-miR-425* | HL |
| hsa-miR-10a*/mmu-miR-10a*/rno-miR-10a-3p | HL |
| hsa-miR-323-3p/mmu-miR-323-3p/rno-miR-323 | HL |
| hsa-miR-519e | HL |
| hsa-miR-502-5p | HL |
| hsa-miR-124*/mmu-miR-124*/rno-miR-124* | HL |
| hsa-miR-345 | HL |
| hsa-miR-584 | HL |
| hsa-miR-654-5p | HL |
| hsa-miR-331-5p/mmu-miR-331-5p | HL |
| hsa-miR-650 | HL |
| hsa-miR-202 | HL |
| hsa-miR-548b-3p | HL |
| hsa-miR-492 | HL |
| hsa-miR-135a*/mmu-miR-135a* | HL |
| ebv-miR-BART20-3p | HL |
| hsa-miR-586 | HL |
| hsa-miR-338-5p/mmu-miR-338-5p/rno-miR-338* | HL |
| hsa-miR-92b* | HL |
| hiv1-miR-H1 | HL |
| hsa-miR-508-5p | HL |
| hsa-miR-542-5p/mmu-miR-542-5p/rno-miR-542-5p | HL |
| hsa-miR-490-5p | HL |
| hsa-miR-663 | HL |
| hsa-miR-433/mmu-miR-433/rno-miR-433 | HL |

We claim:

1. A method of identifying a B cell malignancy in a subject as Hodgkin's Lymphoma, the method comprising:
   determining the level of expression of a microRNA corresponding to SEQ ID NO: 768 in a sample comprising a B cell taken from the subject relative to the level of expression of the microRNA corresponding to SEQ ID NO: 768 in a control sample;
   diagnosing the subject as having Hodgkin's Lymphoma when the expression of the microRNA in the sample is at least two-fold greater than the level of expression in the control; and
   administering a therapy to treat the subject identified as having Hodgkin's Lymphoma.

2. A method of identifying a B cell malignancy in a subject as activated B cell-like (ABC) diffuse large B cell lymphoma (DLBCL), or germinal center-like (GCB) DLBCL, the method comprising:
   determining the level of expression of a microRNA corresponding to SEQ ID NO: 766 in a sample comprising a B cell taken from the subject relative to the level of expression of the microRNA corresponding to SEQ ID NO: 766 in a GCB DLBCL control sample; and
   administering a proteasome inhibitor to treat the subject identified as having ABC DLBCL, wherein the B cell malignancy is identified to be ABC DLBCL when the expression of the microRNA in the sample is 50% or less than the level of expression in the GCB DLBCL control.

3. The method of claim 1, the method further comprising determining the level of expression of at least one additional microRNA in a sample taken from the subject relative to the level of expression of the at least one additional microRNA in a control sample, wherein the at least one additional microRNA corresponds to at least one of SEQ ID NOs: 763, 764, 765, 766, 767, 769, 770, 771, 772, and 773.

4. The method of claim 1, wherein the control comprises normal cells, benign lymph nodes, or other B cell malignancy.

5. A method of identifying a B cell malignancy in a subject as activated B cell-like (ABC) diffuse large B cell lymphoma (DLBCL), the method comprising:
   determining the level of expression of a microRNA corresponding to at least one of SEQ ID NO: 766 and SEQ ID NO: 1061 in a sample comprising a B cell taken from the subject relative to the level of expression of the microRNA in a control sample; and
   administering a proteasome inhibitor to treat the subject identified as having ABC DLBCL, wherein the B cell malignancy is identified to be ABC DLBCL when the expression of the microRNA in the sample is 50% or less than the level of expression in the control.

6. The method of claim 5, wherein the control comprises normal cells, benign lymph nodes, or other B cell malignancy.

7. The method of claim 6, wherein the other B cell malignancy is selected from germinal center-like diffuse large B cell lymphoma (GCB DLBCL), Burkitt lymphoma, follicular lymphoma, and Hodgkin's lymphoma.

* * * * *